US012552853B2

(12) United States Patent
Swanson et al.

(10) Patent No.: US 12,552,853 B2
(45) Date of Patent: Feb. 17, 2026

(54) CD86 VARIANT IMMUNOMODULATORY PROTEINS AND USES THEREOF

(71) Applicant: Alpine Immune Sciences, Inc., Seattle, WA (US)

(72) Inventors: Ryan Swanson, Seattle, WA (US); Dan Ardourel, Seattle, WA (US); Steven Dennis Levin, Seattle, WA (US); Joseph L. Kuijper, Seattle, WA (US)

(73) Assignee: Alpine Immune Sciences, Inc., Seattle, WA (US)

( * ) Notice: Subject to any disclaimer, the term of this patent is extended or adjusted under 35 U.S.C. 154(b) by 1163 days.

(21) Appl. No.: 17/298,506

(22) PCT Filed: Nov. 27, 2019

(86) PCT No.: PCT/US2019/063808

§ 371 (c)(1),
(2) Date: May 28, 2021

(87) PCT Pub. No.: WO2020/113141

PCT Pub. Date: Jun. 4, 2020

(65) Prior Publication Data

US 2022/0372106 A1 Nov. 24, 2022

Related U.S. Application Data

(60) Provisional application No. 62/862,001, filed on Jun. 14, 2019, provisional application No. 62/774,131, filed on Nov. 30, 2018.

(51) Int. Cl.

| | |
|---|---|
| ***C07K 14/705*** | (2006.01) |
| ***A61K 39/395*** | (2006.01) |
| ***C07K 14/47*** | (2006.01) |
| ***C12N 15/10*** | (2006.01) |

(52) U.S. Cl.

CPC ...... *C07K 14/70532* (2013.01); *A61K 39/395* (2013.01); *C07K 14/47* (2013.01); *C12N 15/102* (2013.01); *C07K 2317/24* (2013.01); *C07K 2317/52* (2013.01)

(58) Field of Classification Search

None

See application file for complete search history.

(56) References Cited

U.S. PATENT DOCUMENTS

| | | | |
|---|---|---|---|
| 5,168,062 | A | 12/1992 | Stinski |
| 5,208,020 | A | 5/1993 | Chari et al. |
| 5,385,839 | A | 1/1995 | Stinski |
| 5,443,964 | A | 8/1995 | Pickup et al. |
| 5,457,035 | A | 10/1995 | Baum et al. |
| 5,500,362 | A | 3/1996 | Robinson et al. |
| 5,624,821 | A | 4/1997 | Winter et al. |
| 5,648,260 | A | 7/1997 | Winter et al. |
| 5,698,530 | A | 12/1997 | Schlom et al. |
| 5,716,613 | A | 2/1998 | Guber et al. |
| 5,716,826 | A | 2/1998 | Guber et al. |
| 5,731,168 | A | 3/1998 | Carter et al. |
| 5,767,071 | A | 6/1998 | Palladino et al. |
| 5,780,426 | A | 7/1998 | Palladino et al. |
| 5,821,337 | A | 10/1998 | Carter et al. |
| 5,851,529 | A | 12/1998 | Guber et al. |
| 5,891,432 | A | 4/1999 | Hoo |
| 5,998,205 | A | 12/1999 | Hallenbeck et al. |
| 6,143,290 | A | 11/2000 | Zhang et al. |
| 6,194,551 | B1 | 2/2001 | Idusogie et al. |
| 6,365,619 | B1 | 4/2002 | Shi |
| 6,428,968 | B1 | 8/2002 | Molnar-Kimber et al. |
| 6,596,535 | B1 | 7/2003 | Carter |
| 6,632,670 | B1 | 10/2003 | Wadsworth et al. |
| 6,635,427 | B2 | 10/2003 | Wittwer et al. |
| 6,653,103 | B2 | 11/2003 | Peterson et al. |
| 6,689,871 | B1 | 2/2004 | Wolfe et al. |
| 6,723,316 | B2 | 4/2004 | Laquerre et al. |
| 6,737,056 | B1 | 5/2004 | Presta |
| 6,855,317 | B2 | 2/2005 | Koelle et al. |
| 6,887,471 | B1 | 5/2005 | Linsley et al. |
| 6,897,045 | B2 | 5/2005 | Engelhardt et al. |
| 6,936,257 | B1 | 8/2005 | Bennett |
| 6,998,252 | B1 | 2/2006 | Moss et al. |
| 7,001,765 | B2 | 2/2006 | Maass et al. |
| 7,033,826 | B2 | 4/2006 | Perricaudet et al. |
| 7,094,875 | B2 | 8/2006 | Punnonen et al. |
| 7,125,717 | B2 | 10/2006 | Carter |
| 7,153,510 | B1 | 12/2006 | Rose |

(Continued)

FOREIGN PATENT DOCUMENTS

| | | |
|---|---|---|
| EP | 0757099 | 2/1997 |
| EP | 1385466 | 2/2004 |

(Continued)

OTHER PUBLICATIONS

U.S. Appl. No. 16/959,662, filed Jan. 3, 2019, by Swanson et al.

(Continued)

*Primary Examiner* — Ilia I Ouspenski

(74) *Attorney, Agent, or Firm* — McNeill PLLC

(57) ABSTRACT

Provided herein are variant CD86 polypeptides, immunomodulatory proteins comprising variant CD86 polypeptides, and nucleic acids encoding such proteins. The immunomodulatory proteins provide therapeutic utility for a variety of immunological and oncological conditions. Compositions and methods for making and using such proteins are provided.

23 Claims, 37 Drawing Sheets

Specification includes a Sequence Listing.

(56) References Cited

U.S. PATENT DOCUMENTS

| | | | | |
|---|---|---|---|---|
| 7,172,893 | B2 | 2/2007 | Rabinowitz et al. | |
| 7,238,526 | B2 | 7/2007 | Wilson et al. | |
| 7,241,447 | B1 | 7/2007 | Engelhardt et al. | |
| 7,247,615 | B2 | 7/2007 | Schlom et al. | |
| 7,332,581 | B2 | 2/2008 | Presta | |
| 7,368,116 | B2 | 5/2008 | Schlom et al. | |
| 7,371,826 | B2 | 5/2008 | Presta | |
| 7,378,087 | B2 | 5/2008 | Jefferies et al. | |
| 7,537,924 | B2 | 5/2009 | Coffin | |
| 7,550,296 | B2 | 6/2009 | Hermiston et al. | |
| 7,588,767 | B2 | 9/2009 | Szalay et al. | |
| 7,588,771 | B2 | 9/2009 | Szalay et al. | |
| 7,662,398 | B2 | 2/2010 | Szalay et al. | |
| 7,662,627 | B2 | 2/2010 | Johnson et al. | |
| 7,731,952 | B2 | 6/2010 | Mohr et al. | |
| 7,731,974 | B2 | 6/2010 | Bell et al. | |
| 7,754,221 | B2 | 7/2010 | Szalay et al. | |
| 7,811,814 | B2 | 10/2010 | Bohn et al. | |
| 7,897,146 | B2 | 3/2011 | Brown et al. | |
| 7,906,111 | B2 | 3/2011 | Wilson et al. | |
| 7,927,585 | B2 | 4/2011 | Snyder | |
| 7,943,374 | B2 | 5/2011 | Hildinger | |
| 7,968,340 | B2 | 6/2011 | Hallek et al. | |
| 8,007,780 | B2 | 8/2011 | Arbetman et al. | |
| 8,911,726 | B2 | 12/2014 | Takahashi et al. | |
| 8,956,619 | B2 | 2/2015 | Ostrand-Rosenberg | |
| 9,029,315 | B2 | 5/2015 | Chen et al. | |
| 9,103,831 | B2 | 8/2015 | O'Sullivan et al. | |
| 9,453,227 | B2 | 9/2016 | Diamond et al. | |
| 9,709,568 | B2 | 7/2017 | Pierce et al. | |
| 9,884,902 | B2 | 2/2018 | Minter et al. | |
| 11,078,282 | B2 | 8/2021 | Swanson et al. | |
| 11,096,988 | B2 | 8/2021 | Swanson et al. | |
| 11,117,948 | B2 | 9/2021 | Swanson et al. | |
| 11,117,949 | B2 | 9/2021 | Swanson et al. | |
| 11,117,950 | B2 | 9/2021 | Swanson et al. | |
| 11,230,588 | B2 | 1/2022 | Swanson et al. | |
| 11,319,359 | B2 | 5/2022 | Swanson et al. | |
| 11,359,022 | B2 | 6/2022 | Swanson et al. | |
| 11,479,609 | B2 | 10/2022 | Swanson et al. | |
| 11,498,967 | B2 | 11/2022 | Swanson et al. | |
| 11,639,375 | B2 | 5/2023 | Swanson et al. | |
| 11,753,458 | B2 | 9/2023 | Evans et al. | |
| 12,065,476 | B2 * | 8/2024 | Swanson ................ | C12N 15/86 |
| 2002/0009454 | A1 | 1/2002 | Boone et al. | |
| 2002/0168714 | A1 | 11/2002 | Barbas et al. | |
| 2003/0138881 | A1 | 7/2003 | Punnonen et al. | |
| 2003/0232323 | A1 | 12/2003 | Freeman et al. | |
| 2004/0009604 | A1 | 1/2004 | Zhang et al. | |
| 2004/0063094 | A1 | 4/2004 | Coffin et al. | |
| 2004/0072283 | A1 | 4/2004 | Seed et al. | |
| 2004/0146488 | A1 | 7/2004 | Hu et al. | |
| 2005/0014934 | A1 | 1/2005 | Hinton et al. | |
| 2005/0220818 | A1 | 10/2005 | Lorence | |
| 2005/0260601 | A1 | 11/2005 | Whitt et al. | |
| 2006/0024298 | A1 | 2/2006 | Lazar et al. | |
| 2006/0039894 | A1 | 2/2006 | Mohr et al. | |
| 2007/0098743 | A1 | 5/2007 | Bell et al. | |
| 2007/0110720 | A1 | 5/2007 | Brown et al. | |
| 2007/0202572 | A1 | 8/2007 | Szalay et al. | |
| 2007/0212727 | A1 | 9/2007 | Szalay et al. | |
| 2009/0010889 | A1 | 1/2009 | Brown et al. | |
| 2009/0053244 | A1 | 2/2009 | Chen et al. | |
| 2009/0098529 | A1 | 4/2009 | Chen et al. | |
| 2009/0117034 | A1 | 5/2009 | Chen et al. | |
| 2009/0136917 | A1 | 5/2009 | Szalay et al. | |
| 2009/0155287 | A1 | 6/2009 | Chen et al. | |
| 2009/0162288 | A1 | 6/2009 | Chen et al. | |
| 2009/0215147 | A1 | 8/2009 | Zhang et al. | |
| 2009/0274728 | A1 | 11/2009 | Brown et al. | |
| 2009/0285860 | A1 | 11/2009 | Martuza et al. | |
| 2010/0062016 | A1 | 3/2010 | Szalay et al. | |
| 2010/0092515 | A1 | 4/2010 | Conner et al. | |
| 2010/0113567 | A1 | 5/2010 | Barber | |
| 2010/0172877 | A1 | 7/2010 | van den Pol et al. | |
| 2010/0178276 | A1 | 7/2010 | Sadelain et al. | |
| 2010/0178684 | A1 | 7/2010 | Woo et al. | |
| 2010/0196325 | A1 | 8/2010 | Szalay et al. | |
| 2010/0233078 | A1 | 9/2010 | Szalay et al. | |
| 2010/0261660 | A1 | 10/2010 | Punnonen et al. | |
| 2010/0322893 | A1 | 12/2010 | Franks et al. | |
| 2011/0064650 | A1 | 3/2011 | Szalay | |
| 2011/0064763 | A1 | 3/2011 | Allen et al. | |
| 2011/0158948 | A1 | 6/2011 | Brown et al. | |
| 2011/0177032 | A1 | 7/2011 | Martuza | |
| 2011/0212530 | A1 | 9/2011 | Baltimore et al. | |
| 2011/0293705 | A1 | 12/2011 | Irvine et al. | |
| 2011/0305712 | A1 | 12/2011 | Akamatsu et al. | |
| 2013/0017199 | A1 | 1/2013 | Langermann | |
| 2013/0149305 | A1 | 6/2013 | Ostrand-Rosenberg | |
| 2014/0011370 | A1 | 1/2014 | Camphausen | |
| 2014/0154216 | A1 | 6/2014 | Coffin | |
| 2014/0186401 | A1 | 7/2014 | Diamond et al. | |
| 2014/0322129 | A1 | 10/2014 | Leong et al. | |
| 2014/0348832 | A1 | 11/2014 | Zhu et al. | |
| 2015/0232532 | A1 | 8/2015 | Ostrand-Rosenberg | |
| 2015/0359909 | A1 | 12/2015 | O'Sullivan et al. | |
| 2016/0017041 | A1 | 1/2016 | Violette et al. | |
| 2016/0339066 | A1 | 11/2016 | Szalay et al. | |
| 2016/0347849 | A1 | 12/2016 | Cai et al. | |
| 2016/0376346 | A1 | 12/2016 | Camphausen et al. | |
| 2017/0028040 | A1 | 2/2017 | Lan et al. | |
| 2017/0189476 | A1 | 7/2017 | Sung et al. | |
| 2018/0118805 | A1 | 5/2018 | Bernett et al. | |
| 2018/0208639 | A1 | 7/2018 | Minter et al. | |
| 2018/0244749 | A1 | 8/2018 | Swanson et al. | |
| 2018/0256644 | A1 | 9/2018 | Swanson et al. | |
| 2018/0319861 | A1 | 11/2018 | Lan et al. | |
| 2019/0135922 | A1 | 5/2019 | Swanson et al. | |
| 2019/0175654 | A1 | 6/2019 | Swanson et al. | |
| 2020/0040059 | A1 | 2/2020 | Swanson et al. | |
| 2021/0130436 | A1 | 5/2021 | Swanson et al. | |
| 2021/0155668 | A1 | 5/2021 | Swanson et al. | |
| 2021/0155669 | A1 | 5/2021 | Swanson et al. | |
| 2021/0163571 | A1 | 6/2021 | Swanson et al. | |
| 2021/0171603 | A1 | 6/2021 | Swanson et al. | |
| 2021/0188942 | A1 | 6/2021 | Swanson et al. | |
| 2021/0347897 | A1 | 11/2021 | Swanson et al. | |
| 2021/0363219 | A1 * | 11/2021 | Swanson .......... | C07K 14/70503 |
| 2022/0242930 | A1 | 8/2022 | Swanson et al. | |
| 2023/0101432 | A1 | 3/2023 | Swanson | |
| 2023/0136723 | A1 | 5/2023 | Swanson et al. | |
| 2023/0220039 | A1 | 7/2023 | Swanson et al. | |
| 2023/0250152 | A1 | 8/2023 | Evans et al. | |
| 2024/0002466 | A1 | 1/2024 | Swanson et al. | |
| 2024/0158463 | A1 | 5/2024 | Evans et al. | |
| 2024/0360197 | A1 * | 10/2024 | Swanson .......... | C07K 14/70503 |

FOREIGN PATENT DOCUMENTS

| | | |
|---|---|---|
| EP | 1391213 | 2/2004 |
| EP | 1520175 | 4/2005 |
| EP | 1606411 | 12/2005 |
| EP | 3020816 | 5/2016 |
| WO | WO-1993/010151 | 5/1993 |
| WO | WO-1994/011026 | 5/1994 |
| WO | WO-1994/029351 | 12/1994 |
| WO | WO-1998/050431 | 11/1998 |
| WO | WO-1999/002711 | 1/1999 |
| WO | WO-1999/038955 | 8/1999 |
| WO | WO-1999/051642 | 10/1999 |
| WO | WO-2000/042072 | 7/2000 |
| WO | WO-2001/030843 | 5/2001 |
| WO | WO-2002/000717 | 1/2002 |
| WO | WO 2003/002722 | 1/2003 |
| WO | WO-2004/029197 | 4/2004 |
| WO | WO 2004/030636 | 4/2004 |
| WO | WO-2004/056312 | 7/2004 |
| WO | WO-2005/063816 | 7/2005 |
| WO | WO-2005/100402 | 10/2005 |
| WO | WO-2006/019447 | 2/2006 |
| WO | WO-2006/029879 | 3/2006 |
| WO | WO-2007/052029 | 5/2007 |
| WO | WO-2008/011636 | 1/2008 |

(56) References Cited

FOREIGN PATENT DOCUMENTS

| | | |
|---|---|---|
| WO | WO-2008/047150 | 4/2008 |
| WO | WO-2008/155134 | 12/2008 |
| WO | WO 2009/029342 | 3/2009 |
| WO | WO-2009/067800 | 6/2009 |
| WO | WO-2009/076524 | 6/2009 |
| WO | WO 2009/105671 | 8/2009 |
| WO | WO 2010/027827 | 3/2010 |
| WO | WO-2011/020024 | 2/2011 |
| WO | WO-2011/056983 | 5/2011 |
| WO | WO-2011/103584 | 8/2011 |
| WO | WO-2011/113019 | 9/2011 |
| WO | WO-2011/133886 | 10/2011 |
| WO | WO-2012/079000 | 6/2012 |
| WO | WO-2012/125850 | 9/2012 |
| WO | WO-2012/141984 | 10/2012 |
| WO | WO-2012/149364 | 11/2012 |
| WO | WO-2015/184228 | 12/2012 |
| WO | WO-2013/003761 | 1/2013 |
| WO | WO 2013/079174 | 6/2013 |
| WO | WO-2013/130683 | 9/2013 |
| WO | WO-2013/149167 | 10/2013 |
| WO | WO-2013/169338 | 11/2013 |
| WO | WO 2014/138188 | 9/2014 |
| WO | WO-2014/198002 | 12/2014 |
| WO | WO-2014/207063 | 12/2014 |
| WO | WO-2015/009606 | 1/2015 |
| WO | WO-2015/107026 | 7/2015 |
| WO | WO-2016/011083 | 1/2016 |
| WO | WO-2016/191643 | 1/2016 |
| WO | WO 2016/022994 | 2/2016 |
| WO | WO 2016/034678 | 3/2016 |
| WO | WO-2016/073704 | 5/2016 |
| WO | WO-2016/118577 | 7/2016 |
| WO | WO-2016/164428 | 10/2016 |
| WO | WO-2016/168771 | 10/2016 |
| WO | WO 2017/019846 | 2/2017 |
| WO | WO-2017/029389 | 2/2017 |
| WO | WO-2017/048878 | 3/2017 |
| WO | WO-2017/055547 | 4/2017 |
| WO | WO 2017/079117 | 5/2017 |
| WO | WO 2017/106061 | 6/2017 |
| WO | WO-2017/181148 | 10/2017 |
| WO | WO-2017/181152 | 10/2017 |
| WO | WO 2017/201131 | 11/2017 |
| WO | WO-2018/022945 | 2/2018 |
| WO | WO-2018/022946 | 2/2018 |
| WO | WO-2018/075978 | 4/2018 |
| WO | WO-2018/170021 | 9/2018 |
| WO | WO-2018/170026 | 9/2018 |
| WO | WO-2019/136179 | 7/2019 |
| WO | WO-2019/241758 | 12/2019 |
| WO | WO 2001/092337 | 12/2021 |

OTHER PUBLICATIONS

U.S. Appl. No. 16/493,752, filed Sep. 12, 2019, by Swanson et al.

U.S. Appl. No. 17/252,233, filed Dec. 14, 2020, by Swanson et al.

"Database accession No. A0A2K5E9H6," Retrieved from UNIPROT, https://www.uniprot.org/uniprot/A0A2K5E9H6. Retrieved Sep. 13, 2019.

"Database accession No. BDH56778," Retrieved from GENESEQ, Retrieved on Sep. 13, 2019.

"Database accession No. BDV07959," Retrieved from GENESEQ, Retrieved on Sep. 12, 2019.

"Database accession No. ADM18706." Retrieved from IBIS, http://ibis/exam/dbfetch.jsp?id=GSP:ADM18706. Retrieved on Oct. 10, 2017.

"Database accession No. ADM18913." Retrieved from IBIS, http://ibis/exam/dbfetch.jsp?id=GSP:ADM18913. Retrieved on Oct. 10, 2017.

"Database accession No. BCD07227." Retrieved from IBIS, http://ibis/exam/dbfetch.jsp?id=GSP:BCD07227. Retrieved on Oct. 10, 2017.

"Database accession No. BCD07228." Retrieved from IBIS, http://ibis/exam/dbfetch.jsp?id=GSP:BCD07228. Retrieved on Oct. 10, 2017.

"Database accession No. BD020821," Retrieved from GENESEQ, https://www.ebi.ac.uk/ena/data/view/BD020821. Retrieved on May 16, 2018.

"Database accession No. BD020825," Retrieved from GENESEQ, https://www.ebi.ac.uk/ena/data/view/BD020825. Retrieved on May 16, 2018.

"Database accession No. F7DZ76," version 32. Retrieved from UNIPROT, http://www.uniprot.org/uniprot/F7DZ76. Retrieved on Jun. 6, 2018.

"Database accession No. G1SUI3," version 36. Retrieved from UNIPROT, http://www.uniprot.org/uniprot/G1SUI3.txt. Retrieved on Jun. 6, 2018.

Baban et al., "Bacteria as vectors for gene therapy of cancer," Bioeng Bugs. (2010) 1(6):385-394.

Behr et al., "Trastuzumab and breast cancer," N Engl J Med.(2001) 345:995-996.

Benson et al., "GenBank," Nucleic Acids Res (2013) 41 (Database issue):D36-D42.

Biasini et al., "Swiss-Model: modelling protein tertiary and quaternary structure using evolutionary information," Nucleic Acids Res (2014) 42:W252-258.

Boder et al.. "Optimal screening of surface-displayed polypeptide libraries," Biotechnol Prog. (1998) 14:55-62.

Brandt et al., The B7 family member B7-H6 is a tumor cell ligand for the activating natural killer cell receptor NKp30 in humans. J Exp Med. (2009) 206:1495-1503.

Brown et al., "Structure-based mutagenesis of the human immunodeficiency virus type 1 DNA attachment site: effects on integration and cDNA synthesis," J Virol. (1999) 73(11):9011-9020.

Bruggemann et al., "Comparison of the effector functions of human immunoglobulins using a matched set of chimeric antibodies," J Exp Med. (1987) 166(5):1351-1361.

Buchschacher et al., "Human immunodeficiency virus vectors for inducible expression of foreign genes," J Virol. (1992) 66(5):2731-2739.

Burmeister et al., ICOS controls the pool size of effector-memory and regulatory T cells. J Immunol.(2008) 180:774-82.

Busch et al., "Dimers, leucine zippers and DNA-binding domains," Trends Genet. (1990) 6(2): 36-40.

Carter et al., "Cytotoxic T-lymphocyte antigen-4 and programmed death-1 function as negative regulators of lymphocyte activation," Immunol Res (2003) 28:49-59.

Carter et al., "Humanization of an anti-p185HER2 antibody for human cancer therapy," Proc Natl Acad Sci USA (1992) 89:4285-4289.

Chakrabarti et al., "A mutant B7-1/Ig fusion protein that selectively binds to CTLA-4 ameliorates anti-tumor DNA vaccination and counters regulatory T cell activity", Vaccine, Elsevier, Amsterdam, NL, vol. 23, No. 37, Aug. 31, 2005 pp. 4553-4564.

Chang et al., "The discovery of small molecule carbamates as potent dual alpha(4)beta(1)/alpha(4)beta(7) integrin antagonists," Bioorg Med Chem Lett. Jan. 21, 2002;12(2):159-63.

Chao et al., "Isolating and engineering human antibodies using yeast surface display," Nat Protoc. (2006) 1:755-768.

Chari et al., "Immunoconjugates containing novel maytansinoids: promising anticancer drugs," Cancer Res. (1992) 52(1):127-131.

Chattopadhyay et al., "Structural basis of inducible costimulator ligand costimulatory function: determination of the cell surface oligomeric state and functional mapping of the receptor binding site of the protein," J Immunol. Sep. 15, 2006;177(6):3920-9.

Clynes et al., "Fc receptors are required in passive and active immunity to melanoma," Proc Natl Acad Sci U S A. (1998) 95(2):652-656.

Colcher et al., "Use of monoclonal antibodies as radiopharmaceuticals for the localization of human carcinoma xenografts in athymic mice," Methods Enzymol. (1986); 121: 802-16.

Cornetta et al., "No retroviremia or pathology in long-term follow-up of monkeys exposed to a murine amphotropic retrovirus," Hum Gene Ther. (1991) Fall;2(3):215-9.

(56) References Cited

OTHER PUBLICATIONS

Cragg et al., "Antibody specificity controls in vivo effector mechanisms of anti-CD20 reagents," Blood. (2004) 103(7):2738-2743.
Cragg et al., "Complement-mediated lysis by anti-CD20 mAb correlates with segregation into lipid rafts," Blood. (2003) 101(3):1045-1052.
David et al., "Protein iodination with solid state lactoperoxidase," Biochemistry. Feb. 26, 1974;13(5):1014-21.
Deisenhofer et al., "Crystallographic refinement and atomic models of a human Fc fragment and its complex with fragment B of protein A from *Staphylococcus aureus* at 2.9- and 2.8-A resolution," Biochemistry. Apr. 28, 1981;20(9):2361-70.
Derer et al., Complement in antibody-based tumor therapy. Crit Rev Immunol. (2014) 34:199-214.
Doty et al., "Two regions in the CD80 cytoplasmic tail regulate CD80 redistribution and T cell costimulation," J Immunol. (1998) 161(6): 2700-2707.
Dull et al., "A Third-Generation Lentivirus Vector with a Conditional Packaging System," J Virology (1998) 72(11): 8463-8471.
Duncan et al., "The binding site for C1q on IgG," Nature. Apr. 21, 1988;332(6166):738-40.
Ellis et al., "Interactions of CD80 and CD86 with CD28 and CTLA4," J Immunol (1996) 156:2700-2709.
Engelman et al., "Multiple effects of mutations in human immunodeficiency virus type 1 integrase on viral replication," J Virol. 1995 69(5):2729-2736.
Fraker et al., "Protein and cell membrane iodinations with a sparingly soluble chloroamide, 1,3,4,6-tetrachloro-3a,6a-diphrenylglycoluril," Biochem Biophys Res Commun. Feb. 28, 1978;80(4):849-57.
Freeman et al., "Engagement of the PD-1 immunoinhibitory receptor by a novel B7 family member leads to negative regulation of lymphocyte activation," J Exp Med (2000) 192(7):1027-1034.
Garcia-Aragoncillo et al., "Design of virotherapy for effective tumor treatment," Curr Opin Mol Ther. Aug. 2010;12(4):403-11.
Gazzano-Santoro et al., "A non-radioactive complement-dependent cytotoxicity assay for anti-CD20 monoclonal antibody," J Immunol Methods. Mar. 28, 1997;202(2):163-71.
Gentz et al., "Parallel association of Fos and Jun leucine zippers juxtaposes DNA binding domains," Science. (1989) 243(4899): 1695-1699.
Gherardi et al., "Recombinant poxviruses as mucosal vaccine vectors," J Gen Virol. (2005) 86(Pt 11):2925-2936.
Gregoire-Gauthier et al., "Use of immunoglobulins in the prevention of GvHD in a xenogeneic NOD/SCID/gammac-mouse model," Bone Marrow Transplant (2012) 47:439-450.
Guerra et al., "Host response to the attenuated poxvirus vector NYVAC: upregulation of apoptotic genes and NF-kappaB-responsive genes in infected HeLa cells," J Virol. (2006) 80(2): 985-98.
Haile et al., "Tumor Cell Programmed Death Ligand 1-Mediated T Cell Suppression ins overcome by coexpression of CD80," J Immunol (2011) 186(12):6822-6829.
Halaby et al., "The immunoglobulin superfamily: an insight on its tissular, species, and functional diversity," J Mol Evol (1998) 46:89-400.
Hallden et al., "Oncolytic virotherapy with modified adenoviruses and novel therapeutic targets," Expert Opin Ther Targets. Oct. 2012;16(10):945-58.
Harris et al., "CD80 costimulation is essential for the induction of airway eosinophilia," J Exp Med. Jan. 6, 1997;185(1):177-82.
Hellstrom et al., "Antitumor effects of L6, an IgG2a antibody that reacts with most human carcinomas," Proc Natl Acad Sci U S A. (1986) 83(18):7059-7063.
Hellstrom et al., "Strong antitumor activities of IgG3 antibodies to a human melanoma-associated ganglioside," Proc Natl Acad Sci U S A. (1985) 82(5):1499-1502.
Hinman et al., "Preparation and characterization of monoclonal antibody conjugates of the calicheamicins: a novel and potent family of antitumor antibiotics," Cancer Res. (1993) 53(14):3336-3342.
Hu et al., "Yaba-like disease virus: an alternative replicating poxvirus vector for cancer gene therapy," J Virol. (2001) 75(21):10300-10308.
Idusogie et al., "Mapping of the C1q binding site on rituxan, a chimeric antibody with a human IgG1 Fc," J Immunol. (2000) 164(8):4178-4184.
Jenkins et al., "CD28 delivers a costimulatory signal involved in antigen-specific IL-2 production by human T cells," J Immunol. (1991) 147:2461-6.
Johann et al., "GLVR1, a receptor for gibbon ape leukemia virus, is homologous to a phosphate permease of Neurospora crassa and is expressed at high levels in the brain and thymus," J Virol. (1992) 66(3):1635-1640.
Kabat et al., "Sequences of Proteins of Immunological Interest," Fifth Edition, U.S. Department of Health and Human Services, NIH Publication No. 91-3242 (1991), 83 pages.
Khalil et al., "The future of cancer treatment: immunomodulation, CARs and combination immunotherapy," Nat Rev Clin Oncol. (2016) 13(5):273-90.
Kirn et al., "Targeted and armed oncolytic poxviruses: a novel multi-mechanistic therapeutic class for cancer," Nat Rev Cancer. Jan. 2009;9(1):64-71.
Kolberg, "Gene-transfer virus contaminant linked to monkey's cancer," J NIH Res. (1992) 4:43-44.
Kremer et al., "Treatment of rheumatoid arthritis by selective inhibition of T-cell activation with fusion protein CTLA4Ig," N Engl J Med (2003) 349(20):1907-1915.
Labrijn et al., "Therapeutic IgG4 antibodies engage in Fab-arm exchange with endogenous human IgG4 in vivo," Nat Biotechnol. Aug. 2009;27(8):767-71.
Larsen et al., "Rational development of LEA29Y (belatacept), a high-affinity variant of CTLA4-Ig with potent immunosuppressive properties," Am J Transplant. Mar. 2005;5(3):443-53.
Leabman et al., "Effects of altered FcγR binding on antibody pharmacokinetics in cynomolgus monkeys," MAbs. (2013) 5(6):896-903.
Li et al., "Comparison of anti-CD3 and anti-CD28-coated beads with soluble anti-CD3 for expanding human T cells: differing impact on CD8 T cell phenotype and responsiveness to restimulation," J Transl Med. (2010) 8:104.
Lin et al., "Specific and dual antagonists of alpha(4)beta(1) and alpha(4)beta(7) integrins," Bioorg Med Chem Lett. Jan. 21, 2002;12(2):133-6.
Lindblad-Toh et al., "A high-resolution map of human evolutionary constraint using 29 mammals," Nature (2011) 478(7370):476-482.
Linderholm et al (Bio Process International, 2014, 12(10): 20-27.
Linsley et al., "Human B7-1 (CD80) and B7-2 (CD86) bind with similar avidities but distinct kinetics to CD28 and CTLA-4 receptors," Immunity. (1994) 1(9): 793-801.
Liu et al., "Eradication of large colon tumor xenografts by targeted delivery of maytansinoids," Proc Natl Acad Sci U S A. (1996) 93(16):8618-8623.
Lode et al., "Targeted therapy with a novel enediyene antibiotic calicheamicin theta(I)1 effectively suppresses growth and dissemination of liver metastases in a syngeneic model of murine neuroblastoma," Cancer Res. (1998) 58(14):2925-2928.
Mandler et al., "Immunoconjugates of geldanamycin and anti-HER2 monoclonal antibodies: antiproliferative activity on human breast carcinoma cell lines," J Natl Cancer Inst. Oct. 4, 2000;92(19):1573-81.
Mandler et al., "Modifications in synthesis strategy improve the yield and efficacy of geldanamycin-herceptin immunoconjugates," Bioconjug Chem. Jul.-Aug. 2002;13(4):786-91.
Mandler et al., "Synthesis and evaluation of antiproliferative activity of a geldanamycin-Herceptin immunoconjugate," Bioorg Med Chem Lett. May 15, 2000;10(10):1025-8.
Maurer et al., "ALPN-202 combines checkpoint inhibition with conditional T cell costimulation to overcome T cell suppression by M2c macrophages and improve the durability of engineered T cell

(56) References Cited

OTHER PUBLICATIONS anti-tumor responses," AACR Annual Meeting 2020;Cancer Res (2020) 80(16suppl): Abstract nr LB-085.
Maute et al., "Engineering high-affinity PD-1 variants for optimized immunotherapy and immuno-PET imaging," Proc Natl Acad Sci U S A. (2015) 112(47): E6506-14.
Mayr et al., "Passage history, properties, and applicability of the attenuated vaccinia virus strain MVA," Infection. (1975);3:6-14. (English translation of abstract provided).
Mcloughlin et al., "TNFerade, an adenovector carrying the transgene for human tumor necrosis factor alpha, for patients with advanced solid tumors: surgical experience and long-term follow-up," Ann Surg Oncol. Oct. 2005;12(10):825-30.
Mcwilliams et al., "Mutations in the 5' end of the human immunodeficiency virus type 1 polypurine tract affect RNase H cleavage specificity and virus titer," J Virol. (2003) 77(20):11150-11157.
Merchant et al., "An efficient route to human bispecific IgG," Nat Biotechnol. (1998) 16(7): 677-681.
Mercier et al., "A chimeric adenovirus vector encoding reovirus attachment protein sigma1 targets cells expressing junctional adhesion molecule 1," Proc Natl Acad Sci U S A. (2004) 101(16): 6188-6193.
Miller et al., "Construction and properties of retrovirus packaging cells based on gibbon ape leukemia virus," J Virol. (1991) 65(5):2220-2224.
Miller et al., "Construction and screening of antigen targeted immune yeast surface display antibody libraries," Curr Protoc Cytom. Jul. 2008;Chapter 4:Unit4.7.
Miller et al., "Gene transfer by retrovirus vectors occurs only in cells that are actively replicating at the time of infection," Mol Cell Biol. (1990) 10(8):4239-4242.
Miller, "Protein-protein recognition and the association of immunoglobulin constant domains," J Mol Biol. Dec. 20, 1990;216(4):965-73.
Milone et al., "Chimeric receptors containing CD137 signal transduction domains mediate enhanced survival of T cells and increased antileukemic efficacy in vivo," Mol Ther. (2009) 17(8):1453-64.
Miyoshi et al. "Development of a self-inactivating lentivirus vector," J Virol. (1998) 72(10):8150-8157.
Molin et al., "Two novel adenovirus vector systems permitting regulated protein expression in gene transfer experiments," J Virol. (1998) 72(10):8358-8361.
Morton et al., "Differential effects of CTLA-4 substitutions on the binding of human CD80 (B7-1) and CD86 (B7-2)," J Immunol. (1996) 156(3):1047-1054.
Narumi et al., "Adenovirus vector-mediated perforin expression driven by a glucocorticoid-inducible promoter inhibits tumor growth in vivo," Am J Respir Cell Mol Biol. (1998) 19(6):936-941.
Nightingale et al., "Transient gene expression by nonintegrating lentiviral vectors," Mol Ther. (2006) 13(6):1121-1132.
Nygren, "Conjugation of horseradish peroxidase to Fab fragments with different homobifunctional and heterobifunctional cross-linking reagents. A comparative study," J Histochem Cytochem. May 1982;30(5):407-12.
Pain et al., "Preparation of protein A-peroxidase monoconjugate using a heterobifunctional reagent, and its use in enzyme immunoassays," J Immunol Methods. (1981);40(2):219-30.
Patyar et al., "Bacteria in cancer therapy: a novel experimental strategy," J Biomed Sci. (2010) 17(1):21.
Peach et al., "Both extracellular immunoglobin-like domains of CD80 contain residues critical for binding T cell surface receptors CTLA-4 and CD28," J Biol Chem. (1995) 270(36):21181-7.
Penix et al., "Two essential regulatory elements in the human interferon gamma promoter confer activation specific expression in T cells," J Exp Med. (1993) 178(5):1483-1496.
Peper et al., "An impedance-based cytotoxicity assay for real-time and label-free assessment of T-cell-mediated killing of adherent cells," J Immunol Methods. Mar. 2014;405:192-8.
Pérez De La Lastra et al., "Epitope mapping of 10 monoclonal antibodies against the pig analogue of human membrane cofactor protein (MCP)," Immunology. (1999) 96(4):663-70.
Petkova et al., "Enhanced half-life of genetically engineered human IgG1 antibodies in a humanized FcRn mouse model: potential application in humorally mediated autoimmune disease," Int Immunol. (2006) 18(12):1759-1769.
Pfeifer et al., "Gene therapy: promises and problems," Annu Rev Genomics Hum Genet. (2001);2:177-211.
Philpott et al., "Use of nonintegrating lentiviral vectors for gene therapy," Hum Gene Ther. (2007) 18(6): 483-9.
Powell et al., "Sequence and structural determinants required for priming of plus-strand DNA synthesis by the human immunodeficiency virus type 1 polypurine tract," J Virol. (1996) 70(8):5288-5296.
Ravetch et al., "Fc receptors," Annu Rev Immunol. (1991) 9:457-492.
Rennert et al., "The IgV domain of human B7-2 (CD86) is sufficient to co-stimulate T lymphocytes and induce cytokine secretion," International Immunology (1997) 9(6):805-813.
Ridgway et al., "'Knobs-into-holes' engineering of antibody CH3 domains for heavy chain heterodimerization," Protein Eng. Jul. 1996;9(7):617-21.
Rosenberg et al., "Use of tumor-infiltrating lymphocytes and interleukin-2 in the immunotherapy of patients with metastatic melanoma. A preliminary report," N Engl J Med. (1988) 319(25):1676-1680.
Rowland et al., "Drug localisation and growth inhibition studies of vindesine-monoclonal anti-CEA conjugates in a human tumour xenograft," Cancer Immunol Immunother. (1986);21(3):183-7.
Ruperto et al., Abatacept in children with juvenile idiopathic arthritis: a randomised, double-blind, placebo-controlled withdrawal trial. Lancet. (2008) 372:383-391.
Sadelain, M. et al., "The basic principles of chimeric antigen receptor design." Cancer Discov., Apr. 2013, vol. 3, No. 4, pp. 388-398.
Sarmay, Gabriella, et al. "Mapping and comparison of the interaction sites on the Fc region of IgG responsible for triggering antibody dependent cellular cytotoxicity (ADCC) through different types of human Fcγ receptor." Molecular immunology 29.5 (1992): 633-639.
Schilderg et al., "Coinhibitory Pathways in the B7-CD28 Ligand-Receptor Family," Immunity. (2016) 44(5): 955-72.
Scholten et al., "Promiscuous behavior of HPV16E6 specific T cell receptor beta chains hampers functional expression in TCR transgenic T cells, which can be restored in part by genetic modification," Cell Oncol. (2010) 32:43-56.
Seow et al., "Biological gene delivery vehicles: beyond viral vectors," Mol Ther. (2009) 17(5):767-777.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. (2001) 276(9):6591-6604.
Sommerfelt et al., "Receptor interference groups of 20 retroviruses plating on human cells," Virology. (1990) 176(1): 58-69.
Srinivasan et al., "Immunomodulatory peptides from IgSF proteins: a review," Curr Protein Pept Sci. (2005) 6(2):185-96.
Srivastava et al., "Engineering CAR-T cells: Design Concepts," Trends in Immunology (2015) 36(8):494-502.
Swanson et al., "CD80 vIgD-Fc proteins combine checkpoint antagonism and costimulatory signaling for elicit potent anti-tumor immunity in vitro and in vivo" American Association for Cancer Research (AACR). Chicago, IL, Apr. 14-18, 2018, Abstract 4550, 1 page, published Jul. 2018.
Tangney et al., "The use of Listeria monocytogenes as a DNA delivery vector for cancer gene therapy," Bioeng Bugs. (2010) 1(4):284-287.
Tareen et al., "Design of a novel integration-deficient lentivector technology that incorporates genetic and posttranslational elements to target human dendritic cells," Mol Ther. (2014) 22(3):575-587.
Tartaglia et al., "Highly attenuated poxvirus vectors," AIDS Res Hum Retroviruses. (1992) 8(8):1445-1447.

(56) References Cited

OTHER PUBLICATIONS

Terawaki et al., "Specific and high-affinity binding of tetramerized PD-L1 extracellular domain to PD-1-expressing cells: possible application to enhance T cell function," Int Immunol (2007) 19(7):881-890.
Thompson et al., "cis-acting sequences required for inducible interleukin-2 enhancer function bind a novel Ets-related protein, Elf-1," Mol Cell Biol. (1992) 12(3):1043-1053.
Todd et al., "Transcription of the interleukin 4 gene is regulated by multiple promoter elements," J Exp Med. (1993) 177(6):1663-1674.
Topalian et al., "Safety, activity, and immune correlates of anti-PD-1 antibody in cancer," N engl J Med (2012) 366:2443-2454.
Vafa et al., "An engineered Fc variant of an IgG eliminates all immune effector functions via structural perturbations," Methods. (2014) 65(1):114-26.
Van Der Merwe et al.. "CD80 (B7-1) binds both CD28 and CTLA-4 with a low affinity and very fast kinetics," J exp Med (1997) 185:393-403.
Van Pijkeren et al., "A novel Listeria monocytogenes-based DNA delivery system for cancer gene therapy," Hum Gene Ther. Apr. 2010;21(4):405-16.
Vincenti et al., "Costimulation blockade with belatacept in renal transplantation," N Engl J Med. (2005) 353:770-81.
Vitetta et al., "Redesigning nature's poisons to create anti-tumor reagents," Science. Nov. 20, 1987;238(4830):1098-104.
Wade et al., "Genome sequence, comparative analysis, and population genetics of the domestic horse," Science. Nov. 6, 2009;326(5954):865-867.
Wang et al., "In vitro characterization of the anti-PD-1 antibody nivolumab, BMS-936558, and in vivo toxicology in non-human primates," Cancer Immunol Res. (2014) 2(9):846-856.
Wang et al., "Molecular modeling and functional mapping of B7-H1 and B7-DC uncouple costimulatory function from PD-1 interaction," J Exp Med. 2003 197(9):1083-91.
Weber et al., "ICOS maintains the T follicular helper cell phenotype by down-regulating Kruppel-like factor 2," J Exp Med. (2015) 212:217-33.
Wekerle et al., "Belatacept: from rational design to clinical application," Transplant International (2012) 25:139-150.
Wilson et al., "Formation of infectious hybrid virions with gibbon ape leukemia virus and human T-cell leukemia virus retroviral envelope glycoproteins and the gag and pol proteins of Moloney murine leukemia virus," J Virol. (1989) 63(5):2374-2378.
Wolchok et al., Development of ipilimumab: a novel immunotherapeutic approach for the treatment of advanced melanoma. Ann N Y Acad Sci. (2013) 1291:1-13.
Wu et al., "CTLA-4-B7 Interaction Is Sufficient to Costimulate T Cell Clonal Expansion," J. Exp. Med. (1997) 185(7):1327-1335.
Wu et al., "IL-24 modulates IFN-gamma expression in patients with tuberculosis," Immunol Lett. (2008) 117(1):57-62.
Xu et al., "Affinity and cross-reactivity engineering of CTLA4-Ig to modulate T cell costimulation," J Immunol (2012) 189(9):4470-4477.
Yao et al., "B7-h2 is a costimulatory ligand for CD28 in human," Immunity. (2011) 34(5):729-40.
Yoshinaga et al., cell co-stimulation through B7RP-1 and ICOS. Nature. (1999) 402:827-832.
Yu et al., "The role of B7-CD28 co-stimulation in tumor rejection," Int Imm (1998) 10(6):791-797.
Zhang et al., "An NKp30-Based Chimeric Anitgen Receptor Promotes T Cell Effector Functions and Antitumor Efficacy In Vivo," J Immunol (2012) 189:2290-2299.
Zhao et al., "TIGIT overexpression diminishes the function of CD4 T cells and ameliorates the severity of rheumatoid arthritis in mouse models," Exp Cell Res. Jan. 1, 2016;340(1):132-8.
Zufferey et al., "Self-inactivating lentivirus vector for safe and efficient in vivo gene delivery," J Virol. (1998) 72(12):9873-9880.
"Database accession No. A0A2K5Q1G1" Retrieved from UNIPROT, https://www.uniprot.org/uniprot/A0A2K5Q1G1.txt. Retrieved on Aug. 12, 2021.
"Database accession No. ADM18864" Retrieved from GENESEQ, Dated Jul. 1, 2004; XP002780658.
"Database accession No. ADM18719" Retrieved from GENESEQ, Dated Jul. 1, 2004; XP002780659.
"Database accession No. ADM18706" Retrieved from GENESEQ, Dated Jul. 1, 2004; XP002774557.
"Database accession No. ADM18913" Retrieved from GENESEQ, Dated Jul. 1, 2004; XP002774558 (abstract).
"Database accession No. ABP68480" Retrieved from GENESEQ, Dated Jan. 8, 2003; XP002780660 (abstract).
"Database accession No. ABP68546" Retrieved from GENESEQ, Dated Jan. 8, 2003; XP002780661 (abstract).
"Database accession No. BCD07228" Retrieved from GENESEQ, Dated Sep. 24, 2015; XP002774560 (abstract).
"Database accession No. BCD07227" Retrieved from GENESEQ, Dated Sep. 24, 2015; XP002774559.
"Database accession No. G3SBS5" Retrieved from UNIPROT, https://www.uniprot.org/uniprot/G3SBS5.txt. Retrieved on Aug. 12, 2021.
Bork, P. "Powers and pitfalls in sequence analysis: the 70% hurdle," Genome Res. (2000) 10(4):398-400.
Bowie et al., "Deciphering the message in protein sequences: tolerance to amino acid substitutions," Science. (1990) 247(4948):1306-10.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol. (1990) 111(5 Pt 1):2129-38.
Butte et al., "Interaction of human PD-L1 and B7-1," Molecular Immunology (2008) 45:3567-3572.
Chaudhri et al., "PD-L1 Binds to B7-1 Only In Cis on the Same Cell Surface," Cancer Immunol Res (2018) 6(8):921-929.
Ghiotto, M., et al "PD-L 1 and PD-L2 differ in their molecular mechanisms of interaction with PD-1", International Immunology, 2010, vol. 22, No. 8, pp. 651-660.
Greenspan et al., "Defining epitopes: It's not as easy as it seems," Nat Biotechnol. (1999) 17(10):936-7.
Haile et al., "Soluble CD80 restores T cell activation and overcomes tumor cell programmed death ligand 1-mediated immune suppression," J Immunol. (2013) 191(5):2829-36.
Hezareh et al., "Effector function activities of a panel of mutants of a broadly neutralizing antibody against human immunodeficiency virus type 1," J Virol (2001) 75(24):12161-12168.
Hunter et al., "Preparation of iodine-131 labelled human growth hormone of high specific activity," Nature. May 5, 1962;194:495-6.
Lazar et al., "Transforming growth factor alpha: mutation of aspartic acid 47 and leucine 48 results in different biological activities," Mol Cell Biol. (1988) 8(3):1247-52.
Lobner et al., "Engineered IgG1-Fc —one fragment to bind them all," Immunol Rev (2016) 270(1):113-31.
Metzler et al., "Solution structure of human CTLA-4 and delineation of a CD80/CD86 binding site conserved in CD28," Nat Struct Biol (1997) 4(7):527-31.
Mkaddem et al., "Understanding Fc Receptor Involvement in Inflammatory Diseases: From Mechanisms to New Therapeutic Tools," Front Immunol. (2019) 10:811.
Moreland et al., "Abatacept," Nat Rev Drug Discov (2006) 5(3):185-6.
Zhang et al., "Crystal structure of the receptor-binding domain of human B7-2: insights into organization and signaling," Proc Natl Acad Sci U S A. (2003) 100(5):2586-91.
"Chimeric human/porcine CD86." Geneseq Oct. 17, 2003 (Oct. 17, 2003), retrieved from EBI accession No. GSP: AAW14944 Database accession No. AAW14944.

* cited by examiner

FIG. 2B
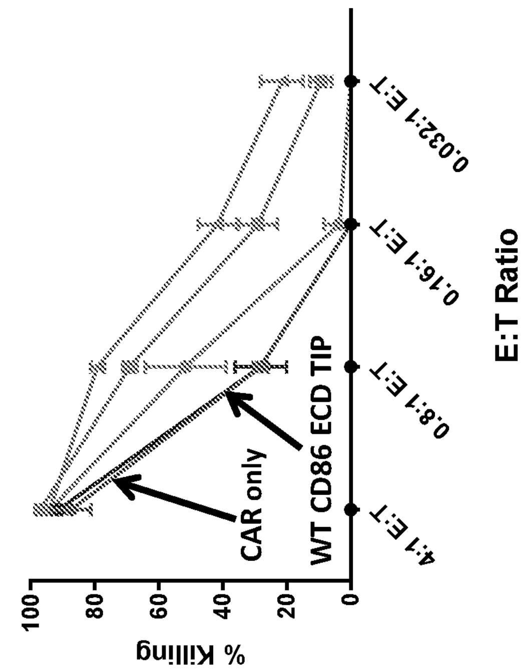
FIG. 2C
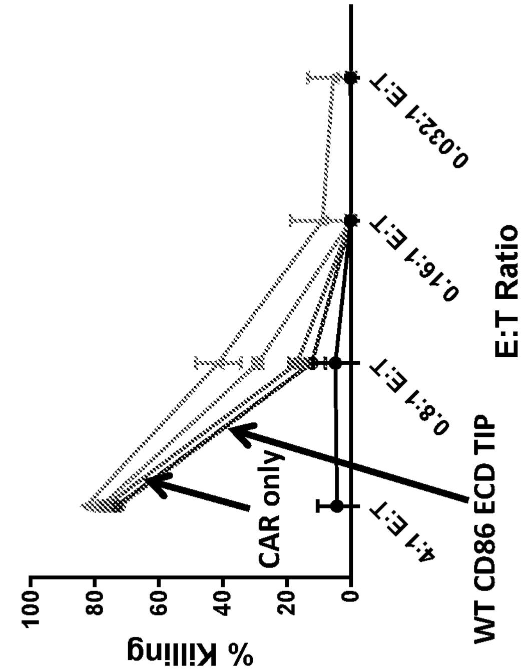
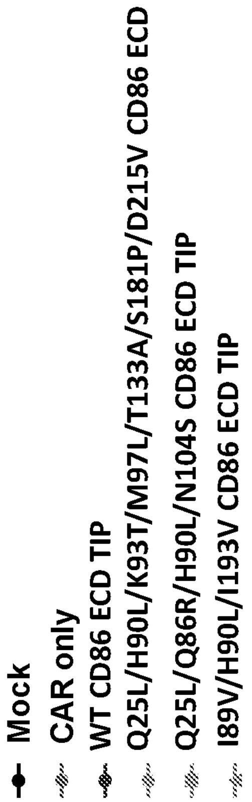

FIG. 3

```
SEQ ID NO: 29     APLKIQAYFNETADLPCQFANSQNQSLSELVVFWQDQENLVLNEVYLGKEKFDSVHSKYM   60
SEQ ID NO: 122    ---------NETADLPCQFANSQNQSLSELVVFWQDQENLVLNEVYLGKEKFDSVHSKYM   51
                           ***************************************************

SEQ ID NO: 29     GRTSFDSDSWTLRLHNLQIKDKGLYQCIIHHKKPTGMIRIHQMNSELSVLANFSQPEIVP   120
SEQ ID NO: 122    GRTSFDSDSWTLRLHNLQIKDKGLYQCIIHHKKPTGMIRIHQMNSELS------------   99
                  ************************************************

SEQ ID NO: 29     ISNITENVYINLTCSSIHGYPEPKKMSVLLRTKNSTIEYDGVMQKSQDNVTELYDVSISL   180
SEQ ID NO: 122    ------------------------------------------------------------   99

SEQ ID NO: 29     SVSFPDVTSNMTIFCILETDKTRLLSSPFSIELEDPQPPPDHIP   224
SEQ ID NO: 122    --------------------------------------------   99
```

Light Chain Constructs

Heavy Chain Constructs

SEQUENCE LISTING

<160> NUMBER OF SEQ ID NOS: 353

<210> SEQ ID NO 1
<211> LENGTH: 288
<212> TYPE: PRT
<213> ORGANISM: Homo sapiens
<220> FEATURE:
<223> OTHER INFORMATION: CD80(B7-1)

<400> SEQUENCE: 1

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

<210> SEQ ID NO 2
<211> LENGTH: 329
<212> TYPE: PRT
<213> ORGANISM: Homo sapiens
<220> FEATURE:
<223> OTHER INFORMATION: CD86(B7-2)

<400> SEQUENCE: 2

```
Met Asp Pro Gln Cys Thr Met Gly Leu Ser Asn Ile Leu Phe Val Met
1               5                   10                  15
```

Ala Phe Leu Leu Ser Gly Ala Ala Pro Leu Lys Ile Gln Ala Tyr Phe
20 25 30

Asn Glu Thr Ala Asp Leu Pro Cys Gln Phe Ala Asn Ser Gln Asn Gln
35 40 45

Ser Leu Ser Glu Leu Val Val Phe Trp Gln Asp Gln Glu Asn Leu Val
50 55 60

Leu Asn Glu Val Tyr Leu Gly Lys Glu Lys Phe Asp Ser Val His Ser
65 70 75 80

Lys Tyr Met Gly Arg Thr Ser Phe Asp Ser Asp Ser Trp Thr Leu Arg
85 90 95

Leu His Asn Leu Gln Ile Lys Asp Lys Gly Leu Tyr Gln Cys Ile Ile
100 105 110

His His Lys Lys Pro Thr Gly Met Ile Arg Ile His Gln Met Asn Ser
115 120 125

Glu Leu Ser Val Leu Ala Asn Phe Ser Gln Pro Glu Ile Val Pro Ile
130 135 140

Ser Asn Ile Thr Glu Asn Val Tyr Ile Asn Leu Thr Cys Ser Ser Ile
145 150 155 160

His Gly Tyr Pro Glu Pro Lys Lys Met Ser Val Leu Leu Arg Thr Lys
165 170 175

Asn Ser Thr Ile Glu Tyr Asp Gly Val Met Gln Lys Ser Gln Asp Asn
180 185 190

Val Thr Glu Leu Tyr Asp Val Ser Ile Ser Leu Ser Val Ser Phe Pro
195 200 205

Asp Val Thr Ser Asn Met Thr Ile Phe Cys Ile Leu Glu Thr Asp Lys
210 215 220

Thr Arg Leu Leu Ser Ser Pro Phe Ser Ile Glu Leu Glu Asp Pro Gln
225 230 235 240

Pro Pro Pro Asp His Ile Pro Trp Ile Thr Ala Val Leu Pro Thr Val
245 250 255

Ile Ile Cys Val Met Val Phe Cys Leu Ile Leu Trp Lys Trp Lys Lys
260 265 270

Lys Lys Arg Pro Arg Asn Ser Tyr Lys Cys Gly Thr Asn Thr Met Glu
275 280 285

Arg Glu Glu Ser Glu Gln Thr Lys Lys Arg Glu Lys Ile His Ile Pro
290 295 300

Glu Arg Ser Asp Glu Ala Gln Arg Val Phe Lys Ser Ser Lys Thr Ser
305 310 315 320

Ser Cys Asp Lys Ser Asp Thr Cys Phe
325

<210> SEQ ID NO 3
<211> LENGTH: 290
<212> TYPE: PRT
<213> ORGANISM: Homo sapiens
<220> FEATURE:
<223> OTHER INFORMATION: CD274 (PD-L1, B7-H1)

<400> SEQUENCE: 3

Met Arg Ile Phe Ala Val Phe Ile Phe Met Thr Tyr Trp His Leu Leu
1 5 10 15

Asn Ala Phe Thr Val Thr Val Pro Lys Asp Leu Tyr Val Val Glu Tyr
20 25 30

Gly Ser Asn Met Thr Ile Glu Cys Lys Phe Pro Val Glu Lys Gln Leu
35 40 45

```
Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 4
<211> LENGTH: 273
<212> TYPE: PRT
<213> ORGANISM: Homo sapiens
<220> FEATURE:
<223> OTHER INFORMATION: PDCD1LG2(PD-L2, CD273)

<400> SEQUENCE: 4

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110
```

Lys Tyr Leu Thr Leu Lys Val Lys Ala Ser Tyr Arg Lys Ile Asn Thr
115 120 125

His Ile Leu Lys Val Pro Glu Thr Asp Glu Val Glu Leu Thr Cys Gln
130 135 140

Ala Thr Gly Tyr Pro Leu Ala Glu Val Ser Trp Pro Asn Val Ser Val
145 150 155 160

Pro Ala Asn Thr Ser His Ser Arg Thr Pro Glu Gly Leu Tyr Gln Val
165 170 175

Thr Ser Val Leu Arg Leu Lys Pro Pro Pro Gly Arg Asn Phe Ser Cys
180 185 190

Val Phe Trp Asn Thr His Val Arg Glu Leu Thr Leu Ala Ser Ile Asp
195 200 205

Leu Gln Ser Gln Met Glu Pro Arg Thr His Pro Thr Trp Leu Leu His
210 215 220

Ile Phe Ile Pro Phe Cys Ile Ile Ala Phe Ile Phe Ile Ala Thr Val
225 230 235 240

Ile Ala Leu Arg Lys Gln Leu Cys Gln Lys Leu Tyr Ser Ser Lys Asp
245 250 255

Thr Thr Lys Arg Pro Val Thr Thr Thr Lys Arg Glu Val Asn Ser Ala
260 265 270

Ile

<210> SEQ ID NO 5
<211> LENGTH: 302
<212> TYPE: PRT
<213> ORGANISM: Homo sapiens
<220> FEATURE:
<223> OTHER INFORMATION: ICOSLG(B7RP1, CD275, ICOSL, B7-H2)

<400> SEQUENCE: 5

Met Arg Leu Gly Ser Pro Gly Leu Leu Phe Leu Leu Phe Ser Ser Leu
1 5 10 15

Arg Ala Asp Thr Gln Glu Lys Glu Val Arg Ala Met Val Gly Ser Asp
20 25 30

Val Glu Leu Ser Cys Ala Cys Pro Glu Gly Ser Arg Phe Asp Leu Asn
35 40 45

Asp Val Tyr Val Tyr Trp Gln Thr Ser Glu Ser Lys Thr Val Val Thr
50 55 60

Tyr His Ile Pro Gln Asn Ser Ser Leu Glu Asn Val Asp Ser Arg Tyr
65 70 75 80

Arg Asn Arg Ala Leu Met Ser Pro Ala Gly Met Leu Arg Gly Asp Phe
85 90 95

Ser Leu Arg Leu Phe Asn Val Thr Pro Gln Asp Glu Gln Lys Phe His
100 105 110

Cys Leu Val Leu Ser Gln Ser Leu Gly Phe Gln Glu Val Leu Ser Val
115 120 125

Glu Val Thr Leu His Val Ala Ala Asn Phe Ser Val Pro Val Val Ser
130 135 140

Ala Pro His Ser Pro Ser Gln Asp Glu Leu Thr Phe Thr Cys Thr Ser
145 150 155 160

Ile Asn Gly Tyr Pro Arg Pro Asn Val Tyr Trp Ile Asn Lys Thr Asp
165 170 175

Asn Ser Leu Leu Asp Gln Ala Leu Gln Asn Asp Thr Val Phe Leu Asn
180 185 190

Met Arg Gly Leu Tyr Asp Val Val Ser Val Leu Arg Ile Ala Arg Thr

```
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300


<210> SEQ ID NO 6
<211> LENGTH: 534
<212> TYPE: PRT
<213> ORGANISM: Homo sapiens
<220> FEATURE:
<223> OTHER INFORMATION: CD276(B7-H3)

<400> SEQUENCE: 6

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
```

```
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530


<210> SEQ ID NO 7
<211> LENGTH: 282
<212> TYPE: PRT
<213> ORGANISM: Homo sapiens
<220> FEATURE:
<223> OTHER INFORMATION: VTCN1(B7-H4)

<400> SEQUENCE: 7

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
```

```
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280


<210> SEQ ID NO 8
<211> LENGTH: 220
<212> TYPE: PRT
<213> ORGANISM: Homo sapiens
<220> FEATURE:
<223> OTHER INFORMATION: CD28

<400> SEQUENCE: 8

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
```

```
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220


<210> SEQ ID NO 9
<211> LENGTH: 223
<212> TYPE: PRT
<213> ORGANISM: Homo sapiens
<220> FEATURE:
<223> OTHER INFORMATION: CTLA4

<400> SEQUENCE: 9

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220


<210> SEQ ID NO 10
<211> LENGTH: 288
<212> TYPE: PRT
<213> ORGANISM: Homo sapiens
<220> FEATURE:
<223> OTHER INFORMATION: PDCD1(PD-1)

<400> SEQUENCE: 10

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30
```

```
Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 11
<211> LENGTH: 199
<212> TYPE: PRT
<213> ORGANISM: Homo sapiens
<220> FEATURE:
<223> OTHER INFORMATION: ICOS

<400> SEQUENCE: 11

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110
```

```
Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195


<210> SEQ ID NO 12
<211> LENGTH: 289
<212> TYPE: PRT
<213> ORGANISM: Homo sapiens
<220> FEATURE:
<223> OTHER INFORMATION: BTLA(CD272)

<400> SEQUENCE: 12

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270
```

```
Arg Asn Val Lys Glu Ala Pro Thr Glu Tyr Ala Ser Ile Cys Val Arg
        275                 280                 285

Ser


<210> SEQ ID NO 13
<211> LENGTH: 458
<212> TYPE: PRT
<213> ORGANISM: Homo sapiens
<220> FEATURE:
<223> OTHER INFORMATION: CD4

<400> SEQUENCE: 13

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
```

340 345 350

Lys Arg Glu Lys Ala Val Trp Val Leu Asn Pro Glu Ala Gly Met Trp
355 360 365

Gln Cys Leu Leu Ser Asp Ser Gly Gln Val Leu Leu Glu Ser Asn Ile
370 375 380

Lys Val Leu Pro Thr Trp Ser Thr Pro Val Gln Pro Met Ala Leu Ile
385 390 395 400

Val Leu Gly Gly Val Ala Gly Leu Leu Leu Phe Ile Gly Leu Gly Ile
405 410 415

Phe Phe Cys Val Arg Cys Arg His Arg Arg Arg Gln Ala Glu Arg Met
420 425 430

Ser Gln Ile Lys Arg Leu Leu Ser Glu Lys Lys Thr Cys Gln Cys Pro
435 440 445

His Arg Phe Gln Lys Thr Cys Ser Pro Ile
450 455

<210> SEQ ID NO 14
<211> LENGTH: 235
<212> TYPE: PRT
<213> ORGANISM: Homo sapiens
<220> FEATURE:
<223> OTHER INFORMATION: CD8A(CD8-alpha)

<400> SEQUENCE: 14

Met Ala Leu Pro Val Thr Ala Leu Leu Leu Pro Leu Ala Leu Leu Leu
1 5 10 15

His Ala Ala Arg Pro Ser Gln Phe Arg Val Ser Pro Leu Asp Arg Thr
20 25 30

Trp Asn Leu Gly Glu Thr Val Glu Leu Lys Cys Gln Val Leu Leu Ser
35 40 45

Asn Pro Thr Ser Gly Cys Ser Trp Leu Phe Gln Pro Arg Gly Ala Ala
50 55 60

Ala Ser Pro Thr Phe Leu Leu Tyr Leu Ser Gln Asn Lys Pro Lys Ala
65 70 75 80

Ala Glu Gly Leu Asp Thr Gln Arg Phe Ser Gly Lys Arg Leu Gly Asp
85 90 95

Thr Phe Val Leu Thr Leu Ser Asp Phe Arg Arg Glu Asn Glu Gly Tyr
100 105 110

Tyr Phe Cys Ser Ala Leu Ser Asn Ser Ile Met Tyr Phe Ser His Phe
115 120 125

Val Pro Val Phe Leu Pro Ala Lys Pro Thr Thr Thr Pro Ala Pro Arg
130 135 140

Pro Pro Thr Pro Ala Pro Thr Ile Ala Ser Gln Pro Leu Ser Leu Arg
145 150 155 160

Pro Glu Ala Cys Arg Pro Ala Ala Gly Gly Ala Val His Thr Arg Gly
165 170 175

Leu Asp Phe Ala Cys Asp Ile Tyr Ile Trp Ala Pro Leu Ala Gly Thr
180 185 190

Cys Gly Val Leu Leu Leu Ser Leu Val Ile Thr Leu Tyr Cys Asn His
195 200 205

Arg Asn Arg Arg Arg Val Cys Lys Cys Pro Arg Pro Val Val Lys Ser
210 215 220

Gly Asp Lys Pro Ser Leu Ser Ala Arg Tyr Val
225 230 235

```
<210> SEQ ID NO 15
<211> LENGTH: 210
<212> TYPE: PRT
<213> ORGANISM: Homo sapiens
<220> FEATURE:
<223> OTHER INFORMATION: CD8B(CD8-beta)

<400> SEQUENCE: 15

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Phe
        195                 200                 205

Tyr Lys
    210


<210> SEQ ID NO 16
<211> LENGTH: 525
<212> TYPE: PRT
<213> ORGANISM: Homo sapiens
<220> FEATURE:
<223> OTHER INFORMATION: LAG3

<400> SEQUENCE: 16

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95
```

```
Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
```

515 520 525

<210> SEQ ID NO 17
<211> LENGTH: 301
<212> TYPE: PRT
<213> ORGANISM: Homo sapiens
<220> FEATURE:
<223> OTHER INFORMATION: HAVCR2(TIM-3)

<400> SEQUENCE: 17

Met Phe Ser His Leu Pro Phe Asp Cys Val Leu Leu Leu Leu Leu Leu
1 5 10 15

Leu Leu Thr Arg Ser Ser Glu Val Glu Tyr Arg Ala Glu Val Gly Gln
20 25 30

Asn Ala Tyr Leu Pro Cys Phe Tyr Thr Pro Ala Ala Pro Gly Asn Leu
35 40 45

Val Pro Val Cys Trp Gly Lys Gly Ala Cys Pro Val Phe Glu Cys Gly
50 55 60

Asn Val Val Leu Arg Thr Asp Glu Arg Asp Val Asn Tyr Trp Thr Ser
65 70 75 80

Arg Tyr Trp Leu Asn Gly Asp Phe Arg Lys Gly Asp Val Ser Leu Thr
85 90 95

Ile Glu Asn Val Thr Leu Ala Asp Ser Gly Ile Tyr Cys Cys Arg Ile
100 105 110

Gln Ile Pro Gly Ile Met Asn Asp Glu Lys Phe Asn Leu Lys Leu Val
115 120 125

Ile Lys Pro Ala Lys Val Thr Pro Ala Pro Thr Arg Gln Arg Asp Phe
130 135 140

Thr Ala Ala Phe Pro Arg Met Leu Thr Thr Arg Gly His Gly Pro Ala
145 150 155 160

Glu Thr Gln Thr Leu Gly Ser Leu Pro Asp Ile Asn Leu Thr Gln Ile
165 170 175

Ser Thr Leu Ala Asn Glu Leu Arg Asp Ser Arg Leu Ala Asn Asp Leu
180 185 190

Arg Asp Ser Gly Ala Thr Ile Arg Ile Gly Ile Tyr Ile Gly Ala Gly
195 200 205

Ile Cys Ala Gly Leu Ala Leu Ala Leu Ile Phe Gly Ala Leu Ile Phe
210 215 220

Lys Trp Tyr Ser His Ser Lys Glu Lys Ile Gln Asn Leu Ser Leu Ile
225 230 235 240

Ser Leu Ala Asn Leu Pro Pro Ser Gly Leu Ala Asn Ala Val Ala Glu
245 250 255

Gly Ile Arg Ser Glu Glu Asn Ile Tyr Thr Ile Glu Glu Asn Val Tyr
260 265 270

Glu Val Glu Glu Pro Asn Glu Tyr Tyr Cys Tyr Val Ser Ser Arg Gln
275 280 285

Gln Pro Ser Gln Pro Leu Gly Cys Arg Phe Ala Met Pro
290 295 300

<210> SEQ ID NO 18
<211> LENGTH: 526
<212> TYPE: PRT
<213> ORGANISM: Homo sapiens
<220> FEATURE:
<223> OTHER INFORMATION: CEACAM1

<400> SEQUENCE: 18

```
Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
```

```
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510

Leu Thr Ala Thr Glu Ile Ile Tyr Ser Glu Val Lys Lys Gln
        515                 520                 525


<210> SEQ ID NO 19
<211> LENGTH: 244
<212> TYPE: PRT
<213> ORGANISM: Homo sapiens
<220> FEATURE:
<223> OTHER INFORMATION: TIGIT

<400> SEQUENCE: 19

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly


<210> SEQ ID NO 20
```

<211> LENGTH: 417
<212> TYPE: PRT
<213> ORGANISM: Homo sapiens
<220> FEATURE:
<223> OTHER INFORMATION: PVR(CD155)

<400> SEQUENCE: 20

```
Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
        115                 120                 125

Pro Gln Gly Ser Arg Ser Val Asp Ile Trp Leu Arg Val Leu Ala Lys
    130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
            180                 185                 190

Pro Gly Phe Leu Ser Gly Thr Val Thr Val Thr Ser Leu Trp Ile Leu
        195                 200                 205

Val Pro Ser Ser Gln Val Asp Gly Lys Asn Val Thr Cys Lys Val Glu
    210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
            260                 265                 270

Glu Pro Thr Gly Tyr Asn Trp Ser Thr Thr Met Gly Pro Leu Pro Pro
        275                 280                 285

Phe Ala Val Ala Gln Gly Ala Gln Leu Leu Ile Arg Pro Val Asp Lys
    290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Ile Ser Arg Asn Ala Ile Ile Phe Leu Val Leu Gly Ile
            340                 345                 350

Leu Val Phe Leu Ile Leu Leu Gly Ile Gly Ile Tyr Phe Tyr Trp Ser
        355                 360                 365

Lys Cys Ser Arg Glu Val Leu Trp His Cys His Leu Cys Pro Ser Ser
    370                 375                 380
```

```
Thr Glu His Ala Ser Ala Ser Ala Asn Gly His Val Ser Tyr Ser Ala
385                 390                 395                 400

Val Ser Arg Glu Asn Ser Ser Ser Gln Asp Pro Gln Thr Glu Gly Thr
                405                 410                 415

Arg


<210> SEQ ID NO 21
<211> LENGTH: 538
<212> TYPE: PRT
<213> ORGANISM: Homo sapiens
<220> FEATURE:
<223> OTHER INFORMATION: PVRL2(CD112)

<400> SEQUENCE: 21

Met Ala Arg Ala Ala Ala Leu Leu Pro Ser Arg Ser Pro Pro Thr Pro
1               5                   10                  15

Leu Leu Trp Pro Leu Leu Leu Leu Leu Leu Leu Glu Thr Gly Ala Gln
            20                  25                  30

Asp Val Arg Val Gln Val Leu Pro Glu Val Arg Gly Gln Leu Gly Gly
        35                  40                  45

Thr Val Glu Leu Pro Cys His Leu Leu Pro Pro Val Pro Gly Leu Tyr
    50                  55                  60

Ile Ser Leu Val Thr Trp Gln Arg Pro Asp Ala Pro Ala Asn His Gln
65                  70                  75                  80

Asn Val Ala Ala Phe His Pro Lys Met Gly Pro Ser Phe Pro Ser Pro
                85                  90                  95

Lys Pro Gly Ser Glu Arg Leu Ser Phe Val Ser Ala Lys Gln Ser Thr
            100                 105                 110

Gly Gln Asp Thr Glu Ala Glu Leu Gln Asp Ala Thr Leu Ala Leu His
        115                 120                 125

Gly Leu Thr Val Glu Asp Glu Gly Asn Tyr Thr Cys Glu Phe Ala Thr
    130                 135                 140

Phe Pro Lys Gly Ser Val Arg Gly Met Thr Trp Leu Arg Val Ile Ala
145                 150                 155                 160

Lys Pro Lys Asn Gln Ala Glu Ala Gln Lys Val Thr Phe Ser Gln Asp
                165                 170                 175

Pro Thr Thr Val Ala Leu Cys Ile Ser Lys Glu Gly Arg Pro Pro Ala
            180                 185                 190

Arg Ile Ser Trp Leu Ser Ser Leu Asp Trp Glu Ala Lys Glu Thr Gln
        195                 200                 205

Val Ser Gly Thr Leu Ala Gly Thr Val Thr Val Thr Ser Arg Phe Thr
    210                 215                 220

Leu Val Pro Ser Gly Arg Ala Asp Gly Val Thr Val Thr Cys Lys Val
225                 230                 235                 240

Glu His Glu Ser Phe Glu Glu Pro Ala Leu Ile Pro Val Thr Leu Ser
                245                 250                 255

Val Arg Tyr Pro Pro Glu Val Ser Ile Ser Gly Tyr Asp Asp Asn Trp
            260                 265                 270

Tyr Leu Gly Arg Thr Asp Ala Thr Leu Ser Cys Asp Val Arg Ser Asn
        275                 280                 285

Pro Glu Pro Thr Gly Tyr Asp Trp Ser Thr Thr Ser Gly Thr Phe Pro
    290                 295                 300

Thr Ser Ala Val Ala Gln Gly Ser Gln Leu Val Ile His Ala Val Asp
305                 310                 315                 320
```

Ser Leu Phe Asn Thr Thr Phe Val Cys Thr Val Thr Asn Ala Val Gly
325 330 335

Met Gly Arg Ala Glu Gln Val Ile Phe Val Arg Glu Thr Pro Asn Thr
340 345 350

Ala Gly Ala Gly Ala Thr Gly Gly Ile Ile Gly Gly Ile Ile Ala Ala
355 360 365

Ile Ile Ala Thr Ala Val Ala Ala Thr Gly Ile Leu Ile Cys Arg Gln
370 375 380

Gln Arg Lys Glu Gln Thr Leu Gln Gly Ala Glu Glu Asp Glu Asp Leu
385 390 395 400

Glu Gly Pro Pro Ser Tyr Lys Pro Pro Thr Pro Lys Ala Lys Leu Glu
405 410 415

Ala Gln Glu Met Pro Ser Gln Leu Phe Thr Leu Gly Ala Ser Glu His
420 425 430

Ser Pro Leu Lys Thr Pro Tyr Phe Asp Ala Gly Ala Ser Cys Thr Glu
435 440 445

Gln Glu Met Pro Arg Tyr His Glu Leu Pro Thr Leu Glu Glu Arg Ser
450 455 460

Gly Pro Leu His Pro Gly Ala Thr Ser Leu Gly Ser Pro Ile Pro Val
465 470 475 480

Pro Pro Gly Pro Pro Ala Val Glu Asp Val Ser Leu Asp Leu Glu Asp
485 490 495

Glu Glu Gly Glu Glu Glu Glu Glu Tyr Leu Asp Lys Ile Asn Pro Ile
500 505 510

Tyr Asp Ala Leu Ser Tyr Ser Ser Pro Ser Asp Ser Tyr Gln Gly Lys
515 520 525

Gly Phe Val Met Ser Arg Ala Met Tyr Val
530 535

<210> SEQ ID NO 22
<211> LENGTH: 336
<212> TYPE: PRT
<213> ORGANISM: Homo sapiens
<220> FEATURE:
<223> OTHER INFORMATION: CD226

<400> SEQUENCE: 22

Met Asp Tyr Pro Thr Leu Leu Leu Ala Leu Leu His Val Tyr Arg Ala
1 5 10 15

Leu Cys Glu Glu Val Leu Trp His Thr Ser Val Pro Phe Ala Glu Asn
20 25 30

Met Ser Leu Glu Cys Val Tyr Pro Ser Met Gly Ile Leu Thr Gln Val
35 40 45

Glu Trp Phe Lys Ile Gly Thr Gln Gln Asp Ser Ile Ala Ile Phe Ser
50 55 60

Pro Thr His Gly Met Val Ile Arg Lys Pro Tyr Ala Glu Arg Val Tyr
65 70 75 80

Phe Leu Asn Ser Thr Met Ala Ser Asn Asn Met Thr Leu Phe Phe Arg
85 90 95

Asn Ala Ser Glu Asp Asp Val Gly Tyr Tyr Ser Cys Ser Leu Tyr Thr
100 105 110

Tyr Pro Gln Gly Thr Trp Gln Lys Val Ile Gln Val Val Gln Ser Asp
115 120 125

Ser Phe Glu Ala Ala Val Pro Ser Asn Ser His Ile Val Ser Glu Pro
130 135 140

-continued

Gly Lys Asn Val Thr Leu Thr Cys Gln Pro Gln Met Thr Trp Pro Val
145 150 155 160

Gln Ala Val Arg Trp Glu Lys Ile Gln Pro Arg Gln Ile Asp Leu Leu
165 170 175

Thr Tyr Cys Asn Leu Val His Gly Arg Asn Phe Thr Ser Lys Phe Pro
180 185 190

Arg Gln Ile Val Ser Asn Cys Ser His Gly Arg Trp Ser Val Ile Val
195 200 205

Ile Pro Asp Val Thr Val Ser Asp Ser Gly Leu Tyr Arg Cys Tyr Leu
210 215 220

Gln Ala Ser Ala Gly Glu Asn Glu Thr Phe Val Met Arg Leu Thr Val
225 230 235 240

Ala Glu Gly Lys Thr Asp Asn Gln Tyr Thr Leu Phe Val Ala Gly Gly
245 250 255

Thr Val Leu Leu Leu Leu Phe Val Ile Ser Ile Thr Thr Ile Ile Val
260 265 270

Ile Phe Leu Asn Arg Arg Arg Arg Arg Glu Arg Arg Asp Leu Phe Thr
275 280 285

Glu Ser Trp Asp Thr Gln Lys Ala Pro Asn Asn Tyr Arg Ser Pro Ile
290 295 300

Ser Thr Ser Gln Pro Thr Asn Gln Ser Met Asp Asp Thr Arg Glu Asp
305 310 315 320

Ile Tyr Val Asn Tyr Pro Thr Phe Ser Arg Arg Pro Lys Thr Arg Val
325 330 335

<210> SEQ ID NO 23
<211> LENGTH: 351
<212> TYPE: PRT
<213> ORGANISM: Homo sapiens
<220> FEATURE:
<223> OTHER INFORMATION: CD2

<400> SEQUENCE: 23

Met Ser Phe Pro Cys Lys Phe Val Ala Ser Phe Leu Leu Ile Phe Asn
1 5 10 15

Val Ser Ser Lys Gly Ala Val Ser Lys Glu Ile Thr Asn Ala Leu Glu
20 25 30

Thr Trp Gly Ala Leu Gly Gln Asp Ile Asn Leu Asp Ile Pro Ser Phe
35 40 45

Gln Met Ser Asp Asp Ile Asp Asp Ile Lys Trp Glu Lys Thr Ser Asp
50 55 60

Lys Lys Lys Ile Ala Gln Phe Arg Lys Glu Lys Glu Thr Phe Lys Glu
65 70 75 80

Lys Asp Thr Tyr Lys Leu Phe Lys Asn Gly Thr Leu Lys Ile Lys His
85 90 95

Leu Lys Thr Asp Asp Gln Asp Ile Tyr Lys Val Ser Ile Tyr Asp Thr
100 105 110

Lys Gly Lys Asn Val Leu Glu Lys Ile Phe Asp Leu Lys Ile Gln Glu
115 120 125

Arg Val Ser Lys Pro Lys Ile Ser Trp Thr Cys Ile Asn Thr Thr Leu
130 135 140

Thr Cys Glu Val Met Asn Gly Thr Asp Pro Glu Leu Asn Leu Tyr Gln
145 150 155 160

Asp Gly Lys His Leu Lys Leu Ser Gln Arg Val Ile Thr His Lys Trp
165 170 175

-continued

Thr Thr Ser Leu Ser Ala Lys Phe Lys Cys Thr Ala Gly Asn Lys Val
180 185 190

Ser Lys Glu Ser Ser Val Glu Pro Val Ser Cys Pro Glu Lys Gly Leu
195 200 205

Asp Ile Tyr Leu Ile Ile Gly Ile Cys Gly Gly Gly Ser Leu Leu Met
210 215 220

Val Phe Val Ala Leu Leu Val Phe Tyr Ile Thr Lys Arg Lys Lys Gln
225 230 235 240

Arg Ser Arg Arg Asn Asp Glu Glu Leu Glu Thr Arg Ala His Arg Val
245 250 255

Ala Thr Glu Glu Arg Gly Arg Lys Pro His Gln Ile Pro Ala Ser Thr
260 265 270

Pro Gln Asn Pro Ala Thr Ser Gln His Pro Pro Pro Pro Pro Gly His
275 280 285

Arg Ser Gln Ala Pro Ser His Arg Pro Pro Pro Pro Gly His Arg Val
290 295 300

Gln His Gln Pro Gln Lys Arg Pro Pro Ala Pro Ser Gly Thr Gln Val
305 310 315 320

His Gln Gln Lys Gly Pro Pro Leu Pro Arg Pro Arg Val Gln Pro Lys
325 330 335

Pro Pro His Gly Ala Ala Glu Asn Ser Leu Ser Pro Ser Ser Asn
340 345 350

<210> SEQ ID NO 24
<211> LENGTH: 180
<212> TYPE: PRT
<213> ORGANISM: Homo sapiens
<220> FEATURE:
<223> OTHER INFORMATION: CD160

<400> SEQUENCE: 24

Met Leu Leu Glu Pro Gly Arg Gly Cys Cys Ala Leu Ala Ile Leu Leu
1 5 10 15

Ala Ile Val Asp Ile Gln Ser Gly Gly Cys Ile Asn Ile Thr Ser Ser
20 25 30

Ala Ser Gln Glu Gly Thr Arg Leu Asn Leu Ile Cys Thr Val Trp His
35 40 45

Lys Lys Glu Glu Ala Glu Gly Phe Val Val Phe Leu Cys Lys Asp Arg
50 55 60

Ser Gly Asp Cys Ser Pro Glu Thr Ser Leu Lys Gln Leu Arg Leu Lys
65 70 75 80

Arg Asp Pro Gly Ile Asp Gly Val Gly Glu Ile Ser Ser Gln Leu Met
85 90 95

Phe Thr Ile Ser Gln Val Thr Pro Leu His Ser Gly Thr Tyr Gln Cys
100 105 110

Cys Ala Arg Ser Gln Lys Ser Gly Ile Arg Leu Gln Gly His Phe Phe
115 120 125

Ser Ile Leu Phe Thr Glu Thr Gly Asn Tyr Thr Val Thr Gly Leu Lys
130 135 140

Gln Arg Gln His Leu Glu Phe Ser His Asn Glu Gly Thr Leu Ser Ser
145 150 155 160

Gly Phe Leu Gln Glu Lys Val Trp Val Met Leu Val Thr Ser Leu Val
165 170 175

Ala Leu Gln Ala
180

<210> SEQ ID NO 25
<211> LENGTH: 278
<212> TYPE: PRT
<213> ORGANISM: Homo sapiens
<220> FEATURE:
<223> OTHER INFORMATION: CD200

<400> SEQUENCE: 25

```
Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Tyr Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Asp Arg Gly Glu Leu Ser Gln
            260                 265                 270

Gly Val Gln Lys Met Thr
        275
```

<210> SEQ ID NO 26
<211> LENGTH: 325
<212> TYPE: PRT
<213> ORGANISM: Homo sapiens
<220> FEATURE:
<223> OTHER INFORMATION: CD200R1(CD200R)

<400> SEQUENCE: 26

```
Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30
```

Gln Ile Thr Gln Asn Tyr Ser Lys Val Leu Ala Glu Val Asn Thr Ser
35 40 45

Trp Pro Val Lys Met Ala Thr Asn Ala Val Leu Cys Cys Pro Pro Ile
50 55 60

Ala Leu Arg Asn Leu Ile Ile Ile Thr Trp Glu Ile Ile Leu Arg Gly
65 70 75 80

Gln Pro Ser Cys Thr Lys Ala Tyr Arg Lys Glu Thr Asn Glu Thr Lys
85 90 95

Glu Thr Asn Cys Thr Asp Glu Arg Ile Thr Trp Val Ser Arg Pro Asp
100 105 110

Gln Asn Ser Asp Leu Gln Ile Arg Pro Val Ala Ile Thr His Asp Gly
115 120 125

Tyr Tyr Arg Cys Ile Met Val Thr Pro Asp Gly Asn Phe His Arg Gly
130 135 140

Tyr His Leu Gln Val Leu Val Thr Pro Glu Val Thr Leu Phe Gln Asn
145 150 155 160

Arg Asn Arg Thr Ala Val Cys Lys Ala Val Ala Gly Lys Pro Ala Ala
165 170 175

Gln Ile Ser Trp Ile Pro Glu Gly Asp Cys Ala Thr Lys Gln Glu Tyr
180 185 190

Trp Ser Asn Gly Thr Val Thr Val Lys Ser Thr Cys His Trp Glu Val
195 200 205

His Asn Val Ser Thr Val Thr Cys His Val Ser His Leu Thr Gly Asn
210 215 220

Lys Ser Leu Tyr Ile Glu Leu Leu Pro Val Pro Gly Ala Lys Lys Ser
225 230 235 240

Ala Lys Leu Tyr Ile Pro Tyr Ile Ile Leu Thr Ile Ile Ile Leu Thr
245 250 255

Ile Val Gly Phe Ile Trp Leu Leu Lys Val Asn Gly Cys Arg Lys Tyr
260 265 270

Lys Leu Asn Lys Thr Glu Ser Thr Pro Val Val Glu Glu Asp Glu Met
275 280 285

Gln Pro Tyr Ala Ser Tyr Thr Glu Lys Asn Asn Pro Leu Tyr Asp Thr
290 295 300

Thr Asn Lys Val Lys Ala Ser Glu Ala Leu Gln Ser Glu Val Asp Thr
305 310 315 320

Asp Leu His Thr Leu
325

<210> SEQ ID NO 27
<211> LENGTH: 201
<212> TYPE: PRT
<213> ORGANISM: Homo sapiens
<220> FEATURE:
<223> OTHER INFORMATION: NC R3 (NKp30)

<400> SEQUENCE: 27

Met Ala Trp Met Leu Leu Leu Ile Leu Ile Met Val His Pro Gly Ser
1 5 10 15

Cys Ala Leu Trp Val Ser Gln Pro Pro Glu Ile Arg Thr Leu Glu Gly
20 25 30

Ser Ser Ala Phe Leu Pro Cys Ser Phe Asn Ala Ser Gln Gly Arg Leu
35 40 45

Ala Ile Gly Ser Val Thr Trp Phe Arg Asp Glu Val Val Pro Gly Lys
50 55 60

```
Glu Val Arg Asn Gly Thr Pro Glu Phe Arg Gly Arg Leu Ala Pro Leu
65                  70                  75                  80

Ala Ser Ser Arg Phe Leu His Asp His Gln Ala Glu Leu His Ile Arg
                85                  90                  95

Asp Val Arg Gly His Asp Ala Ser Ile Tyr Val Cys Arg Val Glu Val
            100                 105                 110

Leu Gly Leu Gly Val Gly Thr Gly Asn Gly Thr Arg Leu Val Val Glu
        115                 120                 125

Lys Glu His Pro Gln Leu Gly Ala Gly Thr Val Leu Leu Leu Arg Ala
    130                 135                 140

Gly Phe Tyr Ala Val Ser Phe Leu Ser Val Ala Val Gly Ser Thr Val
145                 150                 155                 160

Tyr Tyr Gln Gly Lys Cys Leu Thr Trp Lys Gly Pro Arg Arg Gln Leu
                165                 170                 175

Pro Ala Val Val Pro Ala Pro Leu Pro Pro Pro Cys Gly Ser Ser Ala
            180                 185                 190

His Leu Leu Pro Pro Val Pro Gly Gly
        195                 200


<210> SEQ ID NO 28
<211> LENGTH: 208
<212> TYPE: PRT
<213> ORGANISM: Homo sapiens
<220> FEATURE:
<223> OTHER INFORMATION: CD80(B7-1) ECD

<400> SEQUENCE: 28

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205


<210> SEQ ID NO 29
```

<211> LENGTH: 224
<212> TYPE: PRT
<213> ORGANISM: Homo sapiens
<220> FEATURE:
<223> OTHER INFORMATION: CD86 ECD (24-247)

<400> SEQUENCE: 29

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 30
<211> LENGTH: 220
<212> TYPE: PRT
<213> ORGANISM: Homo sapiens
<220> FEATURE:
<223> OTHER INFORMATION: CD274 (PD-L1, B7-H1) ECD

<400> SEQUENCE: 30

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

Phe Val His Gly Glu Glu Asp Leu Lys Val Gln His Ser Ser Tyr Arg
50 55 60

Gln Arg Ala Arg Leu Leu Lys Asp Gln Leu Ser Leu Gly Asn Ala Ala
65 70 75 80

Leu Gln Ile Thr Asp Val Lys Leu Gln Asp Ala Gly Val Tyr Arg Cys
85 90 95

Met Ile Ser Tyr Gly Gly Ala Asp Tyr Lys Arg Ile Thr Val Lys Val

```
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220


<210> SEQ ID NO 31
<211> LENGTH: 201
<212> TYPE: PRT
<213> ORGANISM: Homo sapiens
<220> FEATURE:
<223> OTHER INFORMATION: PDCD1LG2(PD-L2, CD273) ECD

<400> SEQUENCE: 31

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr
        195                 200


<210> SEQ ID NO 32
<211> LENGTH: 238
<212> TYPE: PRT
<213> ORGANISM: Homo sapiens
<220> FEATURE:
<223> OTHER INFORMATION: ICOSLG(B7RP1, CD275, ICOSL, B7-H2) ECD
```

<400> SEQUENCE: 32

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr
225                 230                 235
```

<210> SEQ ID NO 33
<211> LENGTH: 438
<212> TYPE: PRT
<213> ORGANISM: Homo sapiens
<220> FEATURE:
<223> OTHER INFORMATION: CD276(B7-H3) ECD

<400> SEQUENCE: 33

```
Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Ala Glu Gly Gln Asp Gln Gly Ser Ala Tyr Ala Asn Arg
    50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
            100                 105                 110
```

```
Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Gln Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly Ala Val Glu Val Gln Val Pro
    210                 215                 220

Glu Asp Pro Val Val Ala Leu Val Gly Thr Asp Ala Thr Leu Arg Cys
225                 230                 235                 240

Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Pro Asp
        275                 280                 285

Leu Leu Ala Gln Gly Asn Ala Ser Leu Arg Leu Gln Arg Val Arg Val
    290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335

Met Thr Leu Glu Pro Asn Lys Asp Leu Arg Pro Gly Asp Thr Val Thr
            340                 345                 350

Ile Thr Cys Ser Ser Tyr Arg Gly Tyr Pro Glu Ala Glu Val Phe Trp
        355                 360                 365

Gln Asp Gly Gln Gly Val Pro Leu Thr Gly Asn Val Thr Thr Ser Gln
    370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
            420                 425                 430

Thr Phe Pro Pro Glu Ala
        435
```

<210> SEQ ID NO 34
<211> LENGTH: 235
<212> TYPE: PRT
<213> ORGANISM: Homo sapiens
<220> FEATURE:
<223> OTHER INFORMATION: VTCN1(B7-H4) ECD

<400> SEQUENCE: 34

```
Leu Ile Ile Gly Phe Gly Ile Ser Gly Arg His Ser Ile Thr Val Thr
1               5                   10                  15

Thr Val Ala Ser Ala Gly Asn Ile Gly Glu Asp Gly Ile Leu Ser Cys
            20                  25                  30
```

Thr Phe Glu Pro Asp Ile Lys Leu Ser Asp Ile Val Ile Gln Trp Leu
35 40 45

Lys Glu Gly Val Leu Gly Leu Val His Glu Phe Lys Glu Gly Lys Asp
50 55 60

Glu Leu Ser Glu Gln Asp Glu Met Phe Arg Gly Arg Thr Ala Val Phe
65 70 75 80

Ala Asp Gln Val Ile Val Gly Asn Ala Ser Leu Arg Leu Lys Asn Val
85 90 95

Gln Leu Thr Asp Ala Gly Thr Tyr Lys Cys Tyr Ile Ile Thr Ser Lys
100 105 110

Gly Lys Gly Asn Ala Asn Leu Glu Tyr Lys Thr Gly Ala Phe Ser Met
115 120 125

Pro Glu Val Asn Val Asp Tyr Asn Ala Ser Ser Glu Thr Leu Arg Cys
130 135 140

Glu Ala Pro Arg Trp Phe Pro Gln Pro Thr Val Val Trp Ala Ser Gln
145 150 155 160

Val Asp Gln Gly Ala Asn Phe Ser Glu Val Ser Asn Thr Ser Phe Glu
165 170 175

Leu Asn Ser Glu Asn Val Thr Met Lys Val Val Ser Val Leu Tyr Asn
180 185 190

Val Thr Ile Asn Asn Thr Tyr Ser Cys Met Ile Glu Asn Asp Ile Ala
195 200 205

Lys Ala Thr Gly Asp Ile Lys Val Thr Glu Ser Glu Ile Lys Arg Arg
210 215 220

Ser His Leu Gln Leu Leu Asn Ser Lys Ala Ser
225 230 235

<210> SEQ ID NO 35
<211> LENGTH: 134
<212> TYPE: PRT
<213> ORGANISM: Homo sapiens
<220> FEATURE:
<223> OTHER INFORMATION: CD28 ECD

<400> SEQUENCE: 35

Asn Lys Ile Leu Val Lys Gln Ser Pro Met Leu Val Ala Tyr Asp Asn
1 5 10 15

Ala Val Asn Leu Ser Cys Lys Tyr Ser Tyr Asn Leu Phe Ser Arg Glu
20 25 30

Phe Arg Ala Ser Leu His Lys Gly Leu Asp Ser Ala Val Glu Val Cys
35 40 45

Val Val Tyr Gly Asn Tyr Ser Gln Gln Leu Gln Val Tyr Ser Lys Thr
50 55 60

Gly Phe Asn Cys Asp Gly Lys Leu Gly Asn Glu Ser Val Thr Phe Tyr
65 70 75 80

Leu Gln Asn Leu Tyr Val Asn Gln Thr Asp Ile Tyr Phe Cys Lys Ile
85 90 95

Glu Val Met Tyr Pro Pro Pro Tyr Leu Asp Asn Glu Lys Ser Asn Gly
100 105 110

Thr Ile Ile His Val Lys Gly Lys His Leu Cys Pro Ser Pro Leu Phe
115 120 125

Pro Gly Pro Ser Lys Pro
130

<210> SEQ ID NO 36
<211> LENGTH: 126

<212> TYPE: PRT
<213> ORGANISM: Homo sapiens
<220> FEATURE:
<223> OTHER INFORMATION: CTLA4 ECD

<400> SEQUENCE: 36

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp
        115                 120                 125
```

<210> SEQ ID NO 37
<211> LENGTH: 150
<212> TYPE: PRT
<213> ORGANISM: Homo sapiens
<220> FEATURE:
<223> OTHER INFORMATION: PDCD1(PD-1) ECD

<400> SEQUENCE: 37

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 38
<211> LENGTH: 120
<212> TYPE: PRT
<213> ORGANISM: Homo sapiens
<220> FEATURE:
<223> OTHER INFORMATION: ICOS ECD

<400> SEQUENCE: 38

Glu Ile Asn Gly Ser Ala Asn Tyr Glu Met Phe Ile Phe His Asn Gly
1 5 10 15

Gly Val Gln Ile Leu Cys Lys Tyr Pro Asp Ile Val Gln Gln Phe Lys
20 25 30

Met Gln Leu Leu Lys Gly Gly Gln Ile Leu Cys Asp Leu Thr Lys Thr
35 40 45

Lys Gly Ser Gly Asn Thr Val Ser Ile Lys Ser Leu Lys Phe Cys His
50 55 60

Ser Gln Leu Ser Asn Asn Ser Val Ser Phe Phe Leu Tyr Asn Leu Asp
65 70 75 80

His Ser His Ala Asn Tyr Tyr Phe Cys Asn Leu Ser Ile Phe Asp Pro
85 90 95

Pro Pro Phe Lys Val Thr Leu Thr Gly Gly Tyr Leu His Ile Tyr Glu
100 105 110

Ser Gln Leu Cys Cys Gln Leu Lys
115 120

<210> SEQ ID NO 39
<211> LENGTH: 127
<212> TYPE: PRT
<213> ORGANISM: Homo sapiens
<220> FEATURE:
<223> OTHER INFORMATION: BTLA(CD272) ECD

<400> SEQUENCE: 39

Lys Glu Ser Cys Asp Val Gln Leu Tyr Ile Lys Arg Gln Ser Glu His
1 5 10 15

Ser Ile Leu Ala Gly Asp Pro Phe Glu Leu Glu Cys Pro Val Lys Tyr
20 25 30

Cys Ala Asn Arg Pro His Val Thr Trp Cys Lys Leu Asn Gly Thr Thr
35 40 45

Cys Val Lys Leu Glu Asp Arg Gln Thr Ser Trp Lys Glu Glu Lys Asn
50 55 60

Ile Ser Phe Phe Ile Leu His Phe Glu Pro Val Leu Pro Asn Asp Asn
65 70 75 80

Gly Ser Tyr Arg Cys Ser Ala Asn Phe Gln Ser Asn Leu Ile Glu Ser
85 90 95

His Ser Thr Thr Leu Tyr Val Thr Asp Val Lys Ser Ala Ser Glu Arg
100 105 110

Pro Ser Lys Asp Glu Met Ala Ser Arg Pro Trp Leu Leu Tyr Arg
115 120 125

<210> SEQ ID NO 40
<211> LENGTH: 371
<212> TYPE: PRT
<213> ORGANISM: Homo sapiens
<220> FEATURE:
<223> OTHER INFORMATION: CD4 ECD

<400> SEQUENCE: 40

Lys Lys Val Val Leu Gly Lys Lys Gly Asp Thr Val Glu Leu Thr Cys
1 5 10 15

Thr Ala Ser Gln Lys Lys Ser Ile Gln Phe His Trp Lys Asn Ser Asn
20 25 30

Gln Ile Lys Ile Leu Gly Asn Gln Gly Ser Phe Leu Thr Lys Gly Pro
35 40 45

```
Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205

Gly Ser Gly Glu Leu Trp Trp Gln Ala Glu Arg Ala Ser Ser Ser Lys
    210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
        275                 280                 285

Leu Val Val Met Arg Ala Thr Gln Leu Gln Lys Asn Leu Thr Cys Glu
    290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Ser Thr Pro
        355                 360                 365

Val Gln Pro
    370


<210> SEQ ID NO 41
<211> LENGTH: 161
<212> TYPE: PRT
<213> ORGANISM: Homo sapiens
<220> FEATURE:
<223> OTHER INFORMATION: CD8A(CD8-alpha) ECD

<400> SEQUENCE: 41

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30
```

Cys Ser Trp Leu Phe Gln Pro Arg Gly Ala Ala Ala Ser Pro Thr Phe
35 40 45

Leu Leu Tyr Leu Ser Gln Asn Lys Pro Lys Ala Ala Glu Gly Leu Asp
50 55 60

Thr Gln Arg Phe Ser Gly Lys Arg Leu Gly Asp Thr Phe Val Leu Thr
65 70 75 80

Leu Ser Asp Phe Arg Arg Glu Asn Glu Gly Tyr Tyr Phe Cys Ser Ala
85 90 95

Leu Ser Asn Ser Ile Met Tyr Phe Ser His Phe Val Pro Val Phe Leu
100 105 110

Pro Ala Lys Pro Thr Thr Thr Pro Ala Pro Arg Pro Pro Thr Pro Ala
115 120 125

Pro Thr Ile Ala Ser Gln Pro Leu Ser Leu Arg Pro Glu Ala Cys Arg
130 135 140

Pro Ala Ala Gly Gly Ala Val His Thr Arg Gly Leu Asp Phe Ala Cys
145 150 155 160

Asp

<210> SEQ ID NO 42
<211> LENGTH: 149
<212> TYPE: PRT
<213> ORGANISM: Homo sapiens
<220> FEATURE:
<223> OTHER INFORMATION: CD8B(CD8-beta) ECD

<400> SEQUENCE: 42

Leu Gln Gln Thr Pro Ala Tyr Ile Lys Val Gln Thr Asn Lys Met Val
1 5 10 15

Met Leu Ser Cys Glu Ala Lys Ile Ser Leu Ser Asn Met Arg Ile Tyr
20 25 30

Trp Leu Arg Gln Arg Gln Ala Pro Ser Ser Asp Ser His His Glu Phe
35 40 45

Leu Ala Leu Trp Asp Ser Ala Lys Gly Thr Ile His Gly Glu Glu Val
50 55 60

Glu Gln Glu Lys Ile Ala Val Phe Arg Asp Ala Ser Arg Phe Ile Leu
65 70 75 80

Asn Leu Thr Ser Val Lys Pro Glu Asp Ser Gly Ile Tyr Phe Cys Met
85 90 95

Ile Val Gly Ser Pro Glu Leu Thr Phe Gly Lys Gly Thr Gln Leu Ser
100 105 110

Val Val Asp Phe Leu Pro Thr Thr Ala Gln Pro Thr Lys Lys Ser Thr
115 120 125

Leu Lys Lys Arg Val Cys Arg Leu Pro Arg Pro Glu Thr Gln Lys Gly
130 135 140

Pro Leu Cys Ser Pro
145

<210> SEQ ID NO 43
<211> LENGTH: 422
<212> TYPE: PRT
<213> ORGANISM: Homo sapiens
<220> FEATURE:
<223> OTHER INFORMATION: LAG3 ECD

<400> SEQUENCE: 43

Val Pro Val Val Trp Ala Gln Glu Gly Ala Pro Ala Gln Leu Pro Cys
1 5 10 15

```
Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu
            420
```

<210> SEQ ID NO 44
<211> LENGTH: 181
<212> TYPE: PRT
<213> ORGANISM: Homo sapiens
<220> FEATURE:
<223> OTHER INFORMATION: HAVCR2(TIM-3) ECD

<400> SEQUENCE: 44

Ser Glu Val Glu Tyr Arg Ala Glu Val Gly Gln Asn Ala Tyr Leu Pro
1 5 10 15

Cys Phe Tyr Thr Pro Ala Ala Pro Gly Asn Leu Val Pro Val Cys Trp
20 25 30

Gly Lys Gly Ala Cys Pro Val Phe Glu Cys Gly Asn Val Val Leu Arg
35 40 45

Thr Asp Glu Arg Asp Val Asn Tyr Trp Thr Ser Arg Tyr Trp Leu Asn
50 55 60

Gly Asp Phe Arg Lys Gly Asp Val Ser Leu Thr Ile Glu Asn Val Thr
65 70 75 80

Leu Ala Asp Ser Gly Ile Tyr Cys Cys Arg Ile Gln Ile Pro Gly Ile
85 90 95

Met Asn Asp Glu Lys Phe Asn Leu Lys Leu Val Ile Lys Pro Ala Lys
100 105 110

Val Thr Pro Ala Pro Thr Arg Gln Arg Asp Phe Thr Ala Ala Phe Pro
115 120 125

Arg Met Leu Thr Thr Arg Gly His Gly Pro Ala Glu Thr Gln Thr Leu
130 135 140

Gly Ser Leu Pro Asp Ile Asn Leu Thr Gln Ile Ser Thr Leu Ala Asn
145 150 155 160

Glu Leu Arg Asp Ser Arg Leu Ala Asn Asp Leu Arg Asp Ser Gly Ala
165 170 175

Thr Ile Arg Ile Gly
180

<210> SEQ ID NO 45
<211> LENGTH: 394
<212> TYPE: PRT
<213> ORGANISM: Homo sapiens
<220> FEATURE:
<223> OTHER INFORMATION: CEACAM1 ECD

<400> SEQUENCE: 45

Gln Leu Thr Thr Glu Ser Met Pro Phe Asn Val Ala Glu Gly Lys Glu
1 5 10 15

Val Leu Leu Leu Val His Asn Leu Pro Gln Gln Leu Phe Gly Tyr Ser
20 25 30

Trp Tyr Lys Gly Glu Arg Val Asp Gly Asn Arg Gln Ile Val Gly Tyr
35 40 45

Ala Ile Gly Thr Gln Gln Ala Thr Pro Gly Pro Ala Asn Ser Gly Arg
50 55 60

Glu Thr Ile Tyr Pro Asn Ala Ser Leu Leu Ile Gln Asn Val Thr Gln
65 70 75 80

Asn Asp Thr Gly Phe Tyr Thr Leu Gln Val Ile Lys Ser Asp Leu Val
85 90 95

Asn Glu Glu Ala Thr Gly Gln Phe His Val Tyr Pro Glu Leu Pro Lys
100 105 110

Pro Ser Ile Ser Ser Asn Asn Ser Asn Pro Val Glu Asp Lys Asp Ala
115 120 125

Val Ala Phe Thr Cys Glu Pro Glu Thr Gln Asp Thr Thr Tyr Leu Trp
    130                 135                 140

Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
    210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys His Ala Asn Asn Ser Val Thr
            260                 265                 270

Gly Cys Asn Arg Thr Thr Val Lys Thr Ile Ile Val Thr Glu Leu Ser
        275                 280                 285

Pro Val Val Ala Lys Pro Gln Ile Lys Ala Ser Lys Thr Thr Val Thr
    290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
                325                 330                 335

Arg Met Lys Leu Ser Gln Gly Asn Thr Thr Leu Ser Ile Asn Pro Val
            340                 345                 350

Lys Arg Glu Asp Ala Gly Thr Tyr Trp Cys Glu Val Phe Asn Pro Ile
        355                 360                 365

Ser Lys Asn Gln Ser Asp Pro Ile Met Leu Asn Val Asn Tyr Asn Ala
    370                 375                 380

Leu Pro Gln Glu Asn Gly Leu Ser Pro Gly
385                 390

<210> SEQ ID NO 46
<211> LENGTH: 120
<212> TYPE: PRT
<213> ORGANISM: Homo sapiens
<220> FEATURE:
<223> OTHER INFORMATION: TIGIT ECD

<400> SEQUENCE: 46

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

```
Tyr Thr Gly Arg Ile Phe Leu Glu Val Leu Glu Ser Ser Val Ala Glu
            100                 105                 110

His Gly Ala Arg Phe Gln Ile Pro
        115                 120


<210> SEQ ID NO 47
<211> LENGTH: 323
<212> TYPE: PRT
<213> ORGANISM: Homo sapiens
<220> FEATURE:
<223> OTHER INFORMATION: PVR(CD155) ECD

<400> SEQUENCE: 47

Trp Pro Pro Pro Gly Thr Gly Asp Val Val Val Gln Ala Pro Thr Gln
1               5                   10                  15

Val Pro Gly Phe Leu Gly Asp Ser Val Thr Leu Pro Cys Tyr Leu Gln
            20                  25                  30

Val Pro Asn Met Glu Val Thr His Val Ser Gln Leu Thr Trp Ala Arg
        35                  40                  45

His Gly Glu Ser Gly Ser Met Ala Val Phe His Gln Thr Gln Gly Pro
    50                  55                  60

Ser Tyr Ser Glu Ser Lys Arg Leu Glu Phe Val Ala Ala Arg Leu Gly
65                  70                  75                  80

Ala Glu Leu Arg Asn Ala Ser Leu Arg Met Phe Gly Leu Arg Val Glu
                85                  90                  95

Asp Glu Gly Asn Tyr Thr Cys Leu Phe Val Thr Phe Pro Gln Gly Ser
            100                 105                 110

Arg Ser Val Asp Ile Trp Leu Arg Val Leu Ala Lys Pro Gln Asn Thr
        115                 120                 125

Ala Glu Val Gln Lys Val Gln Leu Thr Gly Glu Pro Val Pro Met Ala
    130                 135                 140

Arg Cys Val Ser Thr Gly Gly Arg Pro Pro Ala Gln Ile Thr Trp His
145                 150                 155                 160

Ser Asp Leu Gly Gly Met Pro Asn Thr Ser Gln Val Pro Gly Phe Leu
                165                 170                 175

Ser Gly Thr Val Thr Val Thr Ser Leu Trp Ile Leu Val Pro Ser Ser
            180                 185                 190

Gln Val Asp Gly Lys Asn Val Thr Cys Lys Val Glu His Glu Ser Phe
        195                 200                 205

Glu Lys Pro Gln Leu Leu Thr Val Asn Leu Thr Val Tyr Tyr Pro Pro
    210                 215                 220

Glu Val Ser Ile Ser Gly Tyr Asp Asn Asn Trp Tyr Leu Gly Gln Asn
225                 230                 235                 240

Glu Ala Thr Leu Thr Cys Asp Ala Arg Ser Asn Pro Glu Pro Thr Gly
                245                 250                 255

Tyr Asn Trp Ser Thr Thr Met Gly Pro Leu Pro Pro Phe Ala Val Ala
            260                 265                 270

Gln Gly Ala Gln Leu Leu Ile Arg Pro Val Asp Lys Pro Ile Asn Thr
        275                 280                 285

Thr Leu Ile Cys Asn Val Thr Asn Ala Leu Gly Ala Arg Gln Ala Glu
    290                 295                 300

Leu Thr Val Gln Val Lys Glu Gly Pro Pro Ser Glu His Ser Gly Ile
305                 310                 315                 320

Ser Arg Asn
```

<210> SEQ ID NO 48
<211> LENGTH: 329
<212> TYPE: PRT
<213> ORGANISM: Homo sapiens
<220> FEATURE:
<223> OTHER INFORMATION: PVRL2(CD112) ECD

<400> SEQUENCE: 48

Gln Asp Val Arg Val Gln Val Leu Pro Glu Val Arg Gly Gln Leu Gly
1 5 10 15

Gly Thr Val Glu Leu Pro Cys His Leu Leu Pro Pro Val Pro Gly Leu
20 25 30

Tyr Ile Ser Leu Val Thr Trp Gln Arg Pro Asp Ala Pro Ala Asn His
35 40 45

Gln Asn Val Ala Ala Phe His Pro Lys Met Gly Pro Ser Phe Pro Ser
50 55 60

Pro Lys Pro Gly Ser Glu Arg Leu Ser Phe Val Ser Ala Lys Gln Ser
65 70 75 80

Thr Gly Gln Asp Thr Glu Ala Glu Leu Gln Asp Ala Thr Leu Ala Leu
85 90 95

His Gly Leu Thr Val Glu Asp Glu Gly Asn Tyr Thr Cys Glu Phe Ala
100 105 110

Thr Phe Pro Lys Gly Ser Val Arg Gly Met Thr Trp Leu Arg Val Ile
115 120 125

Ala Lys Pro Lys Asn Gln Ala Glu Ala Gln Lys Val Thr Phe Ser Gln
130 135 140

Asp Pro Thr Thr Val Ala Leu Cys Ile Ser Lys Glu Gly Arg Pro Pro
145 150 155 160

Ala Arg Ile Ser Trp Leu Ser Ser Leu Asp Trp Glu Ala Lys Glu Thr
165 170 175

Gln Val Ser Gly Thr Leu Ala Gly Thr Val Thr Val Thr Ser Arg Phe
180 185 190

Thr Leu Val Pro Ser Gly Arg Ala Asp Gly Val Thr Val Thr Cys Lys
195 200 205

Val Glu His Glu Ser Phe Glu Glu Pro Ala Leu Ile Pro Val Thr Leu
210 215 220

Ser Val Arg Tyr Pro Pro Glu Val Ser Ile Ser Gly Tyr Asp Asp Asn
225 230 235 240

Trp Tyr Leu Gly Arg Thr Asp Ala Thr Leu Ser Cys Asp Val Arg Ser
245 250 255

Asn Pro Glu Pro Thr Gly Tyr Asp Trp Ser Thr Thr Ser Gly Thr Phe
260 265 270

Pro Thr Ser Ala Val Ala Gln Gly Ser Gln Leu Val Ile His Ala Val
275 280 285

Asp Ser Leu Phe Asn Thr Thr Phe Val Cys Thr Val Thr Asn Ala Val
290 295 300

Gly Met Gly Arg Ala Glu Gln Val Ile Phe Val Arg Glu Thr Pro Asn
305 310 315 320

Thr Ala Gly Ala Gly Ala Thr Gly Gly
325

<210> SEQ ID NO 49
<211> LENGTH: 236
<212> TYPE: PRT
<213> ORGANISM: Homo sapiens
<220> FEATURE:
<223> OTHER INFORMATION: CD226 ECD

<400> SEQUENCE: 49

Glu Glu Val Leu Trp His Thr Ser Val Pro Phe Ala Glu Asn Met Ser
1 5 10 15

Leu Glu Cys Val Tyr Pro Ser Met Gly Ile Leu Thr Gln Val Glu Trp
20 25 30

Phe Lys Ile Gly Thr Gln Gln Asp Ser Ile Ala Ile Phe Ser Pro Thr
35 40 45

His Gly Met Val Ile Arg Lys Pro Tyr Ala Glu Arg Val Tyr Phe Leu
50 55 60

Asn Ser Thr Met Ala Ser Asn Asn Met Thr Leu Phe Phe Arg Asn Ala
65 70 75 80

Ser Glu Asp Asp Val Gly Tyr Tyr Ser Cys Ser Leu Tyr Thr Tyr Pro
85 90 95

Gln Gly Thr Trp Gln Lys Val Ile Gln Val Val Gln Ser Asp Ser Phe
100 105 110

Glu Ala Ala Val Pro Ser Asn Ser His Ile Val Ser Glu Pro Gly Lys
115 120 125

Asn Val Thr Leu Thr Cys Gln Pro Gln Met Thr Trp Pro Val Gln Ala
130 135 140

Val Arg Trp Glu Lys Ile Gln Pro Arg Gln Ile Asp Leu Leu Thr Tyr
145 150 155 160

Cys Asn Leu Val His Gly Arg Asn Phe Thr Ser Lys Phe Pro Arg Gln
165 170 175

Ile Val Ser Asn Cys Ser His Gly Arg Trp Ser Val Ile Val Ile Pro
180 185 190

Asp Val Thr Val Ser Asp Ser Gly Leu Tyr Arg Cys Tyr Leu Gln Ala
195 200 205

Ser Ala Gly Glu Asn Glu Thr Phe Val Met Arg Leu Thr Val Ala Glu
210 215 220

Gly Lys Thr Asp Asn Gln Tyr Thr Leu Phe Val Ala
225 230 235

<210> SEQ ID NO 50
<211> LENGTH: 185
<212> TYPE: PRT
<213> ORGANISM: Homo sapiens
<220> FEATURE:
<223> OTHER INFORMATION: CD2 ECD

<400> SEQUENCE: 50

Lys Glu Ile Thr Asn Ala Leu Glu Thr Trp Gly Ala Leu Gly Gln Asp
1 5 10 15

Ile Asn Leu Asp Ile Pro Ser Phe Gln Met Ser Asp Asp Ile Asp Asp
20 25 30

Ile Lys Trp Glu Lys Thr Ser Asp Lys Lys Lys Ile Ala Gln Phe Arg
35 40 45

Lys Glu Lys Glu Thr Phe Lys Glu Lys Asp Thr Tyr Lys Leu Phe Lys
50 55 60

Asn Gly Thr Leu Lys Ile Lys His Leu Lys Thr Asp Asp Gln Asp Ile
65 70 75 80

Tyr Lys Val Ser Ile Tyr Asp Thr Lys Gly Lys Asn Val Leu Glu Lys
85 90 95

Ile Phe Asp Leu Lys Ile Gln Glu Arg Val Ser Lys Pro Lys Ile Ser
100 105 110

```
Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
    130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185


<210> SEQ ID NO 51
<211> LENGTH: 133
<212> TYPE: PRT
<213> ORGANISM: Homo sapiens
<220> FEATURE:
<223> OTHER INFORMATION: CD160 ECD

<400> SEQUENCE: 51

Ile Asn Ile Thr Ser Ser Ala Ser Gln Glu Gly Thr Arg Leu Asn Leu
1               5                   10                  15

Ile Cys Thr Val Trp His Lys Lys Glu Glu Ala Glu Gly Phe Val Val
            20                  25                  30

Phe Leu Cys Lys Asp Arg Ser Gly Asp Cys Ser Pro Glu Thr Ser Leu
        35                  40                  45

Lys Gln Leu Arg Leu Lys Arg Asp Pro Gly Ile Asp Gly Val Gly Glu
    50                  55                  60

Ile Ser Ser Gln Leu Met Phe Thr Ile Ser Gln Val Thr Pro Leu His
65                  70                  75                  80

Ser Gly Thr Tyr Gln Cys Cys Ala Arg Ser Gln Lys Ser Gly Ile Arg
                85                  90                  95

Leu Gln Gly His Phe Phe Ser Ile Leu Phe Thr Glu Thr Gly Asn Tyr
            100                 105                 110

Thr Val Thr Gly Leu Lys Gln Arg Gln His Leu Glu Phe Ser His Asn
        115                 120                 125

Glu Gly Thr Leu Ser
    130


<210> SEQ ID NO 52
<211> LENGTH: 202
<212> TYPE: PRT
<213> ORGANISM: Homo sapiens
<220> FEATURE:
<223> OTHER INFORMATION: CD200 ECD

<400> SEQUENCE: 52

Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45

Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95
```

```
Gly Phe Gly Lys Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys Gly
        195                 200


<210> SEQ ID NO 53
<211> LENGTH: 215
<212> TYPE: PRT
<213> ORGANISM: Homo sapiens
<220> FEATURE:
<223> OTHER INFORMATION: CD200R1(CD200R) ECD

<400> SEQUENCE: 53

Met Asp Glu Lys Gln Ile Thr Gln Asn Tyr Ser Lys Val Leu Ala Glu
1               5                   10                  15

Val Asn Thr Ser Trp Pro Val Lys Met Ala Thr Asn Ala Val Leu Cys
            20                  25                  30

Cys Pro Pro Ile Ala Leu Arg Asn Leu Ile Ile Ile Thr Trp Glu Ile
        35                  40                  45

Ile Leu Arg Gly Gln Pro Ser Cys Thr Lys Ala Tyr Arg Lys Glu Thr
    50                  55                  60

Asn Glu Thr Lys Glu Thr Asn Cys Thr Asp Glu Arg Ile Thr Trp Val
65                  70                  75                  80

Ser Arg Pro Asp Gln Asn Ser Asp Leu Gln Ile Arg Pro Val Ala Ile
                85                  90                  95

Thr His Asp Gly Tyr Tyr Arg Cys Ile Met Val Thr Pro Asp Gly Asn
            100                 105                 110

Phe His Arg Gly Tyr His Leu Gln Val Leu Val Thr Pro Glu Val Thr
        115                 120                 125

Leu Phe Gln Asn Arg Asn Arg Thr Ala Val Cys Lys Ala Val Ala Gly
    130                 135                 140

Lys Pro Ala Ala Gln Ile Ser Trp Ile Pro Glu Gly Asp Cys Ala Thr
145                 150                 155                 160

Lys Gln Glu Tyr Trp Ser Asn Gly Thr Val Thr Val Lys Ser Thr Cys
                165                 170                 175

His Trp Glu Val His Asn Val Ser Thr Val Thr Cys His Val Ser His
            180                 185                 190

Leu Thr Gly Asn Lys Ser Leu Tyr Ile Glu Leu Leu Pro Val Pro Gly
        195                 200                 205

Ala Lys Lys Ser Ala Lys Leu
    210                 215


<210> SEQ ID NO 54
<211> LENGTH: 117
<212> TYPE: PRT
<213> ORGANISM: Homo sapiens
```

<220> FEATURE:
<223> OTHER INFORMATION: NC R3 (NKp30) ECD

<400> SEQUENCE: 54

Leu Trp Val Ser Gln Pro Pro Glu Ile Arg Thr Leu Glu Gly Ser Ser
1 5 10 15

Ala Phe Leu Pro Cys Ser Phe Asn Ala Ser Gln Gly Arg Leu Ala Ile
20 25 30

Gly Ser Val Thr Trp Phe Arg Asp Glu Val Val Pro Gly Lys Glu Val
35 40 45

Arg Asn Gly Thr Pro Glu Phe Arg Gly Arg Leu Ala Pro Leu Ala Ser
50 55 60

Ser Arg Phe Leu His Asp His Gln Ala Glu Leu His Ile Arg Asp Val
65 70 75 80

Arg Gly His Asp Ala Ser Ile Tyr Val Cys Arg Val Glu Val Leu Gly
85 90 95

Leu Gly Val Gly Thr Gly Asn Gly Thr Arg Leu Val Val Glu Lys Glu
100 105 110

His Pro Gln Leu Gly
115

<210> SEQ ID NO 55
<211> LENGTH: 254
<212> TYPE: PRT
<213> ORGANISM: Homo sapiens
<220> FEATURE:
<223> OTHER INFORMATION: Mature CD80(B7-1)

<400> SEQUENCE: 55

Val Ile His Val Thr Lys Glu Val Lys Glu Val Ala Thr Leu Ser Cys
1 5 10 15

Gly His Asn Val Ser Val Glu Glu Leu Ala Gln Thr Arg Ile Tyr Trp
20 25 30

Gln Lys Glu Lys Lys Met Val Leu Thr Met Met Ser Gly Asp Met Asn
35 40 45

Ile Trp Pro Glu Tyr Lys Asn Arg Thr Ile Phe Asp Ile Thr Asn Asn
50 55 60

Leu Ser Ile Val Ile Leu Ala Leu Arg Pro Ser Asp Glu Gly Thr Tyr
65 70 75 80

Glu Cys Val Val Leu Lys Tyr Glu Lys Asp Ala Phe Lys Arg Glu His
85 90 95

Leu Ala Glu Val Thr Leu Ser Val Lys Ala Asp Phe Pro Thr Pro Ser
100 105 110

Ile Ser Asp Phe Glu Ile Pro Thr Ser Asn Ile Arg Arg Ile Ile Cys
115 120 125

Ser Thr Ser Gly Gly Phe Pro Glu Pro His Leu Ser Trp Leu Glu Asn
130 135 140

Gly Glu Glu Leu Asn Ala Ile Asn Thr Thr Val Ser Gln Asp Pro Glu
145 150 155 160

Thr Glu Leu Tyr Ala Val Ser Ser Lys Leu Asp Phe Asn Met Thr Thr
165 170 175

Asn His Ser Phe Met Cys Leu Ile Lys Tyr Gly His Leu Arg Val Asn
180 185 190

Gln Thr Phe Asn Trp Asn Thr Thr Lys Gln Glu His Phe Pro Asp Asn
195 200 205

Leu Leu Pro Ser Trp Ala Ile Thr Leu Ile Ser Val Asn Gly Ile Phe

```
    210                 215                 220

Val Ile Cys Cys Leu Thr Tyr Cys Phe Ala Pro Arg Cys Arg Glu Arg
225                 230                 235                 240

Arg Arg Asn Glu Arg Leu Arg Arg Glu Ser Val Arg Pro Val
                245                 250


<210> SEQ ID NO 56
<211> LENGTH: 306
<212> TYPE: PRT
<213> ORGANISM: Hoo sapiens
<220> FEATURE:
<223> OTHER INFORMATION: Mature CD86(B7-2)

<400> SEQUENCE: 56

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

Arg Val Phe Lys Ser Ser Lys Thr Ser Ser Cys Asp Lys Ser Asp Thr
    290                 295                 300

Cys Phe
305
```

<210> SEQ ID NO 57
<211> LENGTH: 272
<212> TYPE: PRT
<213> ORGANISM: Homo sapiens
<220> FEATURE:
<223> OTHER INFORMATION: Mature CD274 (PD-L1, B7-H1)

<400> SEQUENCE: 57

Phe Thr Val Thr Val Pro Lys Asp Leu Tyr Val Val Glu Tyr Gly Ser
1 5 10 15

Asn Met Thr Ile Glu Cys Lys Phe Pro Val Glu Lys Gln Leu Asp Leu
20 25 30

Ala Ala Leu Ile Val Tyr Trp Glu Met Glu Asp Lys Asn Ile Ile Gln
35 40 45

Phe Val His Gly Glu Glu Asp Leu Lys Val Gln His Ser Ser Tyr Arg
50 55 60

Gln Arg Ala Arg Leu Leu Lys Asp Gln Leu Ser Leu Gly Asn Ala Ala
65 70 75 80

Leu Gln Ile Thr Asp Val Lys Leu Gln Asp Ala Gly Val Tyr Arg Cys
85 90 95

Met Ile Ser Tyr Gly Gly Ala Asp Tyr Lys Arg Ile Thr Val Lys Val
100 105 110

Asn Ala Pro Tyr Asn Lys Ile Asn Gln Arg Ile Leu Val Val Asp Pro
115 120 125

Val Thr Ser Glu His Glu Leu Thr Cys Gln Ala Glu Gly Tyr Pro Lys
130 135 140

Ala Glu Val Ile Trp Thr Ser Ser Asp His Gln Val Leu Ser Gly Lys
145 150 155 160

Thr Thr Thr Thr Asn Ser Lys Arg Glu Glu Lys Leu Phe Asn Val Thr
165 170 175

Ser Thr Leu Arg Ile Asn Thr Thr Thr Asn Glu Ile Phe Tyr Cys Thr
180 185 190

Phe Arg Arg Leu Asp Pro Glu Glu Asn His Thr Ala Glu Leu Val Ile
195 200 205

Pro Glu Leu Pro Leu Ala His Pro Pro Asn Glu Arg Thr His Leu Val
210 215 220

Ile Leu Gly Ala Ile Leu Leu Cys Leu Gly Val Ala Leu Thr Phe Ile
225 230 235 240

Phe Arg Leu Arg Lys Gly Arg Met Met Asp Val Lys Lys Cys Gly Ile
245 250 255

Gln Asp Thr Asn Ser Lys Lys Gln Ser Asp Thr His Leu Glu Glu Thr
260 265 270

<210> SEQ ID NO 58
<211> LENGTH: 254
<212> TYPE: PRT
<213> ORGANISM: Homo sapiens
<220> FEATURE:
<223> OTHER INFORMATION: Mature PDCD1LG2(PD-L2, CD273)

<400> SEQUENCE: 58

Leu Phe Thr Val Thr Val Pro Lys Glu Leu Tyr Ile Ile Glu His Gly
1 5 10 15

Ser Asn Val Thr Leu Glu Cys Asn Phe Asp Thr Gly Ser His Val Asn
20 25 30

Leu Gly Ala Ile Thr Ala Ser Leu Gln Lys Val Glu Asn Asp Thr Ser
35 40 45

```
Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr Trp Leu Leu His Ile Phe Ile
        195                 200                 205

Pro Phe Cys Ile Ile Ala Phe Ile Phe Ile Ala Thr Val Ile Ala Leu
    210                 215                 220

Arg Lys Gln Leu Cys Gln Lys Leu Tyr Ser Ser Lys Asp Thr Thr Lys
225                 230                 235                 240

Arg Pro Val Thr Thr Thr Lys Arg Glu Val Asn Ser Ala Ile
                245                 250
```

<210> SEQ ID NO 59
<211> LENGTH: 284
<212> TYPE: PRT
<213> ORGANISM: Homo sapiens
<220> FEATURE:
<223> OTHER INFORMATION: Mature ICOSLG(B7RP1, CD275, ICOSL, B7-H2)

<400> SEQUENCE: 59

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160
```

```
Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr Trp Ser
225                 230                 235                 240

Ile Leu Ala Val Leu Cys Leu Leu Val Val Val Ala Val Ala Ile Gly
                245                 250                 255

Trp Val Cys Arg Asp Arg Cys Leu Gln His Ser Tyr Ala Gly Ala Trp
            260                 265                 270

Ala Val Ser Pro Glu Thr Glu Leu Thr Gly His Val
        275                 280


<210> SEQ ID NO 60
<211> LENGTH: 506
<212> TYPE: PRT
<213> ORGANISM: Homo sapiens
<220> FEATURE:
<223> OTHER INFORMATION: Mature CD276(B7-H3)

<400> SEQUENCE: 60

Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Ala Glu Gly Gln Asp Gln Gly Ser Ala Tyr Ala Asn Arg
    50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Gln Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly Ala Val Glu Val Gln Val Pro
    210                 215                 220

Glu Asp Pro Val Val Ala Leu Val Gly Thr Asp Ala Thr Leu Arg Cys
225                 230                 235                 240
```

```
Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Pro Asp
        275                 280                 285

Leu Leu Ala Gln Gly Asn Ala Ser Leu Arg Leu Gln Arg Val Arg Val
    290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335

Met Thr Leu Glu Pro Asn Lys Asp Leu Arg Pro Gly Asp Thr Val Thr
            340                 345                 350

Ile Thr Cys Ser Ser Tyr Arg Gly Tyr Pro Glu Ala Glu Val Phe Trp
        355                 360                 365

Gln Asp Gly Gln Gly Val Pro Leu Thr Gly Asn Val Thr Thr Ser Gln
    370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
            420                 425                 430

Thr Phe Pro Pro Glu Ala Leu Trp Val Thr Val Gly Leu Ser Val Cys
        435                 440                 445

Leu Ile Ala Leu Leu Val Ala Leu Ala Phe Val Cys Trp Arg Lys Ile
    450                 455                 460

Lys Gln Ser Cys Glu Glu Glu Asn Ala Gly Ala Glu Asp Gln Asp Gly
465                 470                 475                 480

Glu Gly Glu Gly Ser Lys Thr Ala Leu Gln Pro Leu Lys His Ser Asp
                485                 490                 495

Ser Lys Glu Asp Asp Gly Gln Glu Ile Ala
            500                 505
```

<210> SEQ ID NO 61
<211> LENGTH: 258
<212> TYPE: PRT
<213> ORGANISM: Homo sapiens
<220> FEATURE:
<223> OTHER INFORMATION: Mature VTCN1(B7-H4)

<400> SEQUENCE: 61

```
Leu Ile Ile Gly Phe Gly Ile Ser Gly Arg His Ser Ile Thr Val Thr
1               5                   10                  15

Thr Val Ala Ser Ala Gly Asn Ile Gly Glu Asp Gly Ile Leu Ser Cys
            20                  25                  30

Thr Phe Glu Pro Asp Ile Lys Leu Ser Asp Ile Val Ile Gln Trp Leu
        35                  40                  45

Lys Glu Gly Val Leu Gly Leu Val His Glu Phe Lys Glu Gly Lys Asp
    50                  55                  60

Glu Leu Ser Glu Gln Asp Glu Met Phe Arg Gly Arg Thr Ala Val Phe
65                  70                  75                  80

Ala Asp Gln Val Ile Val Gly Asn Ala Ser Leu Arg Leu Lys Asn Val
                85                  90                  95
```

Gln Leu Thr Asp Ala Gly Thr Tyr Lys Cys Tyr Ile Ile Thr Ser Lys
100 105 110

Gly Lys Gly Asn Ala Asn Leu Glu Tyr Lys Thr Gly Ala Phe Ser Met
115 120 125

Pro Glu Val Asn Val Asp Tyr Asn Ala Ser Ser Glu Thr Leu Arg Cys
130 135 140

Glu Ala Pro Arg Trp Phe Pro Gln Pro Thr Val Val Trp Ala Ser Gln
145 150 155 160

Val Asp Gln Gly Ala Asn Phe Ser Glu Val Ser Asn Thr Ser Phe Glu
165 170 175

Leu Asn Ser Glu Asn Val Thr Met Lys Val Val Ser Val Leu Tyr Asn
180 185 190

Val Thr Ile Asn Asn Thr Tyr Ser Cys Met Ile Glu Asn Asp Ile Ala
195 200 205

Lys Ala Thr Gly Asp Ile Lys Val Thr Glu Ser Glu Ile Lys Arg Arg
210 215 220

Ser His Leu Gln Leu Leu Asn Ser Lys Ala Ser Leu Cys Val Ser Ser
225 230 235 240

Phe Phe Ala Ile Ser Trp Ala Leu Leu Pro Leu Ser Pro Tyr Leu Met
245 250 255

Leu Lys

<210> SEQ ID NO 62
<211> LENGTH: 202
<212> TYPE: PRT
<213> ORGANISM: Homo sapiens
<220> FEATURE:
<223> OTHER INFORMATION: Mature CD28

<400> SEQUENCE: 62

Asn Lys Ile Leu Val Lys Gln Ser Pro Met Leu Val Ala Tyr Asp Asn
1 5 10 15

Ala Val Asn Leu Ser Cys Lys Tyr Ser Tyr Asn Leu Phe Ser Arg Glu
20 25 30

Phe Arg Ala Ser Leu His Lys Gly Leu Asp Ser Ala Val Glu Val Cys
35 40 45

Val Val Tyr Gly Asn Tyr Ser Gln Gln Leu Gln Val Tyr Ser Lys Thr
50 55 60

Gly Phe Asn Cys Asp Gly Lys Leu Gly Asn Glu Ser Val Thr Phe Tyr
65 70 75 80

Leu Gln Asn Leu Tyr Val Asn Gln Thr Asp Ile Tyr Phe Cys Lys Ile
85 90 95

Glu Val Met Tyr Pro Pro Pro Tyr Leu Asp Asn Glu Lys Ser Asn Gly
100 105 110

Thr Ile Ile His Val Lys Gly Lys His Leu Cys Pro Ser Pro Leu Phe
115 120 125

Pro Gly Pro Ser Lys Pro Phe Trp Val Leu Val Val Val Gly Gly Val
130 135 140

Leu Ala Cys Tyr Ser Leu Leu Val Thr Val Ala Phe Ile Ile Phe Trp
145 150 155 160

Val Arg Ser Lys Arg Ser Arg Leu Leu His Ser Asp Tyr Met Asn Met
165 170 175

Thr Pro Arg Arg Pro Gly Pro Thr Arg Lys His Tyr Gln Pro Tyr Ala
180 185 190

Pro Pro Arg Asp Phe Ala Ala Tyr Arg Ser

```
        195                 200


<210> SEQ ID NO 63
<211> LENGTH: 188
<212> TYPE: PRT
<213> ORGANISM: Homo sapiens
<220> FEATURE:
<223> OTHER INFORMATION: Mature CTLA4

<400> SEQUENCE: 63

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Phe Leu
        115                 120                 125

Leu Trp Ile Leu Ala Ala Val Ser Ser Gly Leu Phe Phe Tyr Ser Phe
    130                 135                 140

Leu Leu Thr Ala Val Ser Leu Ser Lys Met Leu Lys Lys Arg Ser Pro
145                 150                 155                 160

Leu Thr Thr Gly Val Tyr Val Lys Met Pro Pro Thr Glu Pro Glu Cys
                165                 170                 175

Glu Lys Gln Phe Gln Pro Tyr Phe Ile Pro Ile Asn
            180                 185


<210> SEQ ID NO 64
<211> LENGTH: 268
<212> TYPE: PRT
<213> ORGANISM: Homo sapiens
<220> FEATURE:
<223> OTHER INFORMATION: Mature PDCD1(PD-1)

<400> SEQUENCE: 64

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110
```

```
Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265


<210> SEQ ID NO 65
<211> LENGTH: 179
<212> TYPE: PRT
<213> ORGANISM: Homo sapiens
<220> FEATURE:
<223> OTHER INFORMATION: Mature ICOS

<400> SEQUENCE: 65

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

Ala Phe Val Val Val Cys Ile Leu Gly Cys Ile Leu Ile Cys Trp Leu
    130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu


<210> SEQ ID NO 66
<211> LENGTH: 259
<212> TYPE: PRT
```

<213> ORGANISM: Homo sapiens
<220> FEATURE:
<223> OTHER INFORMATION: Mature BTLA(CD272)

<400> SEQUENCE: 66

Lys Glu Ser Cys Asp Val Gln Leu Tyr Ile Lys Arg Gln Ser Glu His
1 5 10 15

Ser Ile Leu Ala Gly Asp Pro Phe Glu Leu Glu Cys Pro Val Lys Tyr
20 25 30

Cys Ala Asn Arg Pro His Val Thr Trp Cys Lys Leu Asn Gly Thr Thr
35 40 45

Cys Val Lys Leu Glu Asp Arg Gln Thr Ser Trp Lys Glu Glu Lys Asn
50 55 60

Ile Ser Phe Phe Ile Leu His Phe Glu Pro Val Leu Pro Asn Asp Asn
65 70 75 80

Gly Ser Tyr Arg Cys Ser Ala Asn Phe Gln Ser Asn Leu Ile Glu Ser
85 90 95

His Ser Thr Thr Leu Tyr Val Thr Asp Val Lys Ser Ala Ser Glu Arg
100 105 110

Pro Ser Lys Asp Glu Met Ala Ser Arg Pro Trp Leu Leu Tyr Arg Leu
115 120 125

Leu Pro Leu Gly Gly Leu Pro Leu Leu Ile Thr Thr Cys Phe Cys Leu
130 135 140

Phe Cys Cys Leu Arg Arg His Gln Gly Lys Gln Asn Glu Leu Ser Asp
145 150 155 160

Thr Ala Gly Arg Glu Ile Asn Leu Val Asp Ala His Leu Lys Ser Glu
165 170 175

Gln Thr Glu Ala Ser Thr Arg Gln Asn Ser Gln Val Leu Leu Ser Glu
180 185 190

Thr Gly Ile Tyr Asp Asn Asp Pro Asp Leu Cys Phe Arg Met Gln Glu
195 200 205

Gly Ser Glu Val Tyr Ser Asn Pro Cys Leu Glu Glu Asn Lys Pro Gly
210 215 220

Ile Val Tyr Ala Ser Leu Asn His Ser Val Ile Gly Pro Asn Ser Arg
225 230 235 240

Leu Ala Arg Asn Val Lys Glu Ala Pro Thr Glu Tyr Ala Ser Ile Cys
245 250 255

Val Arg Ser

<210> SEQ ID NO 67
<211> LENGTH: 433
<212> TYPE: PRT
<213> ORGANISM: Homo sapiens
<220> FEATURE:
<223> OTHER INFORMATION: Mature CD4

<400> SEQUENCE: 67

Lys Lys Val Val Leu Gly Lys Lys Gly Asp Thr Val Glu Leu Thr Cys
1 5 10 15

Thr Ala Ser Gln Lys Lys Ser Ile Gln Phe His Trp Lys Asn Ser Asn
20 25 30

Gln Ile Lys Ile Leu Gly Asn Gln Gly Ser Phe Leu Thr Lys Gly Pro
35 40 45

Ser Lys Leu Asn Asp Arg Ala Asp Ser Arg Arg Ser Leu Trp Asp Gln
50 55 60

Gly Asn Phe Pro Leu Ile Ile Lys Asn Leu Lys Ile Glu Asp Ser Asp

```
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205

Gly Ser Gly Glu Leu Trp Trp Gln Ala Glu Arg Ala Ser Ser Ser Lys
    210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
        275                 280                 285

Leu Val Val Met Arg Ala Thr Gln Leu Gln Lys Asn Leu Thr Cys Glu
    290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Ser Thr Pro
        355                 360                 365

Val Gln Pro Met Ala Leu Ile Val Leu Gly Gly Val Ala Gly Leu Leu
    370                 375                 380

Leu Phe Ile Gly Leu Gly Ile Phe Phe Cys Val Arg Cys Arg His Arg
385                 390                 395                 400

Arg Arg Gln Ala Glu Arg Met Ser Gln Ile Lys Arg Leu Leu Ser Glu
                405                 410                 415

Lys Lys Thr Cys Gln Cys Pro His Arg Phe Gln Lys Thr Cys Ser Pro
            420                 425                 430

Ile


<210> SEQ ID NO 68
<211> LENGTH: 214
<212> TYPE: PRT
<213> ORGANISM: Homo sapiens
<220> FEATURE:
<223> OTHER INFORMATION: Mature CD8A(CD8-alpha)

<400> SEQUENCE: 68
```

```
Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp Ile Tyr Ile Trp Ala Pro Leu Ala Gly Thr Cys Gly Val Leu Leu
                165                 170                 175

Leu Ser Leu Val Ile Thr Leu Tyr Cys Asn His Arg Asn Arg Arg Arg
            180                 185                 190

Val Cys Lys Cys Pro Arg Pro Val Val Lys Ser Gly Asp Lys Pro Ser
        195                 200                 205

Leu Ser Ala Arg Tyr Val
    210
```

<210> SEQ ID NO 69
<211> LENGTH: 189
<212> TYPE: PRT
<213> ORGANISM: Homo sapiens
<220> FEATURE:
<223> OTHER INFORMATION: Mature CD8B(CD8-beta)

<400> SEQUENCE: 69

```
Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140
```

```
Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Phe Tyr Lys
            180                 185


<210> SEQ ID NO 70
<211> LENGTH: 497
<212> TYPE: PRT
<213> ORGANISM: Homo sapiens
<220> FEATURE:
<223> OTHER INFORMATION: Mature LAG3

<400> SEQUENCE: 70

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320
```

```
Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu Leu Leu Phe Leu Ile Leu Gly Val Leu Ser
            420                 425                 430

Leu Leu Leu Leu Val Thr Gly Ala Phe Gly Phe His Leu Trp Arg Arg
        435                 440                 445

Gln Trp Arg Pro Arg Arg Phe Ser Ala Leu Glu Gln Gly Ile His Pro
    450                 455                 460

Pro Gln Ala Gln Ser Lys Ile Glu Glu Leu Glu Gln Glu Pro Glu Pro
465                 470                 475                 480

Glu Pro Glu Pro Glu Pro Glu Pro Glu Pro Glu Pro Glu Pro Glu Gln
                485                 490                 495

Leu


<210> SEQ ID NO 71
<211> LENGTH: 280
<212> TYPE: PRT
<213> ORGANISM: Homo sapiens
<220> FEATURE:
<223> OTHER INFORMATION: Mature HAVCR2(TIM-3)

<400> SEQUENCE: 71

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175
```

```
Thr Ile Arg Ile Gly Ile Tyr Ile Gly Ala Gly Ile Cys Ala Gly Leu
            180                 185                 190

Ala Leu Ala Leu Ile Phe Gly Ala Leu Ile Phe Lys Trp Tyr Ser His
        195                 200                 205

Ser Lys Glu Lys Ile Gln Asn Leu Ser Leu Ile Ser Leu Ala Asn Leu
    210                 215                 220

Pro Pro Ser Gly Leu Ala Asn Ala Val Ala Glu Gly Ile Arg Ser Glu
225                 230                 235                 240

Glu Asn Ile Tyr Thr Ile Glu Glu Asn Val Tyr Glu Val Glu Glu Pro
                245                 250                 255

Asn Glu Tyr Tyr Cys Tyr Val Ser Ser Arg Gln Gln Pro Ser Gln Pro
            260                 265                 270

Leu Gly Cys Arg Phe Ala Met Pro
        275                 280


<210> SEQ ID NO 72
<211> LENGTH: 492
<212> TYPE: PRT
<213> ORGANISM: Homo sapiens
<220> FEATURE:
<223> OTHER INFORMATION: Mature CEACAM1

<400> SEQUENCE: 72

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Thr Gln Asp Thr Thr Tyr Leu Trp
    130                 135                 140

Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
    210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
                245                 250                 255
```

```
Val Asn Asn Ser Gly Ser Tyr Thr Cys His Ala Asn Asn Ser Val Thr
            260                 265                 270

Gly Cys Asn Arg Thr Thr Val Lys Thr Ile Ile Val Thr Glu Leu Ser
        275                 280                 285

Pro Val Val Ala Lys Pro Gln Ile Lys Ala Ser Lys Thr Thr Val Thr
    290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
                325                 330                 335

Arg Met Lys Leu Ser Gln Gly Asn Thr Thr Leu Ser Ile Asn Pro Val
            340                 345                 350

Lys Arg Glu Asp Ala Gly Thr Tyr Trp Cys Glu Val Phe Asn Pro Ile
        355                 360                 365

Ser Lys Asn Gln Ser Asp Pro Ile Met Leu Asn Val Asn Tyr Asn Ala
    370                 375                 380

Leu Pro Gln Glu Asn Gly Leu Ser Pro Gly Ala Ile Ala Gly Ile Val
385                 390                 395                 400

Ile Gly Val Val Ala Leu Val Ala Leu Ile Ala Val Ala Leu Ala Cys
                405                 410                 415

Phe Leu His Phe Gly Lys Thr Gly Arg Ala Ser Asp Gln Arg Asp Leu
            420                 425                 430

Thr Glu His Lys Pro Ser Val Ser Asn His Thr Gln Asp His Ser Asn
        435                 440                 445

Asp Pro Pro Asn Lys Met Asn Glu Val Thr Tyr Ser Thr Leu Asn Phe
    450                 455                 460

Glu Ala Gln Gln Pro Thr Gln Pro Thr Ser Ala Ser Pro Ser Leu Thr
465                 470                 475                 480

Ala Thr Glu Ile Ile Tyr Ser Glu Val Lys Lys Gln
                485                 490


<210> SEQ ID NO 73
<211> LENGTH: 222
<212> TYPE: PRT
<213> ORGANISM: Homo sapiens
<220> FEATURE:
<223> OTHER INFORMATION: Mature TIGIT

<400> SEQUENCE: 73

Met Thr Gly Thr Ile Glu Thr Thr Gly Asn Ile Ser Ala Glu Lys Gly
1               5                   10                  15

Gly Ser Ile Ile Leu Gln Cys His Leu Ser Ser Thr Thr Ala Gln Val
            20                  25                  30

Thr Gln Val Asn Trp Glu Gln Gln Asp Gln Leu Leu Ala Ile Cys Asn
        35                  40                  45

Ala Asp Leu Gly Trp His Ile Ser Pro Ser Phe Lys Asp Arg Val Ala
    50                  55                  60

Pro Gly Pro Gly Leu Gly Leu Thr Leu Gln Ser Leu Thr Val Asn Asp
65                  70                  75                  80

Thr Gly Glu Tyr Phe Cys Ile Tyr His Thr Tyr Pro Asp Gly Thr Tyr
                85                  90                  95

Thr Gly Arg Ile Phe Leu Glu Val Leu Glu Ser Ser Val Ala Glu His
            100                 105                 110

Gly Ala Arg Phe Gln Ile Pro Leu Leu Gly Ala Met Ala Ala Thr Leu
        115                 120                 125
```

```
Val Val Ile Cys Thr Ala Val Ile Val Val Val Ala Leu Thr Arg Lys
    130                 135                 140

Lys Lys Ala Leu Arg Ile His Ser Val Glu Gly Asp Leu Arg Arg Lys
145                 150                 155                 160

Ser Ala Gly Gln Glu Glu Trp Ser Pro Ser Ala Pro Ser Pro Pro Gly
                165                 170                 175

Ser Cys Val Gln Ala Glu Ala Ala Pro Ala Gly Leu Cys Gly Glu Gln
            180                 185                 190

Arg Gly Glu Asp Cys Ala Glu Leu His Asp Tyr Phe Asn Val Leu Ser
        195                 200                 205

Tyr Arg Ser Leu Gly Asn Cys Ser Phe Phe Thr Glu Thr Gly
    210                 215                 220


<210> SEQ ID NO 74
<211> LENGTH: 397
<212> TYPE: PRT
<213> ORGANISM: Homo sapiens
<220> FEATURE:
<223> OTHER INFORMATION: Mature PVR(CD155)

<400> SEQUENCE: 74

Trp Pro Pro Pro Gly Thr Gly Asp Val Val Val Gln Ala Pro Thr Gln
1               5                   10                  15

Val Pro Gly Phe Leu Gly Asp Ser Val Thr Leu Pro Cys Tyr Leu Gln
            20                  25                  30

Val Pro Asn Met Glu Val Thr His Val Ser Gln Leu Thr Trp Ala Arg
        35                  40                  45

His Gly Glu Ser Gly Ser Met Ala Val Phe His Gln Thr Gln Gly Pro
    50                  55                  60

Ser Tyr Ser Glu Ser Lys Arg Leu Glu Phe Val Ala Ala Arg Leu Gly
65                  70                  75                  80

Ala Glu Leu Arg Asn Ala Ser Leu Arg Met Phe Gly Leu Arg Val Glu
                85                  90                  95

Asp Glu Gly Asn Tyr Thr Cys Leu Phe Val Thr Phe Pro Gln Gly Ser
            100                 105                 110

Arg Ser Val Asp Ile Trp Leu Arg Val Leu Ala Lys Pro Gln Asn Thr
        115                 120                 125

Ala Glu Val Gln Lys Val Gln Leu Thr Gly Glu Pro Val Pro Met Ala
    130                 135                 140

Arg Cys Val Ser Thr Gly Gly Arg Pro Pro Ala Gln Ile Thr Trp His
145                 150                 155                 160

Ser Asp Leu Gly Gly Met Pro Asn Thr Ser Gln Val Pro Gly Phe Leu
                165                 170                 175

Ser Gly Thr Val Thr Val Thr Ser Leu Trp Ile Leu Val Pro Ser Ser
            180                 185                 190

Gln Val Asp Gly Lys Asn Val Thr Cys Lys Val Glu His Glu Ser Phe
        195                 200                 205

Glu Lys Pro Gln Leu Leu Thr Val Asn Leu Thr Val Tyr Tyr Pro Pro
    210                 215                 220

Glu Val Ser Ile Ser Gly Tyr Asp Asn Asn Trp Tyr Leu Gly Gln Asn
225                 230                 235                 240

Glu Ala Thr Leu Thr Cys Asp Ala Arg Ser Asn Pro Glu Pro Thr Gly
                245                 250                 255

Tyr Asn Trp Ser Thr Thr Met Gly Pro Leu Pro Pro Phe Ala Val Ala
            260                 265                 270
```

```
Gln Gly Ala Gln Leu Leu Ile Arg Pro Val Asp Lys Pro Ile Asn Thr
        275                 280                 285

Thr Leu Ile Cys Asn Val Thr Asn Ala Leu Gly Ala Arg Gln Ala Glu
    290                 295                 300

Leu Thr Val Gln Val Lys Glu Gly Pro Pro Ser Glu His Ser Gly Ile
305                 310                 315                 320

Ser Arg Asn Ala Ile Ile Phe Leu Val Leu Gly Ile Leu Val Phe Leu
                325                 330                 335

Ile Leu Leu Gly Ile Gly Ile Tyr Phe Tyr Trp Ser Lys Cys Ser Arg
            340                 345                 350

Glu Val Leu Trp His Cys His Leu Cys Pro Ser Ser Thr Glu His Ala
        355                 360                 365

Ser Ala Ser Ala Asn Gly His Val Ser Tyr Ser Ala Val Ser Arg Glu
    370                 375                 380

Asn Ser Ser Ser Gln Asp Pro Gln Thr Glu Gly Thr Arg
385                 390                 395


<210> SEQ ID NO 75
<211> LENGTH: 507
<212> TYPE: PRT
<213> ORGANISM: Homo sapiens
<220> FEATURE:
<223> OTHER INFORMATION: Mature PVRL2(CD112)

<400> SEQUENCE: 75

Gln Asp Val Arg Val Gln Val Leu Pro Glu Val Arg Gly Gln Leu Gly
1               5                   10                  15

Gly Thr Val Glu Leu Pro Cys His Leu Leu Pro Pro Val Pro Gly Leu
            20                  25                  30

Tyr Ile Ser Leu Val Thr Trp Gln Arg Pro Asp Ala Pro Ala Asn His
        35                  40                  45

Gln Asn Val Ala Ala Phe His Pro Lys Met Gly Pro Ser Phe Pro Ser
    50                  55                  60

Pro Lys Pro Gly Ser Glu Arg Leu Ser Phe Val Ser Ala Lys Gln Ser
65                  70                  75                  80

Thr Gly Gln Asp Thr Glu Ala Glu Leu Gln Asp Ala Thr Leu Ala Leu
                85                  90                  95

His Gly Leu Thr Val Glu Asp Glu Gly Asn Tyr Thr Cys Glu Phe Ala
            100                 105                 110

Thr Phe Pro Lys Gly Ser Val Arg Gly Met Thr Trp Leu Arg Val Ile
        115                 120                 125

Ala Lys Pro Lys Asn Gln Ala Glu Ala Gln Lys Val Thr Phe Ser Gln
    130                 135                 140

Asp Pro Thr Thr Val Ala Leu Cys Ile Ser Lys Glu Gly Arg Pro Pro
145                 150                 155                 160

Ala Arg Ile Ser Trp Leu Ser Ser Leu Asp Trp Glu Ala Lys Glu Thr
                165                 170                 175

Gln Val Ser Gly Thr Leu Ala Gly Thr Val Thr Val Thr Ser Arg Phe
            180                 185                 190

Thr Leu Val Pro Ser Gly Arg Ala Asp Gly Val Thr Val Thr Cys Lys
        195                 200                 205

Val Glu His Glu Ser Phe Glu Glu Pro Ala Leu Ile Pro Val Thr Leu
    210                 215                 220

Ser Val Arg Tyr Pro Pro Glu Val Ser Ile Ser Gly Tyr Asp Asp Asn
225                 230                 235                 240
```

```
Trp Tyr Leu Gly Arg Thr Asp Ala Thr Leu Ser Cys Asp Val Arg Ser
                245                 250                 255

Asn Pro Glu Pro Thr Gly Tyr Asp Trp Ser Thr Thr Ser Gly Thr Phe
            260                 265                 270

Pro Thr Ser Ala Val Ala Gln Gly Ser Gln Leu Val Ile His Ala Val
        275                 280                 285

Asp Ser Leu Phe Asn Thr Thr Phe Val Cys Thr Val Thr Asn Ala Val
    290                 295                 300

Gly Met Gly Arg Ala Glu Gln Val Ile Phe Val Arg Glu Thr Pro Asn
305                 310                 315                 320

Thr Ala Gly Ala Gly Ala Thr Gly Gly Ile Ile Gly Gly Ile Ile Ala
                325                 330                 335

Ala Ile Ile Ala Thr Ala Val Ala Ala Thr Gly Ile Leu Ile Cys Arg
            340                 345                 350

Gln Gln Arg Lys Glu Gln Thr Leu Gln Gly Ala Glu Glu Asp Glu Asp
        355                 360                 365

Leu Glu Gly Pro Pro Ser Tyr Lys Pro Pro Thr Pro Lys Ala Lys Leu
    370                 375                 380

Glu Ala Gln Glu Met Pro Ser Gln Leu Phe Thr Leu Gly Ala Ser Glu
385                 390                 395                 400

His Ser Pro Leu Lys Thr Pro Tyr Phe Asp Ala Gly Ala Ser Cys Thr
                405                 410                 415

Glu Gln Glu Met Pro Arg Tyr His Glu Leu Pro Thr Leu Glu Glu Arg
            420                 425                 430

Ser Gly Pro Leu His Pro Gly Ala Thr Ser Leu Gly Ser Pro Ile Pro
        435                 440                 445

Val Pro Pro Gly Pro Pro Ala Val Glu Asp Val Ser Leu Asp Leu Glu
    450                 455                 460

Asp Glu Glu Gly Glu Glu Glu Glu Glu Tyr Leu Asp Lys Ile Asn Pro
465                 470                 475                 480

Ile Tyr Asp Ala Leu Ser Tyr Ser Ser Pro Ser Asp Ser Tyr Gln Gly
                485                 490                 495

Lys Gly Phe Val Met Ser Arg Ala Met Tyr Val
            500                 505
```

<210> SEQ ID NO 76
<211> LENGTH: 318
<212> TYPE: PRT
<213> ORGANISM: Homo sapiens
<220> FEATURE:
<223> OTHER INFORMATION: Mature CD226

<400> SEQUENCE: 76

```
Glu Glu Val Leu Trp His Thr Ser Val Pro Phe Ala Glu Asn Met Ser
1               5                   10                  15

Leu Glu Cys Val Tyr Pro Ser Met Gly Ile Leu Thr Gln Val Glu Trp
            20                  25                  30

Phe Lys Ile Gly Thr Gln Gln Asp Ser Ile Ala Ile Phe Ser Pro Thr
        35                  40                  45

His Gly Met Val Ile Arg Lys Pro Tyr Ala Glu Arg Val Tyr Phe Leu
    50                  55                  60

Asn Ser Thr Met Ala Ser Asn Asn Met Thr Leu Phe Phe Arg Asn Ala
65                  70                  75                  80

Ser Glu Asp Asp Val Gly Tyr Tyr Ser Cys Ser Leu Tyr Thr Tyr Pro
                85                  90                  95
```

```
Gln Gly Thr Trp Gln Lys Val Ile Gln Val Val Gln Ser Asp Ser Phe
            100                 105                 110

Glu Ala Ala Val Pro Ser Asn Ser His Ile Val Ser Glu Pro Gly Lys
        115                 120                 125

Asn Val Thr Leu Thr Cys Gln Pro Gln Met Thr Trp Pro Val Gln Ala
    130                 135                 140

Val Arg Trp Glu Lys Ile Gln Pro Arg Gln Ile Asp Leu Leu Thr Tyr
145                 150                 155                 160

Cys Asn Leu Val His Gly Arg Asn Phe Thr Ser Lys Phe Pro Arg Gln
                165                 170                 175

Ile Val Ser Asn Cys Ser His Gly Arg Trp Ser Val Ile Val Ile Pro
            180                 185                 190

Asp Val Thr Val Ser Asp Ser Gly Leu Tyr Arg Cys Tyr Leu Gln Ala
        195                 200                 205

Ser Ala Gly Glu Asn Glu Thr Phe Val Met Arg Leu Thr Val Ala Glu
    210                 215                 220

Gly Lys Thr Asp Asn Gln Tyr Thr Leu Phe Val Ala Gly Gly Thr Val
225                 230                 235                 240

Leu Leu Leu Leu Phe Val Ile Ser Ile Thr Thr Ile Ile Val Ile Phe
                245                 250                 255

Leu Asn Arg Arg Arg Arg Arg Glu Arg Arg Asp Leu Phe Thr Glu Ser
            260                 265                 270

Trp Asp Thr Gln Lys Ala Pro Asn Asn Tyr Arg Ser Pro Ile Ser Thr
        275                 280                 285

Ser Gln Pro Thr Asn Gln Ser Met Asp Asp Thr Arg Glu Asp Ile Tyr
    290                 295                 300

Val Asn Tyr Pro Thr Phe Ser Arg Arg Pro Lys Thr Arg Val
305                 310                 315
```

<210> SEQ ID NO 77
<211> LENGTH: 327
<212> TYPE: PRT
<213> ORGANISM: Homo sapiens
<220> FEATURE:
<223> OTHER INFORMATION: Mature CD2

<400> SEQUENCE: 77

```
Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
    130                 135                 140
```

```
Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp Ile Tyr Leu Ile Ile Gly Ile
            180                 185                 190

Cys Gly Gly Gly Ser Leu Leu Met Val Phe Val Ala Leu Leu Val Phe
        195                 200                 205

Tyr Ile Thr Lys Arg Lys Lys Gln Arg Ser Arg Arg Asn Asp Glu Glu
    210                 215                 220

Leu Glu Thr Arg Ala His Arg Val Ala Thr Glu Glu Arg Gly Arg Lys
225                 230                 235                 240

Pro His Gln Ile Pro Ala Ser Thr Pro Gln Asn Pro Ala Thr Ser Gln
                245                 250                 255

His Pro Pro Pro Pro Pro Gly His Arg Ser Gln Ala Pro Ser His Arg
            260                 265                 270

Pro Pro Pro Pro Gly His Arg Val Gln His Gln Pro Gln Lys Arg Pro
        275                 280                 285

Pro Ala Pro Ser Gly Thr Gln Val His Gln Gln Lys Gly Pro Pro Leu
    290                 295                 300

Pro Arg Pro Arg Val Gln Pro Lys Pro Pro His Gly Ala Ala Glu Asn
305                 310                 315                 320

Ser Leu Ser Pro Ser Ser Asn
                325


<210> SEQ ID NO 78
<211> LENGTH: 154
<212> TYPE: PRT
<213> ORGANISM: Homo sapiens
<220> FEATURE:
<223> OTHER INFORMATION: Mature CD160

<400> SEQUENCE: 78

Ile Asn Ile Thr Ser Ser Ala Ser Gln Glu Gly Thr Arg Leu Asn Leu
1               5                   10                  15

Ile Cys Thr Val Trp His Lys Lys Glu Glu Ala Glu Gly Phe Val Val
            20                  25                  30

Phe Leu Cys Lys Asp Arg Ser Gly Asp Cys Ser Pro Glu Thr Ser Leu
        35                  40                  45

Lys Gln Leu Arg Leu Lys Arg Asp Pro Gly Ile Asp Gly Val Gly Glu
    50                  55                  60

Ile Ser Ser Gln Leu Met Phe Thr Ile Ser Gln Val Thr Pro Leu His
65                  70                  75                  80

Ser Gly Thr Tyr Gln Cys Cys Ala Arg Ser Gln Lys Ser Gly Ile Arg
                85                  90                  95

Leu Gln Gly His Phe Phe Ser Ile Leu Phe Thr Glu Thr Gly Asn Tyr
            100                 105                 110

Thr Val Thr Gly Leu Lys Gln Arg Gln His Leu Glu Phe Ser His Asn
        115                 120                 125

Glu Gly Thr Leu Ser Ser Gly Phe Leu Gln Glu Lys Val Trp Val Met
    130                 135                 140

Leu Val Thr Ser Leu Val Ala Leu Gln Ala
145                 150


<210> SEQ ID NO 79
<211> LENGTH: 248
```

<212> TYPE: PRT
<213> ORGANISM: Homo sapiens
<220> FEATURE:
<223> OTHER INFORMATION: Mature CD200

<400> SEQUENCE: 79

```
Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45

Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

Gly Phe Gly Lys Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys Gly Tyr Trp Phe Ser Val Pro
        195                 200                 205

Leu Leu Leu Ser Ile Val Ser Leu Val Ile Leu Leu Val Leu Ile Ser
    210                 215                 220

Ile Leu Leu Tyr Trp Lys Arg His Arg Asn Gln Asp Arg Gly Glu Leu
225                 230                 235                 240

Ser Gln Gly Val Gln Lys Met Thr
                245
```

<210> SEQ ID NO 80
<211> LENGTH: 297
<212> TYPE: PRT
<213> ORGANISM: Homo sapiens
<220> FEATURE:
<223> OTHER INFORMATION: Mature CD200R1(CD200R)

<400> SEQUENCE: 80

```
Met Asp Glu Lys Gln Ile Thr Gln Asn Tyr Ser Lys Val Leu Ala Glu
1               5                   10                  15

Val Asn Thr Ser Trp Pro Val Lys Met Ala Thr Asn Ala Val Leu Cys
            20                  25                  30

Cys Pro Pro Ile Ala Leu Arg Asn Leu Ile Ile Ile Thr Trp Glu Ile
        35                  40                  45

Ile Leu Arg Gly Gln Pro Ser Cys Thr Lys Ala Tyr Arg Lys Glu Thr
    50                  55                  60

Asn Glu Thr Lys Glu Thr Asn Cys Thr Asp Glu Arg Ile Thr Trp Val
65                  70                  75                  80
```

```
Ser Arg Pro Asp Gln Asn Ser Asp Leu Gln Ile Arg Pro Val Ala Ile
                85                  90                  95

Thr His Asp Gly Tyr Tyr Arg Cys Ile Met Val Thr Pro Asp Gly Asn
            100                 105                 110

Phe His Arg Gly Tyr His Leu Gln Val Leu Val Thr Pro Glu Val Thr
        115                 120                 125

Leu Phe Gln Asn Arg Asn Arg Thr Ala Val Cys Lys Ala Val Ala Gly
    130                 135                 140

Lys Pro Ala Ala Gln Ile Ser Trp Ile Pro Glu Gly Asp Cys Ala Thr
145                 150                 155                 160

Lys Gln Glu Tyr Trp Ser Asn Gly Thr Val Thr Val Lys Ser Thr Cys
                165                 170                 175

His Trp Glu Val His Asn Val Ser Thr Val Thr Cys His Val Ser His
            180                 185                 190

Leu Thr Gly Asn Lys Ser Leu Tyr Ile Glu Leu Leu Pro Val Pro Gly
        195                 200                 205

Ala Lys Lys Ser Ala Lys Leu Tyr Ile Pro Tyr Ile Ile Leu Thr Ile
    210                 215                 220

Ile Ile Leu Thr Ile Val Gly Phe Ile Trp Leu Leu Lys Val Asn Gly
225                 230                 235                 240

Cys Arg Lys Tyr Lys Leu Asn Lys Thr Glu Ser Thr Pro Val Val Glu
                245                 250                 255

Glu Asp Glu Met Gln Pro Tyr Ala Ser Tyr Thr Glu Lys Asn Asn Pro
            260                 265                 270

Leu Tyr Asp Thr Thr Asn Lys Val Lys Ala Ser Glu Ala Leu Gln Ser
        275                 280                 285

Glu Val Asp Thr Asp Leu His Thr Leu
    290                 295


<210> SEQ ID NO 81
<211> LENGTH: 183
<212> TYPE: PRT
<213> ORGANISM: Homo sapiens
<220> FEATURE:
<223> OTHER INFORMATION: Mature NC R3 (NKp30)

<400> SEQUENCE: 81

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

His Pro Gln Leu Gly Ala Gly Thr Val Leu Leu Leu Arg Ala Gly Phe
        115                 120                 125

Tyr Ala Val Ser Phe Leu Ser Val Ala Val Gly Ser Thr Val Tyr Tyr
    130                 135                 140
```

Gln Gly Lys Cys Leu Thr Trp Lys Gly Pro Arg Arg Gln Leu Pro Ala
145 150 155 160

Val Val Pro Ala Pro Leu Pro Pro Pro Cys Gly Ser Ser Ala His Leu
165 170 175

Leu Pro Pro Val Pro Gly Gly
180

<210> SEQ ID NO 82
<211> LENGTH: 414
<212> TYPE: PRT
<213> ORGANISM: Homo sapiens
<220> FEATURE:
<223> OTHER INFORMATION: VSIG8

<400> SEQUENCE: 82

Met Arg Val Gly Gly Ala Phe His Leu Leu Leu Val Cys Leu Ser Pro
1 5 10 15

Ala Leu Leu Ser Ala Val Arg Ile Asn Gly Asp Gly Gln Glu Val Leu
20 25 30

Tyr Leu Ala Glu Gly Asp Asn Val Arg Leu Gly Cys Pro Tyr Val Leu
35 40 45

Asp Pro Glu Asp Tyr Gly Pro Asn Gly Leu Asp Ile Glu Trp Met Gln
50 55 60

Val Asn Ser Asp Pro Ala His His Arg Glu Asn Val Phe Leu Ser Tyr
65 70 75 80

Gln Asp Lys Arg Ile Asn His Gly Ser Leu Pro His Leu Gln Gln Arg
85 90 95

Val Arg Phe Ala Ala Ser Asp Pro Ser Gln Tyr Asp Ala Ser Ile Asn
100 105 110

Leu Met Asn Leu Gln Val Ser Asp Thr Ala Thr Tyr Glu Cys Arg Val
115 120 125

Lys Lys Thr Thr Met Ala Thr Arg Lys Val Ile Val Thr Val Gln Ala
130 135 140

Arg Pro Ala Val Pro Met Cys Trp Thr Glu Gly His Met Thr Tyr Gly
145 150 155 160

Asn Asp Val Val Leu Lys Cys Tyr Ala Ser Gly Gly Ser Gln Pro Leu
165 170 175

Ser Tyr Lys Trp Ala Lys Ile Ser Gly His His Tyr Pro Tyr Arg Ala
180 185 190

Gly Ser Tyr Thr Ser Gln His Ser Tyr His Ser Glu Leu Ser Tyr Gln
195 200 205

Glu Ser Phe His Ser Ser Ile Asn Gln Gly Leu Asn Asn Gly Asp Leu
210 215 220

Val Leu Lys Asp Ile Ser Arg Ala Asp Asp Gly Leu Tyr Gln Cys Thr
225 230 235 240

Val Ala Asn Asn Val Gly Tyr Ser Val Cys Val Val Glu Val Lys Val
245 250 255

Ser Asp Ser Arg Arg Ile Gly Val Ile Ile Gly Ile Val Leu Gly Ser
260 265 270

Leu Leu Ala Leu Gly Cys Leu Ala Val Gly Ile Trp Gly Leu Val Cys
275 280 285

Cys Cys Cys Gly Gly Ser Gly Ala Gly Gly Ala Arg Gly Ala Phe Gly
290 295 300

Tyr Gly Asn Gly Gly Gly Val Gly Gly Gly Ala Cys Gly Asp Leu Ala
305 310 315 320

```
Ser Glu Ile Arg Glu Asp Ala Val Ala Pro Gly Cys Lys Ala Ser Gly
                325                 330                 335

Arg Gly Ser Arg Val Thr His Leu Leu Gly Tyr Pro Thr Gln Asn Val
            340                 345                 350

Ser Arg Ser Leu Arg Arg Lys Tyr Ala Pro Pro Pro Cys Gly Gly Pro
        355                 360                 365

Glu Asp Val Ala Leu Ala Pro Cys Thr Ala Ala Ala Ala Cys Glu Ala
    370                 375                 380

Gly Pro Ser Pro Val Tyr Val Lys Val Lys Ser Ala Glu Pro Ala Asp
385                 390                 395                 400

Cys Ala Glu Gly Pro Val Gln Cys Lys Asn Gly Leu Leu Val
                405                 410


<210> SEQ ID NO 83
<211> LENGTH: 393
<212> TYPE: PRT
<213> ORGANISM: Homo sapiens
<220> FEATURE:
<223> OTHER INFORMATION: Mature VSIG8

<400> SEQUENCE: 83

Val Arg Ile Asn Gly Asp Gly Gln Glu Val Leu Tyr Leu Ala Glu Gly
1               5                   10                  15

Asp Asn Val Arg Leu Gly Cys Pro Tyr Val Leu Asp Pro Glu Asp Tyr
            20                  25                  30

Gly Pro Asn Gly Leu Asp Ile Glu Trp Met Gln Val Asn Ser Asp Pro
        35                  40                  45

Ala His His Arg Glu Asn Val Phe Leu Ser Tyr Gln Asp Lys Arg Ile
    50                  55                  60

Asn His Gly Ser Leu Pro His Leu Gln Gln Arg Val Arg Phe Ala Ala
65                  70                  75                  80

Ser Asp Pro Ser Gln Tyr Asp Ala Ser Ile Asn Leu Met Asn Leu Gln
                85                  90                  95

Val Ser Asp Thr Ala Thr Tyr Glu Cys Arg Val Lys Lys Thr Thr Met
            100                 105                 110

Ala Thr Arg Lys Val Ile Val Thr Val Gln Ala Arg Pro Ala Val Pro
        115                 120                 125

Met Cys Trp Thr Glu Gly His Met Thr Tyr Gly Asn Asp Val Val Leu
    130                 135                 140

Lys Cys Tyr Ala Ser Gly Gly Ser Gln Pro Leu Ser Tyr Lys Trp Ala
145                 150                 155                 160

Lys Ile Ser Gly His His Tyr Pro Tyr Arg Ala Gly Ser Tyr Thr Ser
                165                 170                 175

Gln His Ser Tyr His Ser Glu Leu Ser Tyr Gln Glu Ser Phe His Ser
            180                 185                 190

Ser Ile Asn Gln Gly Leu Asn Asn Gly Asp Leu Val Leu Lys Asp Ile
        195                 200                 205

Ser Arg Ala Asp Asp Gly Leu Tyr Gln Cys Thr Val Ala Asn Asn Val
    210                 215                 220

Gly Tyr Ser Val Cys Val Val Glu Val Lys Val Ser Asp Ser Arg Arg
225                 230                 235                 240

Ile Gly Val Ile Ile Gly Ile Val Leu Gly Ser Leu Leu Ala Leu Gly
                245                 250                 255

Cys Leu Ala Val Gly Ile Trp Gly Leu Val Cys Cys Cys Cys Gly Gly
            260                 265                 270
```

```
Ser Gly Ala Gly Gly Ala Arg Gly Ala Phe Gly Tyr Gly Asn Gly Gly
        275                 280                 285

Gly Val Gly Gly Gly Ala Cys Gly Asp Leu Ala Ser Glu Ile Arg Glu
    290                 295                 300

Asp Ala Val Ala Pro Gly Cys Lys Ala Ser Gly Arg Gly Ser Arg Val
305                 310                 315                 320

Thr His Leu Leu Gly Tyr Pro Thr Gln Asn Val Ser Arg Ser Leu Arg
                325                 330                 335

Arg Lys Tyr Ala Pro Pro Pro Cys Gly Gly Pro Glu Asp Val Ala Leu
            340                 345                 350

Ala Pro Cys Thr Ala Ala Ala Ala Cys Glu Ala Gly Pro Ser Pro Val
        355                 360                 365

Tyr Val Lys Val Lys Ser Ala Glu Pro Ala Asp Cys Ala Glu Gly Pro
    370                 375                 380

Val Gln Cys Lys Asn Gly Leu Leu Val
385                 390


<210> SEQ ID NO 84
<211> LENGTH: 242
<212> TYPE: PRT
<213> ORGANISM: Homo sapiens
<220> FEATURE:
<223> OTHER INFORMATION: VSIG8 ECD

<400> SEQUENCE: 84

Val Arg Ile Asn Gly Asp Gly Gln Glu Val Leu Tyr Leu Ala Glu Gly
1               5                   10                  15

Asp Asn Val Arg Leu Gly Cys Pro Tyr Val Leu Asp Pro Glu Asp Tyr
            20                  25                  30

Gly Pro Asn Gly Leu Asp Ile Glu Trp Met Gln Val Asn Ser Asp Pro
        35                  40                  45

Ala His His Arg Glu Asn Val Phe Leu Ser Tyr Gln Asp Lys Arg Ile
    50                  55                  60

Asn His Gly Ser Leu Pro His Leu Gln Gln Arg Val Arg Phe Ala Ala
65                  70                  75                  80

Ser Asp Pro Ser Gln Tyr Asp Ala Ser Ile Asn Leu Met Asn Leu Gln
                85                  90                  95

Val Ser Asp Thr Ala Thr Tyr Glu Cys Arg Val Lys Lys Thr Thr Met
            100                 105                 110

Ala Thr Arg Lys Val Ile Val Thr Val Gln Ala Arg Pro Ala Val Pro
        115                 120                 125

Met Cys Trp Thr Glu Gly His Met Thr Tyr Gly Asn Asp Val Val Leu
    130                 135                 140

Lys Cys Tyr Ala Ser Gly Gly Ser Gln Pro Leu Ser Tyr Lys Trp Ala
145                 150                 155                 160

Lys Ile Ser Gly His His Tyr Pro Tyr Arg Ala Gly Ser Tyr Thr Ser
                165                 170                 175

Gln His Ser Tyr His Ser Glu Leu Ser Tyr Gln Glu Ser Phe His Ser
            180                 185                 190

Ser Ile Asn Gln Gly Leu Asn Asn Gly Asp Leu Val Leu Lys Asp Ile
        195                 200                 205

Ser Arg Ala Asp Asp Gly Leu Tyr Gln Cys Thr Val Ala Asn Asn Val
    210                 215                 220

Gly Tyr Ser Val Cys Val Val Glu Val Lys Val Ser Asp Ser Arg Arg
225                 230                 235                 240
```

Ile Gly

<210> SEQ ID NO 85
<211> LENGTH: 224
<212> TYPE: PRT
<213> ORGANISM: Artificial Sequence
<220> FEATURE:
<223> OTHER INFORMATION: CD86 ECD v1

<400> SEQUENCE: 85

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Ala Leu Arg Leu His Asn Leu Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220
```

<210> SEQ ID NO 86
<211> LENGTH: 224
<212> TYPE: PRT
<213> ORGANISM: Artificial Sequence
<220> FEATURE:
<223> OTHER INFORMATION: CD86 ECD v2

<400> SEQUENCE: 86

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Gly Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80
```

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Val Leu Glu Asp Pro Gln Pro Pro Pro Asp His Ile Pro
210 215 220

<210> SEQ ID NO 87
<211> LENGTH: 224
<212> TYPE: PRT
<213> ORGANISM: Artificial Sequence
<220> FEATURE:
<223> OTHER INFORMATION: CD86 ECD v3
<220> FEATURE:
<221> NAME/KEY: VARIANT
<222> LOCATION: (215)...(215)
<223> OTHER INFORMATION: Xaa is any amino acid
<220> FEATURE:
<221> NAME/KEY: VARIANT
<222> LOCATION: (217)...(217)
<223> OTHER INFORMATION: Xaa is any amino acid
<220> FEATURE:
<221> NAME/KEY: VARIANT
<222> LOCATION: (218)...(218)
<223> OTHER INFORMATION: Xaa is any amino acid

<400> SEQUENCE: 87

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

```
Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Xaa Pro Xaa Xaa Pro Pro Asp His Ile Pro
    210                 215                 220


<210> SEQ ID NO 88
<211> LENGTH: 224
<212> TYPE: PRT
<213> ORGANISM: Artificial Sequence
<220> FEATURE:
<223> OTHER INFORMATION: CD86 ECD v4

<400> SEQUENCE: 88

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Lys Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Asn Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Thr Ser Leu Ser Val Ser Phe Pro Asp Val Thr Ser Asn Met Thr
            180                 185                 190

Ile Phe Cys Ile Leu Asp Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 89
<211> LENGTH: 224
<212> TYPE: PRT
<213> ORGANISM: Artificial Sequence
<220> FEATURE:
<223> OTHER INFORMATION: CD86 ECD v5

<400> SEQUENCE: 89

Ala Pro Leu Lys Ile Gln Ala Tyr Phe Asn Glu Thr Val Asp Leu Pro
1               5                   10                  15

Cys Gln Phe Ala Asn Ser Gln Asn Leu Ser Leu Ser Glu Leu Val Val
```

```
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Met Glu Thr Asp Lys Thr Arg Leu Leu Thr Ser Pro
        195                 200                 205

Phe Ser Ile Glu Leu Glu Asp Pro Gln Pro Pro Pro Asp His Ile Pro
    210                 215                 220


<210> SEQ ID NO 90
<211> LENGTH: 224
<212> TYPE: PRT
<213> ORGANISM: Artificial Sequence
<220> FEATURE:
<223> OTHER INFORMATION: CD86 ECD v6

<400> SEQUENCE: 90

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Thr Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Met Thr Cys Ser Ser Ile His Gly Tyr Pro Glu Pro Lys
    130                 135                 140

Lys Met Ser Asp Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
```

```
                165                 170                 175

Ser Ile Ser Leu Pro Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp His Gln Pro Pro Pro Asp His Ile Pro
    210                 215                 220


<210> SEQ ID NO 91
<211> LENGTH: 224
<212> TYPE: PRT
<213> ORGANISM: Artificial Sequence
<220> FEATURE:
<223> OTHER INFORMATION: CD86 ECD v7
<220> FEATURE:
<221> NAME/KEY: VARIANT
<222> LOCATION: (201)...(201)
<223> OTHER INFORMATION: Xaa is any amino acid

<400> SEQUENCE: 91

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Ile Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Ala
        115                 120                 125

Tyr Ile Asn Leu Thr Cys Ser Ser Ile His Gly Tyr Ala Glu Pro Lys
    130                 135                 140

Lys Met Ser Val Leu Leu Arg Thr Lys Asn Ser Thr Ile Gly Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Leu Glu Thr Asp Xaa Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 92
<211> LENGTH: 224
<212> TYPE: PRT
<213> ORGANISM: Artificial Sequence
<220> FEATURE:
<223> OTHER INFORMATION: CD86 ECD v8

<400> SEQUENCE: 92

Ala Pro Leu Lys Ile Gln Ala Tyr Phe Asn Glu Thr Ala Asp Leu Pro
1               5                   10                  15
```

```
Cys Gln Phe Ala Asn Ser Gln Asn Leu Ser Leu Ser Glu Leu Val Val
            20                  25                  30

Phe Trp Gln Asp Gln Glu Asp Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Arg
65                  70                  75                  80

Asp Lys Gly Leu Tyr Arg Cys Phe Ile Leu His Lys Thr Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asp Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asp Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 93
<211> LENGTH: 224
<212> TYPE: PRT
<213> ORGANISM: Artificial Sequence
<220> FEATURE:
<223> OTHER INFORMATION: CD86 ECD v9

<400> SEQUENCE: 93

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Thr Pro Thr Gly
                85                  90                  95

Leu Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Ala Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160
```

Gly Val Met Gln Lys Ser Gln Asp Asn Val Thr Glu Leu Tyr Asp Val
165 170 175

Ser Ile Ser Leu Pro Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Val Pro Gln Pro Pro Pro Asp His Ile Pro
210 215 220

<210> SEQ ID NO 94
<211> LENGTH: 224
<212> TYPE: PRT
<213> ORGANISM: Artificial Sequence
<220> FEATURE:
<223> OTHER INFORMATION: CD86 ECD v10

<400> SEQUENCE: 94

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Leu His Lys Lys Pro Thr Gly
85 90 95

Met Ile Arg Ile His Gln Met Ser Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 95
<211> LENGTH: 224
<212> TYPE: PRT
<213> ORGANISM: Artificial Sequence
<220> FEATURE:
<223> OTHER INFORMATION: CD86 ECD v11

<400> SEQUENCE: 95

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val

```
            20                  25                  30

Phe Trp Gln Asp Gln Glu Asn Met Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Ser Ser Val Pro Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 96
<211> LENGTH: 224
<212> TYPE: PRT
<213> ORGANISM: Artificial Sequence
<220> FEATURE:
<223> OTHER INFORMATION: CD86 ECD v12

<400> SEQUENCE: 96

Ala Pro Leu Lys Ile Gln Ala Tyr Phe Asn Glu Thr Ala Asp Leu Pro
1               5                   10                  15

Cys Lys Phe Ala Asn Ser Gln Asn Leu Ser Leu Ser Glu Leu Val Val
            20                  25                  30

Ile Trp Gln Asp Gln Glu Asn Ser Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
```

```
            165                 170                 175

Ser Ile Ser Leu Ser Val Ser Phe Pro Asp Val Thr Ser Asn Met Thr
        180                 185                 190

Ile Phe Cys Ile Leu Glu Thr Asp Lys Thr Arg Leu Leu Ser Ser Pro
    195                 200                 205

Phe Ser Ile Glu Leu Glu Asp Pro Gln Pro Pro Pro Asp His Ile Pro
210                 215                 220


<210> SEQ ID NO 97
<211> LENGTH: 224
<212> TYPE: PRT
<213> ORGANISM: Artificial Sequence
<220> FEATURE:
<223> OTHER INFORMATION: CD86 ECD v13

<400> SEQUENCE: 97

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Lys Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Thr His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 98
<211> LENGTH: 224
<212> TYPE: PRT
<213> ORGANISM: Artificial Sequence
<220> FEATURE:
<223> OTHER INFORMATION: CD86 ECD v14

<400> SEQUENCE: 98

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30
```

```
Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Pro Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Arg Asn Ser Thr Ile Glu Tyr Asp
145                 150                 155                 160

Gly Val Met Gln Lys Ser Gln Asp Asn Asp Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 99
<211> LENGTH: 224
<212> TYPE: PRT
<213> ORGANISM: Artificial Sequence
<220> FEATURE:
<223> OTHER INFORMATION: CD86 ECD v15

<400> SEQUENCE: 99

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Gly Glu Leu Val Val
            20                  25                  30

Ile Trp Gln Asp Gln Glu Asn Leu Val Leu Asn Glu Val Tyr Leu Gly
        35                  40                  45

Lys Glu Lys Leu Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His His Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175
```

Ser Thr Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 100
<211> LENGTH: 224
<212> TYPE: PRT
<213> ORGANISM: Artificial Sequence
<220> FEATURE:
<223> OTHER INFORMATION: CD86 ECD v16
<220> FEATURE:
<221> NAME/KEY: VARIANT
<222> LOCATION: (212)...(212)
<223> OTHER INFORMATION: Xaa is any amino acid
<220> FEATURE:
<221> NAME/KEY: VARIANT
<222> LOCATION: (221)...(221)
<223> OTHER INFORMATION: Xaa is any amino acid

<400> SEQUENCE: 100

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Ile Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Glu
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Ser Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Xaa Leu Glu Asp Pro Gln Pro Pro Pro Xaa His Ile Pro
210 215 220

<210> SEQ ID NO 101
<211> LENGTH: 224
<212> TYPE: PRT
<213> ORGANISM: Artificial Sequence
<220> FEATURE:
<223> OTHER INFORMATION: CD86 ECD v17
<220> FEATURE:
<221> NAME/KEY: VARIANT
<222> LOCATION: (221)...(221)

<223> OTHER INFORMATION: Xaa is any amino acid

<400> SEQUENCE: 101

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Ile Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Glu Asn Ser Thr Ile Glu Tyr Asp
145 150 155 160

Gly Val Met Gln Lys Ser Gln Asp Asn Val Thr Gly Leu Tyr Asp Val
165 170 175

Ser Ile Ser Leu Ser Val Ser Phe Pro Asp Val Thr Ser Asn Met Asn
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Xaa His Ile Pro
210 215 220

<210> SEQ ID NO 102
<211> LENGTH: 224
<212> TYPE: PRT
<213> ORGANISM: Artificial Sequence
<220> FEATURE:
<223> OTHER INFORMATION: CD86 ECD v18
<220> FEATURE:
<221> NAME/KEY: VARIANT
<222> LOCATION: (215)...(215)
<223> OTHER INFORMATION: Xaa is any amino acid

<400> SEQUENCE: 102

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Ile Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Tyr His Lys Lys Pro Thr Gly
85 90 95

Met Ile Arg Ile His Gln Met Asn Ser Glu Leu Ser Val Leu Ala Asn

```
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Glu Val
                165                 170                 175

Ser Ile Ser Leu Ser Val Ser Phe Pro Asp Val Thr Ser Asn Met Thr
            180                 185                 190

Ile Phe Cys Val Leu Asp Thr Asp Lys Thr Arg Leu Leu Ser Ser Pro
        195                 200                 205

Phe Ser Ile Glu Leu Glu Xaa Pro Gln Pro Pro Pro Asp His Ile Pro
    210                 215                 220


<210> SEQ ID NO 103
<211> LENGTH: 224
<212> TYPE: PRT
<213> ORGANISM: Artificial Sequence
<220> FEATURE:
<223> OTHER INFORMATION: CD86 ECD v19
<220> FEATURE:
<221> NAME/KEY: VARIANT
<222> LOCATION: (212)...(212)
<223> OTHER INFORMATION: Xaa is any amino acid
<220> FEATURE:
<221> NAME/KEY: VARIANT
<222> LOCATION: (215)...(215)
<223> OTHER INFORMATION: Xaa is any amino acid

<400> SEQUENCE: 103

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Ile Tyr Leu Gly
        35                  40                  45

Lys Glu Lys Phe Asp Ser Val His Ser Lys Tyr Met Gly Arg Thr Ser
    50                  55                  60

Phe Asp Ser Asn Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Pro Phe Pro Asp Val Thr Ser Asn Met Thr
            180                 185                 190

Ile Phe Cys Ile Leu Glu Thr Asp Lys Thr Arg Leu Ser Ser Ser Pro
        195                 200                 205
```

```
Phe Ser Ile Xaa Leu Glu Xaa Pro Gln Pro Pro Pro Asp His Ile Pro
    210                 215                 220


<210> SEQ ID NO 104
<211> LENGTH: 224
<212> TYPE: PRT
<213> ORGANISM: Artificial Sequence
<220> FEATURE:
<223> OTHER INFORMATION: CD86 ECD v20

<400> SEQUENCE: 104

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Val Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Asn
            100                 105                 110

Phe Gly Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu His Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 105
<211> LENGTH: 224
<212> TYPE: PRT
<213> ORGANISM: Artificial Sequence
<220> FEATURE:
<223> OTHER INFORMATION: CD86 ECD v21

<400> SEQUENCE: 105

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
```

65 70 75 80

Asp Lys Gly Leu Tyr Gln Cys Ile Ile Tyr His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Ser Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 106
<211> LENGTH: 224
<212> TYPE: PRT
<213> ORGANISM: Artificial Sequence
<220> FEATURE:
<223> OTHER INFORMATION: CD86 ECD v22

<400> SEQUENCE: 106

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Tyr His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Asn Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro 210 215 220

<210> SEQ ID NO 107
<211> LENGTH: 224
<212> TYPE: PRT
<213> ORGANISM: Artificial Sequence
<220> FEATURE:
<223> OTHER INFORMATION: CD86 ECD v23

<400> SEQUENCE: 107

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Val Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Val Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 108
<211> LENGTH: 223
<212> TYPE: PRT
<213> ORGANISM: Artificial Sequence
<220> FEATURE:
<223> OTHER INFORMATION: CD86 ECD v24

<400> SEQUENCE: 108

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Glu
65 70 75 80

```
Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp Thr Phe
    210                 215                 220


<210> SEQ ID NO 109
<211> LENGTH: 224
<212> TYPE: PRT
<213> ORGANISM: Artificial Sequence
<220> FEATURE:
<223> OTHER INFORMATION: CD86 ECD v25

<400> SEQUENCE: 109

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Met
65                  70                  75                  80

Asp Lys Gly Leu Tyr Gln Cys Thr Ile His His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220
```

<210> SEQ ID NO 110
<211> LENGTH: 224
<212> TYPE: PRT
<213> ORGANISM: Artificial Sequence
<220> FEATURE:
<223> OTHER INFORMATION: CD86 ECD v26

<400> SEQUENCE: 110

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His His Ile Lys Pro Thr Gly
85 90 95

Met Ile Arg Ile His Gln Met Asn Ser Glu Leu Ser Val Leu Ala Asn
100 105 110

Ser Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 111
<211> LENGTH: 224
<212> TYPE: PRT
<213> ORGANISM: Artificial Sequence
<220> FEATURE:
<223> OTHER INFORMATION: CD86 ECD v27

<400> SEQUENCE: 111

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Lys Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

```
Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 112
<211> LENGTH: 224
<212> TYPE: PRT
<213> ORGANISM: Artificial Sequence
<220> FEATURE:
<223> OTHER INFORMATION: CD86 ECD v28

<400> SEQUENCE: 112

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Ile Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 113
```

<211> LENGTH: 224
<212> TYPE: PRT
<213> ORGANISM: Artificial Sequence
<220> FEATURE:
<223> OTHER INFORMATION: CD86 ECD v29

<400> SEQUENCE: 113

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Ile Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Leu His Lys Thr Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 114
<211> LENGTH: 224
<212> TYPE: PRT
<213> ORGANISM: Artificial Sequence
<220> FEATURE:
<223> OTHER INFORMATION: CD86 ECD v30

<400> SEQUENCE: 114

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala Asn

```
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 115
<211> LENGTH: 224
<212> TYPE: PRT
<213> ORGANISM: Artificial Sequence
<220> FEATURE:
<223> OTHER INFORMATION: CD86 ECD v31

<400> SEQUENCE: 115

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Ser Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 116
<211> LENGTH: 223
<212> TYPE: PRT
```

<213> ORGANISM: Artificial Sequence
<220> FEATURE:
<223> OTHER INFORMATION: CD86 ECD v32

<400> SEQUENCE: 116

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Ser Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile
210 215 220

<210> SEQ ID NO 117
<211> LENGTH: 224
<212> TYPE: PRT
<213> ORGANISM: Artificial Sequence
<220> FEATURE:
<223> OTHER INFORMATION: CD86 ECD v33

<400> SEQUENCE: 117

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala Asn
100 105 110

```
Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Arg Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 118
<211> LENGTH: 224
<212> TYPE: PRT
<213> ORGANISM: Artificial Sequence
<220> FEATURE:
<223> OTHER INFORMATION: CD86 ECD v34

<400> SEQUENCE: 118

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Val Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 119
<211> LENGTH: 224
<212> TYPE: PRT
<213> ORGANISM: Artificial Sequence
<220> FEATURE:
```

```
<223> OTHER INFORMATION: CD86 ECD v35

<400> SEQUENCE: 119

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Thr Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Ser Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Pro Pro
        195                 200                 205

Phe Ser Ile Glu Leu Glu Asp Pro Gln Pro Pro Pro Asp His Ile Pro
    210                 215                 220


<210> SEQ ID NO 120
<211> LENGTH: 224
<212> TYPE: PRT
<213> ORGANISM: Artificial Sequence
<220> FEATURE:
<223> OTHER INFORMATION: CD86 ECD v36

<400> SEQUENCE: 120

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Thr Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125
```

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

<210> SEQ ID NO 121
<211> LENGTH: 224
<212> TYPE: PRT
<213> ORGANISM: Artificial Sequence
<220> FEATURE:
<223> OTHER INFORMATION: CD86 ECD v37

<400> SEQUENCE: 121

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Gly Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

<210> SEQ ID NO 122
<211> LENGTH: 99
<212> TYPE: PRT
<213> ORGANISM: Artificial Sequence
<220> FEATURE:
<223> OTHER INFORMATION: CD86(B7-2) IgV WT

<400> SEQUENCE: 122

Asn Glu Thr Ala Asp Leu Pro Cys Gln Phe Ala Asn Ser Gln Asn Gln
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

His His Lys Lys Pro Thr Gly Met Ile Arg Ile His Gln Met Asn Ser
85 90 95

Glu Leu Ser

<210> SEQ ID NO 123
<211> LENGTH: 111
<212> TYPE: PRT
<213> ORGANISM: Artificial Sequence
<220> FEATURE:
<223> OTHER INFORMATION: CD86(B7-2) IgV (24-134)

<400> SEQUENCE: 123

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu Ala
100 105 110

<210> SEQ ID NO 124
<211> LENGTH: 111
<212> TYPE: PRT
<213> ORGANISM: Artificial Sequence
<220> FEATURE:
<223> OTHER INFORMATION: CD86 IgV v44

<400> SEQUENCE: 124

Ala Pro Leu Lys Ile Gln Ala Tyr Phe Asn Glu Thr Val Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly

```
                85                  90                  95

Met Ile Arg Ile His Gln Met Asn Ser Glu Leu Ser Val Leu Ala
            100                 105                 110


<210> SEQ ID NO 125
<211> LENGTH: 111
<212> TYPE: PRT
<213> ORGANISM: Artificial Sequence
<220> FEATURE:
<223> OTHER INFORMATION: CD86 IgV v45

<400> SEQUENCE: 125

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Thr Pro Thr Gly
                85                  90                  95

Leu Ile Arg Ile His Gln Met Asn Ser Glu Leu Ser Val Leu Ala
            100                 105                 110


<210> SEQ ID NO 126
<211> LENGTH: 111
<212> TYPE: PRT
<213> ORGANISM: Artificial Sequence
<220> FEATURE:
<223> OTHER INFORMATION: CD86 IgV v46

<400> SEQUENCE: 126

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Asn Ser Glu Leu Ser Val Leu Ala
            100                 105                 110


<210> SEQ ID NO 127
<211> LENGTH: 111
<212> TYPE: PRT
<213> ORGANISM: Artificial Sequence
<220> FEATURE:
<223> OTHER INFORMATION: CD86 IgV v47

<400> SEQUENCE: 127

Ala Pro Leu Lys Ile Gln Ala Tyr Phe Asn Glu Thr Ala Asp Leu Pro
1               5                   10                  15
```

```
Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Val Leu His Lys Lys Pro Thr Gly
                85                  90                  95

Met Ile Arg Ile His Gln Met Asn Ser Glu Leu Ser Val Leu Ala
            100                 105                 110


<210> SEQ ID NO 128
<211> LENGTH: 111
<212> TYPE: PRT
<213> ORGANISM: Artificial Sequence
<220> FEATURE:
<223> OTHER INFORMATION: CD86 IgV v48

<400> SEQUENCE: 128

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Lys Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
            100                 105                 110


<210> SEQ ID NO 129
<211> LENGTH: 111
<212> TYPE: PRT
<213> ORGANISM: Artificial Sequence
<220> FEATURE:
<223> OTHER INFORMATION: CD86 IgV v49

<400> SEQUENCE: 129

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Ile Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
```

```
            100                 105                 110


<210> SEQ ID NO 130
<211> LENGTH: 111
<212> TYPE: PRT
<213> ORGANISM: Artificial Sequence
<220> FEATURE:
<223> OTHER INFORMATION: CD86 IgV v50

<400> SEQUENCE: 130

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
            100                 105                 110


<210> SEQ ID NO 131
<211> LENGTH: 224
<212> TYPE: PRT
<213> ORGANISM: Artificial Sequence
<220> FEATURE:
<223> OTHER INFORMATION: CD86 IgC WT v1

<400> SEQUENCE: 131

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190
```

```
Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 132
<211> LENGTH: 224
<212> TYPE: PRT
<213> ORGANISM: Artificial Sequence
<220> FEATURE:
<223> OTHER INFORMATION: CD86 IgC WT v2

<400> SEQUENCE: 132

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Thr Pro Thr Gly
                85                  90                  95

Leu Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220


<210> SEQ ID NO 133
<211> LENGTH: 224
<212> TYPE: PRT
<213> ORGANISM: Artificial Sequence
<220> FEATURE:
<223> OTHER INFORMATION: CD86 IgC WT v3

<400> SEQUENCE: 133

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60
```

Phe Asp Ser Asp Ser Trp Thr Leu Arg Leu His Asn Leu Gln Ile Lys
65 70 75 80

Asp Lys Gly Leu Tyr Gln Cys Ile Val Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 134
<211> LENGTH: 224
<212> TYPE: PRT
<213> ORGANISM: Artificial Sequence
<220> FEATURE:
<223> OTHER INFORMATION: CD86 WT IgC v4

<400> SEQUENCE: 134

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

```
Phe Ser Ile Glu Leu Glu Asp Pro Gln Pro Pro Pro Asp His Ile Pro
    210                 215                 220


<210> SEQ ID NO 135
<211> LENGTH: 355
<212> TYPE: PRT
<213> ORGANISM: Artificial Sequence
<220> FEATURE:
<223> OTHER INFORMATION: CD86 NKP30 Stack v1

<400> SEQUENCE: 135

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Thr Pro Thr Gly
                85                  90                  95

Leu Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Ala Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Val Pro Gln Pro Pro Pro Asp His Ile Pro
    210                 215                 220

Gly Gly Gly Gly Ser Gly Gly Gly Gly Ser Gly Gly Gly Gly Ser Leu
225                 230                 235                 240

Trp Val Ser Gln Pro Pro Glu Ile Arg Thr Leu Glu Gly Ser Ser Ala
                245                 250                 255

Phe Leu Pro Cys Ser Phe Asn Ala Ser Gln Gly Arg Val Ala Ile Gly
            260                 265                 270

Ser Val Thr Trp Phe Arg Asp Glu Val Val Pro Gly Lys Glu Val Arg
        275                 280                 285

Asn Gly Thr Pro Glu Phe Arg Gly Arg Leu Val Pro Leu Ala Pro Ser
    290                 295                 300

Arg Phe Leu His Asp His Gln Ala Glu Leu His Ile Arg Asp Val Arg
305                 310                 315                 320

Gly His Asp Ala Gly Ile Tyr Val Cys Arg Val Glu Val Leu Gly Leu
                325                 330                 335

Gly Val Gly Thr Gly Asn Gly Thr Arg Leu Val Val Glu Lys Glu His
            340                 345                 350
```

```
Pro Gln Leu
        355


<210> SEQ ID NO 136
<211> LENGTH: 355
<212> TYPE: PRT
<213> ORGANISM: Artificial Sequence
<220> FEATURE:
<223> OTHER INFORMATION: CD86 NKP30 Stack v2

<400> SEQUENCE: 136

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Ser Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Gly Gly Gly Gly Ser Gly Gly Gly Gly Ser Gly Gly Gly Gly Ser Leu
225                 230                 235                 240

Trp Val Ser Gln Pro Pro Glu Ile Arg Thr Leu Glu Gly Ser Ser Ala
                245                 250                 255

Phe Leu Pro Cys Ser Phe Asn Ala Ser Gln Gly Arg Val Ala Ile Gly
            260                 265                 270

Ser Val Thr Trp Phe Arg Asp Glu Val Val Pro Gly Lys Glu Val Arg
        275                 280                 285

Asn Gly Thr Pro Glu Phe Arg Gly Arg Leu Val Pro Leu Ala Pro Ser
    290                 295                 300

Arg Phe Leu His Asp His Gln Ala Glu Leu His Ile Arg Asp Val Arg
305                 310                 315                 320

Gly His Asp Ala Gly Ile Tyr Val Cys Arg Val Glu Val Leu Gly Leu
                325                 330                 335

Gly Val Gly Thr Gly Asn Gly Thr Arg Leu Val Val Glu Lys Glu His
            340                 345                 350
```

```
Pro Gln Leu
        355


<210> SEQ ID NO 137
<211> LENGTH: 355
<212> TYPE: PRT
<213> ORGANISM: Artificial Sequence
<220> FEATURE:
<223> OTHER INFORMATION: CD86 NKP30 Stack v3

<400> SEQUENCE: 137

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Lys Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Gly Gly Gly Gly Ser Gly Gly Gly Gly Ser Gly Gly Gly Gly Ser Leu
225                 230                 235                 240

Trp Val Ser Gln Pro Pro Glu Ile Arg Thr Leu Glu Gly Ser Ser Ala
                245                 250                 255

Phe Leu Pro Cys Ser Phe Asn Ala Ser Gln Gly Arg Val Ala Ile Gly
            260                 265                 270

Ser Val Thr Trp Phe Arg Asp Glu Val Val Pro Gly Lys Glu Val Arg
        275                 280                 285

Asn Gly Thr Pro Glu Phe Arg Gly Arg Leu Val Pro Leu Ala Pro Ser
    290                 295                 300

Arg Phe Leu His Asp His Gln Ala Glu Leu His Ile Arg Asp Val Arg
305                 310                 315                 320

Gly His Asp Ala Gly Ile Tyr Val Cys Arg Val Glu Val Leu Gly Leu
                325                 330                 335

Gly Val Gly Thr Gly Asn Gly Thr Arg Leu Val Val Glu Lys Glu His
            340                 345                 350
```

Pro Gln Leu
355

<210> SEQ ID NO 138
<211> LENGTH: 355
<212> TYPE: PRT
<213> ORGANISM: Artificial Sequence
<220> FEATURE:
<223> OTHER INFORMATION: CD86 NKP30 Stack v4

<400> SEQUENCE: 138

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Val Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Val Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

Gly Gly Gly Gly Ser Gly Gly Gly Gly Ser Gly Gly Gly Gly Ser Leu
225 230 235 240

Trp Val Ser Gln Pro Pro Glu Ile Arg Thr Leu Glu Gly Ser Ser Ala
245 250 255

Phe Leu Pro Cys Ser Phe Asn Ala Ser Gln Gly Arg Val Ala Ile Gly
260 265 270

Ser Val Thr Trp Phe Arg Asp Glu Val Val Pro Gly Lys Glu Val Arg
275 280 285

Asn Gly Thr Pro Glu Phe Arg Gly Arg Leu Val Pro Leu Ala Pro Ser
290 295 300

Arg Phe Leu His Asp His Gln Ala Glu Leu His Ile Arg Asp Val Arg
305 310 315 320

Gly His Asp Ala Gly Ile Tyr Val Cys Arg Val Glu Val Leu Gly Leu
325 330 335

Gly Val Gly Thr Gly Asn Gly Thr Arg Leu Val Val Glu Lys Glu His
340 345 350

```
Pro Gln Leu
        355


<210> SEQ ID NO 139
<211> LENGTH: 355
<212> TYPE: PRT
<213> ORGANISM: Artificial Sequence
<220> FEATURE:
<223> OTHER INFORMATION: CD86 NKP30 Stack v5

<400> SEQUENCE: 139

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Arg Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Gly Gly Gly Gly Ser Gly Gly Gly Gly Ser Gly Gly Gly Gly Ser Leu
225                 230                 235                 240

Trp Val Ser Gln Pro Pro Glu Ile Arg Thr Leu Glu Gly Ser Ser Ala
                245                 250                 255

Phe Leu Pro Cys Ser Phe Asn Ala Ser Gln Gly Arg Val Ala Ile Gly
            260                 265                 270

Ser Val Thr Trp Phe Arg Asp Glu Val Val Pro Gly Lys Glu Val Arg
        275                 280                 285

Asn Gly Thr Pro Glu Phe Arg Gly Arg Leu Val Pro Leu Ala Pro Ser
    290                 295                 300

Arg Phe Leu His Asp His Gln Ala Glu Leu His Ile Arg Asp Val Arg
305                 310                 315                 320

Gly His Asp Ala Gly Ile Tyr Val Cys Arg Val Glu Val Leu Gly Leu
                325                 330                 335

Gly Val Gly Thr Gly Asn Gly Thr Arg Leu Val Val Glu Lys Glu His
            340                 345                 350
```

Pro Gln Leu
355

<210> SEQ ID NO 140
<211> LENGTH: 239
<212> TYPE: PRT
<213> ORGANISM: Artificial Sequence
<220> FEATURE:
<223> OTHER INFORMATION: CD86 NKP30 Stack v6

<400> SEQUENCE: 140

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Leu His Lys Lys Pro Thr Gly
85 90 95

Met Ile Arg Ile His Gln Met Ser Ser Glu Leu Ser Gly Gly Gly Gly
100 105 110

Ser Gly Gly Gly Gly Ser Gly Gly Gly Gly Ser Leu Trp Val Ser Gln
115 120 125

Pro Pro Glu Ile Arg Thr Leu Glu Gly Ser Ser Ala Phe Leu Pro Cys
130 135 140

Ser Phe Asn Ala Ser Gln Gly Arg Val Ala Ile Gly Ser Val Thr Trp
145 150 155 160

Phe Arg Asp Glu Val Val Pro Gly Lys Glu Val Arg Asn Gly Thr Pro
165 170 175

Glu Phe Arg Gly Arg Leu Val Pro Leu Ala Pro Ser Arg Phe Leu His
180 185 190

Asp His Gln Ala Glu Leu His Ile Arg Asp Val Arg Gly His Asp Ala
195 200 205

Gly Ile Tyr Val Cys Arg Val Glu Val Leu Gly Leu Gly Val Gly Thr
210 215 220

Gly Asn Gly Thr Arg Leu Val Val Glu Lys Glu His Pro Gln Leu
225 230 235

<210> SEQ ID NO 141
<211> LENGTH: 111
<212> TYPE: PRT
<213> ORGANISM: Artificial Sequence
<220> FEATURE:
<223> OTHER INFORMATION: CD86 IgV v51

<400> SEQUENCE: 141

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser

```
    50                  55                  60

Phe Asp Ser Asp Ser Trp Ala Leu Arg Leu His Asn Leu Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala
            100                 105                 110


<210> SEQ ID NO 142
<211> LENGTH: 111
<212> TYPE: PRT
<213> ORGANISM: Artificial Sequence
<220> FEATURE:
<223> OTHER INFORMATION: CD86 IgV v52

<400> SEQUENCE: 142

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Gly Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala
            100                 105                 110


<210> SEQ ID NO 143
<211> LENGTH: 111
<212> TYPE: PRT
<213> ORGANISM: Artificial Sequence
<220> FEATURE:
<223> OTHER INFORMATION: CD86 IgV v53

<400> SEQUENCE: 143

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
            100                 105                 110


<210> SEQ ID NO 144
<211> LENGTH: 111
<212> TYPE: PRT
<213> ORGANISM: Artificial Sequence
<220> FEATURE:
```

<223> OTHER INFORMATION: CD86 IgV v54

<400> SEQUENCE: 144

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Lys Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Asn Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala
100 105 110

<210> SEQ ID NO 145
<211> LENGTH: 111
<212> TYPE: PRT
<213> ORGANISM: Artificial Sequence
<220> FEATURE:
<223> OTHER INFORMATION: CD86 IgV v55

<400> SEQUENCE: 145

Ala Pro Leu Lys Ile Gln Ala Tyr Phe Asn Glu Thr Val Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala
100 105 110

<210> SEQ ID NO 146
<211> LENGTH: 111
<212> TYPE: PRT
<213> ORGANISM: Artificial Sequence
<220> FEATURE:
<223> OTHER INFORMATION: CD86 IgV v56

<400> SEQUENCE: 146

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys 65 70 75 80

Asp Lys Gly Leu Tyr Arg Cys Ile Ile Leu His Lys Thr Pro Thr Gly
85 90 95

Met Ile Arg Ile His Gln Met Asn Ser Glu Leu Ser Val Leu Ala
100 105 110

<210> SEQ ID NO 147
<211> LENGTH: 111
<212> TYPE: PRT
<213> ORGANISM: Artificial Sequence
<220> FEATURE:
<223> OTHER INFORMATION: CD86 IgV v57

<400> SEQUENCE: 147

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Ile Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Tyr His Lys Lys Pro Thr Gly
85 90 95

Met Ile Arg Ile His Gln Met Asn Ser Glu Leu Ser Val Leu Ala
100 105 110

<210> SEQ ID NO 148
<211> LENGTH: 111
<212> TYPE: PRT
<213> ORGANISM: Artificial Sequence
<220> FEATURE:
<223> OTHER INFORMATION: CD86 IgV v58

<400> SEQUENCE: 148

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asp Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Arg
65 70 75 80

Asp Lys Gly Leu Tyr Arg Cys Phe Ile Leu His Lys Thr Pro Thr Gly
85 90 95

Met Ile Arg Ile His Gln Met Asn Ser Glu Leu Ser Val Leu Ala
100 105 110

<210> SEQ ID NO 149
<211> LENGTH: 111
<212> TYPE: PRT
<213> ORGANISM: Artificial Sequence
<220> FEATURE:
<223> OTHER INFORMATION: CD86 IgV v59

<400> SEQUENCE: 149

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Thr Pro Thr Gly
                85                  90                  95

Leu Ile Arg Ile His Gln Met Asn Ser Glu Leu Ser Val Leu Ala
            100                 105                 110


<210> SEQ ID NO 150
<211> LENGTH: 111
<212> TYPE: PRT
<213> ORGANISM: Artificial Sequence
<220> FEATURE:
<223> OTHER INFORMATION: CD86 IgV v60

<400> SEQUENCE: 150

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Ser Ser Glu Leu Ser Val Leu Ala
            100                 105                 110


<210> SEQ ID NO 151
<211> LENGTH: 111
<212> TYPE: PRT
<213> ORGANISM: Artificial Sequence
<220> FEATURE:
<223> OTHER INFORMATION: CD86 IgV v61

<400> SEQUENCE: 151

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Met Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
```

```
                85                  90                  95

Met Ile Arg Ile His Gln Met Asn Ser Glu Leu Ser Val Leu Ala
            100                 105                 110


<210> SEQ ID NO 152
<211> LENGTH: 111
<212> TYPE: PRT
<213> ORGANISM: Artificial Sequence
<220> FEATURE:
<223> OTHER INFORMATION: CD86 IgV v62

<400> SEQUENCE: 152

Ala Pro Leu Lys Ile Gln Ala Tyr Phe Asn Glu Thr Ala Asp Leu Pro
1               5                   10                  15

Cys Lys Phe Ala Asn Ser Gln Asn Leu Ser Leu Ser Glu Leu Val Val
            20                  25                  30

Ile Trp Gln Asp Gln Glu Asn Ser Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
            100                 105                 110


<210> SEQ ID NO 153
<211> LENGTH: 111
<212> TYPE: PRT
<213> ORGANISM: Artificial Sequence
<220> FEATURE:
<223> OTHER INFORMATION: CD86 IgV v63

<400> SEQUENCE: 153

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Lys Cys Ile Ile Leu His Lys Lys Pro Thr Gly
                85                  90                  95

Met Ile Arg Ile His Gln Met Asn Ser Glu Leu Ser Val Leu Ala
            100                 105                 110


<210> SEQ ID NO 154
<211> LENGTH: 111
<212> TYPE: PRT
<213> ORGANISM: Artificial Sequence
<220> FEATURE:
<223> OTHER INFORMATION: CD86 IgV v64

<400> SEQUENCE: 154

Ala Pro Leu Lys Ile Gln Ala Tyr Phe Asn Glu Thr Ala Asp Leu Pro
1               5                   10                  15
```

```
Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Pro Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala
            100                 105                 110


<210> SEQ ID NO 155
<211> LENGTH: 111
<212> TYPE: PRT
<213> ORGANISM: Artificial Sequence
<220> FEATURE:
<223> OTHER INFORMATION: CD86 IgV v65

<400> SEQUENCE: 155

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Gly Glu Leu Val Val
            20                  25                  30

Ile Trp Gln Asp Gln Glu Asn Leu Val Leu Asn Glu Val Tyr Leu Gly
        35                  40                  45

Lys Glu Lys Leu Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His His Met Asn Ser Glu Leu Ser Val Leu Ala
            100                 105                 110


<210> SEQ ID NO 156
<211> LENGTH: 111
<212> TYPE: PRT
<213> ORGANISM: Artificial Sequence
<220> FEATURE:
<223> OTHER INFORMATION: CD86 IgV v66

<400> SEQUENCE: 156

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Ile Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
```

100 105 110

<210> SEQ ID NO 157
<211> LENGTH: 111
<212> TYPE: PRT
<213> ORGANISM: Artificial Sequence
<220> FEATURE:
<223> OTHER INFORMATION: CD86 IgV v67

<400> SEQUENCE: 157

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Ile Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala
100 105 110

<210> SEQ ID NO 158
<211> LENGTH: 111
<212> TYPE: PRT
<213> ORGANISM: Artificial Sequence
<220> FEATURE:
<223> OTHER INFORMATION: CD86 IgV v68

<400> SEQUENCE: 158

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Ile Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Tyr His Lys Lys Pro Thr Gly
85 90 95

Met Ile Arg Ile His Gln Met Asn Ser Glu Leu Ser Val Leu Ala
100 105 110

<210> SEQ ID NO 159
<211> LENGTH: 111
<212> TYPE: PRT
<213> ORGANISM: Artificial Sequence
<220> FEATURE:
<223> OTHER INFORMATION: CD86 IgV v69

<400> SEQUENCE: 159

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

```
Phe Trp Gln Asp Gln Glu Asn Leu Val Leu Asn Glu Ile Tyr Leu Gly
        35                  40                  45

Lys Glu Lys Phe Asp Ser Val His Ser Lys Tyr Met Gly Arg Thr Ser
    50                  55                  60

Phe Asp Ser Asn Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
            100                 105                 110


<210> SEQ ID NO 160
<211> LENGTH: 111
<212> TYPE: PRT
<213> ORGANISM: Artificial Sequence
<220> FEATURE:
<223> OTHER INFORMATION: CD86 IgV v70

<400> SEQUENCE: 160

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Val Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala
            100                 105                 110


<210> SEQ ID NO 161
<211> LENGTH: 111
<212> TYPE: PRT
<213> ORGANISM: Artificial Sequence
<220> FEATURE:
<223> OTHER INFORMATION: CD86 IgV v71

<400> SEQUENCE: 161

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala
            100                 105                 110
```

<210> SEQ ID NO 162
<211> LENGTH: 111
<212> TYPE: PRT
<213> ORGANISM: Artificial Sequence
<220> FEATURE:
<223> OTHER INFORMATION: CD86 IgV v72

<400> SEQUENCE: 162

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Tyr His Lys Lys Pro Thr Gly
85 90 95

Met Ile Arg Ile His Gln Met Asn Ser Glu Leu Ser Val Leu Ala
100 105 110

<210> SEQ ID NO 163
<211> LENGTH: 111
<212> TYPE: PRT
<213> ORGANISM: Artificial Sequence
<220> FEATURE:
<223> OTHER INFORMATION: CD86 IgV v73

<400> SEQUENCE: 163

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Val Leu His Lys Lys Pro Thr Gly
85 90 95

Met Ile Arg Ile His Gln Met Asn Ser Glu Leu Ser Val Leu Ala
100 105 110

<210> SEQ ID NO 164
<211> LENGTH: 111
<212> TYPE: PRT
<213> ORGANISM: Artificial Sequence
<220> FEATURE:
<223> OTHER INFORMATION: CD86 IgV v74

<400> SEQUENCE: 164

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Glu
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala
            100                 105                 110

<210> SEQ ID NO 165
<211> LENGTH: 111
<212> TYPE: PRT
<213> ORGANISM: Artificial Sequence
<220> FEATURE:
<223> OTHER INFORMATION: CD86 IgV v75

<400> SEQUENCE: 165

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Met
65                  70                  75                  80

Asp Lys Gly Leu Tyr Gln Cys Thr Ile His His Lys Lys Pro Thr Gly
                85                  90                  95

Met Ile Arg Ile His Gln Met Asn Ser Glu Leu Ser Val Leu Ala
            100                 105                 110

<210> SEQ ID NO 166
<211> LENGTH: 111
<212> TYPE: PRT
<213> ORGANISM: Artificial Sequence
<220> FEATURE:
<223> OTHER INFORMATION: CD86 IgV v76

<400> SEQUENCE: 166

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Ile Lys Pro Thr Gly
                85                  90                  95

Met Ile Arg Ile His Gln Met Asn Ser Glu Leu Ser Val Leu Ala
            100                 105                 110

<210> SEQ ID NO 167
<211> LENGTH: 111
<212> TYPE: PRT

<213> ORGANISM: Artificial Sequence
<220> FEATURE:
<223> OTHER INFORMATION: CD86 IgV v77

<400> SEQUENCE: 167

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Lys Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
            100                 105                 110
```

<210> SEQ ID NO 168
<211> LENGTH: 111
<212> TYPE: PRT
<213> ORGANISM: Artificial Sequence
<220> FEATURE:
<223> OTHER INFORMATION: CD86 IgV v78

<400> SEQUENCE: 168

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Ile Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala
            100                 105                 110
```

<210> SEQ ID NO 169
<211> LENGTH: 111
<212> TYPE: PRT
<213> ORGANISM: Artificial Sequence
<220> FEATURE:
<223> OTHER INFORMATION: CD86 IgV v79

<400> SEQUENCE: 169

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Ile Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60
```

Phe Asp Ser Asp Ser Trp Thr Leu Arg Leu His Asn Leu Gln Ile Lys
65 70 75 80

Asp Lys Gly Leu Tyr Arg Cys Ile Ile Leu His Lys Thr Pro Thr Gly
85 90 95

Met Ile Arg Ile His Gln Met Asn Ser Glu Leu Ser Val Leu Ala
100 105 110

<210> SEQ ID NO 170
<211> LENGTH: 111
<212> TYPE: PRT
<213> ORGANISM: Artificial Sequence
<220> FEATURE:
<223> OTHER INFORMATION: CD86 IgV v80

<400> SEQUENCE: 170

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala
100 105 110

<210> SEQ ID NO 171
<211> LENGTH: 111
<212> TYPE: PRT
<213> ORGANISM: Artificial Sequence
<220> FEATURE:
<223> OTHER INFORMATION: CD86 IgV v81

<400> SEQUENCE: 171

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala
100 105 110

<210> SEQ ID NO 172
<211> LENGTH: 111
<212> TYPE: PRT
<213> ORGANISM: Artificial Sequence
<220> FEATURE:
<223> OTHER INFORMATION: CD86 IgV v82

<400> SEQUENCE: 172

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala
100 105 110

<210> SEQ ID NO 173
<211> LENGTH: 111
<212> TYPE: PRT
<213> ORGANISM: Artificial Sequence
<220> FEATURE:
<223> OTHER INFORMATION: CD86 IgV v83

<400> SEQUENCE: 173

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala
100 105 110

<210> SEQ ID NO 174
<211> LENGTH: 111
<212> TYPE: PRT
<213> ORGANISM: Artificial Sequence
<220> FEATURE:
<223> OTHER INFORMATION: CD86 IgV v84

<400> SEQUENCE: 174

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Tyr His Lys Lys Pro Thr Gly
85 90 95

Met Ile Arg Ile His Gln Met Asn Ser Glu Leu Ser Val Leu Ala
100 105 110

<210> SEQ ID NO 175
<211> LENGTH: 111
<212> TYPE: PRT
<213> ORGANISM: Artificial Sequence
<220> FEATURE:
<223> OTHER INFORMATION: CD86 IgV v85

<400> SEQUENCE: 175

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Thr Gly Leu Tyr Gln Cys Ile Ile Leu His Lys Lys Pro Thr Gly
85 90 95

Met Ile Arg Ile His Gln Met Asn Ser Glu Leu Ser Val Leu Ala
100 105 110

<210> SEQ ID NO 176
<211> LENGTH: 111
<212> TYPE: PRT
<213> ORGANISM: Artificial Sequence
<220> FEATURE:
<223> OTHER INFORMATION: CD86 IgV v86

<400> SEQUENCE: 176

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Leu His Lys Thr Pro Thr Gly
85 90 95

Met Ile Arg Ile His Gln Met Asn Ser Glu Leu Ser Val Leu Ala
100 105 110

<210> SEQ ID NO 177
<211> LENGTH: 111
<212> TYPE: PRT
<213> ORGANISM: Artificial Sequence
<220> FEATURE:
<223> OTHER INFORMATION: CD86 IgV v87

<400> SEQUENCE: 177

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Gly Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Tyr His Lys Lys Pro Thr Gly
                85                  90                  95

Met Ile Arg Ile His Gln Met Asn Ser Glu Leu Ser Val Leu Ala
            100                 105                 110


<210> SEQ ID NO 178
<211> LENGTH: 99
<212> TYPE: PRT
<213> ORGANISM: Artificial Sequence
<220> FEATURE:
<223> OTHER INFORMATION: CD86 IgV WT v1

<400> SEQUENCE: 178

Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Ala Leu Arg
    50                  55                  60

Leu His Asn Leu Gln Ile Lys Asp Lys Gly Leu Tyr Gln Cys Ile Ile
65                  70                  75                  80

Tyr His Lys Lys Pro Thr Gly Met Ile Arg Ile His Gln Met Asn Ser
                85                  90                  95

Glu Leu Ser


<210> SEQ ID NO 179
<211> LENGTH: 99
<212> TYPE: PRT
<213> ORGANISM: Artificial Sequence
<220> FEATURE:
<223> OTHER INFORMATION: CD86 IgV WT v2

<400> SEQUENCE: 179

Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Gly Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

His His Lys Lys Pro Thr Gly Met Ile Arg Ile His Gln Met Asn Ser
                85                  90                  95
```

Glu Leu Ser

<210> SEQ ID NO 180
<211> LENGTH: 99
<212> TYPE: PRT
<213> ORGANISM: Artificial Sequence
<220> FEATURE:
<223> OTHER INFORMATION: CD86 IgV WT v3

<400> SEQUENCE: 180

```
Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser
```

<210> SEQ ID NO 181
<211> LENGTH: 99
<212> TYPE: PRT
<213> ORGANISM: Artificial Sequence
<220> FEATURE:
<223> OTHER INFORMATION: CD86 IgV WT v4

<400> SEQUENCE: 181

```
Asn Glu Thr Ala Asp Leu Pro Cys Gln Phe Ala Asn Ser Gln Asn Gln
1               5                   10                  15

Ser Leu Ser Glu Leu Val Val Phe Trp Gln Asp Gln Glu Asn Leu Val
            20                  25                  30

Leu Lys Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Asn Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser
```

<210> SEQ ID NO 182
<211> LENGTH: 99
<212> TYPE: PRT
<213> ORGANISM: Artificial Sequence
<220> FEATURE:
<223> OTHER INFORMATION: CD86 IgV WT v5

<400> SEQUENCE: 182

```
Asn Glu Thr Val Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
```

```
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser


<210> SEQ ID NO 183
<211> LENGTH: 99
<212> TYPE: PRT
<213> ORGANISM: Artificial Sequence
<220> FEATURE:
<223> OTHER INFORMATION: CD86 IgV WT v6

<400> SEQUENCE: 183

Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Arg Cys Ile Ile
65                  70                  75                  80

Leu His Lys Thr Pro Thr Gly Met Ile Arg Ile His Gln Met Asn Ser
                85                  90                  95

Glu Leu Ser


<210> SEQ ID NO 184
<211> LENGTH: 99
<212> TYPE: PRT
<213> ORGANISM: Artificial Sequence
<220> FEATURE:
<223> OTHER INFORMATION: CD86 IgV WT v7

<400> SEQUENCE: 184

Asn Glu Thr Ala Asp Leu Pro Cys Gln Phe Ala Asn Ser Gln Asn Leu
1               5                   10                  15

Ser Leu Ser Glu Leu Val Val Ile Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Tyr His Lys Lys Pro Thr Gly Met Ile Arg Ile His Gln Met Asn Ser
                85                  90                  95

Glu Leu Ser


<210> SEQ ID NO 185
<211> LENGTH: 99
<212> TYPE: PRT
<213> ORGANISM: Artificial Sequence
<220> FEATURE:
```

<223> OTHER INFORMATION: CD86 IgV WT v8

<400> SEQUENCE: 185

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asp Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Arg Asp Lys Gly Leu Tyr Arg Cys Phe Ile
65 70 75 80

Leu His Lys Thr Pro Thr Gly Met Ile Arg Ile His Gln Met Asn Ser
85 90 95

Glu Leu Ser

<210> SEQ ID NO 186
<211> LENGTH: 99
<212> TYPE: PRT
<213> ORGANISM: Artificial Sequence
<220> FEATURE:
<223> OTHER INFORMATION: CD86 IgV WT v9

<400> SEQUENCE: 186

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Thr Pro Thr Gly Leu Ile Arg Ile His Gln Met Asn Ser
85 90 95

Glu Leu Ser

<210> SEQ ID NO 187
<211> LENGTH: 99
<212> TYPE: PRT
<213> ORGANISM: Artificial Sequence
<220> FEATURE:
<223> OTHER INFORMATION: CD86 IgV WT v10

<400> SEQUENCE: 187

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Arg Cys Ile Ile
65 70 75 80

Leu His Lys Lys Pro Thr Gly Met Ile Arg Ile His Gln Met Ser Ser
85 90 95

Glu Leu Ser

<210> SEQ ID NO 188
<211> LENGTH: 99
<212> TYPE: PRT
<213> ORGANISM: Artificial Sequence
<220> FEATURE:
<223> OTHER INFORMATION: CD86 IgV WT v11

<400> SEQUENCE: 188

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Met Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 189
<211> LENGTH: 99
<212> TYPE: PRT
<213> ORGANISM: Artificial Sequence
<220> FEATURE:
<223> OTHER INFORMATION: CD86 IgV WT v12

<400> SEQUENCE: 189

Asn Glu Thr Ala Asp Leu Pro Cys Lys Phe Ala Asn Ser Gln Asn Leu
1 5 10 15

Ser Leu Ser Glu Leu Val Val Ile Trp Gln Asp Gln Glu Asn Ser Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 190
<211> LENGTH: 99
<212> TYPE: PRT
<213> ORGANISM: Artificial Sequence
<220> FEATURE:
<223> OTHER INFORMATION: CD86 IgV WT v13

<400> SEQUENCE: 190

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val

```
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Lys Cys Ile Ile
65                  70                  75                  80

Leu His Lys Lys Pro Thr Gly Met Ile Arg Ile His Gln Met Asn Ser
                85                  90                  95

Glu Leu Ser


<210> SEQ ID NO 191
<211> LENGTH: 99
<212> TYPE: PRT
<213> ORGANISM: Artificial Sequence
<220> FEATURE:
<223> OTHER INFORMATION: CD86 IgV WT v14

<400> SEQUENCE: 191

Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Pro Gln Ile Lys Asp Lys Gly Leu Tyr Gln Cys Ile Ile
65                  70                  75                  80

Tyr His Lys Lys Pro Thr Gly Met Ile Arg Ile His Gln Met Asn Ser
                85                  90                  95

Glu Leu Ser


<210> SEQ ID NO 192
<211> LENGTH: 99
<212> TYPE: PRT
<213> ORGANISM: Artificial Sequence
<220> FEATURE:
<223> OTHER INFORMATION: CD86 IgV WT v15

<400> SEQUENCE: 192

Asn Glu Thr Ala Asp Leu Pro Cys Gln Phe Ala Asn Ser Gln Asn Leu
1               5                   10                  15

Ser Leu Gly Glu Leu Val Val Ile Trp Gln Asp Gln Glu Asn Leu Val
            20                  25                  30

Leu Asn Glu Val Tyr Leu Gly Lys Glu Lys Leu Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His His Met Asn Ser
                85                  90                  95

Glu Leu Ser


<210> SEQ ID NO 193
<211> LENGTH: 99
```

<212> TYPE: PRT
<213> ORGANISM: Artificial Sequence
<220> FEATURE:
<223> OTHER INFORMATION: CD86 IgV WT v16

<400> SEQUENCE: 193

```
Asn Glu Thr Ala Asp Leu Pro Cys Gln Phe Ala Asn Ser Gln Asn Leu
1               5                   10                  15

Ser Leu Ser Glu Leu Val Val Ile Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser
```

<210> SEQ ID NO 194
<211> LENGTH: 99
<212> TYPE: PRT
<213> ORGANISM: Artificial Sequence
<220> FEATURE:
<223> OTHER INFORMATION: CD86 IgV WT v17

<400> SEQUENCE: 194

```
Asn Glu Thr Ala Asp Leu Pro Cys Gln Phe Ala Asn Ser Gln Asn Leu
1               5                   10                  15

Ser Leu Ser Glu Leu Val Val Ile Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser
```

<210> SEQ ID NO 195
<211> LENGTH: 99
<212> TYPE: PRT
<213> ORGANISM: Artificial Sequence
<220> FEATURE:
<223> OTHER INFORMATION: CD86 IgV WT v18

<400> SEQUENCE: 195

```
Asn Glu Thr Ala Asp Leu Pro Cys Gln Phe Ala Asn Ser Gln Asn Leu
1               5                   10                  15

Ser Leu Ser Glu Leu Val Val Ile Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60
```

Leu His Asn Leu Gln Ile Lys Asp Lys Gly Leu Tyr Arg Cys Ile Ile
65 70 75 80

Tyr His Lys Lys Pro Thr Gly Met Ile Arg Ile His Gln Met Asn Ser
85 90 95

Glu Leu Ser

<210> SEQ ID NO 196
<211> LENGTH: 99
<212> TYPE: PRT
<213> ORGANISM: Artificial Sequence
<220> FEATURE:
<223> OTHER INFORMATION: CD86 IgV WT v19

<400> SEQUENCE: 196

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Ile Tyr Leu Gly Lys Glu Lys Phe Asp Ser Val His Ser
35 40 45

Lys Tyr Met Gly Arg Thr Ser Phe Asp Ser Asn Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 197
<211> LENGTH: 99
<212> TYPE: PRT
<213> ORGANISM: Artificial Sequence
<220> FEATURE:
<223> OTHER INFORMATION: CD86 IgV WT v20

<400> SEQUENCE: 197

Asn Glu Thr Ala Asp Leu Pro Cys Gln Phe Ala Asn Ser Gln Asn Gln
1 5 10 15

Ser Leu Ser Glu Leu Val Val Phe Trp Gln Asp Gln Val Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

His His Lys Lys Pro Thr Gly Met Ile Arg Ile His Gln Met Asn Ser
85 90 95

Glu Leu Ser

<210> SEQ ID NO 198
<211> LENGTH: 99
<212> TYPE: PRT
<213> ORGANISM: Artificial Sequence
<220> FEATURE:
<223> OTHER INFORMATION: CD86 IgV WT v21

<400> SEQUENCE: 198

Asn Glu Thr Ala Asp Leu Pro Cys Gln Phe Ala Asn Ser Gln Asn Gln 1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Tyr His Lys Lys Pro Thr Gly Met Ile Arg Ile His Gln Met Asn Ser
85 90 95

Glu Leu Ser

<210> SEQ ID NO 199
<211> LENGTH: 99
<212> TYPE: PRT
<213> ORGANISM: Artificial Sequence
<220> FEATURE:
<223> OTHER INFORMATION: CD86 IgV WT v22

<400> SEQUENCE: 199

Asn Glu Thr Ala Asp Leu Pro Cys Gln Phe Ala Asn Ser Gln Asn Gln
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Tyr His Lys Lys Pro Thr Gly Met Ile Arg Ile His Gln Met Asn Ser
85 90 95

Glu Leu Ser

<210> SEQ ID NO 200
<211> LENGTH: 99
<212> TYPE: PRT
<213> ORGANISM: Artificial Sequence
<220> FEATURE:
<223> OTHER INFORMATION: CD86 IgV WT v23

<400> SEQUENCE: 200

Asn Glu Thr Ala Asp Leu Pro Cys Gln Phe Ala Asn Ser Gln Asn Gln
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Val
65 70 75 80

Leu His Lys Lys Pro Thr Gly Met Ile Arg Ile His Gln Met Asn Ser
85 90 95

Glu Leu Ser

<210> SEQ ID NO 201
<211> LENGTH: 99
<212> TYPE: PRT
<213> ORGANISM: Artificial Sequence
<220> FEATURE:
<223> OTHER INFORMATION: CD86 IgV WT v24

<400> SEQUENCE: 201

```
Asn Glu Thr Ala Asp Leu Pro Cys Gln Phe Ala Asn Ser Gln Asn Gln
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Glu Asp Lys Gly Leu Tyr Gln Cys Ile Ile
65                  70                  75                  80

Tyr His Lys Lys Pro Thr Gly Met Ile Arg Ile His Gln Met Asn Ser
                85                  90                  95

Glu Leu Ser
```

<210> SEQ ID NO 202
<211> LENGTH: 99
<212> TYPE: PRT
<213> ORGANISM: Artificial Sequence
<220> FEATURE:
<223> OTHER INFORMATION: CD86 IgV WT v25

<400> SEQUENCE: 202

```
Asn Glu Thr Ala Asp Leu Pro Cys Gln Phe Ala Asn Ser Gln Asn Gln
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Met Asp Lys Gly Leu Tyr Gln Cys Thr Ile
65                  70                  75                  80

His His Lys Lys Pro Thr Gly Met Ile Arg Ile His Gln Met Asn Ser
                85                  90                  95

Glu Leu Ser
```

<210> SEQ ID NO 203
<211> LENGTH: 99
<212> TYPE: PRT
<213> ORGANISM: Artificial Sequence
<220> FEATURE:
<223> OTHER INFORMATION: CD86 IgV WT v26

<400> SEQUENCE: 203

```
Asn Glu Thr Ala Asp Leu Pro Cys Gln Phe Ala Asn Ser Gln Asn Gln
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45
```

```
Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

His His Ile Lys Pro Thr Gly Met Ile Arg Ile His Gln Met Asn Ser
                85                  90                  95

Glu Leu Ser


<210> SEQ ID NO 204
<211> LENGTH: 99
<212> TYPE: PRT
<213> ORGANISM: Artificial Sequence
<220> FEATURE:
<223> OTHER INFORMATION: CD86 IgV WT v27

<400> SEQUENCE: 204

Asn Glu Thr Ala Asp Leu Pro Cys Gln Phe Ala Asn Ser Gln Asn Gln
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Lys Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser


<210> SEQ ID NO 205
<211> LENGTH: 99
<212> TYPE: PRT
<213> ORGANISM: Artificial Sequence
<220> FEATURE:
<223> OTHER INFORMATION: CD86 IgV WT v28

<400> SEQUENCE: 205

Asn Glu Thr Ala Asp Leu Pro Cys Gln Phe Ala Asn Ser Gln Asn Leu
1               5                   10                  15

Ser Leu Ser Glu Leu Val Val Ile Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser


<210> SEQ ID NO 206
<211> LENGTH: 99
<212> TYPE: PRT
<213> ORGANISM: Artificial Sequence
<220> FEATURE:
<223> OTHER INFORMATION: CD86 IgV WT v29
```

<400> SEQUENCE: 206

Asn Glu Thr Ala Asp Leu Pro Cys Gln Phe Ala Asn Ser Gln Asn Leu
1 5 10 15

Ser Leu Ser Glu Leu Val Val Ile Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Arg Cys Ile Ile
65 70 75 80

Leu His Lys Thr Pro Thr Gly Met Ile Arg Ile His Gln Met Asn Ser
85 90 95

Glu Leu Ser

<210> SEQ ID NO 207
<211> LENGTH: 99
<212> TYPE: PRT
<213> ORGANISM: Artificial Sequence
<220> FEATURE:
<223> OTHER INFORMATION: CD86 IgV WT v30

<400> SEQUENCE: 207

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 208
<211> LENGTH: 99
<212> TYPE: PRT
<213> ORGANISM: Artificial Sequence
<220> FEATURE:
<223> OTHER INFORMATION: CD86 IgV WT v31

<400> SEQUENCE: 208

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 209
<211> LENGTH: 99
<212> TYPE: PRT
<213> ORGANISM: Artificial Sequence
<220> FEATURE:
<223> OTHER INFORMATION: CD86 IgV WT v32

<400> SEQUENCE: 209

```
Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser
```

<210> SEQ ID NO 210
<211> LENGTH: 99
<212> TYPE: PRT
<213> ORGANISM: Artificial Sequence
<220> FEATURE:
<223> OTHER INFORMATION: CD86 IgV WT v33

<400> SEQUENCE: 210

```
Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Ile
65                  70                  75                  80

Leu His Lys Lys Pro Thr Gly Met Ile Arg Ile His Gln Met Asn Ser
                85                  90                  95

Glu Leu Ser
```

<210> SEQ ID NO 211
<211> LENGTH: 99
<212> TYPE: PRT
<213> ORGANISM: Artificial Sequence
<220> FEATURE:
<223> OTHER INFORMATION: CD86 IgV WT v34

<400> SEQUENCE: 211

```
Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30
```

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Tyr His Lys Lys Pro Thr Gly Met Ile Arg Ile His Gln Met Asn Ser
85 90 95

Glu Leu Ser

<210> SEQ ID NO 212
<211> LENGTH: 99
<212> TYPE: PRT
<213> ORGANISM: Artificial Sequence
<220> FEATURE:
<223> OTHER INFORMATION: CD86 IgV WT v35

<400> SEQUENCE: 212

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Thr Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 213
<211> LENGTH: 99
<212> TYPE: PRT
<213> ORGANISM: Artificial Sequence
<220> FEATURE:
<223> OTHER INFORMATION: CD86 IgV WT v36

<400> SEQUENCE: 213

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Arg Cys Ile Ile
65 70 75 80

Leu His Lys Thr Pro Thr Gly Met Ile Arg Ile His Gln Met Asn Ser
85 90 95

Glu Leu Ser

<210> SEQ ID NO 214
<211> LENGTH: 99
<212> TYPE: PRT
<213> ORGANISM: Artificial Sequence
<220> FEATURE:
<223> OTHER INFORMATION: CD86 IgV WT v37

<400> SEQUENCE: 214

Asn Glu Thr Ala Asp Leu Pro Cys Gln Phe Ala Asn Ser Gln Asn Gln
1 5 10 15

Ser Leu Gly Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Tyr His Lys Lys Pro Thr Gly Met Ile Arg Ile His Gln Met Asn Ser
85 90 95

Glu Leu Ser

<210> SEQ ID NO 215
<211> LENGTH: 99
<212> TYPE: PRT
<213> ORGANISM: Artificial Sequence
<220> FEATURE:
<223> OTHER INFORMATION: CD86 IgV WT v81

<400> SEQUENCE: 215

Asn Glu Thr Val Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 216
<211> LENGTH: 99
<212> TYPE: PRT
<213> ORGANISM: Artificial Sequence
<220> FEATURE:
<223> OTHER INFORMATION: CD86 IgV WT v82

<400> SEQUENCE: 216

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

```
Leu His Lys Thr Pro Thr Gly Leu Ile Arg Ile His Gln Met Asn Ser
                85                  90                  95

Glu Leu Ser


<210> SEQ ID NO 217
<211> LENGTH: 99
<212> TYPE: PRT
<213> ORGANISM: Artificial Sequence
<220> FEATURE:
<223> OTHER INFORMATION: CD86 IgV WT v83

<400> SEQUENCE: 217

Asn Glu Thr Ala Asp Leu Pro Cys Gln Phe Ala Asn Ser Gln Asn Leu
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Arg Cys Ile Ile
65                  70                  75                  80

Leu His Lys Lys Pro Thr Gly Met Ile Arg Ile His Gln Met Asn Ser
                85                  90                  95

Glu Leu Ser


<210> SEQ ID NO 218
<211> LENGTH: 99
<212> TYPE: PRT
<213> ORGANISM: Artificial Sequence
<220> FEATURE:
<223> OTHER INFORMATION: CD86 IgV WT v84

<400> SEQUENCE: 218

Asn Glu Thr Ala Asp Leu Pro Cys Gln Phe Ala Asn Ser Gln Asn Gln
1               5                   10                  15

Ser Leu Ser Glu Leu Val Val Phe Trp Gln Asp Gln Glu Asn Leu Val
            20                  25                  30

Leu Asn Glu Val Tyr Leu Gly Lys Glu Lys Phe Asp Ser Val His Ser
        35                  40                  45

Lys Tyr Met Gly Arg Thr Ser Phe Asp Ser Asp Ser Trp Thr Leu Arg
    50                  55                  60

Leu His Asn Leu Gln Ile Lys Asp Lys Gly Leu Tyr Gln Cys Ile Val
65                  70                  75                  80

Leu His Lys Lys Pro Thr Gly Met Ile Arg Ile His Gln Met Asn Ser
                85                  90                  95

Glu Leu Ser


<210> SEQ ID NO 219
<211> LENGTH: 99
<212> TYPE: PRT
<213> ORGANISM: Artificial Sequence
<220> FEATURE:
<223> OTHER INFORMATION: CD86 IgV WT v85

<400> SEQUENCE: 219

Asn Glu Thr Ala Asp Leu Pro Cys Gln Phe Ala Asn Ser Gln Asn Gln
1               5                   10                  15
```

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Lys Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 220
<211> LENGTH: 99
<212> TYPE: PRT
<213> ORGANISM: Artificial Sequence
<220> FEATURE:
<223> OTHER INFORMATION: CD86 IgV WT v86

<400> SEQUENCE: 220

Asn Glu Thr Ala Asp Leu Pro Cys Gln Phe Ala Asn Ser Gln Asn Leu
1 5 10 15

Ser Leu Ser Glu Leu Val Val Ile Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 221
<211> LENGTH: 99
<212> TYPE: PRT
<213> ORGANISM: Artificial Sequence
<220> FEATURE:
<223> OTHER INFORMATION: CD86 IgV WT v87

<400> SEQUENCE: 221

Asn Glu Thr Ala Asp Leu Pro Cys Gln Phe Ala Asn Ser Gln Asn Leu
1 5 10 15

Ser Leu Ser Glu Leu Val Val Phe Trp Gln Asp Gln Glu Asn Leu Val
20 25 30

Leu Asn Glu Val Tyr Leu Gly Lys Glu Lys Phe Asp Ser Val His Ser
35 40 45

Lys Tyr Met Gly Arg Thr Ser Phe Asp Ser Asp Ser Trp Thr Leu Arg
50 55 60

Leu His Asn Leu Gln Ile Lys Asp Lys Gly Leu Tyr Gln Cys Ile Ile
65 70 75 80

Leu His Lys Lys Pro Thr Gly Met Ile Arg Ile His Gln Met Asn Ser
85 90 95

Glu Leu Ser

<210> SEQ ID NO 222

<211> LENGTH: 7
<212> TYPE: PRT
<213> ORGANISM: Artificial Sequence
<220> FEATURE:
<223> OTHER INFORMATION: Linker

<400> SEQUENCE: 222

Gly Ser Gly Gly Gly Gly Ser
1               5

<210> SEQ ID NO 223
<211> LENGTH: 5
<212> TYPE: PRT
<213> ORGANISM: Artificial Sequence
<220> FEATURE:
<223> OTHER INFORMATION: 4GS Linker

<400> SEQUENCE: 223

Gly Gly Gly Gly Ser
1               5

<210> SEQ ID NO 224
<211> LENGTH: 15
<212> TYPE: PRT
<213> ORGANISM: Artificial Sequence
<220> FEATURE:
<223> OTHER INFORMATION: 3x G4S Linker

<400> SEQUENCE: 224

Gly Gly Gly Gly Ser Gly Gly Gly Gly Ser Gly Gly Gly Gly Ser
1               5                   10                  15

<210> SEQ ID NO 225
<211> LENGTH: 10
<212> TYPE: PRT
<213> ORGANISM: Artificial Sequence
<220> FEATURE:
<223> OTHER INFORMATION: 2x G4S Linker

<400> SEQUENCE: 225

Gly Gly Gly Gly Ser Gly Gly Gly Gly Ser
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Linker

<400> SEQUENCE: 226

Gly Gly Gly Gly Ser Gly Gly Gly Gly Ser Ala Ala Ala
1               5                   10

<210> SEQ ID NO 227
<211> LENGTH: 17
<212> TYPE: PRT
<213> ORGANISM: Artificial Sequence
<220> FEATURE:
<223> OTHER INFORMATION: GS(G4S)3 linker

<400> SEQUENCE: 227

Gly Ser Gly Gly Gly Gly Ser Gly Gly Gly Gly Ser Gly Gly Gly Gly
1               5                   10                  15

Ser

<210> SEQ ID NO 228
<211> LENGTH: 27
<212> TYPE: PRT
<213> ORGANISM: Artificial Sequence
<220> FEATURE:
<223> OTHER INFORMATION: GS(G4S)5 linker

<400> SEQUENCE: 228

```
Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser
            20                  25
```

<210> SEQ ID NO 229
<211> LENGTH: 232
<212> TYPE: PRT
<213> ORGANISM: Artificial Sequence
<220> FEATURE:
<223> OTHER INFORMATION: IgG1 Fc

<400> SEQUENCE: 229

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 230
<211> LENGTH: 231
<212> TYPE: PRT
<213> ORGANISM: Artificial Sequence
<220> FEATURE:
<223> OTHER INFORMATION: Stack Fc (homodimeric)

<400> SEQUENCE: 230

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 231
<211> LENGTH: 116
<212> TYPE: PRT
<213> ORGANISM: Artificial Sequence
<220> FEATURE:
<223> OTHER INFORMATION: NKp30 variant

<400> SEQUENCE: 231

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Val Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Val Pro Leu Ala Pro
    50                  55                  60

Ser Arg Phe Leu His Asp His Gln Ala Glu Leu His Ile Arg Asp Val
65                  70                  75                  80

Arg Gly His Asp Ala Gly Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

His Pro Gln Leu
        115

<210> SEQ ID NO 232
<211> LENGTH: 116
<212> TYPE: PRT
<213> ORGANISM: Artificial Sequence
<220> FEATURE:
<223> OTHER INFORMATION: NKp30 variant v2

<400> SEQUENCE: 232

Leu Trp Val Ser Gln Pro Pro Glu Ile Arg Thr Leu Glu Gly Ser Ser
1 5 10 15

Ala Phe Leu Pro Cys Ser Phe Asn Ala Ser Gln Gly Arg Leu Ala Ile
20 25 30

Gly Ser Val Thr Trp Phe Arg Asp Glu Val Val Pro Gly Lys Glu Val
35 40 45

Arg Asn Gly Thr Pro Glu Phe Arg Gly Arg Leu Ala Pro Leu Ala Ser
50 55 60

Ser Arg Phe Leu His Asp His Gln Ala Glu Leu His Ile Arg Asp Val
65 70 75 80

Arg Gly His Asp Ala Ser Ile Tyr Val Cys Arg Val Glu Val Leu Gly
85 90 95

Leu Gly Val Gly Thr Gly Asn Gly Thr Arg Leu Val Val Glu Lys Glu
100 105 110

His Pro Gln Leu
115

<210> SEQ ID NO 233
<211> LENGTH: 306
<212> TYPE: PRT
<213> ORGANISM: Artificial Sequence
<220> FEATURE:
<223> OTHER INFORMATION: CD86 WT ECD TIP

<400> SEQUENCE: 233

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr

```
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

Arg Val Phe Lys Ser Ser Lys Thr Ser Ser Cys Asp Lys Ser Asp Thr
    290                 295                 300

Cys Phe
305


<210> SEQ ID NO 234
<211> LENGTH: 306
<212> TYPE: PRT
<213> ORGANISM: Artificial Sequence
<220> FEATURE:
<223> OTHER INFORMATION: CD86 ECD TIP v1

<400> SEQUENCE: 234

Ala Pro Leu Lys Ile Gln Ala Tyr Phe Asn Glu Thr Val Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Met Glu Thr Asp Lys Thr Arg Leu Leu Thr Ser Pro
        195                 200                 205

Phe Ser Ile Glu Leu Glu Asp Pro Gln Pro Pro Pro Asp His Ile Pro
    210                 215                 220

Trp Ile Thr Ala Val Leu Pro Thr Val Ile Ile Cys Val Met Val Phe
```

```
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

Arg Val Phe Lys Ser Ser Lys Thr Ser Ser Cys Asp Lys Ser Asp Thr
    290                 295                 300

Cys Phe
305


<210> SEQ ID NO 235
<211> LENGTH: 306
<212> TYPE: PRT
<213> ORGANISM: Artificial Sequence
<220> FEATURE:
<223> OTHER INFORMATION: CD86 ECD TIP v2

<400> SEQUENCE: 235

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Thr Pro Thr Gly
                85                  90                  95

Leu Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Ala Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Val Pro Gln Pro Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
```

```
        275                 280                 285

Arg Val Phe Lys Ser Ser Lys Thr Ser Ser Cys Asp Lys Ser Asp Thr
    290                 295                 300

Cys Phe
305


<210> SEQ ID NO 236
<211> LENGTH: 306
<212> TYPE: PRT
<213> ORGANISM: Artificial Sequence
<220> FEATURE:
<223> OTHER INFORMATION: CD86 ECD TIP v3

<400> SEQUENCE: 236

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Ser Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

Arg Val Phe Lys Ser Ser Lys Thr Ser Ser Cys Asp Lys Ser Asp Thr
    290                 295                 300

Cys Phe
305
```

<210> SEQ ID NO 237
<211> LENGTH: 306
<212> TYPE: PRT
<213> ORGANISM: Artificial Sequence
<220> FEATURE:
<223> OTHER INFORMATION: CD86 ECD TIP v4

<400> SEQUENCE: 237

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Val Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Val Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

Arg Val Phe Lys Ser Ser Lys Thr Ser Ser Cys Asp Lys Ser Asp Thr
    290                 295                 300

Cys Phe
305
```

<210> SEQ ID NO 238
<211> LENGTH: 306
<212> TYPE: PRT
<213> ORGANISM: Artificial Sequence
<220> FEATURE:
<223> OTHER INFORMATION: CD86 ECD TIP v5

<400> SEQUENCE: 238

```
Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Lys Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

Arg Val Phe Lys Ser Ser Lys Thr Ser Ser Cys Asp Lys Ser Asp Thr
    290                 295                 300

Cys Phe
305


<210> SEQ ID NO 239
<211> LENGTH: 306
<212> TYPE: PRT
<213> ORGANISM: Artificial Sequence
<220> FEATURE:
<223> OTHER INFORMATION: CD86 ECD TIP v6

<400> SEQUENCE: 239

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Ile Trp Gln Asp Gln Glu Asn Leu Val Leu Asn Glu Val Tyr Leu Gly
        35                  40                  45
```

```
Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

Arg Val Phe Lys Ser Ser Lys Thr Ser Ser Cys Asp Lys Ser Asp Thr
    290                 295                 300

Cys Phe
305


<210> SEQ ID NO 240
<211> LENGTH: 306
<212> TYPE: PRT
<213> ORGANISM: Artificial Sequence
<220> FEATURE:
<223> OTHER INFORMATION: CD86 ECD TIP v7

<400> SEQUENCE: 240

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95
```

```
Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Ser Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Trp Ile Thr Ala Val Leu Pro Thr Val Ile Ile Cys Val Met Val Phe
225                 230                 235                 240

Cys Leu Ile Leu Trp Lys Trp Lys Lys Lys Lys Arg Pro Arg Asn Ser
                245                 250                 255

Tyr Lys Cys Gly Thr Asn Thr Met Glu Arg Glu Glu Ser Glu Gln Thr
            260                 265                 270

Lys Lys Arg Glu Lys Ile His Ile Pro Glu Arg Ser Asp Glu Ala Gln
        275                 280                 285

Arg Val Phe Lys Ser Ser Lys Thr Ser Ser Cys Asp Lys Ser Asp Thr
    290                 295                 300

Cys Phe
305


<210> SEQ ID NO 241
<211> LENGTH: 306
<212> TYPE: PRT
<213> ORGANISM: Artificial Sequence
<220> FEATURE:
<223> OTHER INFORMATION: CD86 ECD TIP v8

<400> SEQUENCE: 241

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140
```

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Arg Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

Trp Ile Thr Ala Val Leu Pro Thr Val Ile Ile Cys Val Met Val Phe
225 230 235 240

Cys Leu Ile Leu Trp Lys Trp Lys Lys Lys Lys Arg Pro Arg Asn Ser
245 250 255

Tyr Lys Cys Gly Thr Asn Thr Met Glu Arg Glu Glu Ser Glu Gln Thr
260 265 270

Lys Lys Arg Glu Lys Ile His Ile Pro Glu Arg Ser Asp Glu Ala Gln
275 280 285

Arg Val Phe Lys Ser Ser Lys Thr Ser Ser Cys Asp Lys Ser Asp Thr
290 295 300

Cys Phe
305

<210> SEQ ID NO 242
<211> LENGTH: 400
<212> TYPE: PRT
<213> ORGANISM: Artificial Sequence
<220> FEATURE:
<223> OTHER INFORMATION: PAS

<400> SEQUENCE: 242

Ala Ser Pro Ala Ala Pro Ala Pro Ala Ser Pro Ala Ala Pro Ala Pro
1 5 10 15

Ser Ala Pro Ala Ala Ser Pro Ala Ala Pro Ala Pro Ala Ser Pro Ala
20 25 30

Ala Pro Ala Pro Ser Ala Pro Ala Ala Ser Pro Ala Ala Pro Ala Pro
35 40 45

Ala Ser Pro Ala Ala Pro Ala Pro Ser Ala Pro Ala Ala Ser Pro Ala
50 55 60

Ala Pro Ala Pro Ala Ser Pro Ala Ala Pro Ala Pro Ser Ala Pro Ala
65 70 75 80

Ala Ser Pro Ala Ala Pro Ala Pro Ala Ser Pro Ala Ala Pro Ala Pro
85 90 95

Ser Ala Pro Ala Ala Ser Pro Ala Ala Pro Ala Pro Ala Ser Pro Ala
100 105 110

Ala Pro Ala Pro Ser Ala Pro Ala Ala Ser Pro Ala Ala Pro Ala Pro
115 120 125

Ala Ser Pro Ala Ala Pro Ala Pro Ser Ala Pro Ala Ala Ser Pro Ala
130 135 140

Ala Pro Ala Pro Ala Ser Pro Ala Ala Pro Ala Pro Ser Ala Pro Ala
145 150 155 160

Ala Ser Pro Ala Ala Pro Ala Pro Ala Ser Pro Ala Ala Pro Ala Pro
165 170 175

Ser Ala Pro Ala Ala Ser Pro Ala Ala Pro Ala Pro Ala Ser Pro Ala
180 185 190

Ala Pro Ala Pro Ser Ala Pro Ala Ala Ser Pro Ala Ala Pro Ala Pro
195 200 205

Ala Ser Pro Ala Ala Pro Ala Pro Ser Ala Pro Ala Ala Ser Pro Ala
210 215 220

Ala Pro Ala Pro Ala Ser Pro Ala Ala Pro Ala Pro Ser Ala Pro Ala
225 230 235 240

Ala Ser Pro Ala Ala Pro Ala Pro Ala Ser Pro Ala Ala Pro Ala Pro
245 250 255

Ser Ala Pro Ala Ala Ser Pro Ala Ala Pro Ala Pro Ala Ser Pro Ala
260 265 270

Ala Pro Ala Pro Ser Ala Pro Ala Ala Ser Pro Ala Ala Pro Ala Pro
275 280 285

Ala Ser Pro Ala Ala Pro Ala Pro Ser Ala Pro Ala Ala Ser Pro Ala
290 295 300

Ala Pro Ala Pro Ala Ser Pro Ala Ala Pro Ala Pro Ser Ala Pro Ala
305 310 315 320

Ala Ser Pro Ala Ala Pro Ala Pro Ala Ser Pro Ala Ala Pro Ala Pro
325 330 335

Ser Ala Pro Ala Ala Ser Pro Ala Ala Pro Ala Pro Ala Ser Pro Ala
340 345 350

Ala Pro Ala Pro Ser Ala Pro Ala Ala Ser Pro Ala Ala Pro Ala Pro
355 360 365

Ala Ser Pro Ala Ala Pro Ala Pro Ser Ala Pro Ala Ala Ser Pro Ala
370 375 380

Ala Pro Ala Pro Ala Ser Pro Ala Ala Pro Ala Pro Ser Ala Pro Ala
385 390 395 400

<210> SEQ ID NO 243
<211> LENGTH: 22
<212> TYPE: PRT
<213> ORGANISM: Artificial Sequence
<220> FEATURE:
<223> OTHER INFORMATION: P2A protein

<400> SEQUENCE: 243

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 244
<211> LENGTH: 237
<212> TYPE: PRT
<213> ORGANISM: Artificial Sequence
<220> FEATURE:
<223> OTHER INFORMATION: eGFP

<400> SEQUENCE: 244

Ser Lys Gly Glu Glu Leu Phe Thr Gly Val Val Pro Ile Leu Val Glu
1 5 10 15

Leu Asp Gly Asp Val Asn Gly His Lys Phe Ser Val Ser Gly Glu Gly
20 25 30

Glu Gly Asp Ala Thr Tyr Gly Lys Leu Thr Leu Lys Phe Ile Cys Thr
35 40 45

Thr Gly Lys Leu Pro Val Pro Trp Pro Thr Leu Val Thr Thr Leu Thr
50 55 60

Tyr Gly Val Gln Cys Phe Ser Arg Tyr Pro Asp His Met Lys Gln His
65 70 75 80

Asp Phe Phe Lys Ser Ala Met Pro Glu Gly Tyr Val Gln Glu Arg Thr
85 90 95

Ile Phe Phe Lys Asp Asp Gly Asn Tyr Lys Thr Arg Ala Glu Val Lys
100 105 110

Phe Glu Gly Asp Thr Leu Val Asn Arg Ile Glu Leu Lys Gly Ile Asp
115 120 125

Phe Lys Glu Asp Gly Asn Ile Leu Gly His Lys Leu Glu Tyr Asn Tyr
130 135 140

Asn Ser His Asn Val Tyr Ile Met Ala Asp Lys Gln Lys Asn Gly Ile
145 150 155 160

Lys Val Asn Phe Lys Ile Arg His Asn Ile Glu Asp Gly Ser Val Gln
165 170 175

Leu Ala Asp His Tyr Gln Gln Asn Thr Pro Ile Gly Asp Gly Pro Val
180 185 190

Leu Leu Pro Asp Asn His Tyr Leu Ser Thr Gln Ser Ala Leu Ser Lys
195 200 205

Asp Pro Asn Glu Lys Arg Asp His Met Val Leu Leu Glu Phe Val Thr
210 215 220

Ala Ala Gly Ile Thr His Gly Met Asp Glu Leu Tyr Lys
225 230 235

<210> SEQ ID NO 245
<211> LENGTH: 237
<212> TYPE: PRT
<213> ORGANISM: Artificial Sequence
<220> FEATURE:
<223> OTHER INFORMATION: Green fluorescent protein

<400> SEQUENCE: 245

Ser Lys Gly Glu Glu Leu Phe Thr Gly Val Val Pro Ile Leu Val Glu
1 5 10 15

Leu Asp Gly Asp Val Asn Gly His Lys Phe Ser Val Ser Gly Glu Gly
20 25 30

Glu Gly Asp Ala Thr Tyr Gly Lys Leu Thr Leu Lys Phe Ile Cys Thr
35 40 45

Thr Gly Lys Leu Pro Val Pro Trp Pro Thr Leu Val Thr Thr Phe Ser
50 55 60

Tyr Gly Val Gln Cys Phe Ser Arg Tyr Pro Asp His Met Lys Gln His
65 70 75 80

Asp Phe Phe Lys Ser Ala Met Pro Glu Gly Tyr Val Gln Glu Arg Thr
85 90 95

Ile Phe Phe Lys Asp Asp Gly Asn Tyr Lys Thr Arg Ala Glu Val Lys
100 105 110

Phe Glu Gly Asp Thr Leu Val Asn Arg Ile Glu Leu Lys Gly Ile Asp
115 120 125

Phe Lys Glu Asp Gly Asn Ile Leu Gly His Lys Leu Glu Tyr Asn Tyr
130 135 140

Asn Ser His Asn Val Tyr Ile Met Ala Asp Lys Gln Lys Asn Gly Ile
145 150 155 160

Lys Val Asn Phe Lys Ile Arg His Asn Ile Glu Asp Gly Ser Val Gln
165 170 175

Leu Ala Asp His Tyr Gln Gln Asn Thr Pro Ile Gly Asp Gly Pro Val
180 185 190

Leu Leu Pro Asp Asn His Tyr Leu Ser Thr Gln Ser Ala Leu Ser Lys
195 200 205

Asp Pro Asn Glu Lys Arg Asp His Met Val Leu Leu Glu Phe Val Thr
210 215 220

Ala Ala Gly Ile Thr His Gly Met Asp Glu Leu Tyr Lys
225 230 235

<210> SEQ ID NO 246
<211> LENGTH: 239
<212> TYPE: PRT
<213> ORGANISM: Artificial Sequence
<220> FEATURE:
<223> OTHER INFORMATION: eGFP

<400> SEQUENCE: 246

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Leu Lys Phe Ile
35 40 45

Cys Thr Thr Gly Lys Leu Pro Val Pro Trp Pro Thr Leu Val Thr Thr
50 55 60

Leu Thr Tyr Gly Val Gln Cys Phe Ser Arg Tyr Pro Asp His Met Lys
65 70 75 80

Gln His Asp Phe Phe Lys Ser Ala Met Pro Glu Gly Tyr Val Gln Glu
85 90 95

Arg Thr Ile Phe Phe Lys Asp Asp Gly Asn Tyr Lys Thr Arg Ala Glu
100 105 110

Val Lys Phe Glu Gly Asp Thr Leu Val Asn Arg Ile Glu Leu Lys Gly
115 120 125

Ile Asp Phe Lys Glu Asp Gly Asn Ile Leu Gly His Lys Leu Glu Tyr
130 135 140

Asn Tyr Asn Ser His Asn Val Tyr Ile Met Ala Asp Lys Gln Lys Asn
145 150 155 160

Gly Ile Lys Val Asn Phe Lys Ile Arg His Asn Ile Glu Asp Gly Ser
165 170 175

Val Gln Leu Ala Asp His Tyr Gln Gln Asn Thr Pro Ile Gly Asp Gly
180 185 190

Pro Val Leu Leu Pro Asp Asn His Tyr Leu Ser Thr Gln Ser Ala Leu
195 200 205

Ser Lys Asp Pro Asn Glu Lys Arg Asp His Met Val Leu Leu Glu Phe
210 215 220

Val Thr Ala Ala Gly Ile Thr Leu Gly Met Asp Glu Leu Tyr Lys
225 230 235

<210> SEQ ID NO 247
<211> LENGTH: 25
<212> TYPE: PRT
<213> ORGANISM: Artificial Sequence
<220> FEATURE:
<223> OTHER INFORMATION: (EAAAK)5 linker

<400> SEQUENCE: 247

Glu Ala Ala Ala Lys Glu Ala Ala Ala Lys Glu Ala Ala Ala Lys Glu
1 5 10 15

Ala Ala Ala Lys Glu Ala Ala Ala Lys
20 25

<210> SEQ ID NO 248
<211> LENGTH: 8
<212> TYPE: PRT
<213> ORGANISM: Artificial Sequence
<220> FEATURE:
<223> OTHER INFORMATION: FLAG-tag

<400> SEQUENCE: 248

Asp Tyr Lys Asp Asp Asp Asp Lys
1               5

<210> SEQ ID NO 249
<211> LENGTH: 6
<212> TYPE: PRT
<213> ORGANISM: Artificial Sequence
<220> FEATURE:
<223> OTHER INFORMATION: 6xHis tag

<400> SEQUENCE: 249

His His His His His His
1               5

<210> SEQ ID NO 250
<211> LENGTH: 228
<212> TYPE: PRT
<213> ORGANISM: Artificial Sequence
<220> FEATURE:
<223> OTHER INFORMATION: rabbit Fc

<400> SEQUENCE: 250

Ala Pro Ser Thr Cys Ser Lys Pro Thr Cys Pro Pro Pro Glu Leu Leu
1               5                   10                  15

Gly Gly Pro Ser Val Phe Ile Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Glu Asp Asp Pro Glu Val Gln Phe Thr Trp Tyr Ile Asn Asn Glu Gln
    50                  55                  60

Val Arg Thr Ala Arg Pro Pro Leu Arg Glu Gln Gln Phe Asn Ser Thr
65                  70                  75                  80

Ile Arg Val Val Ser Thr Leu Pro Ile Ala His Glu Asp Trp Leu Arg
                85                  90                  95

Gly Lys Glu Phe Lys Cys Lys Val His Asn Lys Ala Leu Pro Ala Pro
            100                 105                 110

Ile Glu Lys Thr Ile Ser Lys Ala Arg Gly Gln Pro Leu Glu Pro Lys
        115                 120                 125

Val Tyr Thr Met Gly Pro Pro Arg Glu Glu Leu Ser Ser Arg Ser Val
    130                 135                 140

Ser Leu Thr Cys Met Ile Asn Gly Phe Tyr Pro Ser Asp Ile Ser Val
145                 150                 155                 160

Glu Trp Glu Lys Asn Gly Lys Ala Glu Asp Asn Tyr Lys Thr Thr Pro
                165                 170                 175

Ala Val Leu Asp Ser Asp Gly Ser Tyr Phe Leu Tyr Ser Lys Leu Ser
            180                 185                 190

Val Pro Thr Ser Glu Trp Gln Arg Gly Asp Val Phe Thr Cys Ser Val
        195                 200                 205

Met His Glu Ala Leu His Asn His Tyr Thr Gln Lys Ser Ile Ser Arg
    210                 215                 220

Ser Pro Gly Lys
225

<210> SEQ ID NO 251
<211> LENGTH: 238
<212> TYPE: PRT
<213> ORGANISM: Artificial Sequence
<220> FEATURE:
<223> OTHER INFORMATION: mouse Fc2b

<400> SEQUENCE: 251

```
Glu Pro Ser Gly Pro Ile Ser Thr Ile Asn Pro Cys Pro Pro Cys Lys
1               5                   10                  15

Glu Cys His Lys Cys Pro Ala Pro Asn Leu Glu Gly Gly Pro Ser Val
            20                  25                  30

Phe Ile Phe Pro Pro Asn Ile Lys Asp Val Leu Met Ile Ser Leu Thr
        35                  40                  45

Pro Lys Val Thr Cys Val Val Val Asp Val Ser Glu Asp Asp Pro Asp
    50                  55                  60

Val Gln Ile Ser Trp Phe Val Asn Asn Val Glu Val His Thr Ala Gln
65                  70                  75                  80

Thr Gln Thr His Arg Glu Asp Tyr Asn Ser Thr Ile Arg Val Val Ser
                85                  90                  95

Thr Leu Pro Ile Gln His Gln Asp Trp Met Ser Gly Lys Glu Phe Lys
            100                 105                 110

Cys Lys Val Asn Asn Lys Asp Leu Pro Ser Pro Ile Glu Arg Thr Ile
        115                 120                 125

Ser Lys Ile Lys Gly Leu Val Arg Ala Pro Gln Val Tyr Ile Leu Pro
    130                 135                 140

Pro Pro Ala Glu Gln Leu Ser Arg Lys Asp Val Ser Leu Thr Cys Leu
145                 150                 155                 160

Val Val Gly Phe Asn Pro Gly Asp Ile Ser Val Glu Trp Thr Ser Asn
                165                 170                 175

Gly His Thr Glu Glu Asn Tyr Lys Asp Thr Ala Pro Val Leu Asp Ser
            180                 185                 190

Asp Gly Ser Tyr Phe Ile Tyr Ser Lys Leu Asn Met Lys Thr Ser Lys
        195                 200                 205

Trp Glu Lys Thr Asp Ser Phe Ser Cys Asn Val Arg His Glu Gly Leu
    210                 215                 220

Lys Asn Tyr Tyr Leu Lys Lys Thr Ile Ser Arg Ser Pro Gly
225                 230                 235
```

<210> SEQ ID NO 252
<211> LENGTH: 232
<212> TYPE: PRT
<213> ORGANISM: Artificial Sequence
<220> FEATURE:
<223> OTHER INFORMATION: Knob Fc

<400> SEQUENCE: 252

```
Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
```

65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Cys Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 253
<211> LENGTH: 231
<212> TYPE: PRT
<213> ORGANISM: Artificial Sequence
<220> FEATURE:
<223> OTHER INFORMATION: wild-type human IgG1 Fc - delK

<400> SEQUENCE: 253

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe

```
        195                 200                 205

Ser Cys Ser Val Met His Glu Ala Leu His Asn His Tyr Thr Gln Lys
    210                 215                 220

Ser Leu Ser Leu Ser Pro Gly
225                 230


<210> SEQ ID NO 254
<211> LENGTH: 232
<212> TYPE: PRT
<213> ORGANISM: Artificial Sequence
<220> FEATURE:
<223> OTHER INFORMATION: IgG1 Fc C220S

<400> SEQUENCE: 254

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 255
<211> LENGTH: 232
<212> TYPE: PRT
<213> ORGANISM: Artificial Sequence
<220> FEATURE:
<223> OTHER INFORMATION: Fc

<400> SEQUENCE: 255

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

```
Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Cys Glu Glu Gln
65                  70                  75                  80

Tyr Gly Ser Thr Tyr Arg Cys Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 256
<211> LENGTH: 232
<212> TYPE: PRT
<213> ORGANISM: Artificial Sequence
<220> FEATURE:
<223> OTHER INFORMATION: Fc1.1

<400> SEQUENCE: 256

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160
```

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 257
<211> LENGTH: 231
<212> TYPE: PRT
<213> ORGANISM: Artificial Sequence
<220> FEATURE:
<223> OTHER INFORMATION: Fc

<400> SEQUENCE: 257

Glu Pro Lys Ser Ser Asp Lys Thr His Thr Cys Pro Pro Cys Pro Ala
1 5 10 15

Pro Pro Val Ala Gly Pro Ser Val Phe Leu Phe Pro Pro Lys Pro Lys
20 25 30

Asp Thr Leu Met Ile Ser Arg Thr Pro Glu Val Thr Cys Val Val Val
35 40 45

Asp Val Lys His Glu Asp Pro Glu Val Lys Phe Asn Trp Tyr Val Asp
50 55 60

Gly Val Glu Val His Asn Ala Lys Thr Lys Pro Arg Glu Glu Gln Tyr
65 70 75 80

Asn Ser Thr Tyr Arg Val Val Ser Val Leu Thr Val Leu His Gln Asp
85 90 95

Trp Leu Asn Gly Lys Glu Tyr Lys Cys Lys Val Ser Asn Lys Ala Leu
100 105 110

Pro Ala Pro Ile Glu Lys Thr Ile Ser Lys Ala Lys Gly Gln Pro Arg
115 120 125

Glu Pro Gln Val Tyr Thr Leu Pro Pro Ser Arg Glu Glu Met Thr Lys
130 135 140

Asn Gln Val Ser Leu Thr Cys Leu Val Lys Gly Phe Tyr Pro Ser Asp
145 150 155 160

Ile Ala Val Glu Trp Glu Ser Asn Gly Gln Pro Glu Asn Asn Tyr Lys
165 170 175

Thr Thr Pro Pro Val Leu Asp Ser Asp Gly Ser Phe Phe Leu Tyr Ser
180 185 190

Lys Leu Thr Val Asp Lys Ser Arg Trp Gln Gln Gly Asn Val Phe Ser
195 200 205

Cys Ser Val Met His Glu Ala Leu His Asn His Tyr Thr Gln Lys Ser
210 215 220

Leu Ser Leu Ser Pro Gly Lys
225 230

<210> SEQ ID NO 258
<211> LENGTH: 232
<212> TYPE: PRT
<213> ORGANISM: Artificial Sequence
<220> FEATURE:
<223> OTHER INFORMATION: Stack Fc (homodimeric)

<400> SEQUENCE: 258

```
Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 259
<211> LENGTH: 231
<212> TYPE: PRT
<213> ORGANISM: Artificial Sequence
<220> FEATURE:
<223> OTHER INFORMATION: SEFL

<400> SEQUENCE: 259

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Cys Glu Glu Gln
65                  70                  75                  80

Tyr Gly Ser Thr Tyr Arg Cys Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125
```

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 260
<211> LENGTH: 231
<212> TYPE: PRT
<213> ORGANISM: Artificial Sequence
<220> FEATURE:
<223> OTHER INFORMATION: Fc1.1

<400> SEQUENCE: 260

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 261

<211> LENGTH: 230
<212> TYPE: PRT
<213> ORGANISM: Artificial Sequence
<220> FEATURE:
<223> OTHER INFORMATION: Fc

<400> SEQUENCE: 261

Glu Pro Lys Ser Ser Asp Lys Thr His Thr Cys Pro Pro Cys Pro Ala
1 5 10 15

Pro Pro Val Ala Gly Pro Ser Val Phe Leu Phe Pro Pro Lys Pro Lys
20 25 30

Asp Thr Leu Met Ile Ser Arg Thr Pro Glu Val Thr Cys Val Val Val
35 40 45

Asp Val Lys His Glu Asp Pro Glu Val Lys Phe Asn Trp Tyr Val Asp
50 55 60

Gly Val Glu Val His Asn Ala Lys Thr Lys Pro Arg Glu Glu Gln Tyr
65 70 75 80

Asn Ser Thr Tyr Arg Val Val Ser Val Leu Thr Val Leu His Gln Asp
85 90 95

Trp Leu Asn Gly Lys Glu Tyr Lys Cys Lys Val Ser Asn Lys Ala Leu
100 105 110

Pro Ala Pro Ile Glu Lys Thr Ile Ser Lys Ala Lys Gly Gln Pro Arg
115 120 125

Glu Pro Gln Val Tyr Thr Leu Pro Pro Ser Arg Glu Glu Met Thr Lys
130 135 140

Asn Gln Val Ser Leu Thr Cys Leu Val Lys Gly Phe Tyr Pro Ser Asp
145 150 155 160

Ile Ala Val Glu Trp Glu Ser Asn Gly Gln Pro Glu Asn Asn Tyr Lys
165 170 175

Thr Thr Pro Pro Val Leu Asp Ser Asp Gly Ser Phe Phe Leu Tyr Ser
180 185 190

Lys Leu Thr Val Asp Lys Ser Arg Trp Gln Gln Gly Asn Val Phe Ser
195 200 205

Cys Ser Val Met His Glu Ala Leu His Asn His Tyr Thr Gln Lys Ser
210 215 220

Leu Ser Leu Ser Pro Gly
225 230

<210> SEQ ID NO 262
<211> LENGTH: 235
<212> TYPE: PRT
<213> ORGANISM: Artificial Sequence
<220> FEATURE:
<223> OTHER INFORMATION: IgG2 Fc

<400> SEQUENCE: 262

Thr Lys Val Asp Lys Thr Val Glu Arg Lys Cys Cys Val Glu Cys Pro
1 5 10 15

Pro Cys Pro Ala Pro Pro Val Ala Gly Pro Ser Val Phe Leu Phe Pro
20 25 30

Pro Lys Pro Lys Asp Thr Leu Met Ile Ser Arg Thr Pro Glu Val Thr
35 40 45

Cys Val Val Val Asp Val Ser His Glu Asp Pro Glu Val Gln Phe Asn
50 55 60

Trp Tyr Val Asp Gly Val Glu Val His Asn Ala Lys Thr Lys Pro Arg
65 70 75 80

Glu Glu Gln Phe Asn Ser Thr Phe Arg Val Val Ser Val Leu Thr Val 85 90 95

Val His Gln Asp Trp Leu Asn Gly Lys Glu Tyr Lys Cys Lys Val Ser
100 105 110

Asn Lys Gly Leu Pro Ala Pro Ile Glu Lys Thr Ile Ser Lys Thr Lys
115 120 125

Gly Gln Pro Arg Glu Pro Gln Val Tyr Thr Leu Pro Pro Ser Arg Glu
130 135 140

Glu Met Thr Lys Asn Gln Val Ser Leu Thr Cys Leu Val Lys Gly Phe
145 150 155 160

Tyr Pro Ser Asp Ile Ala Val Glu Trp Glu Ser Asn Gly Gln Pro Glu
165 170 175

Asn Asn Tyr Lys Thr Thr Pro Pro Met Leu Asp Ser Asp Gly Ser Phe
180 185 190

Phe Leu Tyr Ser Lys Leu Thr Val Asp Lys Ser Arg Trp Gln Gln Gly
195 200 205

Asn Val Phe Ser Cys Ser Val Met His Glu Ala Leu His Asn His Tyr
210 215 220

Thr Gln Lys Ser Leu Ser Leu Ser Pro Gly Lys
225 230 235

<210> SEQ ID NO 263
<211> LENGTH: 229
<212> TYPE: PRT
<213> ORGANISM: Artificial Sequence
<220> FEATURE:
<223> OTHER INFORMATION: IgG4 Fc

<400> SEQUENCE: 263

Glu Ser Lys Tyr Gly Pro Pro Cys Pro Ser Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser 210 215 220

Leu Ser Leu Gly Lys
225

<210> SEQ ID NO 264
<211> LENGTH: 229
<212> TYPE: PRT
<213> ORGANISM: Artificial Sequence
<220> FEATURE:
<223> OTHER INFORMATION: IgG4 Fc S228P

<400> SEQUENCE: 264

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 265
<211> LENGTH: 5
<212> TYPE: PRT
<213> ORGANISM: Artificial Sequence
<220> FEATURE:
<223> OTHER INFORMATION: EAAAK linker

<400> SEQUENCE: 265

Glu Ala Ala Ala Lys
1 5

<210> SEQ ID NO 266
<211> LENGTH: 15
<212> TYPE: PRT
<213> ORGANISM: Artificial Sequence
<220> FEATURE:

<223> OTHER INFORMATION: (EAAAK)3 linker

<400> SEQUENCE: 266

Glu Ala Ala Ala Lys Glu Ala Ala Ala Lys Glu Ala Ala Ala Lys
1 5 10 15

<210> SEQ ID NO 267
<211> LENGTH: 225
<212> TYPE: PRT
<213> ORGANISM: Artificial Sequence
<220> FEATURE:
<223> OTHER INFORMATION: Fc1.1 delta EPKSSD

<400> SEQUENCE: 267

Lys Thr His Thr Cys Pro Pro Cys Pro Ala Pro Glu Ala Glu Gly Ala
1 5 10 15

Pro Ser Val Phe Leu Phe Pro Pro Lys Pro Lys Asp Thr Leu Met Ile
20 25 30

Ser Arg Thr Pro Glu Val Thr Cys Val Val Val Asp Val Ser His Glu
35 40 45

Asp Pro Glu Val Lys Phe Asn Trp Tyr Val Asp Gly Val Glu Val His
50 55 60

Asn Ala Lys Thr Lys Pro Arg Glu Glu Gln Tyr Asn Ser Thr Tyr Arg
65 70 75 80

Val Val Ser Val Leu Thr Val Leu His Gln Asp Trp Leu Asn Gly Lys
85 90 95

Glu Tyr Lys Cys Lys Val Ser Asn Lys Ala Leu Pro Ala Pro Ile Glu
100 105 110

Lys Thr Ile Ser Lys Ala Lys Gly Gln Pro Arg Glu Pro Gln Val Tyr
115 120 125

Thr Leu Pro Pro Ser Arg Glu Glu Met Thr Lys Asn Gln Val Ser Leu
130 135 140

Thr Cys Leu Val Lys Gly Phe Tyr Pro Ser Asp Ile Ala Val Glu Trp
145 150 155 160

Glu Ser Asn Gly Gln Pro Glu Asn Asn Tyr Lys Thr Thr Pro Pro Val
165 170 175

Leu Asp Ser Asp Gly Ser Phe Phe Leu Tyr Ser Lys Leu Thr Val Asp
180 185 190

Lys Ser Arg Trp Gln Gln Gly Asn Val Phe Ser Cys Ser Val Met His
195 200 205

Glu Ala Leu His Asn His Tyr Thr Gln Lys Ser Leu Ser Leu Ser Pro
210 215 220

Gly
225

<210> SEQ ID NO 268
<211> LENGTH: 108
<212> TYPE: PRT
<213> ORGANISM: Artificial Sequence
<220> FEATURE:
<223> OTHER INFORMATION: NKp30 v1 IgC-like

<400> SEQUENCE: 268

Leu Trp Val Ser Gln Pro Pro Glu Ile Arg Thr Leu Glu Gly Ser Ser
1 5 10 15

Ala Phe Leu Pro Cys Ser Phe Asn Ala Ser Gln Gly Arg Val Ala Ile
20 25 30

Gly Ser Val Thr Trp Phe Arg Asp Glu Val Val Pro Gly Lys Glu Val

```
        35                  40                  45

Arg Asn Gly Thr Pro Glu Phe Arg Gly Arg Leu Val Pro Leu Ala Pro
    50                  55                  60

Ser Arg Phe Leu His Asp His Gln Ala Glu Leu His Ile Arg Asp Val
65                  70                  75                  80

Arg Gly His Asp Ala Gly Ile Tyr Val Cys Arg Val Glu Val Leu Gly
                85                  90                  95

Leu Gly Val Gly Thr Gly Asn Gly Thr Arg Leu Val
            100                 105


<210> SEQ ID NO 269
<211> LENGTH: 108
<212> TYPE: PRT
<213> ORGANISM: Artificial Sequence
<220> FEATURE:
<223> OTHER INFORMATION: NKp30 v2 IgC-like

<400> SEQUENCE: 269

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Val Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val
            100                 105


<210> SEQ ID NO 270
<211> LENGTH: 108
<212> TYPE: PRT
<213> ORGANISM: Artificial Sequence
<220> FEATURE:
<223> OTHER INFORMATION: NKp30 v3 IgC-like

<400> SEQUENCE: 270

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Val Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val
            100                 105


<210> SEQ ID NO 271
<211> LENGTH: 108
```

<212> TYPE: PRT
<213> ORGANISM: Artificial Sequence
<220> FEATURE:
<223> OTHER INFORMATION: NKp30 v4 IgC-like

<400> SEQUENCE: 271

```
Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Pro
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val
            100                 105
```

<210> SEQ ID NO 272
<211> LENGTH: 108
<212> TYPE: PRT
<213> ORGANISM: Artificial Sequence
<220> FEATURE:
<223> OTHER INFORMATION: NKp30 v5 IgC-like

<400> SEQUENCE: 272

```
Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Gly Ile Tyr Val Cys Arg Val Glu Val Leu Gly
                85                  90                  95

Leu Gly Val Gly Thr Gly Asn Gly Thr Arg Leu Val
            100                 105
```

<210> SEQ ID NO 273
<211> LENGTH: 117
<212> TYPE: PRT
<213> ORGANISM: Artificial Sequence
<220> FEATURE:
<223> OTHER INFORMATION: NKp30 v1 ECD

<400> SEQUENCE: 273

```
Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Val Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Val Pro Leu Ala Pro
```

```
    50                  55                  60

Ser Arg Phe Leu His Asp His Gln Ala Glu Leu His Ile Arg Asp Val
65                  70                  75                  80

Arg Gly His Asp Ala Gly Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

His Pro Gln Leu Gly
        115


<210> SEQ ID NO 274
<211> LENGTH: 117
<212> TYPE: PRT
<213> ORGANISM: Artificial Sequence
<220> FEATURE:
<223> OTHER INFORMATION: NKp30 v2 ECD

<400> SEQUENCE: 274

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Val Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

His Pro Gln Leu Gly
        115


<210> SEQ ID NO 275
<211> LENGTH: 117
<212> TYPE: PRT
<213> ORGANISM: Artificial Sequence
<220> FEATURE:
<223> OTHER INFORMATION: NKp30 v3 ECD

<400> SEQUENCE: 275

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Val Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110
```

His Pro Gln Leu Gly
115

<210> SEQ ID NO 276
<211> LENGTH: 117
<212> TYPE: PRT
<213> ORGANISM: Artificial Sequence
<220> FEATURE:
<223> OTHER INFORMATION: NKp30 v4 ECD

<400> SEQUENCE: 276

Leu Trp Val Ser Gln Pro Pro Glu Ile Arg Thr Leu Glu Gly Ser Ser
1 5 10 15

Ala Phe Leu Pro Cys Ser Phe Asn Ala Ser Gln Gly Arg Leu Ala Ile
20 25 30

Gly Ser Val Thr Trp Phe Arg Asp Glu Val Val Pro Gly Lys Glu Val
35 40 45

Arg Asn Gly Thr Pro Glu Phe Arg Gly Arg Leu Ala Pro Leu Ala Pro
50 55 60

Ser Arg Phe Leu His Asp His Gln Ala Glu Leu His Ile Arg Asp Val
65 70 75 80

Arg Gly His Asp Ala Ser Ile Tyr Val Cys Arg Val Glu Val Leu Gly
85 90 95

Leu Gly Val Gly Thr Gly Asn Gly Thr Arg Leu Val Val Glu Lys Glu
100 105 110

His Pro Gln Leu Gly
115

<210> SEQ ID NO 277
<211> LENGTH: 117
<212> TYPE: PRT
<213> ORGANISM: Artificial Sequence
<220> FEATURE:
<223> OTHER INFORMATION: NKp30 v5 ECD

<400> SEQUENCE: 277

Leu Trp Val Ser Gln Pro Pro Glu Ile Arg Thr Leu Glu Gly Ser Ser
1 5 10 15

Ala Phe Leu Pro Cys Ser Phe Asn Ala Ser Gln Gly Arg Leu Ala Ile
20 25 30

Gly Ser Val Thr Trp Phe Arg Asp Glu Val Val Pro Gly Lys Glu Val
35 40 45

Arg Asn Gly Thr Pro Glu Phe Arg Gly Arg Leu Ala Pro Leu Ala Ser
50 55 60

Ser Arg Phe Leu His Asp His Gln Ala Glu Leu His Ile Arg Asp Val
65 70 75 80

Arg Gly His Asp Ala Gly Ile Tyr Val Cys Arg Val Glu Val Leu Gly
85 90 95

Leu Gly Val Gly Thr Gly Asn Gly Thr Arg Leu Val Val Glu Lys Glu
100 105 110

His Pro Gln Leu Gly
115

<210> SEQ ID NO 278
<211> LENGTH: 108
<212> TYPE: PRT
<213> ORGANISM: Artificial Sequence
<220> FEATURE:
<223> OTHER INFORMATION: NKp30 WT IgC-like

<400> SEQUENCE: 278

Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val
            100                 105

<210> SEQ ID NO 279
<211> LENGTH: 8
<212> TYPE: PRT
<213> ORGANISM: Artificial Sequence
<220> FEATURE:
<223> OTHER INFORMATION: Stuffer

<400> SEQUENCE: 279

His Met Ser Ser Val Ser Ala Gln
1               5

<210> SEQ ID NO 280
<211> LENGTH: 232
<212> TYPE: PRT
<213> ORGANISM: Artificial Sequence
<220> FEATURE:
<223> OTHER INFORMATION: Hole Fc

<400> SEQUENCE: 280

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 281
<211> LENGTH: 71
<212> TYPE: PRT
<213> ORGANISM: Artificial Sequence
<220> FEATURE:
<223> OTHER INFORMATION: CD8-derived hinge and transmembrane domain

<400> SEQUENCE: 281

Lys Pro Thr Thr Thr Pro Ala Pro Arg Pro Pro Thr Pro Ala Pro Thr
1 5 10 15

Ile Ala Ser Gln Pro Leu Ser Leu Arg Pro Glu Ala Ser Arg Pro Ala
20 25 30

Ala Gly Gly Ala Val His Thr Arg Gly Leu Asp Phe Ala Ser Asp Ile
35 40 45

Tyr Ile Trp Ala Pro Leu Ala Gly Thr Cys Gly Val Leu Leu Leu Ser
50 55 60

Leu Val Ile Thr Leu Tyr Cys
65 70

<210> SEQ ID NO 282
<211> LENGTH: 69
<212> TYPE: PRT
<213> ORGANISM: Artificial Sequence
<220> FEATURE:
<223> OTHER INFORMATION: CD8-derived hinge and transmembrane domain (2nd gen CAR)

<400> SEQUENCE: 282

Ala Lys Pro Thr Thr Thr Pro Ala Pro Arg Pro Pro Thr Pro Ala Pro
1 5 10 15

Thr Ile Ala Ser Gln Pro Leu Ser Leu Arg Pro Glu Ala Cys Arg Pro
20 25 30

Ala Ala Gly Gly Ala Val His Thr Arg Gly Leu Asp Phe Ala Cys Asp
35 40 45

Ile Tyr Ile Trp Ala Pro Leu Ala Gly Thr Cys Gly Val Leu Leu Leu
50 55 60

Ser Leu Val Ile Thr
65

<210> SEQ ID NO 283
<211> LENGTH: 68
<212> TYPE: PRT
<213> ORGANISM: Artificial Sequence
<220> FEATURE:
<223> OTHER INFORMATION: CD8 hinge and transmembrane domain

<400> SEQUENCE: 283

Lys Pro Thr Thr Thr Pro Ala Pro Arg Pro Pro Thr Pro Ala Pro Thr
1 5 10 15

Ile Ala Ser Gln Pro Leu Ser Leu Arg Pro Glu Ala Cys Arg Pro Ala
20 25 30

Ala Gly Gly Ala Val His Thr Arg Gly Leu Asp Phe Ala Cys Asp Ile
35 40 45

Tyr Ile Trp Ala Pro Leu Ala Gly Thr Cys Gly Val Leu Leu Leu Ser
50 55 60

Leu Val Ile Thr
65

<210> SEQ ID NO 284
<211> LENGTH: 112
<212> TYPE: PRT
<213> ORGANISM: Artificial Sequence
<220> FEATURE:
<223> OTHER INFORMATION: CD3zeta intracellular signaling domain

<400> SEQUENCE: 284

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 285
<211> LENGTH: 42
<212> TYPE: PRT
<213> ORGANISM: Artificial Sequence
<220> FEATURE:
<223> OTHER INFORMATION: 4-1BB-derived costimulatory domain

<400> SEQUENCE: 285

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 286
<211> LENGTH: 40
<212> TYPE: PRT
<213> ORGANISM: Artificial Sequence
<220> FEATURE:
<223> OTHER INFORMATION: CD28-derived costimulatory domain

<400> SEQUENCE: 286

Ser Lys Arg Ser Arg Leu Leu His Ser Asp Tyr Met Asn Met Thr Pro
1 5 10 15

Arg Arg Pro Gly Pro Thr Arg Lys His Tyr Gln Pro Tyr Ala Pro Pro
20 25 30

Arg Asp Phe Ala Ala Tyr Arg Ser
35 40

<210> SEQ ID NO 287
<211> LENGTH: 41
<212> TYPE: PRT
<213> ORGANISM: Artificial Sequence
<220> FEATURE:
<223> OTHER INFORMATION: CD28-derived costimulatory domain 2

<400> SEQUENCE: 287

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 288
<211> LENGTH: 44
<212> TYPE: PRT
<213> ORGANISM: Artificial Sequence
<220> FEATURE:
<223> OTHER INFORMATION: CD28-derived costimulatory domain 3

<400> SEQUENCE: 288

Phe Trp Val Arg Ser Lys Arg Ser Arg Leu Leu His Ser Asp Tyr Met
1 5 10 15

Asn Met Thr Pro Arg Arg Pro Gly Pro Thr Arg Lys His Tyr Gln Pro
20 25 30

Tyr Ala Pro Pro Arg Asp Phe Ala Ala Tyr Arg Ser
35 40

<210> SEQ ID NO 289
<211> LENGTH: 16
<212> TYPE: PRT
<213> ORGANISM: Artificial Sequence
<220> FEATURE:
<223> OTHER INFORMATION: CD33 Signal Peptide

<400> SEQUENCE: 289

Met Pro Leu Leu Leu Leu Leu Pro Leu Leu Trp Ala Gly Ala Leu Ala
1 5 10 15

<210> SEQ ID NO 290
<211> LENGTH: 22
<212> TYPE: PRT
<213> ORGANISM: Artificial Sequence
<220> FEATURE:
<223> OTHER INFORMATION: IgGkappa light chain

<400> SEQUENCE: 290

Met Asp Met Arg Val Leu Ala Gln Leu Leu Gly Leu Leu Leu Leu Cys
1 5 10 15

Phe Pro Gly Ala Arg Cys
20

<210> SEQ ID NO 291
<211> LENGTH: 18
<212> TYPE: PRT
<213> ORGANISM: Artificial Sequence
<220> FEATURE:
<223> OTHER INFORMATION: HSA signal peptide

<400> SEQUENCE: 291

Met Lys Trp Val Thr Phe Ile Ser Leu Leu Phe Leu Phe Ser Ser Ala
1 5 10 15

Tyr Ser

<210> SEQ ID NO 292
<211> LENGTH: 22
<212> TYPE: PRT
<213> ORGANISM: Artificial Sequence
<220> FEATURE:
<223> OTHER INFORMATION: Ig kappa light chain

<400> SEQUENCE: 292

Met Asp Met Arg Ala Pro Ala Gly Ile Phe Gly Phe Leu Leu Val Leu
1 5 10 15

Phe Pro Gly Tyr Arg Ser
20

<210> SEQ ID NO 293
<211> LENGTH: 19
<212> TYPE: PRT
<213> ORGANISM: Artificial Sequence
<220> FEATURE:
<223> OTHER INFORMATION: human azurocidin preprotein signal sequence

<400> SEQUENCE: 293

Met Thr Arg Leu Thr Val Leu Ala Leu Leu Ala Gly Leu Leu Ala Ser
1 5 10 15

Ser Arg Ala

<210> SEQ ID NO 294
<211> LENGTH: 19
<212> TYPE: PRT
<213> ORGANISM: Artificial Sequence
<220> FEATURE:
<223> OTHER INFORMATION: IgG heavy chain signal peptide

<400> SEQUENCE: 294

Met Glu Leu Gly Leu Ser Trp Ile Phe Leu Leu Ala Ile Leu Lys Gly
1 5 10 15

Val Gln Cys

<210> SEQ ID NO 295
<211> LENGTH: 19
<212> TYPE: PRT
<213> ORGANISM: Artificial Sequence
<220> FEATURE:
<223> OTHER INFORMATION: IgG heavy chain signal peptide

<400> SEQUENCE: 295

Met Glu Leu Gly Leu Arg Trp Val Phe Leu Val Ala Ile Leu Glu Gly
1 5 10 15

Val Gln Cys

<210> SEQ ID NO 296
<211> LENGTH: 19
<212> TYPE: PRT
<213> ORGANISM: Artificial Sequence
<220> FEATURE:
<223> OTHER INFORMATION: IgG heavy chain signal peptide

<400> SEQUENCE: 296

Met Lys His Leu Trp Phe Phe Leu Leu Leu Val Ala Ala Pro Arg Trp
1 5 10 15

Val Leu Ser

<210> SEQ ID NO 297
<211> LENGTH: 19
<212> TYPE: PRT
<213> ORGANISM: Artificial Sequence
<220> FEATURE:
<223> OTHER INFORMATION: IgG heavy chain signal peptide

<400> SEQUENCE: 297

Met Asp Trp Thr Trp Arg Ile Leu Phe Leu Val Ala Ala Ala Thr Gly
1 5 10 15

Ala His Ser

<210> SEQ ID NO 298
<211> LENGTH: 19
<212> TYPE: PRT
<213> ORGANISM: Artificial Sequence
<220> FEATURE:
<223> OTHER INFORMATION: IgG heavy chain signal peptide

<400> SEQUENCE: 298

Met Asp Trp Thr Trp Arg Phe Leu Phe Val Val Ala Ala Ala Thr Gly
1 5 10 15

Val Gln Ser

<210> SEQ ID NO 299
<211> LENGTH: 19
<212> TYPE: PRT
<213> ORGANISM: Artificial Sequence
<220> FEATURE:
<223> OTHER INFORMATION: IgG heavy chain signal peptide

<400> SEQUENCE: 299

Met Glu Phe Gly Leu Ser Trp Leu Phe Leu Val Ala Ile Leu Lys Gly
1 5 10 15

Val Gln Cys

<210> SEQ ID NO 300
<211> LENGTH: 19
<212> TYPE: PRT
<213> ORGANISM: Artificial Sequence
<220> FEATURE:
<223> OTHER INFORMATION: IgG heavy chain signal peptide

<400> SEQUENCE: 300

Met Glu Phe Gly Leu Ser Trp Val Phe Leu Val Ala Leu Phe Arg Gly
1 5 10 15

Val Gln Cys

<210> SEQ ID NO 301
<211> LENGTH: 26
<212> TYPE: PRT
<213> ORGANISM: Artificial Sequence
<220> FEATURE:
<223> OTHER INFORMATION: IgG heavy chain signal peptide

<400> SEQUENCE: 301

Met Asp Leu Leu His Lys Asn Met Lys His Leu Trp Phe Phe Leu Leu
1 5 10 15

Leu Val Ala Ala Pro Arg Trp Val Leu Ser
20 25

<210> SEQ ID NO 302
<211> LENGTH: 22
<212> TYPE: PRT

<213> ORGANISM: Artificial Sequence
<220> FEATURE:
<223> OTHER INFORMATION: IgG Kappa light chain signal sequences

<400> SEQUENCE: 302

Met Asp Met Arg Val Pro Ala Gln Leu Leu Gly Leu Leu Leu Leu Trp
1 5 10 15

Leu Ser Gly Ala Arg Cys
20

<210> SEQ ID NO 303
<211> LENGTH: 22
<212> TYPE: PRT
<213> ORGANISM: Artificial Sequence
<220> FEATURE:
<223> OTHER INFORMATION: IgG Kappa light chain signal sequences

<400> SEQUENCE: 303

Met Lys Tyr Leu Leu Pro Thr Ala Ala Ala Gly Leu Leu Leu Leu Ala
1 5 10 15

Ala Gln Pro Ala Met Ala
20

<210> SEQ ID NO 304
<211> LENGTH: 17
<212> TYPE: PRT
<213> ORGANISM: Artificial Sequence
<220> FEATURE:
<223> OTHER INFORMATION: Gaussia luciferase

<400> SEQUENCE: 304

Met Gly Val Lys Val Leu Phe Ala Leu Ile Cys Ile Ala Val Ala Glu
1 5 10 15

Ala

<210> SEQ ID NO 305
<211> LENGTH: 18
<212> TYPE: PRT
<213> ORGANISM: Artificial Sequence
<220> FEATURE:
<223> OTHER INFORMATION: Human albumin

<400> SEQUENCE: 305

Met Lys Trp Val Thr Phe Ile Ser Leu Leu Phe Leu Phe Ser Ser Ala
1 5 10 15

Tyr Ser

<210> SEQ ID NO 306
<211> LENGTH: 18
<212> TYPE: PRT
<213> ORGANISM: Artificial Sequence
<220> FEATURE:
<223> OTHER INFORMATION: Human chymotrypsinogen

<400> SEQUENCE: 306

Met Ala Phe Leu Trp Leu Leu Ser Cys Trp Ala Leu Leu Gly Thr Thr
1 5 10 15

Phe Gly

<210> SEQ ID NO 307
<211> LENGTH: 14
<212> TYPE: PRT
<213> ORGANISM: Artificial Sequence
<220> FEATURE:

<223> OTHER INFORMATION: Human interleukin-2

<400> SEQUENCE: 307

Met Gln Leu Leu Ser Cys Ile Ala Leu Ile Leu Ala Leu Val
1               5                   10

<210> SEQ ID NO 308
<211> LENGTH: 15
<212> TYPE: PRT
<213> ORGANISM: Artificial Sequence
<220> FEATURE:
<223> OTHER INFORMATION: Human trypsinogen-2

<400> SEQUENCE: 308

Met Asn Leu Leu Leu Ile Leu Thr Phe Val Ala Ala Ala Val Ala
1               5                   10                  15

<210> SEQ ID NO 309
<211> LENGTH: 20
<212> TYPE: PRT
<213> ORGANISM: Artificial Sequence
<220> FEATURE:
<223> OTHER INFORMATION: T2A protein

<400> SEQUENCE: 309

Ser Gly Glu Gly Arg Gly Ser Leu Leu Thr Cys Gly Asp Val Glu Glu
1               5                   10                  15

Asn Pro Gly Pro
            20

<210> SEQ ID NO 310
<211> LENGTH: 18
<212> TYPE: PRT
<213> ORGANISM: Artificial Sequence
<220> FEATURE:
<223> OTHER INFORMATION: T2A protein

<400> SEQUENCE: 310

Glu Gly Arg Gly Ser Leu Leu Thr Cys Gly Asp Val Glu Glu Asn Pro
1               5                   10                  15

Gly Pro

<210> SEQ ID NO 311
<211> LENGTH: 21
<212> TYPE: PRT
<213> ORGANISM: Artificial Sequence
<220> FEATURE:
<223> OTHER INFORMATION: T2A protein

<400> SEQUENCE: 311

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 312
<211> LENGTH: 232
<212> TYPE: PRT
<213> ORGANISM: Artificial Sequence
<220> FEATURE:
<223> OTHER INFORMATION: Blue fluorescent protein

<400> SEQUENCE: 312

Ser Arg Ser Glu Leu Ile Lys Glu Asn Met His Met Lys Leu Tyr Met
1               5                   10                  15

```
Glu Gly Thr Val Asp Asn His His Phe Lys Cys Thr Ser Glu Gly Glu
            20                  25                  30

Gly Lys Pro Tyr Glu Gly Thr Gln Thr Met Arg Ile Lys Val Val Glu
        35                  40                  45

Gly Gly Pro Leu Pro Phe Ala Phe Asp Ile Leu Ala Thr Ser Phe Leu
    50                  55                  60

Tyr Gly Ser Lys Thr Phe Ile Asn His Thr Gln Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Ile Arg Gly Val Asn Phe Thr
        115                 120                 125

Ser Asn Gly Pro Val Met Gln Lys Lys Thr Leu Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

Thr Tyr Val Glu Gln His Glu Val Ala Ala Arg Tyr Cys Asp Leu Pro
    210                 215                 220

Ser Lys Leu Gly His Lys Leu Asn
225                 230
```

<210> SEQ ID NO 313
<211> LENGTH: 232
<212> TYPE: PRT
<213> ORGANISM: Artificial Sequence
<220> FEATURE:
<223> OTHER INFORMATION: Blue fluorescent protein

<400> SEQUENCE: 313

```
Ser Glu Leu Ile Lys Glu Asn Met His Met Lys Leu Tyr Met Glu Gly
1               5                   10                  15

Thr Val Asp Asn His His Phe Lys Cys Thr Ser Glu Gly Glu Gly Lys
            20                  25                  30

Pro Tyr Glu Gly Thr Gln Thr Met Arg Ile Lys Val Val Glu Gly Gly
        35                  40                  45

Pro Leu Pro Phe Ala Phe Asp Ile Leu Ala Thr Ser Phe Leu Tyr Gly
    50                  55                  60

Ser Lys Thr Phe Ile Asn His Thr Gln Gly Ile Pro Asp Phe Phe Lys
65                  70                  75                  80

Gln Ser Phe Pro Glu Gly Phe Thr Trp Glu Arg Val Thr Thr Tyr Glu
                85                  90                  95

Asp Gly Gly Val Leu Thr Ala Thr Gln Asp Thr Ser Leu Gln Asp Gly
            100                 105                 110

Cys Leu Ile Tyr Asn Val Lys Ile Arg Gly Val Asn Phe Thr Ser Asn
        115                 120                 125

Gly Pro Val Met Gln Lys Lys Thr Leu Gly Trp Glu Ala Phe Thr Glu
    130                 135                 140
```

Thr Leu Tyr Pro Ala Asp Gly Gly Leu Glu Gly Arg Asn Asp Met Ala
145 150 155 160

Leu Lys Leu Val Gly Gly Ser His Leu Ile Ala Asn Ile Lys Thr Thr
165 170 175

Tyr Arg Ser Lys Lys Pro Ala Lys Asn Leu Lys Met Pro Gly Val Tyr
180 185 190

Tyr Val Asp Tyr Arg Leu Glu Arg Ile Lys Glu Ala Asn Asn Glu Thr
195 200 205

Tyr Val Glu Gln His Glu Val Ala Val Ala Arg Tyr Cys Asp Leu Pro
210 215 220

Ser Lys Leu Gly His Lys Leu Asn
225 230

<210> SEQ ID NO 314
<211> LENGTH: 224
<212> TYPE: PRT
<213> ORGANISM: Artificial Sequence
<220> FEATURE:
<223> OTHER INFORMATION: CD86 ECD v38

<400> SEQUENCE: 314

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Leu His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

<210> SEQ ID NO 315
<211> LENGTH: 122
<212> TYPE: PRT
<213> ORGANISM: Artificial Sequence
<220> FEATURE:
<223> OTHER INFORMATION: PD-1 v179 (6-127)

<400> SEQUENCE: 315

Asp Ser Pro Asp Arg Pro Trp Asn Pro Pro Thr Phe Ser Pro Ala Leu
1 5 10 15

Leu Val Val Thr Glu Gly Asp Asn Ala Thr Phe Thr Cys Ser Phe Ser
20 25 30

Asn Thr Ser Glu Ser Phe Val Leu Asn Trp Tyr Arg Met Ser Pro Ser
35 40 45

Asn Gln Thr Asp Lys Leu Ala Ala Phe Pro Glu Asp Arg Asn Gln Pro
50 55 60

Gly Gln Asp Arg Arg Phe Arg Val Thr Gln Leu Pro Asn Gly Arg Asp
65 70 75 80

Tyr His Met Ser Val Asp Arg Ala Arg Arg Asn Asp Ser Gly Thr Tyr
85 90 95

Leu Cys Gly Ala Ile Thr Leu Ala Pro Lys Val Gln Ile Asp Glu Ser
100 105 110

Leu Arg Val Glu Leu Arg Val Thr Glu Arg
115 120

<210> SEQ ID NO 316
<211> LENGTH: 361
<212> TYPE: PRT
<213> ORGANISM: Artificial Sequence
<220> FEATURE:
<223> OTHER INFORMATION: CD86 WT ECD/PD1v179 ECD (6-127) Stack v1

<400> SEQUENCE: 316

Ala Pro Leu Lys Ile Gln Ala Tyr Phe Asn Glu Thr Ala Asp Leu Pro
1 5 10 15

Cys Gln Phe Ala Asn Ser Gln Asn Gln Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile His His Lys Lys Pro Thr Gly
85 90 95

Met Ile Arg Ile His Gln Met Asn Ser Glu Leu Ser Val Leu Ala Asn
100 105 110

Phe Ser Gln Pro Glu Ile Val Pro Ile Ser Asn Ile Thr Glu Asn Val
115 120 125

Tyr Ile Asn Leu Thr Cys Ser Ser Ile His Gly Tyr Pro Glu Pro Lys
130 135 140

Lys Met Ser Val Leu Leu Arg Thr Lys Asn Ser Thr Ile Glu Tyr Asp
145 150 155 160

Gly Val Met Gln Lys Ser Gln Asp Asn Val Thr Glu Leu Tyr Asp Val
165 170 175

Ser Ile Ser Leu Ser Val Ser Phe Pro Asp Val Thr Ser Asn Met Thr
180 185 190

Ile Phe Cys Ile Leu Glu Thr Asp Lys Thr Arg Leu Leu Ser Ser Pro
195 200 205

Phe Ser Ile Glu Leu Glu Asp Pro Gln Pro Pro Pro Asp His Ile Pro
210 215 220

Gly Gly Gly Gly Ser Gly Gly Gly Gly Ser Gly Gly Gly Gly Ser Asp

```
225                 230                 235                 240

Ser Pro Asp Arg Pro Trp Asn Pro Pro Thr Phe Ser Pro Ala Leu Leu
                245                 250                 255

Val Val Thr Glu Gly Asp Asn Ala Thr Phe Thr Cys Ser Phe Ser Asn
            260                 265                 270

Thr Ser Glu Ser Phe Val Leu Asn Trp Tyr Arg Met Ser Pro Ser Asn
        275                 280                 285

Gln Thr Asp Lys Leu Ala Ala Phe Pro Glu Asp Arg Asn Gln Pro Gly
    290                 295                 300

Gln Asp Arg Arg Phe Arg Val Thr Gln Leu Pro Asn Gly Arg Asp Tyr
305                 310                 315                 320

His Met Ser Val Asp Arg Ala Arg Arg Asn Asp Ser Gly Thr Tyr Leu
                325                 330                 335

Cys Gly Ala Ile Thr Leu Ala Pro Lys Val Gln Ile Asp Glu Ser Leu
            340                 345                 350

Arg Val Glu Leu Arg Val Thr Glu Arg
        355                 360


<210> SEQ ID NO 317
<211> LENGTH: 361
<212> TYPE: PRT
<213> ORGANISM: Artificial Sequence
<220> FEATURE:
<223> OTHER INFORMATION: CD86 ECD v1 /PD1v179 ECD (6-127) Stack v2

<400> SEQUENCE: 317

Ala Pro Leu Lys Ile Gln Ala Tyr Phe Asn Glu Thr Val Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Lys Pro Thr Gly
                85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Met Glu Thr Asp Lys Thr Arg Leu Leu Thr Ser Pro
        195                 200                 205

Phe Ser Ile Glu Leu Glu Asp Pro Gln Pro Pro Pro Asp His Ile Pro
    210                 215                 220

Gly Gly Gly Gly Ser Gly Gly Gly Gly Ser Gly Gly Gly Gly Ser Asp
```

```
225                 230                 235                 240

Ser Pro Asp Arg Pro Trp Asn Pro Pro Thr Phe Ser Pro Ala Leu Leu
                245                 250                 255

Val Val Thr Glu Gly Asp Asn Ala Thr Phe Thr Cys Ser Phe Ser Asn
            260                 265                 270

Thr Ser Glu Ser Phe Val Leu Asn Trp Tyr Arg Met Ser Pro Ser Asn
        275                 280                 285

Gln Thr Asp Lys Leu Ala Ala Phe Pro Glu Asp Arg Asn Gln Pro Gly
    290                 295                 300

Gln Asp Arg Arg Phe Arg Val Thr Gln Leu Pro Asn Gly Arg Asp Tyr
305                 310                 315                 320

His Met Ser Val Asp Arg Ala Arg Arg Asn Asp Ser Gly Thr Tyr Leu
                325                 330                 335

Cys Gly Ala Ile Thr Leu Ala Pro Lys Val Gln Ile Asp Glu Ser Leu
            340                 345                 350

Arg Val Glu Leu Arg Val Thr Glu Arg
        355                 360


<210> SEQ ID NO 318
<211> LENGTH: 361
<212> TYPE: PRT
<213> ORGANISM: Artificial Sequence
<220> FEATURE:
<223> OTHER INFORMATION: CD86 ECD v2 /PD1v179 ECD (6-127) Stack v3

<400> SEQUENCE: 318

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Thr Pro Thr Gly
                85                  90                  95

Leu Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Ala Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Pro Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Val Pro Gln Pro Pro Pro Asp His Ile Pro
    210                 215                 220

Gly Gly Gly Gly Ser Gly Gly Gly Gly Ser Gly Gly Gly Gly Ser Asp
```

```
225                 230                 235                 240

Ser Pro Asp Arg Pro Trp Asn Pro Pro Thr Phe Ser Pro Ala Leu Leu
                245                 250                 255

Val Val Thr Glu Gly Asp Asn Ala Thr Phe Thr Cys Ser Phe Ser Asn
            260                 265                 270

Thr Ser Glu Ser Phe Val Leu Asn Trp Tyr Arg Met Ser Pro Ser Asn
        275                 280                 285

Gln Thr Asp Lys Leu Ala Ala Phe Pro Glu Asp Arg Asn Gln Pro Gly
    290                 295                 300

Gln Asp Arg Arg Phe Arg Val Thr Gln Leu Pro Asn Gly Arg Asp Tyr
305                 310                 315                 320

His Met Ser Val Asp Arg Ala Arg Arg Asn Asp Ser Gly Thr Tyr Leu
                325                 330                 335

Cys Gly Ala Ile Thr Leu Ala Pro Lys Val Gln Ile Asp Glu Ser Leu
            340                 345                 350

Arg Val Glu Leu Arg Val Thr Glu Arg
        355                 360


<210> SEQ ID NO 319
<211> LENGTH: 361
<212> TYPE: PRT
<213> ORGANISM: Artificial Sequence
<220> FEATURE:
<223> OTHER INFORMATION: CD86 ECD v3 /PD1v179 ECD (6-127) Stack v4

<400> SEQUENCE: 319

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Ser Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Val Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro Asp His Ile Pro
    210                 215                 220

Gly Gly Gly Gly Ser Gly Gly Gly Gly Ser Gly Gly Gly Gly Ser Asp
```

```
225                 230                 235                 240

Ser Pro Asp Arg Pro Trp Asn Pro Pro Thr Phe Ser Pro Ala Leu Leu
                245                 250                 255

Val Val Thr Glu Gly Asp Asn Ala Thr Phe Thr Cys Ser Phe Ser Asn
            260                 265                 270

Thr Ser Glu Ser Phe Val Leu Asn Trp Tyr Arg Met Ser Pro Ser Asn
        275                 280                 285

Gln Thr Asp Lys Leu Ala Ala Phe Pro Glu Asp Arg Asn Gln Pro Gly
    290                 295                 300

Gln Asp Arg Arg Phe Arg Val Thr Gln Leu Pro Asn Gly Arg Asp Tyr
305                 310                 315                 320

His Met Ser Val Asp Arg Ala Arg Arg Asn Asp Ser Gly Thr Tyr Leu
                325                 330                 335

Cys Gly Ala Ile Thr Leu Ala Pro Lys Val Gln Ile Asp Glu Ser Leu
            340                 345                 350

Arg Val Glu Leu Arg Val Thr Glu Arg
        355                 360


<210> SEQ ID NO 320
<211> LENGTH: 248
<212> TYPE: PRT
<213> ORGANISM: Artificial Sequence
<220> FEATURE:
<223> OTHER INFORMATION: CD86 IgV v4 /PD1v179 ECD (6-127) Stack v5

<400> SEQUENCE: 320

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
                85                  90                  95

Met Ile Arg Ile His Gln Met Asn Ser Glu Leu Ser Val Leu Ala Gly
            100                 105                 110

Gly Gly Gly Ser Gly Gly Gly Gly Ser Gly Gly Gly Gly Ser Asp Ser
        115                 120                 125

Pro Asp Arg Pro Trp Asn Pro Pro Thr Phe Ser Pro Ala Leu Leu Val
    130                 135                 140

Val Thr Glu Gly Asp Asn Ala Thr Phe Thr Cys Ser Phe Ser Asn Thr
145                 150                 155                 160

Ser Glu Ser Phe Val Leu Asn Trp Tyr Arg Met Ser Pro Ser Asn Gln
                165                 170                 175

Thr Asp Lys Leu Ala Ala Phe Pro Glu Asp Arg Asn Gln Pro Gly Gln
            180                 185                 190

Asp Arg Arg Phe Arg Val Thr Gln Leu Pro Asn Gly Arg Asp Tyr His
        195                 200                 205

Met Ser Val Asp Arg Ala Arg Arg Asn Asp Ser Gly Thr Tyr Leu Cys
    210                 215                 220

Gly Ala Ile Thr Leu Ala Pro Lys Val Gln Ile Asp Glu Ser Leu Arg
```

225 230 235 240

Val Glu Leu Arg Val Thr Glu Arg
245

<210> SEQ ID NO 321
<211> LENGTH: 248
<212> TYPE: PRT
<213> ORGANISM: Artificial Sequence
<220> FEATURE:
<223> OTHER INFORMATION: CD86 IgV v5 /PD1v179 ECD (6-127) Stack v6

<400> SEQUENCE: 321

Ala Pro Leu Lys Ile Gln Ala Tyr Phe Asn Glu Thr Val Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Gln Cys Ile Ile Leu His Lys Lys Pro Thr Gly
85 90 95

Met Ile Arg Ile His Gln Met Asn Ser Glu Leu Ser Val Leu Ala Gly
100 105 110

Gly Gly Gly Ser Gly Gly Gly Gly Ser Gly Gly Gly Gly Ser Asp Ser
115 120 125

Pro Asp Arg Pro Trp Asn Pro Pro Thr Phe Ser Pro Ala Leu Leu Val
130 135 140

Val Thr Glu Gly Asp Asn Ala Thr Phe Thr Cys Ser Phe Ser Asn Thr
145 150 155 160

Ser Glu Ser Phe Val Leu Asn Trp Tyr Arg Met Ser Pro Ser Asn Gln
165 170 175

Thr Asp Lys Leu Ala Ala Phe Pro Glu Asp Arg Asn Gln Pro Gly Gln
180 185 190

Asp Arg Arg Phe Arg Val Thr Gln Leu Pro Asn Gly Arg Asp Tyr His
195 200 205

Met Ser Val Asp Arg Ala Arg Arg Asn Asp Ser Gly Thr Tyr Leu Cys
210 215 220

Gly Ala Ile Thr Leu Ala Pro Lys Val Gln Ile Asp Glu Ser Leu Arg
225 230 235 240

Val Glu Leu Arg Val Thr Glu Arg
245

<210> SEQ ID NO 322
<211> LENGTH: 248
<212> TYPE: PRT
<213> ORGANISM: Artificial Sequence
<220> FEATURE:
<223> OTHER INFORMATION: CD86 IgV v6 /PD1v179 ECD (6-127) Stack v7

<400> SEQUENCE: 322

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

```
Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile Leu His Lys Thr Pro Thr Gly
                85                  90                  95

Leu Ile Arg Ile His Gln Met Asn Ser Glu Leu Ser Val Leu Ala Gly
            100                 105                 110

Gly Gly Gly Ser Gly Gly Gly Gly Ser Gly Gly Gly Gly Ser Asp Ser
        115                 120                 125

Pro Asp Arg Pro Trp Asn Pro Pro Thr Phe Ser Pro Ala Leu Leu Val
    130                 135                 140

Val Thr Glu Gly Asp Asn Ala Thr Phe Thr Cys Ser Phe Ser Asn Thr
145                 150                 155                 160

Ser Glu Ser Phe Val Leu Asn Trp Tyr Arg Met Ser Pro Ser Asn Gln
                165                 170                 175

Thr Asp Lys Leu Ala Ala Phe Pro Glu Asp Arg Asn Gln Pro Gly Gln
            180                 185                 190

Asp Arg Arg Phe Arg Val Thr Gln Leu Pro Asn Gly Arg Asp Tyr His
        195                 200                 205

Met Ser Val Asp Arg Ala Arg Arg Asn Asp Ser Gly Thr Tyr Leu Cys
    210                 215                 220

Gly Ala Ile Thr Leu Ala Pro Lys Val Gln Ile Asp Glu Ser Leu Arg
225                 230                 235                 240

Val Glu Leu Arg Val Thr Glu Arg
                245
```

<210> SEQ ID NO 323
<211> LENGTH: 248
<212> TYPE: PRT
<213> ORGANISM: Artificial Sequence
<220> FEATURE:
<223> OTHER INFORMATION: CD86 IgV v7 /PD1v179 ECD (6-127) Stack v8

<400> SEQUENCE: 323

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Ser Ser Glu Leu Ser Val Leu Ala Gly
            100                 105                 110

Gly Gly Gly Ser Gly Gly Gly Gly Ser Gly Gly Gly Gly Ser Asp Ser
        115                 120                 125

Pro Asp Arg Pro Trp Asn Pro Pro Thr Phe Ser Pro Ala Leu Leu Val
    130                 135                 140
```

Val Thr Glu Gly Asp Asn Ala Thr Phe Thr Cys Ser Phe Ser Asn Thr
145 150 155 160

Ser Glu Ser Phe Val Leu Asn Trp Tyr Arg Met Ser Pro Ser Asn Gln
165 170 175

Thr Asp Lys Leu Ala Ala Phe Pro Glu Asp Arg Asn Gln Pro Gly Gln
180 185 190

Asp Arg Arg Phe Arg Val Thr Gln Leu Pro Asn Gly Arg Asp Tyr His
195 200 205

Met Ser Val Asp Arg Ala Arg Arg Asn Asp Ser Gly Thr Tyr Leu Cys
210 215 220

Gly Ala Ile Thr Leu Ala Pro Lys Val Gln Ile Asp Glu Ser Leu Arg
225 230 235 240

Val Glu Leu Arg Val Thr Glu Arg
245

<210> SEQ ID NO 324
<211> LENGTH: 231
<212> TYPE: PRT
<213> ORGANISM: Artificial Sequence
<220> FEATURE:
<223> OTHER INFORMATION: Fc knob

<400> SEQUENCE: 324

Glu Pro Lys Ser Ser Asp Lys Thr His Thr Cys Pro Pro Cys Pro Ala
1 5 10 15

Pro Glu Ala Glu Gly Ala Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Cys Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 325
<211> LENGTH: 231

<212> TYPE: PRT
<213> ORGANISM: Artificial Sequence
<220> FEATURE:
<223> OTHER INFORMATION: Fc hole

<400> SEQUENCE: 325

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 326
<211> LENGTH: 604
<212> TYPE: PRT
<213> ORGANISM: Artificial Sequence
<220> FEATURE:
<223> OTHER INFORMATION: PD1 v1 Fc CD86 ECD v10

<400> SEQUENCE: 326

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Asn Gln Pro
    50                  55                  60

Gly Gln Asp Arg Arg Phe Arg Val Thr Gln Leu Pro Asn Gly Arg Asp
65                  70                  75                  80

Tyr His Met Ser Val Asp Arg Ala Arg Arg Asn Asp Ser Gly Thr Tyr
                85                  90                  95

```
Leu Cys Gly Ala Ile Thr Leu Ala Pro Lys Val Gln Ile Asp Glu Ser
            100                 105                 110

Leu Arg Val Glu Leu Arg Val Thr Glu Arg Gly Ser Gly Gly Gly Gly
        115                 120                 125

Ser Glu Pro Lys Ser Ser Asp Lys Thr His Thr Cys Pro Pro Cys Pro
    130                 135                 140

Ala Pro Glu Ala Glu Gly Ala Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Gly Gly Gly Gly Ser Gly Gly Gly
        355                 360                 365

Gly Ser Gly Gly Gly Gly Ser Gly Gly Gly Gly Ser Ala Pro Leu Lys
    370                 375                 380

Ile Gln Ala Tyr Phe Asn Glu Thr Ala Asp Leu Pro Cys Gln Phe Ala
385                 390                 395                 400

Asn Ser Gln Asn Leu Ser Leu Ser Glu Leu Val Val Phe Trp Gln Asp
                405                 410                 415

Gln Glu Asn Leu Val Leu Asn Glu Val Tyr Leu Gly Lys Glu Lys Phe
            420                 425                 430

Asp Ser Val His Ser Lys Tyr Met Gly Arg Thr Ser Phe Asp Ser Asp
        435                 440                 445

Ser Trp Thr Leu Arg Leu His Asn Leu Gln Ile Lys Asp Lys Gly Leu
    450                 455                 460

Tyr Arg Cys Ile Ile Leu His Lys Lys Pro Thr Gly Met Ile Arg Ile
465                 470                 475                 480

His Gln Met Ser Ser Glu Leu Ser Val Leu Ala Asn Phe Ser Gln Pro
                485                 490                 495

Glu Ile Val Pro Ile Ser Asn Ile Thr Glu Asn Val Tyr Ile Asn Leu
            500                 505                 510
```

Thr Cys Ser Ser Ile His Gly Tyr Pro Glu Pro Lys Lys Met Ser Val
515 520 525

Leu Leu Arg Thr Lys Asn Ser Thr Ile Glu Tyr Asp Gly Val Met Gln
530 535 540

Lys Ser Gln Asp Asn Val Thr Glu Leu Tyr Asp Val Ser Ile Ser Leu
545 550 555 560

Ser Val Ser Phe Pro Asp Val Thr Ser Asn Met Thr Ile Phe Cys Ile
565 570 575

Leu Glu Thr Asp Lys Thr Arg Leu Leu Ser Ser Pro Phe Ser Ile Glu
580 585 590

Leu Glu Asp Pro Gln Pro Pro Pro Asp His Ile Pro
595 600

<210> SEQ ID NO 327
<211> LENGTH: 491
<212> TYPE: PRT
<213> ORGANISM: Artificial Sequence
<220> FEATURE:
<223> OTHER INFORMATION: PD1 v1 Fc CD86 IgV v60

<400> SEQUENCE: 327

Asp Ser Pro Asp Arg Pro Trp Asn Pro Pro Thr Phe Ser Pro Ala Leu
1 5 10 15

Leu Val Val Thr Glu Gly Asp Asn Ala Thr Phe Thr Cys Ser Phe Ser
20 25 30

Asn Thr Ser Glu Ser Phe Val Leu Asn Trp Tyr Arg Met Ser Pro Ser
35 40 45

Asn Gln Thr Asp Lys Leu Ala Ala Phe Pro Glu Asp Arg Asn Gln Pro
50 55 60

Gly Gln Asp Arg Arg Phe Arg Val Thr Gln Leu Pro Asn Gly Arg Asp
65 70 75 80

Tyr His Met Ser Val Asp Arg Ala Arg Arg Asn Asp Ser Gly Thr Tyr
85 90 95

Leu Cys Gly Ala Ile Thr Leu Ala Pro Lys Val Gln Ile Asp Glu Ser
100 105 110

Leu Arg Val Glu Leu Arg Val Thr Glu Arg Gly Ser Gly Gly Gly Gly
115 120 125

Ser Glu Pro Lys Ser Ser Asp Lys Thr His Thr Cys Pro Pro Cys Pro
130 135 140

Ala Pro Glu Ala Glu Gly Ala Pro Ser Val Phe Leu Phe Pro Pro Lys
145 150 155 160

Pro Lys Asp Thr Leu Met Ile Ser Arg Thr Pro Glu Val Thr Cys Val
165 170 175

Val Val Asp Val Ser His Glu Asp Pro Glu Val Lys Phe Asn Trp Tyr
180 185 190

Val Asp Gly Val Glu Val His Asn Ala Lys Thr Lys Pro Arg Glu Glu
195 200 205

Gln Tyr Asn Ser Thr Tyr Arg Val Val Ser Val Leu Thr Val Leu His
210 215 220

Gln Asp Trp Leu Asn Gly Lys Glu Tyr Lys Cys Lys Val Ser Asn Lys
225 230 235 240

Ala Leu Pro Ala Pro Ile Glu Lys Thr Ile Ser Lys Ala Lys Gly Gln
245 250 255

Pro Arg Glu Pro Gln Val Tyr Thr Leu Pro Pro Ser Arg Asp Glu Leu
260 265 270

Thr Lys Asn Gln Val Ser Leu Thr Cys Leu Val Lys Gly Phe Tyr Pro
275 280 285

Ser Asp Ile Ala Val Glu Trp Glu Ser Asn Gly Gln Pro Glu Asn Asn
290 295 300

Tyr Lys Thr Thr Pro Pro Val Leu Asp Ser Asp Gly Ser Phe Phe Leu
305 310 315 320

Tyr Ser Lys Leu Thr Val Asp Lys Ser Arg Trp Gln Gln Gly Asn Val
325 330 335

Phe Ser Cys Ser Val Met His Glu Ala Leu His Asn His Tyr Thr Gln
340 345 350

Lys Ser Leu Ser Leu Ser Pro Gly Gly Gly Gly Gly Ser Gly Gly Gly
355 360 365

Gly Ser Gly Gly Gly Gly Ser Gly Gly Gly Gly Ser Ala Pro Leu Lys
370 375 380

Ile Gln Ala Tyr Phe Asn Glu Thr Ala Asp Leu Pro Cys Gln Phe Ala
385 390 395 400

Asn Ser Gln Asn Leu Ser Leu Ser Glu Leu Val Val Phe Trp Gln Asp
405 410 415

Gln Glu Asn Leu Val Leu Asn Glu Val Tyr Leu Gly Lys Glu Lys Phe
420 425 430

Asp Ser Val His Ser Lys Tyr Met Gly Arg Thr Ser Phe Asp Ser Asp
435 440 445

Ser Trp Thr Leu Arg Leu His Asn Leu Gln Ile Lys Asp Lys Gly Leu
450 455 460

Tyr Arg Cys Ile Ile Leu His Lys Lys Pro Thr Gly Met Ile Arg Ile
465 470 475 480

His Gln Met Ser Ser Glu Leu Ser Val Leu Ala
485 490

<210> SEQ ID NO 328
<211> LENGTH: 360
<212> TYPE: PRT
<213> ORGANISM: Artificial Sequence
<220> FEATURE:
<223> OTHER INFORMATION: PD1 ECD v1 FcK

<400> SEQUENCE: 328

Asp Ser Pro Asp Arg Pro Trp Asn Pro Pro Thr Phe Ser Pro Ala Leu
1 5 10 15

Leu Val Val Thr Glu Gly Asp Asn Ala Thr Phe Thr Cys Ser Phe Ser
20 25 30

Asn Thr Ser Glu Ser Phe Val Leu Asn Trp Tyr Arg Met Ser Pro Ser
35 40 45

Asn Gln Thr Asp Lys Leu Ala Ala Phe Pro Glu Asp Arg Asn Gln Pro
50 55 60

Gly Gln Asp Arg Arg Phe Arg Val Thr Gln Leu Pro Asn Gly Arg Asp
65 70 75 80

Tyr His Met Ser Val Asp Arg Ala Arg Arg Asn Asp Ser Gly Thr Tyr
85 90 95

Leu Cys Gly Ala Ile Thr Leu Ala Pro Lys Val Gln Ile Asp Glu Ser
100 105 110

Leu Arg Val Glu Leu Arg Val Thr Glu Arg Gly Ser Gly Gly Gly Gly
115 120 125

Ser Glu Pro Lys Ser Ser Asp Lys Thr His Thr Cys Pro Pro Cys Pro
130 135 140

```
Ala Pro Glu Ala Glu Gly Ala Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Cys Arg Glu Glu Met
            260                 265                 270

Thr Lys Asn Gln Val Ser Leu Trp Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly
        355                 360
```

<210> SEQ ID NO 329
<211> LENGTH: 349
<212> TYPE: PRT
<213> ORGANISM: Artificial Sequence
<220> FEATURE:
<223> OTHER INFORMATION: CD86 IgV v60 FcH

<400> SEQUENCE: 329

```
Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Ser Ser Glu Leu Ser Val Leu Ala Gly
            100                 105                 110

Ser Gly Gly Gly Gly Ser Glu Pro Lys Ser Ser Asp Lys Thr His Thr
        115                 120                 125

Cys Pro Pro Cys Pro Ala Pro Glu Ala Glu Gly Ala Pro Ser Val Phe
    130                 135                 140
```

Leu Phe Pro Pro Lys Pro Lys Asp Thr Leu Met Ile Ser Arg Thr Pro
145 150 155 160

Glu Val Thr Cys Val Val Val Asp Val Ser His Glu Asp Pro Glu Val
165 170 175

Lys Phe Asn Trp Tyr Val Asp Gly Val Glu Val His Asn Ala Lys Thr
180 185 190

Lys Pro Arg Glu Glu Gln Tyr Asn Ser Thr Tyr Arg Val Val Ser Val
195 200 205

Leu Thr Val Leu His Gln Asp Trp Leu Asn Gly Lys Glu Tyr Lys Cys
210 215 220

Lys Val Ser Asn Lys Ala Leu Pro Ala Pro Ile Glu Lys Thr Ile Ser
225 230 235 240

Lys Ala Lys Gly Gln Pro Arg Glu Pro Gln Val Cys Thr Leu Pro Pro
245 250 255

Ser Arg Glu Glu Met Thr Lys Asn Gln Val Ser Leu Ser Cys Ala Val
260 265 270

Lys Gly Phe Tyr Pro Ser Asp Ile Ala Val Glu Trp Glu Ser Asn Gly
275 280 285

Gln Pro Glu Asn Asn Tyr Lys Thr Thr Pro Pro Val Leu Asp Ser Asp
290 295 300

Gly Ser Phe Phe Leu Val Ser Lys Leu Thr Val Asp Lys Ser Arg Trp
305 310 315 320

Gln Gln Gly Asn Val Phe Ser Cys Ser Val Met His Glu Ala Leu His
325 330 335

Asn His Tyr Thr Gln Lys Ser Leu Ser Leu Ser Pro Gly
340 345

<210> SEQ ID NO 330
<211> LENGTH: 362
<212> TYPE: PRT
<213> ORGANISM: Artificial Sequence
<220> FEATURE:
<223> OTHER INFORMATION: FcH CD86 Igv v60

<400> SEQUENCE: 330

Glu Pro Lys Ser Ser Asp Lys Thr His Thr Cys Pro Pro Cys Pro Ala
1 5 10 15

Pro Glu Ala Glu Gly Ala Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Cys Thr Leu Pro Pro Ser Arg Glu Glu Met Thr
130 135 140

Lys Asn Gln Val Ser Leu Ser Cys Ala Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Val
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ala Pro Leu Lys Ile
245 250 255

Gln Ala Tyr Phe Asn Glu Thr Ala Asp Leu Pro Cys Gln Phe Ala Asn
260 265 270

Ser Gln Asn Leu Ser Leu Ser Glu Leu Val Val Phe Trp Gln Asp Gln
275 280 285

Glu Asn Leu Val Leu Asn Glu Val Tyr Leu Gly Lys Glu Lys Phe Asp
290 295 300

Ser Val His Ser Lys Tyr Met Gly Arg Thr Ser Phe Asp Ser Asp Ser
305 310 315 320

Trp Thr Leu Arg Leu His Asn Leu Gln Ile Lys Asp Lys Gly Leu Tyr
325 330 335

Arg Cys Ile Ile Leu His Lys Lys Pro Thr Gly Met Ile Arg Ile His
340 345 350

Gln Met Ser Ser Glu Leu Ser Val Leu Ala
355 360

<210> SEQ ID NO 331
<211> LENGTH: 491
<212> TYPE: PRT
<213> ORGANISM: Artificial Sequence
<220> FEATURE:
<223> OTHER INFORMATION: PD1 ECD v1 FcH CD86 IgV v60

<400> SEQUENCE: 331

Asp Ser Pro Asp Arg Pro Trp Asn Pro Pro Thr Phe Ser Pro Ala Leu
1 5 10 15

Leu Val Val Thr Glu Gly Asp Asn Ala Thr Phe Thr Cys Ser Phe Ser
20 25 30

Asn Thr Ser Glu Ser Phe Val Leu Asn Trp Tyr Arg Met Ser Pro Ser
35 40 45

Asn Gln Thr Asp Lys Leu Ala Ala Phe Pro Glu Asp Arg Asn Gln Pro
50 55 60

Gly Gln Asp Arg Arg Phe Arg Val Thr Gln Leu Pro Asn Gly Arg Asp
65 70 75 80

Tyr His Met Ser Val Asp Arg Ala Arg Arg Asn Asp Ser Gly Thr Tyr
85 90 95

Leu Cys Gly Ala Ile Thr Leu Ala Pro Lys Val Gln Ile Asp Glu Ser
100 105 110

Leu Arg Val Glu Leu Arg Val Thr Glu Arg Gly Ser Gly Gly Gly Gly
115 120 125

Ser Glu Pro Lys Ser Ser Asp Lys Thr His Thr Cys Pro Pro Cys Pro
130 135 140

Ala Pro Glu Ala Glu Gly Ala Pro Ser Val Phe Leu Phe Pro Pro Lys
145 150 155 160

```
Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Cys Thr Leu Pro Pro Ser Arg Glu Glu Met
            260                 265                 270

Thr Lys Asn Gln Val Ser Leu Ser Cys Ala Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Val Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Gly Gly Gly Gly Ser Gly Gly Gly
        355                 360                 365

Gly Ser Gly Gly Gly Gly Ser Gly Gly Gly Gly Ser Ala Pro Leu Lys
    370                 375                 380

Ile Gln Ala Tyr Phe Asn Glu Thr Ala Asp Leu Pro Cys Gln Phe Ala
385                 390                 395                 400

Asn Ser Gln Asn Leu Ser Leu Ser Glu Leu Val Val Phe Trp Gln Asp
                405                 410                 415

Gln Glu Asn Leu Val Leu Asn Glu Val Tyr Leu Gly Lys Glu Lys Phe
            420                 425                 430

Asp Ser Val His Ser Lys Tyr Met Gly Arg Thr Ser Phe Asp Ser Asp
        435                 440                 445

Ser Trp Thr Leu Arg Leu His Asn Leu Gln Ile Lys Asp Lys Gly Leu
    450                 455                 460

Tyr Arg Cys Ile Ile Leu His Lys Lys Pro Thr Gly Met Ile Arg Ile
465                 470                 475                 480

His Gln Met Ser Ser Glu Leu Ser Val Leu Ala
                485                 490
```

<210> SEQ ID NO 332
<211> LENGTH: 231
<212> TYPE: PRT
<213> ORGANISM: Artificial Sequence
<220> FEATURE:
<223> OTHER INFORMATION: Fc

<400> SEQUENCE: 332

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 333
<211> LENGTH: 231
<212> TYPE: PRT
<213> ORGANISM: Artificial Sequence
<220> FEATURE:
<223> OTHER INFORMATION: Fc

<400> SEQUENCE: 333

Glu Pro Lys Ser Ser Asp Lys Thr His Thr Cys Pro Pro Cys Pro Ala
1 5 10 15

Pro Glu Ala Glu Gly Ala Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Thr Cys Leu Val Lys Gly Phe Tyr Pro Ser
145 150 155 160

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230


<210> SEQ ID NO 334
<211> LENGTH: 115
<212> TYPE: PRT
<213> ORGANISM: Artificial Sequence
<220> FEATURE:
<223> OTHER INFORMATION: PD-1 v94 ECD (13-127)

<400> SEQUENCE: 334

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Val Ala
        35                  40                  45

Ala Phe Pro Glu Asp His Ser Gln Pro Gly Gln Asp Cys Arg Phe Arg
    50                  55                  60

Val Thr Gln Leu Pro Asn Gly Arg Asp Tyr His Met Ser Leu Val Arg
65                  70                  75                  80

Ala Arg Arg Asn Asp Ser Gly Thr Tyr Leu Cys Gly Ala Ile Ser Leu
                85                  90                  95

Ala Pro Lys Val Gln Ile Asn Glu Ser Leu Leu Val Glu Leu Arg Val
            100                 105                 110

Thr Glu Arg
        115


<210> SEQ ID NO 335
<211> LENGTH: 111
<212> TYPE: PRT
<213> ORGANISM: Artificial Sequence
<220> FEATURE:
<223> OTHER INFORMATION: PD-1 wt IgV

<400> SEQUENCE: 335

Pro Thr Phe Ser Pro Ala Leu Leu Val Val Thr Glu Gly Asp Asn Ala
1               5                   10                  15

Thr Phe Thr Cys Ser Phe Ser Asn Thr Ser Glu Ser Phe Val Leu Asn
            20                  25                  30

Trp Tyr Arg Met Ser Pro Ser Asn Gln Thr Asp Lys Leu Ala Ala Phe
        35                  40                  45

Pro Glu Asp Arg Ser Gln Pro Gly Gln Asp Cys Arg Phe Arg Val Thr
    50                  55                  60

Gln Leu Pro Asn Gly Arg Asp Phe His Met Ser Val Val Arg Ala Arg
65                  70                  75                  80

Arg Asn Asp Ser Gly Thr Tyr Leu Cys Gly Ala Ile Ser Leu Ala Pro
                85                  90                  95

Lys Ala Gln Ile Lys Glu Ser Leu Arg Ala Glu Leu Arg Val Thr
            100                 105                 110
```

<210> SEQ ID NO 336
<211> LENGTH: 122
<212> TYPE: PRT
<213> ORGANISM: Artificial Sequence
<220> FEATURE:
<223> OTHER INFORMATION: PD-1 wt ECD 6-127

<400> SEQUENCE: 336

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg
        115                 120
```

<210> SEQ ID NO 337
<211> LENGTH: 115
<212> TYPE: PRT
<213> ORGANISM: Artificial Sequence
<220> FEATURE:
<223> OTHER INFORMATION: PD-1 wt ECD (13-127)

<400> SEQUENCE: 337

```
Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Cys Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Ala Gln Ile Lys Glu Ser Leu Arg Ala Glu Leu Arg Val
            100                 105                 110

Thr Glu Arg
        115
```

<210> SEQ ID NO 338
<211> LENGTH: 122
<212> TYPE: PRT
<213> ORGANISM: Artificial Sequence
<220> FEATURE:
<223> OTHER INFORMATION: PD-1 v201 ECD (6-127)

<400> SEQUENCE: 338

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe His Val Ile Trp His Arg Glu Ser Pro Ser
        35                  40                  45

Gly Gln Thr Asp Thr Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Val Cys Gly Val Ile Ser Leu Ala Pro Lys Ile Gln Ile Lys Glu Ser
            100                 105                 110

Leu Arg Ala Glu Leu Arg Val Thr Glu Arg
        115                 120


<210> SEQ ID NO 339
<211> LENGTH: 111
<212> TYPE: PRT
<213> ORGANISM: Artificial Sequence
<220> FEATURE:
<223> OTHER INFORMATION: PD-1 wt IgV

<400> SEQUENCE: 339

Pro Thr Phe Ser Pro Ala Leu Leu Val Val Thr Glu Gly Asp Asn Ala
1               5                   10                  15

Thr Phe Thr Cys Ser Phe Ser Asn Thr Ser Glu Ser Phe Val Leu Asn
            20                  25                  30

Trp Tyr Arg Met Ser Pro Ser Asn Gln Thr Asp Lys Leu Ala Ala Phe
        35                  40                  45

Pro Glu Asp Arg Ser Gln Pro Gly Gln Asp Cys Arg Phe Arg Val Thr
    50                  55                  60

Gln Leu Pro Asn Gly Arg Asp Phe His Met Ser Val Val Arg Ala Arg
65                  70                  75                  80

Arg Asn Asp Ser Gly Thr Tyr Leu Cys Gly Ala Ile Ser Leu Ala Pro
                85                  90                  95

Lys Ala Gln Ile Lys Glu Ser Leu Arg Ala Glu Leu Arg Val Thr
            100                 105                 110


<210> SEQ ID NO 340
<211> LENGTH: 449
<212> TYPE: PRT
<213> ORGANISM: Artificial Sequence
<220> FEATURE:
<223> OTHER INFORMATION: Pertuz HC

<400> SEQUENCE: 340

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 341
<211> LENGTH: 214
<212> TYPE: PRT
<213> ORGANISM: Artificial Sequence
<220> FEATURE:
<223> OTHER INFORMATION: Pertuz LC

<400> SEQUENCE: 341

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 342
<211> LENGTH: 575
<212> TYPE: PRT
<213> ORGANISM: Artificial Sequence
<220> FEATURE:
<223> OTHER INFORMATION: CD86 H3701 IgV HC

<400> SEQUENCE: 342

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Leu His Lys Lys Pro Thr Gly
85 90 95

Met Ile Arg Ile His Gln Met Ser Ser Glu Leu Ser Val Leu Ala Gly
100 105 110

Gly Gly Gly Ser Gly Gly Gly Gly Ser Gly Gly Gly Gly Ser Glu Val
115 120 125

```
Gln Leu Val Glu Ser Gly Gly Gly Leu Val Gln Pro Gly Gly Ser Leu
    130                 135                 140

Arg Leu Ser Cys Ala Ala Ser Gly Phe Thr Phe Thr Asp Tyr Thr Met
145                 150                 155                 160

Asp Trp Val Arg Gln Ala Pro Gly Lys Gly Leu Glu Trp Val Ala Asp
                165                 170                 175

Val Asn Pro Asn Ser Gly Gly Ser Ile Tyr Asn Gln Arg Phe Lys Gly
            180                 185                 190

Arg Phe Thr Leu Ser Val Asp Arg Ser Lys Asn Thr Leu Tyr Leu Gln
        195                 200                 205

Met Asn Ser Leu Arg Ala Glu Asp Thr Ala Val Tyr Tyr Cys Ala Arg
    210                 215                 220

Asn Leu Gly Pro Ser Phe Tyr Phe Asp Tyr Trp Gly Gln Gly Thr Leu
225                 230                 235                 240

Val Thr Val Ser Ser Ala Ser Thr Lys Gly Pro Ser Val Phe Pro Leu
                245                 250                 255

Ala Pro Ser Ser Lys Ser Thr Ser Gly Gly Thr Ala Ala Leu Gly Cys
            260                 265                 270

Leu Val Lys Asp Tyr Phe Pro Glu Pro Val Thr Val Ser Trp Asn Ser
        275                 280                 285

Gly Ala Leu Thr Ser Gly Val His Thr Phe Pro Ala Val Leu Gln Ser
    290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
                325                 330                 335

Thr Lys Val Asp Lys Lys Val Glu Pro Lys Ser Cys Asp Lys Thr His
            340                 345                 350

Thr Cys Pro Pro Cys Pro Ala Pro Glu Leu Leu Gly Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
        435                 440                 445

Cys Lys Val Ser Asn Lys Ala Leu Pro Ala Pro Ile Glu Lys Thr Ile
    450                 455                 460

Ser Lys Ala Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
```

545 550 555 560

His Asn His Tyr Thr Gln Lys Ser Leu Ser Leu Ser Pro Gly Lys
565 570 575

<210> SEQ ID NO 343
<211> LENGTH: 340
<212> TYPE: PRT
<213> ORGANISM: Artificial Sequence
<220> FEATURE:
<223> OTHER INFORMATION: CD86 H3701 IgV LC

<400> SEQUENCE: 343

Ala Pro Leu Lys Ile Gln Ala Tyr Phe Asn Glu Thr Ala Asp Leu Pro
1 5 10 15

Cys Gln Phe Ala Asn Ser Gln Asn Leu Ser Leu Ser Glu Leu Val Val
20 25 30

Phe Trp Gln Asp Gln Glu Asn Leu Val Leu Asn Glu Val Tyr Leu Gly
35 40 45

Lys Glu Lys Phe Asp Ser Val His Ser Lys Tyr Met Gly Arg Thr Ser
50 55 60

Phe Asp Ser Asp Ser Trp Thr Leu Arg Leu His Asn Leu Gln Ile Lys
65 70 75 80

Asp Lys Gly Leu Tyr Arg Cys Ile Ile Leu His Lys Lys Pro Thr Gly
85 90 95

Met Ile Arg Ile His Gln Met Ser Ser Glu Leu Ser Val Leu Ala Gly
100 105 110

Gly Gly Gly Ser Gly Gly Gly Gly Ser Gly Gly Gly Gly Ser Asp Ile
115 120 125

Gln Met Thr Gln Ser Pro Ser Ser Leu Ser Ala Ser Val Gly Asp Arg
130 135 140

Val Thr Ile Thr Cys Lys Ala Ser Gln Asp Val Ser Ile Gly Val Ala
145 150 155 160

Trp Tyr Gln Gln Lys Pro Gly Lys Ala Pro Lys Leu Leu Ile Tyr Ser
165 170 175

Ala Ser Tyr Arg Tyr Thr Gly Val Pro Ser Arg Phe Ser Gly Ser Gly
180 185 190

Ser Gly Thr Asp Phe Thr Leu Thr Ile Ser Ser Leu Gln Pro Glu Asp
195 200 205

Phe Ala Thr Tyr Tyr Cys Gln Gln Tyr Tyr Ile Tyr Pro Tyr Thr Phe
210 215 220

Gly Gln Gly Thr Lys Val Glu Ile Lys Arg Thr Val Ala Ala Pro Ser
225 230 235 240

Val Phe Ile Phe Pro Pro Ser Asp Glu Gln Leu Lys Ser Gly Thr Ala
245 250 255

Ser Val Val Cys Leu Leu Asn Asn Phe Tyr Pro Arg Glu Ala Lys Val
260 265 270

Gln Trp Lys Val Asp Asn Ala Leu Gln Ser Gly Asn Ser Gln Glu Ser
275 280 285

Val Thr Glu Gln Asp Ser Lys Asp Ser Thr Tyr Ser Leu Ser Ser Thr
290 295 300

Leu Thr Leu Ser Lys Ala Asp Tyr Glu Lys His Lys Val Tyr Ala Cys
305 310 315 320

Glu Val Thr His Gln Gly Leu Ser Ser Pro Val Thr Lys Ser Phe Asn
325 330 335

Arg Gly Glu Cys

340

<210> SEQ ID NO 344
<211> LENGTH: 579
<212> TYPE: PRT
<213> ORGANISM: Artificial Sequence
<220> FEATURE:
<223> OTHER INFORMATION: HC CD86 H3701 IgV

<400> SEQUENCE: 344

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr 355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Gly Gly Gly Gly Ser Gly Gly Gly Gly Ser Gly Gly Gly Gly Ser Gly
450 455 460

Gly Gly Gly Ser Ala Pro Leu Lys Ile Gln Ala Tyr Phe Asn Glu Thr
465 470 475 480

Ala Asp Leu Pro Cys Gln Phe Ala Asn Ser Gln Asn Leu Ser Leu Ser
485 490 495

Glu Leu Val Val Phe Trp Gln Asp Gln Glu Asn Leu Val Leu Asn Glu
500 505 510

Val Tyr Leu Gly Lys Glu Lys Phe Asp Ser Val His Ser Lys Tyr Met
515 520 525

Gly Arg Thr Ser Phe Asp Ser Asp Ser Trp Thr Leu Arg Leu His Asn
530 535 540

Leu Gln Ile Lys Asp Lys Gly Leu Tyr Arg Cys Ile Ile Leu His Lys
545 550 555 560

Lys Pro Thr Gly Met Ile Arg Ile His Gln Met Ser Ser Glu Leu Ser
565 570 575

Val Leu Ala

<210> SEQ ID NO 345
<211> LENGTH: 345
<212> TYPE: PRT
<213> ORGANISM: Artificial Sequence
<220> FEATURE:
<223> OTHER INFORMATION: LC CD86 H3701 IgV

<400> SEQUENCE: 345

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Gly Gly Gly Gly Ser
210 215 220

Gly Gly Gly Gly Ser Gly Gly Gly Gly Ser Ala Pro Leu Lys Ile Gln
225 230 235 240

Ala Tyr Phe Asn Glu Thr Ala Asp Leu Pro Cys Gln Phe Ala Asn Ser
245 250 255

Gln Asn Leu Ser Leu Ser Glu Leu Val Val Phe Trp Gln Asp Gln Glu
260 265 270

Asn Leu Val Leu Asn Glu Val Tyr Leu Gly Lys Glu Lys Phe Asp Ser
275 280 285

Val His Ser Lys Tyr Met Gly Arg Thr Ser Phe Asp Ser Asp Ser Trp
290 295 300

Thr Leu Arg Leu His Asn Leu Gln Ile Lys Asp Lys Gly Leu Tyr Arg
305 310 315 320

Cys Ile Ile Leu His Lys Lys Pro Thr Gly Met Ile Arg Ile His Gln
325 330 335

Met Ser Ser Glu Leu Ser Val Leu Ala
340 345

<210> SEQ ID NO 346
<211> LENGTH: 445
<212> TYPE: PRT
<213> ORGANISM: Artificial Sequence
<220> FEATURE:
<223> OTHER INFORMATION: Panit HC

<400> SEQUENCE: 346

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu
35 40 45

Trp Ile Gly His Ile Tyr Tyr Ser Gly Asn Thr Asn Tyr Asn Pro Ser
50 55 60

Leu Lys Ser Arg Leu Thr Ile Ser Ile Asp Thr Ser Lys Thr Gln Phe
65 70 75 80

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser Ala Ser Thr Lys Gly Pro Ser Val Phe
115 120 125

Pro Leu Ala Pro Cys Ser Arg Ser Thr Ser Glu Ser Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Asn Phe Gly Thr Gln Thr Tyr Thr Cys Asn Val Asp His Lys Pro
195 200 205

Ser Asn Thr Lys Val Asp Lys Thr Val Glu Arg Lys Cys Cys Val Glu
210 215 220

Cys Pro Pro Cys Pro Ala Pro Pro Val Ala Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Phe Arg Val Val Ser Val Leu
290 295 300

Thr Val Val His Gln Asp Trp Leu Asn Gly Lys Glu Tyr Lys Cys Lys
305 310 315 320

Val Ser Asn Lys Gly Leu Pro Ala Pro Ile Glu Lys Thr Ile Ser Lys
325 330 335

Thr Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Met Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 347
<211> LENGTH: 214
<212> TYPE: PRT
<213> ORGANISM: Artificial Sequence
<220> FEATURE:
<223> OTHER INFORMATION: Panit LC

<400> SEQUENCE: 347

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

```
Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 348
<211> LENGTH: 571
<212> TYPE: PRT
<213> ORGANISM: Artificial Sequence
<220> FEATURE:
<223> OTHER INFORMATION: CD86 H3701 IgV HC

<400> SEQUENCE: 348

Ala Pro Leu Lys Ile Gln Ala Tyr Phe Asn Glu Thr Ala Asp Leu Pro
1               5                   10                  15

Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Ser Ser Glu Leu Ser Val Leu Ala Gly
            100                 105                 110

Gly Gly Gly Ser Gly Gly Gly Gly Ser Gly Gly Gly Gly Ser Gln Val
        115                 120                 125

Gln Leu Gln Glu Ser Gly Pro Gly Leu Val Lys Pro Ser Glu Thr Leu
    130                 135                 140

Ser Leu Thr Cys Thr Val Ser Gly Gly Ser Val Ser Ser Gly Asp Tyr
145                 150                 155                 160

Tyr Trp Thr Trp Ile Arg Gln Ser Pro Gly Lys Gly Leu Glu Trp Ile
                165                 170                 175

Gly His Ile Tyr Tyr Ser Gly Asn Thr Asn Tyr Asn Pro Ser Leu Lys
            180                 185                 190

Ser Arg Leu Thr Ile Ser Ile Asp Thr Ser Lys Thr Gln Phe Ser Leu
        195                 200                 205

Lys Leu Ser Ser Val Thr Ala Ala Asp Thr Ala Ile Tyr Tyr Cys Val
    210                 215                 220
```

Arg Asp Arg Val Thr Gly Ala Phe Asp Ile Trp Gly Gln Gly Thr Met
225 230 235 240

Val Thr Val Ser Ser Ala Ser Thr Lys Gly Pro Ser Val Phe Pro Leu
245 250 255

Ala Pro Cys Ser Arg Ser Thr Ser Glu Ser Thr Ala Ala Leu Gly Cys
260 265 270

Leu Val Lys Asp Tyr Phe Pro Glu Pro Val Thr Val Ser Trp Asn Ser
275 280 285

Gly Ala Leu Thr Ser Gly Val His Thr Phe Pro Ala Val Leu Gln Ser
290 295 300

Ser Gly Leu Tyr Ser Leu Ser Ser Val Val Thr Val Pro Ser Ser Asn
305 310 315 320

Phe Gly Thr Gln Thr Tyr Thr Cys Asn Val Asp His Lys Pro Ser Asn
325 330 335

Thr Lys Val Asp Lys Thr Val Glu Arg Lys Cys Cys Val Glu Cys Pro
340 345 350

Pro Cys Pro Ala Pro Pro Val Ala Gly Pro Ser Val Phe Leu Phe Pro
355 360 365

Pro Lys Pro Lys Asp Thr Leu Met Ile Ser Arg Thr Pro Glu Val Thr
370 375 380

Cys Val Val Val Asp Val Ser His Glu Asp Pro Glu Val Gln Phe Asn
385 390 395 400

Trp Tyr Val Asp Gly Val Glu Val His Asn Ala Lys Thr Lys Pro Arg
405 410 415

Glu Glu Gln Phe Asn Ser Thr Phe Arg Val Val Ser Val Leu Thr Val
420 425 430

Val His Gln Asp Trp Leu Asn Gly Lys Glu Tyr Lys Cys Lys Val Ser
435 440 445

Asn Lys Gly Leu Pro Ala Pro Ile Glu Lys Thr Ile Ser Lys Thr Lys
450 455 460

Gly Gln Pro Arg Glu Pro Gln Val Tyr Thr Leu Pro Pro Ser Arg Glu
465 470 475 480

Glu Met Thr Lys Asn Gln Val Ser Leu Thr Cys Leu Val Lys Gly Phe
485 490 495

Tyr Pro Ser Asp Ile Ala Val Glu Trp Glu Ser Asn Gly Gln Pro Glu
500 505 510

Asn Asn Tyr Lys Thr Thr Pro Pro Met Leu Asp Ser Asp Gly Ser Phe
515 520 525

Phe Leu Tyr Ser Lys Leu Thr Val Asp Lys Ser Arg Trp Gln Gln Gly
530 535 540

Asn Val Phe Ser Cys Ser Val Met His Glu Ala Leu His Asn His Tyr
545 550 555 560

Thr Gln Lys Ser Leu Ser Leu Ser Pro Gly Lys
565 570

<210> SEQ ID NO 349
<211> LENGTH: 340
<212> TYPE: PRT
<213> ORGANISM: Artificial Sequence
<220> FEATURE:
<223> OTHER INFORMATION: CD86 H3701 IgV LC

<400> SEQUENCE: 349

Ala Pro Leu Lys Ile Gln Ala Tyr Phe Asn Glu Thr Ala Asp Leu Pro
1 5 10 15

```
Cys Gln Phe Ala Asn Ser Gln Asn Leu Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

Phe Asp Ser Asp Ser Trp Thr Leu Arg Leu His Asn Leu Gln Ile Lys
65                  70                  75                  80

Asp Lys Gly Leu Tyr Arg Cys Ile Ile Leu His Lys Lys Pro Thr Gly
                85                  90                  95

Met Ile Arg Ile His Gln Met Ser Ser Glu Leu Ser Val Leu Ala Gly
            100                 105                 110

Gly Gly Gly Ser Gly Gly Gly Gly Ser Gly Gly Gly Gly Ser Asp Ile
        115                 120                 125

Gln Met Thr Gln Ser Pro Ser Ser Leu Ser Ala Ser Val Gly Asp Arg
    130                 135                 140

Val Thr Ile Thr Cys Gln Ala Ser Gln Asp Ile Ser Asn Tyr Leu Asn
145                 150                 155                 160

Trp Tyr Gln Gln Lys Pro Gly Lys Ala Pro Lys Leu Leu Ile Tyr Asp
                165                 170                 175

Ala Ser Asn Leu Glu Thr Gly Val Pro Ser Arg Phe Ser Gly Ser Gly
            180                 185                 190

Ser Gly Thr Asp Phe Thr Phe Thr Ile Ser Ser Leu Gln Pro Glu Asp
        195                 200                 205

Ile Ala Thr Tyr Phe Cys Gln His Phe Asp His Leu Pro Leu Ala Phe
    210                 215                 220

Gly Gly Gly Thr Lys Val Glu Ile Lys Arg Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
        275                 280                 285

Val Thr Glu Gln Asp Ser Lys Asp Ser Thr Tyr Ser Leu Ser Ser Thr
    290                 295                 300

Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
                325                 330                 335

Arg Gly Glu Cys
            340
```

<210> SEQ ID NO 350
<211> LENGTH: 575
<212> TYPE: PRT
<213> ORGANISM: Artificial Sequence
<220> FEATURE:
<223> OTHER INFORMATION: HC CD86 H3701 IgV

<400> SEQUENCE: 350

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30
```

-continued

```
Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445
```

Ser Gly Gly Gly Gly Ser Gly Gly Gly Gly Ser Gly Gly Gly Gly Ser
450 455 460

Ala Pro Leu Lys Ile Gln Ala Tyr Phe Asn Glu Thr Ala Asp Leu Pro
465 470 475 480

Cys Gln Phe Ala Asn Ser Gln Asn Leu Ser Leu Ser Glu Leu Val Val
485 490 495

Phe Trp Gln Asp Gln Glu Asn Leu Val Leu Asn Glu Val Tyr Leu Gly
500 505 510

Lys Glu Lys Phe Asp Ser Val His Ser Lys Tyr Met Gly Arg Thr Ser
515 520 525

Phe Asp Ser Asp Ser Trp Thr Leu Arg Leu His Asn Leu Gln Ile Lys
530 535 540

Asp Lys Gly Leu Tyr Arg Cys Ile Ile Leu His Lys Lys Pro Thr Gly
545 550 555 560

Met Ile Arg Ile His Gln Met Ser Ser Glu Leu Ser Val Leu Ala
565 570 575

<210> SEQ ID NO 351
<211> LENGTH: 345
<212> TYPE: PRT
<213> ORGANISM: Artificial Sequence
<220> FEATURE:
<223> OTHER INFORMATION: LC CD86 H3701 IgV

<400> SEQUENCE: 351

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Phe Cys Gln His Phe Asp His Leu Pro Leu
85 90 95

Ala Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gly Gly Gly Gly Ser Gly Gly Gly Gly Ser
210 215 220

Gly Gly Gly Gly Ser Gly Gly Gly Gly Ser Ala Pro Leu Lys Ile Gln
225 230 235 240

Ala Tyr Phe Asn Glu Thr Ala Asp Leu Pro Cys Gln Phe Ala Asn Ser
245 250 255

Gln Asn Leu Ser Leu Ser Glu Leu Val Val Phe Trp Gln Asp Gln Glu
260 265 270

Asn Leu Val Leu Asn Glu Val Tyr Leu Gly Lys Glu Lys Phe Asp Ser
275 280 285

Val His Ser Lys Tyr Met Gly Arg Thr Ser Phe Asp Ser Asp Ser Trp
290 295 300

Thr Leu Arg Leu His Asn Leu Gln Ile Lys Asp Lys Gly Leu Tyr Arg
305 310 315 320

Cys Ile Ile Leu His Lys Lys Pro Thr Gly Met Ile Arg Ile His Gln
325 330 335

Met Ser Ser Glu Leu Ser Val Leu Ala
340 345

<210> SEQ ID NO 352
<211> LENGTH: 446
<212> TYPE: PRT
<213> ORGANISM: Artificial Sequence
<220> FEATURE:
<223> OTHER INFORMATION: Ramuc HC

<400> SEQUENCE: 352

Glu Val Gln Leu Val Gln Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Thr Asp Ala Phe Asp Ile Trp Gly Gln Gly Thr Met Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly Lys
435 440 445

<210> SEQ ID NO 353
<211> LENGTH: 214
<212> TYPE: PRT
<213> ORGANISM: Artificial Sequence
<220> FEATURE:
<223> OTHER INFORMATION: Ramuc LC

<400> SEQUENCE: 353

Asp Ile Gln Met Thr Gln Ser Pro Ser Ser Val Ser Ala Ser Ile Gly
1 5 10 15

Asp Arg Val Thr Ile Thr Cys Arg Ala Ser Gln Gly Ile Asp Asn Trp
20 25 30

Leu Gly Trp Tyr Gln Gln Lys Pro Gly Lys Ala Pro Lys Leu Leu Ile
35 40 45

Tyr Asp Ala Ser Asn Leu Asp Thr Gly Val Pro Ser Arg Phe Ser Gly
50 55 60

Ser Gly Ser Gly Thr Tyr Phe Thr Leu Thr Ile Ser Ser Leu Gln Ala
65 70 75 80

Glu Asp Phe Ala Val Tyr Phe Cys Gln Gln Ala Lys Ala Phe Pro Pro
85 90 95

Thr Phe Gly Gly Gly Thr Lys Val Asp Ile Lys Gly Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

-continued

```
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210
```

CD86 VARIANT IMMUNOMODULATORY PROTEINS AND USES THEREOF

CROSS-REFERENCE TO RELATED APPLICATIONS

This application is a National Stage application under 35 U.S.C. § 371 of International Application No. PCT/US2019/063808, filed on Nov. 27, 2019 which claims priority from U.S. provisional application No. 62/774,131 filed Nov. 30, 2018, entitled "CD86 VARIANT IMMUNOMODULATORY PROTEINS AND USES THEREOF" and U.S. provisional application No. 62/862,001 filed Jun. 14, 2019, entitled "CD86 VARIANT IMMUNOMODULATORY PROTEINS AND USES THEREOF," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 761612002800SeqList.txt, created May 28, 2021, which is 599,068 bytes in size. The information in the electronic format of the Sequence Listing is incorporated by reference in its entirety.

FIELD

The present disclosure relates to therapeutic compositions for modulating immune response in the treatment of cancer and immunological diseases. In some aspects, the present disclosure relates to particular variants of CD86, and immunomodulatory proteins thereof, that exhibit altered binding affinity for a cognate binding partner, such as increased affinity for CD28. Also provided are methods and uses of such immunomodulatory proteins.

BACKGROUND

Modulation of the immune response by intervening in the processes that occur in the immunological synapse (IS) formed by and between antigen-presenting cells (APCs) or target cells and lymphocytes is of increasing medical interest. Mechanistically, cell surface proteins in the IS can involve the coordinated and often simultaneous interaction of multiple protein targets with a single protein to which they bind. IS interactions occur in close association with the junction of two cells, and a single protein in this structure can interact with both a protein on the same cell (cis) as well as a protein on the associated cell (trans), likely at the same time. Although therapeutics are known that can modulate the IS, improved therapeutics are needed. Provided are immunomodulatory proteins, including soluble proteins or transmembrane immunomodulatory proteins capable of being expressed on cells, that meet such needs.

SUMMARY

Provided herein are variant CD86 polypeptides, containing an extracellular domain or an IgV domain or specific binding fragment thereof, wherein the variant CD86 polypeptide contains one or more amino acid modifications in an unmodified CD86 polypeptide or a specific binding fragment thereof corresponding to position(s) selected from among 13, 18, 25, 28, 33, 38, 39, 40, 43, 45, 52, 53, 60, 68, 71, 77, 79, 80, 82, 86, 88, 89, 90, 92, 93, 97, 102, 104, 113, 114, 123, 128, 129, 132, 133, 137, 141, 143, 144, 148, 153, 154, 158, 170, 172, 175, 178, 180, 181, 183, 185, 192, 193, 196, 197, 198, 205, 206, 207, 212, 215, 216, 222, 223, or 224, with reference to positions set forth in SEQ ID NO:29. In some embodiments, the amino acid modifications contain amino acid substitutions, deletions or insertions. In some embodiments, the unmodified CD86 polypeptide is a mammalian CD86 polypeptide or a specific binding fragment thereof. In some embodiments, the unmodified CD86 polypeptide is a human CD86 polypeptide or a specific binding fragment thereof. In some embodiments, the variant CD86 polypeptide contains the extracellular domain of a human CD86, wherein the one or more amino acid modifications are in one or more residues of the extracellular domain of the unmodified CD86 polypeptide. In some embodiments, the unmodified CD86 polypeptide contains (i) the sequence of amino acids set forth in SEQ ID NO:29, (ii) a sequence of amino acids that has at least 95% sequence identity to SEQ ID NO:29; or (iii) a portion thereof containing an IgV domain or specific binding fragment of the IgV domain. In some embodiments, the unmodified CD86 contains the sequence of amino acids set forth in SEQ ID NO:29. In some embodiments, the portion thereof comprises amino acid residues 33-131 or 24-134 of the IgV domain or specific binding fragment of the IgV domain.

In some embodiments, the unmodified CD86 polypeptide contains (i) the sequence of amino acids set forth in SEQ ID NO: 123, (ii) a sequence of amino acids that has at least 95% sequence identity to SEQ ID NO: 123; or (iii) a portion thereof containing an IgV domain or specific binding fragment of the IgV domain. In some embodiments, the unmodified CD86 contains the sequence of amino acids set forth in SEQ ID NO:123.

In some embodiments, the unmodified CD86 polypeptide contains (i) the sequence of amino acids set forth in SEQ ID NO:122, (ii) a sequence of amino acids that has at least 95% sequence identity to SEQ ID NO:122; or (iii) or a specific binding fragment thereof. In some embodiments, the unmodified CD86 contains the sequence of amino acids set forth in SEQ ID NO:122.

In some embodiments, the specific binding fragment has a length of at least 50, 60, 70, 80, 90, 95 or more amino acids. In some embodiments, the specific binding fragment comprises a length that is at least 80% of the length of the IgV domain set forth as residues 33-131 of SEQ ID NO:2. In some embodiments, the variant CD86 comprises up to 1, 2, 3, 4, 5, 6, 7, 8, 9, 10, 11, 12, 13, 14, 15, 16, 17, 18, 19 or 20 amino acid modifications, optionally amino acid substitutions, insertions, and/or deletions. In some embodiments, the one or more amino acid modifications are substitutions. In some embodiments, the one or more amino acid modifications are insertions. In some embodiments, the one or more amino acid modifications are deletions. In some embodiments, the one or more amino acid modification are one or more amino acid substitutions selected from A13V, Q18K, Q25L, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, H90L, H90Y, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T or I223F, or a conservative amino acid substitution thereof.

In some embodiments, the variant CD86 polypeptide contains one or more amino acid modifications selected from among Q25L/T71A/H90Y, Q25L/D53G/E212V, Q25L/H90L, N43K/I79N/H90L/I178T/E198D, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/528G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S, E38V/S114G/P143H, H90Y/L180S, H90Y/Y129N, I89V/H90L/I193V, K80E/H90Y/H222T/I223F/P224L, K80M/I88T, K92I/F113S, M60K/H90L, Q25L/F33I/H90L, Q25L/F33I/Q86R/H90L/K93T, Q25L/H90L, Q25L/H90L/P185S, Q25L/H90L/P185S/P224L, Q25L/H90L/S179R, Q25L/H90Y/S181P/I193V, Q25L/K82T/H90L/T152S/S207P, Q25L/Q86R/H90L/K93T, or S28G/H90Y. In some embodiments, the one or more amino acid modifications are at position 25 and/or position 90. In some embodiments, the one or more amino acid modifications contain Q25L, H90Y, or H90L. In some embodiments, the one or more amino acid modifications contain Q25L. In some embodiments, the one or more amino acid modification contains H90Y. In some embodiments, the one or more amino acid modifications contain H90L. In some embodiments, the one or more amino acid modifications contain modifications at position 25 and position 90. In some embodiments, the one or more amino acid modifications are selected from Q25L/H90Y or Q25L/H90L. In some embodiments, the one or more amino acid modifications contain Q25L/H90Y or Q25L/H90L and additional amino acid modifications. In some embodiments, the one or more amino acid modifications contain Q25L/H90Y or Q25L/H90L and one or more amino acid modifications selected from A13V, Q18K, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T or I223F, or a conservative amino acid substitution thereof.

In some embodiments, the variant CD86 polypeptide contains one or more amino acid modifications selected from among Q25L/T71A/H90Y, Q25L/D53G/E212V, Q25L/H90L, N43K/I79N/H90L/I178T/E198D, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/S28G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S, H90Y/L180S, H90Y/Y129N, I89V/H90L/I193V, K80E/H90Y/H222T/I223F/P224L, M60K/H90L; Q25L/F33I/H90L; Q25L/F33I/Q86R/H90L/K93T; Q25L/H90L; Q25L/H90L/P185S; Q25L/H90L/P185S/P224L; Q25L/H90L/S179R; Q25L/H90Y/S181P/I193V; Q25L/K82T/H90L/T152S/S207P; Q25L/Q86R/H90L/K93T, S28G/H90Y, A13V/Q25L/H90L, Q25L/H90L/K93T/M97L, Q25L/Q86R/H90L or I89V/H90L.

In some embodiments, the variant CD86 polypeptide contains one or more amino acid modifications A13V/Q25L/H90L. In some embodiments, the variant CD86 polypeptide contains one or more amino acid modifications A13V/Q25L/H90L/S181P/L197M/S206T. In some embodiments, the variant CD86 polypeptide contains one or more amino acid modifications Q25L/H90L/K93T/M97L. In some embodiments, the variant CD86 polypeptide contains one or more amino acid modifications Q25L/H90L/K93T/M97L/T133A/S181P/D215V. In some embodiments, the variant CD86 polypeptide contains one or more amino acid modifications Q25L/Q86R/H90L. In some embodiments, the variant CD86 polypeptide contains one or more amino acid modifications Q25L/Q86R/H90L/N104S. In some embodiments, the variant CD86 polypeptide contains one or more amino acid modifications I89V/H90L. In some embodiments, the variant CD86 polypeptide contains one or more amino acid modifications I89V/H90L/I193V. In some embodiments, the variant CD86 polypeptide contains one or more amino acid modifications M60K/H90L. In some embodiments, the variant CD86 polypeptide contains one or more amino acid modifications Q25L/F33I/H90L. In some embodiments, the variant CD86 polypeptide contains one or more amino acid modifications Q25L/H90L/P185S.

In some embodiments, the variant CD86 polypeptide comprises a sequence of amino acids that exhibits at least 85%, 86%, 87%, 88%, 89%, 90%, 91%, 92%, 93%, 94%, 95%, 96%, 97%, 98% or 99% sequence identity to SEQ ID NO: 29 or a specific binding fragment thereof.

In some embodiments, the variant CD86 polypeptide specifically binds to the ectodomain of CD28 with increased affinity compared to the binding of the unmodified CD86 for the same ectodomain. In some embodiments, the binding affinity is increased at least at or about 1.5-fold, at least at or about 2.0-fold, at least at or about 5.0-fold, at least at or about 10-fold, at least at or about 20-fold, at least at or about 30-fold, at least at or about 40-fold, at least at or about 50-fold, at least at or about 60-fold, at least at or about 70-fold, at least at or about 80-fold, at least at or about 90-fold, at least at or about 100-fold, or at least at or about 125-fold.

In some embodiments, the variant CD86 polypeptide specifically binds to the ectodomain of CTLA-4 with decreased affinity compared to the binding of the unmodified CD86 for the same ectodomain. In some embodiments, the decreased binding affinity is decreased at least at or about 1.2-fold, at least at or about 1.4-fold, at least at or about 1.5-fold, at least at or about 1.75-fold, at least at or about 2.0-fold, at least at or about 2.5-fold, at least at or about 3.0-fold, at least at or about 4.0-fold, or at least at or about 5.0-fold. In some embodiments, the variant CD86 polypeptide specifically binds to the ectodomain of CTLA-4 with the same or similar binding affinity as the binding of the unmodified CD86 for the same ectodomain, optionally wherein the same or similar binding affinity is from at or about 90% to 120% of the binding affinity of the unmodified CD86.

In some embodiments, the variant CD86 polypeptide contains the full extracellular domain. In some embodiments, the variant CD86 polypeptide contains the sequence of amino acids set forth in any of SEQ ID NOS: 85-121 or a specific binding fragment thereof, a sequence of amino acids that exhibits at least 95% sequence identity to any of SEQ ID NOS: 85-121 or a specific binding fragment thereof and that contains the one or more of the amino acid modifications of the respective SEQ ID NO set forth in any of SEQ ID NOS: 85-121. In some embodiments, the variant CD86 polypeptide contains the sequence of amino acids set forth in any of SEQ ID NOS: 141-177 or a specific binding fragment thereof, a sequence of amino acids that exhibits at least 95% sequence identity to any of SEQ ID NOS: 141-177 or a specific binding fragment thereof and that contains the one or more of the amino acid modifications of the respective SEQ ID NO set forth in any of SEQ ID NOS: 141-177.

In some embodiments, the CD28 is a human CD28. In some embodiments, the CTLA-4 is a human CTLA-4. In some embodiments, the variant CD86 polypeptide of is a soluble protein.

In some embodiments, the variant CD86 polypeptide lacks the CD86 transmembrane domain and intracellular signaling domain; and/or the variant CD86 polypeptide is not capable of being expressed on the surface of a cell. In some embodiments, the variant CD86 polypeptide is linked to a multimerization domain. In some embodiments, the multimerization domain is an Fc domain or a variant thereof with reduced effector function. In some embodiments, the variant CD86 polypeptide is linked to an Fc domain or a variant thereof with reduced effector function. In some embodiments, the Fc domain is a human IgG1 or is a variant thereof with reduced effector function. In some embodiments, the Fc domain contains the sequence of amino acids set forth in SEQ ID NO: 229 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 229. In some embodiments, the Fc domain is or contains the sequence of amino acids set forth in SEQ ID NO: 229.

In some embodiments, the Fc domain is a variant IgG1 Fc domain containing one or more amino acid modifications selected from among E233P, L234A, L234V, L235A, L235E, G236del, G237A, S267K, N297G, V302C and K447del, each by EU numbering. In some embodiments, the Fc domain contains the amino acid modifications L234A/L235E/G237A. In some embodiments, the Fc domain contains the amino acid modification C220S by EU numbering. In some embodiments, the Fc domain contains the amino acid modification K447del by EU numbering. In some embodiments, the Fc domain contains the sequence of amino acids set forth in SEQ ID NO: 230 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 230 and contains one or more of the respective amino acid modifications set forth in SEQ ID NO: 230 compared to human IgG1. In some embodiments, the Fc domain is or contains the sequence of amino acids set forth in SEQ ID NO: 230.

In some embodiments, the variant CD86 polypeptide is linked to the multimerization domain or Fc indirectly via a linker, optionally a G4S linker. In some embodiments, the variant CD86 polypeptide is a transmembrane immunomodulatory protein further containing a transmembrane domain, optionally wherein the transmembrane domain is linked, directly or indirectly, to the extracellular domain (ECD) or specific binding fragment thereof of the variant CD86 polypeptide. In some embodiments, the transmembrane domain contains the sequence of amino acids set forth as residues 248-268 of SEQ ID NO: 2 or a functional variant thereof that exhibits at least 85% sequence identity to residues 248-268 of SEQ ID NO: 2. In some embodiments, the variant CD86 polypeptide further contains a cytoplasmic domain, optionally wherein the cytoplasmic domain is linked, directly or indirectly, to the transmembrane domain. In some embodiments, the cytoplasmic domain is or contains a native CD86 cytoplasmic domain. In some embodiments, the cytoplasmic domain contains the sequence of amino acids set forth as residues 269-329 of SEQ ID NO: 2 or a functional variant thereof that exhibits at least 85% sequence identity to residues 269-329 of SEQ ID NO: 2. In some embodiments, the cytoplasmic domain contains an ITAM signaling motif and/or is or contains an intracellular signaling domain of CD3 zeta.

In some embodiments, the variant CD86 polypeptide does not contain a cytoplasmic signaling domain and/or is not capable of mediating or modulating an intracellular signal when expressed on a cell.

Provided herein are immunomodulatory proteins, containing a first variant CD86 polypeptide of any variant CD86 polypeptide described herein and a second variant CD86 polypeptide of any variant CD86 polypeptide described herein. In some embodiments, the first and second variant CD86 polypeptides are linked indirectly via a linker. In some embodiments, the first and second variant CD86 polypeptide are each linked to a multimerization domain, whereby the immunomodulatory protein is a multimer containing the first and second variant CD86 polypeptide. In some embodiments, the multimer is a dimer, optionally a homodimer. In some embodiments, the multimer is a homodimer. In some embodiments, the first variant CD86 polypeptide and the second variant CD86 polypeptide are the same.

Provided herein are immunomodulatory proteins, containing the any of the variant CD86 polypeptide described herein linked, directly or indirectly via a linker, to a second polypeptide containing an immunoglobulin superfamily (IgSF) domain of an IgSF family member. In some embodiments, the IgSF domain is an affinity-modified IgSF domain, said affinity-modified IgSF domain containing one or more amino acid modifications compared to the unmodified or wild-type IgSF domain of the IgSF family member. In some embodiments, the IgSF domain is an affinity modified IgSF domain that exhibits altered binding to one or more of its cognate binding partner(s) compared to the binding of the unmodified or wild-type IgSF domain of the IgSF family member to the same one or more cognate binding partner(s). In some embodiments, the IgSF domain exhibits increased binding to one or more of its cognate binding partner(s) compared to the binding of the unmodified or wild-type IgSF domain of the IgSF family member to the same one or more cognate binding partner(s).

In some embodiments, the IgSF domain of the second polypeptide is a tumor-localizing moiety that binds to a ligand expressed on a tumor or is an inflammatory-localizing moiety that binds to a cell or tissue associated with an inflammatory environment. In some embodiments, the ligand is B7H6. In some embodiments, the IgSF domain is from NKp30. In some embodiments, the immunomodulatory protein further contains a multimerization domain linked to at least one of the variant CD86 polypeptide, or the second polypeptide. In some embodiments, the immunomodulatory protein described herein further contains a third polypeptide containing an IgSF domain of an IgSF family member or an affinity-modified IgSF domain thereof, said affinity-modified IgSF domain containing one or more amino acid modifications compared to the unmodified or wild-type IgSF domain of the IgSF family member. In some embodiments, the third polypeptide is the same as the first and/or second polypeptide; or the third polypeptide is different from the first and/or second polypeptide.

In some embodiments, the immunomodulatory protein further contains a multimerization domain linked to at least one of the variant CD86 polypeptide, the second polypeptide and/or the third polypeptide. In some embodiments, the multimerization domain is an Fc domain of an immunoglobulin, optionally wherein the immunoglobulin protein is human and/or the Fc region is human. In some embodiments, the immunoglobulin protein is human and/or the Fc region is human. In some embodiments, the Fc domain is an IgG1, IgG2 or IgG4, or is a variant thereof with reduced effector function. In some embodiments, the Fc domain is an IgG1 Fc domain, optionally a human IgG1, or is a variant thereof with reduced effector function. In some embodiments, the Fc domain is a human IgG1 Fc domain. In some embodiments, the Fc domain contains the sequence of amino acids set forth in SEQ ID NO: 229 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 229. In some embodiments, the Fc domain is or contains the sequence of amino acids set forth in SEQ ID NO: 229. In some embodiments, the Fc domain is a variant IgG1 containing one or more amino acid substitutions and the one or more amino acid substitutions are selected from E233P, L234A, L234V, L235A, L235E, G236del, G237A, S267K, or N297G, each numbered according to EU index by Kabat. In some embodiments, the Fc domain contains the amino acid substitution N297G, the amino acid substitutions R292C/N297G/V302C, or the amino acid substitutions L234A/L235E/G237A, each numbered according to the EU index of Kabat. In some embodiments, the variant Fc region further contains the amino acid substitution C220S, wherein the residues are numbered according to the EU index of Kabat. In some embodiments, the Fc region contains K447del, wherein the residue is numbered according to the EU index of Kabat. The Fc region may also be referred to herein as an Fc domain.

In some embodiments, the Fc domain contains the sequence of amino acids set forth in SEQ ID NO: 230 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 230 and contains one or more of the respective amino acid modifications set forth in SEQ ID NO: 230 compared to human IgG1. In some embodiments, the Fc domain is contains the sequence of amino acids set forth in SEQ ID NO: 230.

Provided herein is an immunomodulatory protein comprising a first polypeptide and a second polypeptide, wherein: the first polypeptide comprises at least one IgSF domain linked through a linker to a first Fc domain, wherein the at least one IgSF domain comprises one or both of a variant CD86 polypeptide of any variant CD86 polypeptide provided herein or is an IgSF domain of a PD1 polypeptide or a variant thereof; and the second polypeptide comprises at least one IgSF linked through a linker to a second Fc domain, wherein the at least one IgSF domain comprises one or both of a variant CD86 polypeptide of any variant CD86 polypeptide provided herein or is an IgSF domain of a PD1 polypeptide or a variant thereof, wherein the immunomodulatory proteins comprise at least one IgSF domain of CD86 and at least one IgSF domain of PD-1 or a variant thereof.

In some of any of the provided embodiments, the at least one IgSF domain of the first polypeptide comprises a variant CD86 polypeptide that is any variant CD86 polypeptide provided herein. In some of any of the provided embodiments, the at least one IgSF domain of the second polypeptide comprises a variant PD1 polypeptide. In some of any of the provided embodiments, the at least one IgSF domain of the first polypeptide is a first IgSF domain, wherein the first IgSF domain is a variant CD86 polypeptide that is any variant CD86 polypeptide provided herein, and the first polypeptide comprises a second IgSF domain linked through a linker to the first Fc domain. In some of any of the provided embodiments, the second IgSF domain of the first polypeptide comprises a variant PD1 polypeptide. In some of any of the provided embodiments, the at least one IgSF domain of the second polypeptide is a first IgSF domain, wherein the first IgSF domain is variant CD86 polypeptide that is any variant CD86 polypeptide provided herein, and the second polypeptide comprises a second IgSF domain linked through a linker to the second Fc domain. In some of any of the provided embodiments, the second IgSF domain of the second polypeptide comprises a variant PD1 polypeptide.

In some of any of the provided embodiments, the at least one IgSF domain of the first polypeptide is linked through a linker to the N- or C-terminus of the first Fc domain; and the at least one IgSF domain of the second polypeptide is linked through a linker to the N- or C-terminus of the second Fc domain. In some of any of the provided embodiments, the second IgSF domain of the first polypeptide is linked to the first Fc domain terminus opposite to the terminus linked to the first IgSF domain. In some of any of the provided embodiments, the second IgSF domain of the second polypeptide is linked to the second Fc domain terminus opposite to the terminus linked to the first IgSF domain. In some of any of the provided embodiments, wherein the linker independently comprises the sequence of SEQ ID NO: 222 or 224, optionally wherein the linker comprises 1 to 4 repeats of the sequence of SEQ ID NO:222 or 224. In some of any of the provided embodiments, the first Fc domain and the second Fc domain are identical, optionally, wherein the first Fc domain and the second Fc domain comprise the sequence of SEQ ID NO: 230.

In some of any of the provided embodiments, wherein the first polypeptide and the second polypeptide dimerize through the first and second Fc domains to form a homodimer. In some of any of the provided embodiments, the first and second polypeptides of the homodimer comprise from left to right a variant PD1 polypeptide-linker-Fc-linker-variant CD86 polypeptide.

In some of any of the provided embodiments, the variant PD1 polypeptide comprises the sequence of SEQ ID NO: 315. In some of any of the provided embodiments, the variant CD86 polypeptide comprise the sequence of SEQ ID NO: 94 or 150. In some of any of the provided embodiments, the first Fc domain and the second Fc domain are different, optionally wherein the first and second Fc domains comprise knob-into-hole mutations, optionally wherein the first Fc domain or the second Fc domain comprises the sequence of SEQ ID NO: 346, and the other of the first Fc domain or the second Fc domain comprises the sequence of SEQ ID NO:347.

In some of any of the provided embodiments, the first polypeptide and the second polypeptide dimerize through the first and second Fc domains to form a heterodimer. In some of any of the provided embodiments, the first polypeptide of the heterodimer comprises from left to right a variant PD1 polypeptide-linker-Fc and the the second polypeptide of the heterodimer comprises from left to right a variant CD86 polypeptide-linker-Fc, an Fc-linker-variant CD86 polypeptide, or a variant PD1-linker-Fc-linker-variant CD86.

In some of any of the provided embodiments, the variant PD1 polypeptide comprises the sequence of SEQ ID NO: 315. In some some of any of the provided embodiments, the variant CD86 polypeptide comprise the sequence of SEQ ID NO: 94 or 150. In some of any of the provided embodiments, the first polypeptide of the heterodimer comprises the sequence of SEQ ID NO: 350; and the second polypeptide of the heterodimer comprises the sequence of SEQ ID NO: 351, 352, or 353.

Provided herein are conjugates containing any of the variant CD86 polypeptides described herein linked to a targeting moiety that specifically binds to a molecule on the surface of a cell. In some embodiments, the cell is an immune cell or is a tumor cell. In some embodiments, the moiety is a protein, a peptide, nucleic acid, small molecule or nanoparticle. In some embodiments, the moiety is an antibody or antigen-binding fragment. In some embodiments, the conjugate described herein is a fusion protein.

In some of any of the provided embodiments, the variant CD86 polypeptide is linked to the N- or C-terminus of the $V_H$ or $V_L$ of the antibody. In some embodiments, the the variant CD86 polypeptide is linked to the N- or C-terminus of the $V_H$ or $V_L$ of the antibody is any variant CD86 polypeptide provided herein. In some of any of the provided embodiments, the antibody is an anti-HER2 antibody or an anti-EGFR antibody. In some of any of the provided embodiments, the anti-HER2 antibody is pertuzumab. In some of any of the provided embodiments, the variant CD86 polypeptide is linked to the N-terminus of the $V_H$ of pertuzumab, the C-terminus of the $V_H$ of pertuzumab, the N-terminus of the $V_L$ of pertuzumab, or the C-terminus of the $V_L$ of pertuzumab, optionally comprising the sequence of SEQ ID NO:342, 344, 343, or 345, respectively. In some of any of the provided embodiments, the anti-EGFR antibody is panitumumab. In some of any of the provided embodiments, the variant CD86 polypeptide is linked to the N-terminus of the VH of panitumumab, the C-terminus of the VH of panitumumab, the N-terminus of the VL of panitumumab, or the C-terminus of the VL of panitumumab, optionally comprising the sequence of SEQ ID NO:348, 350, 349, or 351, respectively, or an anti-EGFR antibody.

Provided herein are nucleic acid molecules encoding any of the variant CD86 polypeptides described herein, immunomodulatory proteins described herein, or conjugates that are fusion proteins described herein. In some embodiments, the nucleic acid molecule is a synthetic nucleic acid. In some embodiments, the nucleic acid molecule is cDNA.

Provided herein are vectors containing the nucleic acid molecule described herein. In some embodiments, the vector is an expression vector. In some embodiments, the vector is a mammalian expression vector or a viral vector.

Provided herein are cells containing the vector described herein. In some embodiments, the cell is a mammalian cell. In some embodiments, the cell is a human cell.

Provided herein are methods of of producing a protein containing a variant CD86 polypeptide, including introducing the nucleic acid molecule described herein or vector described herein into a host cell under conditions to express the protein in the cell. In some embodiments, the method further includes isolating or purifying the protein from the cell.

Provided herein are methods of engineering a cell expressing a variant CD86 polypeptide, the method including introducing a nucleic acid molecule encoding the variant CD86 polypeptide described herein, immunomodulatory protein described herein or a conjugate that is a fusion protein described herein into a host cell under conditions in which the polypeptide is expressed in the cell.

Provided herein are engineered cells, containing a variant CD86 polypeptide described herein, immunomodulatory protein described herein or a conjugate that is a fusion protein as described herein, a nucleic acid molecule described herein or a vector described herein. In some embodiments, the variant CD86 polypeptide contains a transmembrane domain or is the transmembrane immunomodulatory protein described herein; and/or the protein containing the variant CD86 polypeptide is expressed on the surface of the cell. In some embodiments, the variant CD86 polypeptide does not contain a transmembrane domain and/or is not expressed on the surface of the cell; and/or the variant CD86 polypeptide is capable of being secreted from the engineered cell. In some embodiments, the protein does not contain a cytoplasmic signaling domain or transmembrane domain and/or is not expressed on the surface of the cell; and/or the protein is capable of being secreted from the engineered cell when expressed.

In some embodiments, the engineered cell is an immune cell. In some embodiments, the immune cell is a lymphocyte. In some embodiments, the lymphocyte is a T cell. In some embodiments, the T cell is a CD4+ and/or CD8+ T cell. In some embodiments, the T cell is a regulatory T cell (Treg). In some embodiments, the engineered cell is a primary cell. In some embodiments, the engineered cell is a mammalian cell. In some embodiments, the engineered cell is a human cell. In some embodiments, the engineered cell further contains a chimeric antigen receptor (CAR). In some embodiments, the engineered cell further contains an engineered T-cell receptor (TCR).

Provided herein are infectious agents containing a variant CD86 polypeptide described herein, immunomodulatory protein described herein or a conjugate that is a fusion protein described herein, a nucleic acid molecule described herein or a vector described herein. In some embodiments, the infectious agent is a bacterium or a virus. In some embodiments, the infectious agent is a virus and the virus is an oncolytic virus.

Provided herein are pharmaceutical compositions, containing a variant CD86 polypeptide described herein, immunomodulatory protein described herein or a conjugate that is a fusion protein described herein, an engineered cell described herein or an infectious agent described herein. In some embodiments, the pharmaceutical composition contains a pharmaceutically acceptable excipient. In some embodiments, the pharmaceutical composition is sterile.

Provided herein are articles of manufacture including the pharmaceutical composition described herein in a vial or a container. In some embodiments, the vial or container is sealed.

Provided herein are kits containing the pharmaceutical composition described herein or the article of manufacture described herein and instructions for use.

Provided herein are methods of modulating an immune response in a subject, the methods including administering a variant CD86 polypeptide described herein, immunomodulatory protein described herein or a conjugate that is a fusion protein described herein, an engineered cell described herein, an infectious agent described herein, or the pharmaceutical composition described herein.

Provided herein are methods of modulating an immune response in a subject, including administering the engineered cells described herein. In some embodiments, the engineered cells are autologous to the subject. In some embodiments, the engineered cells are allogenic to the subject. In some embodiments, modulating the immune response treats a disease or condition in the subject.

Provided herein are methods of treating a disease or condition in a subject in need thereof, the methods including administering a variant CD86 polypeptide described herein, immunomodulatory protein described herein or a conjugate that is a fusion protein described herein, an engineered cell described herein, an infectious agent described herein, or the pharmaceutical composition described herein.

Provided herein are methods of of treating a disease or condition in a subject in need thereof, including administering the engineered cells described herein. In some embodiments, the engineered cells are autologous to the subject. In some embodiments, the engineered cells are allogenic to the subject.

In some embodiments, the immune response is increased in the subject. In some embodiments, an immunomodulatory protein or conjugate containing a variant CD86 polypeptide linked to a tumor-localizing moiety is administered to the subject. In some embodiments, the tumor-localizing moiety is or contains a binding molecule that recognizes a tumor antigen. In some embodiments, the binding molecule contains an antibody or an antigen-binding fragment thereof or contains a wild-type IgSF domain or variant thereof.

In some embodiments, a pharmaceutical composition containing the immunomodulatory protein described herein or the conjugate described herein is administered to the subject. In some embodiments, an engineered cell containing a variant CD86 polypeptide that is a transmembrane immunomodulatory protein is administered to the subject, optionally, wherein the engineered cell described herein. In some embodiments, the transmembrane immunomodulatory protein is as described herein.

In some embodiments, the disease or condition is a tumor or cancer. In some embodiments, the disease or condition is selected from melanoma, lung cancer, bladder cancer, a hematological malignancy, liver cancer, brain cancer, renal cancer, breast cancer, pancreatic cancer, colorectal cancer, spleen cancer, prostate cancer, testicular cancer, ovarian cancer, uterine cancer, gastric carcinoma, a musculoskeletal cancer, a head and neck cancer, a gastrointestinal cancer, a germ cell cancer, or an endocrine and neuroendocrine cancer.

In some embodiments, the immune response is decreased. In some embodiment, a variant CD86 polypeptide or immunomodulatory protein that is soluble is administered to the subject. In some embodiments, the soluble polypeptide or immunomodulatory protein is an Fc fusion protein.

In some embodiments, a pharmaceutical composition containing a variant CD86 polypeptide described herein, or the immunomodulatory protein described herein is administered to the subject. In some embodiments, an engineered cell containing a secretable variant CD86 polypeptide is administered to the subject, optionally wherein the engineered cell is any described herein.

In some embodiments, the disease or condition is an inflammatory or autoimmune disease or condition. In some embodiments, the disease or condition is an Antineutrophil cytoplasmic antibodies (ANCA)-associated vasculitis, a vasculitis, an autoimmune skin disease, transplantation, a Rheumatic disease, an inflammatory gastrointestinal disease, an inflammatory eye disease, an inflammatory neurological disease, an inflammatory pulmonary disease, an inflammatory endocrine disease, or an autoimmune hematological disease. In some embodiments, the disease or condition is selected from inflammatory bowel disease, transplant, Crohn's disease, ulcerative colitis, multiple sclerosis, asthma, rheumatoid arthritis, or psoriasis.

BRIEF DESCRIPTION OF THE DRAWINGS

FIG. 2B shows killing activity of Mock transduced T cells and anti-HER2 CAR-transduced T cells expressing the CAR alone or co-expressing an indicated CD86 ECD TIP at different effector to target ratios (E:T) after 24 hours of co-culturing with NCI-N87.

FIG. 2C shows killing activity of Mock transduced T cells and anti-HER2 CAR-transduced T cells expressing the CAR alone or co-expressing an indicated CD86 ECD TIP at different effector to target ratios (E:T) after 24 hours of co-culturing with SCC152.

FIG. 3 depicts an exemplary alignment of the wildtype CD86 extracellular domain (ECD) sequence set forth in SEQ ID NO: 29 containing residues 24-247 of the CD86 designated "CD86(B7-2)" (SEQ ID NO: 2) with the wildtype IgV sequence set forth in SEQ ID NO: 122 containing residues 33-131 of the CD86 designated "CD86(B7-2)" (SEQ ID NO: 2). The symbol "*" indicates that the two aligned residues are identical. The absence of a "*" between two aligned residues indicates that the aligned amino acids are not identical. The symbol "-" indicates a gap in the alignment. Exemplary, non-limiting positions in SEQ ID NO: 122 corresponding to positions with numbering set forth in SEQ ID NO: 29 are indicated by a box.

FIG. 24 depicts various formats of the provided variant IgSF domain molecules.

DETAILED DESCRIPTION

Figure 1A:
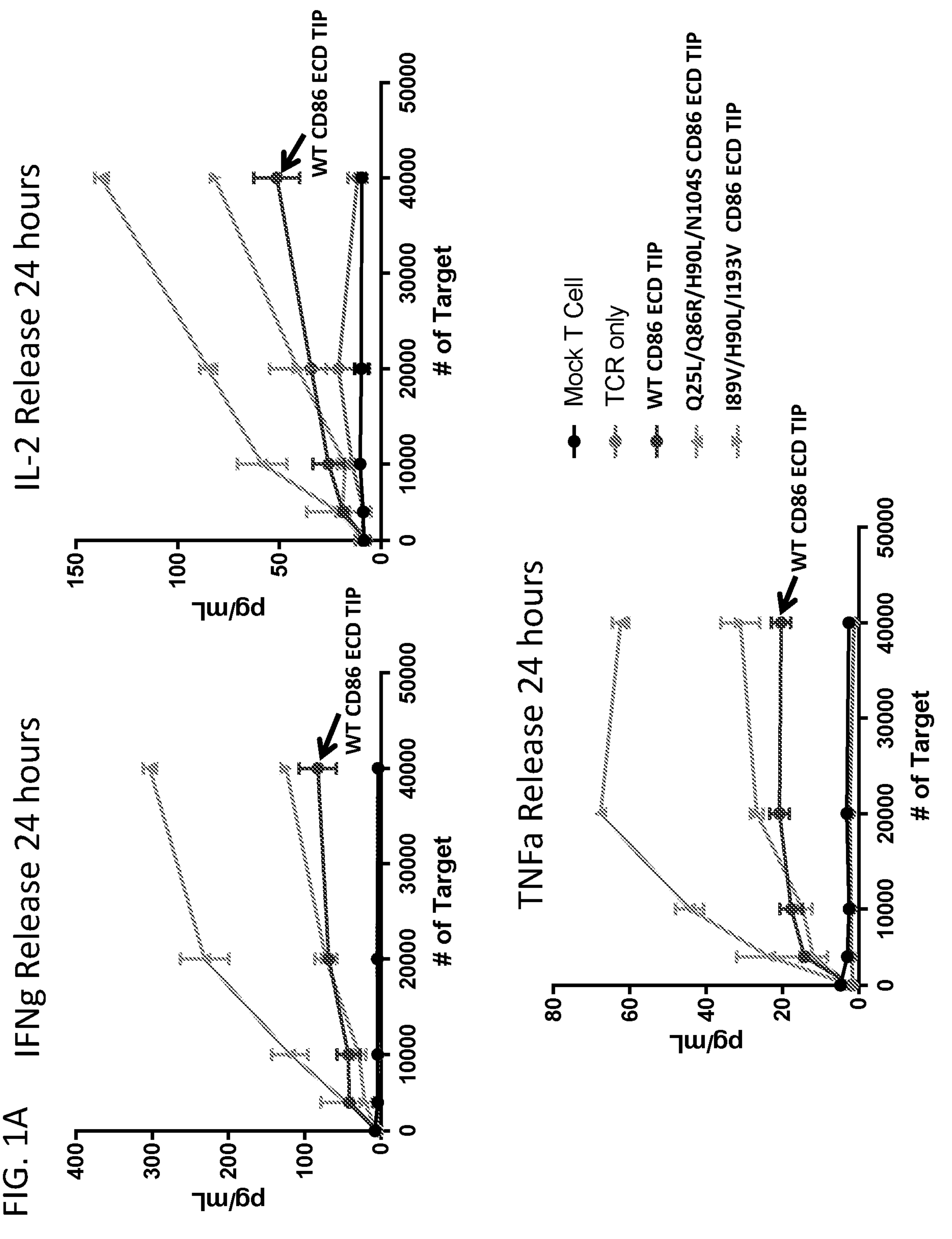
FIG. 1A shows IFN-gamma (IFNγ; top left), IL2 (top right), and TNFα (bottom) release from Mock transduced T cells and E6 TCR-transduced T cells expressing a TCR alone or co-expressing an indicated CD86 ECD TIP in supernatant following 24 hours of co-culture with varying numbers of HLA-A2+HPV+ target cells (SCC152).

Provided herein are immunomodulatory proteins that are or contain variants or mutants of CD86 and specific binding fragments thereof that exhibit altered binding activity or affinity to at least one target ligand cognate binding partner (also called counter-structure ligand protein). In some embodiments, the variant CD86 polypeptides contain one or more amino acid modifications (e.g., amino acid substitutions, deletions, or additions) compared to an unmodified or wild-type CD86 polypeptide. In some embodiments, the variant CD86 polypeptides contain one or more amino acid modifications (e.g., substitutions) compared to an unmodified or wild-type CD86 polypeptide. In some embodiments, the one or more amino acid substitutions are in the extracellular domain, such as are in an IgSF domain (e.g., IgV of IgC), of an unmodified or wild-type CD86 polypeptide. In some embodiments, the variant CD86 polypeptides exhibit altered, such as increased or decreased, binding activity or affinity to one or more of CD28 or CTLA-4 compared to the unmodified or wild-type CD86 not containing the one or more modifications.

In some embodiments, the variant CD86 polypeptides exhibit increased binding affinity to CD28 compared to the unmodified or wild-type CD86 not containing the one or more modifications. In some embodiments, the variant CD86 polypeptides exhibit increased binding affinity to at least CD28 compared to the unmodified or wild-type CD86 not containing the one or more modifications. In some embodiments, the binding affinity is altered (e.g. increased) at least 1.2-fold, 1.4-fold, 1.5-fold, 2.0-fold, 3.0-fold, 4.0-fold, 5.0-fold, 6.0-fold, 7.0-fold, 8.0-fold, 9.0-fold, 10.0-fold, 20.0-fold, 30.0-fold, 40.0-fold, 50.0-fold, 60.0-fold, 70.0-fold, 80.0-fold, 90.0-fold, 100.0-fold, 124.0-fold or more compared to the unmodified or wild-type CD86 not containing the one or more modifications.

In some embodiments, the variant CD86 polypeptides exhibit decreased, no change, or not greater binding affinity to CTLA-4 compared to the unmodified or wild-type CD86 not containing the one or more modifications. In some embodiments, the binding affinity to CTLA-4 is decreased. In some embodiments, the binding affinity is altered (e.g. decreased) at least 1.2-fold, 1.4-fold, 1.5-fold, 2.0-fold, 3.0-fold, 4.0-fold, 5.0-fold, 6.0-fold, 7.0-fold, 8.0-fold, 9.0-fold, 10.0-fold or more compared to the unmodified or wild-type CD86 not containing the one or more modifications.

In some embodiments, the variant CD86 polypeptides and immunomodulatory proteins modulate an immunological immune response, such as increase or decrease an immune response. The particular modulation can be based on the format of the variant CD86 polypeptide, depending on whether a particular format provides an antagonist or blocking activity or an agonist activity. Also provided are various immunomodulatory protein formats of the provided variant polypeptides. As shown herein, alternative formats can facilitate manipulation of the immune response, and hence the therapeutic application. The ability to format the variant polypeptides in various configurations to, depending on the context, antagonize or agonize an immune response, offers flexibility in therapeutic applications based on the same increased binding and activity of a variant CD86 for binding partners. As an example, tethering variant CD86 proteins to a surface can deliver a localized costimulatory signal, while, in other cases, presenting CD86 in a non-localized soluble form can confer antagonistic activity. In some embodiments, the variant CD86 polypeptides and immunomodulatory proteins provided herein can be used for the treatment of diseases or conditions that are associated with a dysregulated immune response.

In some embodiments, the immunomodulatory proteins are soluble. In some embodiments, the immunomodulatory proteins are transmembrane immunomodulatory proteins capable of being expressed on the surface of cells. In some embodiments, the immunomodulatory proteins are secretable immunomodulatory proteins capable of being secreted from a cell in which it is expressed. In some embodiments, also provided herein are one or more other immunomodulatory proteins that are conjugates or fusions containing a variant CD86 polypeptide provided herein and one or more other moiety or polypeptide. In some aspects, provided are engineered cells containing the transmembrane immunomodulatory proteins or secretable immunomodulatory proteins. In some aspects, provided are infectious agents capable of delivering for expression the transmembrane immunomodulatory proteins or secretable immunomodulatory proteins into a cell in which the infectious agent infects. In some embodiments, also provided herein are one or more other immunomodulatory proteins that are conjugates or fusions containing a variant CD86 polypeptide provided herein and one or more other moiety or polypeptide.

In some embodiments, the variant CD86 polypeptide is provided in a format that exhibits agonist activity of its cognate binding partner CD28 and/or that stimulates or initiates costimulatory signaling via CD28. Included among such immunomodulatory protein formats is an engineered cell expressing a variant CD86 polypeptide as a transmembrane immunomodulatory protein. In other cases, the immunomodulatory format can include a fusion with another molecule, such as provided by certain "stack molecules" with other IgSF domains, including tumor-localizing domains (e.g. vCD86-NkP30 constructs), as well as with antibody conjugate formats (e.g. vCD86-anti-HER2 or vCD86-antiHER1 constructs). Such variant CD86 immunomodulatory proteins and formats thereof (e.g. engineered cells or fusion constructs) can be used to treat cancer, viral infections, or bacterial infections. In some embodiments, the variant CD86 immunomodulatory proteins and formats thereof (e.g. engineered cells or fusion constructs) exhibit enhanced costimulatory activity and thereby result in increased T cell activity (e.g. in vivo or in vitro), such as in a primary T cell assay, relative to a wild-type or unmodified CD86 control. In some aspects, T cell activity can be assessed by assessing production of cytokines, such as IL-2, IFN-gamma, or TNFα. In some aspects, the increase, such as the increase in IFN-gamma, IL-2 or TNFα, is by greater than or greater than about 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3.0-fold, 3.5-fold, 4.0-fold, 5.0-fold, 6.0-fold, 7.0-fold, 8.0-fold, 9.0-fold, 10.0-fold or more compared to the unmodified or wild-type CD86 not containing the one or more modifications.

In some embodiments, the variant CD86 polypeptide is provided in a format that exhibits antagonist activity of its cognate binding partner CD28 and/or that blocks or inhibits costimulatory signaling via CD28. Included among such immunomodulatory protein formats is a variant CD86 polypeptide that is soluble (e.g. variant CD86-Fc fusion protein). Such variant CD86 immunomodulatory proteins can be used to treat inflammatory or autoimmune disorders. In some embodiments, the variant CD86 immunomodulatory proteins and formats thereof (e.g. soluble variant CD86-Fc fusion protein) inhibit or block costimulatory signaling and thereby result in decreased T cell activity (e.g. in vivo or in vitro), such as in a primary T cell assay, relative to a wild-type or unmodified CD86 control. In some aspects, T cell activity can be assessed by assessing production of cytokines, such as IL-2, IFN-gamma, or TNFα. In some aspects, the decrease, such as the decrease in IFN-gamma, IL-2, TNFα is by greater than or greater than about 1.1-fold, 1.2-fold, 1.3-fold, 1.4-fold, 1.5-fold, 1.6-fold, 1.7-fold, 1.8-fold, 1.9-fold, 2.0-fold, 3.0-fold, 4.0-fold, 5.0-fold, 6.0-fold, 7.0-fold, 8.0-fold, 9.0-fold, 10.0 fold or more compared to the unmodified or wild-type CD86 not containing the one or more modifications.

In some embodiments, the provided variant CD86 polypeptides modulate T cell activation, expansion, differentiation, and survival via interactions with costimulatory signaling molecules. In general, antigen specific T-cell activation generally requires two distinct signals. The first signal is provided by the interaction of the T-cell receptor (TCR) with major histocompatibility complex (MHC) associated antigens present on antigen presenting cells (APCs). The second signal is costimulatory, e.g., a CD28 costimulatory signal, to TCR engagement and necessary to avoid T-cell apoptosis or anergy.

In some embodiments, under normal physiological conditions, the T cell-mediated immune response is initiated by antigen recognition by the T cell receptor (TCR) and is regulated by a balance of co-stimulatory and inhibitory signals (e.g., immune checkpoint proteins). The immune system relies on immune checkpoints to prevent autoimmunity (i.e., self-tolerance) and to protect tissues from excessive damage during an immune response, for example during an attack against a pathogenic infection. In some cases, however, these immunomodulatory proteins can be dysregulated in diseases and conditions, including tumors, as a mechanism for evading the immune system.

In some embodiments, among known T-cell costimulatory receptors is CD28, which is the T-cell costimulatory receptor for the ligands B7-1 (CD80) and B7-2 (CD86) both of which are present on APCs. These same ligands can also bind to the inhibitory T-cell receptor CTLA4 (cytotoxic T-lymphocyte-associated protein 4) with greater affinity than for CD28; the binding to CTLA4 acts to down-modulate the immune response.

Enhancement or suppression of the activity of CD28 and CTLA-4 receptors has clinical significance for treatment of inflammatory and autoimmune disorders, cancer, and viral infections. In some cases, however, therapies to intervene and alter the costimulatory effects of both receptors are constrained by the spatial orientation requirements as well as size limitations imposed by the confines of the immunological synapse. In some aspects, existing therapeutic drugs, including antibody drugs, may not be able to interact simultaneously with the multiple target proteins involved in modulating these interactions. In addition, in some cases, existing therapeutic drugs may only have the ability to antagonize, but not agonize, an immune response. Additionally, pharmacokinetic differences between drugs that independently target one or the other of these two receptors can create difficulties in properly maintaining a desired blood concentration of such drug combinations throughout the course of treatment. The provided variant CD86 polypeptides and immunomodulatory proteins, and other formats as described, address such problems. Methods of making and using these variants of CD86 polypeptides and immunomodulatory proteins are also provided.

All publications, including patents, patent applications, scientific articles, and databases mentioned in this specification are herein incorporated by reference in their entirety for all purposes to the same extent as if each individual publication, including patent, patent application, scientific article, or database, were specifically and individually indicated to be incorporated by reference. If a definition set forth herein is contrary to or otherwise inconsistent with a definition set forth in the patents, applications, published applications, and other publications that are herein incorporated by reference, the definition set forth herein prevails over the definition that is incorporated herein by reference.

The section headings used herein are for organizational purposes only and are not to be construed as limiting the subject matter described.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms used throughout this specification are defined as follows unless otherwise limited in specific instances. As used in the specification and the appended claims, the singular forms "a," "an," and "the" include plural referents unless the context clearly dictates otherwise. Unless defined otherwise, all technical and scientific terms, acronyms, and abbreviations used herein have the same meaning as commonly understood by one of ordinary skill in the art to which the invention pertains. Unless indicated otherwise, abbreviations and symbols for chemical and biochemical names are per IUPAC-IUB nomenclature. Unless indicated otherwise, all numerical ranges are inclusive of the values defining the range as well as all integer values in-between.

The term "affinity modified" as used in the context of an immunoglobulin superfamily domain, means a mammalian immunoglobulin superfamily (IgSF) domain having an altered amino acid sequence (relative to the corresponding wild-type parental or unmodified IgSF domain) such that it has an increased or decreased binding affinity or avidity to at least one of its cognate binding partners (alternatively "counter-structures") compared to the parental wild-type or unmodified (i.e., non-affinity modified) IgSF control domain. Included in this context is an affinity modified CD86 IgSF domain. In some embodiments, the affinity-modified IgSF domain can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions, in a wildtype or unmodified IgSF domain. An increase or decrease in binding affinity or avidity can be determined using well known binding assays such as flow cytometry. Larsen et al., American Journal of Transplantation, Vol 5: 443-453 (2005). See also, Linsley et al., Immunity, Vol 1(9: 793-801 (1994). An increase in a protein's binding affinity or avidity to its cognate binding partner(s) is to a value at least 10% greater than that of the wild-type IgSF domain control and in some embodiments, at least 20%, 30%, 40%, 50%, 100%, 200%, 300%, 500%, 1000%, 5000%, or 10000% greater than that of the wild-type IgSF domain control value. A decrease in a protein's binding affinity or avidity to at least one of its cognate binding partner is to a value no greater than 90% of the control but no less than 10% of the wild-type IgSF domain control value, and in some embodiments no greater than 80%, 70% 60%, 50%, 40%, 30%, or 20% but no less than 10% of the wild-type IgSF domain control value. An affinity-modified protein is altered in primary amino acid sequence by substitution, addition, or deletion of amino acid residues. The term "affinity modified IgSF domain" is not to be construed as imposing any condition for any particular starting composition or method by which the affinity-modified IgSF domain was created. Thus, the affinity modified IgSF domains of the present invention are not limited to wild type IgSF domains that are then transformed to an affinity modified IgSF domain by any particular process of affinity modification. An affinity modified IgSF domain polypeptide can, for example, be generated starting from wild type mammalian IgSF domain sequence information, then modeled in silico for binding to its cognate binding partner, and finally recombinantly or chemically synthesized to yield the affinity modified IgSF domain composition of matter. In one alternative example, an affinity modified IgSF domain can be created by site-directed mutagenesis of a wild-type IgSF domain. Thus, affinity modified IgSF domain denotes a product and not necessarily a product produced by any given process. A variety of techniques including recombinant methods, chemical synthesis, or combinations thereof, may be employed.

The term "allogeneic" as used herein means a cell or tissue that is removed from one organism and then infused or adoptively transferred into a genetically dissimilar organism of the same species. In some embodiments of the invention, the species is murine or human.

The term "autologous" as used herein means a cell or tissue that is removed from the same organism to which it is later infused or adoptively transferred. An autologous cell or tissue can be altered by, for example, recombinant DNA methodologies, such that it is no longer genetically identical to the native cell or native tissue which is removed from the organism. For example, a native autologous T-cell can be genetically engineered by recombinant DNA techniques to become an autologous engineered cell expressing a transmembrane immunomodulatory protein and/or chimeric antigen receptor (CAR), which in some cases involves engineering a T-cell or TIL (tumor infiltrating lymphocyte). The engineered cells are then infused into a patient from whom the native T-cell was isolated. In some embodiments, the organism is human or murine.

The terms "binding affinity," and "binding avidity" as used herein means the specific binding affinity and specific binding avidity, respectively, of a protein for its counter-structure under specific binding conditions. In biochemical kinetics, avidity refers to the accumulated strength of multiple affinities of individual non-covalent binding interactions, such as between CD86 and its counter-structures CD28 and/or CTLA-4. As such, avidity is distinct from affinity, which describes the strength of a single interaction. An increase or attenuation in binding affinity of a variant CD86 containing an affinity modified CD86 IgSF domain to its counter-structure is determined relative to the binding affinity of the unmodified CD86, such as an unmodified CD86 containing the native or wild-type IgSF domain, such as IgV domain. Methods for determining binding affinity or avidity are known in art. See, for example, Larsen et al., American Journal of Transplantation, Vol. 5: 443-453 (2005). In some embodiments, a variant CD86, such as containing an affinity modified IgSF domain, specifically binds to CD28 and/or CTLA-4 measured by flow cytometry with a binding affinity that yields a Mean Fluorescence Intensity (MFI) value at least 10%, 20%, 30%, 40%, 50%, 60%, 70%, 80%, 90%, or 100% greater than an unmodified CD86 control in a binding assay. In some embodiments, a variant CD86, such as containing an affinity modified IgSF domain, specifically binds to CD28 measured by flow cytometry with a binding affinity that yields a Mean Fluorescence Intensity (MFI) value at least 10%, 20%, 30%, 40%, 50%, 60%, 70%, 80%, 90%, or 100% greater than an unmodified CD86 control in a binding assay. In some embodiments, a variant CD86, such as containing an affinity modified IgSF domain, specifically binds to CTLA-4 measured by flow cytometry with a binding affinity that yields a Mean Fluorescence Intensity (MFI) value at least 10%, 20%, 30%, 40%, 50%, 60%, 70%, 80%, 90%, or 100% less than an unmodified CD86 control in a binding assay. In some embodiments, a variant CD86, such as containing an affinity modified IgSF domain, specifically binds to CTLA-4 measured by flow cytometry with a binding affinity that yields a Mean Fluorescence Intensity (MFI) value that is not significantly different from or is not greater than the binding affinity of an unmodified CD86 control in a binding assay. In some embodiments, a variant CD86, such as containing an affinity modified IgSF domain, specifically binds to CD28 measured by flow cytometry with a binding affinity that yields a Mean Fluorescence Intensity (MFI) value at least 10%, 20%, 30%, 40%, 50%, 60%, 70%, 80%, 90%, or 100% greater than an unmodified CD86 control in a binding assay and exhibits no change in binding affinity or a binding affinity that is not greater for CTLA-4 compared to the unmodified CD86 control in a binding assay. In some embodiments, a variant CD86, such as containing an affinity modified IgSF domain, specifically binds to CD28 measured by flow cytometry with a binding affinity that yields a Mean Fluorescence Intensity (MFI) value at least 10%, 20%, 30%, 40%, 50%, 60%, 70%, 80%, 90%, or 100% greater than an unmodified CD86 control in a binding assay, and exhibits a decrease in binding affinity for CTLA-4 measured by flow cytometry with a binding affinity that yields a Mean Fluorescence Intensity (MFI) value at least 10%, 20%, 30%, 40%, 50%, 60%, 70%, 80%, 90%, or 100% less than an unmodified CD86 control in a binding assay compared to the unmodified CD86 control in a binding assay.

The term "biological half-life" refers to the amount of time it takes for a substance, such as an immunomodulatory polypeptide containing a variant CD86 polypeptide of the present invention, to lose half of its pharmacologic or physiologic activity or concentration. Biological half-life can be affected by elimination, excretion, degradation (e.g., enzymatic) of the substance, or absorption and concentration in certain organs or tissues of the body. In some embodiments, biological half-life can be assessed by determining the time it takes for the blood plasma concentration of the substance to reach half its steady state level ("plasma half-life"). Conjugates that can be used to derivatize and increase the biological half-life of polypeptides of the invention are known in the art and include, but are not limited to, polyethylene glycol (PEG), hydroxyethyl starch (HES), XTEN (extended recombinant peptides; see, WO2013130683), human serum albumin (HSA), bovine serum albumin (BSA), lipids (acylation), poly-Pro-Ala-Ser (PAS), and polyglutamic acid (glutamylation).

The term "chimeric antigen receptor" or "CAR" as used herein refers to an artificial (i.e., man-made) transmembrane protein expressed on a mammalian cell containing at least an ectodomain, a transmembrane, and an endodomain. Optionally, the CAR protein includes a "spacer" which covalently links the ectodomain to the transmembrane domain. A spacer is often a polypeptide linking the ectodomain to the transmembrane domain via peptide bonds. The CAR is typically expressed on a mammalian lymphocyte. In some embodiments, the CAR is expressed on a mammalian cell such as a T-cell or a tumor infiltrating lymphocyte (TIL). A CAR expressed on a T-cell is referred to herein as a "CAR T-cell" or "CAR-T." In some embodiments the CAR-T is a T helper cell, a cytotoxic T-cell, a natural killer T-cell, a memory T-cell, a regulatory T-cell, or a gamma delta T-cell. When used clinically in, e.g., adoptive cell transfer, a CAR-T with antigen binding specificity to the patient's tumor is typically engineered to express on a native T-cell obtained from the patient. The engineered T-cell expressing the CAR is then infused back into the patient. The CAR-T is thus often an autologous CAR-T although allogeneic CAR-Ts are included within the scope of the invention. The ectodomain of a CAR contains an antigen binding region, such as an antibody or antigen binding fragment thereof (e.g., scFv), that specifically binds under physiological conditions with a target antigen, such as a tumor specific antigen. Upon specific binding a biochemical chain of events (i.e., signal transduction) results in modulation of the immunological activity of the CAR-T. Thus, for example, upon specific binding by the antigen binding region of the CAR-T to its target antigen can lead to changes in the immunological activity of the T-cell activity as reflected by changes in cytotoxicity, proliferation, or cytokine production. Signal transduction upon CAR-T activation is achieved in some embodiments by the CD3-zeta chain ("CD3-z") which is involved in signal transduction in native mammalian T-cells. CAR-Ts can further contain multiple signaling domains such as CD28, 4-1BB, or OX40, to further modulate immunomodulatory response of the T-cell. CD3-z contains a conserved motif known as an immunoreceptor tyrosine-based activation motif (ITAM) which is involved in T-cell receptor signal transduction.

The term "collectively" or "collective" when used in reference to cytokine production induced by the presence of two or more variant CD86 polypeptides in an in vitro assay, means the overall cytokine expression level irrespective of the cytokine production induced by individual variant CD86 polypeptides. In some embodiments, the cytokine being assayed is IFN-gamma or IL-2 in an in vitro primary T-cell assay.

The term "cognate binding partner" (used interchangeably with "counter-structure") in reference to a polypeptide, such as in reference to an IgSF domain of a variant CD86, refers to at least one molecule (typically a native mammalian protein) to which the referenced polypeptide specifically binds under specific binding conditions. In some aspects, a variant CD86 containing an affinity modified IgSF domain specifically binds to the counter-structure of the corresponding native or wildtype CD86 but with increased or attenuated affinity. A species of ligand recognized and specifically binding to its cognate receptor under specific binding conditions is an example of a counter-structure or cognate binding partner of that receptor. A "cognate cell surface binding partner" is a cognate binding partner expressed on a mammalian cell surface. A "cell surface molecular species" is a cognate binding partner of ligands of the immunological synapse (IS), expressed on and by cells, such as mammalian cells, forming the immunological synapse.

As used herein, "conjugate," "conjugation" or grammatical variations thereof refer to the joining or linking together of two or more compounds resulting in the formation of another compound, by any joining or linking methods known in the art. It can also refer to a compound which is generated by the joining or linking together two or more compounds. For example, a variant CD86 polypeptide linked directly or indirectly to one or more chemical moieties or polypeptide is an exemplary conjugate. Such conjugates include fusion proteins, those produced by chemical conjugates and those produced by any other methods.

The term "competitive binding" as used herein means that a protein is capable of specifically binding to at least two cognate binding partners but that specific binding of one cognate binding partner inhibits, such as prevents or precludes, simultaneous binding of the second cognate binding partner. Thus, in some cases, it is not possible for a protein to bind the two cognate binding partners at the same time. Generally, competitive binders contain the same or overlapping binding site for specific binding but this is not a requirement. In some embodiments, competitive binding causes a measurable inhibition (partial or complete) of specific binding of a protein to one of its cognate binding partner due to specific binding of a second cognate binding partner. A variety of methods are known to quantify competitive binding such as ELISA (enzyme linked immunosorbent assay) assays.

The term "conservative amino acid substitution" as used herein means an amino acid substitution in which an amino acid residue is substituted by another amino acid residue having a side chain R group with similar chemical properties (e.g., charge or hydrophobicity). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

The term, "corresponding to" with reference to positions of a protein, such as recitation that nucleotides or amino acid positions "correspond to" nucleotides or amino acid positions in a disclosed sequence, such as set forth in the Sequence listing, refers to nucleotides or amino acid positions identified upon alignment with the disclosed sequence based on structural sequence alignment or using a standard alignment algorithm, such as the GAP algorithm. For example, corresponding residues can be determined by alignment of a reference sequence with the sequence of wild-type CD86 set forth in SEQ ID NO: 29 (ECD domain) by structural alignment methods as described herein. By aligning the sequences, one skilled in the art can identify corresponding residues, for example, using conserved and identical amino acid residues as guides. FIG. 3 exemplifies alignment of a sequence with the reference sequence set forth in SEQ ID NO: 29 to identify corresponding residues. For example, in the exemplary alignment shown in FIG. 3, residue 13 of SEQ ID NO: 29 corresponds to residue 4 of SEQ ID NO: 122.

The terms "decrease" or "attenuate" or "suppress" as used herein means to decrease by a statistically significant amount. A decrease can be at least 10%, 20%, 30%, 40%, 50%, 60%, 70%, 80%, 90%, or 100%.

The terms "derivatives" or "derivatized" refer to modification of a protein by covalently linking it, directly or indirectly, to a composition so as to alter such characteristics as biological half-life, bioavailability, immunogenicity, solubility, toxicity, potency, or efficacy while retaining or enhancing its therapeutic benefit. Derivatives of immunomodulatory polypeptides of the invention are within the scope of the invention and can be made by, for example, glycosylation, PEGylation, lipidation, or Fc-fusion.

As used herein, detection includes methods that permit visualization (by eye or equipment) of a protein. A protein can be visualized using an antibody specific to the protein. Detection of a protein can also be facilitated by fusion of the protein with a tag including a label that is detectable or by contact with a second reagent specific to the protein, such as a secondary antibody, that includes a label that is detectable.

As used herein, domain (typically a sequence of three or more, generally 5 or 7 or more amino acids, such as 10 to 200 amino acid residues) refers to a portion of a molecule, such as a protein or encoding nucleic acid, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as binding activity. A protein can have one, or more than one, distinct domains. For example, a domain can be identified, defined or distinguished by homology of the primary sequence or structure to related family members, such as homology to motifs. In another example, a domain can be distinguished by its function, such as an ability to interact with a biomolecule, such as a cognate binding partner. A domain independently can exhibit a biological function or activity such that the domain independently or fused to another molecule can perform an activity, such as, for example binding. A domain can be a linear sequence of amino acids or a non-linear sequence of amino acids. Many polypeptides contain a plurality of domains. Such domains are known, and can be identified by those of skill in the art. For exemplification herein, definitions are provided, but it is understood that it is well within the skill in the art to recognize particular domains by name. If needed appropriate software can be employed to identify domains.

The term "ectodomain" as used herein refers to the region of a membrane protein, such as a transmembrane protein, that lies outside the vesicular membrane. Ectodomains often contain binding domains that specifically bind to ligands or cell surface receptors, such as via a binding domain that specifically binds to the ligand or cell surface receptor. The ectodomain of a cellular transmembrane protein is alternately referred to as an extracellular domain (ECD).

The terms "effective amount" or "therapeutically effective amount" refer to a quantity and/or concentration of a therapeutic composition of the invention, including a protein composition or cell composition, that when administered ex vivo (by contact with a cell from a patient) or in vivo (by administration into a patient) either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient. In the case of cell therapy, the effective amount is an effective dose or number of cells administered to a patient by adoptive cell therapy. In some embodiments the patient is a mammal such as a non-human primate or human patient.

The term "endodomain" as used herein refers to the region found in some membrane proteins, such as transmembrane proteins, that extend into the interior space defined by the cell surface membrane. In mammalian cells, the endodomain is the cytoplasmic region of the membrane protein. In cells, the endodomain interacts with intracellular constituents and can be play a role in signal transduction and thus, in some cases, can be an intracellular signaling domain. The endodomain of a cellular transmembrane protein is alternately referred to as a cytoplasmic domain, which, in some cases, can be a cytoplasmic signaling domain.

The terms "enhanced" or "increased" as used herein in the context of increasing immunological activity of a mammalian lymphocyte means to increase one or more activities the lymphocyte. An increased activity can be one or more of increased cell survival, cell proliferation, cytokine production, or T-cell cytotoxicity, such as by a statistically significant amount. In some embodiments, reference to increased immunological activity means to increase interferon gamma (IFN-gamma), IL-2, or TNFα production, such as by a statistically significant amount. In some embodiments, the immunological activity can be assessed in a mixed lymphocyte reaction (MLR) assay. Methods of conducting MLR assays are known in the art. Wang et al., Cancer Immunol Res. 2014 September: 2(9):846-56. Other methods of assessing activities of lymphocytes are known in the art, including any assay as described herein. In some embodiments, an enhancement can be an increase of at least 10%, 20%, 30%, 40%, 50%, 75%, 100%, 200%, 300%, 400%, or 500% greater than a non-zero control value.

The term "engineered cell" as used herein refers to a mammalian cell that has been genetically modified by human intervention such as by recombinant DNA methods or viral transduction. In some embodiments, the cell is an immune cell, such as a lymphocyte (e.g., T cell, B cell, NK cell) or an antigen presenting cell (e.g., dendritic cell). The cell can be a primary cell from a patient or can be a cell line. In some embodiments, an engineered cell of the invention contains a variant CD86 of the invention engineered to modulate immunological activity of a T-cell expressing CD28 or CTLA-4 to which the variant CD86 polypeptide specifically binds. In some embodiments, the variant CD86 is a transmembrane immunomodulatory protein (hereinafter referred to as "TIP") containing the extracellular domain or a portion thereof containing the IgV domain linked to a transmembrane domain (e.g., a CD86 transmembrane domain) and, optionally, an intracellular signaling domain. In some cases, the TIP is formatted as a chimeric receptor containing a heterologous cytoplasmic signaling domain or endodomain. In some embodiments, an engineered cell is capable of expressing and secreting an immunomodulatory protein as described herein. Among provided engineered cells also are cells further containing an engineered T-cell receptor (TCR) or chimeric antigen receptor (CAR).

The term "engineered T-cell" as used herein refers to a T-cell such as a T helper cell, cytotoxic T-cell (alternatively, cytotoxic T lymphocyte or CTL), natural killer T-cell, regulatory T-cell, memory T-cell, or gamma delta T-cell, that has been genetically modified by human intervention such as by recombinant DNA methods or viral transduction methods. An engineered T-cell contains a variant CD86 transmembrane immunomodulatory protein (TIP) or secreted immunomodulatory protein (SIP) of the present invention that is expressed on the T-cell and is engineered to modulate immunological activity of the engineered T-cell itself, or a mammalian cell to which the variant CD86 expressed on the T-cell specifically binds.

The term "engineered T-cell receptor" or "engineered TCR" refers to a T-cell receptor (TCR) engineered to specifically bind with a desired affinity to a major histocompatibility complex (MHC)/peptide target antigen that is selected, cloned, and/or subsequently introduced into a population of T-cells, often used for adoptive immunotherapy.

The term "expressed on" as used herein is used in reference to a protein expressed on the surface of a cell, such as a mammalian cell. Thus, the protein is expressed as a membrane protein. In some embodiments, the expressed protein is a transmembrane protein. In some embodiments, the protein is conjugated to a small molecule moiety such as a drug or detectable label. Proteins expressed on the surface of a cell can include cell-surface proteins such as cell surface receptors that are expressed on mammalian cells.

The term "half-life extending moiety" refers to a moiety of a polypeptide fusion or chemical conjugate that extends the half-life of a protein circulating in mammalian blood serum compared to the half-life of the protein that is not so conjugated to the moiety. In some embodiments, half-life is extended by greater than or greater than about 1.2-fold, 1.5-fold, 2.0-fold, 3.0-fold, 4.0-fold, 5.0-fold, or 6.0-fold. In some embodiments, half-life is extended by more than 6 hours, more than 12 hours, more than 24 hours, more than 48 hours, more than 72 hours, more than 96 hours or more than 1 week after in vivo administration compared to the protein without the half-life extending moiety. The half-life refers to the amount of time it takes for the protein to lose half of its concentration, amount, or activity. Half-life can be determined for example, by using an ELISA assay or an activity assay. Exemplary half-life extending moieties include an Fc domain, a multimerization domain, polyethylene glycol (PEG), hydroxyethyl starch (HES), XTEN (extended recombinant peptides; see, WO2013130683), human serum albumin (HSA), bovine serum albumin (BSA), lipids (acylation), poly-Pro-Ala-Ser (PAS), and polyglutamic acid (glutamylation).

The term "immunological synapse" or "immune synapse" as used herein means the interface between a mammalian cell that expresses MHC I (major histocompatibility complex) or MHC II, such as an antigen-presenting cell or tumor cell, and a mammalian lymphocyte such as an effector T cell or a Natural Killer (NK) cell.

An Fc (fragment crystallizable) region or domain of an immunoglobulin molecule (also termed an Fc polypeptide) corresponds largely to the constant region of the immunoglobulin heavy chain, and is responsible for various functions, including the antibody's effector function(s). The Fc domain contains part or all of a hinge domain of an immunoglobulin molecule plus a CH2 and a CH3 domain. The Fc domain can form a dimer of two polypeptide chains joined by one or more disulfide bonds. In some embodiments, the Fc is a variant Fc that exhibits reduced (e.g., reduced greater than 30%, 40%, 50%, 60%, 70%, 80%, 90% or more) activity to facilitate an effector function. In some embodiments, reference to amino acid substitutions in an Fc region is by EU numbering system unless described with reference to a specific SEQ ID NO. EU numbering is known and is according to the most recently updated IMGT Scientific Chart (IMGT®, the international ImMunoGeneTics information System®, http://www.imgt.org/IMGTScientific-Chart/Numbering/Hu_IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

An immunoglobulin Fc fusion ("Fc-fusion"), such as an immunomodulatory Fc fusion protein, is a molecule comprising one or more polypeptides (or one or more small molecules) operably linked to an Fc region of an immunoglobulin. An Fc-fusion may comprise, for example, the Fc region of an antibody (which, in some cases, facilitates pharmacokinetics) and a variant CD86 polypeptide. An immunoglobulin Fc region may be linked indirectly or directly to one or more variant CD86 polypeptides or small molecules (fusion partners). Various linkers are known in the art and can optionally be used to link an Fc to a fusion partner to generate an Fc-fusion. Fc-fusions of identical species can be dimerized to form Fc-fusion homodimers, or using non-identical species to form Fc-fusion heterodimers. In some embodiments, the Fc is a mammalian Fc such as a murine, rabbit or human Fc.

The term "host cell" refers to a cell that can be used to express a protein encoded by a recombinant expression vector. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include Chinese hamster ovary (CHO) cells or their derivatives such as Veggie CHO, DG44, Expi CHO, or CHOZN and related cell lines which grow in serum-free media or CHO strain DX-B11, which is deficient in DHFR. In some embodiments, a host cell can be a mammalian cell (e.g., a human cell, a monkey cell, a hamster cell, a rat cell, a mouse cell, or an insect cell).

The term "immunoglobulin" (abbreviated "Ig") as used herein refers to a mammalian immunoglobulin protein including any of the five human classes of antibody: IgA (which includes subclasses IgA1 and IgA2), IgD, IgE, IgG (which includes subclasses IgG1, IgG2, IgG3, and IgG4), and IgM. The term is also inclusive of immunoglobulins that are less than full-length, whether wholly or partially synthetic (e.g., recombinant or chemical synthesis) or naturally produced, such as antigen binding fragment (Fab), variable fragment (Fv) containing $V_H$ and $V_L$, the single chain variable fragment (scFv) containing $V_H$ and $V_L$ linked together in one chain, as well as other antibody V region fragments, such as Fab', $F(ab)_2$, $F(ab')_2$, dsFv diabody, Fc, and Fd polypeptide fragments. Bispecific antibodies, homobispecific and heterobispecific, are included within the meaning of the term.

The term "immunoglobulin superfamily" or "IgSF" as used herein means the group of cell surface and soluble proteins that are involved in the recognition, binding, or adhesion processes of cells. Molecules are categorized as members of this superfamily based on shared structural features with immunoglobulins (i.e., antibodies); they all possess a domain known as an immunoglobulin domain or fold. Members of the IgSF include cell surface antigen receptors, co-receptors and co-stimulatory molecules of the immune system, molecules involved in antigen presentation to lymphocytes, cell adhesion molecules, certain cytokine receptors and intracellular muscle proteins. They are commonly associated with roles in the immune system. Proteins in the immunological synapse are often members of the IgSF. IgSF can also be classified into "subfamilies" based on shared properties such as function. Such subfamilies typically consist of from 4 to 30 IgSF members.

The terms "IgSF domain" or "immunoglobulin domain" or "Ig domain" as used herein refers to a structural domain of IgSF proteins. Ig domains are named after the immunoglobulin molecules. They contain about 70-110 amino acids and are categorized according to their size and function. Ig-domains possess a characteristic Ig-fold, which has a sandwich-like structure formed by two sheets of antiparallel beta strands. Interactions between hydrophobic amino acids on the inner side of the sandwich and highly conserved disulfide bonds formed between cysteine residues in the B and F strands stabilize the Ig-fold. One end of the Ig domain has a section called the complementarity determining region that is important for the specificity of antibodies for their ligands. The Ig like domains can be classified (into classes) as: IgV, IgC1, IgC2, or IgI. Most Ig domains are either variable (IgV) or constant (IgC). IgV domains with 9 beta strands are generally longer than IgC domains with 7 beta strands. Ig domains of some members of the IgSF resemble IgV domains in the amino acid sequence, yet are similar in size to IgC domains. These are called IgC2 domains, while standard IgC domains are called IgC1 domains. T-cell receptor (TCR) chains contain two Ig domains in the extracellular portion; one IgV domain at the N-terminus and one IgC1 domain adjacent to the cell membrane. CD86 contains two Ig domains: IgV and IgC.

The term "IgSF species" as used herein means an ensemble of IgSF member proteins with identical or substantially identical primary amino acid sequence. Each mammalian immunoglobulin superfamily (IgSF) member defines a unique identity of all IgSF species that belong to that IgSF member. Thus, each IgSF family member is unique from other IgSF family members and, accordingly, each species of a particular IgSF family member is unique from the species of another IgSF family member. Nevertheless, variation between molecules that are of the same IgSF species may occur owing to differences in post-translational modification such as glycosylation, phosphorylation, ubiquitination, nitrosylation, methylation, acetylation, and lipidation. Additionally, minor sequence differences within a single IgSF species owing to gene polymorphisms constitute another form of variation within a single IgSF species as do wild type truncated forms of IgSF species owing to, for example, proteolytic cleavage. A "cell surface IgSF species" is an IgSF species expressed on the surface of a cell, generally a mammalian cell.

The term "immunological activity" as used herein in the context of mammalian lymphocytes such as T-cells refers to one or more cell survival, cell proliferation, cytokine production (e.g., interferon-gamma), or T-cell cytotoxicity activities. In some cases, an immunological activity can means their expression of cytokines, such as chemokines or interleukins. Assays for determining enhancement or suppression of immunological activity include the MLR (mixed lymphocyte reaction) assays measuring cytokine levels, such as interferon-gamma or IL-2, in culture supernatants (Wang et al., Cancer Immunol Res. 2014 September: 2(9): 846-56), SEB (staphylococcal enterotoxin B) T cell stimulation assay (Wang et al., Cancer Immunol Res. 2014 September: 2(9):846-56), and anti-CD3 T cell stimulation assays (Li and Kurlander, J Transl Med. 2010: 8: 104). Since T cell activation is associated with secretion of cytokines, such as IFN-gamma or IL-2 cytokines, detecting such cytokine levels in culture supernatants from these in vitro human T cell assays can be assayed using commercial ELISA kits (Wu et al, Immunol Lett 2008 Apr. 15; 117(1): 57-62). Induction of an immune response results in an increase in immunological activity relative to quiescent lymphocytes. An immunomodulatory protein, such as a variant CD86 polypeptide containing an affinity modified IgSF domain, as provided herein can in some embodiments increase or, in alternative embodiments, decrease IFN-gamma (interferon-gamma) or IL-2 expression in a primary T-cell assay relative to a wild-type IgSF member or IgSF domain control. Those of skill will recognize that the format of the primary T-cell assay used to determine an increase in IFN-gamma or IL-2 expression will differ from that employed to assay for a decrease in IFN-gamma or IL-2 expression. In assaying for the ability of an immunomodulatory protein or affinity modified IgSF domain of the invention to decrease IFN-gamma or IL-2 expression in a primary T-cell assay, a Mixed Lymphocyte Reaction (MLR) assay can be used. Conveniently, a soluble form of an affinity modified IgSF domain of the invention can be employed to determine its ability to antagonize and thereby decrease the IFN-gamma or IL-2 expression in a MLR. Alternatively, in assaying for the ability of an immunomodulatory protein or affinity modified IgSF domain of the invention to increase IFN-gamma or IL-2 expression in a primary T-cell assay, a co-immobilization assay can be used. In a co-immobilization assay, a T-cell receptor signal, provided in some embodiments by anti-CD3 antibody, is used in conjunction with a co-immobilized affinity modified IgSF domain, such as a variant CD86, to determine the ability to increase IFN-gamma or IL-2 expression relative to a wild-type IgSF domain control. Methods to assay the immunological activity of engineered cells, including to evaluate the activity of a variant CD86 transmembrane immunomodulatory protein, are known in the art and include, but are not limited to, the ability to expand T cells following antigen stimulation, sustain T cell expansion in the absence of re-stimulation, and anti-cancer activities in appropriate animal models. Assays also include assays to assess cytotoxicity, including a standard $^{51}$Cr-release assay (see e.g., Milone et al., (2009) Molecular Therapy 17: 1453-1464) or flow based cytotoxicity assays, or an impedance based cytotoxicity assay (Peper et al. (2014) Journal of Immunological Methods, 405:192-198).

An "immunomodulatory polypeptide" or "immunomodulatory protein" is a polypeptide or protein molecule that modulates immunological activity. By "modulation" or "modulating" an immune response is meant that immunological activity is either increased or decreased. An immunomodulatory protein can be a single polypeptide chain or a multimer (dimers or higher order multimers) of at least two polypeptide chains covalently bonded to each other by, for example, interchain disulfide bonds. Thus, monomeric, dimeric, and higher order multimeric polypeptides are within the scope of the defined term. Multimeric polypeptides can be homomultimeric (of identical polypeptide chains) or heteromultimeric (of non-identical polypeptide chains). An immunomodulatory protein herein comprises a variant CD86 polypeptide.

The term "increase" as used herein means to increase by a statistically significant amount. An increase can be at least 5%, 10%, 20%, 30%, 40%, 50%, 75%, 100%, or greater than a non-zero control value.

An "isoform" of CD86 is one of a plurality of naturally occurring CD86 polypeptides that differ in amino acid sequence. Isoforms can be the product of splice variants of an RNA transcript expressed by a single gene, or the expression product of highly similar but different genes yielding a functionally similar protein such as may occur from gene duplication. As used herein, the term "isoform" of CD86 also refers to the product of different alleles of a CD86 gene.

The term "label" refers to a compound or composition which can be attached or linked, directly or indirectly to provide a detectable signal or that can interact with a second label to modify a detectable signal. The label can be conjugated directly or indirectly to a polypeptide so as to generate a labeled polypeptide. The label can be detectable by itself (e.g., radioisotope labels or fluorescent labels) or, in the case of an enzymatic label, can catalyze chemical alteration of a substrate compound composition which is detectable. Non-limiting examples of labels included fluorogenic moieties, green fluorescent protein, or luciferase.

The term "lymphocyte" as used herein means any of three subtypes of white blood cell in a mammalian immune system. They include natural killer cells (NK cells) (which function in cell-mediated, cytotoxic innate immunity), T cells (for cell-mediated, cytotoxic adaptive immunity), and B cells (for humoral, antibody-driven adaptive immunity). T cells include: T helper cells, cytotoxic T-cells, natural killer T-cells, memory T-cells, regulatory T-cells, or gamma delta T-cells. Innate lymphoid cells (ILC) are also included within the definition of lymphocyte.

The terms "mammal," or "patient" specifically includes reference to at least one of a: human, chimpanzee, rhesus monkey, cynomolgus monkey, dog, cat, mouse, or rat.

The term "membrane protein" as used herein means a protein that, under physiological conditions, is attached directly or indirectly to a lipid bilayer. A lipid bilayer that forms a membrane can be a biological membrane such as a eukaryotic (e.g., mammalian) cell membrane or an artificial (i.e., man-made) membrane such as that found on a liposome. Attachment of a membrane protein to the lipid bilayer can be by way of covalent attachment, or by way of non-covalent interactions such as hydrophobic or electrostatic interactions. A membrane protein can be an integral membrane protein or a peripheral membrane protein. Membrane proteins that are peripheral membrane proteins are non-covalently attached to the lipid bilayer or non-covalently attached to an integral membrane protein. A peripheral membrane protein forms a temporary attachment to the lipid bilayer such that under the range of conditions that are physiological in a mammal, a peripheral membrane protein can associate and/or disassociate from the lipid bilayer. In contrast to peripheral membrane proteins, integral membrane proteins form a substantially permanent attachment to the membrane's lipid bilayer such that under the range of conditions that are physiological in a mammal, integral membrane proteins do not disassociate from their attachment to the lipid bilayer. A membrane protein can form an attachment to the membrane by way of one layer of the lipid bilayer (monotopic), or attached by way of both layers of the membrane (polytopic). An integral membrane protein that interacts with only one lipid bilayer is an "integral monotopic protein". An integral membrane protein that interacts with both lipid bilayers is an "integral polytopic protein" alternatively referred to herein as a "transmembrane protein".

The terms "modulating" or "modulate" as used herein in the context of an immune response, such as a mammalian immune response, refer to any alteration, such as an increase or a decrease, of existing or potential immune responses that occurs as a result of administration of an immunomodulatory polypeptide comprising a variant CD86 of the present invention or as a result of administration of engineered cells expresses an immunomodulatory protein, such as a variant CD86 transmembrane immunomodulatory protein of the present invention. Thus, it refers to an alteration, such as an increase or decrease, of an immune response as compared to the immune response that occurs or is present in the absence of the administration of the immunomodulatory protein comprising the variant CD86. Such modulation includes any induction, activation, suppression, or alteration in degree or extent of immunological activity of an immune cell. Immune cells include B cells, T cells, NK (natural killer) cells, NK T cells, professional antigen-presenting cells (APCs), non-professional antigen-presenting cells, and inflammatory cells (neutrophils, macrophages, monocytes, eosinophils, and basophils). Modulation includes any change imparted on an existing immune response, a developing immune response, a potential immune response, or the capacity to induce, regulate, influence, or respond to an immune response. Modulation includes any alteration in the expression and/or function of genes, proteins and/or other molecules in immune cells as part of an immune response. Modulation of an immune response or modulation of immunological activity includes, for example, the following: elimination, deletion, or sequestration of immune cells; induction or generation of immune cells that can modulate the functional capacity of other cells such as autoreactive lymphocytes, antigen presenting cells, or inflammatory cells; induction of an unresponsive state in immune cells (i.e., anergy); enhancing or suppressing the activity or function of immune cells, including but not limited to altering the pattern of proteins expressed by these cells. Examples include altered production and/or secretion of certain classes of molecules such as cytokines, chemokines, growth factors, transcription factors, kinases, costimulatory molecules, or other cell surface receptors or any combination of these modulatory events. Modulation can be assessed, for example, by an alteration in IFN-gamma (interferon gamma) or IL-2 expression relative to the wild-type or unmodified CD86 control in a primary T cell assay (see, Zhao and Ji, Exp Cell Res. 2016 Jan. 1; 340(1): 132-138). Modulation can be assessed, for example, by an alteration of an immunological activity of engineered cells, such as an alteration in in cytotoxic activity of engineered cells or an alteration in cytokine secretion of engineered cells relative to cells engineered with a wild-type CD86 transmembrane protein.

The term, a "multimerization domain" refers to a sequence of amino acids that promotes stable interaction of a polypeptide molecule with one or more additional polypeptide molecules, each containing a complementary multimerization domain (e.g., a first multimerization domain and a second multimerization domain), which can be the same or a different multimerization domain. The interactions between complementary multimerization domains, e.g., interaction between a first multimerization domain and a second multimerization domain, form a stable protein-protein interaction to produce a multimer of the polypeptide molecule with the additional polypeptide molecule. In some cases, the multimerization domain is the same and interacts with itself to form a stable protein-protein interaction between two polypeptide chains. Generally, a polypeptide is joined directly or indirectly to the multimerization domain. Exemplary multimerization domains include the immunoglobulin sequences or portions thereof, leucine zippers, hydrophobic regions, hydrophilic regions, and compatible protein-protein interaction domains. The multimerization domain, for example, can be an immunoglobulin constant region or domain, such as, for example, the Fc domain or portions thereof from IgG, including IgG1, IgG2, IgG3, or IgG4 subtypes, IgA, IgE, IgD, IgM and modified forms thereof.

The terms "nucleic acid" and "polynucleotide" are used interchangeably to refer to a polymer of nucleic acid residues (e.g., deoxyribonucleotides or ribonucleotides) in either single- or double-stranded form. Unless specifically limited, the terms encompass nucleic acids containing known analogues of natural nucleotides and that have similar binding properties to it and are metabolized in a manner similar to naturally-occurring nucleotides. Unless otherwise indicated, a particular nucleic acid sequence also implicitly encompasses conservatively modified variants thereof (e.g., degenerate codon substitutions) and complementary nucleotide sequences as well as the sequence explicitly indicated (a "reference sequence"). Specifically, degenerate codon substitutions may be achieved by generating sequences in which the third position of one or more selected (or all) codons is substituted with mixed-base and/or deoxyinosine residues. The term nucleic acid or polynucleotide encompasses cDNA or mRNA encoded by a gene.

The term "molecular species" as used herein means an ensemble of proteins with identical or substantially identical primary amino acid sequence. Each mammalian immunoglobulin superfamily (IgSF) member defines a collection of identical or substantially identical molecular species. Thus, for example, human CD86 is an IgSF member and each human CD86 molecule is a molecular species of CD86. Variation between molecules that are of the same molecular species may occur owing to differences in post-translational modification such as glycosylation, phosphorylation, ubiquitination, nitrosylation, methylation, acetylation, and lipidation. Additionally, minor sequence differences within a single molecular species owing to gene polymorphisms constitute another form of variation within a single molecular species as do wild type truncated forms of a single molecular species owing to, for example, proteolytic cleavage. A "cell surface molecular species" is a molecular species expressed on the surface of a mammalian cell. Two or more different species of protein, each of which is present exclusively on one or exclusively the other (but not both) of the two mammalian cells forming the IS, are said to be in "cis" or "cis configuration" with each other. Two different species of protein, the first of which is exclusively present on one of the two mammalian cells forming the IS and the second of which is present exclusively on the second of the two mammalian cells forming the IS, are said to be in "trans" or "trans configuration." Two different species of protein each of which are present on both of the two mammalian cells forming the IS are in both cis and trans configurations on these cells.

The term "non-competitive binding" as used herein means the ability of a protein to specifically bind simultaneously to at least two cognate binding partners. Thus, the protein is able to bind to at least two different cognate binding partners at the same time, although the binding interaction need not be for the same duration such that, in some cases, the protein is specifically bound to only one of the cognate binding partners. In some embodiments, the binding occurs under specific binding conditions. In some embodiments, the simultaneous binding is such that binding of one cognate binding partner does not substantially inhibit simultaneous binding to a second cognate binding partner. In some embodiments, non-competitive binding means that binding a second cognate binding partner to its binding site on the protein does not displace the binding of a first cognate binding partner to its binding site on the protein. Methods of assessing non-competitive binding are well known in the art such as the method described in Perez de La Lastra et al., Immunology, 1999 April: 96(4): 663-670. In some cases, in non-competitive interactions, the first cognate binding partner specifically binds at an interaction site that does not overlap with the interaction site of the second cognate binding partner such that binding of the second cognate binding partner does not directly interfere with the binding of the first cognate binding partner. Thus, any effect on binding of the cognate binding partner by the binding of the second cognate binding partner is through a mechanism other than direct interference with the binding of the first cognate binding partner. For example, in the context of enzyme-substrate interactions, a non-competitive inhibitor binds to a site other than the active site of the enzyme. Non-competitive binding encompasses uncompetitive binding interactions in which a second cognate binding partner specifically binds at an interaction site that does not overlap with the binding of the first cognate binding partner but binds to the second interaction site only when the first interaction site is occupied by the first cognate binding partner.

The term "pharmaceutical composition" refers to a composition suitable for pharmaceutical use in a mammalian subject, often a human. A pharmaceutical composition typically comprises an effective amount of an active agent (e.g., an immunomodulatory polypeptide comprising a variant CD86 or engineered cells expressing a variant CD86 transmembrane immunomodulatory protein) and a carrier, excipient, or diluent. The carrier, excipient, or diluent is typically a pharmaceutically acceptable carrier, excipient or diluent, respectively.

The terms "polypeptide" and "protein" are used interchangeably herein and refer to a molecular chain of two or more amino acids linked through peptide bonds. The terms do not refer to a specific length of the product. Thus, "peptides," and "oligopeptides," are included within the definition of polypeptide. The terms include post-translational modifications of the polypeptide, for example, glycosylation, acetylation, phosphorylation and the like. The terms also include molecules in which one or more amino acids are amino acid analogs or non-canonical or unnatural amino acids that can be synthesized or expressed recombinantly using known protein engineering techniques. In addition, proteins can be derivatized.

The term "primary T-cell assay" as used herein refers to an in vitro assay to measure a T cell activity, such as production of cytokines, for example interferon-gamma ("IFN-gamma") IL-2, or tumor necrosis factor alpha (TNFα) expression. A variety of such primary T-cell assays are known in the art. In some embodiments, the assay used is an anti-CD3 coimmobilization assay. In this assay, primary T cells are stimulated by anti-CD3 immobilized with or without additional recombinant proteins. Culture supernatants are harvested at timepoints, usually 24-72 hours. In another embodiment, the assay used is a mixed lymphocyte reaction (MLR). In this assay, primary T cells are simulated with allogenic APC. Culture supernatants are harvested at timepoints, usually 24-72 hours. Cytokine levels, such as levels of IFN-gamma, IL-2, or TNFα, are measured in culture supernatants by standard ELISA techniques. Commercial kits are available from vendors and the assay is performed according to manufacturer's recommendation.

The term "purified" as applied to nucleic acids, such as encoding immunomodulatory proteins of the invention, generally denotes a nucleic acid or polypeptide that is substantially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or protein of the invention is at least about 50% pure, usually at least about 75%, 80%, 85%, 90%, 95%, 96%, 99% or more pure (e.g., percent by weight or on a molar basis).

The term "recombinant" indicates that the material (e.g., a nucleic acid or a polypeptide) has been artificially (i.e., non-naturally) altered by human intervention. The alteration can be performed on the material within, or removed from, its natural environment or state. For example, a "recombinant nucleic acid" is one that is made by recombining nucleic acids, e.g., during cloning, affinity modification, DNA shuffling or other well-known molecular biological procedures. A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid or that is otherwise altered by genetic engineering, such as by introducing into the cell a nucleic acid molecule encoding a recombinant protein, such as a transmembrane immunomodulatory protein provided herein. Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. The terms "in operable combination," "in operable order" and "operably linked" as used herein refer to the linkage of nucleic acid sequences in such a manner or orientation that a nucleic acid molecule capable of directing the transcription of a given gene and/or the synthesis of a desired protein molecule is produced.

The term "recombinant expression vector" as used herein refers to a DNA molecule containing a desired coding sequence and appropriate nucleic acid sequences necessary for the expression of the operably linked coding sequence in a particular host cell. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the recombinant expression vector, operably linked to the coding sequence for the recombinant protein, such as a recombinant fusion protein, so that the expressed fusion protein can be secreted by the recombinant host cell, for easier isolation of the fusion protein from the cell, if desired. The term includes the vector as a self-replicating nucleic acid structure as well as the vector incorporated into the genome of a host cell into which it has been introduced. Among the vectors are viral vectors, such as lentiviral vectors.

The term "selectivity" refers to the preference of a subject protein, or polypeptide, for specific binding of one substrate, such as one cognate binding partner, compared to specific binding for another substrate, such as a different cognate binding partner of the subject protein. Selectivity can be reflected as a ratio of the binding activity (e.g., binding affinity) of a subject protein and a first substrate, such as a first cognate binding partner, (e.g., Kai) and the binding activity (e.g., binding affinity) of the same subject protein with a second cognate binding partner (e.g., $K_{d2}$).

The term "sequence identity" as used herein refers to the sequence identity between genes or proteins at the nucleotide or amino acid level, respectively. "Sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned. Methods for the alignment of sequences for comparison are well known in the art, such methods include GAP, BESTFIT, BLAST, FASTA and TFASTA. The BLAST algorithm calculates percent sequence identity and performs a statistical analysis of the similarity between the two sequences. The software for performing BLAST analysis is publicly available through the National Center for Biotechnology Information (NCBI) website.

The term "soluble" as used herein in reference to proteins, means that the protein is not a membrane protein. In general, a soluble protein contains only the extracellular domain of an IgSF family member receptor, or a portion thereof containing an IgSF domain or domains or specific-binding fragments thereof, but does not contain the transmembrane domain. In some cases, solubility of a protein can be improved by linkage or attachment, directly or indirectly via a linker, to an Fc domain, which, in some cases, also can improve the stability and/or half-life of the protein. In some aspects, a soluble protein is an Fc fusion protein.

The term "species" as used herein with respect to polypeptides or nucleic acids means an ensemble of molecules with identical or substantially identical sequences. Variation between polypeptides that are of the same species may occur owing to differences in post-translational modification such as glycosylation, phosphorylation, ubiquitination, nitrosylation, methylation, acetylation, and lipidation. Slightly truncated sequences of polypeptides that differ (or encode a difference) from the full length species at the amino-terminus or carboxyl-terminus by no more than 1, 2, or 3 amino acid residues are considered to be of a single species. Such microheterogeneities are a common feature of manufactured proteins.

The term "specific binding fragment" as used herein in reference to a full-length wild-type mammalian CD86 polypeptide or an ECD, IgV or an IgC domain thereof, means a polypeptide having a subsequence of an ECD, IgV and/or IgC domain and that specifically binds in vitro and/or in vivo to a mammalian CD28 and/or mammalian CTLA-4, such as a human or murine CD28 and/or CTLA-4. In some embodiments, the specific binding fragment of the CD86 ECD, CD86 IgV, or the CD86 IgC is at least 60%, 70%, 75%, 80%, 85%, 90%, 95%, 96%, 97%, 98%, or 99% the sequence length of the full-length wild-type ECD, IgV, or IgC sequence. The specific binding fragment can be altered in sequence to form the variant CD86.

The term "specifically binds" as used herein means the ability of a protein, under specific binding conditions, to bind to a target protein such that its affinity or avidity is at least 5 times as great, but optionally at least 10, 20, 30, 40, 50, 100, 250 or 500 times as great, or even at least 1000 times as great as the average affinity or avidity of the same protein to a collection of random peptides or polypeptides of sufficient statistical size. A specifically binding protein need not bind exclusively to a single target molecule but may specifically bind to a non-target molecule due to similarity in structural conformation between the target and non-target (e.g., paralogs or orthologs). Those of skill will recognize that specific binding to a molecule having the same function in a different species of animal (i.e., ortholog) or to a non-target molecule having a substantially similar epitope as the target molecule (e.g., paralog) is possible and does not detract from the specificity of binding which is determined relative to a statistically valid collection of unique non-targets (e.g., random polypeptides). Thus, a polypeptide of the invention may specifically bind to more than one distinct species of target molecule due to cross-reactivity. Solid-phase ELISA immunoassays or surface plasmon resonance (e.g., Biacore) measurements can be used to determine specific binding between two proteins. Generally, interactions between two binding proteins have dissociation constants ($K_d$) less than $1\times10^{-5}$M, and often as low as $1\times10^{-12}$ M. In certain embodiments of the present disclosure, interactions between two binding proteins have dissociation constants of $1\times10^{-6}$ M, $1\times10^{-7}$ M, $1\times10^{-8}$ M, $1\times10^{-9}$ M, $1\times10^{-10}$ M or $1\times10^{-11}$ M.

The terms "surface expresses" or "surface expression" in reference to a mammalian cell expressing a polypeptide means that the polypeptide is expressed as a membrane protein. In some embodiments, the membrane protein is a transmembrane protein.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods.

The term "targeting moiety" as used herein refers to a composition that is covalently or non-covalently attached to, or physically encapsulates, a polypeptide comprising the variant CD86. The targeting moiety has specific binding affinity for a desired counter-structure such as a cell surface receptor (e.g., CD28), or a tumor antigen such as a tumor specific antigen (TSA) or a tumor associated antigen (TAA) such as B7-H6. Typically, the desired counter-structure is localized on a specific tissue or cell-type. Targeting moieties include: antibodies, antigen binding fragment (Fab), variable fragment (Fv) containing $V_H$ and $V_L$, the single chain variable fragment (scFv) containing $V_H$ and $V_L$ linked together in one chain, as well as other antibody V region fragments, such as Fab', $F(ab)_2$, $F(ab')_2$, dsFv diabody, nanobodies, soluble receptors, receptor ligands, affinity matured receptors or ligands, as well as small molecule (<500 Dalton) compositions (e.g., specific binding receptor compositions). Targeting moieties can also be attached covalently or non-covalently to the lipid membrane of liposomes that encapsulate a polypeptide of the present invention.

The term “transmembrane protein” as used herein means a membrane protein that substantially or completely spans a lipid bilayer such as those lipid bilayers found in a biological membrane such as a mammalian cell, or in an artificial construct such as a liposome. The transmembrane protein comprises a transmembrane domain (“transmembrane domain”) by which it is integrated into the lipid bilayer and by which the integration is thermodynamically stable under physiological conditions. Transmembrane domains are generally predictable from their amino acid sequence via any number of commercially available bioinformatics software applications on the basis of their elevated hydrophobicity relative to regions of the protein that interact with aqueous environments (e.g., cytosol, extracellular fluid). A transmembrane domain is often a hydrophobic alpha helix that spans the membrane. A transmembrane protein can pass through the both layers of the lipid bilayer once or multiple times. A transmembrane protein includes the provided transmembrane immunomodulatory proteins described herein. In addition to the transmembrane domain, a transmembrane immunomodulatory protein of the invention further comprises an ectodomain and, in some embodiments, an endodomain.

The terms “treating,” “treatment,” or “therapy” of a disease or disorder as used herein mean slowing, stopping or reversing the disease or disorders progression, as evidenced by decreasing, cessation or elimination of either clinical or diagnostic symptoms, by administration of a therapeutic composition (e.g., containing an immunomodulatory protein or engineered cells) of the invention either alone or in combination with another compound as described herein. “Treating,” “treatment,” or “therapy” also means a decrease in the severity of symptoms in an acute or chronic disease or disorder or a decrease in the relapse rate as for example in the case of a relapsing or remitting autoimmune disease course or a decrease in inflammation in the case of an inflammatory aspect of an autoimmune disease. As used herein in the context of cancer, the terms “treatment” or, “inhibit,” “inhibiting” or “inhibition” of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS). “Preventing,” “prophylaxis,” or “prevention” of a disease or disorder as used in the context of this invention refers to the administration of an immunomodulatory polypeptide or engineered cells of the invention, either alone or in combination with another compound, to prevent the occurrence or onset of a disease or disorder or some or all of the symptoms of a disease or disorder or to lessen the likelihood of the onset of a disease or disorder.

The term “tumor specific antigen” or “TSA” as used herein refers to a counter-structure that is present primarily on tumor cells of a mammalian subject but generally not found on normal cells of the mammalian subject. A tumor specific antigen need not be exclusive to tumor cells but the percentage of cells of a particular mammal that have the tumor specific antigen is sufficiently high or the levels of the tumor specific antigen on the surface of the tumor are sufficiently high such that it can be targeted by anti-tumor therapeutics, such as immunomodulatory polypeptides of the invention, and provide prevention or treatment of the mammal from the effects of the tumor. In some embodiments, in a random statistical sample of cells from a mammal with a tumor, at least 50% of the cells displaying a TSA are cancerous. In other embodiments, at least 60%, 70%, 80%, 85%, 90%, 95%, or 99% of the cells displaying a TSA are cancerous.

The term “variant” (also “modified” or mutant”) as used in reference to a variant CD86 means a CD86, such as a mammalian (e.g., human or murine) CD86 created by human intervention. The variant CD86 is a polypeptide having an altered amino acid sequence, relative to an unmodified or wild-type CD86. The variant CD86 is a polypeptide which differs from a wild-type CD86 isoform sequence by one or more amino acid substitutions, deletions, additions, or combinations thereof. For purposes herein, the variant CD86 contains at least one affinity modified domain, whereby one or more of the amino acid differences occurs in an IgSF domain (e.g., IgV domain or IgC domain). A variant CD86 can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions. A variant CD86 polypeptide generally exhibits at least 50%, 60%, 70%, 80%, 85%, 86%, 87%, 88%, 89%, 90%, 91%, 92%, 93%, 94%, 95%, 96%, 97%, 98%, 99% or more sequence identity to a corresponding wild-type or unmodified CD86, such as to the sequence of SEQ ID NO: 2, a mature sequence thereof or a portion thereof containing the extracellular domain or an IgSF domain thereof. In some embodiments, a variant CD86 polypeptide exhibits at least 50%, 60%, 70%, 80%, 85%, 86%, 87%, 88%, 89%, 90%, 91%, 92%, 93%, 94%, 95%, 96%, 97%, 98%, 99% or more sequence identity to a corresponding wild-type or unmodified CD86 comprising the sequence set forth in SEQ ID NO: 2, SEQ ID NO: 29, SEQ ID NO: 122, or SEQ ID NO: 123.

Non-naturally occurring amino acids as well as naturally occurring amino acids are included within the scope of permissible substitutions or additions. A variant CD86 is not limited to any particular method of making and includes, for example, de novo chemical synthesis, de novo recombinant DNA techniques, or combinations thereof. A variant CD86 of the invention specifically binds to at least one or more of: CD28 and/or CTLA-4 of a mammalian species. In some embodiments, the altered amino acid sequence results in an altered (i.e., increased or decreased) binding affinity or avidity to CD28 and/or CTLA-4 compared to the unmodified or wild-type CD86 protein. An increase or decrease in binding affinity or avidity can be determined using well known binding assays such as flow cytometry. Larsen et al., American Journal of Transplantation, Vol 5: 443-453 (2005). See also, Linsley et al., Immunity, Vol 1(9): 793-801 (1994). An increase in variant CD86 binding affinity or avidity to CD28 and/or CTLA-4 can be a value at least 5% greater than that of the unmodified or wild-type CD86 and in some embodiments, at least 10%, 15%, 20%, 30%, 40%, 50%, 100% greater than that of the unmodified or wild-type CD86 control value. A decrease in CD86 binding affinity or avidity to CD28 and/or CTLA-4 is to a value no greater than 95% of the of the unmodified or wild-type CD86 control values, and in some embodiments no greater than 80%, 70% 60%, 50%, 40%, 30%, 20%, 10%, 5%, or no detectable binding affinity or avidity of the unmodified or wild-type CD86 control values. In some embodiments, no change in binding affinity or avidity is seen as a lack of significant difference between the binding affinity or avidity of the variant CD86 and the binding affinity or avidity of the unmodified or wild-type CD86. In some embodiments, binding affinity or avidity can be altered for one cognate binding partner and not the other cognate binding partner. For example, a variant CD86 may exhibit increased binding affinity or avidity for CD28, show no change binding affinity or avidity to CTLA-4 compared to the binding affinity or avidity of a wild-type or unmodified CD86 molecule. In some embodiments, binding affinity or avidity can be altered for both cognate binding partners. In some embodiments, the alteration is in the same direction (e.g., both increase or decrease). In some embodiments, the alteration is in different directions (e.g., increased for one cognate binding partner and decreased for the other cognate binding partner). For example, a variant CD86 may exhibit increased binding affinity or avidity for CD28, show decreased binding affinity or avidity to CTLA-4 compared to the binding affinity or avidity of a wild-type or unmodified CD86 molecule. In some embodiments, the CD86 variant or wild-type or unmodified polypeptide binds to the ectodomain of CD28 and/or CTLA-4. Thus, in some embodiments, affinity and avidity are determined based on binding of the CD86 variant or wild-type or unmodified polypeptide to the ectodomain of CD28 and/or CTLA-4. A variant CD86 polypeptide is altered in primary amino acid sequence by substitution, addition, or deletion of amino acid residues. The term "variant" in the context of variant CD86 polypeptide is not to be construed as imposing any condition for any particular starting composition or method by which the variant CD86 is created. A variant CD86 can, for example, be generated starting from wild type mammalian CD86 sequence information, then modeled in silico for binding to CD28 and/or CTLA-4, and finally recombinantly or chemically synthesized to yield the variant CD86. In one alternative example, the variant CD86 can be created by site-directed mutagenesis of an unmodified or wild-type CD86. Thus, variant CD86 denotes a composition and not necessarily a product produced by any given process. A variety of techniques including recombinant methods, chemical synthesis, or combinations thereof, may be employed.

The term "wild-type" or "natural" or "native" as used herein is used in connection with biological materials such as nucleic acid molecules, proteins (e.g., CD86), IgSF members, host cells, and the like, refers to those which are found in nature and not modified by human intervention.

II. VARIANT CD86 POLYPEPTIDES

Provided herein are variant CD86 polypeptides that exhibit altered (increased or decreased) binding activity or affinity for one or more of a CD86 cognate binding partner. In some embodiments, the CD86 cognate binding partner is CD28 or CTLA-4. In some embodiments, the CD86 cognate binding partner is CD28. In some embodiments, the variant CD86 polypeptide contains one or more amino acids modifications, such as one or more substitutions (alternatively, "mutations" or "replacements"), deletions or additions, in an immunoglobulin superfamily (IgSF) domain (IgD) relative to a wild-type or unmodified CD86 polypeptide or a portion of a wild-type or unmodified CD86 containing the IgD or a specific binding fragment thereof. Thus, a provided variant CD86 polypeptide is or comprises a variant IgD (hereinafter called "vIgD") in which the one or more amino acid modifications (e.g. substitutions) is in an IgD.

In some embodiments, the variant is modified in one more IgSF domains relative to the sequence of an unmodified CD86 sequence. In some embodiments, the unmodified CD86 sequence is a wild-type CD86. In some embodiments, the unmodified or wild-type CD86 has the sequence of a native CD86 or an ortholog thereof. In some embodiments, the unmodified CD86 is or comprises the extracellular domain (ECD) of CD86 or a portion thereof containing an IgV domain (see Table 2). In some embodiments, the variant CD86 is or contains the extracellular domain (ECD) of CD86 or a portion thereof containing an IgV domain. In some embodiments, the unmodified or wild-type CD86 polypeptide contains the IgV domain or a specific binding fragment thereof. In some embodiments, the variant CD86 polypeptide contains the IgV domain or a specific binding fragment thereof. In some embodiments, the variant CD86 is soluble and lacks a transmembrane domain. In some embodiments, the variant CD86 further comprises a transmembrane domain and, in some cases, also a cytoplasmic domain.

In some embodiments, the wild-type or unmodified CD86 sequence is a mammalian CD86 sequence. In some embodiments, the wild-type or unmodified CD86 sequence can be a mammalian CD86 that includes, but is not limited to, human, mouse, cynomolgus monkey, or rat. In some embodiments, the wild-type or unmodified CD86 sequence is human.

In some embodiments, the wild-type or unmodified CD86 sequence has (i) the sequence of amino acids set forth in SEQ ID NO: 2 or a mature form thereof lacking the signal sequence, (ii) a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 2 or the mature form thereof, or (iii) is a portion of (i) or (ii) containing an IgV domain or specific binding fragment thereof.

In some embodiments, the wild-type or unmodified CD86 sequence is or comprises an extracellular domain or portion thereof containing the IgV of the CD86 or a specific binding fragment thereof. In some embodiments, the unmodified or wild-type CD86 polypeptide comprises the amino acid sequence set forth in SEQ ID NO: 29, 122, or 123, or an ortholog thereof. In some cases, the unmodified or wild-type CD86 polypeptide can comprise (i) the sequence of amino acids set forth in SEQ ID NO: 29, 122, or 123, (ii) a sequence of amino acids that has at least about 85%, 86%, 87%, 88%, 89%, 90%, 91%, 92%, 93%, 94%, 95%, 96%, 97%, 98%, 99% sequence identity to SEQ ID NO: 29, 122, or 123, or (iii) is a specific binding fragment of the sequence of (i) or (ii). In some embodiments, the wild-type or unmodified CD86 polypeptide comprises the amino acid sequence set forth in SEQ ID NO: 29 (corresponding to amino acid residues 24-247 of SEQ ID NO: 2), or an ortholog thereof. In some embodiments, the wild-type or unmodified CD86 polypeptide comprises the amino acid sequence set forth in SEQ ID NO: 122 (corresponding to amino acid residues 33-131 of SEQ ID NO: 2), or an ortholog thereof. In some embodiments, the wild-type or unmodified CD86 polypeptide comprises the amino acid sequence set forth in SEQ ID NO: 123 (corresponding to amino acid residues 24-134 of SEQ ID NO: 2), or an ortholog thereof. In some embodiments, the wild-type or unmodified CD86 containing the IgV domain or specific binding fragment thereof is capable of binding one or more CD86 cognate binding proteins, such as one or more of CD28 or CTLA-4.

In some embodiments, the wild-type or unmodified CD86 polypeptide contains a specific binding fragment of CD86, such as a specific binding fragment of the IgV domain. In some embodiments the specific binding fragment can bind CD28 and/or CTLA-4. In some embodiments, the specific binding fragment can bind the ectodomain of CD28 and/or CTLA-4. The specific binding fragment can have an amino acid length of at least 50 amino acids, such as at least 60, 70, 80, 90, 100, 110, 120, 130, 140, 150, 160, 170, 180, 190, 200, 210, or 220 amino acids. In some embodiments, a specific binding fragment of the IgV domain contains an amino acid sequence that is at least about 85%, 86%, 87%, 88%, 89%, 90%, 91%, 92%, 93%, 94%, 95%, 96%, 97%, 98%, 99% of the length of the IgV domain set forth as amino acids 33-131 of SEQ ID NO: 2.

In some embodiments, the variant CD86 polypeptide comprises an extracellular domain or a portion thereof comprising one or more affinity modified IgSF domains. In some embodiments, the variant CD86 polypeptides can comprise an IgV domain, or a specific binding fragment of the IgV domain in which the IgSF domain contains the one or more amino acid modifications (e.g. substitutions). In some embodiments, the variant CD86 polypeptide comprises a full-length IgV domain. In some embodiments, the variant CD86 polypeptide comprises a specific binding fragment of the IgV domain. In some embodiments, the variant CD86 polypeptide comprises a full-length extracellular domain (ECD). In some embodiments, the variant CD86 polypeptide comprises a specific binding fragment of the ECD domain. In some embodiments, the variant CD86 polypeptide comprises a specific binding fragment of the ECD domain comprising the full length IgV domain. In some embodiments, the variant CD86 polypeptide comprises a specific binding fragment of the ECD domain comprising a specific binding fragment of the IgV domain.

Generally, each of the various attributes of polypeptides are separately disclosed below (e.g., soluble and membrane bound polypeptides, affinity of CD86 for CD28 and CTLA-4, number of variations per polypeptide chain, number of linked polypeptide chains, the number and nature of amino acid alterations per variant CD86, etc.). However, as will be clear to the skilled artisan, any particular polypeptide can comprise a combination of these independent attributes. It is understood that reference to amino acids, including to a specific sequence set forth as a SEQ ID NO used to describe domain organization of an IgSF domain are for illustrative purposes and are not meant to limit the scope of the embodiments provided. It is understood that polypeptides and the description of domains thereof are theoretically derived based on homology analysis and alignments with similar molecules. Thus, the exact locus can vary, and is not necessarily the same for each protein. Hence, the specific IgSF domain, such as specific IgV domain, can be several amino acids (such as one, two, three or four) longer or shorter.

Further, various embodiments of the invention as discussed below are frequently provided within the meaning of a defined term as disclosed above. The embodiments described in a particular definition are therefore to be interpreted as being incorporated by reference when the defined term is utilized in discussing the various aspects and attributes described herein. Thus, the headings, the order of presentation of the various aspects and embodiments, and the separate disclosure of each independent attribute is not meant to be a limitation to the scope of the present disclosure.

A. Exemplary Modifications

Provided herein are variant CD86 polypeptides containing at least one affinity-modified IgSF domain (e.g., IgV) or a specific binding fragment thereof relative to an IgSF domain contained in a wild-type or unmodified CD86 polypeptide such that the variant CD86 polypeptide exhibits altered (increased or decreased) binding activity or affinity for one or more ligands CD28 or CTLA-4 compared to a wild-type or unmodified CD86 polypeptide. In some embodiments, a variant CD86 polypeptide has a binding affinity for CD28 and/or CTLA-4 that differs from that of a wild-type or unmodified CD86 polypeptide control sequence as determined by, for example, solid-phase ELISA immunoassays, flow cytometry, ForteBio Octet or Biacore assays. In some embodiments, the variant CD86 polypeptide has an increased binding affinity for CD28, relative to a wild-type or unmodified CD86 polypeptide. In some embodiments, the variant CD86 polypeptide has a decreased binding affinity for CTLA-4, relative to a wild-type or unmodified CD86 polypeptide. In some embodiments, the variant CD86 polypeptide exhibits no change in binding affinity for CTLA-4, relative to a wild-type or unmodified CD86 polypeptide. In some embodiments, the variant CD86 polypeptide exhibits no increase in binding affinity for CTLA-4, relative to a wild-type or unmodified CD86 polypeptide. The CD28 and/or the CTLA-4 can be a mammalian protein, such as a human protein or a murine protein. In some embodiments, the variant, wild-type, and unmodified CD86 polypeptides bind to the ectodomain of CD28 and/or CTLA-4. Thus, in some embodiments, affinity or binding activity is determined with respect to the binding of variant, wild-type, and unmodified CD86 polypeptides to the ectodomain of CD28 and/or CTLA-4.

Binding affinities for each of the cognate binding partners are independent; that is, in some embodiments, a variant CD86 polypeptide has an increased binding affinity for CD28 but not CTLA-4, relative to a wild-type or unmodified CD86 polypeptide.

In some embodiments, the variant CD86 polypeptide has an increased binding affinity for CD28, relative to a wild-type or unmodified CD86 polypeptide and has a decreased binding affinity for CTLA-4, relative to a wild-type or unmodified CD86 polypeptide. In some embodiments, the variant CD86 polypeptide has an increased binding affinity for CD28, relative to a wild-type or unmodified CD86 polypeptide and has no change in binding affinity for CTLA-4, relative to a wild-type or unmodified CD86 polypeptide.

In some embodiments, a variant CD86 polypeptide with increased or greater binding affinity to CD28 will have an increase in binding affinity relative to the wild-type or unmodified CD86 polypeptide control of at least about 5%, such as at least about 10%, 15%, 20%, 25%, 35%, or 50% for CD28. In some embodiments, the increase in binding affinity relative to the wild-type or unmodified CD86 polypeptide is more than 1.2-fold, 1.5-fold, 2-fold, 3-fold, 4-fold, 5-fold, 6-fold, 7-fold, 8-fold, 9-fold, 10-fold, 20-fold, 30-fold 40-fold, 50-fold, 60-fold, 70-fold, 80-fold, 90-fold, 100-fold, 125-fold, 150-fold, 175-fold, 200-fold, 225-fold, 250-fold, 275-fold, 300-fold, 325-fold, 350-fold 375-fold, or 400-fold. In such examples, the wild-type or unmodified CD86 polypeptide has the same sequence as the variant CD86 polypeptide except that it does not contain the one or more amino acid modifications (e.g. substitutions).

In some embodiments, a variant CD86 polypeptide with reduced or decreased binding affinity to CTLA-4 will have a decrease in binding affinity relative to the wild-type or unmodified CD86 polypeptide control of at least 5%, such as at least about 10%, 15%, 20%, 30%, 40%, 50%, 60%, 70%, 80%, 90% or more for the CTLA-4. In some embodiments, the decrease in binding affinity relative to the wild-type or unmodified CD86 polypeptide is more than 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 20-fold, 30-fold 40-fold or 50-fold. In some embodiments, a variant CD86 polypeptide does not show a change in binding affinity to CTLA-4 relative to the wild-type or unmodified CD86 polypeptide control. In some embodiments, a variant CD86 polypeptide does not show an increase in binding affinity to CTLA-4 relative to the wild-type or unmodified CD86 polypeptide control. In such examples, the wild-type or unmodified CD86 polypeptide has the same sequence as the variant CD86 polypeptide except that it does not contain the one or more amino acid modifications (e.g. substitutions).

In some embodiments, the equilibrium dissociation constant ($K_d$) of any of the foregoing embodiments to CD28 and/or CTLA-4 can be less than $1\times10^{-5}$M, $1\times10^{-6}$ M, $1\times10^{-7}$ M, $1\times10^{-8}$ M, $1\times10^{-9}$ M, $1\times10^{-1o}$ M or $1\times10^{-11}$M, or $1\times10^{-12}$ M or less.

The wild-type or unmodified CD86 sequence does not necessarily have to be used as a starting composition to generate variant CD86 polypeptides described herein. Therefore, use of the term "modification", such as "substitution", does not imply that the present embodiments are limited to a particular method of making variant CD86 polypeptides. Variant CD86 polypeptides can be made, for example, by de novo peptide synthesis and thus does not necessarily require a modification, such as a "substitution", in the sense of altering a codon to encode for the modification, e.g. substitution. This principle also extends to the terms "addition" and "deletion" of an amino acid residue which likewise do not imply a particular method of making. The means by which the variant CD86 polypeptides are designed or created is not limited to any particular method. In some embodiments, however, a wild-type or unmodified CD86 encoding nucleic acid is mutagenized from wild-type or unmodified CD86 genetic material and screened for desired specific binding affinity and/or induction of IFN-gamma expression or other functional activity. In some embodiments, a variant CD86 polypeptide is synthesized de novo utilizing protein or nucleic acid sequences available at any number of publicly available databases and then subsequently screened. The National Center for Biotechnology Information provides such information and its website is publicly accessible via the internet as is the UniProtKB database.

Unless stated otherwise, as indicated throughout the present disclosure, the amino acid modification(s) are designated by amino acid position number corresponding to the numbering of positions of the unmodified ECD sequence set forth in SEQ ID NO: 29 as follows:

```
                                    (SEQ ID NO: 29)
APLKIQAYFNETADLPCQFANSQNQSLSELVVFWQDQENLVLNEVYLGKE

KFDSVHSKYMGRTSFDSDSWTLRLHNLQIKDKGLYQCIIHHKKPTGMIRI

HQMNSELSVLANFSQPEIVPISNITENVYINLTCSSIHGYPEPKKMSVLL

RTKNSTIEYDGVMQKSQDNVTELYDVSISLSVSFPDVTSNMTIFCILETD

KTRLLSSPFSIELEDPQPPPDHIP
```

Modifications provided herein can be in a wild-type or unmodified CD86 polypeptide set forth in SEQ ID NO: 29 or in a portion thereof containing an IgV domain or a specific binding fragment thereof. In some embodiments, the wild-type or unmodified CD86 polypeptide contains the IgV of CD86 as set forth in SEQ ID NO: 122. In some embodiments, the unmodified CD86 polypeptide contains an IgV that can be several amino acids longer or shorter, such as 1-20, e.g. 1, 2, 3, 4, 5, 6, 7, 8, 9, 10, 11, 12, 13, 14, 15, 16, 17, 18, 19, or 20 amino acids longer or shorter, than the IgV sequence set forth in SEQ ID NO: 122. In some embodiments, the unmodified CD86 polypeptide has 85%, 86%, 87%, 88%, 89%, 90%, 91%, 92%, 93%, 94%, 95%, 96%, 97%, 98%, 99% sequence identity to SEQ ID NO: 29, 122, or 123, or a specific binding fragment thereof. In some embodiments, the unmodified CD86 polypeptide has the sequence set forth in any of SEQ ID NOs: 29, 122, and 123.

```
                                   (SEQ ID NO: 122)
NETADLPCQFANSQNQSLSELVVFWQDQENLVLNEVYLGKEKFDSVHSK

YMGRTSFDSDSWTLRLHNLQIKDKGLYQCIIHHKKPTGMIRIHQMNSEL

S
```

```
                                   (SEQ ID NO: 123)
APLKIQAYFNETADLPCQFANSQNQSLSELVVFWQDQENLVLNEVYLGK

EKFDSVHSKYMGRTSFDSDSWTLRLHNLQIKDKGLYQCIIHHKKPTGMI

RIHQMNSELSVLA
```

It is within the level of a skilled artisan to identify the corresponding position of a modification, e.g. amino acid substitution, in a CD86 polypeptide, including portion thereof containing an IgV domain, such as by alignment of a reference sequence with SEQ ID NO: 29. An exemplary alignment of SEQ ID NO: 29 containing residues 24-247 of wildtype CD86 with SEQ ID NO: 122 containing residues 33-131 of wildtype CD86 is shown in FIG. 3. In the listing of modifications throughout this disclosure, the amino acid position is indicated in the middle, with the corresponding unmodified (e.g. wild-type) amino acid listed before the number and the identified variant amino acid substitution listed after the number. If the modification is a deletion of the position a "del" is indicated and if the modification is an insertion at the position an "ins" is indicated. In some cases, an insertion is listed with the amino acid position indicated in the middle, with the corresponding unmodified (e.g. wild-type) amino acid listed before and after the number and the identified variant amino acid insertion listed after the unmodified (e.g. wild-type) amino acid.

In some embodiments, the variant CD86 polypeptide has one or more amino acid modifications, e.g. substitutions, in a wild-type or unmodified CD86 sequence. The one or more amino acid modifications, e.g. substitutions, can be in the ectodomain (extracellular domain; ECD) of the wild-type or unmodified CD86 sequence. In some embodiments, the one or more amino acid modifications, e.g. substitutions, are in the IgV domain or specific binding fragment thereof. In some embodiments, the one or more amino acid modifications, e.g. substitutions, are in the IgC domain or specific binding fragment thereof. In some embodiments, the one or more amino acid modifications, e.g. substitutions, are in the ECD or specific binding fragment thereof.

In some embodiments, the variant CD86 polypeptide has up to 1, 2, 3, 4, 5, 6, 7, 8, 9, 10, 11, 12, 13, 14, 15, 16, 17, 18, 19, or 20 amino acid modifications, e.g. substitutions. The modifications (e.g. substitutions) can be in the IgV domain. In some embodiments, the modifications are in the ECD. In some embodiments, the modifications are in the ECD and IgV domain. In some embodiments, the modifications are in the IgV domain. In some embodiments, the variant CD86 polypeptide has up to 1, 2, 3, 4, 5, 6, 7, 8, 9, 10, 11, 12, 13, 14, 15, 16, 17, 18, 19, or 20 amino acid modifications, e.g. substitutions, in the IgV domain or specific binding fragment thereof. In some embodiments, the variant CD86 polypeptide has up to 1, 2, 3, 4, 5, 6, 7, 8, 9, 10, 11, 12, 13, 14, 15, 16, 17, 18, 19, or 20 amino acid modifications, e.g. substitutions, in the ECD or specific binding fragment thereof. In some embodiments, the variant CD86 polypeptide has less than 100% sequence identity and at least about 85%, 86%, 86%, 88%, 89%, 90%, 91%, 92%, 93%, 94%, 95%, 96%, 97%, 98%, or 99% sequence identity with the wild-type or unmodified CD86 polypeptide or specific binding fragment thereof, such as with the amino acid sequence of SEQ ID NO: 29, 122, or 123.

In some embodiments, the variant CD86 polypeptide has one or more amino acid modifications, e.g. substitutions, in an unmodified CD86 or specific binding fragment thereof corresponding to position(s) 13, 18, 25, 28, 33, 38, 39, 40, 43, 45, 52, 53, 60, 68, 71, 77, 79, 80, 82, 86, 88, 89, 90, 92, 93, 97, 102, 104, 113, 114, 123, 128, 129, 132, 133, 137, 141, 143, 144, 148, 153, 154, 158, 170, 172, 175, 178, 180, 181, 183, 185, 192, 193, 196, 197, 198, 205, 206, 207, 212, 215, 216, 222, 223, or 224, with reference to positions set forth in SEQ ID NO:29. In some embodiments, the modification at position 224 is a deletion. In some embodiments, such variant CD86 polypeptides exhibit altered binding affinity to one or more of CD28 and/or CTLA-4 compared to the wild-type or unmodified CD86 polypeptide. For example, in some embodiments, the variant CD86 polypeptide exhibits increased binding affinity to CD28 compared to a wild-type or unmodified CD86 polypeptide. In some embodiments, the variant CD86 polypeptide exhibits decreased binding affinity to CTLA-4 compared to a wild-type or unmodified CD86 polypeptide. In some embodiments, the variant CD86 polypeptide does not exhibit any change in binding affinity to CTLA-4 compared to a wild-type or unmodified CD86 polypeptide. In some embodiments, the variant CD86 polypeptide does not exhibit an increase in binding affinity to CTLA-4 compared to a wild-type or unmodified CD86 polypeptide.

In some embodiments, the variant CD86 polypeptide has one or more amino acid substitutions selected from A13V, Q18K, Q25L, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, H90 L, H90Y, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T or I223F, or a conservative amino acid substitution thereof. A conservative amino acid substitution is any amino acid that falls in the same class of amino acids as the substituted amino acids, other than the wild-type or unmodified amino acid. The classes of amino acids are aliphatic (glycine, alanine, valine, leucine, and isoleucine), hydroxyl or sulfur-containing (serine, cysteine, threonine, and methionine), cyclic (proline), aromatic (phenylalanine, tyrosine, tryptophan), basic (histidine, lysine, and arginine), and acidic/amide (aspartate, glutamate, asparagine, and glutamine).

In some embodiments, the variant CD86 polypeptide has two or more amino acid substitutions selected from A13V, Q18K, Q25L, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, H90 L, H90Y, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T or I223F, or a conservative amino acid substitution thereof.

In some embodiments, the variant CD86 polypeptide contains one or more modifications (e.g. amino acid substitutions) at a position corresponding to position(s) selected from 13, 18, 25, 28, 33, 38, 39, 40, 43, 45, 52, 53, 60, 68, 71, 77, 79, 80, 82, 86, 88, 89, 90, 92, 93, 97, 102, 104, 113, 114, 123, 128, 129, 132, 133, 137, 141, 143, 144, 148, 153, 154, 158, 170, 172, 175, 178, 180, 181, 183, 185, 192, 193, 196, 197, 198, 205, 206, 207, 212, 215, 216, 222, 223, or 224 with reference to positions set forth in SEQ ID NO:29. In some embodiments, the amino acid modification is one or more amino acid substitution selected from A13V, Q18K, Q25L, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, H90 L, H90Y, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T or I223F, or a conservative amino acid substitution thereof.

In some embodiments, the variant CD86 polypeptide contains one or more amino acid substitution corresponding to A13V, Q18K, Q25L, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, H90 L, H90Y, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T or I223F, or a conservative substitution thereof.

In some embodiments, the variant CD86 polypeptide contains at least one modification (e.g. substitution) at a position selected from 25 or 90. In some embodiments, at least one amino acid substitution is Q25L, H90Y, or H90L. In some embodiments, at least one amino acid substitution is Q25L. In some embodiments, at least one amino acid substitution is H90Y or H90L.

In some embodiments, the variant CD86 polypeptide contains amino acid substitutions selected from among Q25L/T71A/H90Y, Q25L/D53G/E212V, Q25L/H90L, N43K/I79N/H90L/I178T/E198D, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/S28G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S, E38V/S114G/P143H, H90Y/L180S, H90Y/Y129N, I89V/H90L/I193V, K80E/H90Y/H222T/I223F/P224L, K80M/I88T, K92I/F113S, M60K/H90L, Q25L/F33I/H90L, Q25L/F33I/Q86R/H90L/K93T, Q25L/H90L, Q25L/H90L/P185S, Q25L/H90L/P185S/P224L, Q25L/H90L/S179R, Q25L/H90Y/S181P/I193V, Q25L/K82T/H90L/T152S/S207P, Q25L/Q86R/H90L/K93T, or S28G/H90Y. In some embodiments, the variant CD86 polypeptide contains amino acid substitutions selected from among Q25L/T71A/H90Y, Q25L/D53G/E212V, Q25L/H90L, N43K/I79N/H90L/I178T/E198D, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/S28G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S/E212X, H90Y/L180S, H90Y/Y129N, I89V/H90L/I193V, K80E/H90Y/H222T/I223F/P224L, M60K/H90L, Q25L/F33I/H90L, Q25L/F33I/Q86R/H90L/K93T, Q25L/H90L, Q25L/H90L/P185S, Q25L/H90L/P185S/P224L, Q25L/H90L/S179R, Q25L/H90Y/S181P/I193V, Q25L/K82T/H90L/T152S/S207P, Q25L/Q86R/H90L/K93T, S28G/H90Y, A13V/Q25L/H90L, Q25L/H90L/K93T/M97L, Q25L/Q86R/H90L, or I89V/H90L. In some embodiments, the variant CD86 polypeptide contains amino acid substitutions Q25L/H90Y or Q25L/H90L.

In some embodiments, any of the provided variant CD86 polypeptides can further contain one or more amino acid substitutions from A13V, Q18K, Q25L, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, H90 L, H90Y, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T, or I223F.

In some embodiments, among the provided variant CD86 polypeptides are CD86 polypeptides that have amino acid substitutions Q25L/T71A/H90Y, Q25L/D53G/E212V, Q25L/H90L, N43K/I79N/H90L/I178T/E198D, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/S28G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S, E38V/S114G/P143H, H90Y/L180S, H90Y/Y129N, I89V/H90L/I193V, K80E/H90Y/H222T/I223F/P224L, K80M/I88T, K92I/F113S, M60K/H90L, Q25L/F33I/H90L, Q25L/F33I/Q86R/H90L/K93T, Q25L/H90L, Q25L/H90L/P185S, Q25L/H90L/P185S/P224L, Q25L/H90L/S179R, Q25L/H90Y/S181P/I193V, Q25L/K82T/H90L/T152S/S207P, Q25L/Q86R/H90L/K93T, or S28G/H90Y. In some embodiments, among the provided variant CD86 polypeptides are CD86 polypeptides that have amino acid substitutions Q25L/T71A/H90Y, Q25L/D53G/E212V, Q25L/H90L, N43K/I79N/H90L/I178T/E198D, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/S28G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S/E212X, H90Y/L180S, H90Y/Y129N, I89V/H90L/I193V, K80E/H90Y/H222T/I223F/P224L, M60K/H90L, Q25L/F33I/H90L, Q25L/F33I/Q86R/H90L/K93T, Q25L/H90L, Q25L/H90L/P185S, Q25L/H90L/P185S/P224L, Q25L/H90L/S179R, Q25L/H90Y/S181P/I193V, Q25L/K82T/H90L/T152S/S207P, Q25L/Q86R/H90L/K93T, S28G/H90Y, A13V/Q25L/H90L, Q25L/H90L/K93T/M97L, Q25L/Q86R/H90L, or I89V/H90L.

In some embodiments, the variant CD86 polypeptide comprises any of the substitutions (mutations) listed in Table 1. Table 1 also provides exemplary sequences by reference to SEQ ID NO for the extracellular domain (ECD) or IgV domain of wild-type CD86 or exemplary variant CD86 polypeptides. In some cases, an IgV as indicated in the Table 1 is shorter than an ECD and thus may not include all amino acid substitutions as listed in Table 1, e.g. the amino acid substitutions outside of the IgV domain. As indicated, the exact locus or residues corresponding to a given domain can vary, such as depending on the methods used to identify or classify the domain. Also, in some cases, adjacent N- and/or C-terminal amino acids of a given domain (e.g. ECD or IgV) also can be included in a sequence of a variant IgSF polypeptide, such as to ensure proper folding of the domain when expressed. Thus, it is understood that the exemplification of the SEQ ID NOs in Table 1 is not to be construed as limiting. For example, the particular domain, such as the ECD or IgV domain, of a variant CD86 polypeptide can be several amino acids longer or shorter, such as 1-20, e.g. 1, 2, 3, 4, 5, 6, 7, 8, 9, 10, 11, 12, 13, 14, 15, 16, 17, 18, 19, or 20 amino acids longer or shorter, than the sequence of amino acids set forth in the respective SEQ ID NO.

In some embodiments, the variant CD86 polypeptide is or comprises any of the sequences set forth in SEQ ID NOS: 85-121, 124-134, 141-221, and 314. In some embodiments, the variant CD86 polypeptide is or comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the sequences set forth in any one of SEQ ID NOS: 85-121, 124-134, 141-221, and 314, and that contains the amino acid modification(s), e.g. substitution(s), therein not present in the wild-type or unmodified CD86. In some embodiments, the variant CD86 polypeptide is or comprises a specific binding fragment of any of any one of SEQ ID NOS: 85-121, 124-134, 314, and 141-221 and contains the amino acid modification(s), e.g. substitution(s), therein not present in the wild-type or unmodified CD86. In some embodiments, the variant CD86 is or comprises the sequence set forth by SEQ ID NOS: 89, 93, 94, 107, 111, 112, 115, 117, 124-134, 145, 149, 150, 163, 167, 168, 171, 173, 182, 186, 187, 200, 204, 205, 208, 210, 215-221, or 314. In some embodiments, the variant CD86 polypeptide is or comprises a polypeptide sequence that exhibits at least 90% identity, at least 91% identity, at least 92% identity, at least 93% identity, at least 94% identity, at least 95% identity, such as at least 96% identity, 97% identity, 98% identity, or 99% identity to any of the sequences set forth in any one of SEQ ID NOS: 89, 93, 94, 107, 111, 112, 115, 117, 124-134, 145, 149, 150, 163, 167, 168, 171, 173, 182, 186, 187, 200, 204, 205, 208, 210, 215-221, or 314, and contains the amino acid modification(s), e.g. substitution(s) therein not present in the wild-type or unmodified CD86.

In some embodiments, the variant CD86 polypeptide is or comprises a specific binding fragment of any one of SEQ ID NOS: 85-121, 124-134, 141-221, or 314 and contains the amino acid modification(s), e.g. substitution(s) therein, not present in the wild-type or unmodified CD86. In some embodiments, the variant CD86 polypeptide is or comprises a specific binding fragment of any one of SEQ ID NOS: 89, 93, 94, 107, 111, 112, 115, 117, 124-134, 145, 149, 150, 163, 167, 168, 171, 173, 182, 186, 187, 200, 204, 205, 208, 210, 215-221, or 314 and contains the amino acid modification(s), e.g. substitution(s) therein, not present in the wild-type or unmodified CD86.

TABLE 1

Exemplary variant CD86 polypeptides

| Mutation(s) | SEQ ID NO ECD (24-247) | SEQ ID NO IgV (24-134 ) | SEQ ID NO IgV (33-131) |
|---|---|---|---|
| Wild-type | 29 | 123 | 122 |
| Q25L/T71A/H90Y | 85 | 141 | 178 |
| Q25L/D53G/E212V | 86 | 142 | 179 |
| Q25L/H90L | 87 | 143 | 180 |
| N43K/I79N/H90L/I178T/E198D | 88 | 144 | 181 |
| A13V/Q25L/H90L/S181P/L197M/S206T | 89 | 145 | 182 |
| Q25L/Q86R/H90L/K93T/L132M/V148D/S181P/P216H | 90 | 146 | 183 |
| Q25L/F331/H90Y/V128A/P141A/E158G/S181P | 91 | 147 | 184 |
| Q25L/N39D/K80R/Q86R/I88F/H90L/K93T/N123D/N154D | 92 | 148 | 185 |
| Q25L/H90L/K93T/M97L/T133A/S181P/D215V | 93 | 149 | 186 |
| Q25L/Q86R/H90L/N104S | 94 | 150 | 187 |
| Q25L/L40M/H90L/L180S/S183P | 95 | 151 | 188 |
| Q18K/Q25L/F331/L40S/H90L | 96 | 152 | 189 |
| Q25L/Q86K/H90L/1137T/S181P | 97 | 153 | 190 |
| Q25L/L77P/H90Y/K153R/V170D/S18 IP | 98 | 154 | 191 |
| Q25L/S28G/F331/F52L/H90L/Q102H/I178T | 99 | 155 | 192 |
| Q25L/F331/H90L/K144E/L180S | 100 | 156 | 193 |
| Q25L/F331/H90L/K153E/E172G/T192N | 101 | 157 | 194 |
| Q25L/F331/Q86R/H90Y/D175E/1196V/E198D | 102 | 158 | 195 |
| Q25L/V451/D68N/H90L/S 183P/L205S | 103 | 159 | 196 |
| E38V/S114G/P143H | 104 | 160 | 197 |
| H90Y/L180S | 105 | 161 | 198 |
| H90Y/Y129N | 106 | 162 | 199 |
| I89V/H90L/I193V | 107 | 163 | 200 |
| K80E/H90Y/H222T/I223F/P224L | 108 | 164 | 201 |
| K8OM/I88T | 109 | 165 | 202 |
| K921/F113S | 110 | 166 | 203 |
| M60K/H90L | 111 | 167 | 204 |
| Q25L/F331/H90L | 112 | 168 | 205 |
| Q25L/F331/Q86R/H90L/K93T | 113 | 169 | 206 |
| Q25L/H90L | 114 | 170 | 207 |
| Q25L/H90L/P185S | 115 | 171 | 208 |
| Q25L/H90L/P185S/P224L | 116 | 172 | 209 |
| Q25L/H90L/S179R | 117 | 173 | 210 |
| Q25L/H90Y/S181P/I193 V | 118 | 174 | 211 |
| Q25L/K82T/H90L/T152S/S207P | 119 | 175 | 212 |
| Q25L/Q86R/H90L/K93T | 120 | 176 | 213 |
| S28G/H90Y | 121 | 177 | 214 |
| A13V/Q25L/H90L | 131 | 124 | 215 |
| Q25L/H90L/K93T/M97L | 132 | 125 | 216 |
| Q25L/Q86R/H90L | 314 | 126 | 217 |
| I89V/H9OL | 133 | 127 | 218 |
| M60K/H90L | ill | 128 | 219 |
| Q25L/F331/H90L | 112 | 129 | 220 |
| Q25L/H90L | 134 | 130 | 221 |

In some embodiments, any of the provided variants of CD86 can be included as a polypeptide that is shorter or longer as described, such as by 1-20 amino acids, e.g. 1, 2, 3, 4, 5, 6, 7, 8, 9, 10, 11, 12, 13, 14, 15, 16, 17, 18, 19, or 20 amino acids longer or shorter, than the sequence of amino acids set forth in Table 1 as long as the CD86 polypeptide binds to CD28, including binding with increased affinity compared to the wild-type or unmodified CD86 polypeptide.

In some embodiments, the variant CD86 polypeptide exhibits increased affinity for the ectodomain of CD28 compared to the wild-type or unmodified CD86 polypeptide, such as compared to the sequence set forth in SEQ ID NO: 29, 122, or 123.

In some embodiments, the variant CD86 polypeptide exhibits increased binding affinity for binding the ectodomain of CD28 and exhibits decreased binding affinity for binding to CTLA-4 compared to the wild-type or unmodified CD86 polypeptide, such as compared to the sequence set forth in SEQ ID NO: 29, 122, or 123. In some embodiments, the variant CD86 polypeptide exhibits increased affinity for the ectodomain of CD28, and no change in affinity for the ectodomain of CTLA-4, compared to wild-type or unmodified CD86 polypeptide, such as compared to the sequence set forth in SEQ ID NO: 29, 122, or 123.

In some embodiments, a variant CD86 polypeptide exhibits increased selectivity for CD86 versus CTLA-4 compared to the unmodified CD86 polypeptide (e.g. set forth in SEQ ID NO: 29, 122, or 123) for binding CD28 versus CTLA-4, such as indicated by a ratio of CD28 binding to CTLA-4 binding (CD28:CTLA-4 binding ratio). In some embodiments, the ratio of binding is greater than 1. In some embodiments, the variant CD86 polypeptide exhibits a ratio of binding CD28 versus CTLA-4 that is greater than or greater than about or 1.1, 1.2, 1.3, 1.4, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, or more.

III. FORMAT OF VARIANT POLYPEPTIDES

The immunomodulatory polypeptide comprising a variant CD86 provided herein in which is contained a vIgD can be formatted in a variety of ways, including as a soluble protein, membrane bound protein or secreted protein. In some embodiments, the particular format can be chosen for the desired therapeutic application. In some cases, an immunomodulatory polypeptide comprising a variant CD86 polypeptide is provided in a format to antagonize or block activity of its binding partner, e.g., CTLA-4 and/or CD28. In some cases, an immunomodulatory polypeptide comprising a variant CD86 polypeptide is provided in a format to agonize or stimulate activity of its binding partner, e.g., CD28. In some embodiments, agonism of CD28 may be useful to promote immunity in oncology. A skilled artisan can readily determine the activity of a particular format, such as for antagonizing or agonizing one or more specific binding partner. Exemplary methods for assessing such activities are provided herein, including in the examples. In some embodiments, the modular format of the provided immunomodulatory proteins provides flexibility for engineering or generating immunomodulatory proteins for modulating activity of multiple counter structures (multiple cognate binding partners).

In some aspects, provided are immunomodulatory proteins comprising a vIgD of CD86 in which such proteins are soluble, e.g., fused to an Fc chain. In some aspects, one or more additional IgSF domain, such as one or more additional vIgD, may be linked to a vIgD of CD86 as provided herein (hereinafter called a “stack” or “stacked” immunomodulatory protein). In some embodiments, such “stack” molecules can be provided in a soluble format or, in some cases, may be provided as membrane bound or secreted proteins. In some embodiments, a variant CD86 immunomodulatory protein is provided as a conjugate in which is contained a vIgD of CD86 linked, directly or indirectly, to a targeting agent or moiety, e.g., to an antibody or other binding molecules that specifically binds to a ligand, e.g., an antigen, for example, for targeting or localizing the vIgD to a specific environment or cell, such as when administered to a subject. In some embodiments, the targeting agent, e.g., antibody or other binding molecule, binds to a tumor antigen, thereby localizing the variant CD86 containing the vIgD to the tumor microenvironment, for example, to modulate activity of tumor infiltrating lymphocytes (TILs) specific to the tumor microenvironment.

In some embodiments, provided immunomodulatory proteins are expressed in cells and provided as part of an engineered cellular therapy (ECT). In some embodiments, the variant CD86 polypeptide is expressed in a cell, such as an immune cell (e.g., T cell or antigen presenting cell), in membrane-bound form, thereby providing a transmembrane immunomodulatory protein (hereinafter also called a “TIP”). In some embodiments, depending on the cognate binding partner(s) recognized by the TIP, engineered cells expressing a TIP can agonize a cognate binding partner by providing a costimulatory signal, either positive to negative, to other engineered cells and/or to endogenous T cells. In some embodiments, an engineered cell expressing a TIP binds to a cognate binding partner on a different cell. In some embodiments, when an engineered cell expressing a TIP binds to a cognate binding partner on a different cell, the costimulation is referred to as costimulation in trans. In some embodiments, an engineered cell expressing a TIP binds to a cognate binding partner on itself, thereby inducing costimulating in itself. In some embodiments, when a TIP on a cell binds to a cognate binding partner on itself, the costimulation is referred to as costimulation in cis. In some aspects, the variant CD86 polypeptide is expressed in a cell, such as an immune cell (e.g., T cell or antigen presenting cell), in secretable form to thereby produce a secreted or soluble form of the variant CD86 polypeptide (hereinafter also called a “SIP”), such as when the cells are administered to a subject. In some aspects, depending on the cognate binding partner(s) recognized by the SIP, engineered cells expressing a SIP can antagonize or agonize a cognate binding partner in the environment (e.g., tumor microenvironment) in which it is secreted. In some embodiments, a variant CD86 polypeptide is expressed in an infectious agent (e.g., viral or bacterial agent) which, upon administration to a subject, is able to infect a cell in vivo, such as an immune cell (e.g., T cell or antigen presenting cell), for delivery or expression of the variant polypeptide as a TIP or a SIP in the cell.

In some embodiments, a soluble immunomodulatory polypeptide, such as a variant CD86 containing a vIgD, can be encapsulated within a liposome which itself can be conjugated to any one of or any combination of the provided conjugates (e.g., a targeting moiety). In some embodiments, the soluble or membrane bound immunomodulatory polypeptides of the invention are deglycosylated. In more specific embodiments, the variant CD86 sequence is deglycosylated. In even more specific embodiments, the IgV and/or IgC (e.g., IgC2) domain or domains of the variant CD86 is deglycosylated.

Non-limiting examples of provided formats are further described below.

B. Soluble Protein

In some embodiments, the immunomodulatory protein containing a variant CD86 polypeptide is a soluble protein. Those of skill will appreciate that cell surface proteins typically have an intracellular, transmembrane, and extracellular domain (ECD) and that a soluble form of such proteins can be made using the extracellular domain or an immunologically active subsequence thereof. Thus, in some embodiments, the immunomodulatory protein containing a variant CD86 polypeptide lacks a transmembrane domain or a portion of the transmembrane domain. In some embodiments, the immunomodulatory protein containing a variant CD86 lacks the intracellular (cytoplasmic) domain or a portion of the intracellular domain. In some embodiments, the immunomodulatory protein containing the variant CD86 polypeptide only contains the vIgD portion containing the ECD domain or a portion thereof containing an IgV domain and/or IgC (e.g., IgC2) domain or domains or specific binding fragments thereof containing the amino acid modification(s).

In some embodiments, an immunomodulatory polypeptide comprising a variant CD86 can include one or more variant CD86 polypeptides of the invention. In some embodiments a polypeptide of the invention will comprise exactly 1, 2, 3, 4, 5 variant CD86 sequences. In some embodiments, at least two of the variant CD86 sequences are identical variant CD86 sequences.

In some embodiments, the provided immunomodulatory polypeptide comprises two or more vIgD sequences of CD86. Multiple variant CD86 polypeptides within the polypeptide chain can be identical (i.e., the same species) to each other or be non-identical (i.e., different species) variant CD86 sequences. In addition to single polypeptide chain embodiments, in some embodiments two, three, four, or more of the polypeptides of the invention can be covalently or non-covalently attached to each other. Thus, monomeric, dimeric, and higher order (e.g., 3, 4, 5, or more) multimeric proteins are provided herein. For example, in some embodiments exactly two polypeptides of the invention can be covalently or non-covalently attached to each other to form a dimer. In some embodiments, attachment is made via interchain cysteine disulfide bonds. Compositions comprising two or more polypeptides of the invention can be of an identical species or substantially identical species of polypeptide (e.g., a homodimer) or of non-identical species of polypeptides (e.g., a heterodimer). A composition having a plurality of linked polypeptides of the invention can, as noted above, have one or more identical or non-identical variant CD86 polypeptides of the invention in each polypeptide chain.

In some embodiments, the immunomodulatory protein is or contains a variant CD86 polypeptide that is in monomer form and/or that exhibits monovalent binding to its binding partner. In some aspects, a variant CD86 polypeptide as described, such as a variant CD86 that is soluble and/or that lacks a transmembrane domain and intracellular signaling domain, is linked, directly or indirectly, to a further moiety. In some embodiments, the further moiety is a protein, peptide, small molecule or nucleic acid. In some embodiments, the monovalent immunomodulatory protein is a fusion protein. In some embodiments, the moiety is a half-life extending molecule. Examples of such half-life extending molecules include, but are not limited to, albumin, an albumin-binding polypeptide, Pro/Ala/Ser (PAS), a C-terminal peptide (CTP) of the beta subunit of human chorionic gonadotropin, polyethylene glycol (PEG), long unstructured hydrophilic sequences of amino acids (XTEN), hydroxyethyl starch (HES), an albumin-binding small molecule, or a combination thereof.

In some embodiments, the immunomodulatory polypeptide comprising a variant CD86 can be linked to a moiety that includes conformationally disordered polypeptide sequences composed of the amino acids Pro, Ala, and Ser (See e.g., WO2008/155134, SEQ ID NO: 242). In some cases, the amino acid repeat is at least 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid residues, wherein each repeat comprises (an) Ala, Ser, and Pro residue(s). Thus, provided herein is an immunomodulatory protein that is a PASylated protein wherein the variant CD86 polypeptide is linked, directly or indirectly via a linker, to Pro/Ala/Ser (PAS). In some embodiments, one or more additional linker structures may be used.

In some embodiments, the moiety facilitates detection or purification of the variant CD86 polypeptide. In some cases, the immunomodulatory polypeptide comprises a tag or fusion domain, e.g., affinity or purification tag, linked, directly or indirectly, to the N- and/or C-terminus of the CD86 polypeptide. Various suitable polypeptide tags and/or fusion domains are known, and include but are not limited to, a poly-histidine (His) tag, a FLAG-tag (SEQ ID NO: 248), a Myc-tag, and fluorescent protein-tags (e.g., EGFP, set forth in SEQ ID NOs: 244-246). In some cases, the immunomodulatory polypeptide comprising a variant CD86 comprises at least six histidine residues (set forth in SEQ ID NO: 249). In some cases, the immunomodulatory polypeptide comprising a variant CD86 further comprises various combinations of moieties. For example, the immunomodulatory polypeptide comprising a variant CD86 further comprises one or more polyhistidine-tag and FLAG tag.

In some embodiments, the CD86 polypeptide is linked to a modified immunoglobulin heavy chain constant region (Fc) that remains in monovalent form such as set forth in SEQ ID NO: 252.

In some embodiments, the immunomodulatory protein contains a variant CD86 polypeptide that is linked, directly or indirectly, via a linker to a multimerization domain. In some aspects, the multimerization domain increases the half-life of the molecule. Interaction of two or more variant CD86 polypeptides can be facilitated by their linkage, either directly or indirectly, to any moiety or other polypeptide that are themselves able to interact to form a stable structure. For example, separate encoded variant CD86 polypeptide chains can be joined by multimerization, whereby multimerization of the polypeptides is mediated by a multimerization domain. Typically, the multimerization domain provides for the formation of a stable protein-protein interaction between a first variant CD86 polypeptide and a second variant CD86 polypeptide.

Homo- or heteromultimeric polypeptides can be generated from co-expression of separate variant CD86 polypeptides. The first and second variant CD86 polypeptides can be the same or different. In particular embodiments, the first and second variant CD86 polypeptides are the same in a homodimer, and each is linked to a multimerization domain that is the same. In other embodiments, heterodimers can be formed by linking first and second variant CD86 polypeptides that are different. In some of such embodiments, the first and second variant CD86 polypeptides are linked to different multimerization domains capable of promoting heterodimer formation.

In some embodiments, a multimerization domain includes any capable of forming a stable protein-protein interaction. The multimerization domains can interact via an immunoglobulin sequence (e.g. Fc domain; see e.g., International Patent Pub. Nos. WO 93/10151 and WO 2005/063816 US; U.S. Pub. No. 2006/0024298; U.S. Pat. No. 5,457,035); leucine zipper (e.g., from nuclear transforming proteins fos and jun or the proto-oncogene c-myc or from General Control of Nitrogen (GCN4)) (see e.g., Busch and Sassone-Corsi (1990) Trends Genetics, 6:36-40; Gentz et al., (1989) Science, 243:1695-1699); a hydrophobic region; a hydrophilic region; or a free thiol which forms an intermolecular disulfide bond between the chimeric molecules of a homo- or heteromultimer. In addition, a multimerization domain can include an amino acid sequence comprising a protuberance complementary to an amino acid sequence comprising a hole, such as is described, for example, in U.S. Pat. No. 5,731,168; International Patent Pub. Nos. WO 98/50431 and WO 2005/063816; Ridgway et al. (1996) Protein Engineering, 9:617-621. Such a multimerization region can be engineered such that steric interactions not only promote stable interaction, but further promote the formation of heterodimers over homodimers from a mixture of chimeric monomers. Generally, protuberances are constructed by replacing small amino acid side chains from the interface of the first polypeptide with larger side chains (e.g., tyrosine or tryptophan). Compensatory cavities of identical or similar size to the protuberances are optionally created on the interface of the second polypeptide by replacing large amino acid side chains with smaller ones (e.g., alanine or threonine). Exemplary multimerization domains are described below.

The variant CD86 polypeptide can be joined anywhere, but typically via its N- or C-terminus, to the N- or C-terminus of a multimerization domain to form a chimeric polypeptide. The linkage can be direct or indirect via a linker. The chimeric polypeptide can be a fusion protein or can be formed by chemical linkage, such as through covalent or non-covalent interactions. For example, when preparing a chimeric polypeptide containing a multimerization domain, nucleic acid encoding all or part of a variant CD86 polypeptide can be operably linked to nucleic acid encoding the multimerization domain sequence, directly or indirectly or optionally via a linker domain. In some cases, the construct encodes a chimeric protein where the C-terminus of the variant CD86 polypeptide is joined to the N-terminus of the multimerization domain. In some instances, a construct can encode a chimeric protein where the N-terminus of the variant CD86 polypeptide is joined to the C-terminus of the multimerization domain.

A polypeptide multimer contains multiple, such as two, chimeric proteins created by linking, directly or indirectly, two of the same or different variant CD86 polypeptides directly or indirectly to a multimerization domain. In some examples, where the multimerization domain is a polypeptide, a gene fusion encoding the variant CD86 polypeptide and multimerization domain is inserted into an appropriate expression vector. The resulting chimeric or fusion protein can be expressed in host cells transformed with the recombinant expression vector, and allowed to assemble into multimers, where the multimerization domains interact to form multivalent polypeptides. Chemical linkage of multimerization domains to variant CD86 polypeptides can be carried out using heterobifunctional linkers.

The resulting chimeric polypeptides, such as fusion proteins, and multimers formed therefrom, can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

In some embodiments, the multimerization domain is an Fc domain or portions thereof from an immunoglobulin. In some embodiments, the immunomodulatory protein comprises a variant CD86 polypeptide attached to an immunoglobulin Fc (yielding an "immunomodulatory Fc fusion," such as a "variant CD86-Fc fusion," also termed a CD86 vIgD-Fc fusion). In some embodiments, the attachment of the variant CD86 polypeptide is at the N-terminus of the Fc. In some embodiments, the attachment of the variant CD86 polypeptide is at the C-terminus of the Fc. In some embodiments, two or more CD86 variant polypeptides (the same or different) are independently attached at the N-terminus and at the C-terminus. In some embodiments, CD86-Fc variant fusion provided herein contains a variant CD86 polypeptide in accord with the description set forth in Section II above.

In some embodiments, the Fc is murine or human Fc. In some embodiments, the Fc is a mammalian or human IgG1, IgG2, IgG3, or IgG4 Fc regions. In some embodiments, the Fc is derived from IgG1, such as human IgG1. In some embodiments, the Fc comprises the amino acid sequence set forth in SEQ ID NO: 229, 230, or 253 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 229, 230, or 253.

In some embodiments, the Fc region contains one more modifications to alter (e.g., reduce) one or more of its normal functions. In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments, such functions can be reduced or altered in an Fc for use with the provided Fc fusion proteins.

In some embodiments, one or more amino acid modifications may be introduced into the Fc region of a CD86-Fc variant fusion provided herein, thereby generating an Fc region variant. In some embodiments, the Fc region variant has decreased effector function. There are many examples of changes or mutations to Fc sequences that can alter effector function. For example, WO 00/42072, WO2006019447, WO2012125850, WO2015/107026, US2016/0017041 and Shields et al. J Biol. Chem. 9(2): 6591-6604 (2001) describe exemplary Fc variants with improved or diminished binding to FcRs. The contents of those publications are specifically incorporated herein by reference.

In some embodiments, the provided variant CD86-Fc fusions comprise an Fc region that exhibits reduced effector functions, which makes it a desirable candidate for applications in which the half-life of the CD86-Fc variant fusion in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the CD86-Fc variant fusion lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g., Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox96™ non-radioactive cytotoxicity assay (Promega, Madison, Wis.)). Useful effector cells for such assays include peripheral blood mononuclear cells (PBMC) and Natural Killer (NK) cells. Alternatively or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the CD86-Fc variant fusion is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:

1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., Intl Immunol. 18(12):1759-1769 (2006)).

CD86-Fc variant fusions with reduced effector function include those with substitution of one or more of Fc region residues 238, 265, 269, 270, 297, 327 and 329 by EU numbering (U.S. Pat. No. 6,737,056). Such Fc mutants include Fc mutants with substitutions at two or more of amino acid positions 265, 269, 270, 297 and 327 by EU numbering, including the so-called "DANA" Fc mutant with substitution of residues 265 and 297 to alanine (U.S. Pat. No. 7,332,581).

In some embodiments, the Fc region of CD86-Fc variant fusions has an Fc region in which any one or more of amino acids at positions 234, 235, 236, 237, 238, 239, 270, 297, 298, 325, and 329 (indicated by EU numbering) are substituted with different amino acids compared to the native Fc region. Such alterations of Fc region are not limited to the above-described alterations, and include, for example, alterations such as deglycosylated chains (N297A and N297Q), IgG1-N297G, IgG1-L234A/L235A, IgG1-L234A/L235E/G237A, IgG1-A325A/A330S/P331S, IgG1-C226S/C229S, IgG1-C226S/C229S/E233P/L234V/L235A, IgG1-E233P/L234V/L235A/G236del/S267K, IgG1-L234F/L235E/P331S, IgG1-S267E/L328F, IgG2-V234A/G237A, IgG2-H268Q/V309L/A330S/A331S, IgG4-L235A/G237A/E318A, and IgG4-L236E described in Current Opinion in Biotechnology (2009) 20 (6), 685-691; alterations such as G236R/L328R, L235G/G236R, N325A/L328R, and N325LL328R described in WO 2008/092117; amino acid insertions at positions 233, 234, 235, and 237 (indicated by EU numbering); and alterations at the sites described in WO 2000/042072.

Certain Fc variants with improved or diminished binding to FcRs are described. (See, e.g., U.S. Pat. No. 6,737,056; WO 2004/056312, WO2006019447 and Shields et al., J. Biol. Chem. 9(2): 6591-6604 (2001).)

In some embodiments, there is provided a CD86-Fc variant fusion comprising a variant CD86 polypeptide as described herein and a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.) or WO2015107026. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434 by EU numbering, e.g., substitution of Fc region residue 434 (U.S. Pat. No. 7,371,826).

In some embodiments, the Fc region of a CD86-Fc variant fusion comprises one or more amino acid substitution E356D and M358L by EU numbering. In some embodiments, the Fc region of a CD86-Fc variant fusion comprises one or more amino acid substitutions C220S, C226S and/or C229S by EU numbering. In some embodiments, the Fc region of a CD86 variant fusion comprises one or more amino acid substitutions R292C and V302C. See also Duncan & Winter, Nature 322:738-40 (1988); U.S. Pat. Nos. 5,648,260; 5,624,821; and WO 94/29351 concerning other examples of Fc region variants.

In some embodiments, the wild-type IgG1 Fc can be the Fc set forth in SEQ ID NO: 229 having an allotype containing residues Glu (E) and Met (M) at positions 356 and 358 by EU numbering (e.g., f allotype). In other embodiments, the wild-type IgG1 Fc contains amino acids of the human G1m1 allotype, such as residues containing Asp (D) and Leu (L) at positions 356 and 358, e.g. as set forth in SEQ ID NO 332. Thus, in some cases, an Fc provided herein can contain amino acid substitutions E356D and M358L to reconstitute residues of allotype G1 ml (e.g., alpha allotype). In some aspects, a wild-type Fc is modified by one or more amino acid substitutions to reduce effector activity or to render the Fc inert for Fc effector function. Exemplary effectorless or inert mutations include those described herein. Among effectorless mutations that can be included in an Fc of constructs provided herein are L234A, L235E, and G237A by EU numbering. In some embodiments, a wild-type Fc is further modified by the removal of one or more cysteine residues, such as by replacement of the cysteine residues to a serine residue at position 220 (C220S) by EU numbering. Exemplary inert Fc regions having reduced effector function are set forth in SEQ ID NO: 333 or 256 and SEQ ID NO: 258 or 230, which are based on allotypes set forth in SEQ ID NO: 229 or SEQ ID NO: 332, respectively. In some embodiments, an Fc region used in a construct provided herein can further lack a C-terminal lysine residue.

In some embodiments, alterations are made in the Fc region that result in diminished C1q binding and/or Complement Dependent Cytotoxicity (CDC), e.g., as described in U.S. Pat. No. 6,194,551, WO 99/51642, and Idusogie et al., J. Immunol. 164: 4178-4184 (2000).

In some embodiments, there is provided a CD86-Fc variant fusion comprising a variant Fc region comprising one or more amino acid modifications, wherein the variant Fc region is derived from IgG1, such as human IgG1. In some embodiments, the variant Fc region is derived from the amino acid sequence set forth in SEQ ID NO: 229. In some embodiments, the Fc contains at least one amino acid substitution that is N82G by numbering of SEQ ID NO: 229 (corresponding to N297G by EU numbering). In some embodiments, the Fc further contains at least one amino acid substitution that is R77C or V87C by numbering of SEQ ID NO: 229 (corresponding to R292C or V302C by EU numbering). In some embodiments, the variant Fc region further comprises a C5S amino acid modification by numbering of SEQ ID NO: 229 (corresponding to C220S by EU numbering), such as the Fc region set forth in SEQ ID NO: 254. For example, in some embodiments, the variant Fc region comprises the following amino acid modifications: V297G and one or more of the following amino acid modifications C220S, R292C, or V302C by EU numbering (corresponding to N82G and one or more of the following amino acid modifications C5S, R77C, or V87C with reference to SEQ ID NO: 229), e.g., the Fc region comprises the sequence set forth in SEQ ID NO: 255. In some embodiments, the variant Fc region comprises one or more of the amino acid modifications C220S, L234A, L235E, or G237A, e.g., the Fc region comprises the sequence set forth in SEQ ID NO: 256. In some embodiments, the variant Fc region comprises one or more of the amino acid modifications C220S, L235P, L234V, L235A, G236del, or S267K, e.g., the Fc region comprises the sequence set forth in SEQ ID NO:257. In some embodiments, the variant Fc comprises one or more of the amino acid modifications C220S, L234A, L235E, G237A, E356D, or M358L, e.g., the Fc region comprises the sequence set forth in SEQ ID NO:258.

In some embodiments, CD86-Fc variant fusion provided herein contains a variant CD86 polypeptide in accord with the description set forth in Section II above. In some embodiments, there is provided a CD86-Fc variant fusion comprising any one of the described variant CD86 polypeptide linked to a variant Fc region, wherein the variant Fc region is not a human IgG1 Fc containing the mutations R292C, N297G, and V302C (corresponding to R77C, N82G and V87C with reference to wild-type human IgG1 Fc set forth in SEQ ID NO: 229). In some embodiments, there is provided a CD86-Fc variant fusion comprising any one of the variant CD86 polypeptide linked to an Fc region or variant Fc region, wherein the variant CD86 polypeptide is not linked to the Fc with a linker consisting of three alanines.

In some embodiments, the Fc region lacks the C-terminal lysine corresponding to position 232 of the wild-type or unmodified Fc set forth in SEQ ID NO: 229 (corresponding to K447del by EU numbering). In some aspects, such an Fc region can additionally include one or more additional modifications, e.g., amino acid substitutions, such as any as described. Examples of such an Fc region are set forth in SEQ ID NO: 255-257, 258, or 259-261.

In some embodiments, there is provided a CD86-Fc variant fusion comprising a variant Fc region in which the variant Fc comprises the sequence of amino acids set forth in any of SEQ ID NOS: 255, 258, 256, 257, 254, or 259-261 or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 255, 258, 256, 257, 254, or 259-261.

In some embodiments, the Fc is derived from IgG2, such as human IgG2. In some embodiments, the Fc comprises the amino acid sequence set forth in SEQ ID NO: 262 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 262.

In some embodiments, the Fc comprises the amino acid sequence set forth in SEQ ID NO: 263 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 263. In some embodiments, the IgG4 Fc is a stabilized Fc in which the CH3 domain of human IgG4 is substituted with the CH3 domain of human IgG1 and which exhibits inhibited aggregate formation, an antibody in which the CH3 and CH2 domains of human IgG4 are substituted with the CH3 and CH2 domains of human IgG1, respectively, or an antibody in which arginine at position 409 indicated in the EU index proposed by Kabat et al. of human IgG4 is substituted with lysine and which exhibits inhibited aggregate formation (see e.g., U.S. Pat. No. 8,911,726). In some embodiments, the Fc is an IgG4 containing the S228P mutation, which has been shown to prevent recombination between a therapeutic antibody and an endogenous IgG4 by Fab-arm exchange (see e.g., Labrijin et al. (2009) Nat. Biotechnol., 27(8): 767-71). In some embodiments, the Fc comprises the amino acid sequence set forth in SEQ ID NO: 264 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 264.

In some embodiments, the variant CD86 polypeptide is indirectly linked to the Fc sequence, such as via a linker. In some embodiments, one or more "peptide linkers" link the variant CD86 polypeptide and the Fc domain. In some embodiments, a peptide linker can be a single amino acid residue or greater in length. In some embodiments, the peptide linker has at least one amino acid residue but is no more than 20, 19, 18, 17, 16, 15, 14, 13, 12, 11, 10, 9, 8, 7, 6, 5, 4, 3, 2, or 1 amino acid residues in length. In some embodiments, the linker is a flexible linker. In some embodiments, the linker is (in one-letter amino acid code): GGGGS ("4GS" or "$G_4S$"; SEQ ID NO: 223) or multimers of the 4GS linker, such as repeats of 2, 3, 4, or 5 4GS linkers, such as set forth in SEQ ID NO: 225 (2×GGGGS; $(G_4S)_2$) or SEQ ID NO: 224 (3×GGGGS; $(G_4S)_3$). In some embodiments, the linker can include a series of alanine residues alone or in addition to another peptide linker (such as a 4GS linker or multimer thereof). In some embodiments, the number of alanine residues in each series is 2, 3, 4, 5, or 6 alanines. In some embodiments, the linker is three alanines (AAA). In some embodiments, the variant CD86 polypeptide is indirectly linked to the Fc sequence via a linker, wherein the linker does not consist of three alanines. In some examples, the linker is a 2×GGGGS followed by three alanines (GGGGSGGGGSAAA; SEQ ID NO: 226). In some embodiments, the linker can further include amino acids introduced by cloning and/or from a restriction site, for example the linker can include the amino acids GS (in one-letter amino acid code) as introduced by use of the restriction site BAMHI. For example, in some embodiments, the linker (in one-letter amino acid code) is GSGGGGS (SEQ ID NO:222), $GS(G_4S)_3$ (SEQ ID NO: 227), or $GS(G_4S)_5$ (SEQ ID NO: 228). In some embodiments, the linker is a rigid linker. For example, the linker is an α-helical linker. In some embodiments, the linker is (in one-letter amino acid code): EAAAK or multimers of the EAAAK linker, such as repeats of 2, 3, 4, or 5 EAAAK linkers, such as set forth in SEQ ID NO: 265 (1×EAAAK), SEQ ID NO: 266 (3×EAAAK), or SEQ ID NO: 247 (5×EAAAK). In some cases, the immunomodulatory polypeptide comprising a variant CD86 comprises various combinations of peptide linkers.

In some embodiments, the variant CD86 polypeptide is directly linked to the Fc sequence. In some embodiments, the variant CD86 polypeptide is directly linked to an Fc, such as an inert Fc, that additionally lacks all or a portion of the hinge region. An exemplary Fc, lacking a portion (6 amino acids) of the hinge region is set forth in SEQ ID NO: 267.

In some embodiments, where the CD86 polypeptide is directly linked to the Fc sequence, the CD86 polypeptide can be truncated at the C-terminus by 1, 2, 3, 4, 5, 6, 7, 8, 9, 10, 11, 12, 13, 14, 15, or more amino acids. In some embodiments, the variant CD86 polypeptide is truncated to remove 1, 2, 3, 4, 5, 6, 7, 8, 9, 10, or more amino acids that connect the IgV region to the IgC region.

In some embodiments, the variant CD86-Fc fusion protein is a dimer formed by two variant CD86 Fc polypeptides linked to an Fc domain. In some specific embodiments, identical or substantially identical species (allowing for 3 or fewer N-terminus or C-terminus amino acid sequence differences) of CD86-Fc variant fusion polypeptides will be dimerized to create a homodimer. In some embodiments, the dimer is a homodimer in which the two variant CD86 Fc polypeptides are the same. Alternatively, different species of CD86-Fc variant fusion polypeptides can be dimerized to yield a heterodimer. Thus, in some embodiments, the dimer is a heterodimer in which the two variant CD86 Fc polypeptides are different.

Also provided are nucleic acid molecules encoding the variant CD86-Fc fusion protein. In some embodiments, for production of an Fc fusion protein, a nucleic acid molecule encoding a variant CD86-Fc fusion protein is inserted into an appropriate expression vector. The resulting variant CD86-Fc fusion protein can be expressed in host cells transformed with the expression vector where assembly between Fc domains occurs by interchain disulfide bonds formed between the Fc moieties to yield dimeric, such as divalent, variant CD86-Fc fusion proteins.

The resulting Fc fusion proteins can be easily purified by affinity chromatography over Protein A or Protein G columns. For the generation of heterodimers, additional steps for purification can be necessary. For example, where two nucleic acids encoding different variant CD86 polypeptides are transformed into cells, the formation of heterodimers must be biochemically achieved since variant CD86 molecules carrying the Fc-domain will be expressed as disulfide-linked homodimers as well. Thus, homodimers can be reduced under conditions that favor the disruption of interchain disulfides, but do no effect intra-chain disulfides. In some cases, different variant CD86-Fc monomers are mixed in equimolar amounts and oxidized to form a mixture of homo- and heterodimers. The components of this mixture are separated by chromatographic techniques. Alternatively, the formation of this type of heterodimer can be biased by genetically engineering and expressing Fc fusion molecules that contain a variant CD86 polypeptide using knob-into-hole methods described below.

C. Stack Molecules with Additional IgSF Domains

In some embodiments, the immunomodulatory proteins can contain any of the variant CD86 polypeptides provided herein linked, directly or indirectly, to one or more other immunoglobulin superfamily (IgSF) domain ("stacked" immunomodulatory protein construct and also called a "Type II" immunomodulatory protein). In some aspects, this can create unique multi-domain immunomodulatory proteins that bind two or more, such as three or more, cognate binding partners, thereby providing a multi-targeting modulation of the immune synapse.

In some embodiments, an immunomodulatory protein comprises a combination (a "non-wild-type combination") and/or arrangement (a "non-wild type arrangement" or "non-wild-type permutation") of a variant CD86 domain with one or more other affinity modified and/or non-affinity modified IgSF domain sequences of another IgSF family member (e.g., a mammalian IgSF family member) that are not found in wild-type IgSF family members. In some embodiments, the immunomodulatory protein contains 2, 3, 4, 5 or 6 immunoglobulin superfamily (IgSF) domains, where at least one of the IgSF domains is a variant CD86 IgSF domain (vIgD of CD86) according to the provided description.

In some embodiments, the sequences of the additional IgSF domains can be a modified IgSF domain that contains one or more amino acid modifications, e.g., substitutions, compared to a wildtype or unmodified IgSF domain. In some embodiments, the IgSF domain can be non-affinity modified (e.g., wild-type) or have been affinity modified. In some embodiments, the unmodified or wild-type IgSF domain can be from mouse, rat, cynomolgus monkey, or human origin, or combinations thereof. In some embodiments, the additional IgSF domains can be an IgSF domain of an IgSF family member set forth in Table 2. In some embodiments, the additional IgSF domain can be an affinity-modified IgSF domain containing one or more amino acid modifications, e.g., substitutions, compared to an IgSF domain contained in an IgSF family member set forth in Table 2.

In some embodiments, the additional IgSF domain is an affinity or non-affinity modified IgSF domain contained in an IgSF family member of a family selected from the Signal-Regulatory Protein (SIRP) Family, Triggering Receptor Expressed On Myeloid Cells Like (TREML) Family, Carcinoembryonic Antigen-related Cell Adhesion Molecule (CEACAM) Family, Sialic Acid Binding Ig-Like Lectin (SIGLEC) Family, Butyrophilin Family, B7 family, CD28 family, V-set and Immunoglobulin Domain Containing (VSIG) family, V-set transmembrane Domain (VSTM) family, Major Histocompatibility Complex (MHC) family, Signaling lymphocytic activation molecule (SLAM) family, Leukocyte immunoglobulin-like receptor (LIR), Nectin (Nec) family, Nectin-like (NECL) family, Poliovirus receptor related (PVR) family, Natural cytotoxicity triggering receptor (NCR) family, T cell immunoglobulin and mucin (TIM) family or Killer-cell immunoglobulin-like receptors (KR) family. In some embodiments, the additional IgSF domains are independently derived from an IgSF protein selected from the group consisting of CD80(B7-1), CD86 (B7-2), CD274 (PD-L1, B7-H1), PDCD1LG2(PD-L2, CD273), ICOSLG(B7RP1, CD275, ICOSL, B7-H2), CD276(B7-H3), VTCN1(B7-H4), CD28, CTLA4, PDCD1 (PD-1), ICOS, BTLA(CD272), CD4, CD8A(CD8-alpha), CD8B(CD8-beta), LAG3, HAVCR2(TIM-3), CEACAM1, TIGIT, PVR(CD155), PVRL2(CD112), CD226, CD2, CD160, CD200, CD200R1(CD200R), and NC R3 (NKp30).

The first column of Table 2 provides the name and, optionally, the name of some possible synonyms for that particular IgSF member. The second column provides the protein identifier from the UniProtKB database, a publicly available database accessible via the internet at uniprot.org or, in some cases, the GenBank Number. The Universal Protein Resource (UniProt) is a comprehensive resource for protein sequence and annotation data. The UniProt databases include the UniProt Knowledgebase (UniProtKB). UniProt is a collaboration between the European Bioinformatics Institute (EMBL-EBI), the SIB Swiss Institute of Bioinformatics and the Protein Information Resource (PIR) and supported mainly by a grant from the U.S. National Institutes of Health (NIH). GenBank is the NIH genetic sequence database, an annotated collection of all publicly available DNA sequences (Nucleic Acids Research, 2013 January; 41(D1):D36-42). The third column provides the region where the indicated IgSF domain is located. The region is specified as a range where the domain is inclusive of the residues defining the range. Column 3 also indicates the IgSF domain class for the specified IgSF region. Column 4 provides the region where the indicated additional domains are located (signal peptide, S; extracellular domain, E; transmembrane domain, T; cytoplasmic domain, C). It is understood that description of domains can vary depending on the methods used to identify or classify the domain, and may be identified differently from different sources. The description of residues corresponding to a domain in Table 2 is for exemplification only and can be several amino acids (such as one, two, three or four) longer or shorter. Column 5 indicates for some of the listed IgSF members, some of its cognate cell surface binding partners.

TABLE 2

IgSF members according to the present disclosure.

| IgSF Member (Synonyms) | NCBI Protein Accession Number/ UniProtKB Protein Identifier | IgSF Region & Domain Class | Other Domains | Cognate Cell Surface Binding Partners | IgSF Member Amino Acid Sequence (SEQ ID NO) Precursor (mature residues) | Mature | ECD |
|---|---|---|---|---|---|---|---|
| CD80 (B7-1) | NP_005182.1 P33681 | 35-135, 35-138, 37-138, or 35-141 IgV, 145-230 or 154-232 IgC | S: 1-34, E: 35-242, T: 243-263, C: 264-288 | CD28, CTLA4, PD-L1 | SEQ ID NO: 1 (35-288) | SEQ ID NO: 55 | SEQ ID NO: 28 |
| CD86 (B7-2) | P42081.2 | 33-131 IgV, 150-225 IgC2 | S: 1-23, E: 24-247, T: 248-268, C: 269-329 | CD28, CTLA4 | SEQ ID NO: 2 (24-329) | SEQ ID NO: 56 | SEQ ID NO: 29 |
| CD274 (PD-L1, B7-H1) | Q9NZQ7.1 NP_054862.1 | 24-130 or 19-127 IgV, 133-225 IgC2 | S: 1-18, E: 19-238, T: 239-259, C: 260-290 | PD-1, B7-1 | SEQ ID NO: 3 (19-290) | SEQ ID NO: 57 | SEQ ID NO: 30 |
| PDCD1LG2 (PD-L2, CD273) | Q9BQ51.2 | 21-118 IgV, 122-203 IgC2 | S: 1-19, E: 20-220, T: 221-241, C: 242-273 | PD-1, RGMb | SEQ ID NO: 4 (20-273) | SEQ ID NO: 58 | SEQ ID NO: 31 |
| ICOSLG (B7RP1, CD275, ICOSL, B7-H2) | O75144.2 | 19-129 IgV, 141-227 IgC2 | S: 1-18, E: 19-256, T: 257-277, C: 278-302 | ICOS, CD28, CTLA4 | SEQ ID NO: 5 (19-302) | SEQ ID NO: 59 | SEQ ID NO: 32 |
| CD276 (B7-H3) | Q5ZPR3.1 | 29-139 IgV, 145-238 IgC2, 243-357 IgV2, 363-456, 367-453 IgC2 | S: 1-28, E: 29-466, T: 467-487, C: 488-534 | | SEQ ID NO: 6 (29-534) | SEQ ID NO: 60 | SEQ ID NO: 33 |
| VTCN1 (B7-H4) | Q7Z7D3.1 | 35-146 IgV, 153-241 IgV | S: 1-24, E: 25-259, T: 260-280, C: 281-282 | | SEQ ID NO: 7 (25-282) | SEQ ID NO: 61 | SEQ ID NO: 34 |
| CD28 | P10747.1 | 28-137 IgV | S: 1-18, E: 19-152, T: 153-179, C: 180-220 | B7-1, B7-2, B7RP1 | SEQ ID NO: 8 (19-220) | SEQ ID NO: 62 | SEQ ID NO: 35 |
| CTLA-4 | P16410.3 | 39-140 IgV | S: 1-35, E: 36-161, T: 162-182, C: 183-223 | B7-1, B7-2, B7RP1 | SEQ ID NO: 9 (36-223) | SEQ ID NO: 63 | SEQ ID NO: 36 |
| PDCD1 (PD-1) | Q15116.3 | 35-145 IgV | S: 1-20, E: 21-170, T: 171-191, C: 192-288 | PD-L1, PD-L2 | SEQ ID NO: 10 (21-288) | SEQ ID NO: 64 | SEQ ID NO: 37 |
| ICOS | Q9Y6W8.1 | 30-132 IgV | S: 1-20, E: 21-140, T: 141-161, C: 162-199 | B7RP1 | SEQ ID NO: 11 (21-199) | SEQ ID NO: 65 | SEQ ID NO: 38 |
| BTLA (CD272) | Q7Z6A9.3 | 31-132 IgV | S: 1-30, E: 31-157, T: 158-178, C: 179-289 | HVEM | SEQ ID NO: 12 (31-289) | SEQ ID NO: 66 | SEQ ID NO: 39 |
| CD4 | P01730.1 | 26-125 IgV, 126-203 IgC2, 204-317 IgC2, 317-389, 318-374 IgC2 | S: 1-25, E: 26-396, T: 397-418, C: 419-458 | MHC class II | SEQ ID NO: 13 (26-458) | SEQ ID NO: 67 | SEQ ID NO: 40 |
| CD8A (CD8-alpha) | P01732.1 | 22-135 IgV | S: 1-21, E: 22-182, T: 183-203, C: 204-235 | MHC class I | SEQ ID NO: 14 (22-235) | SEQ ID NO: 68 | SEQ ID NO: 41 |
| CD8B (CD8-beta) | P10966.1 | 22-132 IgV | S: 1-21, E: 22-170, T: 171-191, C: 192-210 | MHC class I | SEQ ID NO: 15 (22-210) | SEQ ID NO: 69 | SEQ ID NO: 42 |

TABLE 2-continued

IgSF members according to the present disclosure.

| IgSF Member (Synonyms) | NCBI Protein Accession Number/ UniProtKB Protein Identifier | IgSF Region & Domain Class | Other Domains | Cognate Cell Surface Binding Partners | IgSF Member Amino Acid Sequence (SEQ ID NO) Precursor (mature residues) | Mature | ECD |
|---|---|---|---|---|---|---|---|
| LAG3 | P18627.5 | 37-167 IgV, 168-252 IgC2, 265-343 IgC2, 349-419 IgC2 | S: 1-28, E: 29-450, T: 451-471, C: 472-525 | MHC class II | SEQ ID NO: 16 (29-525) | SEQ ID NO: 70 | SEQ ID NO: 43 |
| HAVCR2 (TIM-3) | Q8TDQ0.3 | 22-124 IgV | S: 1-21, E: 22-202, T: 203-223, C: 224-301 | CEACAM-1, phosphatidylserine, Galectin-9, HMGB1 | SEQ ID NO: 17 (22-301) | SEQ ID NO: 71 | SEQ ID NO: 44 |
| CEACAM1 | P13688.2 | 35-142 IgV, 145-232 IgC2, 237-317 IgC2, 323-413 IgC2 | S: 1-34, E: 35-428, T: 429-452, C: 453-526 | TIM-3 | SEQ ID NO: 18 (35-526) | SEQ ID NO: 72 | SEQ ID NO: 45 |
| TIGIT | Q495A1.1 | 22-124 IgV | S: 1-21, E: 22-141, T: 142-162, C: 163-244 | CD155, CD112 | SEQ ID NO: 19 (22-244) | SEQ ID NO: 73 | SEQ ID NO: 46 |
| PVR (CD155) | P15151.2 | 24-139 IgV, 145-237 IgC2, 244-328 IgC2 | S: 1-20, E: 21-343, T: 344-367, C: 368-417 | TIGIT, CD226, CD96, poliovirus | SEQ ID NO: 20 (21-417) | SEQ ID NO: 74 | SEQ ID NO: 47 |
| PVRL2 (CD112) | Q92692.1 | 32-156 IgV, 162-256 IgC2, 261-345 IgC2 | S: 1-31, E: 32-360, T: 361-381, C: 382-538 | TIGIT, CD226, CD112R | SEQ ID NO: 21 (32-538) | SEQ ID NO: 75 | SEQ ID NO: 48 |
| CD226 | Q15762.2 | 19-126 IgC2, 135-239 IgC2 | S: 1-18, E: 19-254, T: 255-275, C: 276-336 | CD155, CD112 | SEQ ID NO: 22 (19-336) | SEQ ID NO: 76 | SEQ ID NO: 49 |
| CD2 | P06729.2 | 25-128 IgV, 129-209 IgC2 | S: 1-24, E: 25-209, T: 210-235, C: 236-351 | CD58 | SEQ ID NO: 23 (25-351) | SEQ ID NO: 77 | SEQ ID NO: 50 |
| CD160 | O95971.1 | 27-122 IgV | N/A | HVEM, MHC family of proteins | SEQ ID NO: 24 (27-159) | SEQ ID NO: 78 | SEQ ID NO: 51 |
| CD200 | P41217.4 | 31-141 IgV, 142-232 IgC2 | S: 1-30, E: 31-232, T: 233-259, C: 260-278 | CD200R | SEQ ID NO: 25 (31-278) | SEQ ID NO: 79 | SEQ ID NO: 52 |
| CD200R1 (CD200R) | Q8TD46.2 | 53-139 IgV, 140-228 IgC2 | S: 1-28, E: 29-243, T: 244-264, C: 265-325 | CD200 | SEQ ID NO: 26 (29-325) | SEQ ID NO: 80 | SEQ ID NO: 53 |
| NCR3 (NKp30) | O14931.1 | 19-126 IgC-like | S: 1-18, E: 19-135, T: 136-156, C: 157-201 | B7-H6 | SEQ ID NO: 27 (19-201) | SEQ ID NO: 81 | SEQ ID NO: 54 |
| VSIG8 | Q5VU13 | 22-141 IgV1, 146-257 IgV2 | S: 1-21 E: 22-263 T: 264-284 C: 285-414 | VISTA | SEQ ID NO: 82 (22-414) | SEQ ID NO: 83 | SEQ ID NO: 84 |

The number of such non-affinity modified or affinity modified IgSF domains present in a "stacked" immunomodulatory protein construct (whether non-wild type combinations or non-wild type arrangements) is at least 2, 3, 4, or 5 and in some embodiments exactly 2, 3, 4, or 5 IgSF domains (whereby determination of the number of affinity modified IgSF domains disregards any non-specific binding fractional sequences thereof and/or substantially immunologically inactive fractional sequences thereof).

In some embodiments of a stacked immunomodulatory protein provided herein, the number of IgSF domains is at least 2 wherein the number of affinity modified and the number of non-affinity modified IgSF domains is each independently at least: 0, 1, 2, 3, 4, 5, or 6. Thus, the number of affinity modified IgSF domains and the number of non-affinity modified IgSF domains, respectively, (affinity modified IgSF domain: non-affinity modified IgSF domain), can be exactly or at least: 2:0 (affinity modified:wild-type), 0:2, 2:1, 1:2, 2:2, 2:3, 3:2, 2:4, 4:2, 1:1, 1:3, 3:1, 1:4, 4:1, 1:5, or 5:1.

In some embodiments of a stacked immunomodulatory protein, at least two of the non-affinity modified and/or affinity modified IgSF domains are identical IgSF domains.

In some embodiments, a stacked immunomodulatory protein provided herein comprises at least two affinity modified and/or non-affinity modified IgSF domains from a single IgSF member but in a non-wild-type arrangement (alternatively, "permutation"). One illustrative example of a non-wild type arrangement or permutation is an immunomodulatory protein comprising a non-wild-type order of affinity modified and/or non-affinity modified IgSF domain sequences relative to those found in the wild-type CD86 whose IgSF domain sequences served as the source of the variant IgSF domains as provided herein. Thus, in one example, the immunomodulatory protein can comprise an IgV proximal and an IgC distal to the transmembrane domain albeit in a non-affinity modified and/or affinity modified form. The presence, in an immunomodulatory protein provided herein, of both non-wild-type combinations and non-wild-type arrangements of non-affinity modified and/or affinity modified IgSF domains, is also within the scope of the provided subject matter.

In some embodiments of a stacked immunomodulatory protein, the non-affinity modified and/or affinity modified IgSF domains are non-identical (i.e., different) IgSF domains. Non-identical affinity modified IgSF domains specifically bind, under specific binding conditions, different cognate binding partners and are "non-identical" irrespective of whether or not the wild-type or unmodified IgSF domains from which they are engineered was the same. Thus, for example, a non-wild-type combination of at least two non-identical IgSF domains in an immunomodulatory protein can comprise at least one IgSF domain sequence whose origin is from and unique to one CD86, and at least one of a second IgSF domain sequence whose origin is from and unique to another IgSF family member that is not CD86, wherein the IgSF domains of the immunomodulatory protein are in non-affinity modified and/or affinity modified form. However, in alternative embodiments, the two non-identical IgSF domains originate from the same IgSF domain sequence but at least one is affinity modified such that they specifically bind to different cognate binding partners.

In some embodiments, the provided immunomodulatory proteins, in addition to containing a variant CD86 polypeptide, also contains at least 1, 2, 3, 4, 5 or 6 additional immunoglobulin superfamily (IgSF) domains, such as an IgD domain of an IgSF family member set forth in Table 2. In some embodiments, the provided immunomodulatory protein contains at least one additional IgSF domain (e.g., second IgSF domain). In some embodiments, the provided immunomodulatory protein contains at least two additional IgSF domains (e.g., second and third IgSF domain). In some embodiments, the provided immunomodulatory protein contains at least three additional IgSF domains (e.g., second, third and fourth). In some embodiments, the provided immunomodulatory protein contains at least four additional IgSF domains (e.g., second, third, fourth and fifth). In some embodiments, the provided immunomodulatory protein contains at least five additional IgSF domains (e.g., second, third, fourth, fifth and sixth). In some embodiments, the provided immunomodulatory protein contains at least six additional IgSF domains (e.g., second, third, fourth, fifth, sixth, and seventh). In some embodiments, each of the IgSF domains in the immunomodulatory protein are different. In some embodiments, at least one of the additional IgSF domains is the same as at least one other IgSF domain in the immunomodulatory protein. In some embodiments, each of the IgSF domains is from or derived from a different IgSF family member. In some embodiments, at least two of the IgSF domains are from or derived from the same IgSF family member.

In some embodiments, the additional IgSF domain comprises an IgV domain or an IgC (e.g., IgC2) domain or domains, or a specific binding fragment of the IgV domain or a specific binding fragment of the IgC (e.g., IgC2) domain or domains. In some embodiments, the additional IgSF domain is or comprises a full-length IgV domain. In some embodiments, the additional IgSF domain is or comprises a full-length IgC (e.g., IgC2) domain or domains. In some embodiments, the additional IgSF domain is or comprises a specific binding fragment of the IgV domain. In some embodiments, the additional IgSF domain is or comprises a specific binding fragment of the IgC (e.g., IgC2) domain or domains. In some embodiments, the immunomodulatory protein contains at least two additional IgSF domains from a single (same) IgSF member. For example, in some aspects, the immunomodulatory protein contains an ECD or portion thereof of an IgSF member containing a full-length IgV domain and a full-length IgC (e.g., IgC2) domain or domains or specific binding fragments thereof.

In some embodiments, the provided immunomodulatory proteins contains at least one additional IgSF domain (e.g., a second or, in some cases, also a third IgSF domain and so on) in which at least one additional or second IgSF domain is an IgSF domain set forth in a wild-type or unmodified IgSF domain or a specific binding fragment thereof contained in the sequence of amino acids set forth in any of SEQ ID NOS: 2-27 and 82. In some embodiments, the wild-type or unmodified IgSF domain is an IgV domain or an IgC domain, such as an IgC1 or IgC2 domain.

In some embodiments, the provided immunomodulatory proteins, in addition to containing a variant CD86 polypeptide, also contains at least one additional affinity-modified IgSF domain (e.g., a second or, in some cases, also a third affinity-modified IgSF domain and so on) in which at least one additional IgSF domain is a vIgD that contains one or more amino acid modifications (e.g., substitution, deletion or mutation) compared to an IgSF domain in a wild-type or unmodified IgSF domain, such as an IgSF domain in an IgSF family member set forth in Table 2. In some embodiments, the additional e.g., second or third, affinity-modified IgSF domain comprises at least 85%, 86%, 87%, 88%, 89%, 90%, 91%, 92%, 93%, 94%, 95%, 96%, 97%, 98%, 99% or more sequence identity to a wild-type or unmodified IgSF domain or a specific binding fragment thereof contained in the sequence of amino acids set forth in any of SEQ ID NOS: 2-27 and 82. In some embodiments, the wild-type or unmodified IgSF domain is an IgV domain or an IgC domain, such as an IgC1 or IgC2 domain. In some embodiments, the additional, e.g., second or third, IgSF domain is an affinity-modified IgV domain and/or IgC domain. In some embodiments, the one or more additional IgSF domain is an affinity-modified IgSF domain that contains an IgV domain and/or an IgC (e.g., IgC2) domain or domains, or a specific binding fragment of the IgV domain and/or a specific binding fragment of the IgC (e.g., IgC2) domain or domains, in which the IgV and/or IgC domain contains the amino acid modification(s) (e.g., substitution(s)). In some embodiments, the one or more additional affinity-modified IgSF domain contains an IgV domain containing the amino acid modification(s) (e.g., substitution(s)). In some embodiments, the one or more additional affinity-modified IgSF domain include IgSF domains present in the ECD or a portion of the ECD of the corresponding unmodified IgSF family member, such as a full-length IgV domain and a full-length IgC (e.g., IgC2) domain or domains, or specific binding fragments thereof, in which one or both of the IgV and IgC contain the amino acid modification(s) (e.g., substitution(s)).

In some embodiments, the provided immunomodulatory protein contains at least one additional or second IgSF domain that is a vIgD that contains one or more amino acid substitutions compared to an IgSF domain (e.g., IgV) of a wild-type or unmodified IgSF domain other than CD86.

The stack molecule immunomodulatory proteins containing at least one IgSF domain of a variant CD86 and one or more second or additional IgSF domain can be provided in various construct formats as described in Section III.C.3. Non-limiting examples of constructs are set forth below.

1. PD-1 IgSF Domains

In some embodiments, the at least one additional (e.g., second or third) vIgD is an IgSF domain (e.g., IgV) of a variant PD-1 polypeptide that contains one or more amino acid modifications (e.g., substitutions, deletions or additions) in the IgSF domain (e.g., IgV) compared to unmodified or wild-type PD-1. In some embodiments, the IgSF domain of PD-1 comprises an IgV domain or specific binding fragment of the IgV domain. In some embodiments, the IgD can be an IgV only, including the entire extracellular domain (ECD), or any combination of Ig domains of PD-1. In some embodiments, the wild-type or unmodified PD-1 polypeptide has (i) the sequence of amino acids set forth in SEQ ID NO: 10 or a mature form thereof lacking the signal sequence, (ii) a sequence of amino acids that exhibits at least about 85%, 86%, 87%, 88%, 89%, 90%, 91%, 92%, 93%, 94%, 95%, 96%, 97%, 98%, 99% sequence identity to SEQ ID NO: 10 or a mature form thereof, or (iii) is a portion of (i) or (ii) containing an IgV domain or specific binding fragments thereof. In some embodiments, the wild-type or unmodified PD-1 polypeptide has (i) the sequence of amino acids set forth in SEQ ID NO: 37, (ii) a sequence of amino acids that exhibits at least about 85%, 86%, 87%, 88%, 89%, 90%, 91%, 92%, 93%, 94%, 95%, 96%, 97%, 98%, 99% sequence identity to SEQ ID NO: 37, or (iii) is a portion of (i) or (ii) containing an IgV domain or specific binding fragments thereof. In some embodiments, the unmodified PD-1 polypeptide has 85%, 85%, 87%, 88%, 89%, 90%, 91%, 92%, 93%, 94%, 95%, 96%, 97%, 98%, 99% sequence identity to SEQ ID NO: 37, 335, 336, or 337, or a specific binding fragment thereof. In some embodiments, the unmodified PD-1 polypeptide has the sequence set forth in any of SEQ ID NOs: 37, 335, 336, or 337.

In some embodiments, the IgSF domain of PD-1 is a variant PD-1 polypeptide containing at least one affinity-modified IgSF domain (e.g. IgV or IgC) or a specific binding fragment thereof is an IgSF domain contained in a wild-type or unmodified PD-1 polypeptide such that the variant PD-1 polypeptide exhibits altered (increased or decreased) binding activity or affinity for PD-L1 or PD-L2 compared to a wild-type or unmodified PD-1 polypeptide. In some embodiments, the variant PD-1 polypeptides containing at least one affinity-modified IgSF domain (e.g., IgV) or a specific binding fragment thereof relative to an IgSF domain contained in a wild-type or unmodified PD-1 polypeptide such that the variant PD-1 polypeptide exhibits altered (increased or decreased) binding activity or affinity for one or more ligands PD-L1 or PD-L2 compared to a wild-type or unmodified PD-1 polypeptide. In some embodiments, a variant PD-1 polypeptide has a binding affinity for PD-L1 and/or PD-L2 that differs from that of a wild-type or unmodified PD-1 polypeptide control sequence as determined by, for example, solid-phase ELISA immunoassays, flow cytometry, ForteBio Octet or Biacore assays. In some embodiments, the variant PD-1 polypeptide has an increased binding affinity for PD-L1 and/or PD-L2. In some embodiments, the variant PD-1 polypeptide has a decreased binding affinity for PD-L2, relative to a wild-type or unmodified PD-L1 polypeptide. The PD-L1 and/or the PD-L2 can be a mammalian protein, such as a human protein or a murine protein.

Binding affinities for each of the cognate binding partners are independent; that is, in some embodiments, a variant PD-1 polypeptide has an increased binding affinity for one or both of PD-L1 and/or PD-L2, and a decreased binding affinity for one or both of PD-L1 and PD-L2, relative to a wild-type or unmodified PD-1 polypeptide.

In some embodiments, the variant PD-1 polypeptide has an increased binding affinity for PD-L1, relative to a wild-type or unmodified PD-1 polypeptide. In some embodiments, the variant PD-1 polypeptide has an increased or decreased binding affinity for PD-L2, relative to a wild-type or unmodified PD-L1 polypeptide. In some embodiments, the variant PD-1 polypeptide has an increased binding affinity for PD-L1, relative to a wild-type or unmodified PD-1 polypeptide and has a decreased binding affinity for PD-L2, relative to a wild-type or unmodified PD-1 polypeptide.

In some embodiments, a variant PD-1 polypeptide with increased or greater binding affinity to PD-L1 and/or PD-L2 will have an increase in binding affinity relative to the wild-type or unmodified PD-1 polypeptide control of at least about 5%, such as at least about 10%, 15%, 20%, 25%, 35%, or 50% for the PD-L1 and/or PD-L2. In some embodiments, the increase in binding affinity relative to the wild-type or unmodified PD-1 polypeptide is more than 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold. In such examples, the wild-type or unmodified PD-1 polypeptide has the same sequence as the variant PD-1 polypeptide except that it does not contain the one or more amino acid modifications (e.g. substitutions).

In some embodiments, a variant PD-1 polypeptide with reduced or decreased binding affinity to PD-L2 will have decrease in binding affinity relative to the wild-type or unmodified PD-1 polypeptide control of at least 5%, such as at least about 10%, 15%, 20%, 30%, 40%, 50%, 60%, 70%, 80%, 90% or more for the PD-L2. In some embodiments, the decrease in binding affinity relative to the wild-type or unmodified PD-1 polypeptide is more than 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold. In such examples, the wild-type or unmodified PD-1 polypeptide has the same sequence as the variant PD-1 polypeptide except that it does not contain the one or more amino acid modifications (e.g. substitutions).

The PD-L1 and/or PD-L2 can be a mammalian protein, such as a human protein or a murine protein. In some embodiments, the PD-L1 is a human protein. In some embodiments, the PD-L2 is a human protein.

In some embodiments, the equilibrium dissociation constant ($K_d$) of any of the foregoing embodiments to PD-L1 and/or PD-L2 can be less than $1\times10^{-5}$M, $1\times10^{-6}$ M, $1\times10^{-7}$ M, $1\times10^{-8}$ M, $1\times10^{-9}$ M, $1\times10^{-1o}$ M or $1\times10^{-11}$M, or $1\times10^{-12}$ M or less.

The wild-type or unmodified PD-1 sequence does not necessarily have to be used as a starting composition to generate variant PD-1 polypeptides described herein. Therefore, use of the term "modification", such as "substitution" does not imply that the present embodiments are limited to a particular method of making variant PD-1 polypeptides.

Variant PD-1 polypeptides can be made, for example, by de novo peptide synthesis and thus does not necessarily require a modification, such as a "substitution", in the sense of altering a codon to encode for the modification, e.g. substitution. This principle also extends to the terms "addition" and "deletion" of an amino acid residue which likewise do not imply a particular method of making. The means by which the variant PD-1 polypeptides are designed or created is not limited to any particular method. In some embodiments, however, a wild-type or unmodified PD-1 encoding nucleic acid is mutagenized from wild-type or unmodified PD-1 genetic material and screened for desired specific binding affinity and/or induction of IFN-gamma expression or other functional activity. In some embodiments, a variant PD-1 polypeptide is synthesized de novo utilizing protein or nucleic acid sequences available at any number of publicly available databases and then subsequently screened. The National Center for Biotechnology Information provides such information and its website is publicly accessible via the internet as is the UniProtKB database as discussed previously.

Unless stated otherwise, as indicated throughout the present disclosure, the amino acid substitution(s) are designated by amino acid position number corresponding to the numbering of positions of the unmodified ECD sequence set forth in SEQ ID NO: 37 or, where applicable, the unmodified IgV sequence containing residues 35-145 of SEQ ID NO: 10.

Modifications provided herein can be in a wild-type or unmodified PD-1 polypeptide set forth in SEQ ID NO: 37 or in a portion thereof containing an IgV domain or a specific binding fragment thereof. In some embodiments, the wild-type or unmodified PD-1 polypeptide contains the IgV of PD-1 as set forth in SEQ ID NO: 335. In some embodiments, the unmodified PD-1 polypeptide contains an IgV that can be several amino acids longer or shorter, such as 1-15, e.g. 1, 2, 3, 4, 5, 6, 7, 8, or 9 amino acids longer or shorter, than the sequence of amino acids set forth by SEQ ID NO: 335. In some embodiments, the unmodified PD-1 polypeptide has 85%, 85%, 87%, 88%, 89%, 90%, 91%, 92%, 93%, 94%, 95%, 96%, 97%, 98%, 99% sequence identity to SEQ ID NO: 37, 335, 336, or 337. In some embodiments, the unmodified PD-1 polypeptide has the sequence set forth in any of SEQ ID NO: 37. In some embodiments, the unmodified PD-1 polypeptide has the sequence set forth by SEQ ID NO: 335. In some embodiments, the unmodified PD-1 polypeptide has the sequence set forth by SEQ ID NO: 336. In some embodiments, the unmodified PD-1 polypeptide has the sequence set forth by SEQ ID NO: 337. In some embodiments, the unmodified PD-1 polypeptide has the sequence set forth by SEQ ID NO: 339.

It is within the level of a skilled artisan to identify the corresponding position of a modification, e.g. amino acid substitution, in a PD-1 polypeptide, including portion thereof containing an IgSF domain (e.g. IgV) thereof, such as by alignment of a reference sequence with SEQ ID NO: 37. For example, following alignment, residue 112 of SEQ ID NO: 37 corresponds to residue 107 of SEQ ID NO: 336.

In some embodiments, the variant PD-1 polypeptide has one or more amino acid modifications, e.g. substitutions, in a wild-type or unmodified PD-1 sequence. The one or more amino acid modifications, e.g. substitutions, can be in the ectodomain (extracellular domain) of the wild-type or unmodified PD-1 sequence. In some embodiments, the one or more amino acid modifications, e.g. substitutions, are in the IgV domain or specific binding fragment thereof.

In some embodiments, the variant PD-1 polypeptide has up to 1, 2, 3, 4, 5, 6, 7, 8, 9, 10, 11, 12, 13, 14, 15, 16, 17, 18, 19, or 20 amino acid modifications, e.g. substitutions. The modifications (e.g. substitutions) can be in the IgV domain. In some embodiments, the variant PD-1 polypeptide has up to 1, 2, 3, 4, 5, 6, 7, 8, 9, 10, 11, 12, 13, 14, 15, 16, 17, 18, 19, or 20 amino acid modifications, e.g. substitutions, in the IgV domain or specific binding fragment thereof. In some embodiments, the variant PD-1 polypeptide has less than 100% sequence identity and at least about 85%, 86%, 86%, 88%, 89%, 90%, 91%, 92%, 93%, 94%, 95%, 96%, 97%, 98%, or 99% sequence identity with the wild-type or unmodified PD-1 polypeptide or specific binding fragment thereof, such as with the amino acid sequence of SEQ ID NO: 37, 335, 336, 337, or 339.

In some embodiments, the variant PD-1 polypeptide has one or more amino acid modifications, e.g. substitutions, in an unmodified PD-1 or specific binding fragment thereof corresponding to position(s) 8, 9, 11, 12, 13, 14, 16, 17, 18, 20, 21, 22, 23, 24, 25, 28, 29, 30, 31, 33, 34, 35, 36, 37, 38, 39, 40, 41, 42, 43, 44, 45, 46, 48, 50, 51, 52, 53, 54, 55, 56, 57, 58, 59, 60, 64, 66, 67, 68, 69, 70, 71, 72, 73, 75, 76, 77, 78, 79, 80, 81, 84, 85, 86, 87, 89, 90, 91, 92, 93, 94, 95, 96, 100, 102, 104, 105, 107, 109, 111, 112, 113, 114, 115, 116, 119, 120, 125, 127, 128, 129, 130, 131, 132, 133, 134, 135, 136, 137, 138, 139, 140, 141, 142, 143, or 144, with reference to positions set forth in SEQ ID NO: 37. In some embodiments, such variant PD-1 polypeptides exhibit altered binding affinity to one or more of PD-L1 and/or PD-L2 compared to the wild-type or unmodified PD-1 polypeptide. For example, in some embodiments, the variant PD-1 polypeptide exhibits increased binding affinity to PD-L1 and/or PD-L2 compared to a wild-type or unmodified PD-1 polypeptide. In some embodiments, the variant PD-1 polypeptide exhibits decreased binding affinity to PD-L1 or PD-L2 compared to a wild-type or unmodified PD-1 polypeptide.

In some embodiments, the variant PD-1 polypeptide has one or more amino acid substitutions selected from P8T, D9E, D9G, D9N, D9V, P11A, W12G, W12L, W12R, N13D, N13S, N13Y, P14H, P14L, P145, T16A, T16I, T165, F17I, F17L, F17V, F17Y, S18T, A205, A20T, A20V, L21V, L22I, V23E, V23G, V24L, T25A, D28E, N29D, N29S, A30V, T31I, T31N, T31S, T33I, C34Y, S35N, F36I, F36L, F36Y, S37P, S37T, N38D, N38S, N38T, T39A, T39R, T39S, 540P, 540T, E41D, E41V, S42G, S42R, F43L, F43Y, V44H, V44M, V44R, L45I, L45V, N46I, N46V, Y48F, Y48H, Y48N, R49Y, R49L, M50D, M50E, M50I, M50L, M50Q, M50V, M50T, S51G, P52A, P52L, S53D, S53G, 553L, S53N, S53T, S53V, N54C, N54H, N54D, N54G, N54S, N54Y, Q55E, Q55H, Q55K, Q55R, T56A, T56L, T56M, T56P, T56S, T56V, D57F, D57R, D57V, D57Y, K58L, K58R, K58T, L59M, L59R, L59V, A61L, A61S, E64D, E64K, R66H, R66S, S67C, S67G, S67I, S67N, S67R, Q68E, Q68I, Q68L, Q68P, Q68R, Q68T, P69H, P69L, P69S, G70C, G70E, G70F, G70I, G70L, G70N, G70R, G70V, G705, Q71H, Q71K, Q71L, Q71P, Q71R, D72A, D72G, D72N, C73A, C73G, C73H, C73P, C73S, C73R, C73Y, F75Y, R76G, R76H, R76S, V77D, V77I, T78I, T78S, Q79A, Q79P, Q79R, L80Q, P81S, N82S, R84H, R84Q, D85G, D85N, F86Y, H87L, H87Q, H87R, M88L, M88F, S89G, S89N, V90L, V90M, V91A, V91D, V91I, R92G, R92N, R92S, A93V, R94Q, R95L, R95K, R95G, N96D, N96S, N96T, T100A, T100I, T100S, Y101F, L102F, L102I, L102Y, L102V, G104A, G104T, G104S, G104V, A105C, A105G, A105I, A105L, A105V, 1106L, S107A, S107F, S107L, S107T, S107V, L108F, L108I, L108T, L108Y, A109D, A109G, A109H, A109S, P110A, K111E, K111G, K111I, K111M, K111N, K111R, K111T, K111V, A112I, A112P, A112V, Q113R, Q113W, I114T, K115D, K115E, K115IN, K115N, K115Q, K115R, E116D, R119G, R119H, R119L, R119P, R119Q, R119W, A120V, T125A, T125K, T125I, T125S, T125V, R127F, R127L, R127K, R127S, R127V, R128G, R128M, A129S, E130K, V131A, V131E, V131I, V131R, P132H, P132R, P132S, P132T, T133A, T133R, T133S, A134D, A134V, H135N, H135R, H135Y, P136L, P136T, S137C, P138S, P138T, S139T, P140A, P140L, P140R, R141G, R141M, R141S, R141W, P142A, P142L, P142R, P142T, A143D, A143S, A143V, G144D, or G144S, or a conservative amino acid substitution thereof.

In some embodiments, the variant PD-1 is a variant PD-1 that contains one or more amino acid substitutions from N13D, N13S, F17L, T25A, N29S, A30V, N38D, T39A, V44H, V44R, L45I, L45V, N46I, N46V, Y48F, Y48H, R49Y, R49L, M50D, M50E, M50I, M50L, M50Q, M50V, S53D, S53G, S53L, S53N, S53V, N54C, N54D, N54G, N54S, N54Y, Q55E, Q55H, Q55K, T56A, T56L, T56V, D57F, D57R, D57V, D57Y, K58L, K58T, A61L, A61S, S67G, Q68E, Q68I, Q68L, Q68P, Q68R, Q68T, P69L, P69S, G70F, G70I, G70L, G70N, G70R, G70V, Q71P, Q71R, D72A, D72G, C73S, C73R, R76G, V77I, T78I, Q79A, Q79R, N82S, H87Q, H87R, M88L, M88F, R92G, R95K, R95G, N96D, N96S, Y101F, L102I, L102Y, L102V, G104S, A105I, A105V, S107A, S107F, S107L, S107T, S107V, L108F, L108I, L108Y, A109D, A109H, A109S, P110A, K111E, K111G, K111I, K111R, K111T, K111V, A112I, A112P, A112V, K115R, R119G, A120V, T125A, T125I, T125V, R127F, R127L, R127K, R127V, R128G, V131I, V131R, or a conservative amino acid substitution thereof. In some embodiments, the variant PD-1 polypeptide contains the amino acid substitutions S67N/C73R/F86Y/V91D/S107T/A112V/K115D/A120V. In some embodiments, the variant PD-1 polypeptide has the sequence of amino acids set forth in SEQ ID NO: 315, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 315. In some embodiments, the variant PD-1 polypeptide contains the amino acid substitutions V44H/L45V/N461/Y48H/M50E/N54G/K58T/L102V/A105V/A112I. In some embodiments, the variant PD-1 polypeptide has the sequence of amino acids set forth in SEQ ID NO:334, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:334. Such variant PD-1 polypeptides can be linked, directly or indirectly, to one or more other immunoglobulin superfamily (IgSF) domains as described.

Provided herein are immunomodulatory proteins containing a variant CD86 polypeptide, such as any described in Section II, and an IgSF domain of a PD-1 polypeptide or variant thereof that binds to PD-L1 and/or PD-L2 (CD86/PD-1 immunomodulatory protein). In some embodiments, the variant CD86 polypeptide is or contains the extracellular domain of CD86 or an IgSF (e.g. IgV) domain thereof or a specific binding fragment thereof containing one or more modifications (e.g. substitutions), such as any as described herein. In some embodiments, the variant PD-1 polypeptide is or contains the extracellular domain of PD-1 or an IgSF (e.g. IgV) domain thereof or a specific binding fragment thereof containing one or more modifications (e.g. substitutions), such as any as described herein. The CD86/PD-1 immunomodulatory proteins can be provided in various construct formats as described in Section III.C.3.

2. Tumor Antigen Binding IgSF Domains

In some embodiments, the one or more additional IgSF domain (e.g., second or third IgSF) domain is an IgSF domain (e.g., IgV) of another IgSF family member that binds or recognizes a tumor antigen. In such embodiments, the IgSF family member serves as a tumor-localizing moiety, thereby bringing the vIgD of CD86 in close proximity to immune cells in the tumor microenvironment. In some embodiments, the additional IgSF domain (e.g., second IgSF) is an IgSF domain of NKp30, which binds or recognizes B7-H6 expressed on a tumor cell.

In some embodiments, the at least one additional (e.g., second) IgSF domain, e.g., NKp30, is an affinity-modified IgSF domain or vIgD that contains one or more amino acid modifications (e.g., substitutions, deletions or additions). In some embodiments, the one or more amino acid modifications increase binding affinity and/or selectivity to B7-H6 compared to unmodified IgSF domain, e.g., NKp30, such as by at least or at least about 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold. Exemplary amino acid modifications, such as substitutions, deletions or additions, in an IgSF domain (e.g., IgC-like or full ECD) of a variant NKp30 polypeptide are set forth in Table 2. Among the exemplary polypeptides is an NKp30 variant that contains the mutations L30V/A60V/S64P/S86G with reference to positions in the NKp30 extracellular domain corresponding to positions set forth in SEQ ID NO: 54. In some embodiments, there is provided an immunomodulatory protein containing any of the provided variant CD86 polypeptides and a variant NKp30 polypeptide containing an IgC-like domain including any of the amino acid modifications set forth in Table 3, such as the IgC-like domain set forth in any of SEQ ID NOS: 268-272 or an IgV domain that has at least 85%, 86%, 87%, 88%, 89%, 90%, 91%, 92%, 93%, 94%, 95%, 96%, 97%, 98%, 99% to any of SEQ ID NOS: 268-272 and contains the one or more amino acid modifications. In some embodiments, there is provided an immunomodulatory protein containing any of the provided variant CD86 polypeptides and a variant NKp30 polypeptide containing an ECD or a portion thereof containing an IgSF domain or domains, in which is contained any of the amino acid modifications set forth in Table 3, such as the ECD set forth in any of SEQ ID NOS: 273-277 or an ECD that contains at least 85%, 86%, 87%, 88%, 89%, 90%, 91%, 92%, 93%, 94%, 95%, 96%, 97%, 98%, 99% to any of SEQ ID NOS: 273-277 and contains the one or more amino acid modifications.

Table 3 provides exemplary polypeptides containing one or more affinity-modified IgSF domains that can be used in stack constructs provided herein.

TABLE 3

Exemplary variant NKp30 polypeptides

| Mutation(s) | ECD SEQ ID NO | IgC SEQ ID NO |
|---|---|---|
| Wild-type | 54 | 278 |
| L30V/A60V/S64P/S86G | 273 | 268 |
| L30V | 274 | 269 |
| A60V | 275 | 270 |
| S64P | 276 | 271 |
| S86G | 277 | 272 |
| L30V/A60V/S64P/S86G/G117del | 231 | 268 |

Provided herein are immunomodulatory proteins containing a variant CD86 polypeptide, such as any described in Section II, and an NKp30 polypeptide or variant thereof that binds to B7-H6 (CD86/NkP30 immunomodulatory protein). In some embodiments, the variant CD86 polypeptide is or contains the extracellular domain of CD86 or an IgSF (e.g. IgV) domain thereof or a specific binding fragment thereof containing one or more modifications (e.g. substitutions), such as any as described herein. In some embodiments, the variant NkP30 polypeptide is or contains the extracellular domain of Nkp30 or an IgSF (e.g. IgV) domain thereof or a specific binding fragment thereof containing one or more modifications (e.g. substitutions), such as any as described herein. The CD86/Nkp30 immunomodulatory proteins can be provided in various construct formats as described in Section III.C.3. In some embodiments, the CD86/Nkp30 immunomodulatory proteins exhibit at least 85%, 86%, 87%, 88%, 89%, 90%, 91%, 92%, 93%, 94%, 95%, 96%, 97%, 98% or 99% sequence identity to a sequence set forth in any of SEQ ID NOS:135, 136, 137, 138, 139 or 140. In some embodiments, the variant CD86/Nkp30 immunomodulatory protein has the sequence set forth in SEQ ID NOS: 135, 136, 137, 138, 139 or 140.

3. Constructs

In some embodiments, the two or more IgSF domain, including a vIgD of CD86 and one or more additional IgSF domain (e.g., second or third variant IgSF domain) from another IgSF family member, are covalently or non-covalently linked. A plurality of non-affinity modified and/or affinity modified IgSF domains in a stacked immunomodulatory protein polypeptide chain need not be covalently linked directly to one another. In some embodiments, the two or more IgSF domains are linked directly or indirectly, such as via a linker. In some embodiments, an intervening span of one or more amino acid residues indirectly covalently bonds IgSF domains to each other. The linkage can be via the N-terminal to C-terminal residues. In some embodiments, the linkage can be made via side chains of amino acid residues that are not located at the N-terminus or C-terminus of the IgSF domain(s). Thus, linkages can be made via terminal or internal amino acid residues or combinations thereof.

Figure 23A:
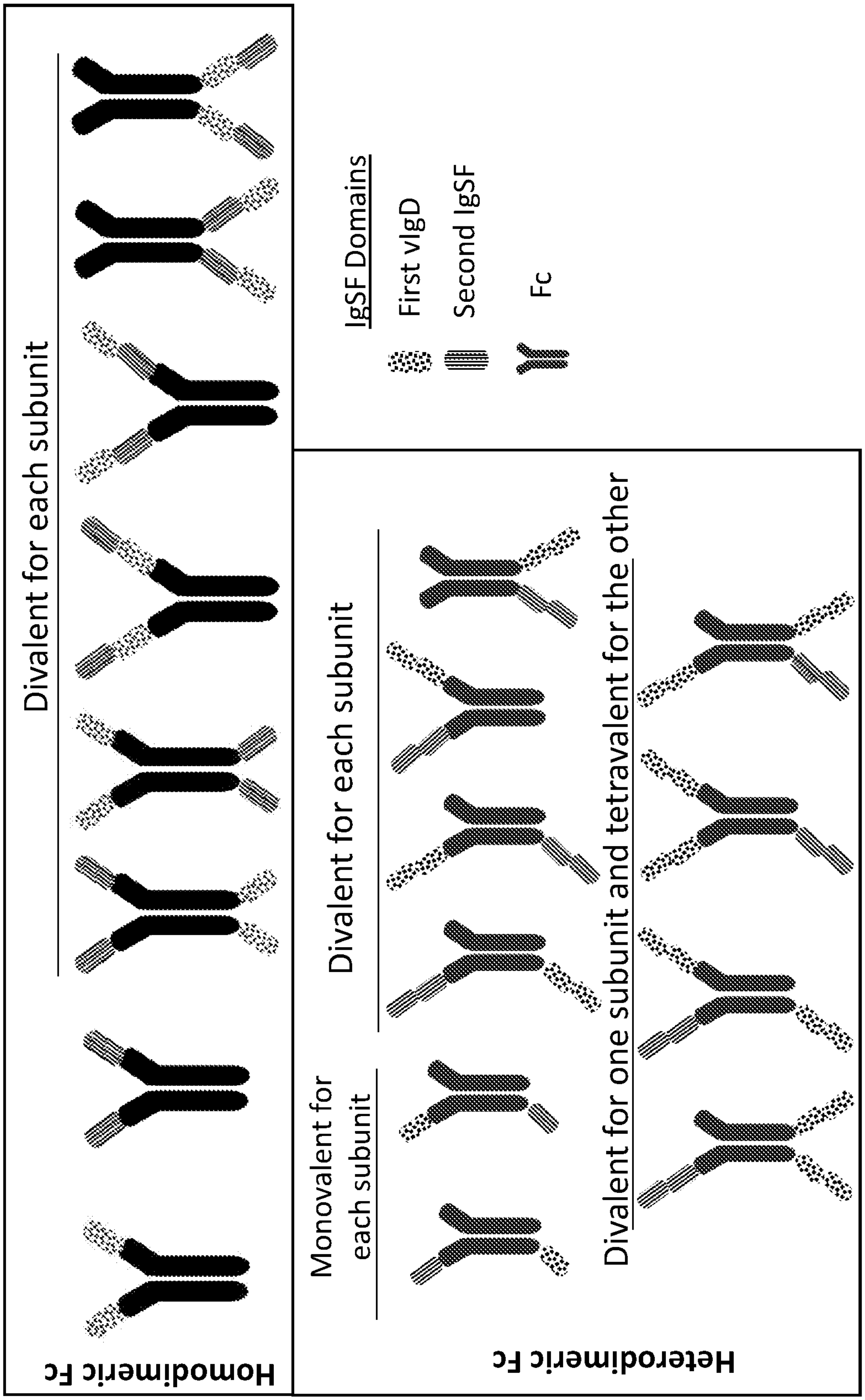
FIG. 23A depicts various exemplary configurations of a stack molecule containing a first variant IgSF domain (first vIgD) and a second IgSF domain, such as a second variant IgSF domain (second vIgD).
Figure 23B:
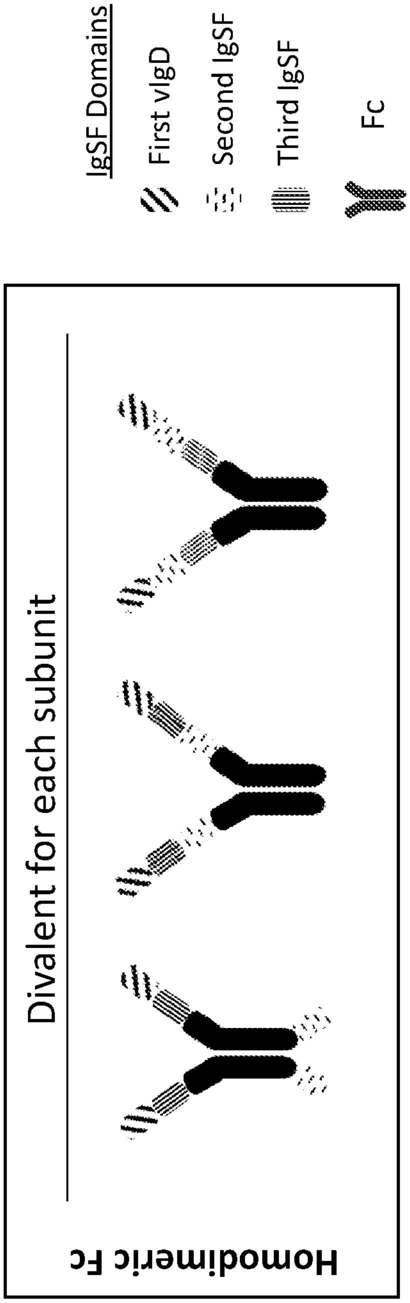
FIG. 23B depicts various exemplary configurations of a stack molecule containing a first variant IgSF domain (first vIgD), a second IgSF domain, such as a second variant IgSF domain (second vIgD), and a third IgSF domain, such as a third variant IgSF domain (third vIgD).
Figure 24A:
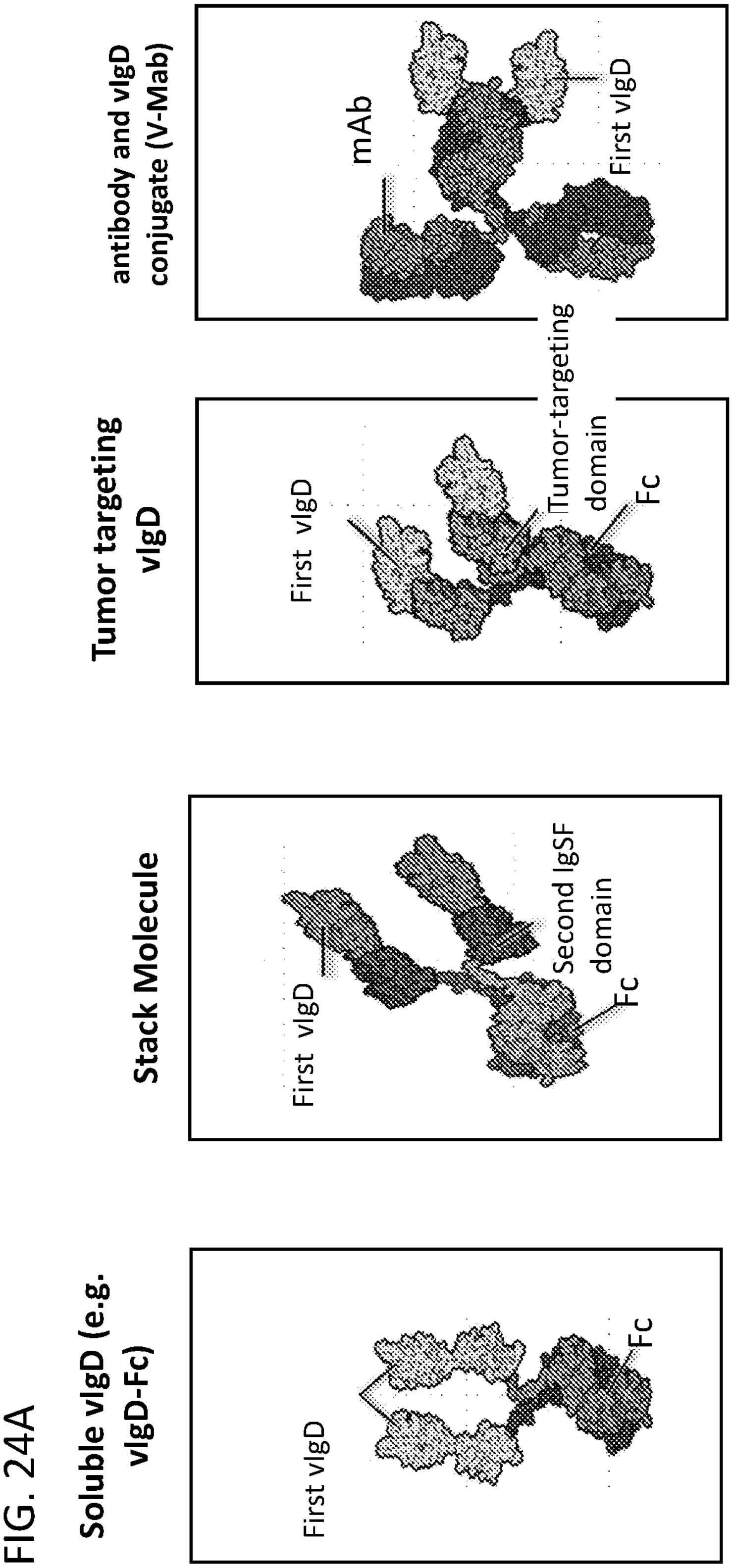
FIG. 24A depicts soluble molecules and FIG. 24B depicts a transmembrane immunomodulatory protein (TIP) containing a variant IgSF domain (vIgD) expressed on the surface of a cell.
Figure 24B:
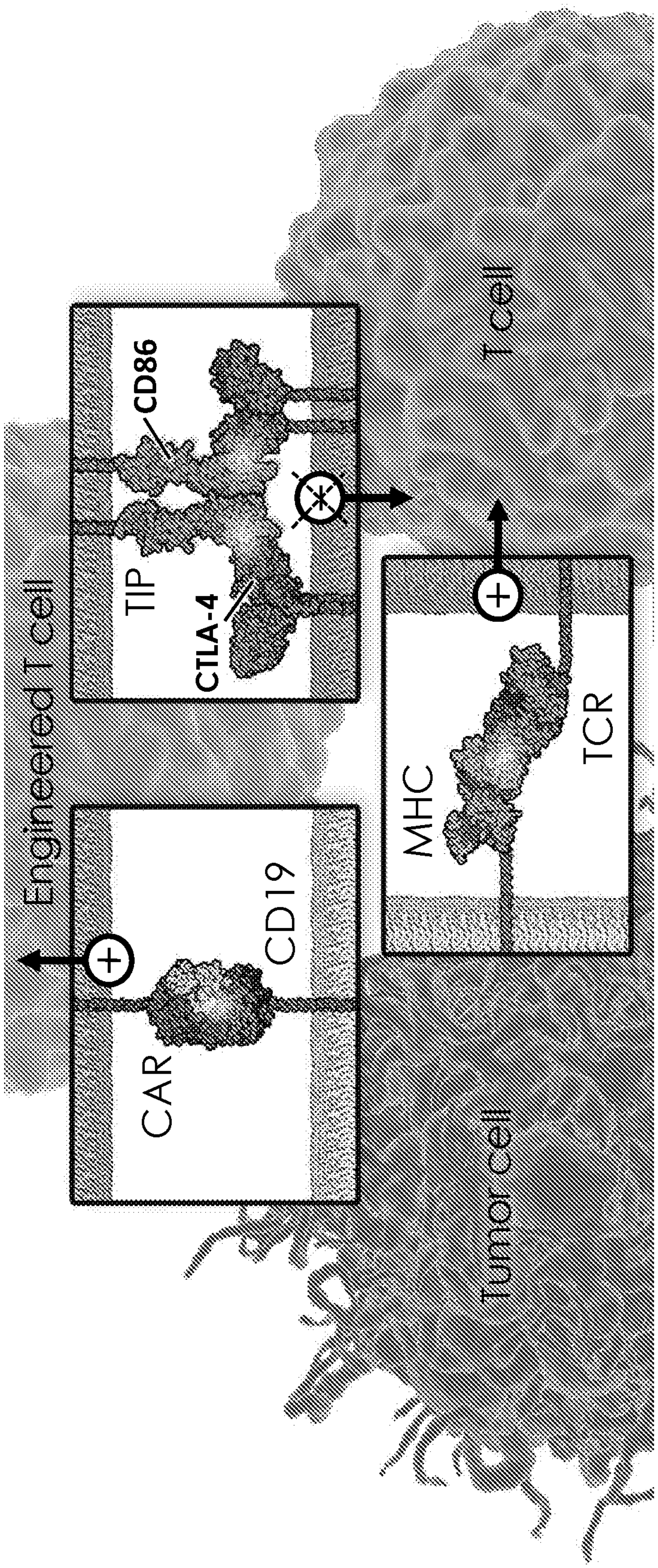
Figure 25:
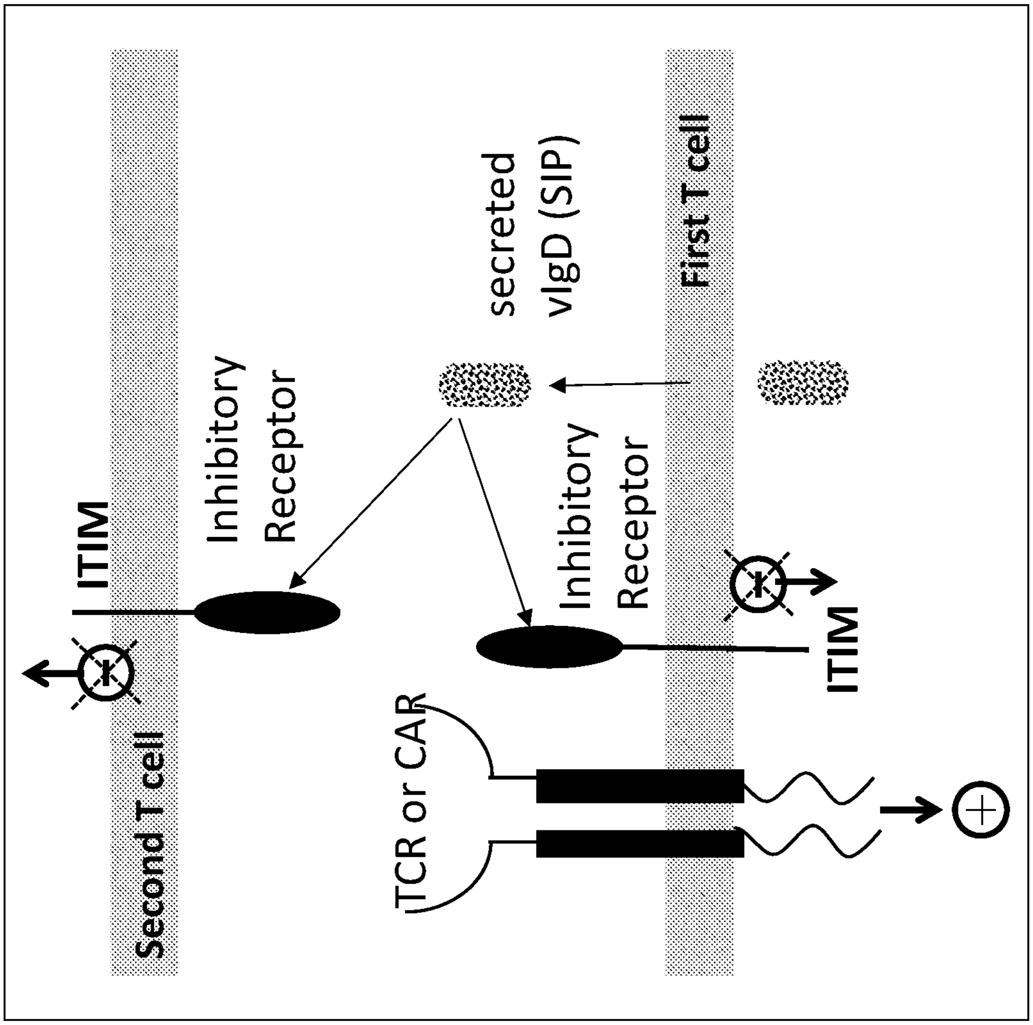
FIG. 25 depicts a secreted immunomodulatory protein (SIP) in which a variant IgSF domain (vIgD) is secreted from a cell, such as a first T cell (e.g., CAR T cell).

In some embodiments, the immunomodulatory protein contains at least two IgSF domains, each linked directly or indirectly via a linker. In some embodiments, the immunomodulatory protein contains at least three immunomodulatory proteins, each linked directly or indirectly via a linker. Various configurations are shown in FIGS. 23A and 23B.

In some embodiments, one or more "peptide linkers" link the vIgD of CD86 and one or more additional IgSF domain (e.g., second or third variant IgSF domain). In some embodiments, a peptide linker can be a single amino acid residue or greater in length. In some embodiments, the peptide linker has at least one amino acid residue but is no more than 20, 19, 18, 17, 16, 15, 14, 13, 12, 11, 10, 9, 8, 7, 6, 5, 4, 3, 2, or 1 amino acid residues in length. In some embodiments, the linker is a flexible linker. In some embodiments, the linker is (in one-letter amino acid code): GGGGS ("4GS") or multimers of the 4GS linker, such as repeats of 2, 3, 4, or 5 4GS linkers. In some embodiments, the peptide linker is $(GGGGS)_2$ (SEQ ID NO: 225) or $(GGGGS)_3$ (SEQ ID NO: 224). In some embodiments, the linker also can include a series of alanine residues alone or in addition to another peptide linker (such as a 4GS linker or multimer thereof). In some embodiments, the number of alanine residues in each series is: 2, 3, 4, 5, or 6 alanines. In some embodiments, the linker also can include a series of alanine residues alone or in addition to another peptide linker (such as a 4GS linker or multimer thereof). In some embodiments, the number of alanine residues in each series is: 2, 3, 4, 5, or 6 alanines. In some embodiments, the linker is a rigid linker. For example, the linker is an α-helical linker. In some embodiments, the linker is (in one-letter amino acid code): EAAAK or multimers of the EAAAK linker, such as repeats of 2, 3, 4, or 5 EAAAK linkers, such as set forth in SEQ ID NO: 265 (1×EAAAK), SEQ ID NO: 266 (3×EAAAK) or SEQ ID NO: 247 (5×EAAAK). In some embodiments, the linker can further include amino acids introduced by cloning and/or from a restriction site, for example the linker can include the amino acids GS (in one-letter amino acid code) as introduced by use of the restriction site BAMHI. For example, in some embodiments, the linker (in one-letter amino acid code) is GSGGGGS (SEQ ID NO:222), $GS(G_4S)_3$ (SEQ ID NO: 227), or $GS(G_4S)_5$ (SEQ ID NO: 228). In some examples, the linker is a 2×GGGGS followed by three alanines (GGGGSGGGGSAAA; SEQ ID NO: 226). In some cases, the immunomodulatory polypeptide comprising a variant CD86 comprises various combinations of peptide linkers.

In some embodiments, the immunomodulatory protein includes a variant CD86 molecule and a variant NKp30 molecule. In some embodiments, the immunomodulatory protein includes or has a sequence having at least 70, 75, 80, 85, 90, 91, 92, 93, 94, 95, 96, 97, 98, or 99% sequence identity to the sequence set forth by SEQ ID NO: 135, 136, 137, 138, 139, or 140. In some embodiments, the immunomodulatory protein includes or has a sequence set forth by SEQ ID NO: 135, 136, 137, 138, 139, or 140. In some embodiments, any of the foregoing sequences form a homodimer. In some embodiments, the homodimer is formed via a multimerization domain that is an Fc domain contained in the immunomodulatory protein. In some embodiments, the homodimer includes the sequence of SEQ ID NO: SEQ ID NO: 135. In some embodiments, the homodimer includes the sequence of SEQ ID NO: SEQ ID NO: 136. In some embodiments, the homodimer includes the sequence of SEQ ID NO: SEQ ID NO: 137. In some embodiments, the homodimer includes the sequence of SEQ ID NO: SEQ ID NO: 138. In some embodiments, the homodimer includes the sequence of SEQ ID NO: SEQ ID NO: 139. In some embodiments, the homodimer includes the sequence of SEQ ID NO: SEQ ID NO: 140.

In some embodiments, the immunomodulatory protein includes a variant CD86 molecule and a variant PD-1 molecule. In some embodiments, the immunomodulatory protein includes or has a sequence having at least 70, 75, 80, 85, 90, 91, 92, 93, 94, 95, 96, 97, 98, or 99% sequence identity to the sequence set forth by SEQ ID NO: 316, 317, 318, 319, 320, 321, 322, or 323. In some embodiments, the immunomodulatory protein includes or has a sequence set forth by SEQ ID NO: 316, 317, 318, 319, 320, 321, 322, or 323. In some embodiments, the immunomodulatory protein includes or has a sequence having at least 70, 75, 80, 85, 90, 91, 92, 93, 94, 95, 96, 97, 98, or 99% sequence identity to the sequence set forth by SEQ ID NO: 326 or 327. In some embodiments, the immunomodulatory protein includes or has the sequence set forth by SEQ ID NO: 326 or 327. In some embodiments, any of the foregoing sequences form a homodimer. In some embodiments, the homodimer is formed via a multimerization domain that is an Fc domain contained in the immunomodulatory protein. In some embodiments, the homodimer includes or has the sequence of SEQ ID NO: 326. In some embodiments, the homodimer includes or has the sequence of SEQ ID NO: 327.

In some embodiments, the immunomodulatory protein includes or has a sequence having at least 70, 75, 80, 85, 90, 91, 92, 93, 94, 95, 96, 97, 98, or 99% sequence identity to the sequence set forth by SEQ ID NO: 328, 329, 330, or 331. In some embodiments, the immunomodulatory protein includes or has the sequence set forth by SEQ ID NO: 328, 329, 330, or 331. In some embodiments any of the foregoing sequences form a heterodimer. In some embodiments, the heterodimer is formed via a multimerization domain that is an Fc domain contained in the immunomodulatory protein. In some embodiments, the first polypeptide of the heterodimer comprises the sequence of SEQ ID NO: 350 and the second polypeptide of the heterodimer comprises the sequence of SEQ ID NO: 351. In some embodiments, the first polypeptide of the heterodimer comprises the sequence of SEQ ID NO: 350 and the second polypeptide of the heterodimer comprises the sequence of SEQ ID NO: 352. In some embodiments, the first polypeptide of the heterodimer comprises the sequence of SEQ ID NO: 350 and the second polypeptide of the heterodimer comprises the sequence of SEQ ID NO: 353.

In some embodiments, the non-affinity modified and/or affinity modified IgSF domains are linked by "wild-type peptide linkers" inserted at the N-terminus and/or C-terminus of a non-affinity modified and/or affinity modified IgSF domains. These linkers are also called leading sequences (N-terminal to non-affinity modified or affinity modified IgSF domain) or trailing sequences (C-terminal to non-affinity modified or affinity modified IgSF domain), and sequences that exist in the wild-type protein that span immediately outside the structural prediction of the Ig fold of the IgSF. In some embodiments, the "wild-type linker" is an amino acid sequence that exists after the signal sequence, but before in the IgSF domain, such as the defined IgV domain, in the amino acid sequence of the wild-type protein. In some embodiments, the "wild-type" linker is an amino acid sequence that exists immediately after the IgSF domain, such as immediately after the defined IgV domain but before the IgC domain, in the amino acid sequence of the wild-type protein. These linker sequences can contribute to the proper folding and function of the neighboring IgSF domain(s). In some embodiments, there is present a leading peptide linker inserted at the N-terminus of the first IgSF domain and/or a trailing sequence inserted at the C-terminus of the first non-affinity modified and/or affinity modified IgSF domain. In some embodiments, there is present a second leading peptide linker inserted at the N-terminus of the second IgSF domain and/or a second trailing sequence inserted at the C-terminus of the second non-affinity modified and/or affinity modified IgSF domain. When the first and second non-affinity modified and/or affinity modified IgSF domains are derived from the same parental protein and are connected in the same orientation, wild-type peptide linkers between the first and second non-affinity modified and/or affinity modified IgSF domains are not duplicated. For example, when the first trailing wild-type peptide linker and the second leading wild-type peptide linker are the same, the Type II immunomodulatory protein does not comprise either the first trailing wild-type peptide linker or the second leading wild-type peptide linker.

In some embodiments, the Type II immunomodulatory protein comprises a first leading wild-type peptide linker inserted at the N-terminus of the first non-affinity modified and/or affinity modified IgSF domain, wherein the first leading wild-type peptide linker comprises at least 5 (such as at least about any of 6, 7, 8, 9, 10, 11, 12, 13, 14, 15, or more) consecutive amino acids from the intervening sequence in the wild-type protein from which the first non-affinity modified and/or affinity modified IgSF domain is derived between the parental IgSF domain and the immediately preceding domain (such as a signal peptide or an IgSF domain). In some embodiments, the first leading wild-type peptide linker comprises the entire intervening sequence in the wild-type protein from which the first non-affinity modified and/or affinity modified IgSF domain is derived between the parental IgSF domain and the immediately preceding domain (such as a signal peptide or an IgSF domain).

In some embodiments, the Type II immunomodulatory protein further comprises a first trailing wild-type peptide linker inserted at the C-terminus of the first non-affinity modified and/or affinity modified IgSF domain, wherein the first trailing wild-type peptide linker comprises at least 5 (such as at least about any of 6, 7, 8, 9, 10, 11, 12, 13, 14, 15, or more) consecutive amino acids from the intervening sequence in the wild-type protein from which the first non-affinity modified and/or affinity modified IgSF domain is derived between the parental IgSF domain and the immediately following domain (such as an IgSF domain or a transmembrane domain). In some embodiments, the first trailing wild-type peptide linker comprises the entire intervening sequence in the wild-type protein from which the first non-affinity modified and/or affinity modified IgSF domain is derived between the parental IgSF domain and the immediately following domain (such as an IgSF domain or a transmembrane domain).

In some embodiments, the Type II immunomodulatory protein further comprises a second leading wild-type peptide linker inserted at the N-terminus of the second non-affinity modified and/or affinity modified IgSF domain, wherein the second leading wild-type peptide linker comprises at least 5 (such as at least about any of 6, 7, 8, 9, 10, 11, 12, 13, 14, 15, or more) consecutive amino acids from the intervening sequence in the wild-type protein from which the second non-affinity modified and/or affinity modified IgSF domain is derived between the parental IgSF domain and the immediately preceding domain (such as a signal peptide or an IgSF domain). In some embodiments, the second leading wild-type peptide linker comprises the entire intervening sequence in the wild-type protein from which the second non-affinity modified and/or affinity modified IgSF domain is derived between the parental IgSF domain and the immediately preceding domain (such as a signal peptide or an IgSF domain).

In some embodiments, the Type II immunomodulatory protein further comprises a second trailing wild-type peptide linker inserted at the C-terminus of the second non-affinity modified and/or affinity modified IgSF domain, wherein the second trailing wild-type peptide linker comprises at least 5 (such as at least about any of 6, 7, 8, 9, 10, 11, 12, 13, 14, 15, or more) consecutive amino acids from the intervening sequence in the wild-type protein from which the second non-affinity modified and/or affinity modified IgSF domain is derived between the parental IgSF domain and the immediately following domain (such as an IgSF domain or a transmembrane domain). In some embodiments, the second trailing wild-type peptide linker comprises the entire intervening sequence in the wild-type protein from which the second non-affinity modified and/or affinity modified IgSF domain is derived between the parental IgSF domain and the immediately following domain (such as an IgSF domain or a transmembrane domain).

In some embodiments, the two or more IgSF domain, including a vIgD of CD86 and one or more additional IgSF domain (e.g., second and/or third variant IgSF domain) from another IgSF family member, are linked or attached to an Fc to form an Fc fusion, which, upon expression in a cell can, in some aspects, produce a dimeric multi-domain stack immunomodulatory protein. Thus, also provided are dimeric multi-domain immunomodulatory proteins.

In some embodiments, the variant CD86 polypeptide and one or more IgSF domain are independently linked, directly or indirectly, to the N- or C-terminus of an Fc region. In some embodiments, the variant CD86 polypeptide and at least one of the one or more additional IgSF domain are linked, directly or indirectly, and one of the variant CD86 and one of the one or more additional IgSF domain is also linked, directly or indirectly, to the N- or C-terminus of an Fc region. In some embodiments, the N- or C-terminus of the Fc region is linked to the variant CD86 polypeptide or the one or more additional IgSF domain and the other of the N- or C-terminus of the Fc region is linked to the other of the CD86 variant or another of the one or more additional IgSF domain. In some embodiments, linkage to the Fc is via a peptide linker, e.g., a peptide linker, such as described above. In some embodiments, linkage between the variant CD86 and the one or more additional IgSF domain is via a peptide linker, e.g., a peptide linker, such as described above. In some embodiments, the vIgD of CD86, the one or more additional IgSF domains, and the Fc domain can be linked together in any of numerous configurations. Exemplary configurations are described in the Examples. See for example, FIGS. 14A-14D.

In some embodiments, the stacked immunomodulatory protein is a dimer formed by two immunomodulatory Fc fusion polypeptides. Also provided are nucleic acid molecules encoding any of the stacked immunomodulatory proteins. In some embodiments, the dimeric multi-domain stack immunomodulatory protein can be produced in cells by expression, or in some cases co-expression, of stack immunomodulatory Fc fusion polypeptides, such as described above in accord with generating dimeric Fc fusion proteins.

In some embodiments, the dimeric multi-domain stack immunomodulatory protein is divalent for each Fc region, monovalent for each subunit, or divalent for one subunit and tetravalent for the other.

In some embodiments, the dimeric multi-domain stack immunomodulatory protein is a homodimeric multi-domain stack Fc protein. In some embodiments, the dimeric multi-domain stack immunomodulatory protein comprises a first stack immunomodulatory Fc fusion polypeptide and a second stack immunomodulatory Fc fusion polypeptide in which the first and second polypeptide are the same. In some embodiments, the multi-domain stack molecule contains a first Fc fusion polypeptide containing a variant CD86 and a second IgSF domain and a second Fc fusion polypeptide containing the variant CD86 and the second IgSF domain. In some embodiments, the multi-domain stack molecule contains a first Fc fusion polypeptide containing a variant CD86, a second IgSF domain, and a third IgSF domain and a second Fc fusion polypeptide containing the variant CD86, the second IgSF domain, and the third IgSF domain. In some embodiments, the Fc portion of the first and/or second fusion polypeptide can be any Fc as described above. In some embodiments, the Fc portion or region of the first and second fusion polypeptide is the same.

In some embodiments, the multi-domain stack molecule is heterodimeric, comprising two different Fc fusion polypeptides, e.g., a first and a second Fc fusion polypeptide, wherein at least one is an Fc fusion polypeptide containing at least one variant CD86 polypeptide and/or at least one is an Fc fusion polypeptide containing a second IgSF domain (e.g., second variant IgSF domain). In some embodiments, the first or second Fc fusion polypeptide further contains a third IgSF domain (e.g., third variant IgSF domain). In some embodiments, the multi-domain stack molecule contains a first Fc fusion polypeptide containing a variant CD86 and a second Fc fusion polypeptide containing a second IgSF domain, in which, in some cases, the first or second Fc fusion polypeptide additionally contains a third IgSF domain. In some embodiments, the multi-domain stack molecule contains a first Fc fusion polypeptide containing a variant CD86, a second IgSF domain, and in some cases, a third IgSF domain and a second Fc fusion polypeptide that is not linked to either a variant CD86 polypeptide or an additional IgSF domain. In some embodiments, the Fc portion or region of the first and second fusion polypeptide is the same. In some embodiments, the Fc portion or region of the first and second fusion polypeptide is different.

In some embodiments, the multi-domain stack molecule contains a first Fc fusion polypeptide containing 1, 2, 3, 4 or more variant CD86 polypeptides and 1, 2, 3, 4 or more additional IgSF domains, wherein the total number of IgSF domains in the first stack Fc fusion polypeptide is greater than 2, 3, 4, 5, 6 or more. In one example of such an embodiment, the second stack Fc fusion polypeptide contains 1, 2, 3, 4 or more variant CD86 polypeptides and 1, 2, 3, 4 or more additional IgSF domains, wherein the total number of IgSF domains in the first stack Fc fusion polypeptide is greater than 2, 3, 4, 5, 6 or more. In another example of such an embodiment, the second Fc fusion polypeptide is not linked to either a variant CD86 polypeptide or additional IgSF domain.

In some embodiments, the heterodimeric stack molecule contains a first stack immunomodulatory Fc fusion polypeptide and a second stack immunomodulatory Fc fusion polypeptide in which the first and second polypeptide are different. In some embodiments, a heterodimeric stack molecule contains a first Fc polypeptide fusion containing an Fc region and a first variant CD86 polypeptide and/or second IgSF domain (e.g., second variant IgSF domain) and a second Fc polypeptide fusion containing an Fc region and the other of the first variant CD86 polypeptide or the second IgSF domain. In some embodiments, a heterodimeric stack molecule contains a first Fc polypeptide fusion containing an Fc region and a first variant CD86 polypeptide and/or second IgSF domain (e.g., second variant IgSF domain) and a second Fc polypeptide fusion containing an Fc region and both the first variant CD86 polypeptide and second IgSF domain (e.g., second variant IgSF domain) but in a different orientation or configuration from the first Fc region. In some embodiments, the first and/or second Fc fusion polypeptide also contains a third IgSF domain (e.g., third variant IgSF domain).

In some embodiments, the Fc domain of one or both of the first and second stacked immunomodulatory Fc fusion polypeptide comprises a modification (e.g., substitution) such that the interface of the Fc molecule is modified to facilitate and/or promote heterodimerization. In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a sequence of amino acids is added preceding the Fc sequence for constructs in which the Fc sequence is the N-terminal portion of the sequence. In some cases, the sequence of amino acids HMSSVSAQ (SEQ ID NO: 279) is added immediately preceding the Fc sequence for constructs in which the Fc sequence is the N-terminal portion of the sequence. In some embodiments, a heterodimeric stack molecule contains a first Fc polypeptide fusion containing an Fc region (knob; e.g., the Fc sequence set forth in SEQ ID NOS: 252 or 324) and a first variant polypeptide and/or second IgSF domain (e.g., second variant IgSF domain) and a second Fc polypeptide fusion containing an Fc region (hole; e.g., the Fc sequence set forth in SEQ ID NO: 280 or 325) and a stuffer sequence HMSSVSAQ (SEQ ID NO:279) is added immediately preceding both Fc regions of the first and second Fc polypeptide fusion.

In some embodiments, a first polypeptide that is modified to contain protuberance (knob) amino acids includes replacement of a native or original amino acid with an amino acid that has at least one side chain which projects from the interface of the first polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine (S), threonine (T), and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 A2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731,168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

In some embodiments, the heterodimeric molecule contains a T366W mutation in the CH3 domain of the "knob chain" and T366S, L368A, Y407V mutations in the CH3 domain of the "hole chain". In some cases, an additional interchain disulfide bridge between the CH3 domains can also be used (Merchant, A. M., et al., Nature Biotech. 16 (1998) 677-681) e.g., by introducing a Y349C mutation into the CH3 domain of the "knob" or "hole" chain and a E356C mutation or a S354C mutation into the CH3 domain of the other chain. In some embodiments, the heterodimeric molecule contains S354CT366W mutations in one of the two CH3 domains and Y349C, T366S, L368A, Y407V mutations in the other of the two CH3 domains. In some embodiments, the heterodimeric molecule comprises E356C, T366W mutations in one of the two CH3 domains and Y349C, T366S, L368A, Y407V mutations in the other of the two CH3 domains. In some embodiments, the heterodimeric molecule comprises Y349C, T366W mutations in one of the two CH3 domains and E356C, T366S, L368A, Y407V mutations in the other of the two CH3 domains. In some embodiments, the heterodimeric molecule comprises Y349C, T366W mutations in one of the two CH3 domains and S354C, T366S, L368A, Y407V mutations in the other of the two CH3 domains. Examples of other knobs-in-holes technologies are known in the art, e.g., as described by EP 1 870 459 A1.

In some embodiments, the Fc regions of the heterodimeric molecule additionally can contain one or more other Fc mutation, such as any described above. In some embodiments, the heterodimer molecule contains an Fc region with a mutation that reduces effector function.

In some embodiments, an Fc variant containing CH3 protuberance (knob) or cavity (hole) modifications can be joined to a stacked immunomodulatory polypeptide anywhere, but typically via its N- or C-terminus, to the N- or C-terminus of a first and/or second stacked immunomodulatory polypeptide, such as to form a fusion polypeptide. The linkage can be direct or indirect via a linker. Typically, a knob and hole molecule is generated by co-expression of a first stacked immunomodulatory polypeptide linked to an Fc variant containing CH3 protuberance modification(s) with a second stacked immunomodulatory polypeptide linked to an Fc variant containing CH3 cavity modification(s).

D. Conjugates and Fusions of Variant Polypeptides and Immunomodulatory Proteins

In some embodiments, the variant polypeptides provided herein, which are immunomodulatory proteins comprising variants of an Ig domain of the IgSF family (vIgD), can be conjugated with or fused with a moiety, such as an effector moiety, such as another protein, directly or indirectly, to form a conjugate ("IgSF conjugate"). In some embodiments, the attachment can be covalent or non-covalent, e.g., via a biotin-streptavidin non-covalent interaction. In some embodiments of a CD86-Fc variant fusion, any one or combination of any two or more of the foregoing conjugates can be attached to the Fc or to the variant CD86 polypeptide or to both.

In some embodiments, the moiety can be a targeting moiety, a small molecule drug (non-polypeptide drug of less than 500 Daltons molar mass), a toxin, a cytostatic agent, a cytotoxic agent, an immunosuppressive agent, a radioactive agent suitable for diagnostic purposes, a radioactive metal ion for therapeutic purposes, a prodrug-activating enzyme, an agent that increases biological half-life, or a diagnostic or detectable agent.

In some embodiments, the effector moiety is a therapeutic agent, such as a cancer therapeutic agent, which is either cytotoxic, cytostatic, or otherwise provides some therapeutic benefit. In some embodiments, the effector moiety is a targeting moiety or agent, such as an agent that targets a cell surface antigen, e.g., an antigen on the surface of a tumor cell. In some embodiments, the effector moiety is a label, which can generate a detectable signal, either directly or indirectly. In some embodiments, the effector moiety is a toxin. In some embodiments, the effector moiety is a protein, peptide, nucleic acid, small molecule, or nanoparticle.

In some embodiments, 1, 2, 3, 4, 5 or more effector moieties, which can be the same or different, are conjugated, linked or fused to the variant polypeptide or protein to form an IgSF conjugate. In some embodiments, such effector moieties can be attached to the variant polypeptide or immunomodulatory protein using various molecular biological or chemical conjugation and linkage methods known in the art and described below. In some embodiments, linkers such as peptide linkers, cleavable linkers, non-cleavable linkers or linkers that aid in the conjugation reaction, can be used to link or conjugate the effector moieties to the variant polypeptide or immunomodulatory protein.

In some embodiments, the IgSF conjugate comprises the following components: (protein or polypeptide), $(L)_q$ and $(\text{effector moiety})_m$, wherein the protein or polypeptide is any of the described variant polypeptides or immunomodulatory proteins capable of binding one or more cognate counter structure ligands as described; L is a linker for linking the protein or polypeptide to the moiety; m is at least 1; q is 0 or more; and the resulting IgSF conjugate binds to the one or more counter structure ligands. In particular embodiments, m is 1 to 4 and q is 0 to 8.

In some embodiments, there is provided an IgSF conjugate comprising a variant polypeptide or immunomodulatory protein provided herein conjugated with a targeting agent that binds to a cell surface molecule, for example, for targeted delivery of the variant polypeptide or immunomodulatory protein to a specific cell. In some embodiments, the targeting agent is a molecule(s) that has the ability to localize and bind to a molecule present on a normal cell/tissue and/or tumor cell/tumor in a subject. In other words, IgSF conjugates comprising a targeting agent can bind to a ligand (directly or indirectly), which is present on a cell, such as a tumor cell. The targeting agents of the invention contemplated for use include antibodies, polypeptides, peptides, aptamers, other ligands, or any combination thereof, that can bind a component of a target cell or molecule.

In some embodiments, the targeting agent binds a tumor cell(s) or can bind in the vicinity of a tumor cell(s) (e.g., tumor vasculature or tumor microenvironment) following administration to the subject. The targeting agent may bind to a receptor or ligand on the surface of the cancer cell. In another aspect of the invention, a targeting agent is selected which is specific for a noncancerous cells or tissue. For example, a targeting agent can be specific for a molecule present normally on a particular cell or tissue. Furthermore, in some embodiments, the same molecule can be present on normal and cancer cells. Various cellular components and molecules are known. For example, if a targeting agent is specific for EGFR, the resulting IgSF conjugate can target cancer cells expressing EGFR as well as normal skin epidermal cells expressing EGFR. Therefore, in some embodiments, an IgSF conjugate of the invention can operate by two separate mechanisms (targeting cancer and non-cancer cells).

In various aspects of the invention disclosed herein an IgSF conjugate of the invention comprises a targeting agent which can bind/target a cellular component, such as a tumor antigen, a bacterial antigen, a viral antigen, a mycoplasma antigen, a fungal antigen, a prion antigen, an antigen from a parasite. In some aspects, a cellular component, antigen, or molecule can each be used to mean a desired target for a targeting agent. For example, in various embodiments, a targeting agent is specific for or binds to a component, which includes but is not limited to, epidermal growth factor receptor (EGFR, ErbB-1, HER1), ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family; platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family; TRK receptor family; ephrin (EPH) receptor family; AXL receptor family; leukocyte tyrosine kinase (LTK) receptor family; TIE receptor family, angiopoietin 1,2; receptor tyrosine kinase-like orphan receptor (ROR) receptor family, e.g., ROR1; CD171 (L1CAM); B7-H6 (NCR3LG1); CD80, tumor glycosylation antigen, e.g., sTn or Tn, such as sTn Ag of MUC1; LHR (LHCGR); phosphatidylserine, discoidin domain receptor (DDR) family; RET receptor family; KLG receptor family; RYK receptor family; MuSK receptor family; Transforming growth factor-α (TGF-α) receptors, TGF-β; Cytokine receptors, Class I (hematopoietin family) and Class II (interferon/IL-10 family) receptors, tumor necrosis factor (TNF) receptor superfamily (TNFRSF), death receptor family; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), β-catenin (CTNNB1), cell division cycle 27 (CDC27), cyclin-dependent kinase 4 (CDK4), CDKN2A, COA-I, dek-can fusion protein, EFTUD-2, Elongation factor 2 (ELF2), Ets variant gene 6/acute myeloid leukemia 1 gene ETS (ETC6-AML1) fusion protein, fibronectin (FN), e.g., the extradomain A (EDA) of fibronectin, GPNMB, low density lipid receptor/GDP-L fucose: β-D-galactose 2-α-L-fucosyltransferase (LDLR/FUT) fusion protein, HLA-A2, arginine to isoleucine exchange at residue 170 of the α-helix of the α2-domain in the HLA-A2gene (HLA-A*201-R170I), HLA-Al 1, heat shock protein 70-2 mutated (HSP70-2M), K1AA0205, MART2, melanoma ubiquitous mutated 1, 2, 3 (MUM-I, 2, 3), prostatic acid phosphatase (PAP), neo-PAP, Myosin class I, NFYC, OGT, OS-9, pml-RARα fusion protein, PRDX5, PTPRK, K-ras (KRAS2), N-ras (NRAS), HRAS, RBAF600, SIRT2, SNRPD1, SYT-SSX1 or -SSX2 fusion protein, Triosephosphate Isomerase, BAGE, BAGK-1, BAGE-2,3,4,5, GAGE-1,2,3,4,5,6,7,8, GnT-V (aberrant N-acetyl glucosaminyl transferase V, MGATS), HERV-K-MEL, KK-LC, KM-HN-I, LAGE, LAGE-I, CTL-recognized antigen on melanoma (CAMEL), MAGE-A1 (MAGE-I), MAGE-A2, MAGE-A3, MAGE-A4, MAGE-A5, MAGE-A6, MAGE-A8, MAGE-A9, MAGE-A10, MAGE-AI 1, MAGE-A12, MAGE-3, MAGE-B1, MAGE-B2, MAGE-B5, MAGE-B6, MAGE-Cl, MAGE-C2, mucin 1 (MUC1), MART-1/Melan-A (MLANA), gp100, gp100/Pme117 (SILV), tyrosinase (TYR), TRP-I, HAGE, NA-88, NY-ESO-I, NY-ESO-1/LAGE-2, SAGE, Sp17, SSX-1,2,3,4, TRP2-INT2, carcino-embryonic antigen (CEA), Kallikrein 4, mammaglobin-A, OA1, prostate specific antigen (PSA), TRP-1/gp75, TRP-2, adipophilin, interferon inducible protein absent in melanoma 2 (AIM-2), BING-4, CPSF, cyclin D1, epithelial cell adhesion molecule (Ep-CAM), EphA3, fibroblast growth factor-5 (FGF-5), glycoprotein 250 (gp250), EGFR (ERBB1), HER-2/neu (ERBB2), interleukin 13 receptor a2 chain (IL13Rα2), IL-6 receptor, intestinal carboxyl esterase (iCE), alpha-feto protein (AFP), M-CSF, mdm-2, MUC1, p53 (TP53), PBF, PRAME, PSMA, RAGE-I, RNF43, RU2AS, SOX1O, STEAP1, survivin (BIRC5), human telomerase reverse transcriptase (hTERT), telomerase, Wilms' tumor gene (WT1), SYCP1, BRDT, SPANX, XAGE, ADAM2, PAGE-5, L1P1, CTAGE-I, CSAGE, MMA1, CAGE, BORIS, HOM-TES-85, AF15q14, HCA661, LDHC, MORC, SGY-I, SPO1 1, TPX1, NY-SAR-35, FTHL17, NXF2, TDRD1, TEX15, FATE, TPTE, immunoglobulin idiotypes, Bence-Jones protein, estrogen receptors (ER), androgen receptors (AR), CD40, CD30, CD20, CD 19, CD33, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), β-human chorionic gonadotropin, β-2 microglobulin, squamous cell carcinoma antigen, neuron-specific enolase, heat shock protein gp96, GM2, sargramostim, CTLA-4, 707 alanine proline (707-AP), adenocarcinoma antigen recognized by T cells 4 (ART-4), carcinoembryonic antigen peptide-1 (CAP-I), calcium-activated chloride channel-2 (CLCA2), cyclophilin B (Cyp-B), human signet ring tumor-2 (HST-2), Human papilloma virus (HPV) proteins (HPV-E6, HPV-E7, major or minor capsid antigens, others), Epstein-Barr virus (EBV) proteins (EBV latent membrane proteins—LMP1, LMP2; others), Hepatitis B or C virus proteins, and HIV proteins.

In some embodiments, an IgSF conjugate, through its targeting agent, will bind a cellular component of a tumor cell, tumor vasculature or tumor microenvironment, thereby promoting killing of targeted cells via modulation of the immune response, (e.g., by activation of co-stimulatory molecules or inhibition of negative regulatory molecules of immune cell activation), inhibition of survival signals (e.g., growth factor or cytokine or hormone receptor antagonists), activation of death signals, and/or immune-mediated cytotoxicity, such as through antibody dependent cellular cytotoxicity. Such IgSF conjugates can function through several mechanisms to prevent, reduce or eliminate tumor cells, such as to facilitate delivery of conjugated effector moieties to the tumor target, such as through receptor-mediated endocytosis of the IgSF conjugate; or such conjugates can recruit, bind, and/or activate immune cells (e.g., NK cells, monocytes/macrophages, dendritic cells, T cells, B cells). Moreover, in some instances one or more of the foregoing pathways may operate upon administration of one or more IgSF conjugates of the invention.

In some embodiments, an IgSF conjugate, through its targeting agent, will be localized to, such as bind to, a cellular component of a tumor cell, tumor vasculature or tumor microenvironment, thereby modulating cells of the immune response in the vicinity of the tumor. In some embodiments, the targeting agent facilitates delivery of the conjugated IgSF (e.g., vIgD) to the tumor target, such as to interact with its cognate binding partner to alter signaling of immune cells (e.g., NK cells, monocytes/macrophages, dendritic cells, T cells, B cells) bearing the cognate binding partner.

In some embodiments, the targeting agent is an immunoglobulin. As used herein, the term "immunoglobulin" includes natural or artificial mono- or polyvalent antibodies including, but not limited to, polyclonal, monoclonal, multispecific, human, humanized or chimeric antibodies, single chain antibodies, Fab fragments, F(ab') fragments, fragments produced by a Fab expression library, single chain Fv (scFv); anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, e.g., molecules that contain an antigen binding site that immunospecifically binds an antigen. The immunoglobulin molecules of the invention can be of any type (e.g., IgG, IgE, IgM, IgD, IgA, and IgY), class (e.g., IgG1, IgG2, IgG3, IgG4, IgA1, and IgA2) or subclass of immunoglobulin molecule.

In some embodiments, an IgSF conjugate, through its antibody targeting moiety, will bind a cellular component of a tumor cell, tumor vasculature, or tumor microenvironment, thereby promoting apoptosis of targeted cells via modulation of the immune response, (e.g., by activation of co-stimulatory molecules or inhibition of negative regulatory molecules of immune cell activation), inhibition of survival signals (e.g., growth factor or cytokine or hormone receptor antagonists), activation of death signals, and/or immune-mediated cytotoxicity, such as through antibody dependent cellular cytotoxicity. Such IgSF conjugates can function through several mechanisms to prevent, reduce, or eliminate tumor cells, such as to facilitate delivery of conjugated effector moieties to the tumor target, such as through receptor-mediated endocytosis of the IgSF conjugate; or such conjugates can recruit, bind, and/or activate immune cells (e.g., NK cells, monocytes/macrophages, dendritic cells, T cells, B cells).

In some embodiments, an IgSF conjugate, through its antibody targeting moiety, will bind a cellular component of a tumor cell, tumor vasculature or tumor microenvironment, thereby modulating the immune response (e.g., by activation of co-stimulatory molecules or inhibition of negative regulatory molecules of immune cell activation). In some embodiments, such conjugates can recognize, bind, and/or modulate (e.g., inhibit or activate) immune cells (e.g., NK cells, monocytes/macrophages, dendritic cells, T cells, B cells).

Antibody targeting moieties of the invention include antibody fragments that include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. Also included in the invention are Fc fragments, antigen-Fc fusion proteins, and Fc-targeting moiety conjugates or fusion products (Fc-peptide, Fc-aptamer). The antibody targeting moieties of the invention may be from any animal origin including birds and mammals. In one aspect, the antibody targeting moieties are human, murine (e.g., mouse and rat), donkey, sheep, rabbit, goat, guinea pig, camel, horse, or chicken. Further, such antibodies may be humanized or chimeric versions of animal antibodies. The antibody targeting moieties of the invention may be monospecific, bispecific, trispecific, or of greater multispecificity.

In various embodiments, an antibody/targeting moiety recruits, binds, and/or activates immune cells (e.g., NK cells, monocytes/macrophages, dendritic cells) via interactions between Fc (in antibodies) and Fc receptors (on immune cells) and via the conjugated variant polypeptides or immunomodulatory proteins provided herein. In some embodiments, an antibody/targeting moiety recognizes or binds a tumor agent and localizes to the tumor cell via the conjugated variant polypeptides or immunomodulatory proteins provided herein to facilitate modulation of immune cells in the vicinity of the tumor.

Examples of antibodies which can be incorporated into IgSF conjugates include but are not limited to antibodies such as Pertuzumab (Perjeta®), Cetuximab (IMC-C225; Erbitux®), Trastuzumab (Herceptin®), Rituximab (Rituxan®; MabThera®), Bevacizumab (Avastin®), Alemtuzumab (Campath®; Campath-1H®; Mabcampath®), Panitumumab (ABX-EGF; Vectibix®), Ranibizumab (Lucentis®), Ibritumomab, Ibritumomab tiuxetan, (Zevalin®), Tositumomab, Iodine I 131 Tositumomab (BEXXAR®), Catumaxomab (Removab®), Gemtuzumab, Gemtuzumab ozogamicine (Mylotarg®), Abatacept (CTLA4-Ig; Orencia®), Belatacept (L104EA29YIg; LEA29Y; LEA), Ipilimumab (MDX-010; MDX-101), Tremelimumab (ticilimumab; CP-675,206), PRS-010, PRS-050, Aflibercept (VEGF Trap, AVE005), Volociximab (M200), F200, MORAb-009, SS1P (CAT-5001), Cixutumumab (IMC-A12), Matuzumab (EMD72000), Nimotuzumab (h-R3), Zalutumumab (HuMax-EGFR), Necitumumab IMC-11F8, mAb806/ch806, Sym004, mAb-425, Panorex@ (17-1A) (murine monoclonal antibody); Panorex@ (17-1A) (chimeric murine monoclonal antibody); IDEC-Y2B8 (murine, anti-CD20 MAb); BEC2 (anti-idiotypic MAb, mimics the GD epitope) (with BCG); Oncolym (Lym-1 monoclonal antibody); SMART MI95 Ab, humanized 13' I LYM-I (Oncolym), Ovarex (B43.13, anti-idiotypic mouse MAb); MDX-210 (humanized anti-HER-2 bispecific antibody); 3622W94 MAb that binds to EGP40 (17-1A) pancarcinoma antigen on adenocarcinomas; Anti-VEGF, Zenapax (SMART Anti-Tac (IL-2 receptor); SMART MI95 Ab, humanized Ab, humanized); MDX-210 (humanized anti-HER-2 bispecific antibody); MDX-447 (humanized anti-EGF receptor bispecific antibody); NovoMAb-G2 (pancarcinoma specific Ab); TNT (chimeric MAb to histone antigens); TNT (chimeric MAb to histone antigens); Gliomab-H (Monoclon s—Humanized Abs); GNI-250 Mab; EMD-72000 (chimeric-EGF antagonist); LymphoCide (humanized LL2 antibody); and MDX-260 bispecific, targets GD-2, ANA Ab, SMART IDlO Ab, SMART ABL 364 Ab or ImmuRAIT-CEA. As illustrated by the forgoing list, it is conventional to make antibodies to a particular target epitope.

In some embodiments, the antibody or antigen-binding fragment of the provided conjugates, including fusion molecules, is cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Dinutuximab (Unituxin™), Erlotinib, Everolimus, Ibrutinib, Imatinib, Lapatinib, Lenvatinib, Nilotinib, Olaparib, Olaratumab (Lartruvo™), Palbociclib, Pazopanib, Pertuzumab (Perjeta®), Ramucirumab (Cyramza®), Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, MPDL3280A, Pidilizumab (CT-011), AMP-224, MSB001078C, or MEDI4736, BMS-935559, LY3300054, atezolizumab, avelumab or durvalumab or is an antigen-binding fragment thereof. In some the antibody or antigen-binding fragment of the provided conjugates, including fusion molecules, is Pertuzumab (Perjeta®), panitumumab or an antigen-binding fragment thereof. In some embodiments, the antibody targeting moiety is a full length antibody, or antigen-binding fragment thereof, containing an Fc domain. In some embodiments, the variant polypeptide or immunomodulatory protein is conjugated to the Fc portion of the antibody targeting moiety, such as by conjugation to the N-terminus of the Fc portion of the antibody.

Figure 18A:
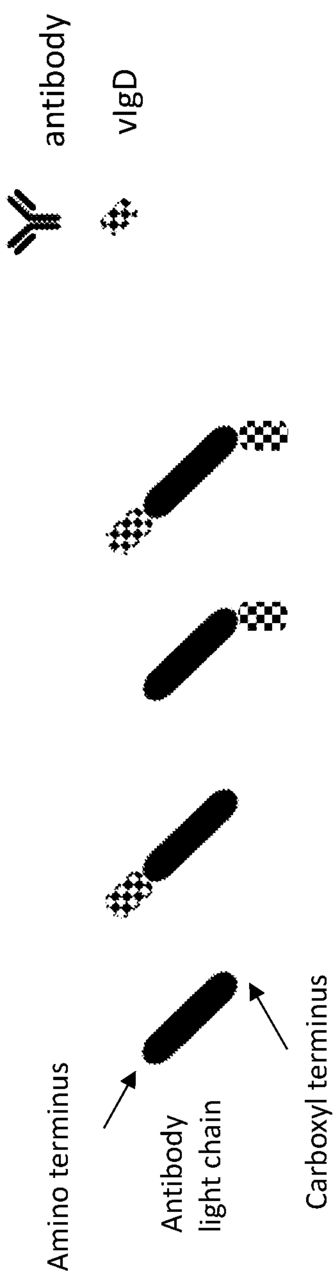
FIG. 18A, FIG. 18B, and FIG. 18C depict exemplary configurations of conjugates of exemplary variant CD86 IgV molecules with HER2 and EGFR targeting antibodies.
Figure 18B:
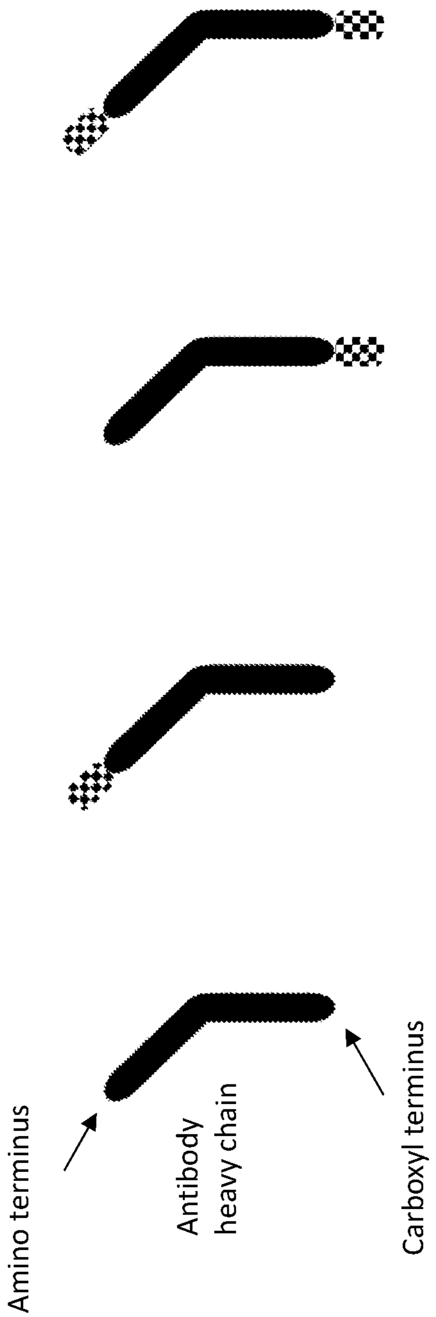
Figure 18C:
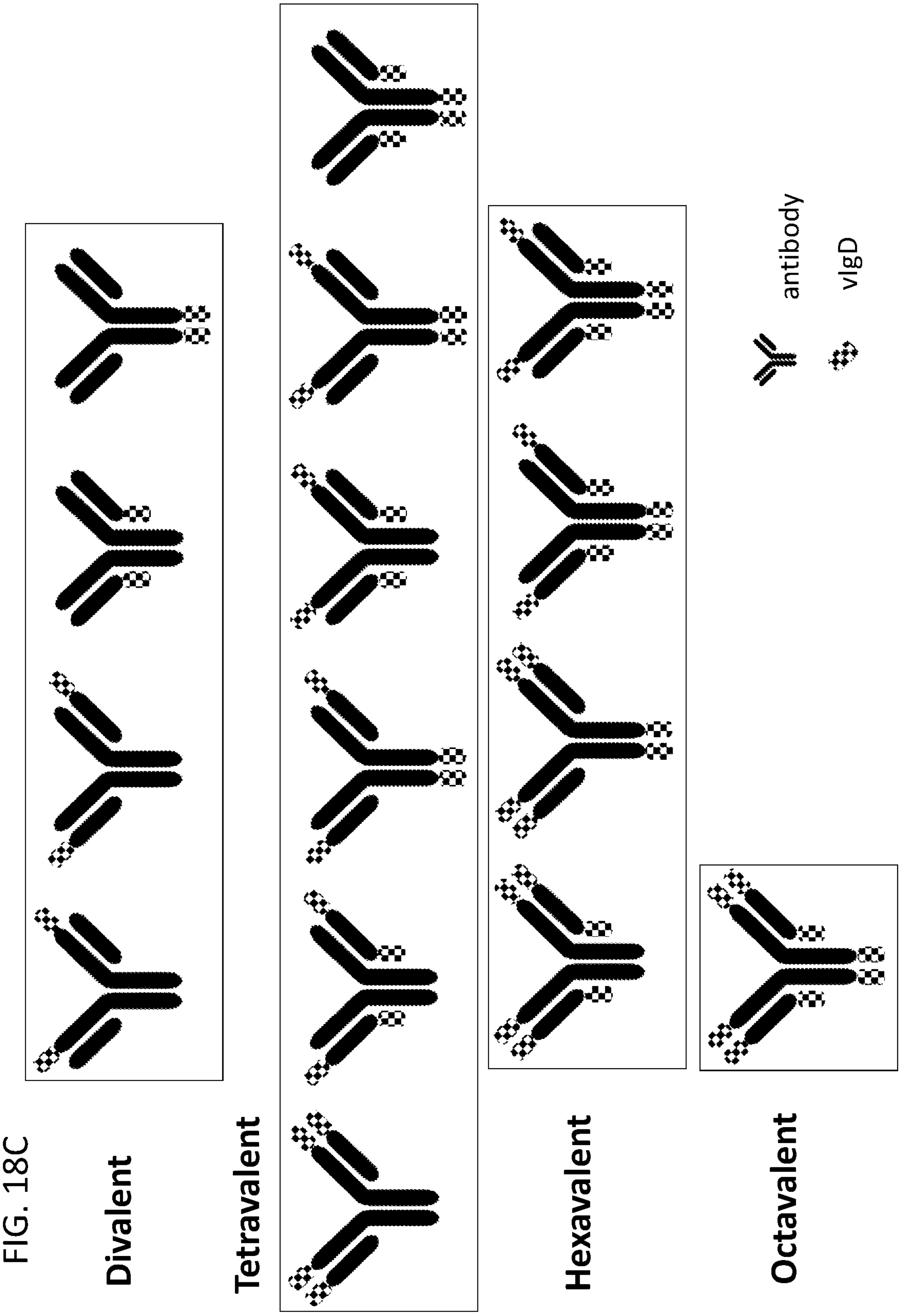

In some embodiments, the vIgD is linked, directly or indirectly, to the N- or C-terminus of the light and/or heavy chain of the antibody. In some embodiments, linkage can be via a peptide linker, such as any described above. In some embodiments, the linker can further include amino acids introduced by cloning and/or from a restriction site. In some embodiments, the linker may include additional amino acids on either end introduced by a restriction site. For example, the linker can include additional amino acids such as SA (in one-letter amino acid code) as introduced by use of the restriction site AFEI. Various configurations can be constructed. FIGS. 18A-18C depict exemplary configurations. In some embodiments, the antibody conjugate can be produced by co-expression of the heavy and light chain of the antibody in a cell.

In some embodiments, HER2 antibodies or antigen binding fragments thereof can be incorporated into the IgSF conjugates. Examples of HER2 antibodies which can be incorporated into IgSF conjugates include but are not limited to antibodies such as Pertuzumab (Perjeta®) and traztuzumab. In some embodiments, the vIgD is linked, directly or indirectly, to the N- or C-terminus of the light and/or heavy chain of an anti-HER2 antibody. In some embodiments, the anti-HER2 antibody is Pertuzumab (Perjeta®). An exemplary light chain and heavy chain of an anti-HER2 antibody Pertuzumab are set forth in SEQ ID NO: 341 and 340, respectively. In some embodiments, the variant CD86 polypeptide described herein is linked to the to the N- or C-terminus of the light and/or heavy chain of Pertuzumab. In some embodiments, a conjugate including Pertuzumab includes or has the $V_H$ sequence of SEQ ID NO:342. In some embodiments, a conjugate including Pertuzumab includes or has the $V_L$ sequence of SEQ ID NO:343. In some embodiments, a conjugate including Pertuzumab includes or has the $V_H$ sequence of SEQ ID NO:344. In some embodiments, a conjugate including Pertuzumab includes or has the $V_L$ sequence of SEQ ID NO:345. In some embodiments, a conjugate including Pertuzumab includes a heavy chain sequence having at least 70, 75, 80, 85, 90, 91, 92, 93, 94, 95, 96, 97, 98, or 99% sequence identity to SEQ ID NO: 342 and a light chain sequence having at least 70, 75, 80, 85, 90, 91, 92, 93, 94, 95, 96, 97, 98, or 99% sequence identity to SEQ ID NO: 341. In some embodiments, a conjugate including Pertuzumab include a heavy chain sequence having at least 70, 75, 80, 85, 90, 91, 92, 93, 94, 95, 96, 97, 98, or 99% sequence identity to SEQ ID NO: 340 and a light chain sequence having at least 70, 75, 80, 85, 90, 91, 92, 93, 94, 95, 96, 97, 98, or 99% sequence identity to SEQ ID NO: 343. In some embodiments, a conjugate including Pertuzumab includes a heavy chain sequence having at least 70, 75, 80, 85, 90, 91, 92, 93, 94, 95, 96, 97, 98, or 99% sequence identity to SEQ ID NO: 344 and a light chain sequence having at least 70, 75, 80, 85, 90, 91, 92, 93, 94, 95, 96, 97, 98, or 99% sequence identity to SEQ ID NO: 341. In some embodiments, a conjugate including Pertuzumab includes the heavy chain sequence having at least 70, 75, 80, 85, 90, 91, 92, 93, 94, 95, 96, 97, 98, or 99% sequence identity to SEQ ID NO: 340 and a light chain sequence having at least 70, 75, 80, 85, 90, 91, 92, 93, 94, 95, 96, 97, 98, or 99% sequence identity to SEQ ID NO: 345. In some embodiments, a conjugate including Pertuzumab includes a heavy chain sequence of SEQ ID NO: 342 and a light chain sequence of SEQ ID NO: 341. In some embodiments, a conjugate including Pertuzumab includes a heavy chain sequence of SEQ ID NO: 340 and a light chain sequence of SEQ ID NO: 343. In some embodiments, a conjugate including Pertuzumab includes a heavy chain sequence of SEQ ID NO: 344 and a light chain sequence of SEQ ID NO: 341. In some embodiments, a conjugate including Pertuzumab includes a heavy chain sequence of SEQ ID NO: 340 and a light chain sequence of SEQ ID NO: 345.

In some embodiments, EGFR (HER1) antibodies or antigen binding fragments thereof can be incorporated into the IgSF conjugates. Examples of EGFR antibodies which can be incorporated into IgSF conjugates include but are not limited to antibodies such as panitumumab and cetuximab. In some embodiments, the vIgD is linked, directly or indirectly, to the N- or C-terminus of the light and/or heavy chain of an anti-EGFR antibody. In some embodiments, the anti-EGFR antibody is Panitumumab. In some embodiments, the variant CD86 polypeptide described herein is linked to the to the N- or C-terminus of the light and/or heavy chain of Panitumumab. An exemplary light chain and heavy chain of an anti-EGFR antibody Panitumumab are set forth in SEQ ID NO: 347 and 346, respectively. In some embodiments, a conjugate including Panitumumab includes or has the $V_H$ sequence of SEQ ID NO:348. In some embodiments, a conjugate including Panitumumab includes or has the $V_L$ sequence of SEQ ID NO:349. In some embodiments, a conjugate including Panitumumab includes or has the $V_H$ sequence of SEQ ID NO:350. In some embodiments, a conjugate including Panitumumab includes or has the $V_L$ sequence of SEQ ID NO:351. In some embodiments, a conjugate including Panitumumab includes a heavy chain sequence having at least 70, 75, 80, 85, 90, 91, 92, 93, 94, 95, 96, 97, 98, or 99% sequence identity to SEQ ID NO: 348 and a light chain sequence having at least 70, 75, 80, 85, 90, 91, 92, 93, 94, 95, 96, 97, 98, or 99% sequence identity to SEQ ID NO: 347. In some embodiments, a conjugate including Panitumumab include a heavy chain sequence having at least 70, 75, 80, 85, 90, 91, 92, 93, 94, 95, 96, 97, 98, or 99% sequence identity to SEQ ID NO: 346 and a light chain sequence having at least 70, 75, 80, 85, 90, 91, 92, 93, 94, 95, 96, 97, 98, or 99% sequence identity to SEQ ID NO: 349. In some embodiments, a conjugate including Panitumumab includes a heavy chain sequence having at least 70, 75, 80, 85, 90, 91, 92, 93, 94, 95, 96, 97, 98, or 99% sequence identity to SEQ ID NO: 350 and a light chain sequence having at least 70, 75, 80, 85, 90, 91, 92, 93, 94, 95, 96, 97, 98, or 99% sequence identity to SEQ ID NO: 347. In some embodiments, a conjugate including Panitumumab includes the heavy chain sequence having at least 70, 75, 80, 85, 90, 91, 92, 93, 94, 95, 96, 97, 98, or 99% sequence identity to SEQ ID NO: 346 and a light chain sequence having at least 70, 75, 80, 85, 90, 91, 92, 93, 94, 95, 96, 97, 98, or 99% sequence identity to SEQ ID NO: 351. In some embodiments, a conjugate including Panitumumab includes a heavy chain sequence of SEQ ID NO: 348 and a light chain sequence of SEQ ID NO: 347. In some embodiments, a conjugate including Panitumumab includes a heavy chain sequence of SEQ ID NO: 346 and a light chain sequence of SEQ ID NO: 349. In some embodiments, a conjugate including Panitumumab includes a heavy chain sequence of SEQ ID NO: 350 and a light chain sequence of SEQ ID NO: 347. In some embodiments, a conjugate including Panitumumab includes a heavy chain sequence of SEQ ID NO: 346 and a light chain sequence of SEQ ID NO: 351.

In one aspect of the invention, the targeting agent is an aptamer molecule. For example, in some embodiments, the aptamer is comprised of nucleic acids that function as a targeting agent. In various embodiments, an IgSF conjugate of the invention comprises an aptamer that is specific for a molecule on a tumor cell, tumor vasculature, and/or a tumor microenvironment. In some embodiments, the aptamer itself can comprise a biologically active sequence, in addition to the targeting module (sequence), wherein the biologically active sequence can induce an immune response to the target cell. In other words, such an aptamer molecule is a dual use agent. In some embodiments, an IgSF conjugate of the invention comprises conjugation of an aptamer to an antibody, wherein the aptamer and the antibody are specific for binding to separate molecules on a tumor cell, tumor vasculature, tumor microenvironment, and/or immune cells.

The term "aptamer" includes DNA, RNA, or peptides that are selected based on specific binding properties to a particular molecule. For example, an aptamer(s) can be selected for binding a particular gene or gene product in a tumor cell, tumor vasculature, tumor microenvironment, and/or an immune cell, as disclosed herein, where selection is made by methods known in the art and familiar to one of skill in the art.

In some aspects of the invention the targeting agent is a peptide. For example, the variant polypeptides or immunomodulatory proteins provided herein can be conjugated to a peptide which can bind with a component of a cancer or tumor cells. Therefore, such IgSF conjugates of the invention comprise peptide targeting agents which binds to a cellular component of a tumor cell, tumor vasculature, and/or a component of a tumor microenvironment. In some embodiments, targeting agent peptides can be an antagonist or agonist of an integrin. Integrins, which comprise an alpha and a beta subunit, include numerous types well known to a skilled artisan.

In one embodiment, the targeting agent is Vvβ3. Integrin Vvβ3 is expressed on a variety of cells and has been shown to mediate several biologically relevant processes, including adhesion of osteoclasts to bone matrix, migration of vascular smooth muscle cells, and angiogenesis. Suitable targeting molecules for integrins include RGD peptides or peptidomimetics as well as non-RGD peptides or peptidomimetics (see, e.g., U.S. Pat. Nos. 5,767,071 and 5,780,426) for other integrins such as V4. βi (VLA-4), V4-P7 (see, e.g., U.S. Pat. No. 6,365,619; Chang et al, Bioorganic & Medicinal Chem Lett, 12:159-163 (2002); Lin et al., Bioorganic & Medicinal Chem Lett, 12:133-136 (2002)), and the like.

In some embodiments, there is provided an IgSF conjugate comprising a variant polypeptide or immunomodulatory protein provided herein conjugated with a therapeutic agent. In some embodiments, the therapeutic agent includes, for example, daunomycin, doxorubicin, methotrexate, and vindesine (Rowland et al., Cancer Immunol. Immunother. 21:183-187, 1986). In some embodiments, the therapeutic agent has an intracellular activity. In some embodiments, the IgSF conjugate is internalized and the therapeutic agent is a cytotoxin that blocks the protein synthesis of the cell, therein leading to cell death. In some embodiments, the therapeutic agent is a cytotoxin comprising a polypeptide having ribosome-inactivating activity including, for example, gelonin, bouganin, saporin, ricin, ricin A chain, bryodin, diphtheria toxin, restrictocin, Pseudomonas exotoxin A and variants thereof. In some embodiments, where the therapeutic agent is a cytotoxin comprising a polypeptide having a ribosome-inactivating activity, the IgSF conjugate must be internalized upon binding to the target cell in order for the protein to be cytotoxic to the cells.

In some embodiments, there is provided an IgSF conjugate comprising a variant polypeptide or immunomodulatory protein provided herein conjugated with a toxin. In some embodiments, the toxin includes, for example, bacterial toxins such as diphtheria toxin, plant toxins such as ricin, small molecule toxins such as geldanamycin (Mandler et al., J. Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may exert their cytotoxic and cytostatic effects by mechanisms including tubulin binding, DNA binding, or topoisomerase inhibition.

In some embodiments, there is provided an IgSF conjugate comprising a variant polypeptide or immunomodulatory protein provided herein conjugated with a label, which can generate a detectable signal, indirectly or directly. These IgSF conjugates can be used for research or diagnostic applications, such as for the in vivo detection of cancer. The label is preferably capable of producing, either directly or indirectly, a detectable signal. For example, the label may be radio-opaque or a radioisotope, such as 3H, 14C, 32P, 35S, 123I, 125I, 131I; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example 99Tc or 1231, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983). In some embodiments, the IgSF conjugate is detectable indirectly. For example, a secondary antibody that is specific for the IgSF conjugate and contains a detectable label can be used to detect the IgSF conjugate.

The IgSF conjugates may be prepared using any methods known in the art. See, e.g., WO 2009/067800, WO 2011/133886, and U.S. Patent Application Publication No. 2014322129, incorporated by reference herein in their entirety.

The variant polypeptides or immunomodulatory proteins of an IgSF conjugate may be "attached to" the effector moiety by any means by which the variant polypeptides or immunomodulatory proteins can be associated with, or linked to, the effector moiety. For example, the variant polypeptides or immunomodulatory proteins of an IgSF conjugate may be attached to the effector moiety by chemical or recombinant means. Chemical means for preparing fusions or conjugates are known in the art and can be used to prepare the IgSF conjugate. The method used to conjugate the variant polypeptides or immunomodulatory proteins and effector moiety must be capable of joining the variant polypeptides or immunomodulatory proteins with the effector moiety without interfering with the ability of the variant polypeptides or immunomodulatory proteins to bind to their one or more counter structure ligands.

The variant polypeptides or immunomodulatory proteins of an IgSF conjugate may be linked indirectly to the effector moiety. For example, the variant polypeptides or immunomodulatory proteins of an IgSF conjugate may be directly linked to a liposome containing the effector moiety of one of several types. The effector moiety(s) and/or the variant polypeptides or immunomodulatory proteins may also be bound to a solid surface.

In some embodiments, the variant polypeptides or immunomodulatory proteins of an IgSF conjugate and the effector moiety are both proteins and can be conjugated using techniques well known in the art. There are several hundred crosslinkers available that can conjugate two proteins. (See for example "Chemistry of Protein Conjugation and Crosslinking," 1991, Shans Wong, CRC Press, Ann Arbor). The crosslinker is generally chosen based on the reactive functional groups available or inserted on the variant polypeptides or immunomodulatory proteins and/or effector moiety. In addition, if there are no reactive groups, a photoactivatable crosslinker can be used. In certain instances, it may be desirable to include a spacer between the variant polypeptides or immunomodulatory proteins and the effector moiety. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

In some embodiments, the variant polypeptides or immunomodulatory proteins of an IgSF conjugate may be engineered with specific residues for chemical attachment of the effector moiety. Specific residues used for chemical attachment of molecule known to the art include lysine and cysteine. The crosslinker is chosen based on the reactive functional groups inserted on the variant polypeptides or immunomodulatory proteins, and available on the effector moiety.

An IgSF conjugate may also be prepared using recombinant DNA techniques. In such a case a DNA sequence encoding the variant polypeptides or immunomodulatory proteins is fused to a DNA sequence encoding the effector moiety, resulting in a chimeric DNA molecule. The chimeric DNA sequence is transfected into a host cell that expresses the fusion protein. The fusion protein can be recovered from the cell culture and purified using techniques known in the art.

Examples of attaching an effector moiety, which is a label, to the variant polypeptides or immunomodulatory proteins include the methods described in Hunter, et al., Nature 144:945 (1962); David, et al., Biochemistry 13:1014 (1974); Pain, et al., J. Immunol. Meth. 40:219 (1981); Nygren, J. Histochem. and Cytochem. 30:407 (1982); Wensel and Meares, Radioimmunoimaging And Radioimmunotherapy, Elsevier, N.Y. (1983); and Colcher et al., "Use Of Monoclonal Antibodies As Radiopharmaceuticals For The Localization Of Human Carcinoma Xenografts In Athymic Mice", Meth. Enzymol., 121:802-16 (1986).

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as 99Tc or 1231, 186Re, 188Re and 111In can be attached via a cysteine residue in the peptide. Yttrium-90 can be attached via a lysine residue. The IODOGEN method (Fraker et al., Biochem. Biophys. Res. Commun. 80:49-57 (1978)) can be used to incorporate iodine-123. "Monoclonal Antibodies in Immunoscintigraphy" (Chatal, CRC Press 1989) describes other methods in detail.

Conjugates of the variant polypeptides or immunomodulatory proteins and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-p-isothiocyanatobenzyl-3-methyldiethylenetriaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The IgSF conjugates of the invention expressly contemplate, but are not limited to, drug conjugates prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A). See pages 467-498, 2003-2004 Applications Handbook and Catalog.

E. Transmembrane and Secretable Immunomodulatory Proteins and Engineered Cells

Provided herein are engineered cells which express the immunomodulatory variant CD86 polypeptides (alternatively, "engineered cells"). In some embodiments, the expressed immunomodulatory variant CD86 polypeptide is a transmembrane protein and is surface expressed. In some embodiments, the expressed immunomodulatory variant CD86 polypeptide is expressed and secreted from the cell.

1. Transmembrane Immunomodulatory Proteins

In some embodiments, an immunomodulatory polypeptide comprising a variant CD86 can be a membrane bound protein. As described in more detail below, the immunomodulatory polypeptide can be a transmembrane immunomodulatory polypeptide comprising a variant CD86 in which is contained: an ectodomain containing at least one affinity modified IgSF domain (IgV or IgC), a transmembrane domain and, optionally, a cytoplasmic domain. In some embodiments, the transmembrane immunomodulatory protein can be expressed on the surface of an immune cell, such as a mammalian cell, including on the surface of a lymphocyte (e.g., T cell or NK cell) or antigen presenting cell. In some embodiments, the transmembrane immunomodulatory protein is expressed on the surface of a mammalian T-cell, including such T-cells as: a T helper cell, a cytotoxic T-cell (alternatively, cytotoxic T lymphocyte or CTL), a natural killer T-cell, a regulatory T-cell, a memory T-cell, or a gamma delta T-cell. In some embodiments, the mammalian cell is an antigen presenting cell (APC). Typically, but not exclusively, the ectodomain (alternatively, "extracellular domain") comprises the one or more amino acid variations (e.g., amino acid substitutions) of the variant CD86 of the invention. Thus, for example, in some embodiments a transmembrane protein will comprise an ectodomain that comprises one or more amino acid substitutions of a variant CD86 of the invention.

In some embodiments, the engineered cells express variant CD86 polypeptides that are transmembrane immunomodulatory polypeptides (TIPs) that can be a membrane protein such as a transmembrane protein. In typical embodiments, the ectodomain of a membrane protein comprises an extracellular domain or IgSF domain thereof of a variant CD86 provided herein in which is contained one or more amino acid substitutions in at least one IgSF domain as described. The transmembrane immunomodulatory proteins provided herein further contain a transmembrane domain linked to the ectodomain. In some embodiments, the transmembrane domain results in an encoded protein for cell surface expression on a cell. In some embodiments, the transmembrane domain is linked directly to the ectodomain. In some embodiments, the transmembrane domain is linked indirectly to the ectodomain via one or more linkers or spacers. In some embodiments, the transmembrane domain contains predominantly hydrophobic amino acid residues, such as leucine and valine.

In some embodiments, a full length transmembrane anchor domain can be used to ensure that the TIPs will be expressed on the surface of the engineered cell, such as engineered T cell. Conveniently, this could be from a particular native protein that is being affinity modified (e.g., CD86 or other native IgSF protein), and simply fused to the sequence of the first membrane proximal domain in a similar fashion as the native IgSF protein (e.g., CD86). In some embodiments, the transmembrane immunomodulatory protein comprises a transmembrane domain of the corresponding wild-type or unmodified IgSF member, such as a transmembrane domain contained in the sequence of amino acids set forth in SEQ ID NO:2 (Table 2). In some embodiments, the membrane bound form comprises a transmembrane domain of the corresponding wild-type or unmodified polypeptide, such as corresponding to residues 248-268 of SEQ ID NO:2.

In some embodiments, the transmembrane domain is a non-native transmembrane domain that is not the transmembrane domain of native CD86. In some embodiments, the transmembrane domain is derived from a transmembrane domain from another non-CD86 family member polypeptide that is a membrane-bound or is a transmembrane protein. In some embodiments, a transmembrane anchor domain from another protein on T cells can be used. In some embodiments, the transmembrane domain is derived from CD8. In some embodiments, the transmembrane domain can further contain an extracellular portion of CD8 that serves as a spacer domain. An exemplary CD8 derived transmembrane domain is set forth in SEQ ID NO: 281, 282, or 283 or a portion thereof containing the CD8 transmembrane domain. In some embodiments, the transmembrane domain is a synthetic transmembrane domain.

In some embodiments, the transmembrane immunomodulatory protein further contains an endodomain, such as a cytoplasmic signaling domain, linked to the transmembrane domain. In some embodiments, the cytoplasmic signaling domain induces cell signaling. In some embodiments, the endodomain of the transmembrane immunomodulatory protein comprises the cytoplasmic domain of the corresponding wild-type or unmodified polypeptide, such as a cytoplasmic domain contained in the sequence of amino acids set forth in SEQ ID NO:2, such as amino acids 269-329 of SEQ ID NO:2 (see Table 2).

In some embodiments, a provided transmembrane immunomodulatory protein that is or comprises a variant CD86 comprises a sequence of amino acids that exhibits at least 85%, 86%, 87%, 88%, 89%, 90%, 91%, 92%, 93%, 94%, 95%, 96%, 97%, 98% or 99% sequence identity to SEQ ID NO: 56 and contains an ectodomain comprising at least one affinity-modified CD86 IgSF domain as described herein and a transmembrane domain. In some embodiments, the transmembrane immunomodulatory protein contains any one or more amino acid substitutions in an IgSF domain (e.g., IgV domain) as described. In some embodiments, the transmembrane immunomodulatory protein can further comprise a cytoplasmic domain as described.

Provided herein are CD86 transmembrane immunomodulatory proteins. In some embodiments the CD86 TIP exhibits at least 85%, 86%, 87%, 88%, 89%, 90%, 91%, 92%, 93%, 94%, 95%, 96%, 97%, 98% or 99% sequence identity to SEQ ID NO: 233. In some embodiments, the CD86 TIP is a variant CD86 TIP that contains one or more amino acid modifications (e.g. substitutions) in the ecotodomain (extracellular portion) or an IgSF (e.g. IgV) domain thereof or a specific binding portion thereof. Exemplary amino acid modifications (e.g. substitutions) include any as described in Section II. In some embodiments, the variant CD86 TIP exhibits at least 85%, 86%, 87%, 88%, 89%, 90%, 91%, 92%, 93%, 94%, 95%, 96%, 97%, 98% or 99% sequence identity to a sequence set forth in any of SEQ ID NOS: 234, 235, 236, 237, 238, 239, 240, or 241. In some embodiments, the variant CD86 TIP has the sequence set forth in SEQ ID NOS: 234, 235, 236, 237, 238, 239, 240, or 241.

In some embodiments, the transmembrane immunomodulatory protein can further contain a signal peptide. In some embodiments, the signal peptide is the native signal peptide of wild-type IgSF member, such as contained in the sequence of amino acids set forth in SEQ ID NO: 2 (see e.g., Table 2).

Also provided is a nucleic acid molecule encoding such transmembrane immunomodulatory proteins. In some embodiments, a nucleic acid molecule encoding a transmembrane immunomodulatory protein comprises a nucleotide sequence that encodes a sequence of amino acids that exhibits at least 85%, 86%, 87%, 88%, 89%, 90%, 91%, 92%, 93%, 94%, 95%, 96%, 97%, 98% or 99% sequence identity to SEQ ID NOS: 56 and contains an ectodomain comprising at least one affinity-modified IgSF domain as described herein, a transmembrane domain and, optionally, a cytoplasmic domain. In some embodiments, the nucleic acid molecule can further comprise a sequence of nucleotides encoding a signal peptide. In some embodiments, the signal peptide is the native signal peptide of the corresponding wild-type IgSF member (see e.g., Table 2). In some embodiments, the signal peptide is a heterologous signal peptide, such as any set forth in Table 4.

In some embodiments, provided are CAR-related transmembrane immunomodulatory proteins in which the endodomain of a transmembrane immunomodulatory protein comprises a cytoplasmic signaling domain that comprises at least one ITAM (immunoreceptor tyrosine-based activation motif)-containing signaling domain. ITAM is a conserved motif found in a number of protein signaling domains involved in signal transduction of immune cells, including in the CD3-zeta chain ("CD3-z") involved in T-cell receptor signal transduction. In some embodiments, the endodomain comprises at CD3-zeta signaling domain. In some embodiments, the CD3-zeta signaling domain comprises the sequence of amino acids set forth in SEQ ID NO: 284 or a sequence of amino acids that exhibits at least 85%, 86%, 87%, 88%, 89%, 90%, 91%, 92%, 93%, 94%, 95%, 96%, 97%, 98% or 99% to SEQ ID NO:284 and retains the activity of T cell signaling. In some embodiments, the endodomain of a CAR-related transmembrane immunomodulatory protein can further comprise a costimulatory signaling domain to further modulate immunomodulatory responses of the T-cell. In some embodiments, the costimulatory signaling domain is CD28, ICOS, 4-1BB, or OX40. In some embodiments, the costimulatory signaling domain is a derived from CD28 or 4-1BB and comprises the sequence of amino acids set forth in any of SEQ ID NOS: 285-288 or a sequence of amino acids that exhibits at least 85%, 86%, 87%, 88%, 89%, 90%, 91%, 92%, 93%, 94%, 95%, 96%, 97%, 98% or 99% to SEQ ID NO: 285-288 and retains the activity of T cell costimulatory signaling. In some embodiments, the provided CAR-related transmembrane immunomodulatory proteins have features of CARs to stimulate T cell signaling upon binding of an affinity modified IgSF domain to a cognate binding partner or counter structure. In some embodiments, upon specific binding by the affinity-modified IgSF domain to its counter structure can lead to changes in the immunological activity of the T-cell activity as reflected by changes in cytotoxicity, proliferation or cytokine production.

In some embodiments, the transmembrane immunomodulatory protein does not contain an endodomain capable of mediating cytoplasmic signaling. In some embodiments, the transmembrane immunomodulatory protein lacks the signal transduction mechanism of the wild-type or unmodified polypeptide and therefore does not itself induce cell signaling. In some embodiments, the transmembrane immunomodulatory protein lacks an intracellular (cytoplasmic) domain or a portion of the intracellular domain of the corresponding wild-type or unmodified polypeptide, such as a cytoplasmic signaling domain contained in the sequence of amino acids set forth in SEQ ID NO:2 (see Table 2). In some embodiments, the transmembrane immunomodulatory protein does not contain an ITIM (immunoreceptor tyrosine-based inhibition motif), such as contained in certain inhibitory receptors, including inhibitory receptors of the IgSF family (e.g., PD-1 or TIGIT). Thus, in some embodiments, the transmembrane immunomodulatory protein only contains the ectodomain and the transmembrane domain, such as any as described.

2. Secreted Immunomodulatory Proteins and Engineered Cells

In some embodiments, the CD86 variant immunomodulatory polypeptide containing any one or more of the amino acid mutations as described herein, is secretable, such as when expressed from a cell. Such a variant CD86 immunomodulatory protein does not comprise a transmembrane domain. In some embodiments, the variant CD86 immunomodulatory protein is not conjugated to a half-life extending moiety (such as an Fc domain or a multimerization domain). In some embodiments, the variant CD86 immunomodulatory protein comprises a signal peptide, e.g., an antibody signal peptide or other efficient signal sequence to get domains outside of the cell. When the immunomodulatory protein comprises a signal peptide and is expressed by an engineered cell, the signal peptide causes the immunomodulatory protein to be secreted by the engineered cell. Generally, the signal peptide, or a portion of the signal peptide, is cleaved from the immunomodulatory protein with secretion. The immunomodulatory protein can be encoded by a nucleic acid (which can be part of an expression vector). In some embodiments, the immunomodulatory protein is expressed and secreted by a cell (such as an immune cell, for example a primary immune cell).

Thus, in some embodiments, there are provided variant CD86 immunomodulatory proteins that further comprises a signal peptide. In some embodiments, provided herein is a nucleic acid molecule encoding the variant CD86 immunomodulatory protein operably connected to a secretion sequence encoding the signal peptide.

A signal peptide is a sequence on the N-terminus of an immunomodulatory protein that signals secretion of the immunomodulatory protein from a cell. In some embodiments, the signal peptide is about 5 to about 40 amino acids in length (such as about 5 to about 7, about 7 to about 10, about 10 to about 15, about 15 to about 20, about 20 to about 25, or about 25 to about 30, about 30 to about 35, or about 35 to about 40 amino acids in length).

In some embodiments, the signal peptide is a native signal peptide from the corresponding wild-type CD86 (see Table 2). In some embodiments, the signal peptide is a non-native signal peptide. For example, in some embodiments, the non-native signal peptide is a mutant native signal peptide from the corresponding wild-type CD86, and can include one or more (such as 2, 3, 4, 5, 6, 7, 8, 9, or 10 or more) substitutions insertions or deletions. In some embodiments, the non-native signal peptide is a signal peptide or mutant thereof of a family member from the same IgSF family as the wild-type IgSF family member. In some embodiments, the non-native signal peptide is a signal peptide or mutant thereof from an IgSF family member from a different IgSF family than the wild-type IgSF family member. In some embodiments, the signal peptide is a signal peptide or mutant thereof from a non-IgSF protein family, such as a signal peptide from an immunoglobulin (such as IgG heavy chain or IgG-kappa light chain), a cytokine (such as interleukin-2 (IL-2) or CD33), a serum albumin protein (e.g., HSA or albumin), a human azurocidin preprotein signal sequence, a luciferase, a trypsinogen (e.g., chymotrypsinogen or trypsinogen), or other signal peptide able to efficiently secrete a protein from a cell. Exemplary signal peptides include any described in the Table 4.

TABLE 4

Exempary Signal Peptides

| SEQ ID NO | Signal Peptide | Peptide Sequence |
|---|---|---|
| 289 | CD33 Signal Peptide | MPLLLLLPLLWAGALA |
| 290 | IgGkappa light chain: | MDMRVLAQLL GLLLLCFPGA RC |
| 291 | HSA signal peptide | MKWVTFISLLFLFSSAYS |
| 292 | Ig kappa light chain | MDMRAPAGIFGFLLVLFPGYRS |
| 293 | human azurocidin preprotein signal sequence | MTRLTVLALLAGLLASSRA |
| 294 | IgG heavy chain signal peptide | MELGLSWIFLLAILKGVQC |
| 295 | IgG heavy chain signal peptide | MELGLRWVFLVAILEGVQC |
| 296 | IgG heavy chain signal peptide | MKHLWFFLLLVAAPRWVLS |
| 297 | IgG heavy chain signal peptide | MDWTWRILFLVAAATGAHS |
| 298 | IgG heavy chain signal peptide | MDWTWRFLFVVAAATGVQS |
| 299 | IgG heavy chain signal peptide | MEFGLSWLFLVAILKGVQC |
| 300 | IgG heavy chain signal peptide | MEFGLSWVFLVALFRGVQC |
| 301 | IgG heavy chain signal peptide | MDLLHKNMKHLWFFLLLVAAPRWVLS |
| 302 | IgG Kappa light chain signal sequences: | MDMRVPAQLLGLLLLWLSGARC |
| 303 | IgG Kappa light chain signal sequences: | MKYLLPTAAAGLLLLAAQPAMA |
| 304 | Gaussia luciferase | MGVKVLFALICIAVAEA |
| 305 | Human albumin | MKWVTFISLLFLFSSAYS |
| 306 | Human chymotrypsinogen | MAFLWLLSCWALLGTTFG |
| 307 | Human interleukin-2 | MQLLSCIALILALV |
| 308 | Human trypsinogen-2 | MNLLLILTFVAAAVA |

In some embodiments of a secretable variant CD86 immunomodulatory protein, the immunomodulatory protein comprises a signal peptide when expressed, and the signal peptide (or a portion thereof) is cleaved from the immunomodulatory protein upon secretion.

In some embodiments, the engineered cells express variant CD86 polypeptides that are secreted from the cell. In some embodiments, such a variant CD86 polypeptide is encoded by a nucleic acid molecule encoding an immunomodulatory protein under the operable control of a signal sequence for secretion. In some embodiments, the encoded immunomodulatory protein is secreted when expressed from a cell. In some embodiments, the immunomodulatory protein encoded by the nucleic acid molecule does not comprise a transmembrane domain. In some embodiments, the immunomodulatory protein encoded by the nucleic acid molecule does not comprise a half-life extending moiety (such as an Fc domain or a multimerization domain). In some embodiments, the immunomodulatory protein encoded by the nucleic acid molecule comprises a signal peptide. In some embodiments, a nucleic acid of the invention further comprises nucleotide sequence that encodes a secretory or signal peptide operably linked to the nucleic acid encoding the immunomodulatory protein, thereby allowing for secretion of the immunomodulatory protein.

3. Cells and Engineering Cells

Provided herein are engineered cells expressing any of the provided immunomodulatory polypeptides. In some embodiments, the engineered cells express on their surface any of the provided transmembrane immunomodulatory polypeptides. In some embodiments, the engineered cells express and are capable of or are able to secrete the immunomodulatory protein from the cells under conditions suitable for secretion of the protein. In some embodiments, the immunomodulatory protein is expressed on a lymphocyte such as a tumor infiltrating lymphocyte (TIL), T-cell or NK cell, or on a myeloid cell. In some embodiments, the engineered cells are antigen presenting cells (APCs). In some embodiments, the engineered cells are engineered mammalian T-cells or engineered mammalian antigen presenting cells (APCs). In some embodiments, the engineered T-cells or APCs are human or murine cells.

In some embodiments, engineered T-cells include, but are not limited to, T helper cell, cytotoxic T-cell (alternatively, cytotoxic T lymphocyte or CTL), natural killer T-cell, regulatory T-cell, memory T-cell, or gamma delta T-cell. In some embodiments, the engineered T cells are CD4+ or CD8+. In addition to the signal of the MHC, engineered T-cells also require a co-stimulatory signal. In some embodiments, engineered T cells also can be modulated by an inhibitory signal, which, in some cases, is provided by a variant CD86 transmembrane immunomodulatory polypeptide expressed in membrane bound form as discussed previously.

In some embodiments, the engineered APCs include, for example, MHC II expressing APCs such as macrophages, B cells, and dendritic cells, as well as artificial APCs (aAPCs) including both cellular and acellular (e.g., biodegradable polymeric microparticles) aAPCs. Artificial APCs (aAPCs) are synthetic versions of APCs that can act in a similar manner to APCs in that they present antigens to T-cells as well as activate them. Antigen presentation is performed by the MHC (Class I or Class II). In some embodiments, in engineered APCs such as aAPCs, the antigen that is loaded onto the MHC is, in some embodiments, a tumor specific antigen or a tumor associated antigen. The antigen loaded onto the MHC is recognized by a T-cell receptor (TCR) of a T cell, which, in some cases, can express CTLA-4, CD28, or other molecules recognized by the variant CD86 polypeptides provided herein. Materials which can be used to engineer an aAPC include: poly (glycolic acid), poly(lactic-co-glycolic acid), iron-oxide, liposomes, lipid bilayers, sepharose, and polystyrene.

In some embodiments a cellular aAPC can be engineered to contain a TIP and TCR agonist which is used in adoptive cellular therapy. In some embodiments, a cellular aAPC can be engineered to contain a TIP and TCR agonist which is used in ex vivo expansion of human T cells, such as prior to administration, e.g., for reintroduction into the patient. In some aspects, the aAPC may include expression of at least one anti-CD3 antibody clone, e.g., such as, for example, OKT3 and/or UCHT1. In some aspects, the aAPCs may be inactivated (e.g., irradiated). In some embodiments, the TIP can include any variant IgSF domain that exhibits binding affinity for a cognate binding partner on a T cell.

In some embodiments, an immunomodulatory protein provided herein, such as a transmembrane immunomodulatory protein or a secretable immunomodulatory protein, is co-expressed or engineered into a cell that expresses an antigen-binding receptor, such as a recombinant receptor, such as a chimeric antigen receptor (CAR) or T cell receptor (TCR). In some embodiments, the engineered cell, such as an engineered T cell, recognizes a desired antigen associated with cancer, inflammatory and autoimmune disorders, or a viral infection. In specific embodiments, the antigen-binding receptor contains an antigen-binding moiety that specifically binds a tumor specific antigen or a tumor associated antigen. In some embodiments, the engineered T-cell is a CAR (chimeric antigen receptor) T-cell that contains an antigen-binding domain (e.g., scFv) that specifically binds to an antigen, such as a tumor specific antigen or tumor associated antigen. In some embodiments, the TIP protein is expressed in an engineered T-cell receptor cell or an engineered chimeric antigen receptor cell. In such embodiments, the engineered cell co-expresses the TIP and the CAR or TCR. In some embodiments, the SIP protein is expressed in an engineered T-cell receptor cell or an engineered chimeric antigen receptor cell. In such embodiments, the engineered cell co-expresses the SIP and the CAR or TCR.

Chimeric antigen receptors (CARs) are recombinant receptors that include an antigen-binding domain (ectodomain), a transmembrane domain, and an intracellular signaling region (endodomain) that is capable of inducing or mediating an activation signal to the T cell after the antigen is bound. In some examples, CAR-expressing cells are engineered to express an extracellular single chain variable fragment (scFv) with specificity for a particular tumor antigen linked to an intracellular signaling part comprising an activating domain and, in some cases, a costimulatory domain. The costimulatory domain can be derived from, e.g., CD28, OX-40, 4-1BB/CD137, inducible T cell costimulator (ICOS). The activating domain can be derived from, e.g., CD3, such as CD3 zeta, epsilon, delta, gamma, or the like. In certain embodiments, the CAR is designed to have two, three, four, or more costimulatory domains. The CAR scFv can be designed to target an antigen expressed on a cell associated with a disease or condition, e.g., a tumor antigen, such as, for example, HER2, which is an oncogene shown to play a role in the development and progression of certain types of aggressive breast cancer.

In some aspects, the antigen-binding domain is an antibody or antigen-binding fragment thereof, such as a single chain fragment (scFv). In some embodiments, the antigen is expressed on a tumor or cancer cell. Exemplary of an antigen is HER2. Exemplary of a CAR is an anti-HER2 CAR, such as a CAR containing an anti-HER2 scFv. Other exemplary CARs include anti-CD19 CARs, anti-BCMA CARs, anti-CD22 CARs and other CARs specific to tumor-associated antigens. In some embodiments, the CAR further contains a spacer, a transmembrane domain, and an intracellular signaling domain or region comprising an ITAM signaling domain, such as a CD3-zeta signaling domain. In some embodiments, the CAR further includes a costimulatory signaling domain. In some embodiments, the spacer and transmembrane domain are the hinge and transmembrane domain derived from CD8, such as having an exemplary sequence set forth in SEQ ID NO: 281, 282, or 283 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 281, 282, or 283. In some embodiments, the endodomain comprises a CD3-zeta signaling domain. In some embodiments, the CD3-zeta signaling domain comprises the sequence of amino acids set forth in SEQ ID NO: 284 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO:284 and retains the activity of T-cell signaling. In some embodiments, the endodomain of a CAR can further comprise a costimulatory signaling domain or region to further modulate immunomodulatory responses of the T-cell. In some embodiments, the costimulatory signaling domain is or comprises a costimulatory region, or is derived from a costimulatory region, of CD28, ICOS, 4-1BB or OX40. In some embodiments, the costimulatory signaling domain is a derived from CD28 or 4-1BB and comprises the sequence of amino acids set forth in any of SEQ ID NOS: 285-288 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 285-288 and retains the activity of T cell costimulatory signaling.

In some embodiments, the construct encoding the CAR further encodes a second protein, such as a marker, e.g., detectable protein, separated from the CAR by a self-cleaving peptide sequence. In some embodiments, the self-cleaving peptide sequence is an F2A, T2A, E2A, or P2A self-cleaving peptide. Exemplary sequences of a T2A self-cleaving peptide are set for the in any one of SEQ ID NOS: 309, 310, 311 or a sequence of amino acids that exhibits at least 85%, 86%, 87%, 88%, 89%, 90%, 91%, 92%, 93%, 94%, 95%, 96%, 97%, 98% or 99% or more sequence identity to any of SEQ ID NOS: 309, 310, 311. In some embodiments, the T2A is encoded by the sequence of nucleotides set forth in SEQ ID NO: 311 or a sequence that exhibits at least 85%, 86%, 87%, 88%, 89%, 90%, 91%, 92%, 93%, 94%, 95%, 96%, 97%, 98% or 99% or more sequence identity to any of SEQ ID NO: 311. An exemplary sequence of a P2A self-cleaving peptide is set in SEQ ID NO: 243 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 243. In some cases, a nucleic acid construct that encodes more than one P2A self-cleaving peptide (such as a P2A1 and P2A2), in which the nucleotide sequence P2A1 and P2A2 each encode the P2A set forth in SEQ ID NO: 243, the nucleotide sequence may be different to avoid recombination between sequences.

In some embodiments, the marker is a detectable protein, such as a fluorescent protein, e.g., a green fluorescent protein (GFP) or blue fluorescent protein (BFP). Exemplary sequences of a fluorescent protein marker are set forth in SEQ ID NO: 313, 312, 244-246, or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 313, 312, 244-246.

In some embodiments, the CAR comprises an anti-HER scFv, a CD8 hinge region, and transmembrane signaling domains derived from 4-1BB and CD3-zeta signalling domains. In some embodiments, the CAR comprises an scFv containing a variable heavy and light chains of trastuzumab.

In another embodiment, the engineered T-cell possesses a TCR, including a recombinant or engineered TCR. In some embodiments, the TCR can be a native TCR. Those of skill in the art will recognize that generally native mammalian T-cell receptors comprise an alpha and a beta chain (or a gamma and a delta chain) involved in antigen specific recognition and binding. In some embodiments, the TCR is an engineered TCR that is modified. In some embodiments, the TCR of an engineered T-cell specifically binds to a tumor associated or tumor specific antigen presented by an APC. In some embodiments, the TCR is an HPV16 E6 peptide (E6 TCR). In some embodiments, the TCR is an HPV16 E7 peptide (E7 TCR). Exemplary HPV TCRs include those described in International published PCT Appl. No. WO2015009606 or WO2015184228.

In some embodiments, the immunomodulatory polypeptides, such as transmembrane immunomodulatory polypeptides or secretable immunomodulatory polypeptides, can be incorporated into engineered cells, such as engineered T cells or engineered APCs, by a variety of strategies such as those employed for recombinant host cells. A variety of methods to introduce a DNA construct into primary T-cells are known in the art. In some embodiments, viral transduction or plasmid electroporation are employed. In typical embodiments, the nucleic acid molecule encoding the immunomodulatory protein, or the expression vector, comprises a signal peptide that localizes the expressed transmembrane immunomodulatory proteins to the cellular membrane or for secretion. In some embodiments, a nucleic acid encoding a transmembrane immunomodulatory protein of the invention is sub-cloned into a viral vector, such as a retroviral vector, which allows expression in the host mammalian cell. The expression vector can be introduced into a mammalian host cell and, under host cell culture conditions, the immunomodulatory protein is expressed on the surface or is secreted.

In an exemplary example, primary T-cells can be purified ex vivo (CD4+ cells or CD8+ cells or both) and stimulated with an activation protocol consisting of various TCR/CD28 agonists, such as anti-CD3/anti-CD28 coated beads. After a 2 or 3 day activation process, a recombinant expression vector containing an immunomodulatory polypeptide can be stably introduced into the primary T-cells through art standard lentiviral or retroviral transduction protocols or plasmid electroporation strategies. Cells can be monitored for immunomodulatory polypeptide expression by, for example, flow cytometry using an anti-epitope tag or antibodies that cross-react with native parental molecule and polypeptides comprising variant CD86. T-cells that express the immunomodulatory polypeptide can be enriched through sorting with anti-epitope tag antibodies or enriched for high or low expression depending on the application.

Upon immunomodulatory polypeptide expression the engineered T-cell can be assayed for appropriate function by a variety of means. The engineered CAR or TCR co-expression can be validated to show that this part of the engineered T-cell was not significantly impacted by the expression of the immunomodulatory protein. Once validated, standard in vitro cytotoxicity, proliferation, or cytokine assays (e.g., IFN-gamma, IL2, TNFα expression) can be used to assess the function of engineered T-cells. Exemplary standard endpoints are percent lysis of the tumor line, proliferation of the engineered T-cell, or IFN-gamma protein expression in culture supernatants. An engineered construct which results in statistically significant increased lysis of tumor line, increased proliferation of the engineered T-cell, or increased IFN-gamma expression over the control construct can be selected for. Additionally, non-engineered, such as native primary or endogenous T-cells could also be incorporated into the same in vitro assay to measure the ability of the immunomodulatory polypeptide construct expressed on the engineered cells, such as engineered T-cells, to modulate activity, including, in some cases, to activate and generate effector function in bystander, native T-cells. Increased expression of activation or differentiation markers such as CD25, CD69, or CD44 could be monitored on endogenous T cells, and increased proliferation and/or cytokine production could indicate desired activity of the immunomodulatory protein expressed on the engineered T cells.

In some embodiments, similar assays can be used to compare the function of engineered T cells containing the CAR or TCR alone to those containing the CAR or TCR and a TIP construct. Typically, these in vitro assays are performed by plating various ratios of the engineered T cell and a "tumor" cell line containing the cognate CAR or TCR antigen together in culture. Standard endpoints are percent lysis of the tumor line, proliferation of the engineered T cell, or IFN-gamma production in culture supernatants. An engineered immunomodulatory protein which resulted in statistically significant increased lysis of tumor line, increased proliferation of the engineered T cell, or increased IFN-gamma production over the same TCR or CAR construct alone, can be selected for. Engineered human T cells can be analyzed in immunocompromised mice, like the NSG strain, which lacks mouse T, NK, and B cells. Engineered human T cells in which the CAR or TCR binds a target counter-structure on the xenograft and is co-expressed with the TIP affinity modified IgSF domain can be adoptively transferred in vivo at different cell numbers and ratios compared to the xenograft. In a common embodiment, the xenograft is introduced into the murine model, followed by the engineered T cells several days later. Engineered T cells containing the immunomodulatory protein can be assayed for increased survival, tumor clearance, or expanded engineered T cells numbers relative to engineered T cells containing the CAR or TCR alone. As in the in vitro assay, endogenous, native (i.e., non-engineered) human T cells could be co-adoptively transferred to look for successful epitope spreading in that population, resulting in better survival or tumor clearance.

In some embodiments, provided engineered T cells expressing a provided immunomodulatory protein exhibits one or more improved properties or activities compared to reference cells that have not been so engineered with an immunomodulatory protein (e.g. TIP) as described herein. In some embodiments, the reference cell, such as a reference T cells, reference CAR-engineered T cells, or reference TCR-engineered T cells, are cells that have been produced or engineered by similar ex vivo procedures but that do not express or have not been engineered to express the immunomodulatory protein. In some embodiments, the property or activity is associated with or related to T-cell function. In some embodiments, the one or more properties or activities include, but are not limited to, cellular proliferation, cytotoxic activity, cytokine production (e.g. IFN-gamma, IL-2 or TNF-alpha), and/or expression of one or more activation markers (e.g. CD69 or CD25). In some embodiments, the activity or property is increased by at least or at least about 1.2-fold, 1.4-fold, 1.5-fold, 1.6-fold, 1.7-fold, 1.8-fold, 1.9-fold, 2.0-fold, 2.5-fold, 3.0-fold, 4.0-fold, 5.0-fold, or more compared to the reference cell or reference cell composition F. Infectious Agents Expressing Variant Polypeptides and Immunomodulatory Proteins Also provided are infectious agents that contain nucleic acids encoding any of the variant polypeptides, such as CD86 vIgD polypeptides, including secretable or transmembrane immunomodulatory proteins described herein. In some embodiments, such infectious agents can deliver the nucleic acids encoding the variant immunomodulatory polypeptides described herein, such as CD86 vIgD polypeptides, to a target cell in a subject, e.g., immune cell and/or antigen-presenting cell (APC) or tumor cell in a subject. Also provided are nucleic acids contained in such infectious agents, and/or nucleic acids for generation or modification of such infectious agents, such as vectors and/or plasmids, and compositions containing such infectious agents.

In some embodiments, the infectious agent is a microorganism or a microbe. In some embodiments, the infectious agent is a virus or a bacterium. In some embodiments, the infectious agent is a virus. In some embodiments, the infectious agent is a bacterium. In some embodiments, such infectious agents can deliver nucleic acid sequences encoding any of the variant polypeptides, such as CD86 vIgD polypeptides, including secretable or transmembrane immunomodulatory proteins, described herein. Thus, in some embodiments, the cell in a subject that is infected or contacted by the infectious agents can be rendered to express on the cell surface or secrete the variant immunomodulatory polypeptides. In some embodiments, the infectious agent can also deliver one or more other therapeutics or nucleic acids encoding other therapeutics to the cell and/or to an environment within the subject. In some embodiments, other therapeutics that can be delivered by the infectious agents include cytokines or other immunomodulatory molecules.

In some embodiments, the infectious agent, e.g., virus or bacteria, contains nucleic acid sequences that encode any of the variant polypeptides, such as CD86 vIgD polypeptides, including secretable or transmembrane immunomodulatory proteins, described herein, and by virtue of contact and/or infection of a cell in the subject, the cell expresses the variant polypeptides, such as CD86 vIgD polypeptides, including secretable or transmembrane immunomodulatory proteins, encoded by the nucleic acid sequences contained in the infectious agent. In some embodiments, the infectious agent can be administered to the subject. In some embodiments, the infectious agent can be contacted with cells from the subject ex vivo.

In some embodiments, the variant polypeptides, such as CD86 vIgD polypeptides, including transmembrane immunomodulatory proteins, expressed by the cell infected by the infectious agent is a transmembrane protein and is surface expressed. In some embodiments, the variant polypeptides, such as CD86 vIgD polypeptides, including secretable immunomodulatory proteins, expressed by the cell infected by the infectious agent is expressed and secreted from the cell. The transmembrane immunomodulatory protein or secreted immunomodulatory protein can be any described herein.

In some embodiments, the cell in the subject that is targeted by the infectious agent include a tumor cell, an immune cell, and/or an antigen-presenting cell (APC). In some embodiments, the infectious agent targets a cell in the tumor microenvironment (TME). In some embodiments, the infectious agent delivers the nucleic acids encoding the variant polypeptides, such as CD86 vIgD polypeptides, including secretable or transmembrane immunomodulatory proteins, to an appropriate cell (for example, an APC, such as a cell that displays a peptide/MHC complex on its cell surface, such as a dendritic cell) or tissue (e.g., lymphoid tissue) that will induce and/or augment the desired effect, e.g., immunomodulation and/or a specific cell-medicated immune response, e.g., CD4 and/or CD8 T-cell response, which CD8 T-cell response may include a cytotoxic T-cell (CTL) response. In some embodiments, the infectious agent targets an APC, such as a dendritic cell (DC). In some embodiments, the nucleic acid molecule delivered by the infectious agents described herein include appropriate nucleic acid sequences necessary for the expression of the operably linked coding sequences encoding the variant immunomodulatory polypeptides, in a particular target cell, e.g., regulatory elements such as promoters.

In some embodiments, the infectious agent that contains nucleic acid sequences encoding the immunomodulatory polypeptides can also contain nucleic acid sequences that encode one or more additional gene products, e.g., cytokines, prodrug converting enzymes, cytotoxins, and/or detectable gene products. For example, in some embodiments, the infectious agent is an oncolytic virus and the virus can include nucleic acid sequences encoding additional therapeutic gene products (see, e.g., Kirn et al., (2009) Nat Rev Cancer 9:64-71; Garcia-Aragoncillo et al., (2010) Curr Opin Mol Ther 12:403-411; see U.S. Pat. Nos. 7,588,767, 7,588,771, 7,662,398 and 7,754,221 and U.S. Pat. Publ. Nos. 2007/0202572, 2007/0212727, 2010/0062016, 2009/0098529, 2009/0053244, 2009/0155287, 2009/0117034, 2010/0233078, 2009/0162288, 2010/0196325, 2009/0136917 and 2011/0064650. In some embodiments, the additional gene product can be a therapeutic gene product that can result in death of the target cell (e.g., tumor cell) or gene products that can augment or boost or regulate an immune response (e.g., cytokine). Exemplary gene products also include among an anticancer agent, an anti-metastatic agent, an antiangiogenic agent, an immunomodulatory molecule, an immune checkpoint inhibitor, an antibody, a cytokine, a growth factor, an antigen, a cytotoxic gene product, a pro-apoptotic gene product, an anti-apoptotic gene product, a cell matrix degradative gene, genes for tissue regeneration or reprogramming human somatic cells to pluripotency, and other genes described herein or known to one of skill in the art. In some embodiments, the additional gene product is Granulocyte-macrophage colony-stimulating factor (GM-CSF).

1. Viruses

In some embodiments, the infectious agent is a virus. In some embodiments, the infectious agent is an oncolytic virus, or a virus that targets particular cells, e.g., immune cells. In some embodiments, the infectious agent targets a tumor cell and/or cancer cell in the subject. In some embodiments, the infectious agent targets an immune cell or an antigen-presenting cell (APC).

In some embodiments, the infectious agent is an oncolytic virus. Oncolytic viruses are viruses that accumulate in tumor cells and replicate in tumor cells. By virtue of replication in the cells, and optional delivery of nucleic acids encoding variant immunomodulatory variant CD86 polypeptides or immunomodulatory proteins described herein, tumor cells are lysed, and the tumor shrinks and can be eliminated. Oncolytic viruses can also have a broad host and cell type range. For example, oncolytic viruses can accumulate in immunoprivileged cells or immunoprivileged tissues, including tumors and/or metastases, and also including wounded tissues and cells, thus allowing the delivery and expression of nucleic acids encoding the variant immunomodulatory polypeptides described herein in a broad range of cell types. Oncolytic viruses can also replicate in a tumor cell specific manner, resulting in tumor cell lysis and efficient tumor regression.

Exemplary oncolytic viruses include adenoviruses, adeno-associated viruses, herpes viruses, Herpes Simplex Virus, Reovirus, Newcastle Disease virus, parvovirus, measles virus, vesicular stomatitis virus (VSV), Coxsackie virus and Vaccinia virus. In some embodiments, oncolytic viruses can specifically colonize solid tumors, while not infecting other organs, and can be used as an infectious agent to deliver the nucleic acids encoding the variant immunomodulatory polypeptides described herein to such solid tumors.

Oncolytic viruses for use in delivering the nucleic acids encoding variant CD86 polypeptides or immunomodulatory proteins described herein, can be any of those known to one of skill in the art and include, for example, vesicular stomatitis virus, see, e.g., U.S. Pat. Nos. 7,731,974, 7,153,510, 6,653,103 and U.S. Pat. Pub. Nos. 2010/0178684, 2010/0172877, 2010/0113567, 2007/0098743, 20050260601, 20050220818 and EP Pat. Nos. 1385466, 1606411 and 1520175; herpes simplex virus, see, e.g., U.S. Pat. Nos. 7,897,146, 7,731,952, 7,550,296, 7,537,924, 6,723,316, 6,428,968 and U.S. Pat. Pub. Nos., 2014/0154216, 2011/0177032, 2011/0158948, 2010/0092515, 2009/0274728, 2009/0285860, 2009/0215147, 2009/0010889, 2007/0110720, 2006/0039894, 2004/0009604, 2004/0063094, International Patent Pub. Nos., WO 2007/052029, WO 1999/038955; retroviruses, see, e.g., U.S. Pat. Nos. 6,689,871, 6,635,472, 5,851,529, 5,716,826, 5,716,613 and U.S. Pat. Pub. No. 20110212530; vaccinia viruses, see, e.g., 2016/0339066, and adeno-associated viruses, see, e.g., U.S. Pat. Nos. 8,007,780, 7,968,340, 7,943,374, 7,906,111, 7,927,585, 7,811,814, 7,662,627, 7,241,447, 7,238,526, 7,172,893, 7,033,826, 7,001,765, 6,897,045, and 6,632,670.

Oncolytic viruses also include viruses that have been genetically altered to attenuate their virulence, to improve their safety profile, enhance their tumor specificity, and they have also been equipped with additional genes, for example cytotoxins, cytokines, prodrug converting enzymes to improve the overall efficacy of the viruses (see, e.g., Kim et al., (2009) Nat Rev Cancer 9:64-71; Garcia-Aragoncillo et al., (2010) Curr Opin Mol Ther 12:403-411; see U.S. Pat. Nos. 7,588,767, 7,588,771, 7,662,398 and 7,754,221 and U.S. Pat. Publ. Nos. 2007/0202572, 2007/0212727, 2010/0062016, 2009/0098529, 2009/0053244, 2009/0155287, 2009/0117034, 2010/0233078, 2009/0162288, 2010/0196325, 2009/0136917 and 2011/0064650). In some embodiments, the oncolytic viruses can be those that have been modified so that they selectively replicate in cancerous cells, and, thus, are oncolytic. For example, the oncolytic virus is an adenovirus that has been engineered to have modified tropism for tumor therapy and also as gene therapy vectors. Exemplary of such is ONYX-015, H101 and Ad5ΔCR (Hallden and Portella (2012) Expert Opin Ther Targets, 16:945-58) and TNFerade (McLoughlin et al. (2005) Ann. Surg. Oncol., 12:825-30), or a conditionally replicative adenovirus Oncorine®.

In some embodiments, the infectious agent is a modified herpes simplex virus. In some embodiments, the infectious agent is a modified version of Talimogene laherparepvec (also known as T-Vec, Imlygic or OncoVex GM-CSF), that is modified to contain nucleic acids encoding any of the variant immunomodulatory polypeptides described herein, such as any of the variant CD86 polypeptides or immunomodulatory proteins described herein. In some embodiments, the infectious agent is a modified herpes simplex virus that is described, e.g., in WO 2007/052029, WO 1999/038955, US 2004/0063094, US 2014/0154216, or, variants thereof.

In some embodiments, the infectious agent is a virus that targets a particular type of cells in a subject that is administered the virus, e.g., a virus that targets immune cells or antigen-presenting cells (APCs). Dendritic cells (DCs) are essential APCs for the initiation and control of immune responses. DCs can capture and process antigens, migrate from the periphery to a lymphoid organ, and present the antigens to resting T cells in a major histocompatibility complex (MHC)-restricted fashion. In some embodiments, the infectious agent is a virus that specifically can target DCs to deliver nucleic acids encoding the variant CD86 polypeptides or immunomodulatory proteins for expression in DCs. In some embodiments, the virus is a lentivirus or a variant or derivative thereof, such as an integration-deficient lentiviral vector. In some embodiments, the virus is a lentivirus that is pseudotyped to efficiently bind to and productively infect cells expressing the cell surface marker dendritic cell-specific intercellular adhesion molecule-3-grabbing non-integrin (DC-SIGN), such as DCs. In some embodiments, the virus is a lentivirus pseudotyped with a Sindbis virus E2 glycoprotein or modified form thereof, such as those described in WO 2013/149167. In some embodiments, the virus allows for delivery and expression of a sequence of interest (e.g., a nucleic acid encoding any of the variant CD86 polypeptides or immunomodulatory proteins described herein) to a DC. In some embodiments, the virus includes those described in WO 2008/011636 or US 2011/0064763, Tareen et al. (2014) Mol. Ther., 22:575-587, or variants thereof. Exemplary of a dendritic cell-tropic vector platform is ZVex™

2. Bacteria

In some embodiments, the infectious agent is a bacterium. For example, in some embodiments, the bacteria can deliver nucleic acids encoding any of the variant immunomodulatory polypeptides described herein, e.g., variant CD86 polypeptide or immunomodulatory protein, to a target cell in the subject, such as a tumor cell, an immune cell, an antigen-presenting cell and/or a phagocytic cell. In some embodiments, the bacterium can be preferentially targeted to a specific environment within a subject, such as a tumor microenvironment (TME), for expression and/or secretion of the variant immunomodulatory polypeptides and/or to target specific cells in the environment for expression of the variant immunomodulatory polypeptides.

In some embodiments, the bacterium delivers the nucleic acids to the cells via bacterial-mediated transfer of plasmid DNA to mammalian cells (also referred to as "bactofection"). For example, in some embodiments, delivery of genetic material is achieved through entry of the entire bacterium into target cells. In some embodiments, spontaneous or induced bacterial lysis can lead to the release of plasmid for subsequent eukaryotic cell expression. In some embodiments, the bacterium can deliver nucleic acids to non-phagocytic mammalian cells (e.g., tumor cells) and/or to phagocytic cells, e.g., certain immune cells and/or APCs. In some embodiments, the nucleic acids delivered by the bacterium can be transferred to the nucleus of the cell in the subject for expression. In some embodiments, the nucleic acids also include appropriate nucleic acid sequences necessary for the expression of the operably linked sequences encoding the variant immunomodulatory polypeptides in a particular host cell, e.g., regulatory elements such as promoters or enhancers. In some embodiments, the infectious agent that is a bacterium can deliver nucleic acids encoding the immunomodulatory proteins in the form of an RNA, such as a pre-made translation-competent RNA delivered to the cytoplasm of the target cell for translation by the target cell's machinery.

In some embodiments, the bacterium can replicate and lyse the target cells, e.g., tumor cells. In some embodiments, the bacterium can contain and/or release nucleic acid sequences and/or gene products in the cytoplasm of the target cells, thereby killing the target cell, e.g., tumor cell. In some embodiments, the infectious agent is a bacterium that can replicate specifically in a particular environment in the subject, e.g., tumor microenvironment (TME). For example, in some embodiments, the bacterium can replicate specifically in anaerobic or hypoxic microenvironments. In some embodiments, conditions or factors present in particular environments, e.g., aspartate, serine, citrate, ribose or galactose produced by cells in the TME, can act as chemoattractants to attract the bacterium to the environment. In some embodiments, the bacterium can express and/or secrete the immunomodulatory proteins described herein in the environment, e.g., TME.

In some embodiments, the infectious agent is a bacterium that is a *Listeria* sp., a *Bifidobacterium* sp., an *Escherichia* sp., a *Clostridium* sp., a *Salmonella* sp., a *Shigella* sp., a *Vibrio* sp. or a *Yersinia* sp. In some embodiments, the bacterium is selected from among one or more of *Listeria monocytogenes, Salmonella typhimurium, Salmonella choleraesuis, Escherichia coli, Vibrio cholera, Clostridium perfringens, Clostridium butyricum, Clostridium novyi, Clostridium acetobutylicum, Bifidobacterium infantis, Bifidobacterium longum* and *Bifidobacterium adolescentis*. In some embodiments, the bacterium is an engineered bacterium. In some embodiments, the bacterium is an engineered bacterium such as those described in, e.g., Seow and Wood (2009) Molecular Therapy 17(5):767-777; Baban et al. (2010) Bioengineered Bugs 1:6, 385-394; Patyar et al. (2010) J Biomed Sci 17:21; Tangney et al. (2010) Bioengineered Bugs 1:4, 284-287; van Pijkeren et al. (2010) Hum Gene Ther. 21(4):405-416; WO 2012/149364; WO 2014/198002; U.S. Pat. Nos. 9,103,831; 9,453,227; US 2014/0186401; US 2004/0146488; US 2011/0293705; US 2015/0359909 and EP 3020816. The bacterium can be modified to deliver nucleic acid sequences encoding any of the variant immunomodulatory polypeptides, conjugates and/or fusions provided herein, and/or to express such variant immunomodulatory polypeptides in the subject.

G. Nucleic Acids, Vectors and Methods for Producing the Polypeptides or Cells

Provided herein are isolated or recombinant nucleic acids collectively referred to as "nucleic acids" which encode any of the various provided embodiments of the variant CD86 polypeptides or immunomodulatory polypeptides provided herein. In some embodiments, nucleic acids provided herein, including all described below, are useful in recombinant production (e.g., expression) of variant CD86 polypeptides or immunomodulatory polypeptides provided herein. In some embodiments, nucleic acids provided herein, including all described below, are useful in expression of variant CD86 polypeptides or immunomodulatory polypeptides provided herein in cells, such as in engineered cells, e.g., immune cells, or infectious agent cells. The nucleic acids provided herein can be in the form of RNA or in the form of DNA, and include mRNA, cRNA, recombinant or synthetic RNA and DNA, and cDNA. The nucleic acids provided herein are typically DNA molecules, and usually double-stranded DNA molecules. However, single-stranded DNA, single-stranded RNA, double-stranded RNA, and hybrid DNA/

RNA nucleic acids or combinations thereof comprising any of the nucleotide sequences of the invention also are provided.

Also provided herein are recombinant expression vectors and recombinant host cells useful in producing the variant CD86 polypeptides or immunomodulatory polypeptides provided herein.

Also provided herein are engineered cells, such as engineered immune cells, containing any of the provided immunomodulatory polypeptides, such as any of the transmembrane immunomodulatory polypeptides or secretable immunomodulatory polypeptides.

Also provided herein are infectious agents, such as bacterial or viral cells, containing any of the provided immunomodulatory polypeptides, such as any of the transmembrane immunomodulatory polypeptides or secretable immunomodulatory polypeptides.

In any of the above provided embodiments, the nucleic acids encoding the immunomodulatory polypeptides provided herein can be introduced into cells using recombinant DNA and cloning techniques. To do so, a recombinant DNA molecule encoding an immunomodulatory polypeptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidite method. Also, a combination of these techniques could be used. In some instances, a recombinant or synthetic nucleic acid may be generated through polymerase chain reaction (PCR). In some embodiments, a DNA insert can be generated encoding one or more variant CD86 polypeptides containing at least one affinity-modified IgSF domain and, in some embodiments, a signal peptide, a transmembrane domain and/or an endodomain in accord with the provided description. This DNA insert can be cloned into an appropriate transduction/transfection vector as is known to those of skill in the art. Also provided are expression vectors containing the nucleic acid molecules.

In some embodiments, the expression vectors are capable of expressing the immunomodulatory proteins in an appropriate cell under conditions suited to expression of the protein. In some aspects, a nucleic acid molecule or an expression vector comprises the DNA molecule that encodes the immunomodulatory protein operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

In some embodiments, expression of the immunomodulatory protein is controlled by a promoter or enhancer to control or regulate expression. The promoter is operably linked to the portion of the nucleic acid molecule encoding the variant polypeptide or immunomodulatory protein. In some embodiments, the promotor is a constitutively active promotor (such as a tissue-specific constitutively active promotor or other constitutive promotor). In some embodiments, the promotor is an inducible promotor, which may be responsive to an inducing agent (such as a T-cell activation signal).

In some embodiments, a constitutive promoter is operatively linked to the nucleic acid molecule encoding the variant polypeptide or immunomodulatory protein. Exemplary constitutive promoters include the Simian vacuolating virus 40 (SV40) promoter, the cytomegalovirus (CMV) promoter, the ubiquitin C (UbC) promoter, and the EF-1 alpha (EF1a) promoter. In some embodiments, the constitutive promoter is tissue specific. For example, in some embodiments, the promoter allows for constitutive expression of the immunomodulatory protein in specific tissues, such as immune cells, lymphocytes, or T-cells. Exemplary tissue-specific promoters are described in U.S. Pat. No. 5,998,205, including, for example, a fetoprotein, DF3, tyrosinase, CEA, surfactant protein, and ErbB2 promoters.

In some embodiments, an inducible promoter is operatively linked to the nucleic acid molecule encoding the variant polypeptide or immunomodulatory protein such that expression of the nucleic acid is controllable by controlling the presence or absence of the appropriate inducer of transcription. For example, the promoter can be a regulated promoter and transcription factor expression system, such as the published tetracycline-regulated systems or other regulatable systems (see, e.g., published International PCT Appl. No. WO 01/30843), to allow regulated expression of the encoded polypeptide. An exemplary regulatable promoter system is the Tet-On (and Tet-Off) system available, for example, from Clontech (Palo Alto, CA). This promoter system allows the regulated expression of the transgene controlled by tetracycline or tetracycline derivatives, such as doxycycline. Other regulatable promoter systems are known (see e.g., published U.S. Application No. 2002-0168714, entitled "Regulation of Gene Expression Using Single-Chain, Monomeric, Ligand Dependent Polypeptide Switches," which describes gene switches that contain ligand binding domains and transcriptional regulating domains, such as those from hormone receptors).

In some embodiments, the promotor is responsive to an element responsive to T-cell activation signaling. Solely by way of example, in some embodiments, an engineered T cell comprises an expression vector encoding the immunomodulatory protein and a promotor operatively linked to control expression of the immunomodulatory protein. The engineered T cell can be activated, for example by signaling through an engineered T cell receptor (TCR) or a chimeric antigen rector (CAR), and thereby triggering expression and secretion of the immunomodulatory protein through the responsive promotor.

In some embodiments, an inducible promoter is operatively linked to the nucleic acid molecule encoding the immunomodulatory protein such that the immunomodulatory protein is expressed in response to a nuclear factor of activated T-cells (NFAT) or nuclear factor kappa-light-chain enhancer of activated B cells (NF-κB). For example, in some embodiments, the inducible promoter comprises a binding site for NFAT or NF-κB. For example, in some embodiments, the promoter is an NFAT or NF-κB promoter or a functional variant thereof. Thus, in some embodiments, the nucleic acids make it possible to control the expression of immunomodulatory protein while also reducing or eliminating the toxicity of the immunomodulatory protein. In particular, engineered immune cells comprising the nucleic acids of the invention express and secrete the immunomodulatory protein only when the cell (e.g., a T-cell receptor (TCR) or a chimeric antigen receptor (CAR) expressed by the cell) is specifically stimulated by an antigen and/or the cell (e.g., the calcium signaling pathway of the cell) is non-specifically stimulated by, e.g., phorbol myristate acetate (PMA)/Ionomycin. Accordingly, the expression and, in some cases, secretion, of immunomodulatory protein can be controlled to occur only when and where it is needed (e.g., in the presence of an infectious disease-causing agent, cancer, or at a tumor site), which can decrease or avoid undesired immunomodulatory protein interactions.

In some embodiments, the nucleic acid encoding an immunomodulatory protein described herein comprises a suitable nucleotide sequence that encodes a NFAT promoter, NF-κB promoter, or a functional variant thereof. "NFAT promoter" as used herein means one or more NFAT responsive elements linked to a minimal promoter. "NF-κB promoter" refers to one or more NF-κB responsive elements linked to a minimal promoter. In some embodiments, the minimal promoter of a gene is a minimal human IL-2 promoter or a CMV promoter. The NFAT responsive elements may comprise, e.g., NFAT1, NFAT2, NFAT3, and/or NFAT4 responsive elements. The NFAT promoter, NF-κB promoter, or a functional variant thereof may comprise any number of binding motifs, e.g., at least two, at least three, at least four, at least five, or at least six, at least seven, at least eight, at least nine, at least ten, at least eleven, or up to twelve binding motifs.

The resulting recombinant expression vector having the DNA molecule thereon is used to transform an appropriate host. This transformation can be performed using methods well known in the art. In some embodiments, a nucleic acid provided herein further comprises nucleotide sequence that encodes a secretory or signal peptide operably linked to the nucleic acid encoding an immunomodulatory polypeptide such that a resultant soluble immunomodulatory polypeptide is recovered from the culture medium, host cell, or host cell periplasm. In other embodiments, the appropriate expression control signals are chosen to allow for membrane expression of an immunomodulatory polypeptide. Furthermore, commercially available kits as well as contract manufacturing companies can also be utilized to make engineered cells or recombinant host cells provided herein.

In some embodiments, the resulting expression vector having the DNA molecule thereon is used to transform, such as transduce, an appropriate cell. The introduction can be performed using methods well known in the art. Exemplary methods include those for transfer of nucleic acids encoding the receptors, including via viral, e.g., retroviral or lentiviral, transduction, transposons, and electroporation. In some embodiments, the expression vector is a viral vector. In some embodiments, the nucleic acid is transferred into cells by lentiviral or retroviral transduction methods.

Any of a large number of publicly available and well-known mammalian host cells, including mammalian T-cells or APCs, can be used in the preparing the polypeptides or engineered cells. The selection of a cell is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all cells can be equally effective for the expression of a particular DNA sequence.

In some embodiments, the host cells can be a variety of eukaryotic cells, such as in yeast cells, or with mammalian cells such as Chinese hamster ovary (CHO) or HEK293 cells. In some embodiments, the host cell is a suspension cell and the polypeptide is engineered or produced in cultured suspension, such as in cultured suspension CHO cells, e.g., CHO—S cells. In some examples, the cell line is a CHO cell line that is deficient in DHFR (DHFR−), such as DG44 and DUXB11. In some embodiments, the cell is deficient in glutamine synthase (GS), e.g., CHO—S cells, CHOK1 SV cells, and CHOZN((R)) GS−/− cells. In some embodiments, the CHO cells, such as suspension CHO cells, may be CHO—S-2H2 cells, CHO—S-clone 14 cells, or ExpiCHO—S cells.

In some embodiments, host cells can also be prokaryotic cells, such as with *E. coli*. The transformed recombinant host is cultured under polypeptide expressing conditions, and then purified to obtain a soluble protein. Recombinant host cells can be cultured under conventional fermentation conditions so that the desired polypeptides are expressed. Such fermentation conditions are well known in the art. Finally, the polypeptides provided herein can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, and affinity chromatography. Protein refolding steps can be used, as desired, in completing configuration of the mature protein. Finally, high performance liquid chromatography (HPLC) can be employed in the final purification steps.

In some embodiments, the cell is an immune cell, such as any described above in connection with preparing engineered cells. In some embodiments, such engineered cells are primary cells. In some embodiments, the engineered cells are autologous to the subject. In some embodiment, the engineered cells are allogeneic to the subject. In some embodiments, the engineered cells are obtained from a subject, such as by leukapheresis, and transformed ex vivo for expression of the immunomodulatory polypeptide, e.g., transmembrane immunomodulatory polypeptide or secretable immunomodulatory polypeptide.

Also provided are nucleic acids encoding any of the variant immunomodulatory polypeptides contained in infectious agents described herein. In some embodiments, the infectious agents deliver the nucleic acids to a cell in the subject, and/or permit expression of the encoded variant polypeptides in the cell. Also provided are nucleic acids that are used to generate, produce or modify such infectious agents. For example, in some embodiments, provided are vectors and/or plasmids that contain nucleic acids encoding the variant immunomodulatory polypeptides, for generation of the infectious agents, delivery to the cells in a subject and/or expression of the variant immunomodulatory polypeptides in the cells in the subject.

In some embodiments, the provided nucleic acids are recombinant viral or bacterial vectors containing nucleic acid sequences encoding the variant immunomodulatory polypeptides. In some embodiments, the recombinant vectors can be used to produce an infectious agent that contains nucleic acid sequences encoding the variant immunomodulatory polypeptides and/or to be delivered to a target cell in the subject for expression by the target cell. In some embodiments, the recombinant vector is an expression vector. In some embodiments, the recombinant vector includes appropriate sequences necessary for generation and/or production of the infectious agent and expression in the target cell.

In some embodiments, the recombinant vector is a plasmid or cosmid. Plasmid or cosmid containing nucleic acid sequences encoding the variant immunomodulatory polypeptides, as described herein, is readily constructed using standard techniques well known in the art. For generation of the infectious agent, the vector or genome can be constructed in a plasmid form that can then be transfected into a packaging or producer cell line or a host bacterium. The recombinant vectors can be generated using any of the recombinant techniques known in the art. In some embodiments, the vectors can include a prokaryotic origin of replication and/or a gene whose expression confers a detectable or selectable marker such as a drug resistance for propagation and/or selection in prokaryotic systems.

In some embodiments, the recombinant vector is a viral vector. Exemplary recombinant viral vectors include a lentiviral vector genome, poxvirus vector genome, vaccinia virus vector genome, adenovirus vector genome, adenovirus-associated virus vector genome, herpes virus vector genome, and alpha virus vector genome. Viral vectors can be live, attenuated, replication conditional or replication deficient, non-pathogenic (defective), replication competent viral vector, and/or is modified to express a heterologous gene product, e.g., the variant immunomodulatory polypeptides provided herein. Vectors for generation of viruses also can be modified to alter attenuation of the virus, which includes any method of increasing or decreasing the transcriptional or translational load.

Exemplary viral vectors that can be used include modified vaccinia virus vectors (see, e.g., Guerra et al., J. Virol. 80:985-98 (2006); Tartaglia et al., AIDS Research and Human Retroviruses 8: 1445-47 (1992); Gheradi et al., J. Gen. Virol. 86:2925-36 (2005); Mayr et al., Infection 3:6-14 (1975); Hu et al., J. Virol. 75: 10300-308 (2001); U.S. Pat. Nos. 5,698,530, 6,998,252, 5,443,964, 7,247,615 and 7,368, 116); adenovirus vector or adenovirus-associated virus vectors (see., e.g., Molin et al., J. Virol. 72:8358-61 (1998); Narumi et al., Am J. Respir. Cell Mol. Biol. 19:936-41 (1998); Mercier et al., Proc. Natl. Acad. Sci. USA 101:6188-93 (2004); U.S. Pat. Nos. 6,143,290; 6,596,535; 6,855,317; 6,936,257; 7,125,717; 7,378,087; 7,550,296); retroviral vectors including those based upon murine leukemia virus (MuLV), gibbon ape leukemia virus (GaLV), ecotropic retroviruses, simian immunodeficiency virus (SIV), human immunodeficiency virus (HIV), and combinations (see, e.g., Buchscher et al., J. Virol. 66:2731-39 (1992); Johann et al., J. Virol. 66: 1635-40 (1992); Sommerfelt et al., Virology 176:58-59 (1990); Wilson et al., J. Virol. 63:2374-78 (1989); Miller et al., J. Virol. 65:2220-24 (1991); Miller et al., Mol. Cell Biol. 10:4239 (1990); Kolberg, NIH Res. 4:43 1992; Cornetta et al., Hum. Gene Ther. 2:215 (1991)); lentiviral vectors including those based upon Human Immunodeficiency Virus (HIV-1), HIV-2, feline immunodeficiency virus (FIV), equine infectious anemia virus, Simian Immunodeficiency Virus (SIV), and maedi/visna virus (see, e.g., Pfeifer et al., Annu. Rev. Genomics Hum. Genet. 2: 177-211 (2001); Zufferey et al., J. Virol. 72: 9873, 1998; Miyoshi et al., J. Virol. 72:8150, 1998; Philpott and Thrasher, Human Gene Therapy 18:483, 2007; Engelman et al., J. Virol. 69: 2729, 1995; Nightingale et al., Mol. Therapy, 13: 1121, 2006; Brown et al., J. Virol. 73:9011 (1999); WO 2009/076524; WO 2012/141984; WO 2016/011083; McWilliams et al., J. Virol. 77: 11150, 2003; Powell et al., J. Virol. 70:5288, 1996) or any, variants thereof, and/or vectors that can be used to generate any of the viruses described above. In some embodiments, the recombinant vector can include regulatory sequences, such as promoter or enhancer sequences, that can regulate the expression of the viral genome, such as in the case for RNA viruses, in the packaging cell line (see, e.g., U.S. Pat. Nos. 5,385,839 and 5,168,062).

In some embodiments, the recombinant vector is an expression vector, e.g., an expression vector that permits expression of the encoded gene product when delivered into the target cell, e.g., a cell in the subject, e.g., a tumor cell, an immune cell and/or an APC. In some embodiments, the recombinant expression vectors contained in the infectious agent are capable of expressing the immunomodulatory proteins in the target cell in the subject, under conditions suited to expression of the protein.

In some aspects, nucleic acids or an expression vector comprises a nucleic acid sequence that encodes the immunomodulatory protein operatively linked to appropriate expression control sequences. Methods of affecting this operative linking, either before or after the nucleic acid sequence encoding the immunomodulatory protein is inserted into the vector, are well known. Expression control sequences include promoters, activators, enhancers, operators, ribosomal binding sites, start signals, stop signals, cap signals, polyadenylation signals, and other signals involved with the control of transcription or translation. The promoter can be operably linked to the portion of the nucleic acid sequence encoding the immunomodulatory protein. In some embodiments, the promotor is a constitutively active promotor in the target cell (such as a tissue-specific constitutively active promotor or other constitutive promotor). For example, the recombinant expression vector may also include, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson et al., Mol. Cell. Biol. 12:1043-53 (1992); Todd et al., J. Exp. Med. 177: 1663-74 (1993); Penix et al., J. Exp. Med. 178:1483-96 (1993)). In some embodiments, the promotor is an inducible promotor, which may be responsive to an inducing agent (such as a T cell activation signal). In some embodiments, nucleic acids delivered to the target cell in the subject, e.g., tumor cell, immune cell and/or APC, can be operably linked to any of the regulatory elements described above.

In some embodiments, the vector is a bacterial vector, e.g., a bacterial plasmid or cosmid. In some embodiments, the bacterial vector is delivered to the target cell, e.g., tumor cells, immune cells and/or APCs, via bacterial-mediated transfer of plasmid DNA to mammalian cells (also referred to as "bactofection"). In some embodiments, the delivered bacterial vector also contains appropriate expression control sequences for expression in the target cells, such as a promoter sequence and/or enhancer sequences, or any regulatory or control sequences described above. In some embodiments, the bacterial vector contains appropriate expression control sequences for expression and/or secretion of the encoded variant polypeptides in the infectious agent, e.g., the bacterium.

In some embodiments, polypeptides provided herein can also be made by synthetic methods. Solid phase synthesis is the preferred technique of making individual peptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Peptides can then be assembled into the polypeptides as provided herein.

IV. METHODS OF ASSESSING ACTIVITY IMMUNE MODULATION OF VARIANT CD86 POLYPEPTIDES AND IMMUNOMODULATORY PROTEINS

In some embodiments, the variant CD86 polypeptides provided herein (full-length and/or specific binding fragments or conjugates, stack constructs or fusion thereof or engineered cells) exhibit immunomodulatory activity to modulate T cell activation. In some embodiments, CD86 polypeptides modulate cytokine production, such as IFN-gamma, TNFα, or IL-2 expression, in a T cell assay relative to a wild-type or unmodified CD86 control. In some cases, modulation of expression cell activity can increase or decrease cytokine production, such as IFN-gamma, TNFα, or IL-2 expression, by or from T cells relative to the control CD86. Assays to determine specific binding and cytokine product, such as IFN-gamma, TNFα, or IL-2 expression, are well-known in the art and include the MLR (mixed lymphocyte reaction) assays measuring cytokine levels in culture supernatants (Wang et al., Cancer Immunol Res. 2014 September: 2(9):846-56), SEB (staphylococcal enterotoxin B) T cell stimulation assay (Wang et al., Cancer Immunol Res. 2014 September: 2(9):846-56), and anti-CD3 T cell stimulation assays (Li and Kurlander, J Transl Med. 2010: 8: 104).

In some embodiments, a variant CD86 polypeptide can in some embodiments increase or, in alternative embodiments, decrease cytokine production, such as IFN-gamma (interferon-gamma), TNFα, or IL-2 expression, in a primary T-cell assay relative to a wild-type CD86 control. In some embodiments, such activity may depend on whether the variant CD86 polypeptide is provided in a form for antagonist activity or in a form for agonist activity. Those of skill will recognize that different formats of the primary T-cell assay used to determine an increase or decrease in IFN-gamma, TNFα, or IL-2 expression exist.

In assaying for the ability of a variant CD86 to increase or decrease IFN-gamma, TNFα, or IL-2 expression in a primary T-cell assay, a Mixed Lymphocyte Reaction (MLR) assay can be used. In some embodiments, a variant CD86 polypeptide or immunomodulatory protein provided in antagonist form, such as soluble form, e.g., variant CD86-Fc or secretable immunomodulatory protein, block activity of the CD28 and thereby decreases MLR activity in the assay, such as observed by decreased production of IFN-gamma, TNFα, or IL-2 in the assay. In some embodiments, a variant CD86 polypeptide or immunomodulatory protein provided in agonist form, such as a localizing vIgD stack or conjugate containing a tumor-localizing moiety or an engineered cell expressing a transmembrane immunomodulatory protein as provided, may stimulate activity of CD28 and thereby increase MLR activity, such as evidenced by increased IFN-gamma, TNFα, or IL-2 production.

Alternatively, in assaying for the ability of a variant CD86 to modulate an increase or decrease in IFN-gamma or IL-2 expression in a primary T-cell assay, a co-immobilization assay can be used. In a co-immobilization assay, a TCR signal, provided in some embodiments by anti-CD3 antibody, is used in conjunction with a co-immobilized variant CD86 to determine the ability to increase or decrease IFN-gamma, TNFα, or IL-2 expression relative to a CD86 unmodified or wild-type control. In some embodiments, a variant CD86 polypeptide or immunomodulatory protein, e.g., a co-immobilized variant CD86 (e.g., CD86-Fc), increases IFN-gamma production in a co-immobilization assay.

In some embodiments, in assaying for the ability of a variant CD86 to modulate an increase or decrease in IFN-gamma, TNFα, or IL-2 expression a T cell reporter assay can be used. In some embodiments, the T cell is a Jurkat T cell line or is derived from Jurkat T cell lines. In reporter assays, the reporter cell line (e.g., Jurkat reporter cell) also can be generated to overexpress an inhibitory receptor, e.g. CTLA-4, that is a cognate binding partner of the variant IgSF domain polypeptide. In some embodiments, the reporter T cells also contain a reporter construct containing an inducible promoter responsive to T cell activation operably linked to a reporter. In some embodiments, the reporter is a fluorescent or luminescent reporter. In some embodiments, the reporter is luciferase. In some embodiments, the promoter is responsive to CD3 signaling. In some embodiments, the promoter is an NFAT promoter. In some embodiments, the promoter is responsive to costimulatory signaling, e.g., CD28 costimulatory signaling. In some embodiments, the promoter is an IL-2 promoter.

In aspects of a reporter assay, a reporter cell line is stimulated, such as by co-incubation with antigen presenting cells (APCs) expressing the wild-type ligand, e.g., CD86. In some embodiments, the APCs are artificial APCs. Artificial APCs are well known to a skilled artisan. In some embodiments, artificial APCs are derived from one or more mammalian cell line, such as K562, CHO or 293 cells. In some embodiments, the artificial APCs are engineered to express an anti-CD3 antibody and, in some cases, a costimulatory ligand. In some embodiments, the artificial APC is generated to overexpress the cognate binding partner of the variant IgSF domain polypeptide. For example, in the case of a variant CD86, the reporter cell line (e.g., Jurkat reporter cell) is generated to overexpress the ligandCD28. In some embodiments, the Jurkat reporter cells are co-incubated with artificial APCs overexpressing in the presence of the variant IgSF domain molecule or immunomodulatory protein, e.g., variant CD86 polypeptide or immunomodulatory protein. In some embodiments, reporter expression is monitored, such as by determining the luminescence or fluorescence of the cells. Agonist or antagonist (blocking) activity of a cognate binding partner can be monitored.

Use of proper controls is known to those of skill in the art, however, in the aforementioned embodiments, a control typically involves use of the unmodified CD86, such as a wild-type of native CD86 isoform from the same mammalian species from which the variant CD86 was derived or developed. In some embodiments, the wild-type or native CD86 is of the same form or corresponding form as the variant. For example, if the variant CD86 is a soluble form containing a variant ECD fused to an Fc protein, then the control is a soluble form containing the wild-type or native ECD of CD86 fused to the Fc protein.

In some embodiments, a variant CD86 polypeptide or immunomodulatory protein, increases IFN-gamma, TNFα, or IL-2 expression (i.e., protein expression) relative to a wild-type or unmodified CD86 control by at least: 5%, 10%, 20%, 30%, 40%, 50%, 60%, 70%, 80%, 90%, or higher. In other embodiments, a variant CD86 or immunomodulatory protein decreases IFN-gamma, TNFα, or IL-2 expression (i.e. protein expression) relative to a wild-type or unmodified CD86 control by at least: 5%, 10%, 20%, 30%, 40%, 50%, 60%, 70%, 80%, 90%, or higher. In some embodiments, the wild-type CD86 control is murine CD86, such as would typically be used for a variant CD86 altered in sequence from that of a wild-type murine CD86 sequence. In some embodiments, the wild-type CD86 control is human CD86, such as would typically be used for a variant CD86 altered in sequence from that of a corresponding wild-type human CD86 sequence such as an CD86 sequence comprising the sequence of amino acids of SEQ ID NO: 2, SEQ ID NO: 122 or SEQ ID NO: 123.

V. PHARMACEUTICAL FORMULATIONS

Provided herein are compositions containing any of the variant CD86 polypeptides, immunomodulatory proteins, conjugates, engineered cells or infectious agents described herein. The pharmaceutical composition can further comprise a pharmaceutically acceptable excipient. For example, the pharmaceutical composition can contain one or more excipients for modifying, maintaining or preserving, for example, the pH, osmolarity, viscosity, clarity, color, isotonicity, odor, sterility, stability, rate of dissolution or release, adsorption, or penetration of the composition. In some aspects, a skilled artisan understands that a pharmaceutical composition containing cells may differ from a pharmaceutical composition containing a protein.

In some embodiments, the pharmaceutical composition is a solid, such as a powder, capsule, or tablet. For example, the components of the pharmaceutical composition can be lyophilized. In some embodiments, the solid pharmaceutical composition is reconstituted or dissolved in a liquid prior to administration.

In some embodiments, the pharmaceutical composition is a liquid, for example variant CD86 polypeptides dissolved in an aqueous solution (such as physiological saline or Ringer's solution). In some embodiments, the pH of the pharmaceutical composition is between about 4.0 and about 8.5 (such as between about 4.0 and about 5.0, between about 4.5 and about 5.5, between about 5.0 and about 6.0, between about 5.5 and about 6.5, between about 6.0 and about 7.0, between about 6.5 and about 7.5, between about 7.0 and about 8.0, or between about 7.5 and about 8.5).

In some embodiments, the pharmaceutical composition comprises a pharmaceutically-acceptable excipient, for example a filler, binder, coating, preservative, lubricant, flavoring agent, sweetening agent, coloring agent, a solvent, a buffering agent, a chelating agent, or stabilizer. Examples of pharmaceutically-acceptable fillers include cellulose, dibasic calcium phosphate, calcium carbonate, microcrystalline cellulose, sucrose, lactose, glucose, mannitol, sorbitol, maltol, pregelatinized starch, corn starch, or potato starch. Examples of pharmaceutically-acceptable binders include polyvinylpyrrolidone, starch, lactose, xylitol, sorbitol, maltitol, gelatin, sucrose, polyethylene glycol, methyl cellulose, or cellulose. Examples of pharmaceutically-acceptable coatings include hydroxypropyl methylcellulose (HPMC), shellac, corn protein zein, or gelatin. Examples of pharmaceutically-acceptable disintegrants include polyvinylpyrrolidone, carboxymethyl cellulose, or sodium starch glycolate. Examples of pharmaceutically-acceptable lubricants include polyethylene glycol, magnesium stearate, or stearic acid. Examples of pharmaceutically-acceptable preservatives include methyl parabens, ethyl parabens, propyl paraben, benzoic acid, or sorbic acid. Examples of pharmaceutically-acceptable sweetening agents include sucrose, saccharine, aspartame, or sorbitol. Examples of pharmaceutically-acceptable buffering agents include carbonates, citrates, gluconates, acetates, phosphates, or tartrates.

In some embodiments, the pharmaceutical composition further comprises an agent for the controlled or sustained release of the product, such as injectable microspheres, bio-erodible particles, polymeric compounds (polylactic acid, polyglycolic acid), beads, or liposomes.

In some embodiments, the pharmaceutical composition is sterile. Sterilization may be accomplished by filtration through sterile filtration membranes or radiation. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

In some embodiments, provided are pharmaceutical compositions containing the transmembrane immunomodulatory proteins, including engineered cells expressing such transmembrane immunomodulatory proteins. In some embodiments, the pharmaceutical compositions and formulations include one or more optional pharmaceutically acceptable carrier or excipient. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Such a formulation may, for example, be in a form suitable for intravenous infusion. A pharmaceutically acceptable carrier may be a pharmaceutically acceptable material, composition, or vehicle that is involved in carrying or transporting cells of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

In some embodiments, the pharmaceutical composition is administered to a subject. Generally, dosages and routes of administration of the pharmaceutical composition are determined according to the size and condition of the subject, according to standard pharmaceutical practice. For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy.

Long-acting pharmaceutical compositions may be administered every 3 to 4 days, every week, or biweekly depending on the half-life and clearance rate of the particular formulation. The frequency of dosing will depend upon the pharmacokinetic parameters of the molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data. A number of biomarkers or physiological markers for therapeutic effect can be monitored including T cell activation or proliferation, cytokine synthesis or production (e.g., production of TNF-α, IFN-γ, IL-2), induction of various activation markers (e.g., CD25, IL-2 receptor), inflammation, joint swelling or tenderness, serum level of C-reactive protein, anti-collagen antibody production, and/or T cell-dependent antibody response(s).

In some embodiments, the pharmaceutical composition is administered to a subject through any route, including orally, transdermally, by inhalation, intravenously, intra-arterially, intramuscularly, direct application to a wound site, application to a surgical site, intraperitoneally, by suppository, subcutaneously, intradermally, transcutaneously, by nebulization, intrapleurally, intraventricularly, intra-articularly, intraocularly, or intraspinally.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2 or more, about 3 or more, about 4 or more, about 5 or more, about 6 or more, or about 7 or more) doses are given in a week. In some embodiments, multiple doses are given over the course of days, weeks, months, or years. In some embodiments, a course of treatment is about 1 or more doses (such as about 2 or more does, about 3 or more doses, about 4 or more doses, about 5 or more doses, about 7 or more doses, about 10 or more doses, about 15 or more doses, about 25 or more doses, about 40 or more doses, about 50 or more doses, or about 100 or more doses).

In some embodiments, an administered dose of the pharmaceutical composition is about 1 μg of protein per kg subject body mass or more (such as about 2 μg of protein per kg subject body mass or more, about 5 μg of protein per kg subject body mass or more, about 10 μg of protein per kg subject body mass or more, about 25 μg of protein per kg subject body mass or more, about 50 μg of protein per kg subject body mass or more, about 100 μg of protein per kg subject body mass or more, about 250 μg of protein per kg subject body mass or more, about 500 μg of protein per kg subject body mass or more, about 1 mg of protein per kg subject body mass or more, about 2 mg of protein per kg subject body mass or more, or about 5 mg of protein per kg subject body mass or more).

In some embodiments, a therapeutic amount of a cell composition is administered. Typically, precise amount of the compositions of the present invention to be administered can be determined by a physician with consideration of individual differences in age, weight, tumor size, extent of infection or metastasis, and condition of the patient (subject). It can generally be stated that a pharmaceutical composition comprising engineered cells, e.g., T cells, as described herein may be administered at a dosage of $10^4$ to $10^9$ cells/kg body weight, such as $10^5$ to $10^6$ cells/kg body weight, including all integer values within those ranges. Engineered cell compositions, such as T cell compositions, may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

In some embodiments, the pharmaceutical composition contains infectious agents containing nucleic acid sequences encoding the immunomodulatory variant polypeptides. In some embodiments, the pharmaceutical composition contains a dose of infectious agents suitable for administration to a subject that is suitable for treatment. In some embodiments, the pharmaceutical composition contains an infectious agent that is a virus, at a single or multiple dosage amount, of between about between or between about $1\times10^5$ and about $1\times10^{12}$ plaque-forming units (pfu), $1\times10^6$ and $1\times10^{10}$ pfu, or $1\times10^7$ and $1\times10^{10}$ pfu, each inclusive, such as at least or at least about or at about $1\times10^6$, $1\times10^7$, $1\times10^8$, $1\times10^9$, $2\times10^9$, $3\times10^9$, $4\times10^9$, $5\times10^9$ pfu or about $1\times10^{10}$ pfu. In some embodiments, the pharmaceutical composition can contain a virus concentration of from or from about $10^5$ to about $10^{10}$ pfu/mL, for example, $5\times10^6$ to $5\times10^9$ or $1\times10^7$ to $1\times10^9$ pfu/mL, such as at least or at least about or at about $10^6$ pfu/mL, $10^7$ pfu/mL, $10^8$ pfu/mL or $10^9$ pfu/mL. In some embodiments, the pharmaceutical composition contains an infectious agent that is a bacterium, at a single or multiple dosage amount, of between about between or between about $1\times10^3$ and about $1\times10^9$ colony-forming units (cfu), $1\times10^4$ and $1\times10^9$ cfu, or $1\times10^5$ and $1\times10^7$ cfu, each inclusive, such as at least or at least about or at about $1\times10^4$, $1\times10^5$, $1\times10^6$, 1×10, $1\times10^8$ or $1\times10^9$ cfu. In some embodiments, the pharmaceutical composition can contain a bacterial concentration of from or from about $10^3$ to about $10^8$ cfu/mL, for example, $5\times10^5$ to $5\times10^7$ or $1\times10^6$ to $1\times10^7$ cfu/mL, such as at least or at least about or at about $10^5$ cfu/mL, $10^6$ cfu/mL, $10^7$ cfu/mL or $10^8$ cfu/mL.

A variety of means are known for determining if administration of a therapeutic composition of the invention sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity (using clinical scores known to the ordinarily skilled artisan) in the case of multiple sclerosis, measuring blood glucose in the case of type I diabetes, or joint inflammation in the case of rheumatoid arthritis.

VI. ARTICLES OF MANUFACTURE AND KITS

Also provided herein are articles of manufacture that comprise the pharmaceutical compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

Further provided are kits comprising the pharmaceutical compositions (or articles of manufacture) described herein, which may further comprise instruction(s) on methods of using the composition, such as uses described herein. The kits described herein may also include other materials desirable from a commercial and user standpoint, including other buffers, diluents, filters, needles, syringes, and package inserts with instructions for performing any methods described herein.

VII. THERAPEUTIC APPLICATIONS

Provided herein are methods using the provided pharmaceutical compositions containing a variant CD86 polypeptides immunomodulatory protein, engineered cell or infectious agent described herein, for modulating an immune response, including in connection with treating a disease or condition in a subject, such as in a human patient. The pharmaceutical compositions described herein (including pharmaceutical composition comprising the variant CD86 polypeptides, the immunomodulatory proteins, the conjugates, and the engineered cells described herein) can be used in a variety of therapeutic applications, such as the treatment of a disease. For example, in some embodiments the pharmaceutical composition is used to treat inflammatory or autoimmune disorders, cancer, organ transplantation, viral infections, and/or bacterial infections in a mammal. The pharmaceutical composition can modulate (e.g., increase or decrease) an immune response to treat the disease. In some embodiments, the methods are carried out with variant CD86 polypeptides in a format to increase an immune response in a subject. In some such aspects, increasing an immune response treats a disease or condition in the subject, such as a tumor or cancer. In some embodiments, the methods are carried out with variant CD86 polypeptides in a format to decrease an immune response in a subject. In some such aspects, decreasing an immune response treats a disease or condition in a subject, such as an inflammatory disease or condition, e.g. an autoimmune disease.

In some embodiments, the provided methods are applicable to therapeutic administration of variant CD86 polypeptides, the immunomodulatory proteins, the conjugates, the engineered cells and infectious agents described herein. It is within the level of a skilled artisan, in view of the provided disclosure, to choose a format for the indication depending on the type of modulation of the immune response, e.g., increase or decrease that is desired.

In some embodiments, a pharmaceutical composition provided herein that stimulates or increases the immune response is administered, which can be useful, for example, in the treatment of cancer, viral infections, or bacterial infections. In some embodiments, the pharmaceutical composition contains a variant CD86 polypeptide in a format that exhibits agonist activity of its cognate binding partner CD28 and/or that stimulates or initiates costimulatory signaling via CD28. Exemplary formats of a CD86 polypeptide for use in connection with such therapeutic applications include, for example, an immunomodulatory protein or "stack" of a variant CD86 polypeptide and an IgSF domain or variant thereof that binds to a tumor antigen (e.g. Nkp30 or affinity-modified variant) (also called a "tumor-localizing IgSF domain), a conjugate containing a variant CD86 polypeptide linked to a tumor-targeting moiety (also called a tumor-localizing moiety), an engineered cell expressing a transmembrane immunomodulatory protein, or an infectious agent comprising a nucleic acid molecule encoding a transmembrane immunomodulatory protein, such as for expression of the transmembrane immunomodulatory protein in an infected cell (e.g. tumor cell or APC, e.g. dendritic cell).

The provided methods to modulate an immune response can be used to treat a disease or condition, such as a tumor or cancer. In some embodiments, the pharmaceutical composition can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient. Thus, the present invention provides ex vivo and in vivo methods to inhibit, halt, or reverse progression of the tumor, or otherwise result in a statistically significant increase in progression-free survival (i.e., the length of time during and after treatment in which a patient is living with cancer that does not get worse), or overall survival (also called "survival rate;" i.e., the percentage of people in a study or treatment group who are alive for a certain period of time after they were diagnosed with or treated for cancer) relative to treatment with a control.

The cancers that can be treated by the pharmaceutical compositions and the treatment methods described herein include, but are not limited to, melanoma, bladder cancer, hematological malignancies (leukemia, lymphoma, myeloma), liver cancer, brain cancer, renal cancer, breast cancer, pancreatic cancer (adenocarcinoma), colorectal cancer, lung cancer (small cell lung cancer and non-small-cell lung cancer), spleen cancer, cancer of the thymus or blood cells (i.e., leukemia), prostate cancer, testicular cancer, ovarian cancer, uterine cancer, gastric carcinoma, a musculoskeletal cancer, a head and neck cancer, a gastrointestinal cancer, a germ cell cancer, or an endocrine and neuroendocrine cancer. In some embodiments, the cancer is Ewing's sarcoma. In some embodiments, the cancer is selected from melanoma, lung cancer, bladder cancer, and a hematological malignancy. In some embodiments, the cancer is a lymphoma, lymphoid leukemia, myeloid leukemia, cervical cancer, neuroblastoma, or multiple myeloma. In some embodiments, the cancer is breast cancer.

In some embodiments, the pharmaceutical composition is administered as a monotherapy (i.e., as a single agent) or as a combination therapy (i.e., in combination with one or more additional anticancer agents, such as a chemotherapeutic drug, a cancer vaccine, or an immune checkpoint inhibitor. In some embodiments, the pharmaceutical composition can also be administered with radiation therapy. In some aspects of the present disclosure, the immune checkpoint inhibitor is nivolumab, Tremelimumab, pembrolizumab, ipilimumab, or the like.

In some embodiments, the pharmaceutical composition suppresses an immune response, which can be useful in the treatment of inflammatory or autoimmune disorders, or organ transplantation. In some embodiments, the pharmaceutical composition contains a variant CD86 polypeptide in a format that exhibits antagonist activity of its cognate binding partner CD28 and/or that blocks or inhibits costimulatory signaling via CD28. Exemplary formats of a CD86 polypeptide for use in connection with such therapeutic applications include, for example, a variant CD86 polypeptide that is soluble (e.g. variant CD86-Fc fusion protein), an immunomodulatory protein or "stack" of a variant CD86 polypeptide and another IgSF domain, including soluble forms thereof that are Fc fusions, an engineered cell expressing a secretable immunomodulatory protein, or an infectious agent comprising a nucleic acid molecule encoding a secretable immunomodulatory protein, such as for expression and secretion of the secretable immunomodulatory protein in an infected cell (e.g. tumor cell or APC, e.g. dendritic cell).

In some embodiments, the pharmaceutical composition contains a variant CD86 polypeptide in a format that exhibits agonizes activity of its cognate binding partner CD28 and/or that facilitates costimulatory signaling via CD28. Exemplary formats of a CD86 polypeptide for use in connection with such therapeutic applications include, for example, a variant CD86 polypeptide that is a transmembrane immunomodulatory polypeptide, an engineered cell expressing a transmembrane immunomodulatory polypeptide, or an infectious agent comprising a nucleic acid molecule encoding a transmembrane immunomodulatory polypeptide, such as for expressing the transmembrane immunomodulatory protein on an infected cell (e.g. T cell, APC, e.g. dendritic cell).

In some embodiments, the inflammatory or autoimmune disorder is antineutrophil cytoplasmic antibodies (ANCA)-associated vasculitis, a vasculitis, an autoimmune skin disease, transplantation, a Rheumatic disease, an inflammatory gastrointestinal disease, an inflammatory eye disease, an inflammatory neurological disease, an inflammatory pulmonary disease, an inflammatory endocrine disease, or an autoimmune hematological disease.

In some embodiments, the inflammatory and autoimmune disorders that can be treated by the pharmaceutical composition described herein is Addison's Disease, allergies, alopecia areata, Alzheimer's, anti-neutrophil cytoplasmic antibodies (ANCA)-associated vasculitis, ankylosing spondylitis, antiphospholipid syndrome (Hughes Syndrome), asthma, atherosclerosis, rheumatoid arthritis, autoimmune hemolytic anemia, autoimmune hepatitis, autoimmune inner ear disease, autoimmune lymphoproliferative syndrome, autoimmune myocarditis, autoimmune oophoritis, autoimmune orchitis, azoospermia, Behcet's Disease, Berger's Disease, bullous pemphigoid, cardiomyopathy, cardiovascular disease, celiac Sprue/coeliac disease, chronic fatigue immune dysfunction syndrome (CFIDS), chronic idiopathic polyneuritis, chronic inflammatory demyelinating, polyradicalneuropathy (CIDP), chronic relapsing polyneuropathy (Guillain-Barré syndrome), Churg-Strauss Syndrome (CSS), cicatricial pemphigoid, cold agglutinin disease (CAD), COPD (chronic obstructive pulmonary disease), CREST syndrome, Crohn's disease, dermatitis, herpetiformus, dermatomyositis, diabetes, discoid lupus, eczema, epidermolysis bullosa acquisita, essential mixed cryoglobulinemia, Evan's Syndrome, exopthalmos, fibromyalgia, Goodpasture's Syndrome, Graves' Disease, Hashimoto's thyroiditis, idiopathic pulmonary fibrosis, idiopathic thrombocytopenia purpura (ITP), IgA nephropathy, immunoproliferative disease or disorder, inflammatory bowel disease (IBD), interstitial lung disease, juvenile arthritis, juvenile idiopathic arthritis (JIA), Kawasaki's Disease, Lambert-Eaton Myasthenic Syndrome, lichen planus, lupus nephritis, lymphocytic hypophysitis, Ménière's Disease, Miller Fish Syndrome/acute disseminated encephalomyeloradiculopathy (EMR), mixed connective tissue disease, multiple sclerosis (MS), muscular rheumatism, myalgic encephalomyelitis (ME), myasthenia gravis, ocular inflammation, pemphigus foliaceus, pemphigus vulgaris, pernicious anemia, polyarteritis nodosa, polychondritis, polyglandular syndromes (Whitaker's syndrome), polymyalgia rheumatica, polymyositis, primary agammaglobulinemia, primary biliary cirrhosis/autoimmune cholangiopathy, psoriasis, psoriatic arthritis, Raynaud's Phenomenon, Reiter's Syndrome/reactive arthritis, restenosis, rheumatic fever, rheumatic disease, sarcoidosis, Schmidt's syndrome, scleroderma, Sjörgen's Syndrome, stiff-man syndrome, systemic lupus erythematosus (SLE), systemic scleroderma, Takayasu arteritis, temporal arteritis/giant cell arteritis, thyroiditis, Type 1 diabetes, ulcerative colitis, uveitis, vasculitis, vitiligo, interstitial bowel disease or Wegener's Granulomatosis. In some embodiments, the inflammatory or autoimmune disorder is selected from interstitial bowel disease, transplant, Crohn's disease, ulcerative colitis, multiple sclerosis, asthma, rheumatoid arthritis, and psoriasis.

In some embodiments, the pharmaceutical composition is administered to modulate an autoimmune condition. For example, suppressing an immune response can be beneficial in methods for inhibiting rejection of a tissue, cell, or organ transplant from a donor by a recipient. Accordingly, in some embodiments, the pharmaceutical compositions described herein are used to limit or prevent graft-related or transplant related diseases or disorders, such as graft versus host disease (GVHD). In some embodiments, the pharmaceutical compositions are used to suppress autoimmune rejection of transplanted or grafted bone marrow, organs, skin, muscle, neurons, islets, or parenchymal cells.

Pharmaceutical compositions comprising engineered cells and the methods described herein can be used in adoptive cell transfer applications. In some embodiments, cell compositions comprising engineered cells can be used in associated methods to, for example, modulate immunological activity in an immunotherapy approach to the treatment of, for example, a mammalian cancer or, in other embodiments the treatment of autoimmune disorders. The methods employed generally comprise a method of contacting a TIP of the present invention with a mammalian cell under conditions that are permissive to specific binding of the affinity modified IgSF domain and modulation of the immunological activity of the mammalian cell. In some embodiments, immune cells (such as tumor infiltrating lymphocytes (TILs), T-cells (including CD8+ or CD4+ T-cells), or APCs) are engineered to express as a membrane protein and/or as a soluble variant CD86 polypeptide, immunomodulatory protein, or conjugate as described herein. The engineered cells can then be contact a mammalian cell, such as an APC, a second lymphocyte or tumor cell in which modulation of immunological activity is desired and under conditions that are permissive of specific binding of the affinity modified IgSF domain to a counter-structure on the mammalian cell such that immunological activity can be modulated in the mammalian cell. Cells can be contacted in vivo or ex vivo.

In some embodiments, the engineered cells are autologous cells. In other embodiments, the cells are allogeneic. In some embodiments, the cells are autologous engineered cells reinfused into the mammal from which it was isolated. In some embodiments, the cells are allogenic engineered cells infused into the mammal. In some embodiments, the cells are harvested from a patient's blood or tumor, engineered to express a polypeptide (such as the variant CD86 polypeptide, immunomodulatory protein, or conjugate as described herein), expanded in an in vitro culture system (for example, by stimulating the cells), and reinfused into the patient to mediate tumor destruction. In some embodiments, the method is conducted by adoptive cell transfer wherein cells expressing the TIP (e.g., a T-cell) are infused back into the patient. In some embodiments, the therapeutic compositions and methods of the invention are used in the treatment of a mammalian patient of cancers such as lymphoma, lymphoid leukemia, myeloid leukemia, cervical cancer, neuroblastoma, or multiple myeloma.

In some embodiments, the provided methods are for treating a subject that is or is suspected of having the disease or condition for which the therapeutic application is directed. In some cases, the subject for treatment can be selected prior to treatment based on one or more features or parameters, such as to determine suitability for the therapy or to identify or select subjects for treatment in accord with any of the provided embodiments, including treatment with any of the provided variant CD86 polypeptides, immunomodulatory proteins, conjugates, engineered cells or infectious agents.

VIII. EXEMPLARY EMBODIMENTS

Among the provided embodiments are:

1. A variant CD86 polypeptide, comprising an extracellular domain or an IgV domain or specific binding fragment thereof, wherein the variant CD86 polypeptide comprises one or more amino acid modifications in an unmodified CD86 polypeptide or a specific binding fragment thereof corresponding to position(s) selected from among 13, 18, 25, 28, 33, 38, 39, 40, 43, 45, 52, 53, 60, 68, 71, 77, 79, 80, 82, 86, 88, 89, 90, 92, 93, 97, 102, 104, 113, 114, 123, 128, 129, 132, 133, 137, 141, 143, 144, 148, 153, 154, 158, 170, 172, 175, 178, 180, 181, 183, 185, 192, 193, 196, 197, 198, 205, 206, 207, 212, 215, 216, 222, 223, or 224, with reference to positions set forth in SEQ ID NO:29.
2. The variant CD86 polypeptide of embodiment 1, wherein the amino acid modifications comprise amino acid substitutions, deletions or insertions.
3. The variant CD86 polypeptide of embodiment 1 or embodiment 2, wherein the unmodified CD86 polypeptide is a mammalian CD86 polypeptide or a specific binding fragment thereof.
4. The variant CD86 polypeptide of embodiment 3, wherein the unmodified CD86 polypeptide is a human CD86 polypeptide or a specific binding fragment thereof.
5. The variant CD86 polypeptide of any of embodiments 1-4, wherein the variant CD86 polypeptide comprises the extracellular domain of a human CD86, wherein the one or more amino acid modifications are in one or more residues of the extracellular domain of the unmodified CD86 polypeptide.
6. The variant CD86 polypeptide of any of embodiments 1-5, wherein the unmodified CD86 polypeptide comprises (i) the sequence of amino acids set forth in SEQ ID NO:29, (ii) a sequence of amino acids that has at least 95% sequence identity to SEQ ID NO:29; or (iii) a portion thereof comprising an IgV domain or specific binding fragment of the IgV domain.
7. The variant CD86 polypeptide of any of embodiments 1-6, wherein the unmodified CD86 comprises the sequence of amino acids set forth in SEQ ID NO:29.
8. The variant CD86 polypeptide of embodiment 6, wherein the portion thereof comprises amino acid residues 33-131 or 24-134 of the IgV domain or specific binding fragment of the IgV domain.
9. The variant CD86 polypeptide of any of embodiments 1-6 and embodiment 8, wherein the unmodified CD86 polypeptide comprises (i) the sequence of amino acids set forth in SEQ ID NO: 123, (ii) a sequence of amino acids that has at least 95% sequence identity to SEQ ID NO: 123; or (iii) a portion thereof comprising an IgV domain or specific binding fragment of the IgV domain.
10. The variant CD86 polypeptide of any of embodiments 1-6, wherein the unmodified CD86 comprises the sequence of amino acids set forth in SEQ ID NO:123.
11. The variant CD86 polypeptide of any of embodiments 1-6, 8 and 9, wherein the unmodified CD86 polypeptide comprises (i) the sequence of amino acids set forth in SEQ ID NO:122, (ii) a sequence of amino acids that has at least 95% sequence identity to SEQ ID NO:122; or (iii) or a specific binding fragment thereof.
12. The variant CD86 polypeptide of any of embodiments 1-6, 8, 9 and 11, wherein the unmodified CD86 comprises the sequence of amino acids set forth in SEQ ID NO:122.
13. The variant CD86 polypeptide of any of embodiments 1-12, wherein:
    the specific binding fragment has a length of at least 50, 60, 70, 80, 90, 95 or more amino acids; or
    the specific binding fragment comprises a length that is at least 80% of the length of the IgV domain set forth as residues 33-131 of SEQ ID NO:2.
14. The variant CD86 polypeptide of any of embodiments 1-13, wherein the variant CD86 comprises up to 1, 2, 3, 4, 5, 6, 7, 8, 9, 10, 11, 12, 13, 14, 15, 16, 17, 18, 19 or 20 amino acid modifications, optionally amino acid substitutions, insertions and/or deletions.
15. The variant CD86 polypeptide of any of embodiments 1-14, wherein the one or more amino acid modification are one or more amino acid substitutions selected from A13V, Q18K, Q25L, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, H90 L, H90Y, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T or I223F, or a conservative amino acid substitution thereof.

16. The variant CD86 polypeptide of any of embodiments 1-15, comprising one or more amino acid modifications selected from among Q25L/T71A/H90Y, Q25L/D53G/E212V, Q25L/H90L, N43K/I79N/H90L/I178T/E198D, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/528G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S, E38V/S114G/P143H, H90Y/L180S, H90Y/Y129N, I89V/H90L/I193V, K80E/H90Y/H222T/I223F/P224L, K80M/I88T, K92I/F113S, M60K/H90L, Q25L/F33I/H90L, Q25L/F33I/Q86R/H90L/K93T, Q25L/H90L, Q25L/H90L/P185S, Q25L/H90L/P185S/P224L, Q25L/H90L/S179R, Q25L/H90Y/S181P/I193V, Q25L/K82T/H90L/T152S/S207P, Q25L/Q86R/H90L/K93T, or S28G/H90Y.

17. The variant CD86 polypeptide of any of embodiments 1-14, wherein the one or more amino acid modifications are at position 25 and/or position 90.

18. The variant CD86 polypeptide of any of embodiments 1-14 and 17, wherein the one or more amino acid modifications comprise Q25L, H90Y, or H90L.

19. The variant CD86 polypeptide of any of embodiments 1-14 and 17, wherein the one or more amino acid modifications comprise modification at position 25 and position 90.

20. The variant CD86 polypeptide of embodiment 19, wherein the one or more amino acid modifications are selected from Q25L/H90Y or Q25L/H90L.

21. The variant CD86 polypeptide of any of embodiments 1-20, comprising one or more amino acid modifications selected from among Q25L/T71A/H90Y, Q25L/D53G/E212V, Q25L/H90L, N43K/I79N/H90L/I178T/E198D, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/S28G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S/E212X, H90Y/L180S, H90Y/Y129N, I89V/H90L/I193V, K80E/H90Y/H222T/I223F/P224L, M60K/H90L; Q25L/F33I/H90L; Q25L/F33I/Q86R/H90L/K93T; Q25L/H90L; Q25L/H90L/P185S; Q25L/H90L/P185S/P224L; Q25L/H90L/S179R; Q25L/H90Y/S181P/I193V; Q25L/K82T/H90L/T152S/S207P; Q25L/Q86R/H90L/K93T, S28G/H90Y, A13V/Q25L/H90L, Q25L/H90L/K93T/M97L, Q25L/Q86R/H90L or I89V/H90L.

22. The variant CD86 polypeptide of any of embodiments 1-21, comprising one or more amino acid modifications A13V/Q25L/H90L.

23. The variant CD86 polypeptide of any of embodiments 1-22, comprising one or more amino acid modifications A13V/Q25L/H90L/S181P/L197M/S206T.

24. The variant CD86 polypeptide of any of embodiments 1-21, comprising one or more amino acid modifications Q25L/H90L/K93T/M97L.

25. The variant CD86 polypeptide of any of embodiments 1-21 and 24, comprising one or more amino acid modifications Q25L/H90L/K93T/M97L/T133A/S181P/D215V.

26. The variant CD86 polypeptide of any of embodiments 1-21 and 24, comprising one or more amino acid modifications Q25L/Q86R/H90L.

27. The variant CD86 polypeptide of any of embodiments 1-21 and 26, comprising one or more amino acid modifications Q25L/Q86R/H90L/N104S.

28. The variant CD86 polypeptide of any of embodiments 1-21, comprising one or more amino acid modifications I89V/H90L.

29. The variant CD86 polypeptide of any of embodiments 1-21 and 28, comprising one or more amino acid modifications I89V/H90L/I193V.

30. The variant CD86 polypeptide of any of embodiments 1-21, comprising one or more amino acid modifications M60K/H90L.

31. The variant CD86 polypeptide of any of embodiments 1-21, comprising one or more amino acid modifications Q25L/F33I/H90L.

32. The variant CD86 polypeptide of any of embodiments 1-21, comprising one or more amino acid modifications Q25L/H90L/P185S.

33. The variant CD86 polypeptide of any of embodiments 1-32, wherein the variant CD86 polypeptide comprises a sequence of amino acids that exhibits at least 85%, 86%, 87%, 88%, 89%, 90%, 91%, 92%, 93%, 94%, 95%, 96%, 97%, 98% or 99% sequence identity to SEQ ID NO:29 or a specific binding fragment thereof.

34. The variant CD86 polypeptide of any of embodiments 1-33, wherein the variant CD86 polypeptide specifically binds to the ectodomain of CD28 with increased affinity compared to the binding of the unmodified CD86 for the same ectodomain.

35. The variant CD86 polypeptide of embodiment 34, wherein the binding affinity is increased at least at or about 1.5-fold, at least at or about 2.0-fold, at least at or about 5.0-fold, at least at or about 10-fold, at least at or about 20-fold, at least at or about 30-fold, at least at or about 40-fold, at least at or about 50-fold, at least at or about 60-fold, at least at or about 70-fold, at least at or about 80-fold, at least at or about 90-fold, at least at or about 100-fold, or at least at or about 125-fold.

36. The variant CD86 polypeptide of any of embodiments 1-35, wherein the variant CD86 polypeptide specifically binds to the ectodomain of CTLA-4 with decreased affinity compared to the binding of the unmodified CD86 for the same ectodomain.

37. The variant CD86 polypeptide of embodiment 36, wherein the decreased binding affinity is decreased at least at or about 1.2-fold, at least at or about 1.4-fold, at least at or about 1.5-fold, at least at or about 1.75-fold, at least at or about 2.0-fold, at least at or about 2.5-fold, at least at or about 3.0-fold, at least at or about 4.0-fold, or at least at or about 5.0-fold.

38. The variant CD86 polypeptide of any of embodiments 1-37, wherein the variant CD86 polypeptide specifically binds to the ectodomain of CTLA-4 with the same or similar binding affinity as the binding of the unmodified CD86 for the same ectodomain, optionally wherein the same or similar binding affinity is from at or about 90% to 120% of the binding affinity of the unmodified CD86.

39. The variant CD86 polypeptide of any of embodiments 1-38, wherein the variant CD86 polypeptide comprises the full extracellular domain.

40. The variant CD86 polypeptide of any of embodiments 1-39, wherein the variant CD86 polypeptide comprises the sequence of amino acids set forth in any of SEQ ID NOS: 85-121 or a specific binding fragment thereof, a sequence of amino acids that exhibits at least 95% sequence identity to any of SEQ ID NOS: 85-121 or a specific binding fragment thereof and that contains the one or more of the amino acid modifications of the respective SEQ ID NO set forth in any of SEQ ID NOS: 85-121.

41. The variant CD86 polypeptide of any of embodiments 1-40, wherein the variant CD86 polypeptide comprises the sequence of amino acids set forth in any of SEQ ID NOS: 141-177 or a specific binding fragment thereof, a sequence of amino acids that exhibits at least 95% sequence identity to any of SEQ ID NOS: 141-177 or a specific binding fragment thereof and that contains the one or more of the amino acid modifications of the respective SEQ ID NO set forth in any of SEQ ID NOS: 141-177.

42. The variant CD86 polypeptide of any of embodiments 34-41, wherein the CD28 is a human CD28.

43. The variant CD86 polypeptide of any of embodiments 34-42, wherein the CTLA-4 is a human CTLA-4.

44. The variant CD86 polypeptide of any of embodiments 1-43 that is a soluble protein.

45. The variant CD86 polypeptide of any of embodiments 1-44, wherein:
   - the variant CD86 polypeptide lacks the CD86 transmembrane domain and intracellular signaling domain; and/or
   - the variant CD86 polypeptide is not capable of being expressed on the surface of a cell.

46. The variant CD86 polypeptide of any of embodiments 1-45 that is linked to a multimerization domain.

47. The variant CD86 polypeptide of embodiment 46, wherein the multimerization domain is an Fc domain or a variant thereof with reduced effector function.

48. The variant CD86 polypeptide of any of embodiments 1-47 that is linked to an Fc domain or a variant thereof with reduced effector function.

49. The variant CD86 polypeptide of embodiment 47 or embodiment 48, wherein the Fc domain is a human IgG1 or is a variant thereof with reduced effector function.

50. The variant CD86 polypeptide of any of embodiments 47-49, wherein the Fc domain comprises the sequence of amino acids set forth in SEQ ID NO: 229 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 229.

51. The variant CD86 polypeptide of any of embodiments 47-50, wherein the Fc domain is or comprises the sequence of amino acids set forth in SEQ ID NO: 229.

52. The variant CD86 polypeptide of any of embodiments 47-50, wherein the Fc domain is a variant IgG1 Fc domain comprising one or more amino acid modifications selected from among E233P, L234A, L234V, L235A, L235E, G236del, G237A, S267K, N297G, V302C and K447del, each by EU numbering.

53. The variant CD86 polypeptide of any of embodiments 47-50 and 52, wherein the Fc domain comprises the amino acid modifications L234A/L235E/G237A.

54. The variant CD86 polypeptide of any of embodiments 47-50, 52 and 53, wherein the Fc domain comprises the amino acid modification C220S by EU numbering.

55. The variant CD86 polypeptide of any of embodiments 47-50 and 52-54, wherein the Fc domain comprises the amino acid modification K447del by EU numbering.

56. The variant CD86 polypeptide of any of embodiments 47-50 and 52-55, wherein the Fc domain comprises the sequence of amino acids set forth in SEQ ID NO: 230 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 230 and comprises one or more of the respective amino acid modifications set forth in SEQ ID NO: 230 compared to human IgG1.

57. The variant CD86 polypeptide of any of embodiments 47-50 and 52-56, wherein the Fc domain is or comprises the sequence of amino acids set forth in SEQ ID NO: 230.

58. The variant CD86 polypeptide of any of embodiments 47-57, wherein the variant CD86 polypeptide is linked to the multimerization domain or Fc indirectly via a linker, optionally a G4S linker.

59. The variant CD86 polypeptide of any of embodiments 1-43, wherein the variant CD86 polypeptide is a transmembrane immunomodulatory protein further comprising a transmembrane domain, optionally wherein the transmembrane domain is linked, directly or indirectly, to the extracellular domain (ECD) or specific binding fragment thereof of the variant CD86 polypeptide.

60. The variant CD86 polypeptide of embodiment 59, wherein the transmembrane domain comprises the sequence of amino acids set forth as residues 248-268 of SEQ ID NO:2 or a functional variant thereof that exhibits at least 85% sequence identity to residues 248-268 of SEQ ID NO:2.

61. The variant CD86 polypeptide of embodiment 59 or embodiment 60, further comprising a cytoplasmic domain, optionally wherein the cytoplasmic domain is linked, directly or indirectly, to the transmembrane domain.

62. The variant CD86 polypeptide of embodiment 61, wherein the cytoplasmic domain is or comprises a native CD86 cytoplasmic domain.

63. The variant CD86 polypeptide of embodiment 61 or embodiment 62, wherein the cytoplasmic domain comprises the sequence of amino acids set forth as residues 269-329 of SEQ ID NO:2 or a functional variant thereof that exhibits at least 85% sequence identity to residues 269-329 of SEQ ID NO:2.

64. The variant CD86 polypeptide of embodiment 61, wherein the cytoplasmic domain comprises an ITAM signaling motif and/or is or comprises an intracellular signaling domain of CD3 zeta.

65. The variant CD86 polypeptide of embodiment 59 or embodiment 60, wherein the polypeptide does not comprise a cytoplasmic signaling domain and/or is not capable of mediating or modulating an intracellular signal when expressed on a cell.
66. An immunomodulatory protein, comprising a first variant CD86 polypeptide of any of embodiments 1-65 and second variant CD86 polypeptide of any of embodiments 1-58.
67. The immunomodulatory protein of embodiment 66, wherein the first and second variant CD86 polypeptides are linked indirectly via a linker.
68. The immunomodulatory protein of embodiment 66 or embodiment 67, wherein the first and second variant CD86 polypeptide are each linked to a multimerization domain, whereby the immunomodulatory protein is a multimer comprising the first and second variant CD86 polypeptide.
69. The immunomodulatory protein of embodiment 68, wherein the multimer is a dimer, optionally a homodimer.
70. The immunomodulatory protein of any of embodiments 66-69, wherein the first variant CD86 polypeptide and the second variant CD86 polypeptide are the same.
71. An immunomodulatory protein, comprising the variant CD86 polypeptide of any of embodiments 1-65 linked, directly or indirectly via a linker, to a second polypeptide comprising an immunoglobulin superfamily (IgSF) domain of an IgSF family member.
72. The immunomodulatory protein of embodiment 71, wherein the IgSF domain is an affinity-modified IgSF domain, said affinity-modified IgSF domain comprising one or more amino acid modifications compared to the unmodified or wild-type IgSF domain of the IgSF family member.
73. The immunomodulatory protein of embodiment 72, wherein the IgSF domain is an affinity modified IgSF domain that exhibits altered binding to one or more of its cognate binding partner(s) compared to the binding of the unmodified or wild-type IgSF domain of the IgSF family member to the same one or more cognate binding partner(s).
74. The immunomodulatory protein of embodiment 73, wherein the IgSF domain exhibits increased binding to one or more of its cognate binding partner(s) compared to the binding of the unmodified or wild-type IgSF domain of the IgSF family member to the same one or more cognate binding partner(s).
75. The immunomodulatory protein of any of embodiments 71-74, wherein the IgSF domain of the second polypeptide is a tumor-localizing moiety that binds to a ligand expressed on a tumor or that binds to a ligand expressed on a tumor or is an inflammatory-localizing moiety that binds to a cell or tissue associated with an inflammatory environment.
76. The immunomodulatory polypeptide of embodiment 75, wherein the ligand is B7H6.
77. The immunomodulatory polypeptide of embodiment 75 or embodiment 76, wherein the IgSF domain is from NKp30.
78. The immunomodulatory protein of any of embodiments 71-77 wherein the immunomodulatory protein further comprises a multimerization domain linked to at least one of the variant CD86 polypeptide, or the second polypeptide.
79. The immunomodulatory protein of any of embodiments 71-78, further comprising a third polypeptide comprising an IgSF domain of an IgSF family member or an affinity-modified IgSF domain thereof, said affinity-modified IgSF domain comprising one or more amino acid modifications compared to the unmodified or wild-type IgSF domain of the IgSF family member.
80. The immunomodulatory protein of embodiment 79, wherein:
   - the third polypeptide is the same as the first and/or second polypeptide; or
   - the third polypeptide is different from the first and/or second polypeptide.
81. The immunomodulatory protein of embodiment 79 or embodiment 80, wherein the immunomodulatory protein further comprises a multimerization domain linked to at least one of the variant CD86 polypeptide, the second polypeptide and/or the third polypeptide.
82. The immunomodulatory protein of any of embodiments 68-70, 78 and 81, wherein the multimerization domain is an Fc domain of an immunoglobulin, optionally wherein the immunoglobulin protein is human and/or the Fc region is human.
83. The immunomodulatory protein of embodiment 82, wherein the Fc domain is an IgG1, IgG2 or IgG4, or is a variant thereof with reduced effector function.
84. The immunomodulatory protein of embodiment 83, wherein the Fc domain is an IgG1 Fc domain, optionally a human IgG1, or is a variant thereof with reduced effector function.
85. The immunomodulatory protein of any of embodiments 82-84, wherein the Fc domain comprises the sequence of amino acids set forth in SEQ ID NO: 229 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 229.
86. The immunomodulatory protein of any of embodiments 82-85, wherein the Fc domain is or comprises the sequence of amino acids set forth in SEQ ID NO: 229.
87. The immunomodulatory protein of embodiment 84 or embodiment 85, wherein the Fc domain is a variant IgG1 comprising one or more amino acid substitutions and the one or more amino acid substitutions are selected from E233P, L234A, L234V, L235A, L235E, G236del, G237A, S267K, or N297G, each numbered according to EU index by Kabat.
88. The immunomodulatory protein of embodiment 87, wherein the Fc domain comprises the amino acid substitution N297G, the amino acid substitutions R292C/N297G/V302C, or the amino acid substitutions L234A/L235E/G237A, each numbered according to the EU index of Kabat.
89. The immunomodulatory protein of embodiment 87 or embodiment 88, wherein the variant Fc region further comprises the amino acid substitution C220S, wherein the residues are numbered according to the EU index of Kabat.
90. The immunomodulatory protein of any of embodiments 87-89, wherein the Fc region comprises K447del, wherein the residue is numbered according to the EU index of Kabat.
91. The immunomodulatory protein of any of embodiments 84, 85 and 87-90, wherein the Fc domain comprises the sequence of amino acids set forth in SEQ ID NO: 230 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 230 and comprises one or more of the respective amino acid modifications set forth in SEQ ID NO: 230 compared to human IgG1.

92. The immunomodulatory protein of any of embodiments 84, 85 and 87-91, wherein the Fc domain is comprises the sequence of amino acids set forth in SEQ ID NO: 230.

93. A conjugate, comprising a variant CD86 polypeptide of any of embodiments 1-65 linked to a targeting moiety that specifically binds to a molecule on the surface of a cell.

94. The conjugate of embodiment 93, wherein the cell is an immune cell or is a tumor cell.

95. The conjugate of embodiment 93 or embodiment 94, wherein the moiety is a protein, a peptide, nucleic acid, small molecule or nanoparticle.

96. The conjugate of any of embodiments 93-95, wherein the moiety is an antibody or antigen-binding fragment.

97. The conjugate of any of embodiments 93-96 that is a fusion protein.

98. A nucleic acid molecule(s) encoding a variant CD86 polypeptide of any of embodiments 1-65, an immunomodulatory protein of any of embodiments 66-92 or a conjugate that is a fusion protein of any of embodiments 93-97.

99. The nucleic acid molecule of embodiment 98 that is a synthetic nucleic acid.

100. The nucleic acid molecule of embodiment 98 or embodiment 99 that is a cDNA.

101. A vector, comprising the nucleic acid molecule of any of embodiments 98-100.

102. The vector of embodiment 101 that is an expression vector.

103. The vector of embodiment 101 or embodiment 102, wherein the vector is a mammalian expression vector or a viral vector.

104. A cell, comprising the vector of any of embodiments 101-103.

105. The cell of embodiment 104 that is a mammalian cell.

106. The cell of embodiment 104 or embodiment 105 that is a human cell.

107. A method of producing a protein comprising a variant CD86 polypeptide, comprising introducing the nucleic acid molecule of any of embodiments 98-100 or vector of any of embodiments 101-103 into a host cell under conditions to express the protein in the cell.

108. The method of embodiment 107, further comprising isolating or purifying the protein from the cell.

109. A method of engineering a cell expressing a variant CD86 polypeptide, the method comprising introducing a nucleic acid molecule encoding the variant CD86 polypeptide of any of embodiments 1-65, immunomodulatory protein of any of embodiments 66-92 or a conjugate that is a fusion protein of any of embodiments 93-97 into a host cell under conditions in which the polypeptide is expressed in the cell.

110. An engineered cell, comprising a variant CD86 polypeptide of any of embodiments 1-65, immunomodulatory protein of any of embodiments 66-92 or a conjugate that is a fusion protein of any of embodiments 93-97, a nucleic acid molecule of any of embodiments 98-100 or a vector of any of embodiments 101-103.

111. The engineered cell of embodiment 110, wherein:
the variant CD86 polypeptide comprises a transmembrane domain or is the transmembrane immunomodulatory protein of any of embodiments 59-65; and/or
the protein comprising the variant CD86 polypeptide is expressed on the surface of the cell.

112. The engineered cell of embodiment 110, wherein:
the variant CD86 polypeptide does not comprise a transmembrane domain and/or is not expressed on the surface of the cell; and/or
the variant CD86 polypeptide is capable of being secreted from the engineered cell.

113. The engineered cell of embodiment 110 or embodiment 112, wherein:
the protein does not comprise a cytoplasmic signaling domain or transmembrane domain and/or is not expressed on the surface of the cell; and/or
the protein is capable of being secreted from the engineered cell when expressed.

114. The engineered cell of any of embodiments 110-113, wherein the cell is an immune cell.

115. The engineered cell of embodiment 114, wherein the immune cell is a lymphocyte.

116. The engineered cell of embodiment 115, wherein the lymphocyte is a T cell.

117. The engineered cell of embodiment 116, wherein the T cell is a CD4+ and/or CD8+ T cell.

118. The engineered cell of embodiment 116 or embodiment 117, wherein the T cell is a regulatory T cell (Treg).

119. The engineered cell of any of embodiments 110-118 that is a primary cell.

120. The engineered cell of any of embodiments 110-119, wherein the cell is a mammalian cell.

121. The engineered cell of any of embodiments 110-120, wherein the cell is a human cell.

122. The engineered cell of any of embodiments 110-121, further comprising a chimeric antigen receptor (CAR).

123. The engineered cell of any of embodiments 110-121, further comprising an engineered T-cell receptor (TCR).

124. An infectious agent, comprising a variant CD86 polypeptide of any of embodiments 1-65, immunomodulatory protein of any of embodiments 66-92 or a conjugate that is a fusion protein of any of embodiments 93-97, a nucleic acid molecule of any of embodiments 98-100 or a vector of any of embodiments 101-103.

125. The infectious agent of embodiment 124, wherein the infectious agent is a bacterium or a virus.

126. The infectious agent of embodiment 125, wherein the infectious agent is a virus and the virus is an oncolytic virus.

127. A pharmaceutical composition, comprising a variant CD86 polypeptide of any of embodiments 1-65, immunomodulatory protein of any of embodiments 66-92 or a conjugate that is a fusion protein of any of embodiments 93-97, an engineered cell of any of embodiment 110-123 or an infectious agent of any of embodiments 124-126.

128. The pharmaceutical composition of embodiment 127, comprising a pharmaceutically acceptable excipient.

129. The pharmaceutical composition of embodiment 127 or embodiment 128, wherein the pharmaceutical composition is sterile.

130. An article of manufacture comprising the pharmaceutical composition of any of embodiments 127-129 in a vial or a container.

131. The article of manufacture of embodiment 130, wherein the vial or container is sealed.

132. A kit comprising the pharmaceutical composition of any of embodiments 127-129 or the article of manufacture of embodiment 131 or embodiment 132 and instructions for use.

133. A method of modulating an immune response in a subject, the method comprising administering a variant CD86 polypeptide of any of embodiments 1-65, immunomodulatory protein of any of embodiments 66-92 or a conjugate that is a fusion protein of any of embodiments 93-97, an engineered cell of any of embodiment 110-123, an infectious agent of any of embodiments 124-126, or the pharmaceutical composition of any of embodiments 127-129.

134. A method of modulating an immune response in a subject, comprising administering the engineered cells of any of embodiments 110-123.

135. The method of embodiment 134, wherein the engineered cells are autologous to the subject.

136. The method of embodiment 134, wherein the engineered cells are allogenic to the subject.

137. The method of any of embodiments 133-136, wherein modulating the immune response treats a disease or condition in the subject.

138. A method of treating a disease or condition in a subject in need thereof, the method comprising administering a variant CD86 polypeptide of any of embodiments 1-65, immunomodulatory protein of any of embodiments 66-92 or a conjugate that is a fusion protein of any of embodiments 93-97, an engineered cell of any of embodiment 110-123, an infectious agent of any of embodiments 124-126, or the pharmaceutical composition of any of embodiments 127-129.

139. A method of treating a disease or condition in a subject in need thereof, comprising administering the engineered cells of any of embodiments 110-123.

140. The method of embodiment 139, wherein the engineered cells are autologous to the subject.

141. The method of embodiment 139, wherein the engineered cells are allogenic to the subject.

142. The method of any of embodiments 133-141, wherein the immune response is increased in the subject.

143. The method of any of embodiments 133, 137, 138 and 142, wherein an immunomodulatory protein or conjugate comprising a variant CD86 polypeptide linked to a tumor-localizing moiety is administered to the subject.

144. The method of embodiment 143, wherein the tumor-localizing moiety is or comprises a binding molecule that recognizes a tumor antigen.

145. The method of embodiment 144, wherein the binding molecule comprises an antibody or an antigen-binding fragment thereof or comprises a wild-type IgSF domain or variant thereof.

146. The method of any of embodiments 133 and 137-145, wherein a pharmaceutical composition comprising the immunomodulatory protein of any of embodiments 71-90 or the conjugate of any of embodiments 93-97 is administered to the subject.

147. The method of any of embodiments 133-142, wherein an engineered cell comprising a variant CD86 polypeptide that is a transmembrane immunomodulatory protein is administered to the subject, optionally, wherein the engineered cell is of embodiment 110, 111 and 114-123.

148. The method of any of embodiment 147, wherein the transmembrane immunomodulatory protein is of any of embodiments 59-65.

149. The method of any of embodiments 137-148, wherein the disease or condition is a tumor or cancer.

150. The method of any one of embodiments 137-149, wherein the disease or condition is selected from melanoma, lung cancer, bladder cancer, a hematological malignancy, liver cancer, brain cancer, renal cancer, breast cancer, pancreatic cancer, colorectal cancer, spleen cancer, prostate cancer, testicular cancer, ovarian cancer, uterine cancer, gastric carcinoma, a musculoskeletal cancer, a head and neck cancer, a gastrointestinal cancer, a germ cell cancer, or an endocrine and neuroendocrine cancer.

151. The method of any of embodiments 133-141, wherein the immune response is decreased.

152. The method of any of embodiments 133, 137, 138 and 151, wherein a variant CD86 polypeptide or immunomodulatory protein that is soluble is administered to the subject.

153. The method of embodiment 152, wherein the soluble polypeptide or immunomodulatory protein is an Fc fusion protein.

154. The method of any of embodiments 133, 137, 138 and 151-153, wherein a pharmaceutical composition comprising a variant CD86 polypeptide of any of embodiments 1-58, or the immunomodulatory protein of any of embodiments 66-74 and 78-91 is administered to the subject.

155. The method of any of embodiments 133, 137, 138 and 151, wherein an engineered cell comprising a secretable variant CD86 polypeptide is administered to the subject, optionally wherein the engineered cell is of any of embodiments 110 and 112-123.

156. The method of any of embodiments any of embodiments 133, 137, 138 and 151-155, wherein the disease or condition is an inflammatory or autoimmune disease or condition.

157. The method of any of embodiments 133, 137, 138 and 151-155, wherein the disease or condition is an Antineutrophil cytoplasmic antibodies (ANCA)-associated vasculitis, a vasculitis, an autoimmune skin disease, transplantation, a Rheumatic disease, an inflammatory gastrointestinal disease, an inflammatory eye disease, an inflammatory neurological disease, an inflammatory pulmonary disease, an inflammatory endocrine disease, or an autoimmune hematological disease.

158. The method of embodiment 156 or embodiment 157, wherein the disease or condition is selected from inflammatory bowel disease, transplant, Crohn's disease, ulcerative colitis, multiple sclerosis, asthma, rheumatoid arthritis, or psoriasis.

IX. EXAMPLES

The following examples are included for illustrative purposes only and are not intended to limit the scope of the invention.

Example 1

Generation of Mutant DNA Constructs of CD86 IgSF Domains

Example 1 describes the generation of mutant DNA constructs of human CD86 IgSF domains for translation and expression on the surface of yeast as yeast display libraries, introduction of DNA libraries into yeast, and selection of yeast cells expressing affinity-modified variants of CD86 ECD.

Constructs were generated based on a wildtype human CD86 sequence set forth in SEQ ID NO: 29 containing the extracellular domain (ECD; corresponding to residues 24-247 as set forth in UniProt Accession No. P42081), designated "CD86 ECD (24-247)" as follows:

```
CD86 ECD (24-247) (SEQ ID NO: 29):
APLKIQAYFNETADLPCQFANSQNQSLSELVVFWQDQENLVLNEVYLGKE

KFDSVHSKYMGRTSFDSDSWTLRLHNLQIKDKGLYQCIIHHKKPTGMIRI

HQMNSELSVLANFSQPEIVPISNITENVYINLTCSSIHGYPEPKKMSVLL

RTKNSTIEYDGVMQKSQDNVTELYDVSISLSVSFPDVTSNMTIFCILETD

KTRLLSSPFSIELEDPQPPPDHIP
```

Random DNA libraries were constructed to identify variants of the ECD of CD86 set forth in SEQ ID NO: 29. DNA encoding the wild-type ECD domain was cloned between the BamHI and KpnI sites of the modified yeast expression vector PBYDS03 (Life Technologies USA) which places the CD86 ECD N-terminal to the yeast surface anchoring domain Sag1 (the C-terminal domain of yeast α-agglutinin) with an in-frame HA fusion tag N-terminal to the CD86 ECD sequence and a c-Myc fusion tag C-terminal to the CD86 ECD sequence. Expression in this vector is driven off of the inducible gal-1 promoter. After verification of the correct DNA sequence, and proper display of the wild-type CD86 ECD protein on the yeast surface, the wild type DNA construct was used as template for error-prone PCR to introduce random mutations across the CD86 ECD sequence. After error-prone PCR, the mutagenized CD86 ECD DNA was gel purified and then PCR amplified using primers containing 40 bp overlap regions homologous to the upstream sequence of BamHI and the downstream sequence of KpnI in pBYDS03 for preparation of large scale yeast electroporation. The gel-purified, mutated CD86 ECD DNA insert was resuspended in sterile, deionized water.

The mutated CD86 library DNA was inserted into electroporation-competent BJ5464 yeast cells (ATCC) along with BamHI and KpnI digested pBYDS03 vector DNA by electroporation using a BTX ECM399 electroporation system at 2500V. Library size was determined by plating serial dilutions of freshly recovered cells on SCD-Leu agar plates. The remainder of the electroporated culture was grown to saturation under selection in SCD-Leu selection medium. Cells from this culture were subcultured 1/100 into the same medium once more and grown to saturation to minimize the fraction of untransformed cells and to allow for segregation of plasmid from cells that may contain two or more library variants. To maintain library diversity, this subculturing step was carried out using an inoculum that contained at least 10× more cells than the calculated library size. Cells from the second saturated culture were resuspended in fresh medium and frozen and stored at −80° C. (frozen library stock).

Cells from the library were thawed from individual library stocks and grown overnight. The next day cells were resuspending in galactose containing induction media (SCDG-Leu media) and grown overnight at 30° C. to induce expression of library proteins on the yeast cell surface. One liter of SCDG-Leu induction media contained 5.4 grams $Na_2HPO_4$, 8.56 grams $NaH_2PO_4H_2O$, 20 grams galactose, 2.0 grams dextrose, 6.7 grams yeast nitrogen base, and 1.6 grams yeast synthetic drop out media supplement without leucine dissolved in water and sterilized through a 0.22 μm membrane filter device.

10× induced library cells were sorted once using Protein A magnetic beads (New England Biolabs, USA) loaded with CD28-Fc to reduce non-binders and enrich for all CD86 ECD variants with the ability to bind their exogenous recombinant counter-structure proteins. This was then followed by three rounds of positive CD28 selection by protein staining with decreasing concentrations of CD28-Fc (20 nM, 1 nM or 250 pM) and fluorescence activated cell sorting (FACS) to enrich the fraction of yeast cells that displayed improved binders. Magnetic bead enrichment and selections by flow cytometry were carried out essentially as described in Miller K. D. et al., Current Protocols in Cytometry 4.7.1-4.7.30, July 2008. Hits were chosen from the third round of positive selection yeast cell outputs described above.

A second cycle of random mutagenesis was carried out from yeast cell outputs from the third round of CD28 positive selected cells. Further hits were chosen following three rounds of FACs positive selection using decreasing concentrations of CD28-Fc as described above. From yeast cell outputs from the third round of CD28-Fc positive selection, a further negative FACS selection of CTLA-4 was preformed after protein staining with 100 nM CTLA-4 Fc.

Inserts from selected FACS outputs were subcloned into an Fc fusion vector for sequence analysis of individual clones. Hits were chosen for protein production and binding and functional activity screening based on the frequency of variant amino acids that were enriched over the selection process as described in Example 2.

Example 2

Reformatting Selection Outputs as Fc-Fusions and in Various Immunomodulatory Protein Formats Exemplary Hits chosen in Example 1 were reformatted as immunomodulatory proteins containing an affinity modified (variant) CD86 fused to an Fc molecule.

Output cell pools from selected CD86 FACS sorts were grown to terminal density in SCD-Leu selection medium and plasmid DNA was isolated using a yeast plasmid DNA isolation kit (Zymoresearch, USA). For generation of Fc fusions, the affinity matured CD86 ECD variants were PCR amplified with primers containing 40 bp homologous regions on either end with an AfeI and BamHI digested Fc fusion vector encoding and in-frame with the Fc region to carry out in vitro recombination using Gibson Assembly Master Mix (New England Biolabs). The Gibson Assembly reaction was added to the *E. coli* strain NEB5alpha (New England Biolabs, USA) for heat shock transformation following the manufacturer's instructions.

Dilutions of transformation reactions were plated onto LB-agar containing 100 μg/mL carbenicillin (Teknova, USA) to isolate single colonies for selection. Generally, up to 96 colonies from each transformation were then grown in 96 well plates to saturation overnight at 37° C. in LB-broth containing 100 μg/mL carbenicillin (Teknova cat #L8112) and a small aliquot from each well was submitted for DNA sequencing to identify mutation(s) in all clones.

After sequence analysis and identification of clones of interest, plasmid DNA was prepared using the MidiPlus kit (Qiagen).

The DNA encoded generated affinity-modified (variant) CD86 Fc fusion proteins as follows: variant CD86 domain followed by a linker of 7 amino acids (GSGGGGS) followed by a human IgG1 effectorless Fc sequence set forth in SEQ ID NO: 230 containing the mutations L234A, L235E and G237A, by the Eu Index numbering system for immunoglobulin proteins. Since the construct does not include any antibody light chains that can form a covalent bond with a cysteine, the human IgG1 Fc also contained replacement of the cysteine residues to a serine residue at position 220 (C220S) by Eu Index numbering system for immunoglobulin proteins (corresponding to position 5 (C5S) with reference to the wild-type or unmodified Fc set forth in SEQ ID NO: 299). The Fc region also lacked the C-terminal lysine at position 447 (designated K447del) normally encoded in the wild type human IgG1 constant region gene (corresponding to position 232 of the wild-type or unmodified Fc) set forth in SEQ ID NO: 229.

```
                                    SEQ ID NO: 230
EPKSSDKTHTCPPCPAPEAEGAPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPG
```

Recombinant variant Fc fusion proteins were produced from suspension-adapted human embryonic kidney (HEK) 293 cells using the Expi293 expression system (Invitrogen, USA). Supernatant was harvested and the Fc Protein was captured on Mab SelectSure. (GE Healthcare cat. no. 17543801) Protein was eluted from the column using 50 mM Acetate pH3.6. The MabSelect Sure eluate is pooled and the pH is adjusted to above pH5.0. This material was then polished on a Preparative SEC column, to generate highly purified monomeric material. This material is buffer exchanged into 10 mM Acetate, 9% Sucrose pH 5.0. (A5Su) The protein purity is assessed by analytic SEC. Material is vialed and stored at −80.

Example 3

Assessment of Binding of Affinity-Matured IgSF Domain-Containing Molecules to Cell-Expressed Counter Structure This Example describes Fc-fusion binding studies of purified proteins from the above Examples to assess specificity and affinity of CD86 domain variant immunomodulatory proteins for a cognate binding partner.

Binding of the CD86 domain variants described above were assayed for binding to CD28 using Jurkat cells or to CTLA-4 using Chinese Hamster Ovary (CHO) cells that were transduced to stably express CTLA-4 (CHO/CTLA-4). For staining by flow cytometry, approximately 100,000 ligand-expressing cells were incubated with various concentrations of each candidate CD86 variant Fc fusion protein. Controls included an extracellular domain (ECD) of wild-type CD86 ("Wt CD86-Fc") and an Fc only control. To assess binding, cells were stained with an anti-human Fc secondary antibody (Jackson ImmunoResearch, USA), and samples were analyzed on an LSRII (BD Biosciences, Inc., USA) flow cytometer.

Mean Fluorescence Intensity (MFI) was calculated and compared to binding of wildtype CD86 ECD-Fc control with FlowJo Version 10 (FlowJo Version 10, USA). Results for the binding studies for binding of 11 nM of exemplary tested variant CD86 ECD-Fc fusion molecules for CD28- or CTLA-4-expressing cells are shown in Table E1. The Table also indicates amino acid substitutions in the ECD of the variant CD86 selected in the screening described above. In the Table, the exemplary amino acid substitutions and insertions in the ECD domain are designated by amino acid position number corresponding to amino acid positions in the respective reference unmodified mature CD86 extracellular domain (ECD) sequence set forth in SEQ ID NO:29. The amino acid position is indicated in the middle, with the corresponding unmodified (e.g. wild-type) amino acid listed before the number and the identified variant amino acid substitution listed after the number. Column 2 sets forth the SEQ ID NO identifier for each variant ECD domain contained in the variant ECD-Fc fusion molecule.

As shown in Table E1, the selections resulted in the identification of a number of CD86 IgSF (e.g. ECD) domain variants that were affinity-modified to exhibit increased binding for CD28. The selected variants, in some cases, exhibited altered (e.g. decreased) binding to CTLA4.

TABLE E1

Binding of CD86 ECD Variants to Cognate Binding Partners

| | | Binding to CD28 on Jurkat Cells(11 nM) | | Binding to CHO/CTLA4 Transfectants (11 nM) | |
|---|---|---|---|---|---|
| Mutations | SEQ ID NO (ECD) | MFI | Fold Increase over WT CD86 ECD | MFI | Fold Increase over WT CD86 ECD |
| Q25L, T71A, H90Y | 85 | 4062 | 286.1 | 20435 | 1.0 |
| Q25L, D53G, E212V | 86 | 166 | 11.7 | 23346 | 1.2 |
| Q25L, H90L | 87 | 3464 | 243.9 | 16961 | 0.8 |
| N43K, I79N, H90L, I178T, E198D | 88 | 11.6 | 0.8 | 13204 | 0.7 |
| A13V, Q25L, H90L, S181P, L197M, S206T | 89 | 2235 | 157.4 | 18271 | 0.9 |

TABLE E1-continued

Binding of CD86 ECD Variants to Cognate Binding Partners

| Mutations | SEQ ID NO (ECD) | Binding to CD28 on Jurkat Cells(11 nM) MFI | Binding to CD28 on Jurkat Cells(11 nM) Fold Increase over WT CD86 ECD | Binding to CHO/CTLA4 Transfectants (11 nM) MFI | Binding to CHO/CTLA4 Transfectants (11 nM) Fold Increase over WT CD86 ECD |
|---|---|---|---|---|---|
| Q25L, Q86R, H90L, K93T, L132M, V148D, S181P, P216H | 90 | 1639 | 115.4 | 21502 | 1.1 |
| Q25L, F33I, H90Y, V128A, P141A, E158G, S181P | 91 | 1445 | 101.8 | 17459 | 0.9 |
| Q25L, N39D, K80R, Q86R, I88F, H90L, K93T, N123D, N154D | 92 | 1928 | 135.8 | 19889 | 1.0 |
| Q25L, H90L, K93T, M97L, T133A, S181P, D215V | 93 | 373 | 26.3 | 17275 | 0.9 |
| Q25L, Q86R, H90L, N104S | 94 | 3834 | 270.0 | 19636 | 1.0 |
| Q25L, L40M, H90L, L180S, S183P | 95 | 2482 | 174.8 | 19802 | 1.0 |
| Q18K, Q25L, F33I, L40S, H90L | 96 | 3781 | 266.3 | 18971 | 0.9 |
| Q25L, Q86K, H90L, I137T, S181P | 97 | 387 | 27.3 | 19575 | 1.0 |
| Q25L, L77P, H90Y, K153R, V170D, S181P | 98 | 15.7 | 1.1 | 18797 | 0.9 |
| Q25L, S28G, F33I, F52L, H90L, Q102H, I178T | 99 | 749 | 52.7 | 21177 | 1.0 |
| Q25L, F33I, H90L, K144E, L180S | 100 | 1636 | 115.2 | 23546 | 1.2 |
| Q25L, F33I, H90L, K153E, E172G, T192N | 101 | 13.2 | 0.9 | 8657 | 0.4 |
| Q25L, F33I, Q86R, H90Y, D175E, 1196V, E198D | 102 | 528 | 37.2 | 22641 | 1.1 |
| Q25L, V45I, D68N, H90L, S183P, L205S | 103 | 466 | 32.8 | 17446 | 0.9 |
| E38V, S114G, P143H | 104 | | No Protein | | |
| H90Y,L180S | 105 | 11.4 | 0.8 | 6078 | 0.3 |
| H90Y, Y129N | 106 | 154 | 10.8 | 17640 | 0.9 |
| 189V, H90L, 1193V | 107 | 1248 | 87.9 | 22070 | 1.1 |
| K80E, H90Y, H222T, I223F, P224L | 108 | | No Protein | | |
| K80M, I88T | 109 | 1966 | 138.5 | 18532 | 0.9 |
| K92I, F113S | 110 | 369 | 26.0 | 20421 | 1.0 |
| M60K, H90L | 111 | 1049 | 73.9 | 17319 | 0.9 |
| Q25L, F33I, H90L | 112 | 115 | 8.1 | 20888 | 1.0 |
| Q25L, F33I, Q86R, H90L, K93T | 113 | 1316 | 92.7 | 14705 | 0.7 |
| Q25L, H90L | 114 | 1810 | 127.5 | 21873 | 1.1 |
| Q25L, H90L, P185S | 115 | 135 | 9.5 | 18546 | 0.9 |
| Q25L, H90L, P185S, P224L | 116 | 11.9 | 0.8 | 9355 | 0.5 |
| Q25L, H90L, S179R | 117 | 2397 | 168.8 | 23282 | 1.1 |
| Q25L, H90Y, S181P, 1193V | 118 | 256 | 18.0 | 16648 | 0.8 |
| Q25L, K82T, H90L, T152S, S207P | 119 | 1027 | 72.3 | 18161 | 0.9 |
| Q25L, Q86R, H90L, K93T | 120 | 1500 | 105.6 | 19777 | 1.0 |
| S28G, H90Y | 121 | | No Protein | | |
| CD86 WT ECD-Fc | 29 | 14.2 | 1.0 | 20294 | 1.0 |
| Fe only control | 230 | 11.4 | 0.8 | 32.9 | 0.0 |

Example 4

Generation and Binding Activity of CD86 IgV-Fc Immunomodulatory Proteins

Exemplary CD86 ECD variants identified and generated in Examples 1-3 were converted to an immunomodulatory protein containing the IgV domain as the only IgSF domain of the molecule. The generated variant IgV constructs were based on a wildtype human CD86 sequence set forth in SEQ ID NO: 123 containing the IgV domain (corresponding to residues 24-134 as set forth in UniProt Accession No. P42081), designated "CD86 IgV (24-134)" as follows:

```
CD86 IgV (24-134) (SEQ ID NO: 123):
APLKIQAYFNETADLPCQFANSQNQSLSELVVFWQDQENLVLNEVYLGK

EKFDSVHSKYMGRTSFDSDSWTLRLHNLQIKDKGLYQCIIHHKKPTGMI

RIHQMNSELSVLA
```

The variant CD86 IgV molecules were formatted as Fc fusion proteins as described in Example 2, and tested for binding to CD28 or CTLA-4 as described in Example 3. Results for the binding studies for binding of 25 nM of exemplary tested variant CD86 IgV-Fc fusion molecules for CD28- or CTLA-4-expressing cells are shown in Table E2. In the Table, the exemplary amino acid substitutions and insertions in the IgV domain are designated by amino acid position number corresponding to amino acid positions in the respective reference unmodified mature CD86 extracellular domain (ECD) sequence set forth in SEQ ID NO:29. The amino acid position is indicated in the middle, with the corresponding unmodified (e.g. wild-type) amino acid listed before the number and the identified variant amino acid substitution listed after the number. Column 2 sets forth the SEQ ID NO identifier for each variant IgV domain contained in the variant IgV-Fc fusion molecule.

The assay plate was briefly spun down (10 seconds at 1200 RPM) and incubated at 37° C. for 5 hours. After the 5 hour incubation, the plate was removed and equilibrated to room temperature for 15 minutes. 100 μL of Bio-Glo (Promega) were added/well of the assay plate, which was then placed on an orbital shaker for 10 minutes. Luminescence was measured with a 1 second per well integration time using a BioTek Cytation 3 luminometer.

An average relative luminescence value was determined for each variant CD86 ECD-Fc and variant CD86 IgV-Fc and a fold increase in IL-2 reporter signal was calculated for each variant compared to wildtype CD86 ECD-Fc protein. The results for the 50 nM concentrations are provided in Table E3 (CD86 ECD-Fc) or Table E4 (CD86 IgV-Fc) below. As shown, co-culturing exemplary variant CD86 ECD-Fc or variant CD86 IgV-Fc molecules with Jurkat effector cells expressing IL-2-luciferase reporter, resulted in increased CD28 costimulation (i.e., agonism) compared to WT CD86 ECD-Fc or the Fc-only negative control.

TABLE E2

Binding of CD86 IgV Variants to Cognate Binding Partners

| | | Binding to CD28 on Jurkat Cells (25 nM) | | Binding to CHO/CTLA4 Transfectants (25 nM) | |
|---|---|---|---|---|---|
| Mutations | SEQ ID NO (IgV) | MFI | Fold Increase over WT CD86 ECD | MFI | Fold Increase over WT CD86 ECD |
| A13V, Q25L, H90L | 124 | 1370 | 111.4 | 3980 | 1.0 |
| Q25L, H90L, K93T, M97L | 125 | 1425 | 115.9 | 4239 | 1.1 |
| Q25L, Q86R, H90L | 126 | 1569 | 127.6 | 4940 | 1.3 |
| 189V, H90L | 127 | 213 | 17.3 | 1660 | 0.4 |
| M60K, H90L | 128 | 20 | 1.6 | 134 | 0.0 |
| Q25L, F33I, H90L | 129 | 1383 | 112.4 | 5901 | 1.5 |
| Q25L, H90L | 130 | 1194 | 97.1 | 3587 | 0.9 |
| WT CD86 IgV-Fc | 123 | 12.3 | 1.0 | 87 | 0.0 |
| WT CD86 ECD-Fc | 29 | 12.3 | 1.0 | 3951 | 1.0 |
| Fc control | 230 | 10.5 | 0.9 | 35.9 | 0.0 |

Example 5

Assessment of Bioactivity of Affinity-Matured CD86 IgSF Domain-Containing Molecules Using a Jurkat/IL2 Reporter Assay This Example describes a Jurkat/IL2 reporter assay to assess bioactivity of CD86 domain variant immunomodulatory proteins for CD28 costimulation.

The day before the assay, the assay plate was prepared. To prepare the assay plate, 10 nM anti-CD3 antibody (clone OKT3; BioLegend, catalog no. 317315) was combined with a titration of CD86-Fc variants (concentrations ranging from 200 nM to 12 pM) or control proteins (WT CD86-Fc and Fc control) in PBS. 100 μL/well of OKT3+CD86-Fc was aliquoted into a white, flat-bottom 96-well plate (Costar). The plate was incubated overnight at 4° C. to allow the antibody and CD86-Fc variant protein to adhere to the surface of the plate. The next day, the wells of the assay plate were washed twice with 150 μL PBS prior to the assay.

The day of the assay, Jurkat effector cells expressing IL-2-luciferase reporter were counted and resuspended in assay buffer to a concentration of $1\times10^6$ cells/mL. 100 μL/well of the Jurkat cell suspension were then added assay plate.

TABLE E3

Luciferase Activity (CD86 ECD Variants)

| | | Jurkat/IL2 Luciferase Assay (10 nM OKT3 + 50 nM CD86 ECD-Fc) | |
|---|---|---|---|
| Mutations | SEQ ID NO (ECD) | Relative luminescence units (RLU) | Fold Increase over WT CD86 ECD |
| A13V, Q25L, H90L, S181P, L197M, S206T | 89 | 1125 | 8.5 |
| Q25L, H90L, K93T, M97L, T133A, S181P, D215V | 93 | 997 | 7.6 |
| Q25L, Q86R, H90L, N104S | 94 | 717 | 5.4 |
| 189V, H90L, 1193V | 107 | 218 | 1.7 |
| M60K, H90L | 111 | 202 | 1.5 |
| Q25L, F33I, H90L | 112 | 428 | 3.2 |
| Q25L, H90L, P185S | 113 | 416 | 3.2 |
| WT CD86 ECD-Fc | 29 | 132 | 1.0 |
| Fc control | 230 | 112 | 0.8 |

TABLE E4

| Luciferase Activity (CD86 IgV Variants) | | | |
|---|---|---|---|
| | | Jurkat/IL2 Luciferase Assay (10 nM OKT3 + 50 nM CD86 IgV-Fc) | |
| Mutations | SEQ ID NO (IgV) | Relative luminescence units (RLU) | Fold Increase over WT CD86 ECD |
| A13V, Q25L, H90L | 124 | 719 | 5.4 |
| Q25L, H90L, K93T, M97L | 125 | 406 | 3.1 |
| Q25L, Q86R, H90L | 126 | 800 | 6.1 |
| 189V, H90L | 127 | 562 | 4.3 |
| M60K, H90L | 128 | 818 | 6.2 |
| Q25L, F33I, H90L | 129 | 1137 | 8.6 |
| Q25L, H90L | 130 | 691 | 5.2 |
| WT CD86 ECD-Fc | 29 | 132 | 1.0 |
| Fc control | 230 | 112 | 0.8 |

Example 6

Generation and Assessment of Engineered Cells Expressing a Transmembrane Immunomodulatory Protein and a T Cell Receptor or Chimeric Antigen Receptor (CAR)

This Example describes the expression of variant CD86 IgSF domain-containing transmembrane immunomodulatory proteins (TIPs) with an exemplary recombinant HPV16 E6-specific T cell receptor (TCR) or anti-HER2 CAR in human T cells. The CD86-TIPs had an affinity-modified ECD domain and also included a wild-type CD86 transmembrane and cytoplasmic domain corresponding to residues 248-268 and 269-329 of SEQ ID NO: 2, respectively. Exemplary TIPs included a CD86 TIP containing amino acid mutations corresponding to either Q25L/Q86R/H90L/N104S (SEQ ID NO:94), I89V/H90L/I193V (SEQ ID NO:107) or Q25L/H90L/K93T/M97L/T133A/S181P/D215V (SEQ ID NO:93), wherein numbering of mutations is with reference to positions in the CD86 extracellular domain set forth in SEQ ID NO: 29.

The nucleic acid molecules encoding the TIPs were individually cloned into a lentiviral vector, which was used to transduced T cells. Briefly, lentivirus particles containing the nucleic acid sequences were produced after co-transfection of HEK293 cells with the vectors and lentivirus packaging constructs. The lentivirus particles were collected with the culture medium. Human pan T cells were isolated from peripheral blood mononuclear cells (PBMC) of normal blood donors using EasySep™ Human T Cell Isolation Kit. The pan T cells were cultured with anti-CD3 and anti-CD28 magnetic beads and IL-2 for 6 hours, and then were co-transduced with the TIP lentivirus and with lentivirus for expression of either an exemplary TCR recognizing the MHC class I presented HPV16 E6 peptide (E6 TCR) or an anti-HER2 CAR. For co-transduction, the lentiviruses were transduced at a 1:1 ratio in the presence of polybrene. Transduction was performed by using spinfection at 1000×G for 30 minutes at 30° C.

Lentivirus was removed and replaced with fresh IL-2 containing media the next day. Culture media were changed with fresh IL-2 every 2 days and transduced T cells were expanded for 10 days. After 10 days of culture, engineered cells were accessed for activity as described below. As a control, activity was compared to control T cells transduced with a WT CD86 TIP (SEQ ID NO:2), a CAR or TCR only, or to mock transduced T cells.

A. CD86 TIPs/TCR Engineered T Cells

After 10 days of culture, T cells co-transduced with a CD86 TIP and E6 TCR, or control TCR only, TIP only or mock transduced T cells, were analyzed for cytokine production following co-culture with target antigen-expressing cells using MAGPIX® Luminex, which measures the amount of cytokine in the culture media. HLA-A2+HPV+ target cells line (SCC152) were seeded into a 96-well plate starting at 40,000 cells per well, titrated at 1:2 dilution for 4-point titrations. Target cells were cultured for 6 hours to form a mono cell layer. The transduced or control T cells were added to the wells at 40,000 cells per well and cultured for another 24 hours. Culture supernatant were collected and analyzed by MAGPIX®. The results were displayed and recorded as the raw value of cytokine production in pg/mL. FIG. 1A shows release of Interferon-gamma, IL-2, and TNFα from engineered cells that co-expressed variant CD86 TIPS, plotted as pg/mL versus target cell number. Error bars represent standard deviation from triplicate wells. Increased cytokine production was observed from E6 TCR-expressing cells that co-expressed a CD86 TIP. Greater cytokine production was observed in cells co-transduced with the exemplary variant CD86 TIP compared to the WT CD86 TIP. Table E5 shows exemplary raw values of IFNg detected in supernatant following 24 hour incubation of engineered cells expressing TCR alone or in combination with wild-type or variant CD86 TIPs as indicated.

TABLE E5

| IFNg Cytokine Production (pg/mL) | | | | | | |
|---|---|---|---|---|---|---|
| | SEQ ID NO | Target Cell # | | | | |
| Mutations | (CD86 ECD) | 0 | 5000 | 10000 | 20000 | 40000 |
| TCR only | | 1.2 | 1.8 | 2.0 | 3.5 | 24.5 |
| WT CD86 and TCR | 29 | 1.2 | 1.4 | 2.9 | 7.5 | 44.7 |
| A13V/Q25L/H90L/S181P/L197M, S206T (CD86 ECD) and TCR | 89 | 1.2 | 2.3 | 3.1 | 11.1 | 56.2 |

TABLE E5-continued

| IFNg Cytokine Production (pg/mL) | | | | | | |
|---|---|---|---|---|---|---|
| | SEQ ID NO | Target Cell # | | | | |
| Mutations | (CD86 ECD) | 0 | 5000 | 10000 | 20000 | 40000 |
| Q25L/90L/93T/97L/133A/S181P/215V (CD86 ECD) and TCR | 93 | 1.2 | 1.6 | 2.9 | 17.3 | 93.0 |
| Q25L/Q86R/H90L/N104S (CD86 ECD) and TCR | 94 | 1.2 | 2.6 | 5.7 | 49.5 | 162.2 |
| I89V/H90L/I193V (CD86 ECD) and TCR | 107 | 1.3 | 2.0 | 2.7 | 10.6 | 82.2 |
| M60K/H90L (CD86 ECD) and TCR | 111 | 1.4 | 2.1 | 3.8 | 7.9 | 31.3 |
| Q25L/F33I/H90L (CD86 ECD) and TCR | 112 | 1.2 | 1.5 | 2.4 | 10.4 | 36.3 |
| Q25L/H90L/P185S (CD86 ECD) and TCR | 115 | 1.1 | 1.7 | 3.4 | 11.5 | 74.6 |
| Q25L/H90L/S179R (CD86 ECD) and TCR | 117 | 1.3 | 1.4 | 2.0 | 10.2 | 102.4 |

Figures 1B, 1C:
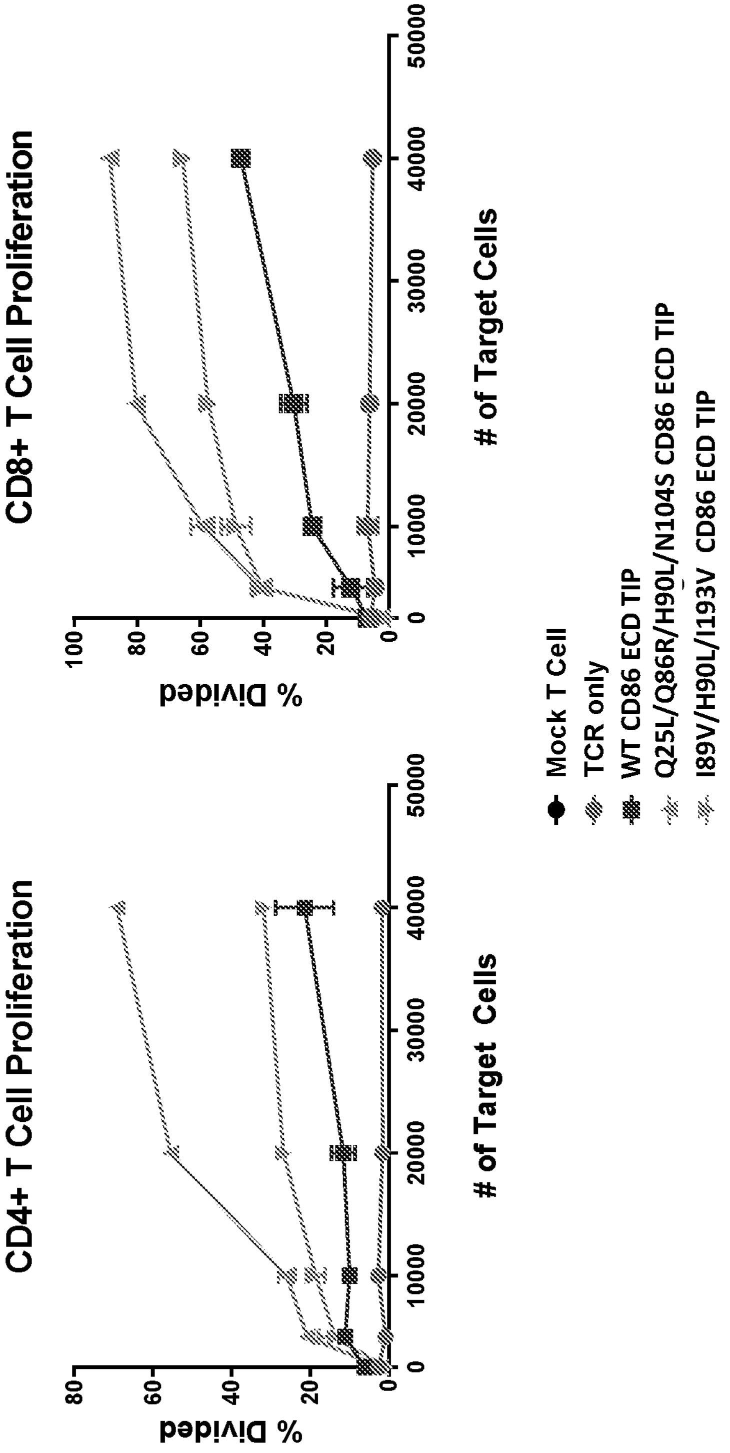
FIGS. 1B and 1C show CD4+ and CD8+ T cell proliferation, respectively, 3 days after initiation of co-culture of Mock transduced T cells or E6 TCR-transduced T cells expressing a TCR alone or co-expressing an indicated CD86 ECD TIP with varying numbers of HLA-A2+HPV+ target cells (SCC152).

Transduced cells were also Cell Trace Violet (CTV) labeled and incubated with titrated amount of SCC152 target cells and proliferation was evaluated after 3 days on TCR+CD4+(FIG. 1B) or TCR+CD8+(FIG. 1C) T cells. % Divided are plotted +/−standard deviation of triplicate wells. As shown in FIGS. 1B-1C, engineered cells that co-expressed variant CD86 TIPS had increased proliferation in response to the target SCC-152 cell line compared to control or cells expressing the wildtype CD86 TIP.

Figure 1D:
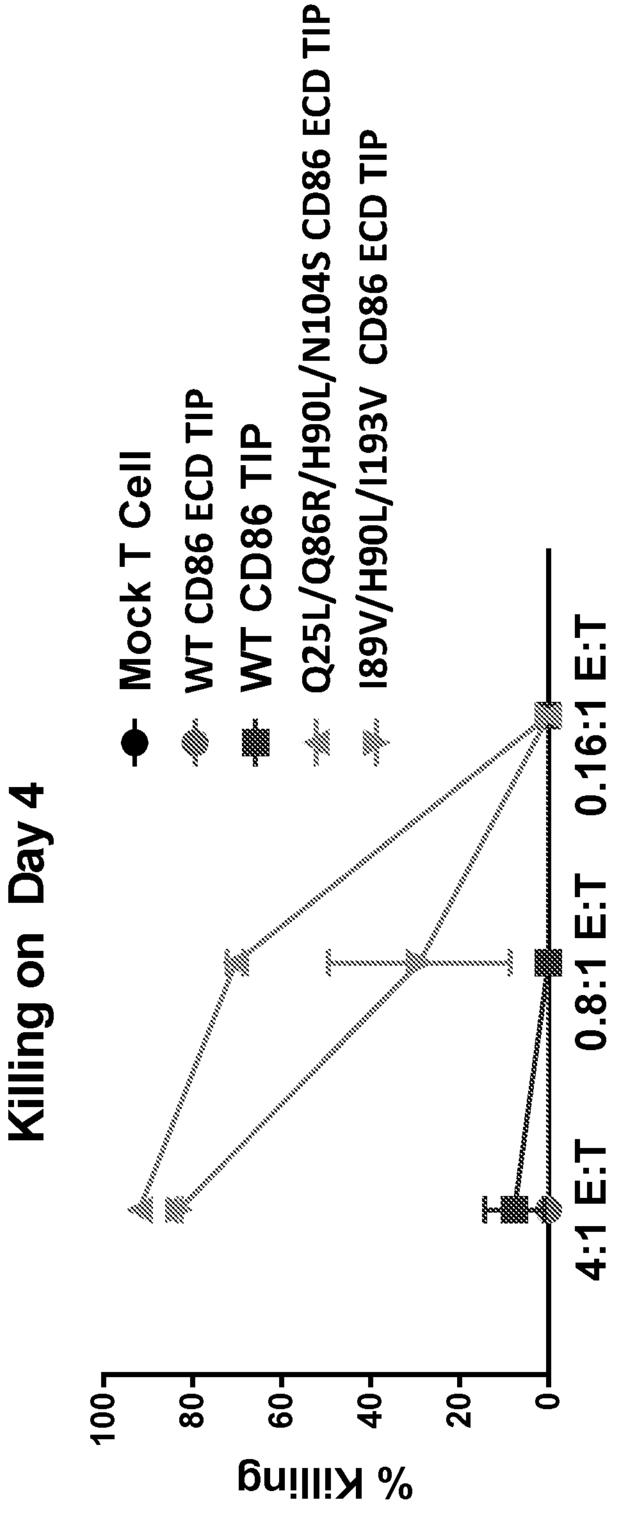
FIG. 1D shows killing activity of Mock transduced T cells and E6 TCR-transduced T cells expressing a TCR alone or co-expressing an indicated CD86 ECD TIP at different effector to target ratios (E:T) after 4 days of co-culturing with HLA-A2+HPV+ target cells (SCC152).

To assess cytotoxic activity of the engineered T cells, the HLA-A2+HPV+tumor target cell line SCC-152 was stably transduced with a virus encoding a constitutively active expression vector, which drives expression of firefly luciferase. Transduced T cells or control T cells were seeded at varying numbers to give a range of effector to target ratios (E:T ratios). T cells were incubated with target cells for 4 days at 37° C. and luciferase activity was measured. The percent killing was calculated by the formula: % Killing=(1−(luciferase signal in T cells+targets/luciferase signal from target cells only))*100%, and was plotted versus the E:T ratio. As shown in FIG. 1D, killing was observed with engineered cells that co-expressed a CD86 TIP, with little killing detected in TCR only expressing T cells. Compared to co-expression of WT CD86 TIP, co-expression of variant CD86 TIPs resulted in substantially enhanced killing activity by E6 TCR-expressing T cells. Data is shown with +/−standard deviation of triplicate wells.

B. CD86 TIP/CAR Engineered T Cells

Figure 2A:
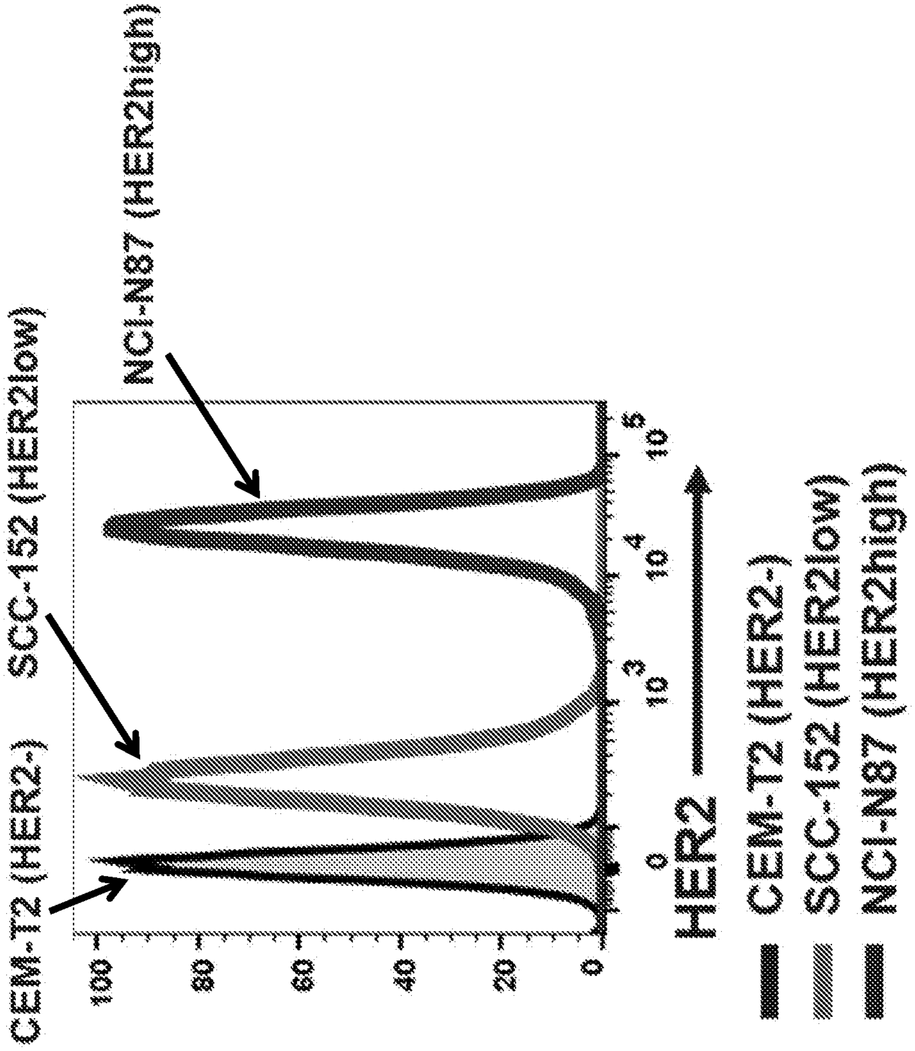
FIG. 2A depicts HER2 expression levels on CEM-T2, SCC152, and NCI-N87 cell lines.
Figure 4A:
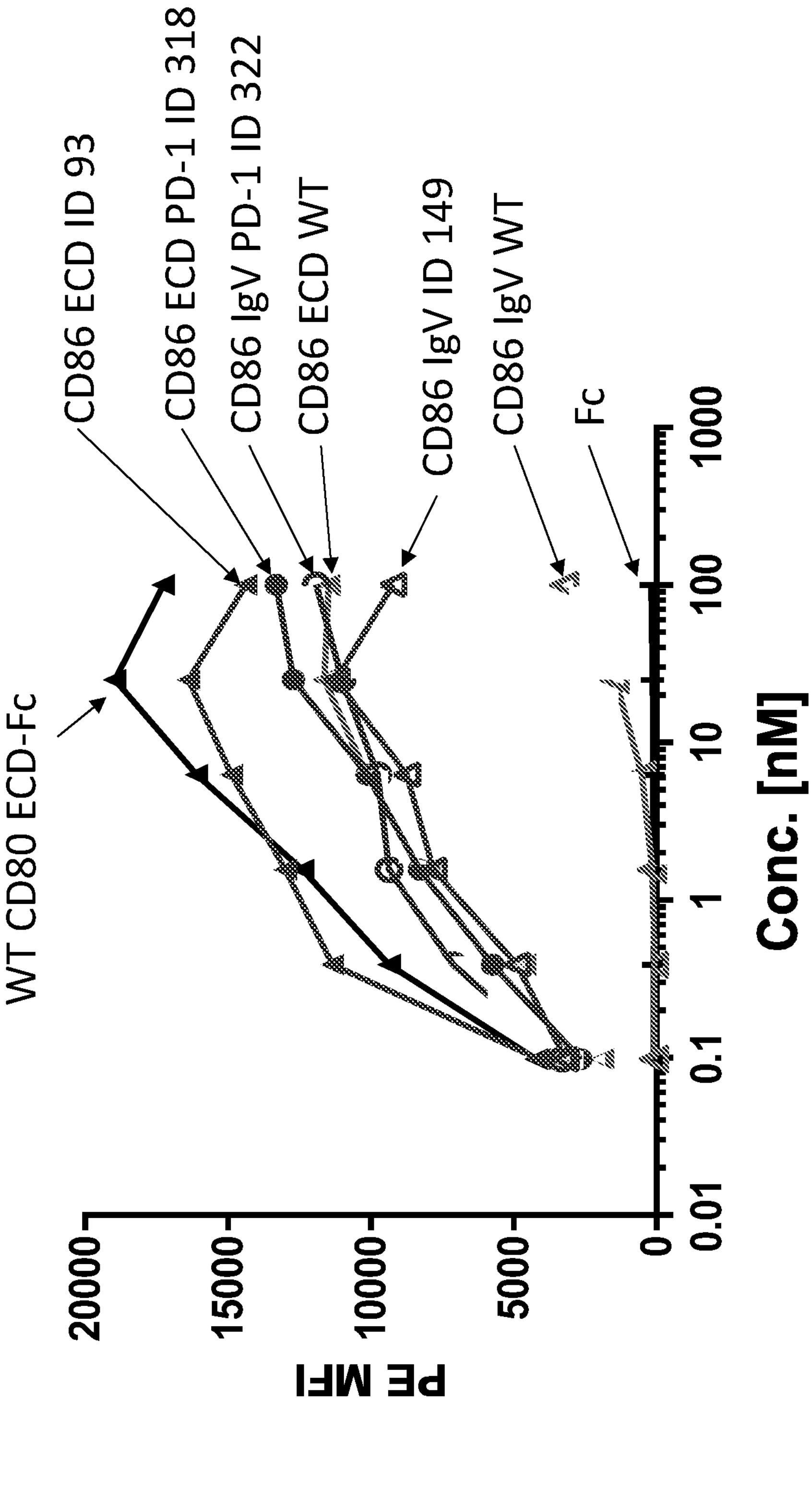
FIG. 4A and FIG. 4B depict binding of exemplary PD1-CD86 stack constructs at various concentrations (0.1 nM to 100 nM) to cognate binding partner CTLA-4, determined by Mean Fluorescence Intensity (MFI) assessed by flow cytometry.
Figure 4B:
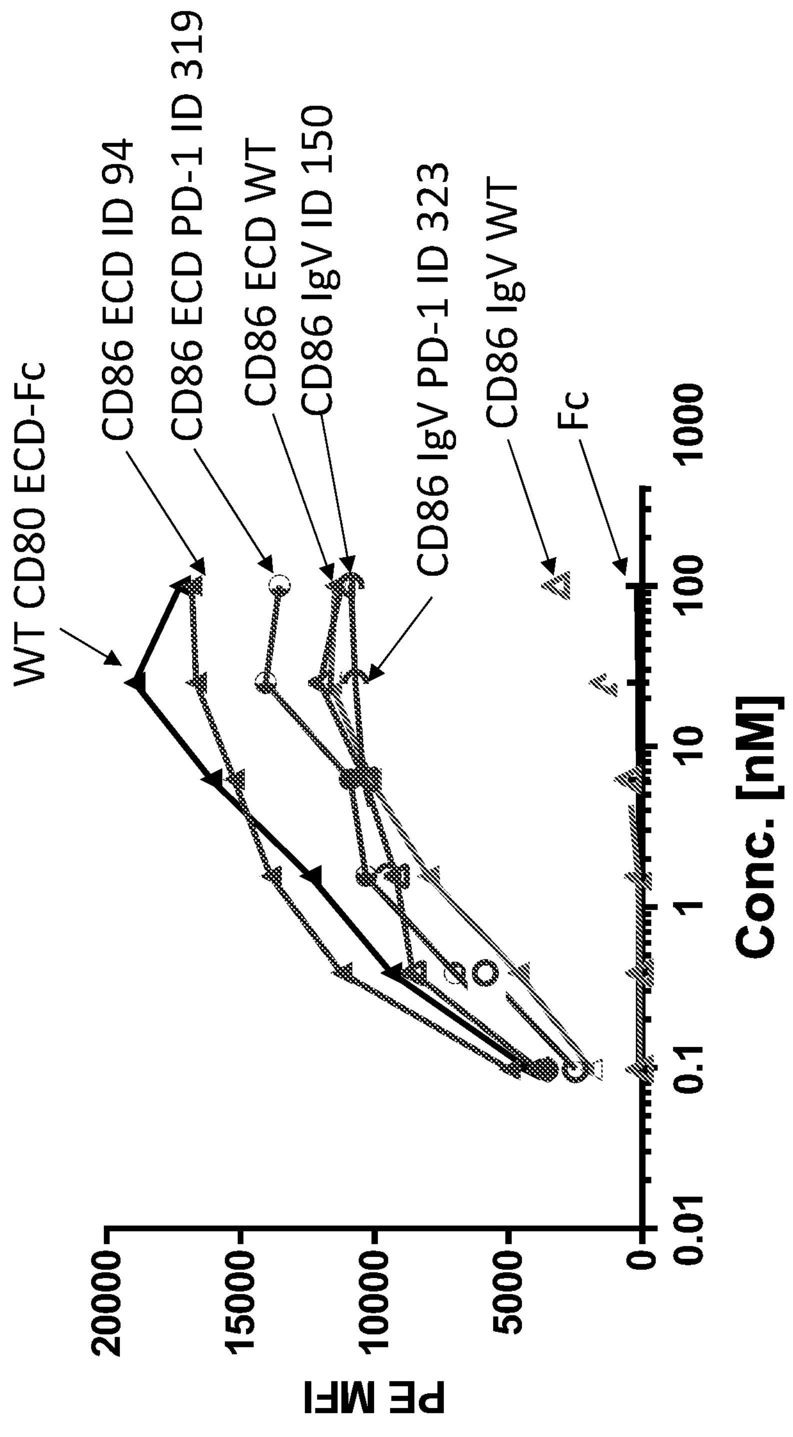
Figure 5A:
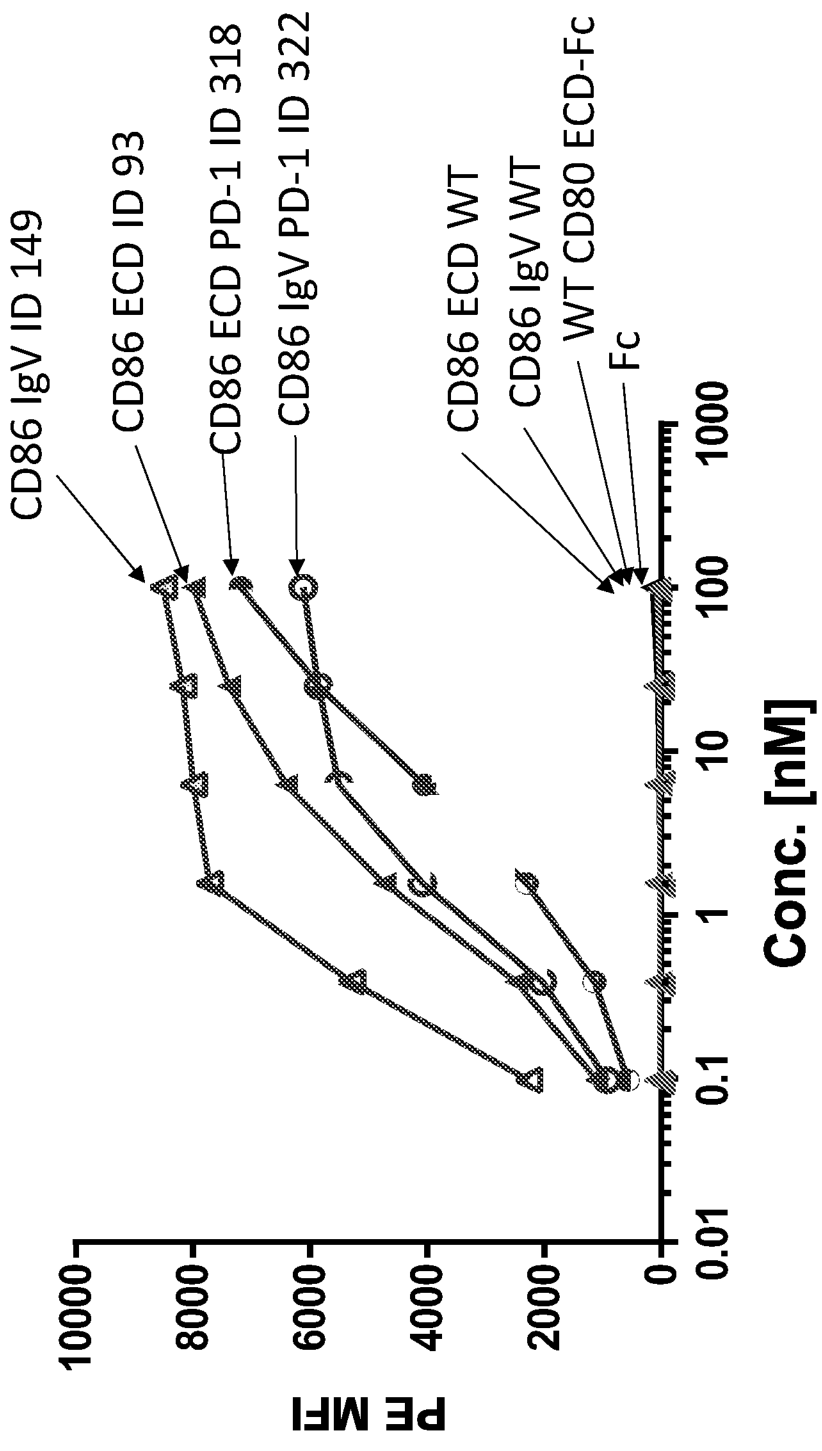
FIG. 5A and FIG. 5B depict binding of exemplary PD1-CD86 stack constructs at various concentrations (0.1 nM to 100 nM) to cognate binding partner CD28, determined by Mean Fluorescence Intensity (MFI) assessed by flow cytometry.
Figure 5B:
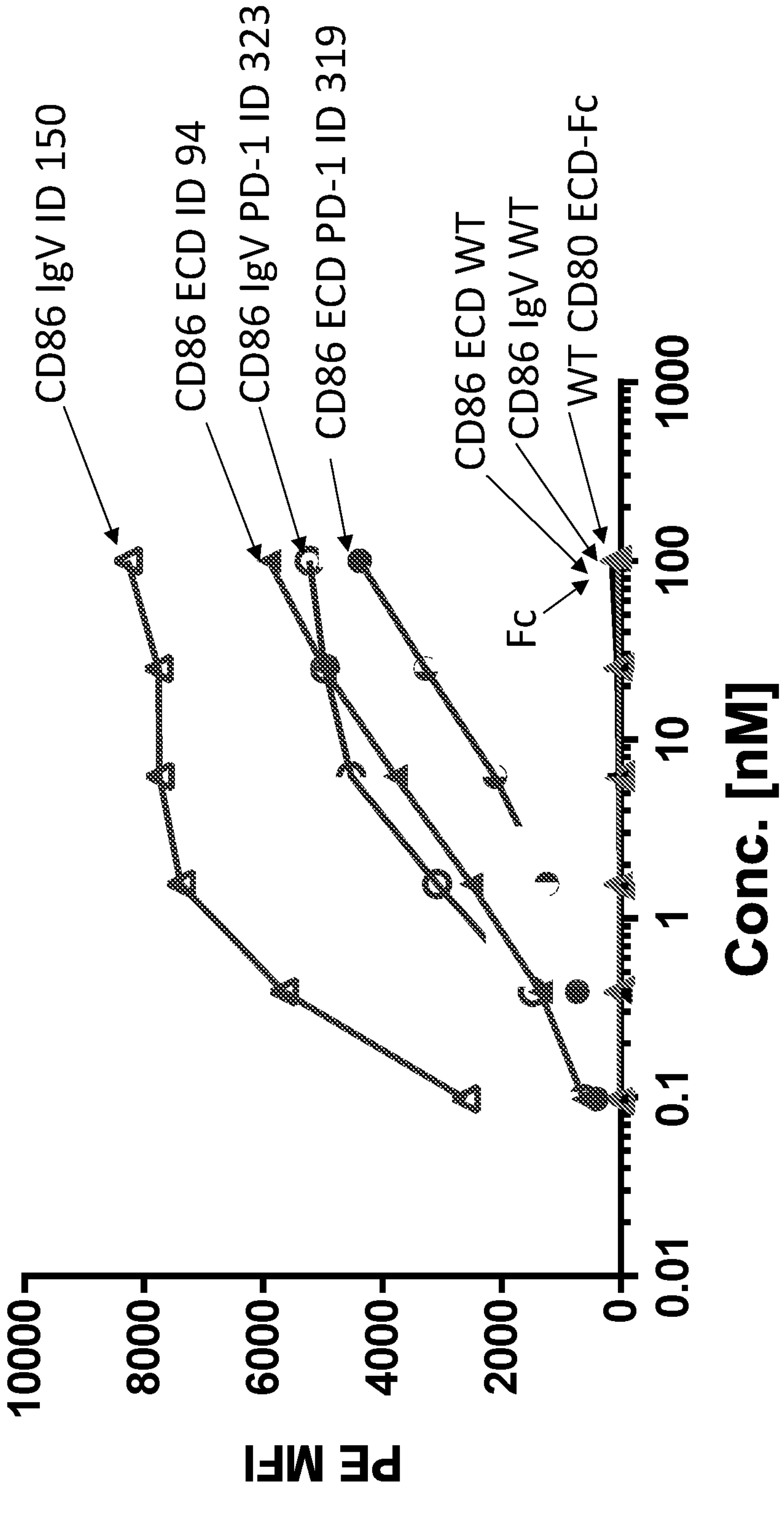
Figure 6A:
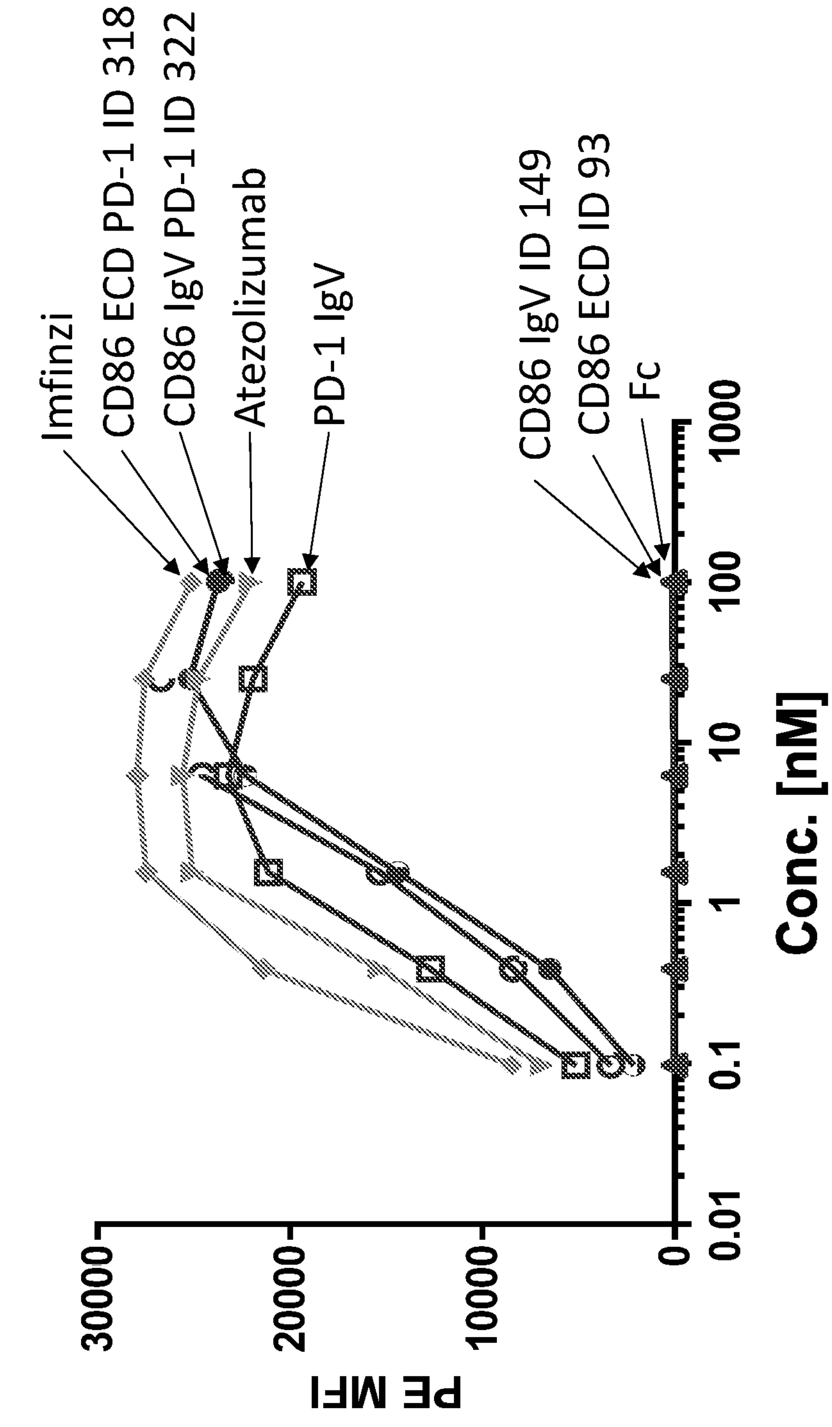
FIG. 6A and FIG. 6B depict binding of exemplary PD1-CD86 stack constructs at various concentrations (0.1 nM to 100 nM) to cognate binding partner PD-L1, determined by Mean Fluorescence Intensity (MFI) assessed by flow cytometry
Figure 6B:
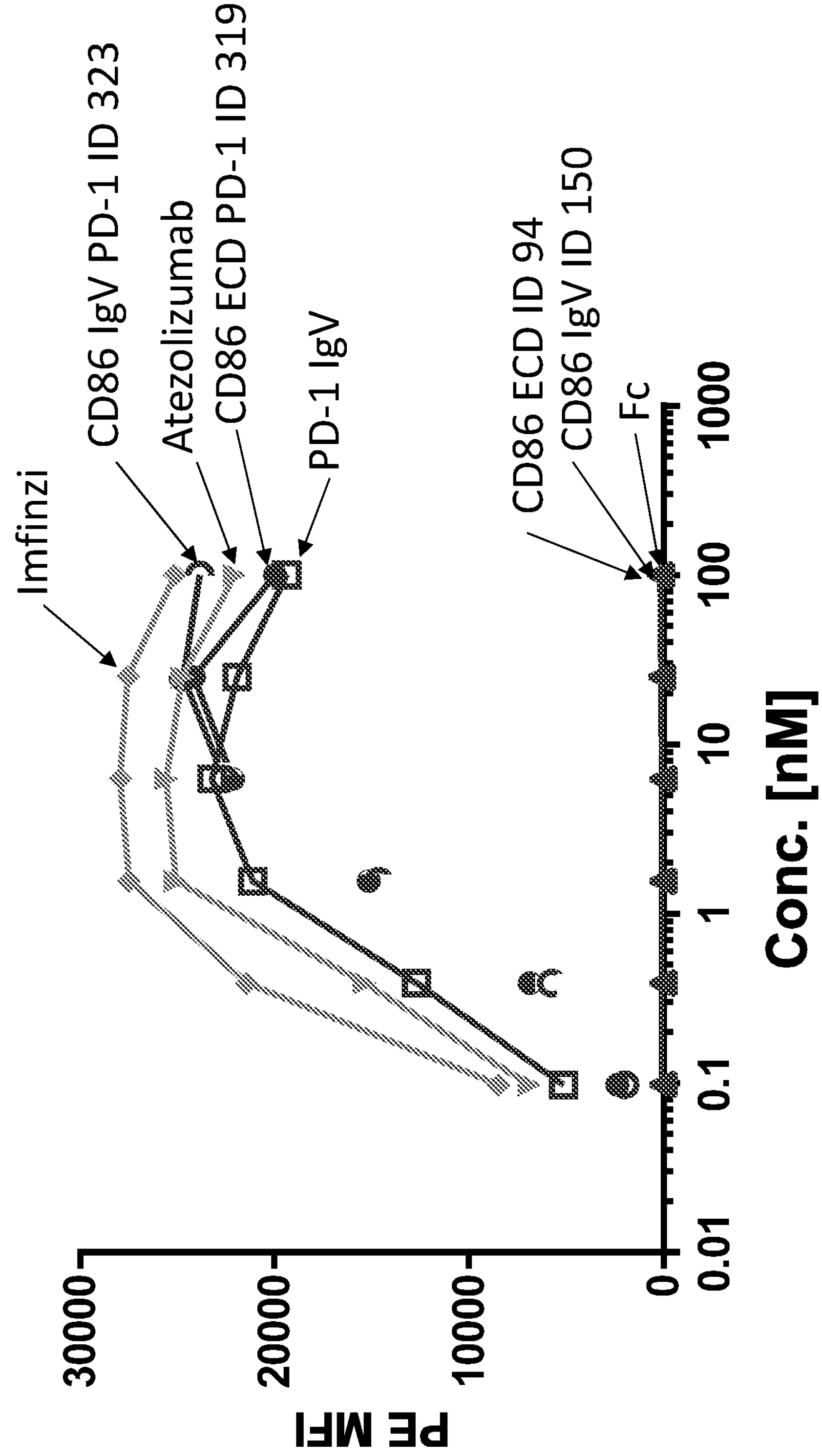

To assess cytotoxic activity, the engineered cells were incubated with target cells expressing high (NCI-N87) or low (SCC-152) levels of HER2 antigen (FIG. 2A). The target cells were stably transduced with a virus encoding a constitutively active expression vector, which drives expression of firefly luciferase, and cytotoxic activity was assessed similar to above. Anti-HER2 CAR transduced T cells were seeded at varying numbers to give a range of effector to target ratios (E:T ratios). T cells were incubated with target cells NCI-N87 or SCC-152 at 37° C. and killing activity was assessed after 24 hours by measuring luciferase activity. The percent killing was calculated by the formula: % Killing=(1−(luciferase signal in T cells+targets/luciferase signal from target cells only))*100%, and was plotted versus the E:T ratios.

As shown in FIGS. 2B and 2C, expression of a variant CD86 TIPs enhanced anti-HER2 CAR-T cell killing of target cells expressing either high antigen (FIG. 2B) or low antigen (FIG. 2C). Data is shown with +/−standard deviation of triplicate wells.

Example 7

Generation and Assessment of CD86 Stacked Molecules Containing Different Affinity-Modified Domains Selected variant CD86 molecules described in Examples 1~4 that were affinity-modified for increased binding to CD28 were used to generate "stack" Fc fusion molecules with a variant NKp30 IgV domain as a tumor localizing domain (designated "L"). The exemplary variant NKp30 was identified from screening a yeast display library containing mutagenized DNA encoding NKp30 variants for increased binding affinity to B7-H6. Following two rounds of FACS screening by staining with recombinant B7H6.Fc (rB7H6.Fc), outputs gave MFI values of 533 when stained with 16.6 nM rB7H6.Fc, whereas the parental NKp30 strain MFI was measured at 90 when stained with the same concentration of rB7H6.Fc (6-fold improvement). Among the NKp30 variants that were identified, was a variant that contained mutations L30V/A60V/S64P/S86G (SEQ ID NO:231), with reference to positions in the NKp30 extracellular domain corresponding to positions set forth in SEQ ID NO:54. The generated CD86-Nkp30 stack constructs were assessed for binding and activity.

A. Generation of CD86-NkP30 Stack Constructs

Stack constructs were obtained by combining PCR products or geneblocks (Integrated DNA Technologies, Coralville, IA) that encoded the stack in a format that enabled its fusion to Fc by standard Gibson assembly using a Gibson assembly kit (New England Biolabs, USA). The stacks were generated in a homodimer format containing two identical polypeptides by fusion with a human IgG1 effectorless Fc sequence (e.g. set forth in SEQ ID NO: 230). The encoding nucleic acid molecule of all stacks was generated to encode a protein designed as follows: a first variant CD86 ECD or IgV, followed by a 15 amino acid linker composed of three GGGGS(G4S) motifs (SEQ ID NO: 224), followed by a variant NKp30 IgV domain, followed by a GSGGGGS linker (SEQ ID NO: 222), followed by the human IgG1 effectorless Fc sequence set forth in SEQ ID NO: 230 as described above.

Expression constructs encoding Fc fusion proteins were transfected into Expi293 HEK293 cells (e.g. Invitrogen). Supernatants were harvested and protein was captured and eluted from a Protein A column using an AKTA protein purification system.

TABLE E5

| CD86-NKp30 Stacks | | |
|---|---|---|
| SEQ ID NO of | IgSF components of Stack Construct | |
| stack construct | CD86 | NKp30 |
| 135 | CD86 ECD: Q25L/H90L/K93T/M97L/T133A/S181P/D215V (ECD set forth in SEQ ID NO: 93) | SEQ ID NO: 231 |
| 136 | CD86 ECD Q25L/Q86R/H90L/N104S (ECD set forth in SEQ ID NO: 94) | SEQ ID NO: 231 |
| 137 | CD86ECD M60K/H90L (ECD set forth in SEQ ID NO: 111) | SEQ ID NO: 231 |
| 138 | CD86 ECD I89V/H90L/I193V (ECD set forth in SEQ ID NO: 107) | SEQ ID NO: 231 |
| 139 | CD86ECD Q25L/H90L/S179R (ECD set forth in SEQ ID NO: 117) | SEQ ID NO: 231 |
| 140 | CD86 IgV Q25L, Q86R, H90L, N104S (IgV set forth in SEQ ID NO: 150) | SEQ ID NO: 231 |

B. Binding

Jurkat/IL-2 cells expressing CD28 and CHO cells transduced to express CTLA-4 were used to test binding of the variant CD86 domain of the stack constructs to its cognate binding partners CD28 and CTLA-4. Cells were incubated with various concentrations (100,000 pM to 98 pM, 6 points, 1:4 dilution series) of the exemplary constructs set forth in Table E5. For comparison, binding of multiple exemplary variant CD86-Fc constructs, as described in Example 2 and Table E1, and effectorless Fc alone (SEQ ID NO: 230) were also tested. Binding was assessed by flow cytometry using an anti-Fc antibody-PE and Mean Fluorescence Intensity (MFI) was determined.

Figure 10:
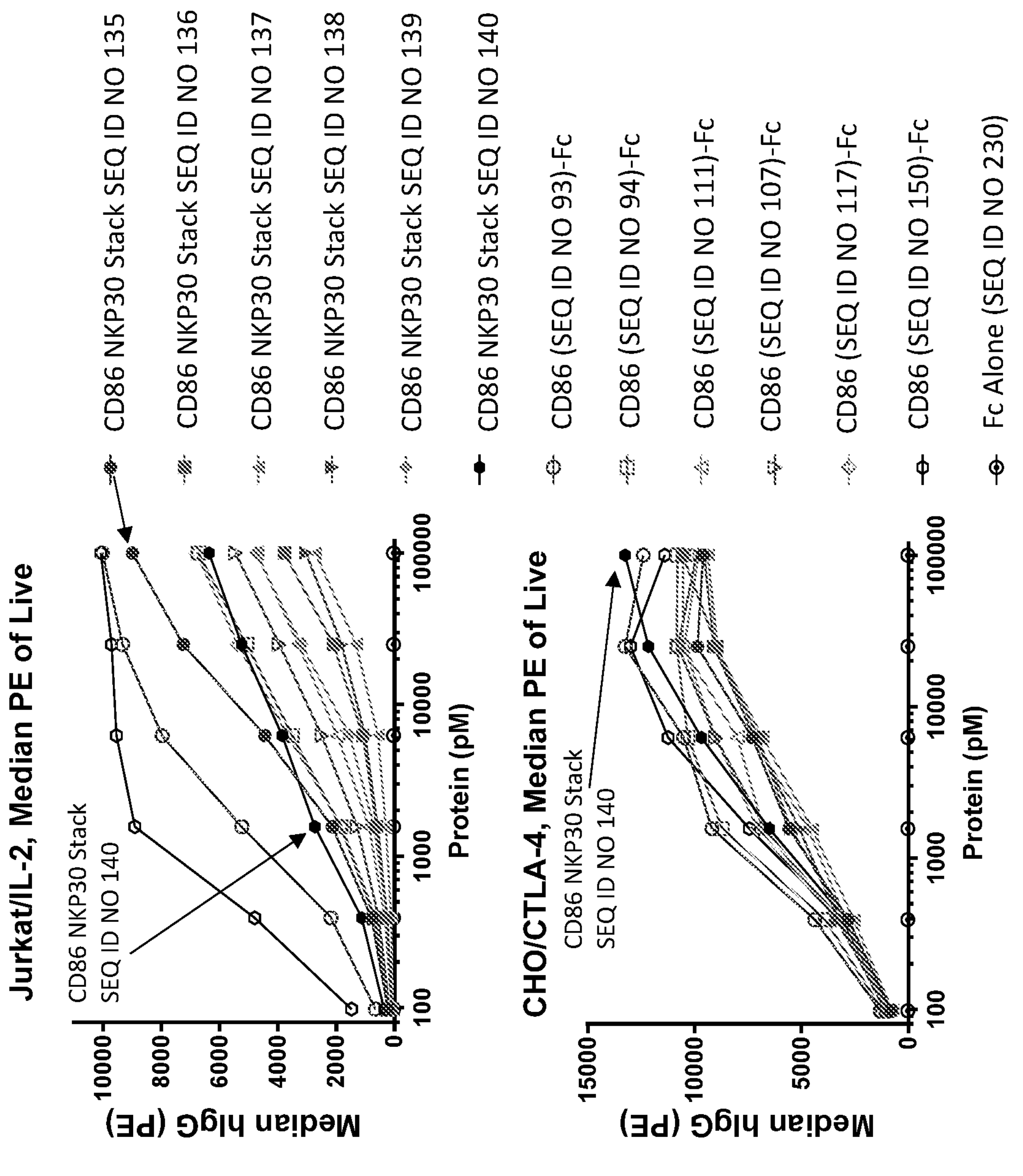
FIG. 10 depicts the binding of exemplary NKp30-CD86 stack constructs at various concentrations (100 to 100,000 pM) to CD28 and CTLA-4, determined as median hIgG PE.

As shown in FIG. 10, exemplary NKp30-CD86 stack constructs retain binding to CD28 and CTLA-4 compared to exemplary variant CD86-Fc constructs and Fc alone. Although the stack constructs generally bound less well than the corresponding variant CD86 vIgD-Fc construct, binding to CD28 and CTLA-4 was observed for all stack constructs with particularly high binding shown for the stack construct set forth in SEQ ID NO: 135.

C. T Cell Costimulation

Exemplary variant NKp30-CD86 stack constructs were assessed for their ability to costimulate primary T cells in a coimmobilization assay. Flat-bottom 96-well plates were coated with 5 nM anti-human CD3 (OKT3) and 40 nM B7H6 diluted in PBS and incubated overnight at 4° C. The following day, plates were rinsed 3 times with sterile PBS, and $1\times10^5$ CFSE-labelled human Pan T cells were added to each well. T cells were incubated for 72 hrs with 100 nM, 8.333 nM, or 0.694 nM of the exemplary NKp30-CD86 stack constructs (see Table E5). For comparison, an exemplary variant CD86 set forth by SEQ ID NO: 93 (generated as a Fc fusion as described in Example 4), an exemplary variant NKp30 set forth by SEQ ID NO: 231 (generated as a Fc fusion as described in Example 4), and effectorless Fc alone (SEQ ID NO: 230) were also tested. Experiments were performed in triplicate.

Figure 11A:
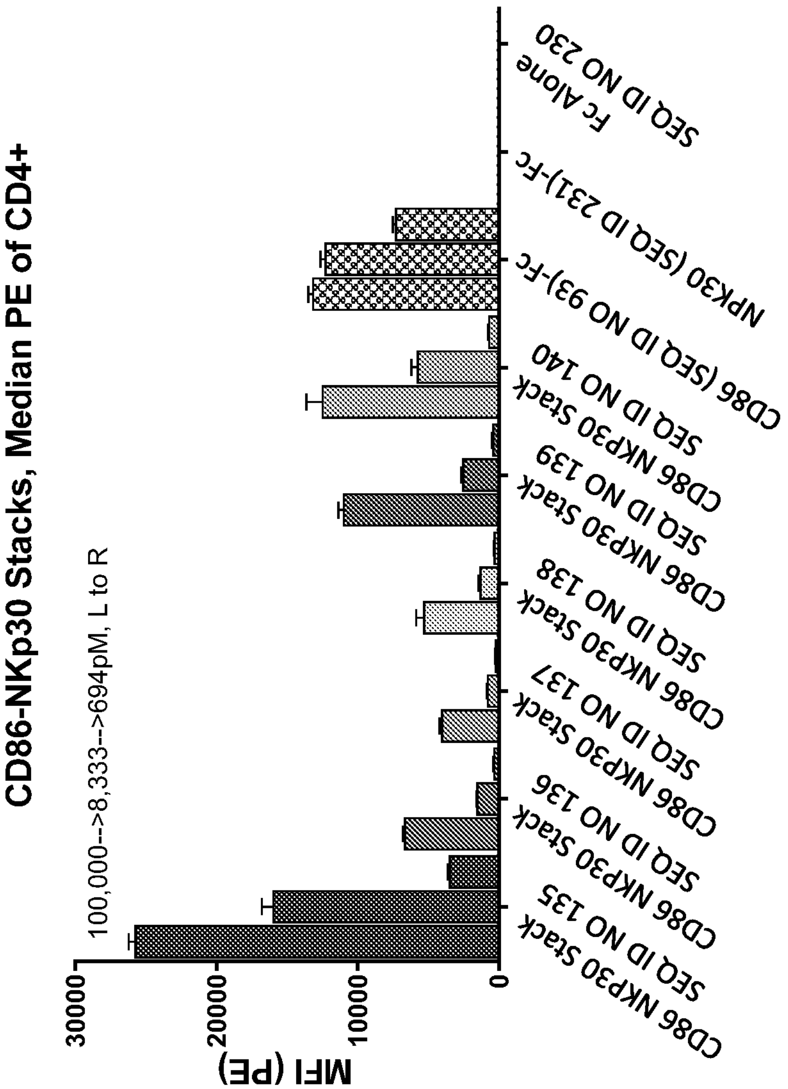
FIG. 11A depicts the binding ability of exemplary NKp30-CD86 stack constructs to primary T cells, determined by Mean Flourescence Intensity (MFI) assessed by flow cytometry.
Figure 11B:
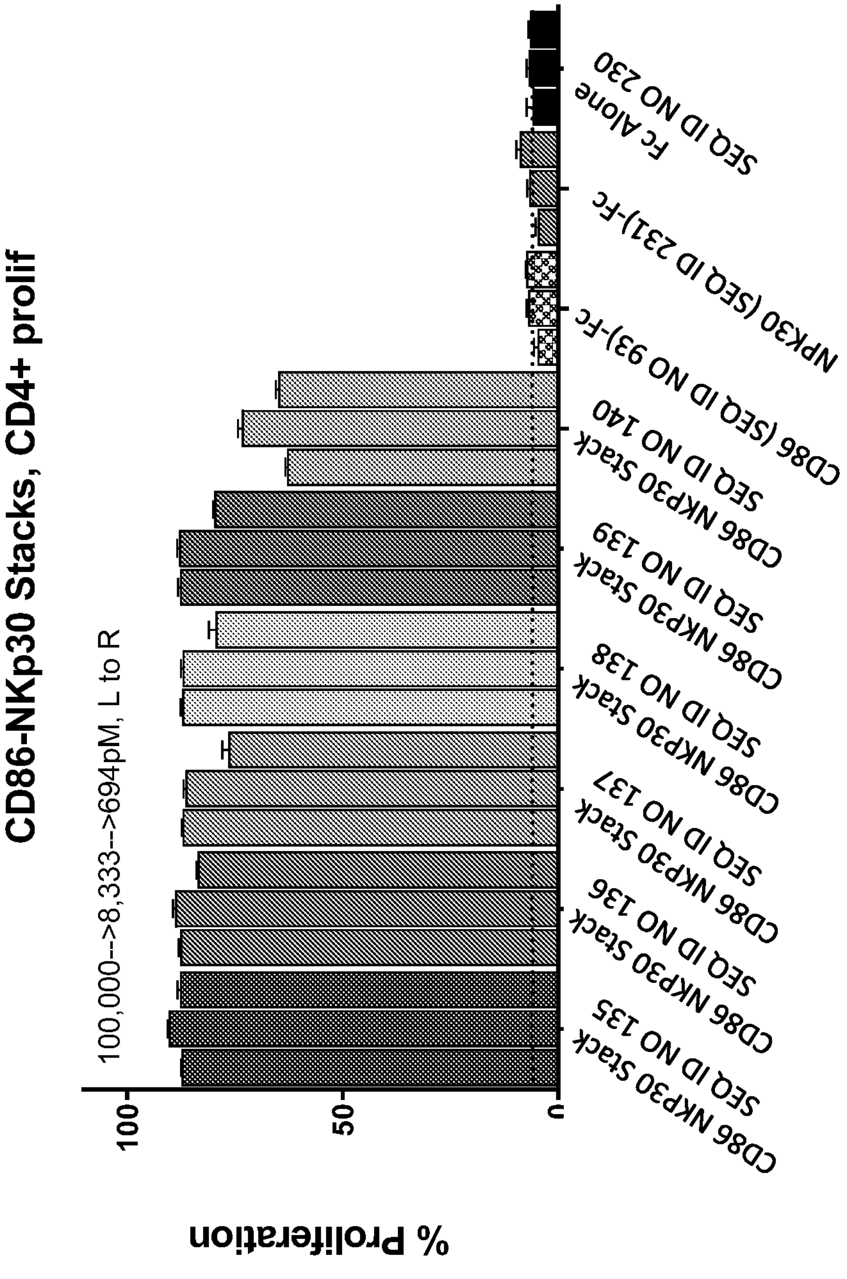
FIG. 11B shows percent T cell proliferation assessed by flow cytometry using CFSE dye.

Binding of stack constructs to primary T cells was determined by flow cytometry after staining with an anti-Fc antibody-PE and mean fluorescence intensity (MFI) was determined. T cell proliferation was assessed by flow cytometric measurement of CFSE dye dilution and percent proliferation was determined. FIG. 11A shows binding of exemplary stack constructs to primary human CD4+ T cells. As shown in FIG. 11B, incubation with the exemplary stack constructs at each concentration induced T cell proliferation compared to the exemplary variant CD86-Fc, the exemplary variant NKp30-Fc, and Fc alone. Similar binding and proliferation results were observed for CD8+ T cells.

Figure 12:
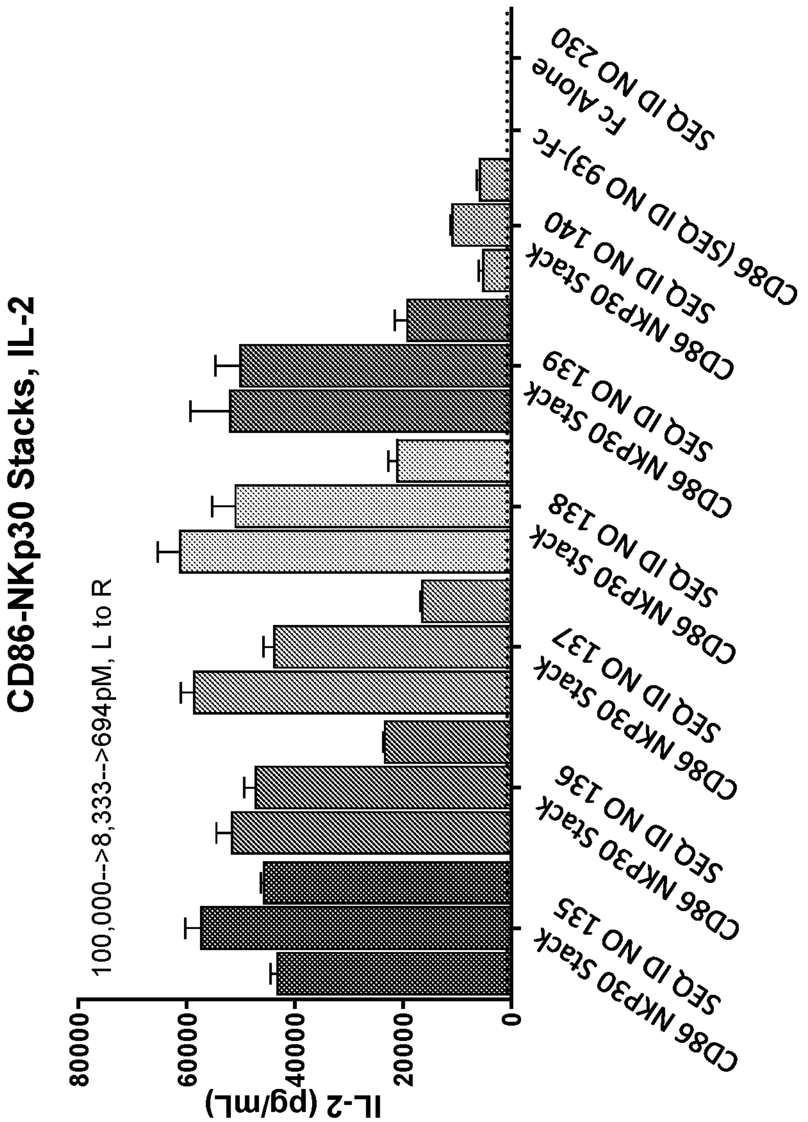
FIG. 12 depicts the concentration of IL-2 (pg/mL) harvested from T cell supernatants as assessed by ELISA.

To assess T cell cytokine production, supernatant was harvested after 24 hrs of incubation and IL-2 concentration was determined by ELISA. As shown in FIG. 12, incubation with exemplary stack constructs increased IL-2 production compared to the exemplary variant CD86-Fc and Fc alone.

Figure 13:
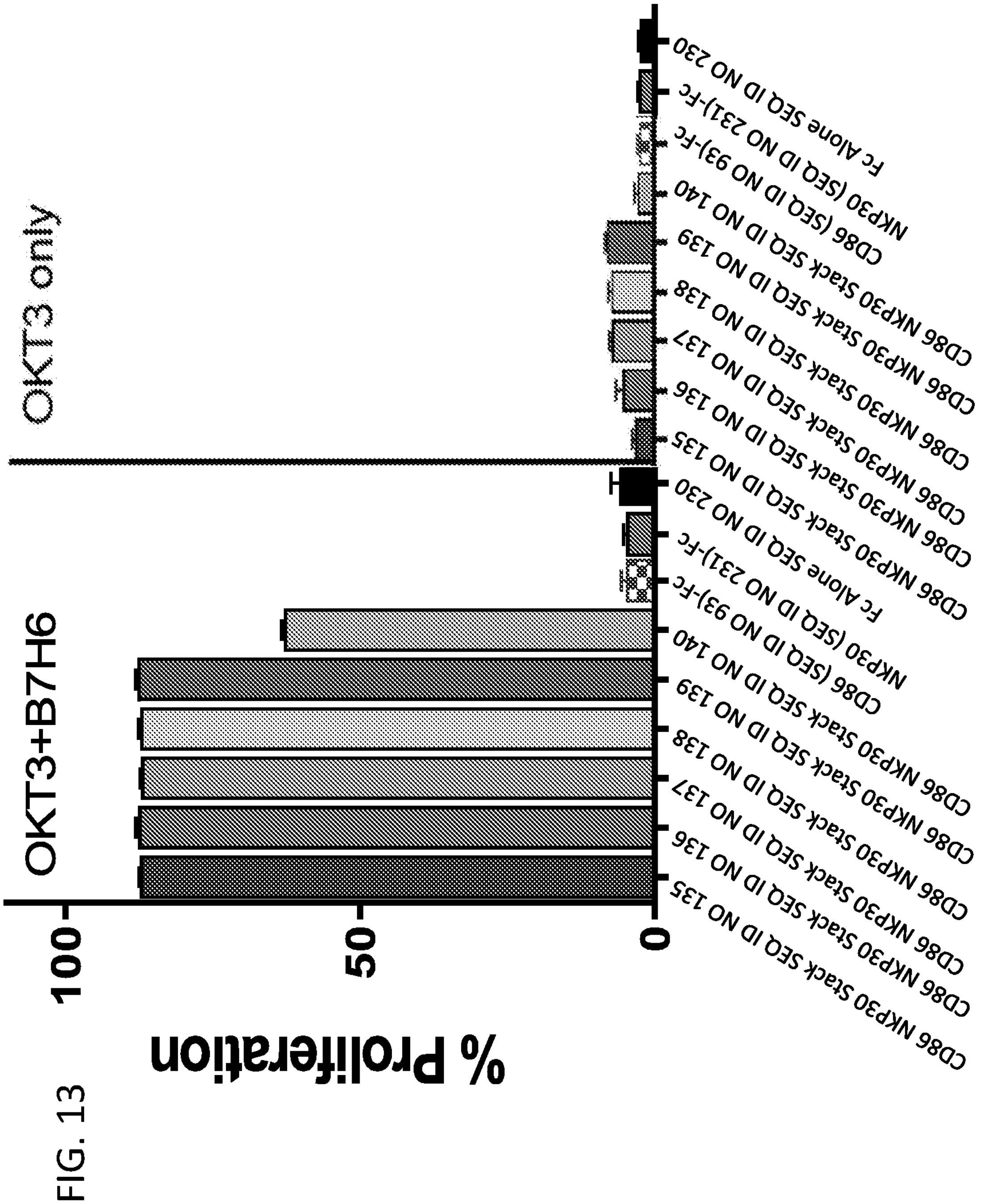
FIG. 13 depicts exemplary NKp30-CD86 stack construct costimulation in the presence (left) and absence (right) of B7H6. Percent T cell proliferation assessed by flow cytometry.

Together the above results demonstrate that the stack constructs are able to bind to primary T cells and provide costimulation. To assess whether stack construct activity depended on the presence of B7H6, the cognate binding partner of NKp30, a separate coimmobilization experiment was performed as described above, but plates were coated with anti-CD3 (OKT3) only. FIG. 13 shows that primary T cells incubated with exemplary stack constructs (100 nM) in the absence of B7H6 resulted in reduced CD4+ T cell proliferative activity compared to incubation in the presence of B7H6. Similar results were observed for CD8+ T cells. These data indicate that costimulation activity of CD86-NKp30 stack constructs is B7H6-dependent.

Example 8

Generation of Stacked Molecules Containing Variant PD-1 Molecules and Variant CD86 Molecules Exemplary variant CD86 molecules described in Examples 1-5 that were affinity-modified were used to generate "stack" Fc fusion molecules with a an exemplary variant PD-1 IgSF domain that was affinity-modified with increased binding to PD-L1 (e.g. set forth in SEQ ID NO:315). The stack constructs contained either a wild-type CD86 extracellular domain (ECD; SEQ ID NO: 29), a wild-type CD86 IgV domain (SEQ ID NO: 123), or a CD86 ECD or IgV domain affinity-modified for increased binding to CD28 as described in Table E18. Stack constructs were obtained via overlap PCR of CD86 and PD-1 sequences that encoded the stack in a format that enabled its fusion to Fc by standard Gibson assembly using a Gibson assembly kit (New England Biolabs, USA). The encoding nucleic acid molecule of all stacks was generated to encode a protein designed as follows: a first wild-type or variant CD86 ECD or IgV domain, followed by a 15 amino acid linker composed of three GGGGS(G4S) motifs (SEQ ID NO: 224), followed by a variant PD-1 domain, followed by a GSGGGGS linker (SEQ ID NO: 222), followed by the human IgG1 effectorless Fc sequence set forth in SEQ ID NO: 230 as described above.

Table E6 sets forth exemplary generated CD86-PD-1 Stacks.

TABLE E6

| CD86-PD-1 Stacks | | |
|---|---|---|
| SEQ ID NO of | IgSF components of Stack Construct | |
| stack construct | CD86 | PD-1 |
| 316 | WT CD86 ECD (ECD set forth in SEO ID NO: 29) | SEQ ID NO: 315 |
| 317 | CD86 ECD: A13V/Q25L/H90L/S181P/L197M/S206T (ECD set forth in SEQ ID NO: 89 ) | SEQ ID NO: 315 |
| 318 | CD86 ECD: Q25L/H90L/K93T/M97L/T133A/S181P/D215V (ECD set forth in SEQ ID NO: 93) | SEQ ID NO: 315 |
| 319 | CD86 ECD: Q25L/Q86R/H90L/N104S (ECD set forth in SEQ ID NO: 94) | SEQ ID NO: 315 |
| 320 | CD86 IgV domain (IgV set forth in SEQ ID NO: 123) | SEQ ID NO: 315 |
| 321 | CD86 IgV: A13V/Q25L/H90L/S181P/L197M/S206T (IgV set forth in SEQ ID NO: 145) | SEQ ID NO: 315 |
| 322 | CD86 IgV: Q25L/H90L/K93T/M97L/T133A/S181P/D215V (IgV set forth in SEQ ID NO: 149) | SEQ ID NO: 315 |
| 323 | CD86 IgV: Q25L/Q86R/H90L/N104S (IgV set forth in SEQ ID NO: 150) | SEQ ID NO: 315 |

Example 9

Assessment of Binding and Activity of Stacked Molecules Containing Variant PD-1 Molecules and Variant CD86 Molecules Exemplary stack constructs were generated substantially as described in Example 8, containing a variant PD-1 IgSF domain (e.g. SEQ ID NO:315) with either a wild-type CD86 extracellular domain (ECD; e.g. SEQ ID NO: 29), a wild-type CD86 IgV domain (e.g. SEQ ID NO: 123), or a variant CD86 IgSF domain (ECD, e.g. SEQ ID NO: 89 or 93 or 94; or IgV, e.g SEQ ID NO: 145, 149 or 150), and were assessed for binding and activity.

A. Binding

To assess binding to cognate binding partners, cells were transduced to express huCTLA, huCD28 and huPD-L1 full-length mammalian proteins. Cells were incubated with various concentrations (0.1 nM to 100 nM) of the exemplary constructs set forth in Table E6. For comparison, binding of wild-type CD80-Fc was also tested. For binding to PD-L1, binding also was compared to anti-PD-1 antibodies (Imfinzi and Atezolizumab). An Fc only molecule was also tested as a control. Binding was assessed by flow cytometry and mean Fluorescence Intensity (MFI) was determined.

As shown in FIGS. 4A-6B, exemplary PD1-CD86 stack constructs retain binding to CTLA-4, CD28 and PD-L1 compared to molecules containing only individual wild-type or variant IgSF domains. Stack constructs containing mutations Q25L/H90L/K93T/M97L/T133A/S181P/D215V in IgV (SEQ ID NO:149, e.g. stack set forth in SEQ ID NO:322) or ECD (SEQ ID NO:93, e.g. stack set forth in SEQ ID NO:318) retain binding to CTLA-4 (FIG. 4A), CD28 (FIG. 5A) and PD-L1 (FIG. 6A), compared to molecules containing only individual wild-type or variant IgSF domains. Stack constructs containing mutations Q25L/Q86R/H90L/N104S in IgV (SEQ ID NO:150, e.g. stack set forth in SEQ ID NO:323) or ECD (SEQ ID NO:94, e.g. stack set forth in SEQ ID NO:319) retain binding to CTLA-4 (FIG. 4B), CD28 (FIG. 5B) and PD-L1 (FIG. 6B), B. PD-L1-Dependent CD28 Costimulation Exemplary variant stack constructs were assessed for their ability to deliver PD-L1 dependent costimulation of CD28 using Jurkat/IL-2 reporter cells expressing PD-1. K562/OKT3/PD-L1 or K562/OKT3 artificial antigen presenting cells (aAPCs) were plated at 20,000 cells/well and pre-incubated with various amounts of exemplary variant stack constructs from 0.01 nM to 100 nM. An Fc only molecule was also tested as control. Jurkat effector cells expressing an IL-2-luciferase reporter were added at a total of 100,000 cells per well, such that each well had a final ratio of 1:5 K562: Jurkat cells. Jurkat cells, K562 cells, and exemplary stack constructs were incubated for 6 hours at 37 degrees Celsius. 100 μL of a cell lysis and luciferase substrate solution (BioGlo luciferase reagent, Promega) were added to each well and luminescence was measured.

Figure 7A:
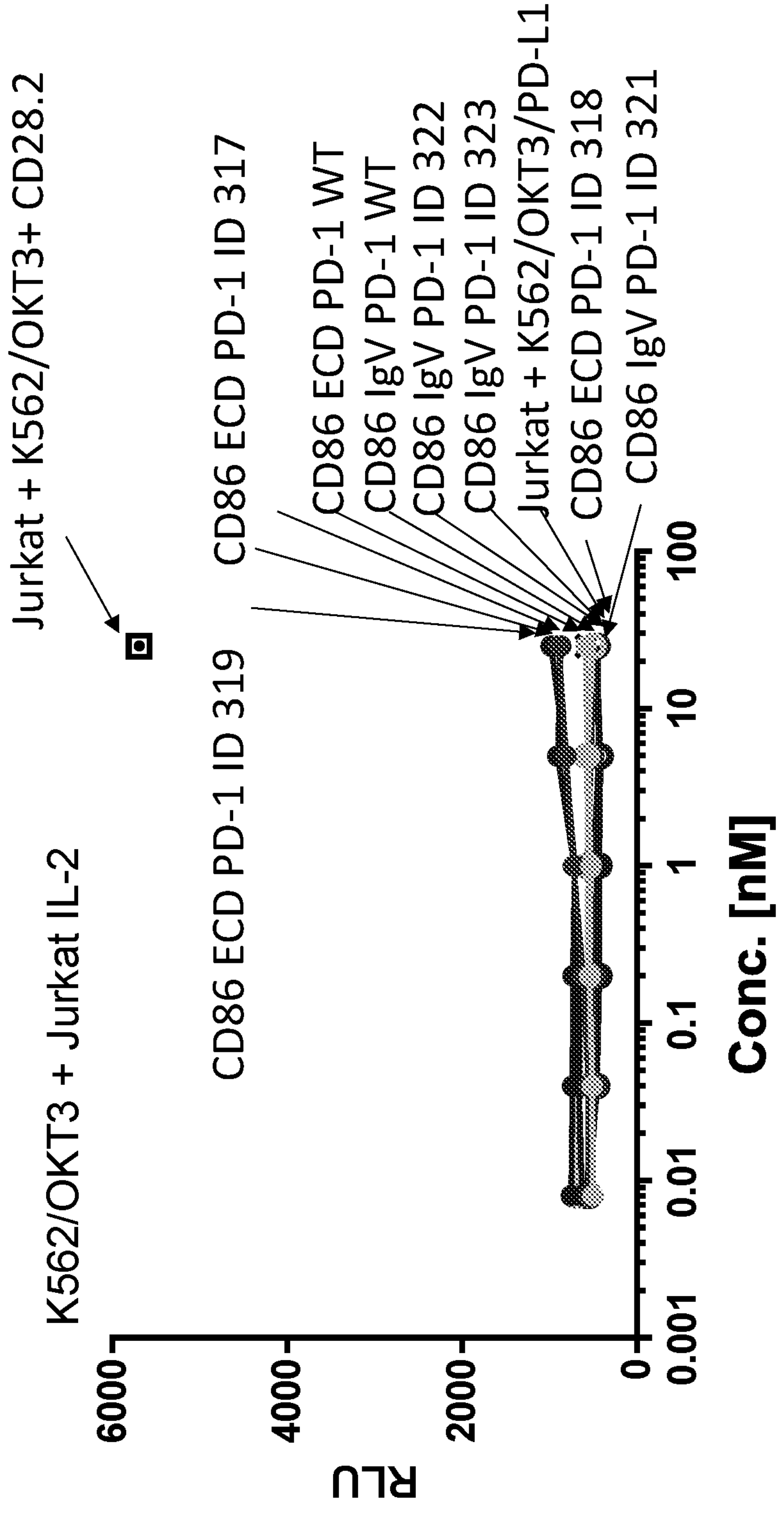
FIG. 7A and FIG. 7B depict the ability of exemplary variant PD1-CD86 stack constructs to deliver PD-L1 dependent costimulation of CD28 using Jurkat/IL-2 reporter cells (FIG. 7A) or Jurkat/IL-2 reporter cells expressing PD-L1 (FIG. 7B), as measured by IL-2 luminiscence relative luminescence units (RLU).
Figure 7B:
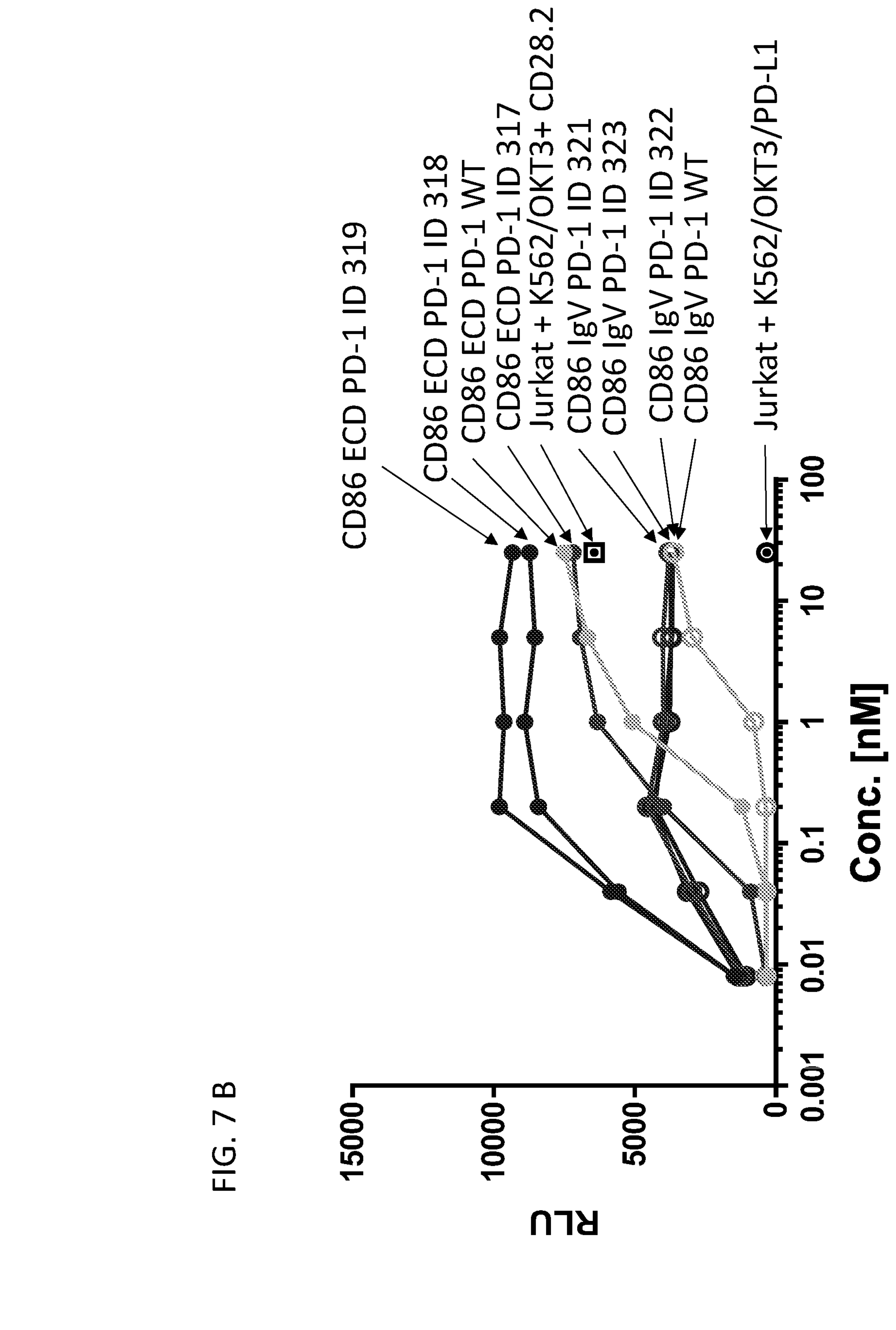

As shown in FIG. 7A, the addition of the exemplary variant stack constructs in the absence of PD-L1 exhibited little to no co-stimulatory signal consistent with the observation that PD-1/CD86 containing stack proteins require PD-L1 binding to induce a costimulatory signal via CD28. As shown in FIG. 7B, the addition of both ECD and IgV exemplary variant stack constructs in the presence of PD-L1 agonized CD28 dependent luminescent activity, as measured by IL-2 luminiescence relative luminescence units (RLU). The level of costimulation correlated with the CD28 and/or PD-L1 binding affinity of the variant molecules. This result is consistent with the activity of the variant PD-1-containing stack immunomodulatory proteins to exhibit PD-L1-dependent CD28-mediated costimulation.

C. T Cell Response

A cytomegalovirus (CMV) antigen-specific functional assay was used to assess the effect of exemplary variant stack molecules on T cell responses.

Peripheral blood mononuclear cells (PBMC) obtained from CMV seropositive donor were thawed and CMV lysate added at 1 μg/mL to 250,000/well PBMC in the presence of tested exemplary variant stack constructs (diluted at 1:3 dilutions from 100,000 pM to 46 pm). An Fc only molecule was also tested as control. Supernatant was collected 48 hours after incubation to assay IL-2 by ELISA, and 96 hours after incubation to assay IFNg by ELISA.

Figure 8:
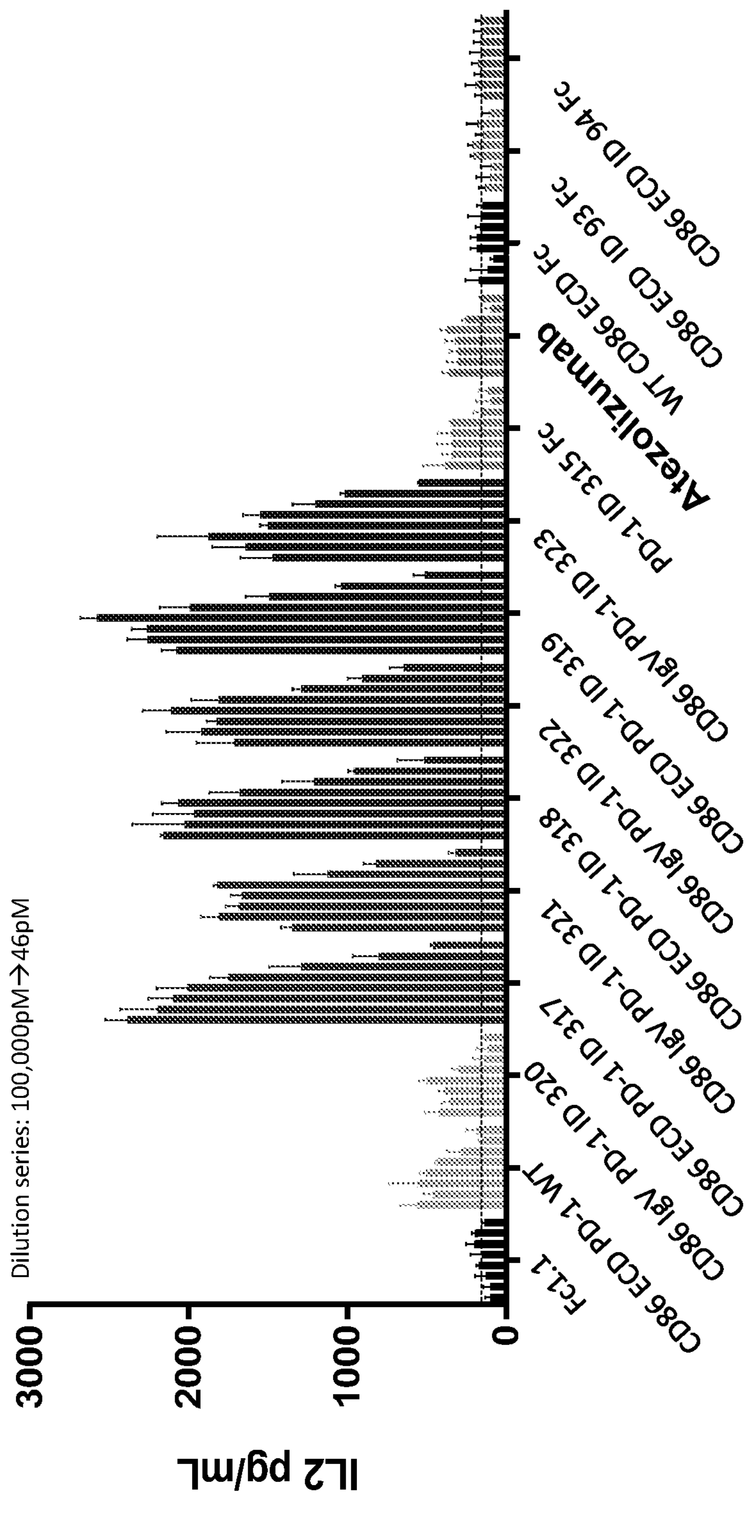
FIG. 8 and FIG. 9 depict cytokine concentrations (pg/mL) of T cell supernatants from a cytomegalovirus (CMV) antigen-specific functional assay. Supernatants were determined for IL-2 (FIG. 8) and IFNg (FIG. 9), as assessed by ELISA.
Figure 9:
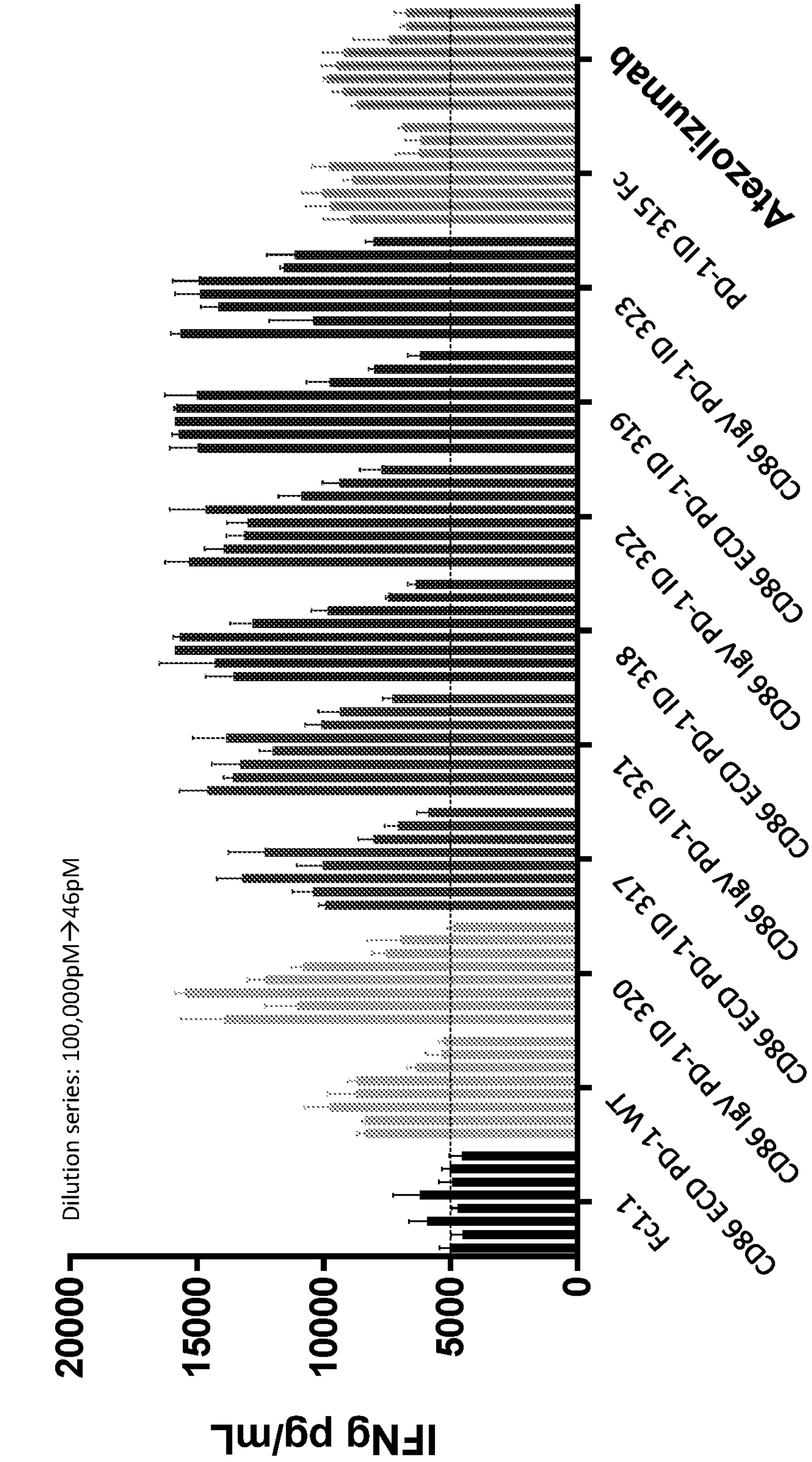

The exemplary PD1-CD86 stack constructs showed a concentration dependent increase in IL-2 production (FIG. 8) and IFNg production (FIG. 9). The PD1-CD86 stack constructs stimulated the production of cytokines to a greater degree than PD-L1 control antibody (atezolizumab) or the individual variant PD1 IgV-Fc molecule. The PD1-CD86 stack constructs also stimulated the production of cytokines to a greater degree than wild-type CD86 ECD-Fc or the individual variant CD86 ECD-Fc molecules.

These results are consistent with PD1-CD86 stack molecules displaying costimulatory effects to stimulate CD28 in a PD-L1-dependent manner. These results were observed for constructs with varying degrees of binding to CD28 on Jurkat cells as shown in Example 18.B above, including stack constructs containing a wild-type CD86 ECD that was observed to have low detectable binding to CD28.

Example 10

Generation and Assessment of Binding and Activity of Formatted Stacked Molecules Containing Variant PD-1 Molecules and Variant CD86 Molecules Exemplary variant CD86 molecules and exemplary variant PD-1 molecules that were affinity-modified as described in Examples 1-5 and Example 8, respectively, were used to generate "stack" Fc fusion molecules. The generated CD86-PD1 stack constructs were assessed for binding and activity.

A. Generation of CD86-PD-1 Stack Constructs

The stacks were generated by combining PCR products or geneblocks (Integrated DNA Technologies, Coralville, IA) that encoded the stack in a format that enabled its fusion to Fc by standard Gibson assembly using a Gibson assembly kit (New England Biolabs, USA). Stacks constructs had a homodimer format containing two identical polypeptides by fusion with a human IgG1 effectorless Fc sequence (e.g., set forth in SEQ ID NO: 230). Alternatively, stack constructs had a heterodimer format by "knobs-into-hole" Fc engineering to promote association of two different individual chains of the heterodimer, in which one polypeptide was fused to a "knob" Fc subunit (SEQ ID NO:346) and the second polypeptide was fused to a "hole" Fc subunit (SEQ ID NO:347).

Expression constructs encoding Fc fusion proteins were transfected into Expi293 HEK293 cells (e.g. Invitrogen). Supernatants were harvested and protein was captured and eluted from a Protein A column using an AKTA protein purification system.

Table E7 sets forth exemplary generated PD-1-CD86 stacks and formats. FIGS. 14A-14D depicts the structure of exemplary formatted stack constructs.

TABLE E7

Exemplary CD86-PD1 Stacks Formatted

Figure 14A:
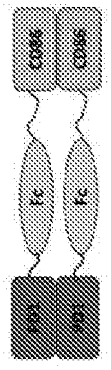
FIGS. 14A-14D depict the structure of exemplary formatted stack constructs.
Figure 14B:
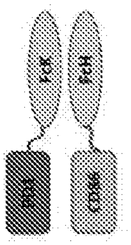
Figure 14C:
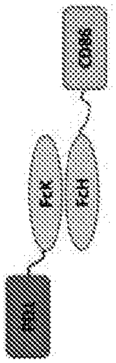
Figure 14D:
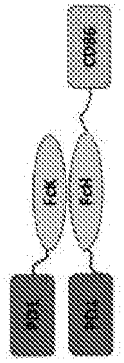

| Exemplary Format (FIG.) | SEQ ID NOs of stack construct | Domain 1 | Linker | Domain 2 | Linker | Domain 3 |
|---|---|---|---|---|---|---|
| FIG. 14A | 326 | Variant PD1 ECD (SEQ ID NO: 315) | GSG4S (SEQ ID NO: 222) | Fc (SEQ ID NO: 230) | four GGGGS (G4S) motifs (SEQ ID NO: 224) | Variant CD86 ECD (SEQ ID NO: 94) |
| | 326 | Variant PD1 ECD (SEQ ID NO: 315) | GSG4S (SEQ ID NO: 222) | Fc (SEQ ID NO: 230) | four GGGGS (G4S) motifs (SEQ ID NO: 224) | Variant CD86 ECD (SEQ ID NO: 94) |
| FIG. 14A | 327 | Variant PD1 ECD (SEQ ID NO: 315) | GSG4S (SEQ ID NO: 222) | Fc (SEQ ID NO: 230) | four GGGGS (G4S) motifs (SEQ ID NO: 224) | Variant CD86 IgV (SEQ ID NO: 150) |
| | 327 | Variant PD1 ECD (SEQ ID NO: 315) | GSG4S (SEQ ID NO: 222) | Fc (SEQ ID NO: 230) | four GGGGS (G4S) motifs (SEQ ID NO: 224) | Variant CD86 IgV (SEQ ID NO: 150) |
| FIG. 14B | 329 | Variant PD1 ECD (SEQ ID NO: 315) | GSG4S linker (SEQ ID NO: 222) | Fc (SEQ ID NO: 324) | — | — |
| | 329 | Variant PD1 ECD (SEQ ID NO: 315) | GSG4S linker (SEQ ID NO: 222) | Fc (SEQ ID NO: 325) | — | — |
| FIG. 14C | 328 | Variant PD1 ECD (SEQ ID NO: 315) | GSG4S linker (SEQ ID NO: 222) | Fc (SEQ ID NO: 324) | — | — |
| | 330 | Fc (SEQ ID NO: 325) | four GGGGS (G4S) motifs (SEQ ID NO: 224) | Variant CD86 IgV (SEQ ID NO: 150) | — | — |
| FIG. 14D | 328 | Variant PD1 ECD (SEQ ID NO: 315) | GSG4S linker (SEQ ID NO: 222) | Fc (SEQ ID NO: 324) | — | — |
| | 331 | Variant PD1 ECD (SEQ ID NO: 315) | GSG4S linker (SEQ ID NO: 222) | Fc (SEQ ID NO: 325) | four GGGGS (G4S) motifs (SEQ ID NO: 224) | Variant CD86 IgV (SEQ ID NO: 150) |

B. Binding

To assess binding activity, the exemplary formatted stack constructs were incubated with Jurkat cells expressing CD28, the cognate binding partner of CD86, and with K562 cells transduced to express PDL1, the cognate binding partner of PD-1. The cells (50,000 cells/well) were incubated on ice for 30 min with the formatted stack constructs set forth in Table E7 at various concentrations (starting concentration 100 nM, 8 serial 1:4 dilutions titrated down). Cells were then washed with FACS buffer and resuspended with 50 μL anti-Fc antibody-PE for 30 min. Binding was assessed by flow cytometry and Mean Fluorescence Intensity (MFI) was determined.

Figure 15A:
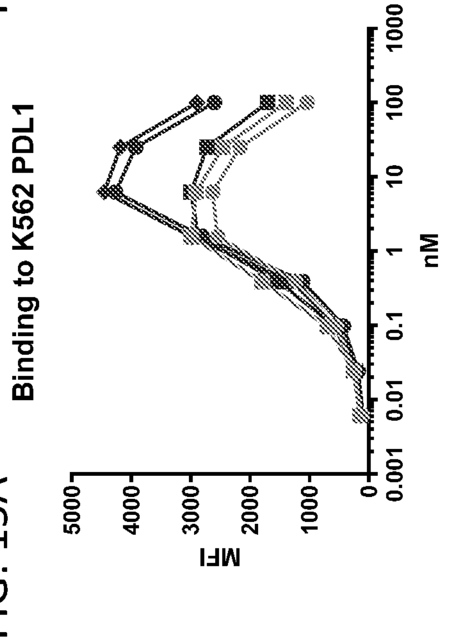
FIG. 15A and FIG. 15B depict binding of the exemplary formatted stack constructs at various concentrations (100 nM serial diluted 8 times to 1:4) to cognate binding partners PD-L1 (left) and CD28 (right) as assessed by flow cytometry and measured by Mean Fluorescence Intensity (MFI).
Figure 15B:
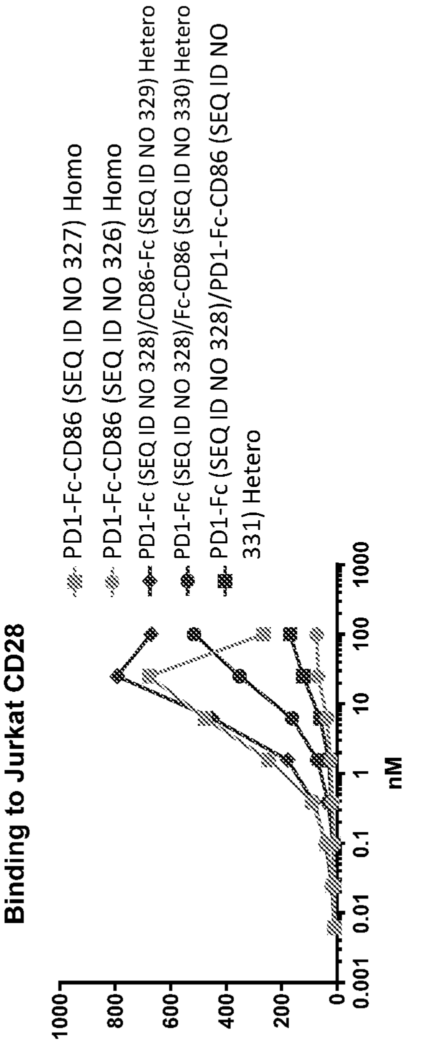

As shown in FIGS. 15A and 15B, exemplary PD-1-CD86 stack construct formats retain binding to PDL1 and CD28 compared to exemplary variant unformatted control stacks. These data indicate that the different stacked molecule formats retain binding activity to cognate binding partners.

C. T Cell Costimulation

To test whether exemplary stack constructs could drive target-specific costimulation of T cells, a transfected cell system including a T cell reporter line for measuring costimulation was used. Jurkat cells including an IL-2 promoter luciferase reporter and that expressed or did not express PD1 were used to evaluate costimulatory function. To stimulate the Jurkat cells, K562 cells were engineered for use as artificial antigen presenting cells. Specifically, K562 cells were transduced with a lentivirus encoding a single-chain Fv version of the anti-CD3 antibody OKT3 with or without transduction with a separate lentivirus directing PDL1 expression. K562 cells displaying cell surface anti-CD3 single chain Fv (OKT3) with or without surface PDL1 expression were plated in culture media at $2\times10^4$ cells/well. Target cells were incubated for 10 min with exemplary PD1-CD86 stack constructs (titrated down from 2 nM in 8 serial, 1:3 dilutions) at 37° C. The Jurkat effector cells expressing an IL-2-luciferase reporter gene (Promega) were added at $1\times10^5$ cells/well to bring the final volume/well to 100 μl. Target and Jurkat cells in the presence or absence of exemplary stack constructs were incubated for 5 hours at 37° C. Plates were removed from the incubator and acclimated to room temperature for 15 minutes. 100 μL of cell lysis and luciferase substrate solution (BioGlo luciferase reagent, Promega) was added to each well and the plates were incubated on an orbital shaker for 10 minutes. Luminescence was measured with a 1 second per well integration time using a Cytation 3 imaging reader (BioTek Instruments). Relative luminescence values (RLU) were determined for each test sample and reported.

Figure 16A:
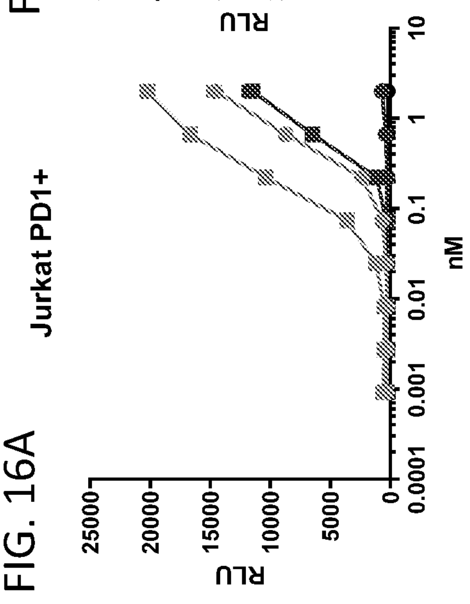
FIG. 16A and FIG. 16B depict the costimulatory ability of the exemplary formatted stack constructs tested in a luciferase reporter cell system and determined using Relative Luminescence Units (RLU).
Figure 16B:
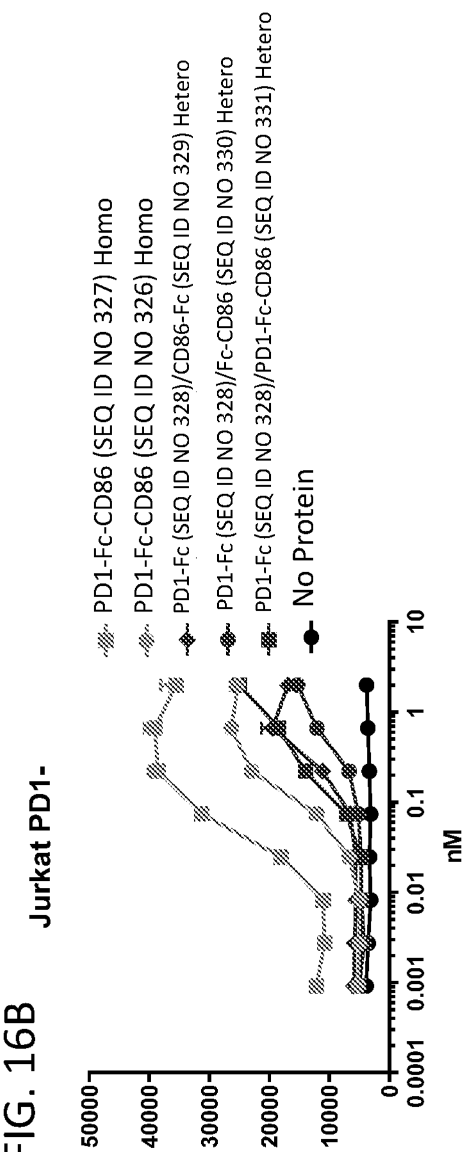

As shown in FIGS. 16A and 16B, incubation with the exemplary stack constructs provided costimulation to the T cells in the presence of PDL1+K562/OKT3 cells regardless of whether the T cells were PD1+ or PD1−. These results suggest that stack constructs are capable of delivering a T cell costimulatory signal even in the presence of strong checkpoint blockade.

D. Cytokine Production

To assess the ability of exemplary CD86-PD-1 stack constructs (see Table E7) to facilitate cytokine production in T cells, an HLA-A2+HPV+ target cell line known to express PD-L1 (SCC152 PDL1+) was co-cultured with T cells transduced to express an exemplary recombinant HPV16 E6-specific T cell receptor (TCR) in the presence of various concentrations of the exemplary formatted stacks. SCC152 PDL1+ cells were seeded into a 96-well plate at 40,000 cells/well with culture media and incubated overnight at 37° C. The following day, various concentrations of the exemplary formatted stack constructs (0.666 nM, titrated at 1:3 dilution for 5-point titration) and 40,000 T cells expressing the recombinant HPV16 E6-specific T cell receptor (TCR) were added to each well. For comparison, cells were incubated with a variant CD80 IgV-Fc fusion protein known to bind CD28 and PD-L1, with mock transduced T cells (mock), or incubated in the absence of formatted stack constructs (no protein). Plates were incubated at 37° C., and supernatant was collected after 24 hrs of incubation to test for secreted cytokines, e.g., IFNg, IL-2, TNFα.

Figure 17A:
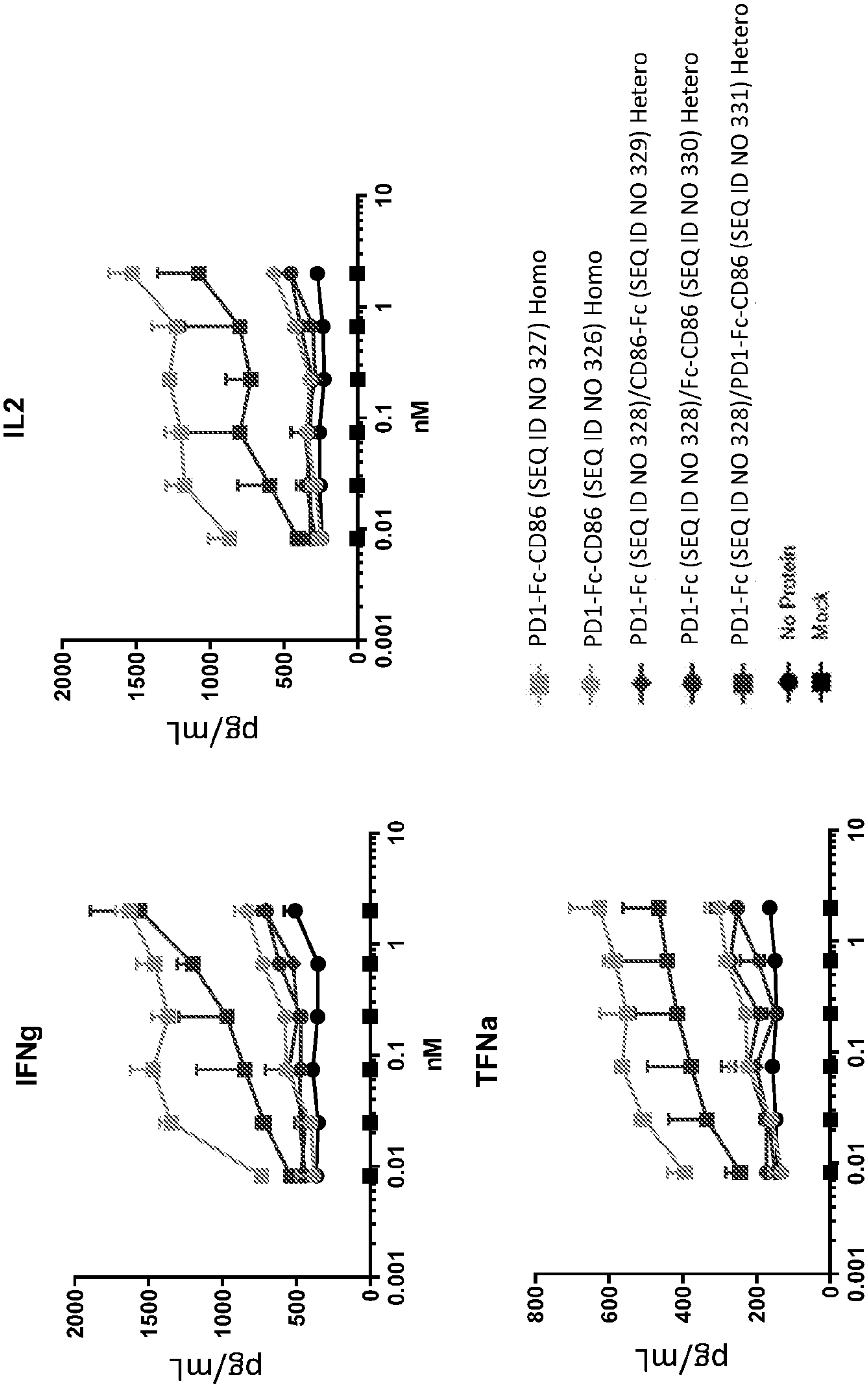
FIG. 17A depicts the ability of exemplary CD86-PD-1 stack constructs to facilitate cytokine production in T cells as measured by the concentration of IFNg, IL2, and TNFα (pg/mL).

As shown in FIG. 17A, formatted CD86-PD-1 stack constructs induced higher levels of IFNg, IL-2, and TNFα cytokine production at 24 hrs relative to control. These data indicate that formatted CD86-PD-1 stack constructs facilitate costimulation and cytokine production in target specific T cells.

E. Cytotoxic Activity

Exemplary CD86-PD-1 stack constructs (see Table E7) were assessed for their ability to facilitate T cell cytotoxic activity. HLA-A2+HPV+ target cell line SCC152 PDL1+ were seeded into a 96-well plate at 20,000 cells per well with culture media and incubated overnight at 37° C. The following day, the culture media was discarded, and the cells were incubated for 10 min at 37° C. with 100 μL of luciferin. Various concentrations of the exemplary formatted stack constructs (0.666 nM, titrated at 1:3 dilution for 5-point titration) and 20,000 T cells transduced with an exemplary recombinant HPV16 E6-specific T cell receptor (TCR) were added to each well and incubated for 10 min at 37° C. before being centrifuged (1300 rpm) for 30 sec. For comparison, cells were incubated with a variant CD80 IgV-Fc fusion protein known to bind CD28 and PD-L1, mock transduced T cells (mock), or in the absence of formatted stack constructs (no protein). Plates were incubated at 37° C., and relative luminescence values (RLU) were determined after 24, 48, and 72 hrs of incubation.

Figure 17B:
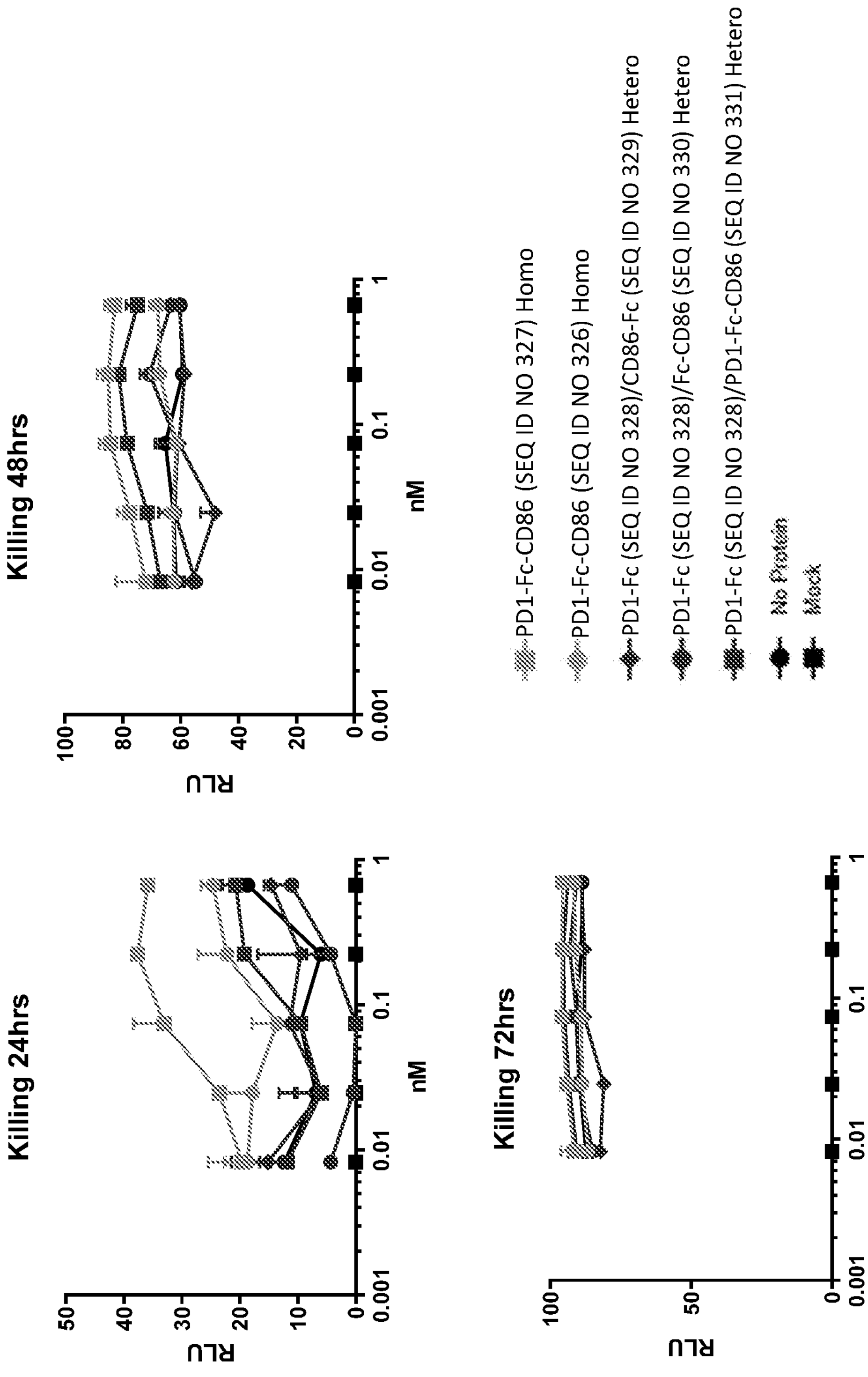
FIG. 17B depicts the ability of exemplary CD86-PD-1 stack constructs to facilitate T cell cytoxic activity against HLA-A2+HPV+ target cells at 24 hours, 48 hours, and 72 hours post incubation assessed by Relative Lumiescence Units (RLU).

FIG. 17B shows cell killing, as measured by RLU, at 24, 48, and 72 hrs at each concentration. CD86-PD-1 stack constructs enhanced T cell cytotoxic activity at 24 hours compared to control. These data support that the CD86-PD-1 stack constructs are capable of costimulating T cells to induce T cell cytotoxic activity.

Example 11

Assessment of Binding and Costimulatory Function of Conjugates HER2 and EGFR Targeting Antibody Exemplary variant CD86 IgV molecules were conjugated to HER2 and EGFR targeting antibodies to form conjugates (fusion proteins). The variant CD86 IgV domain set forth by SEQ ID NO: 150 was fused to the amino or carboxyl termini of the light chain or heavy chain of the HER2 targeting antibody pertuzumab or the EGFR targeting antibody panitumumab with intervening G4S linkers (see Table E8). Exemplary configurations of conjugates (fusion proteins) are shown in FIG. 18. DNA encoding each of the constructs diagrammed in FIGS. 19A and 19B was transfected into HEK-293 cells and secreted proteins were purified by Protein A and size exclusion chromatography. The resultant conjugate proteins were next assessed for retention of appropriate binding properties.

TABLE E8

| Description | Heavy Chain (HC) SEQ ID NO | Light Chain (LC) SEQ ID NO |
|---|---|---|
| Exemplary CD86-Antibody Conjugates and Control Antibodies | | |
| Pertuzumab | 340 | 341 |
| CD86-HC Pertuzumab | 342 | 341 |
| CD86-LC Pertuzumab | 340 | 343 |
| HC-CD86 Pertuzumab | 344 | 341 |
| LC-CD86 Pertuzumab | 340 | 345 |
| Panitumumab | 346 | 347 |
| CD86-HC Panitumumab | 348 | 347 |
| CD86-LC Panitumumab | 346 | 349 |
| HC-CD86 Panitumumab | 350 | 347 |
| LC-CD86 Panitumumab | 346 | 351 |
| Control Antibody | | |
| Ramucirumab | 352 | 353 |

A. Binding

Figure 19A:
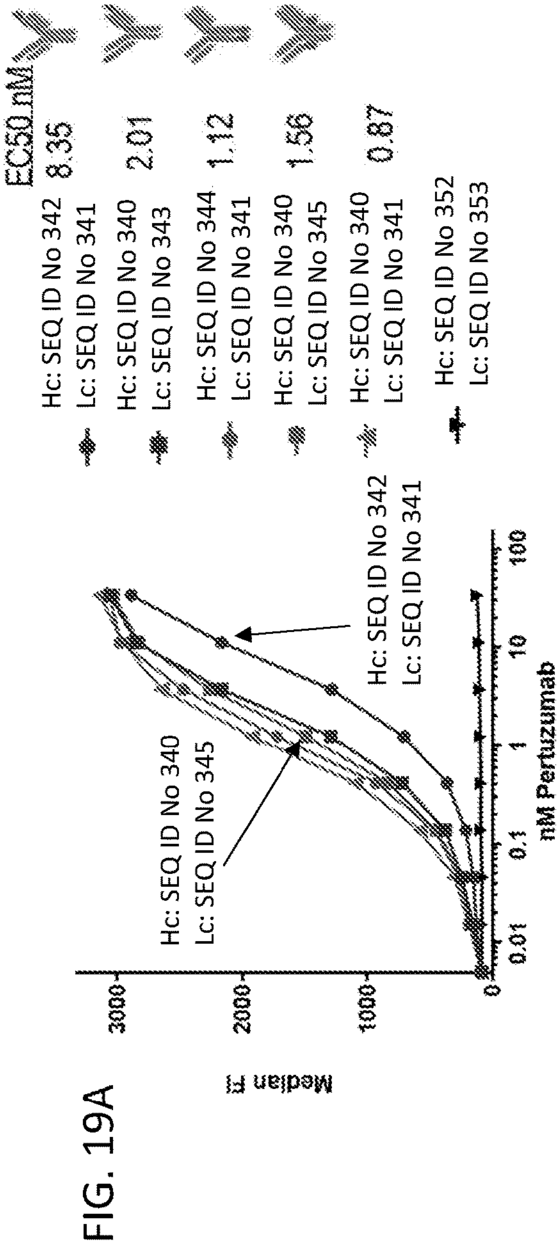
FIG. 19 depicts binding of exemplary pertuzumab-CD86 conjugates to HER2 (FIG. 19A) and exemplary panitumumab-CD86 conjugates to EGFR (FIG. 19B) as determined by Mean Fluorescence Intensity.

To assess the ability of the exemplary pertuzumab-CD86 conjugates (fusion proteins) to bind HER2, SCC-152 cells were incubated with various concentrations of exemplary conjugates (see Table E8), pertuzumab, or control antibody (ramucirumab). SCC152 cells (50,000 cells/well) were incubated on ice for 30 min with the CD86 antibody conjugates (fusion proteins) set forth in Table E8 at various concentrations (starting concentration 33 nM, 9 serial 1:3 dilutions titrated down). Cells were then washed with FACS buffer and resuspended with 50 μL anti-Fc antibody-PE for 30 min. Binding was assessed by flow cytometry and Median Fluorescence Intensity (MFI) was determined. As shown in FIG. 19A, conjugates retained binding to HER2.

Figure 19B:
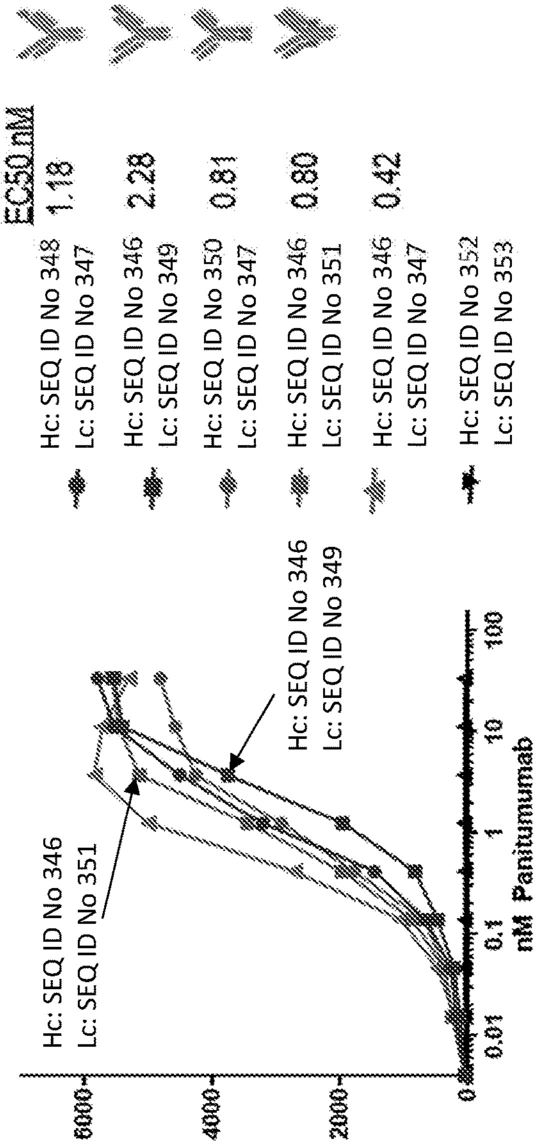

To assess the ability of the exemplary panitumumab-CD86 conjugates to bind EGFR, CHO cells transduced to express EGFR were incubated with various concentrations of exemplary conjugates (see Table E8), panitumumab, or control antibody (ramucirumab). CHO-EGFR cells (50,000 cells/well) were incubated on ice for 30 min with the CD86 antibody fusion conjugate constructs set forth in Table E8 at various concentrations (starting concentration 33 nM, 9 serial 1:3 dilutions titrated down). Cells were then washed with FACS buffer and resuspended with 50 μL anti-Fc antibody-PE for 30 min. Binding was assessed by flow cytometry and Median Fluorescence Intensity (MFI) was determined. As shown in FIG. 19B, conjugates retained binding to EGFR.

B. T cell Costimulation

To test whether exemplary conjugates (fusion proteins) could drive target-specific costimulation of T cells, a transfected cell system including Jurkat cells with an IL-2 promoter luciferase reporter were used to evaluate costimulatory function. To stimulate the Jurkat cells, target SCC-152 cells, which constitutively express HPV viral proteins, were plated in culture media at $2\times10^4$ cells/well. Target cells were incubated for 10 min with CD86 antibody fusion conjugates (titrated down from 2 nM in 8 serial, 1:4 dilutions) at 37° C. The Jurkat effector cells expressing an IL-2-luciferase reporter gene (Promega) were added at $1\times10^5$ cells/well to bring the final volume/well to 100 μl. Target and Jurkat cells in the presence or absence of exemplary conjugates were incubated for 5 hours at 37° C. Plates were removed from the incubator and acclimated to room temperature for 15 minutes. 100 μL of cell lysis and luciferase substrate solution (BioGlo luciferase reagent, Promega) was added to each well and the plates were incubated on an orbital shaker for 10 minutes. Luminescence was measured with a 1 second per well integration time using a Cytation 3 imaging reader (BioTek Instruments). Relative luminescence values (RLU) were determined for each test sample and reported.

Figure 20A:
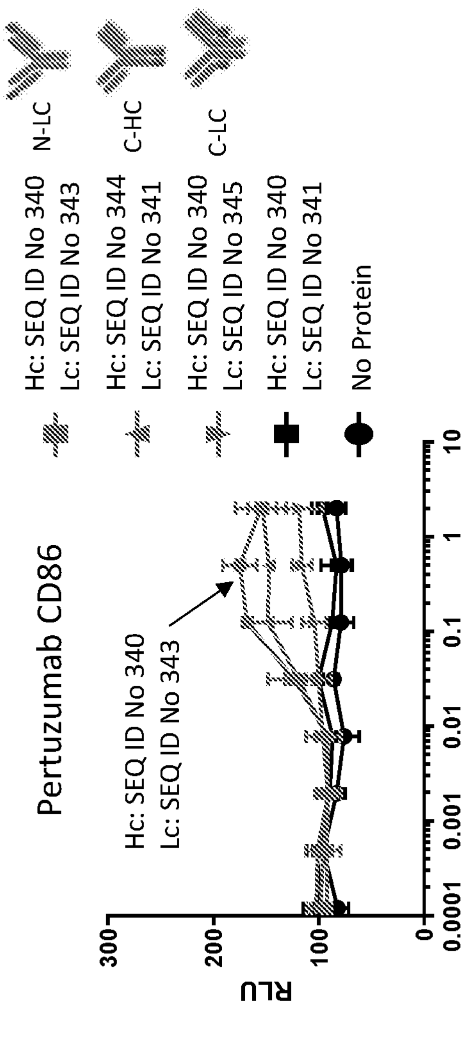
FIG. 20 depicts the ability of pertuzumab-CD86 conjugates (FIG. 20A) and exemplary panitumumab-CD86 conjugates (FIG. 20B) to provide costimulation to T cells in an IL-2 luciferase reporter assay as measured in Relative Luminescence Units (RLU).
Figure 20B:
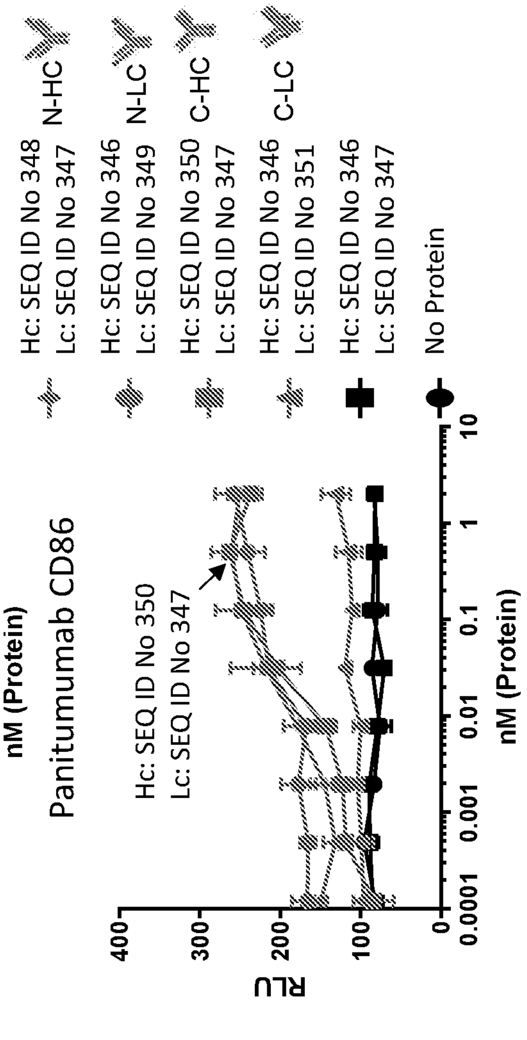

SCC-152 cells were co-cultured with the Jurkat IL2 reporter cell line transduced with an TCR specific for the HPV peptide E6 in the presence or absence of various concentrations of conjugates or control antibody. As shown in FIGS. 20A and 20B, RLU measures revealed that T cells experienced increased costimulation in the presence of conjugates compared to control antibody.

C. Cytotoxic Activity

Exemplary conjugates were assessed for their ability to facilitate T cell cytotoxic activity. Target cell lines SCC-152 were seeded into a 96-well plate at 20,000 cells per well with culture media and incubated overnight at 37° C. The following day, the culture media was discarded, and the cells were incubated for 10 min at 37° C. with 100 μL of luciferin. 20,000 primary human T cells transduced with E6 TCR were added to each well at various effector to target ratios (E:T) in the presence of 2 nM of an exemplary conjugate and incubated for 10 min at 37° C. before being centrifuged (1300 rpm) for 30 sec. For comparison, cells were incubated with pertuzumab only, panitumumab only, control antibody ramucirumab (mock), or in the absence of protein. Plates were incubated at 37° C., and the percentage of target cell killing was determined after 24 hrs of incubation.

Figure 21A:
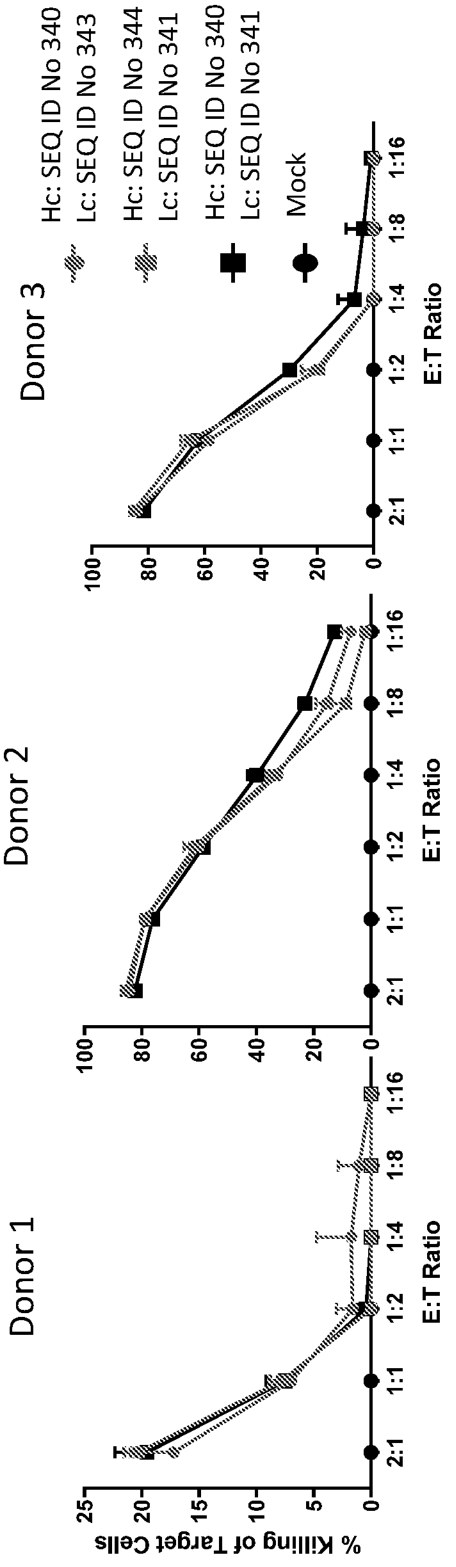
FIG. 21 depicts the ability of exemplary pertuzumab-CD86 conjugates (FIG. 21A) and exemplary panitumumab-CD86 conjugates (FIG. 21B) to facilitate T cell cytotoxic activity as tested at various effector to target ratios (E:T) of primary human T cells measured by percent killing of SCC-152 target cells.
Figure 21B:
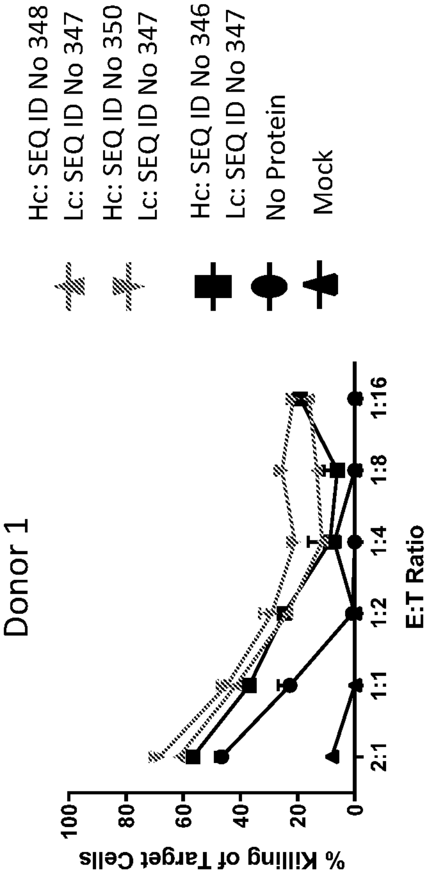

FIGS. 21A and 21B demonstrate minimal increases in percent cell killing after 24 hrs at each E:T in the presence of exemplary conjugates.

C. Cytokine Production

To assess the ability of exemplary conjugate to facilitate cytokine production in T cells, SCC-152 cells were co-cultured with primary human T cells transduced with E6 TCR (three donors) in the presence of various concentrations of the exemplary conjugates (see Table E8). SCC-152 cells were seeded into 96-well plates at 40,000 cells/well with culture media and incubated overnight at 37° C. The following day, various concentrations of the exemplary conjugates and 40,000 T cells were added to each well. For comparison, cells were incubated with pertuzumab only, panitumumab only, control antibody ramucirumab (mock), or in the absence of protein. Plates were incubated at 37° C., and supernatant was collected after 24 hrs of incubation to test for secreted cytokines, e.g., IFNg, IL-2, TNFa.

Figure 22A:
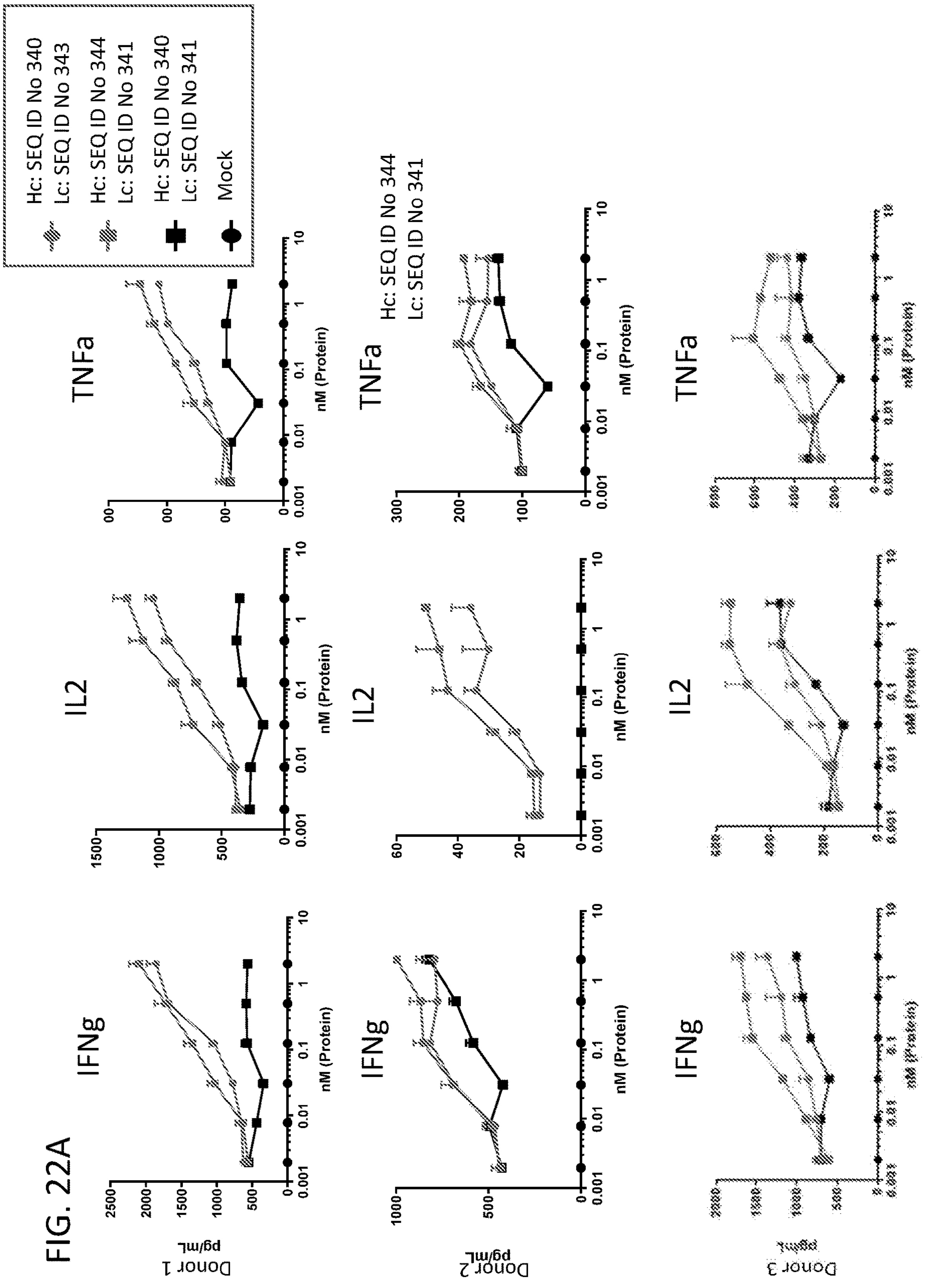
FIG. 22 depicts the ability of pertuzumab-CD86 conjugates (FIG. 22A) and exemplary panitumumab-CD86 conjugates (FIG. 22B) to facilitate cytokine production in T cells by determining the concentration of IFNg, IL2, and TNFα (nM protein) in the cellular supernatant.
Figure 22B:
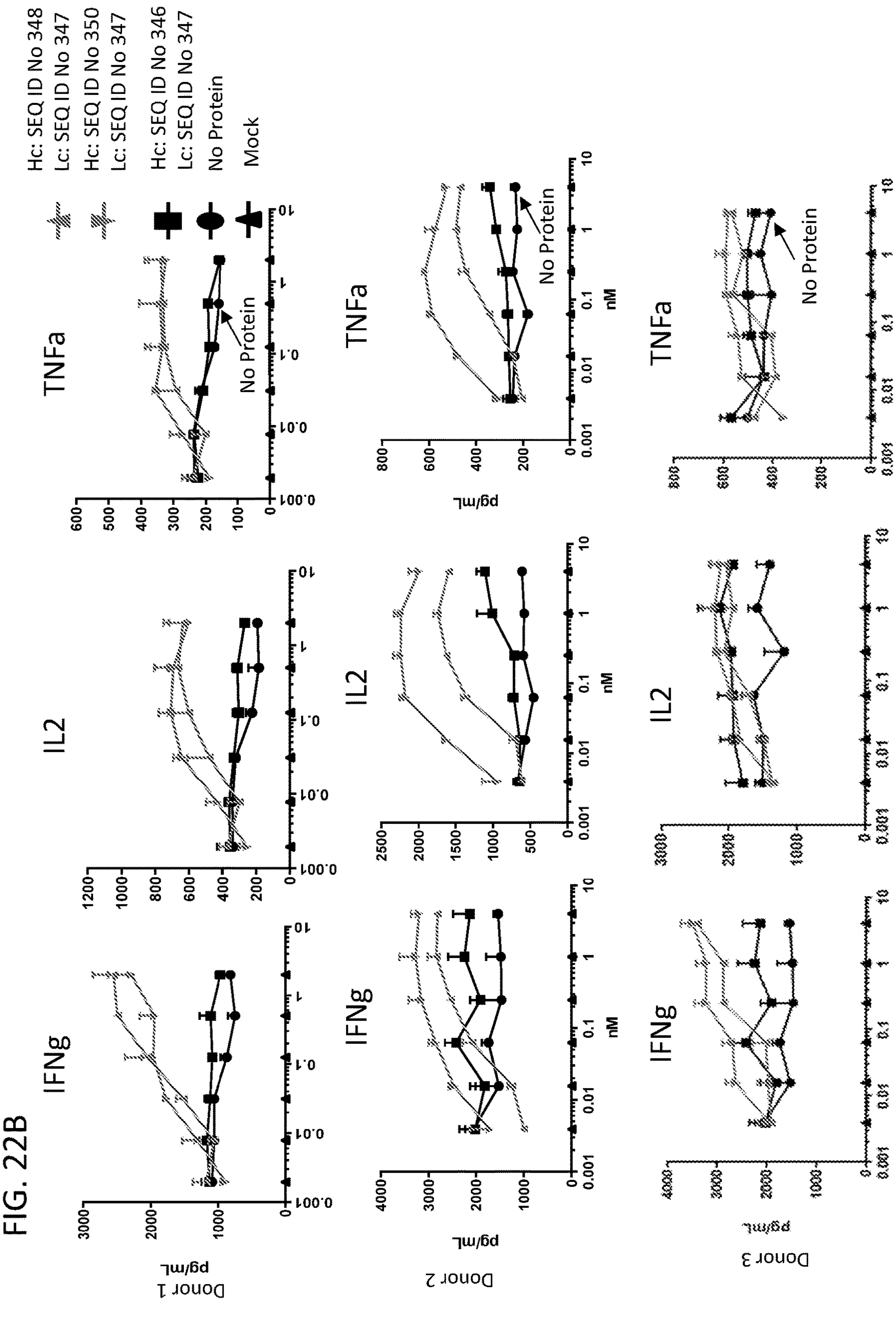

FIGS. 22A and 22B show the concentration of IFNg, IL-2, and TNFa for each donor. As shown, CD86-antibody conjugates resulted in cells exhibiting enhanced cytokine production compared to antibody only controls. These data demonstrate that conjugates are able to facilitate costimulation and cytokine production in T cells.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

What is claimed:

1. A variant CD86 polypeptide, comprising a CD86 extracellular domain or a portion thereof comprising a CD86 IgV domain, wherein the variant CD86 polypeptide comprises an amino acid modification at position 25 with reference to an unmodified CD86 polypeptide, and further comprises one or more amino acid modifications at position(s) selected from 13, 18, 28, 33, 38, 39, 40, 43, 45, 52, 53, 60, 68, 71, 77, 79, 80, 82, 86, 88, 89, 90, 92, 93, 97, 102, 104, 113, 114, 123, 128, 129, 132, 133, 137, 141, 143, 144, 148, 153, 154, 158, 170, 172, 175, 178, 180, 181, 183, 185, 192, 193, 196, 197, 198, 205, 206, 207, 212, 215, 216, 222, 223, or 224, with reference to positions set forth in SEQ ID NO:29.

2. The variant CD86 polypeptide of claim 1, wherein the unmodified CD86 polypeptide comprises:

(i) the sequence of amino acids set forth in SEQ ID NO:29, (ii) the sequence of amino acids set forth in SEQ ID NO:123;

(iii) the sequence of amino acids set forth in SEQ ID NO:122;

or (iv) a portion of any of (i)-(iii) comprising an IgV domain.

3. The variant CD86 polypeptide of claim 1, wherein the variant CD86 comprises up to 1, 2, 3, 4, 5, 6, 7, 8, 9, 10, 11, 12, 13, 14, 15, 16, 17, 18, 19 or 20 amino acid modifications.

4. The variant CD86 polypeptide of claim 1, wherein the one or more amino acid modification comprises Q25L and further comprises one or more amino acid substitutions selected from A13V, Q18K, S28G, F33I, E38V, N39D, L40M, L40S, N43K, V45I, F52L, D53G, M60K, D68N, T71A, L77P, I79N, K80E, K80M, K80R, K82T, Q86K, Q86R, I88F, I88T, I89V, H90 L, H90Y, K92I, K93T, M97L, Q102H, N104S, F113S, S114G, N123D, V128A, Y129N, L132M, T133A, I137T, P141A, P143H, K144E, V148D, K153E, K153R, N154D, E158G, V170D, E172G, D175E, I178T, L180S, S181P, S183P, P185S, T192N, I193V, I196V, L197M, E198D, L205S, S206T, S207P, E212V, D215V, P216H, H222T or I223F.

5. The variant CD86 polypeptide of claim 1, comprising one or more amino acid modifications selected from Q25L/H90Y, A13V/Q25L/H90L, Q25L/Q86R/H90L, I89V/H90L, Q25L/T71A/H90Y, Q25L/D53G/E212V, Q25L/H90L, A13V/Q25L/H90L/S181P/L197M/S206T, Q25L/Q86R/H90L/K93T/L132M/V148D/S181P/P216H, Q25L/F33I/H90Y/V128A/P141A/E158G/S181P, Q25L/N39D/K80R/Q86R/I88F/H90L/K93T/N123D/N154D, Q25L/H90L/K93T/M97L/T133A/S181P/D215V, Q25L/Q86R/H90L/N104S, Q25L/L40M/H90L/L180S/S183P, Q18K/Q25L/F33I/L40S/H90L, Q25L/Q86K/H90L/I137T/S181P, Q25L/L77P/H90Y/K153R/V170D/S181P, Q25L/S28G/F33I/F52L/H90L/Q102H/I178T, Q25L/F33I/H90L/K144E/L180S, Q25L/F33I/H90L/K153E/E172G/T192N, Q25L/F33I/Q86R/H90Y/D175E/I196V/E198D, Q25L/V45I/D68N/H90L/S183P/L205S, Q25L/F33I/H90L, Q25L/F33I/Q86R/H90L/K93T, Q25L/H90L, Q25L/H90L/P185S, Q25L/H90L/P185S/P224L, Q25L/H90L/S179R, Q25L/H90Y/S181P/I193V, Q25L/K82T/H90L/T152S/S207P, or Q25L/Q86R/H90L/K93T.

6. The variant CD86 polypeptide of claim 1, wherein the variant CD86 polypeptide comprises a sequence of amino acids that exhibits at least 85%, 86%, 87%, 88%, 89%, 90%, 91%, 92%, 93%, 94%, 95%, 96%, 97%, 98% or 99% sequence identity to SEQ ID NO:29.

7. The variant CD86 polypeptide of claim 1, wherein the variant CD86 polypeptide specifically binds to the ectodomain of CD28 with increased affinity compared to the binding of the unmodified CD86 for the same ectodomain.

8. The variant CD86 polypeptide of claim 1, wherein the variant CD86 polypeptide specifically binds to the ectodomain of CTLA-4 with decreased affinity compared to the binding of the unmodified CD86 for the same ectodomain.

9. The variant CD86 polypeptide of claim 1, wherein the variant CD86 polypeptide comprises:

(i) the sequence of amino acids set forth in any of SEQ ID NOS: 85-87, 89-103, or 112-120 or a portion thereof comprising an IgV domain, (ii) a sequence of amino acids that exhibits at least 95% sequence identity to any of SEQ ID NOS: 85-87, 89-103, or 112-120 or a portion thereof comprising an IgV domain and that contains the one or more of the amino acid modifications of the respective SEQ ID NO set forth in any of SEQ ID NOS: 85-87, 89-103, or 112-120, (iii) the sequence of amino acids set forth in any of SEQ ID NOs: 141-143, 145-159, or 168-176, or (iv) a sequence of amino acids that exhibits at least 95% sequence identity to any of SEQ ID NOs: 141-143, 145-159, or 168-176 and that contains the one or more of the amino acid modifications of the respective SEQ ID NO set forth in any of SEQ ID NOs: 141-143, 145-159, or 168-176.

10. An immunomodulatory protein comprising a variant CD86 polypeptide of claim 1 linked to a multimerization domain.

11. The immunomodulatory protein of claim 10, wherein the multimerization domain is an Fc domain or a variant thereof with reduced effector function.

12. An infectious agent, comprising the variant CD86 polypeptide of claim 1, or an immunomodulatory protein comprising the variant CD86 polypeptide of claim 1 linked to a multimerization domain.

13. A pharmaceutical composition, comprising the variant CD86 polypeptide of claim 1, or an immunomodulatory protein comprising the variant CD86 polypeptide of claim 1 linked to a multimerization domain.

14. An article of manufacture comprising the pharmaceutical composition of claim 13 in a vial or a container.

15. The variant CD86 polypeptide of claim 1, wherein the unmodified CD86 comprises the sequence of amino acids set forth in SEQ ID NO:122.

16. The variant CD86 polypeptide of claim 1, comprising one or more amino acid modifications Q25L/Q86R/H90L/N104S.

17. The variant CD86 polypeptide of claim 1, comprising the sequence of amino acid set forth in SEQ ID NO: 150.

18. The variant CD86 polypeptide of claim 1, comprising the sequence of amino acid set forth in SEQ ID NO: 94.

19. The immunomodulatory protein of claim 11, wherein the Fc domain comprises the sequence of amino acids set forth in SEQ ID NO: 229 or a sequence of amino acids that exhibits at least 85% sequence identity to the sequence of amino acids set forth in SEQ ID NO: 229.

20. The immunomodulatory protein of claim 11, wherein the Fc domain is or comprises the sequence of amino acids set forth in SEQ ID NO: 229.

21. The immunomodulatory protein of claim 11, wherein the Fc domain is a variant IgG1 Fc domain comprising one or more amino acid modifications selected from among C220S, E233P, L234A, L234V, L235A, L235E, G236del, G237A, S267K, N297G, V302C and K447del, each by EU numbering.

22. The immunomodulatory protein of claim 11, wherein the Fc domain is a variant IgG1 Fc domain comprising the amino acid modifications L234A/L235E/G237A, each by EU numbering.

23. The immunomodulatory protein of claim 11, wherein the Fc domain is or comprises the sequence of amino acids set forth in SEQ ID NO: 230 or a sequence of amino acids that exhibits at least 85% sequence identity to the sequence of amino acids set forth in SEQ ID NO: 230.

* * * * *